(12) United States Patent
Monroe et al.

(10) Patent No.: US 11,084,875 B2
(45) Date of Patent: Aug. 10, 2021

(54) ANTI-TREM2 ANTIBODIES AND METHODS OF USE THEREOF

(71) Applicant: ALECTOR LLC, South San Francisco, CA (US)

(72) Inventors: Kate Monroe, Berkeley, CA (US); Tina Schwabe, San Francisco, CA (US); Francesca Avogadri-Connors, South San Francisco, CA (US); Ilaria Tassi, San Francisco, CA (US); Helen Lam, Union City, CA (US); Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 149 days.

(21) Appl. No.: 16/382,117

(22) Filed: Apr. 11, 2019

(65) Prior Publication Data
US 2019/0315858 A1    Oct. 17, 2019

Related U.S. Application Data

(63) Continuation of application No. 15/502,766, filed as application No. PCT/US2015/044396 on Aug. 8, 2015, now abandoned.

(Continued)

(51) Int. Cl.
*C07K 16/28* (2006.01)
*A61K 39/00* (2006.01)

(52) U.S. Cl.
CPC .......... *C07K 16/2803* (2013.01); *C07K 16/28* (2013.01); *C07K 16/283* (2013.01); *A61K 2039/505* (2013.01); *C07K 2317/21* (2013.01); *C07K 2317/31* (2013.01); *C07K 2317/33* (2013.01); *C07K 2317/34* (2013.01); *C07K 2317/52* (2013.01); *C07K 2317/55* (2013.01);
(Continued)

(58) Field of Classification Search
None
See application file for complete search history.

(56) References Cited

U.S. PATENT DOCUMENTS

| | | | |
|---|---|---|---|
| 4,657,760 A | 4/1987 | Kung et al. | |
| 4,816,567 A | 3/1989 | Cabilly et al. | |

(Continued)

FOREIGN PATENT DOCUMENTS

| | | |
|---|---|---|
| EP | 0404097 B1 | 9/1996 |
| JP | 200473182 A | 9/2005 |

(Continued)

OTHER PUBLICATIONS

Alegre, M.-L. et al. (Jun. 1, 1994). "A Non-Activating "Humanized" Anti-cd3 Monoclonal Antibody Retains Immunosuppressive Properties in Vivo," *Transplantation* 57(11):1537-1543.

(Continued)

*Primary Examiner* — Adam Weidner
(74) *Attorney, Agent, or Firm* — Morrison & Foerster LLP

(57) ABSTRACT

The invention is generally directed to methods and compositions that include antibodies, e.g., monoclonal, chimeric, humanized antibodies, antibody fragments, etc., that specifically bind a TREM2 protein, e.g., a mammalian TREM2 and/or human TREM2. The methods provided herein find use in preventing, reducing risk, or treating an individual having dementia, frontotemporal dementia, Alzheimer's disease, Nasu-Hakola disease, or multiple sclerosis.

26 Claims, 68 Drawing Sheets

Specification includes a Sequence Listing.

Related U.S. Application Data

(60) Provisional application No. 62/135,110, filed on Mar. 18, 2015, provisional application No. 62/135,122, filed on Mar. 18, 2015, provisional application No. 62/035,336, filed on Aug. 8, 2014.

(52) U.S. Cl.
CPC ...... *C07K 2317/56* (2013.01); *C07K 2317/75* (2013.01); *C07K 2317/76* (2013.01); *C07K 2317/92* (2013.01)

(56) References Cited

U.S. PATENT DOCUMENTS

| | | |
|---|---|---|
| 5,206,344 A | 4/1993 | Katre et al. |
| 5,225,212 A | 7/1993 | Martin et al. |
| 5,229,275 A | 7/1993 | Goroff |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Weis et al. |
| 5,573,905 A | 11/1996 | Lerner et al. |
| 5,587,458 A | 12/1996 | King et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,731,168 A | 3/1998 | Carter et al. |
| 5,739,277 A | 4/1998 | Presta et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,417,429 B1 | 7/2002 | Hein et al. |
| 6,420,548 B1 | 7/2002 | Vézina et al. |
| 6,982,321 B2 | 1/2006 | Winter |
| 7,087,409 B2 | 8/2006 | Barbas, III et al. |
| 7,125,978 B1 | 10/2006 | Vezina et al. |
| 7,556,926 B2 | 7/2009 | Tojo et al. |
| 8,093,360 B2 | 1/2012 | Casey |
| 8,231,878 B2 | 7/2012 | Colonna et al. |
| 8,614,299 B2 | 12/2013 | Baurin et al. |
| 8,981,061 B2 | 3/2015 | Colonna et al. |
| 9,587,036 B2 | 3/2017 | Kufer et al. |
| 9,975,966 B2 | 5/2018 | Lee et al. |
| 10,676,525 B2 | 6/2020 | Schwabe et al. |
| 2003/0165875 A1 | 9/2003 | Colonna et al. |
| 2004/0175744 A1 | 9/2004 | Hu et al. |
| 2005/0155089 A1 | 7/2005 | La et al. |
| 2005/0260670 A1 | 11/2005 | Colonna et al. |
| 2006/0014679 A1 | 1/2006 | Tojo et al. |
| 2006/0263774 A1 | 11/2006 | Clark et al. |
| 2007/0148167 A1 | 6/2007 | Strohl |
| 2009/0081199 A1 | 3/2009 | Colonna et al. |
| 2009/0181855 A1 | 7/2009 | Vasquez et al. |
| 2010/0056386 A1 | 3/2010 | Vasquez et al. |
| 2010/0280227 A1 | 11/2010 | Ambrose et al. |
| 2013/0150559 A1 | 6/2013 | Colonna et al. |
| 2016/0251434 A1 | 9/2016 | Colonna et al. |
| 2017/0240631 A1 | 8/2017 | Monroe et al. |
| 2019/0010230 A1 | 1/2019 | Monroe et al. |
| 2019/0040130 A1 | 2/2019 | Schwabe et al. |
| 2019/0330335 A1 | 10/2019 | Schwabe et al. |
| 2020/0317776 A1 | 10/2020 | Schwabe et al. |

FOREIGN PATENT DOCUMENTS

| | | |
|---|---|---|
| WO | WO-1987/04462 A1 | 7/1987 |
| WO | WO-1991/10741 A1 | 7/1991 |
| WO | WO-1993/08829 A1 | 5/1993 |
| WO | WO-1993/11161 A1 | 6/1993 |
| WO | WO-1993/16185 A2 | 8/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/58572 A1 | 11/1999 |
| WO | WO-2001/27160 A1 | 4/2001 |
| WO | WO-2004/042072 A2 | 5/2004 |
| WO | WO-2007/106585 A1 | 9/2007 |
| WO | WO-2008/045443 A2 | 4/2008 |
| WO | WO-2008/079246 A2 | 7/2008 |
| WO | WO-2009/036379 A2 | 3/2009 |
| WO | WO-2010/056386 A1 | 5/2010 |
| WO | WO-2010/105256 A1 | 9/2010 |
| WO | WO-2012/009568 A2 | 1/2012 |
| WO | WO-2014074942 A1 | 5/2014 |
| WO | WO-2016/023019 A2 | 2/2016 |
| WO | WO-2016/049641 A1 | 3/2016 |
| WO | WO-2016/064895 A1 | 4/2016 |
| WO | WO-2017/058866 A1 | 4/2017 |
| WO | WO-2017/062672 A2 | 4/2017 |
| WO | WO-2018015573 A2 | 1/2018 |
| WO | WO-2018195506 A1 | 10/2018 |
| WO | WO-2019028292 A1 | 2/2019 |
| WO | WO-2019055841 A1 | 3/2019 |
| WO | WO-2019118513 A1 | 6/2019 |

OTHER PUBLICATIONS

Almagro, J.C. et al. (2008). "Humanization of Antibodies," *Frontiers in Bio-Science* 13:1619-1633.

Al-Shawi, R.et al. (2008). "Neurotoxic and Neurotrophic Roles of proNGF and the Receptor Sortilin in the Adult and Ageing Nervous System," *European Journal of Neuroscience* 27:2103-2114.

Angal, S. et al. (1993). "A Single Amino Acid Substitution Abolishes the Heterogeneity of Chimeric Mouse/Human (IgG4) Antibody," *Molecular Immunology* 30(1):105-108.

Armour, K.L. et al. (1999). "Recombinant Human IgG Molecules Lacking Fcγ Receptor I Binding and Monocyte Triggering Activities," *Eur. J. Immunol.* 29:2613-2624.

Armour, K.L. et al. (2003). "Differential Binding to Human FcγRIIa and FcγRIIb Receptors by Human IgG Wildtype and Mutant Antibodies," *Molecular Immunology* 40:585-593.

Armour, K.L. et al. (Jun. 25-28, 2000). "Mutant IgG Lacking FcγRIII Binding and ADCC Activities,"*The Haematology Journal*, poster Session 1, *Presented at the 5th Annual Meeting of the European Haematology Association*, Birmingham, UK, 1(Suppl. 1):27, 2 pages.

Arnett, M.G. et al. (Dec. 5, 2007; e-published on Oct. 26, 2007). "proNGF, Sortilin, and p75$^{NTR}$: Potential Mediators of Injury-Induced Apoptosis in the Mouse Dorsal Root Ganglion," *Brain Res.* 1183:32-42.

Asquith, D.L. et al. (2009). "Animal Models of Rheumatoid Arthritis," *Eur. J. Immunol.* 39:2040-2044.

Author Unknown. (2006). "Anti-TREM2, Clone 78, Cat. # MABN755, Lot 3013362," Certificate of Analysis, located at <http://www.merckmillipore.com/SG/en/product/Anti-TREM-2-Antibody-clone-78,MM_NF-MABN755>, 2 pages.

Author Unknown. (Jan. 1, 2016). "Anti-TREM2 Monoclonal Antibody Clone 78," Millipore Sigma NF-MABN755, located at <http://www.emdmillipore.com/US/en/product/Anti-TREM-2-Antibody-clone-78,MM_NF-MABN755#overview>, pp. 1-3 (Datasheet).

Baca, M. et al. (1997). "Antibody Humanization Using Monovalent Phage Display," *The Journal of Biological Chemistry* 272(16):10678-10684.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," *Proc Nat. Acad. Sci. USA* 91:3809-3813.

(56) References Cited

OTHER PUBLICATIONS

Bartholomaeus, P. et al. (2014). "Cell Contact-Dependent Priming and Fc Interaction with CD32+ Immune Cells Contribute to the TGN1412-Triggered Cytokine Response," *The Journal of Immunology* 192:2091-2098.
Basso, D.M. et al. (May 2006). "Basso Mouse Scale for Locomotion Detects Differences in Recovery after Spinal Cord Injury in Five Common Mouse Strains," *J. Neurotrauma* 23(5):635-659.
Bates, M.K. et al. (Feb. 2006). "Genetic Immunization for Antibody Generation in Research Animals by Intravenous Delivery of Plasmid DNA," *Biotechniques* 40(2):199-207.
Beattie, M.S. et al. (Oct. 24, 2002). "ProNGF Induces p75-Mediated Death of Oligodendrocytes following Spinal Cord Injury," *Neuron* 36(3):375-386.
Boerner, P. et al. (1991). "Production of Antigen-Specific Human Monoclonal Antibodies From In Vitro-Primed Human Splenocytes," *Journal of Immunology* 147(1):86-95.
Bolt, S. et al. (1993). "The Generation of a Humanized, Non-Mitogenic Cd3 Monoclonal Antibody Which Retains In Vitro Immunosuppressive Properties," *European Journal Immunol.* 23:403-411.
Borroni, B. et al. (Apr. 2014; e-pub. Oct. 16, 2013). "Heterozygous *TREM2* Mutations in Frontotemporal Dementia," *Neurobiol Aging.* 35(4):934.e7-934.e10.
Bouchon et al. (2001). "A DAP12-Mediated Pathway Regulates Expression of CC Chemokine Receptor 7 and Maturation of Human Dendritic Cells," *J. Exp. Med.* 194(8):1111-1122.
Brennan, M. et al. (Jul. 5, 1985). "Preparation of Bispecific Antibodies by Chemical Recombination of Monoclonal Immunoglobulin $G_1$ Fragments," *Science* 229:81-83.
Bross, P.F. et al. (Jun. 2001). "Approval Summary: Gemtuzumab Ozogamicin in Relapsed Acute Myeloid Leukemia," *Clinical Cancer Research* 7(6):1490-1496.
Bruggemann, M. et al. (1993). "Designer Mice: The Production of Human Antibody Repertoires in Transgenic Animals," *Year in Immunol.* 7:33-40.
Cady, J. et al. (Apr. 2014). "*TREM2* Variant p. R47H as a Risk Factor for Sporadic Amyotrophic Lateral Sclerosis," *JAMA Neurol.* 71(4):449-453.
Cantoni, C. et al. (Mar. 2015). "Trem2 Regulates Microglial Cell Activation in Response to Demyelination In Vivo," *Acta Neuropathol*, 129(3):429-447, thirty three pages.
Cao, X. et al. (Sep. 2011). "Macrophage Polarization in the Maculae of Age-Related Macular Degeneration: A Pilot Study," *Pathology International* 61(9):528-535, fourteen pages.
Capel, P.J.A. et al. (1994). "Heterogeneity of Human IgG Fc Receptors," *Immunomethods* 4:25-34.
Carter, P. et al. (Feb. 1992). "High Level *Escherichia coli* Expression and Production of a Bivalent Humanized Antibody Fragment," *Bio/technology* 10:163-167.
Carter, P. et al. (May 1992). "Humanization of an Anti-p185$^{HER2}$ Antibody for Human Cancer Therapy," *Proc. Natl. Acad. Sci. USA* 89:4285-4289.
Chang et al. (2002). "Retinal Degeneration Mutants in the Mouse," *Vision Research* 42:517-525.
Chen, Y. et al. (Oct. 1996). "An Experimental Model of Closed Head Injury in Mice: Pathophysiology, Histopathology, and Cognitive Deficits," *J. Neurotrauma* 13(10):557-568.
Chothia, C. et al. (1987). "Canonical Structures for the Hypervariable Regions of Immunoglobulins," *J. Mol. Biol*, 196(4):901-917.
Chu, S.Y. et al. (2008, e-pub. Aug. 8, 2008). "Inhibition of B cell Receptor-Mediated Activation of Primary Human B Cells by Coengagement of CD19 and FcγRIIb with Fc-Engineered Antibodies," *Molecular Immunology* 45(15):3926-3933.
Clackson, T. et al. (Aug. 15, 1991). "Making Antibody Fragments Using Phage Display Libraries," *Nature* 352(6336):624-628.
Cole, M.S. et al. (Aug. 27, 1999). "HuM291, a Humanized Anti-Cd3 Antibody is Immunosuppressive to T Cells While Exhibiting Reduced Mitogenicity in Vitro," *Transplantation* 68(4):563-571.

Colonna, M. (Jun. 1, 2003). "TREMS in the Immune System and Beyond," *The Journal of Immunology* 3(6):445-453.
Correale, C. et al. (Feb. 2013). "Bacterial Sensor Triggering Receptor Expressed on Myeloid Cells-2 Regulates the Mucosal Inflammatory Response," *Gastroenterology* 144(2):346-356.
Cruts, M. et al. (2008). "Loss of Progranulin Function in Frontotemporal Lobar Degeneration," *Trends Genetics* 24(4):186-194.
Cunningham, B.C. et al. (Jun. 2, 1989). "High-Resolution Epitope Mapping of Hgh-Receptor Interactions by Alanine-Scanning Mutagenesis," *Science* 244(4908):1081-1085.
Cuyvers, E. et al. (Oct. 9, 2013). "Investigating the Role of Rare Heterozygous *TREM2* Variants in Alzheimer's Disease and Frontotemporal Dementia," *Neurobiol Aging* 35(3):726:e11-e19.
Daëron, M. (1997). "FC Receptor Biology," *Annu. Rev. Immunol.* 15:203-234.
Dall' Acqua, W.F. et al. (Aug. 18, 2006). "Properties of Human IgG1s Engineered for Enhanced Binding to the Neonatal Fc Receptor (FcRn)," *The Journal of Biological Chemistry* 281(33):23514-23524.
Damani, M.R. et al. (2011). "Age-Related Alterations in the Dynamic Behavior of Microglia," *Aging Cell* 10:263-176.
Daneman, R. et al. (Oct., 29, 2010). "The Mouse Blood-Brain Barrier Transcriptome: A New Resource for Understanding the Development and Function of Brain Endothelial Cells," *PLoS One* 5(10):e13741, sixteen pages.
Davidson, E. et al. (Sep. 2014). "A High-Throughput Shotgun Mutagenesis Approach to Mapping B-Cell Antibody Epitopes," *Immunology* 143(1):13-20.
Davis, P.M. et al. (2007). "Abatacept Binds to the Fc Receptor Cd64 But Does Not Mediate Complement-Dependent Cytotoxicity or Antibody-Dependent Cellular Cytotoxicity," *The Journal of Rheumatology* 34(11):2204-2210.
De Haas, M. et al. (Oct. 1995). "Fc Gamma Receptors of Phagocytes," *J. Lab. Clin. Med.* 126(4):330-341.
Ducry, L. et al. (Jan. 2010; e-pub. Sep. 21, 2009). "Antibody-Drug Conjugates: Linking Cytotoxic Payloads to Monoclonal Antibodies," *Bioconjug. Chem.* 21(1):5-13.
Edwards, B.E. et al. (2003). "The Remarkable Flexibility of the Human Antibody Repertoire; Isolation of Over One Thousand Different Antibodies to a Single Protein, BLyS," *J. Mol. Biol.* 334(1):103-118.
El-Danaf, R.N. et al. (Feb. 11, 2015). "Characteristic Patterns of Dendritic Remodeling in Early-Stage Glaucoma: Evidence from Genetically Identified Retinal Ganglion Cell Types," *The Journal of Neuroscience* 35(6):2329-2343.
Estep, P. et al. (Mar.- Apr. 2013). "High Throughput Solution-Based Measurement of Antibody-Antigen Affinity and Epitope Binning," *mAbs.* 5(2):270-278.
Fahnestock, M. et al. (2001). "The Precursor Pro-Nerve Growth Factor Is the Predominant Form of Nerve Growth Factor in Brain and Is Increased in Alzheimer's Disease," *Molecular and Cellular Neuroscience* 18:210-220.
Fan, Y.-J. (2008). "Differential effects of Pro-BDNF on Sensory Neurons after Sciatic Nerve Transection in Neonatal Rats," *European Journal of Neuroscience* 27(9):2380-2390.
Feldhaus, M.J. et al. (Jul. 2004, e-pub. May 31, 2004). "Yeast Display of Antibody Fragments: A Discovery and Characterization Platform," *J. Immunological Methods* 290(1-2):69-80.
Fellouse, F.A. et al. (Aug. 24, 2004). "Synthetic Antibodies from a Four-Amino-Acid Code: A Dominant Role for Tyrosine in Antigen Recognition," *PNAS* 101(34):12467-12472.
Fishwild, D.M. et al. (Jul. 1996). "High-Avidity Human IgGk Monoclonal Antibodies from a Novel Strain of Minilocus Transgenic Mice," *Nature Biotechnology* 14(7):845-851.
Gabathuler, R. (2010; e-pub. Aug. 5, 2009). "Approaches to Transport Therapeutic Drugs across the Blood-Brain Barrier to Treat Brain Diseases," *Neurobiology of Disease* 37(1):48-57.
Garber, K. (Nov. 2014). "Bispecific Antibodies Rise Again," *Nature Reviews Drug Discovery* 13(11):799-801.
Gattis, J.L. et al. (May 12, 2006). "The Structure of the Extracellular Domain of Triggering Receptor Expressed on Myeloid Cells Like Transcript-1 and Evidence for a Naturally Occurring Soluble Fragment," *The Journal of Biological Chemistry* 281(19):13396-13403.

(56) References Cited

OTHER PUBLICATIONS

Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," *The FASEB Journal* 29(4):1247-1257.
Gerngross, T.U. (Nov. 2004). "Advances in the Production of Human Therapeutic Proteins in Yeasts and Filamentous Fungi," *Nature Biotechnology* 22(11):1409-1414.
Gibot, S. et al. (May 2006). "Modulation of the Triggering Receptor Expressed on the Myeloid Cell Type 1 Pathway in Murine Septic Shock," *Infection and Immunity* 74(5):2823-2830.
Gonçalves, L.A. et al. (Nov. 26, 2013). "TREM2 Governs Kupffer Cell Activation and Explains belr1 Genetic Resistance to Malaria liver Stage Infection," *PNAS* 110(48):19531-19536.
Gordon, M.N. et al. (May 2001). "Correlation Between Cognitive Deficits and Aβ Deposits in Transgenic APP+PS1 Mice," *Nuerobiol. Aging* 22(3):377-385.
Graham, F.L. et al. (1977). "Characteristics of a Human Cell Line Transformed by DNA from Human Adenovirus Type 5," *Journal of General Virology* 36:59-72.
Gravestein, L.A. et al. (1994). "Novel mAbs Reveal Potent Co-Stimulatory Activity of Murine CD27," *International Immunology* 7(4):551-557.
Gravestein, L.A. et al. (Aug. 1, 1996). "CD27 Cooperates with the Pre-T Cell Receptor in the Regulation of Murine T Cell Development," *J. Exp. Med.* 184(2):675-685.
Griffith, A.D. et al. (Feb. 1993). "Human Anti-Self Antibodies with High Specificity from Phage Display Libraries," *EMBO J.* 12(2):725-734.
Gruber, M. et al. (1994). "Efficient Tumor Cell Lysis Mediated by a Bispecific Single Chain Antibody Expressed in *Escherichia coli*," *The Journal of Immunology* 152(11):5368-5374.
Guerreiro, R. et al. (Jan. 10, 2013). "TREM2 Variants in Alzheimer's Disease," *The New England Journal of Medicine* 368(2):117-127.
Guerreiro, R.J. et al. (Jan. 2013). "Using Exome Sequencing to Reveal Mutations in TREM2 Presenting as a Frontotemporal Dementia-like Syndrome Without Bone Involvement," *JAMA Neural.* 70(1):78-84, fifteen pages.
Guerreiro, R.J. et al. (Oct. 2012). "TOMM40 Association with Alzheimer Disease: Tales of APOE and Linkage Disequilibrium," *Arch Neural.* 69(10):1243-1244.
Gupta, N. et al. (2003). "Activated Microglia in Human Retinitis Pigmentosa, Late-Onset Retinal Degeneration, and Age-Related Macular Degeneration," *Experimental Eye Research* 76(4):463-471.
Hamann, P.R. et al. (2002, e-pub. Dec. 19, 2001). "Gemtuzumab Ozogamicin, A Potent and Selective Anti-CD33 Antibody-Calicheamicin Conjugate for Treatment of Acute Myeloid Leukemia," *Bioconjugate Chemistry* 13(1):47-58.
Hamerman, J.A. et al. (Aug. 15, 2006). "Cutting Edge: Inhibition of TLR and FcR Responses in Macrophages by Triggering Receptor Expressed on Myeloid Cells (TREM)-2 and DAP12," *The Journal of Immunology* 177(4):2051-2055.
Hamerman, J.A. et al. (Jun. 2005; e-pub. May 15, 2005). "Enhanced Toll-Like Receptor Responses in the Absence of Signaling Adaptor DAP12," *Nat Immunol.* 6(6):579-586, twenty pages.
Hamers-Casterman, C. et al. (Jun. 3, 1993). "Naturally Occurring Antibodies Devoid of Light Chains," *Nature* 363(6428):446-448.
Han, S. et al. (Apr. 2010; e-pub. Apr. 5, 2010). "Rescuing Vasculature With Intravenous Angiopoietin-1 and aVβ3 Integrin Peptide is Protective After Spinal Cord Injury," *Brain* 133(4):1026-1042.
Harrington, A.W. et al. (Apr. 20, 2004). "Secreted proNGF is a Pathophysiological Death-Inducing Ligand After Adult CNS Injury," *Proc. Natl. Acad. Sci USA* 101(16): 6226-6230.
Harris, W.J. (Nov. 1, 1995). "Therapeutic Monoclonals—Production of Humanized Monoclonal Antibodies for In Vivo Imaging and Therapy," *Biochem. Soc. Transactions* 23(4):1035-1038.

Hawkins, R.E. et al. (1992). "Selection of Phage Antibodies by Binding Affinity: Mimicking Affinity Maturation," *Journal of Molecular Biology* 226(3):889-896.
Hazen, M. et al. (Jan.-Feb. 2014). "An Improved and Robust DNA Immunization Method to Develop Antibodies Against Extracellular Loops of Multi-Transmembrane Proteins," *MAbs* 6(1):95-107.
Hezareh, M. et al. (Dec. 2001). "Effector Function Activities of a Panel of Mutants of a Broadly Neutralizing Antibody against Human Immunodeficiency Virus Type 1," *Journal of Virology* vol. 75(24):12161-12168.
Hickman, S.E. et al. (Aug. 13, 2008). "Microglial Dysfunction and Defective β-Amyloid Clearance Pathways in Aging Alzheimer's Disease Mice," *J Neurosci.* 28(33):8354-8360.
Holliger, P. et al. (Jul. 1993). ""Diabodies": Small Bivalent and Bispecific Antibody Fragments," *Proceedings of the National Academy of Sciences* 90(14):6444-6448.
Hongo, J.S. et al. (1995). "Development and Characterization of Murine Monoclonal Antibodies to the Latency-Associated Peptide of Transforming Growth Factor $β_1$," *Hybridoma* 14(3):253-260.
Hoogenboom, H.R. et al. (1992). "By-Passing Immunisation. Human Antibodies from Synthetic Repertoires of Germline Hh Gene Segments Rearranged in Vitro," *Journal of Molecular Biology* 227(2):381-388.
Hsieh, C.L. et al. (May 2009; e-pub. Mar. 19, 2009). "A Role for TREM2 Ligands in the Phagocytosis of Apoptotic Neuronal Cells by Microglia," *Journal of Neurochemistry* 109(4):1144-1156, twenty one pages.
Humphrey, M.B. et al. (2006). "TREM2, a DAP12-Associated Receptor, Regulates Osteoclast Differentiation and Function," *J Bone Miner Res.* 21(2):237-245.
Hurle, M.R. et al. (Aug. 1994)."Protein Engineering Techniques for Antibody Humanization," *Current Opinion in Biotechnology* 5(4):428-433.
Hutchins, J.T. et al. (Dec. 1995). "Improved Biodistribution, Tumor Targeting, and Reduced Immunogenicity in Mice with a γ 4 Variant of Campath-IH," *Proc. Natl. Acad. Sci.* 92(26):11980-11984.
Hutton, M. et al. (Jun. 18, 1998). "Association of Missense and 5'-Splice-Site Mutations in Tau with the Inherited Dementia FTDP-17," *Nature* 393(6689):702-705.
Idusogie, E.E. et al. (Feb. 15, 2001). "Engineered Antibodies With Increased Activity to Recruit Complement," *J. Immunol.* 166(4):2571-2575.
Ito, H. et al. (Jan. 2012; e-pub. Dec. 12, 2011). "TREM-2, Triggering Receptor Expressed on Myeloid cell-2, Negatively Regulates TLR responses in Dendritic Cells," *Eur. J. Immunol.* 42(1):176-185.
Jackson, J.R. et al. (Apr. 1, 1995). "In Vitro Antibody Maturation. Improvement of a High Affinity, Neutralizing Antibody against IL-13β" *The Journal of Immunology* 157(7):3310-3319.
Jakobovits, A. et al. (Mar. 18, 1993) "Germ-line Transmission and Expression of a Human-derived Yeast Artificial Chromosome," *Nature* 362(6417):255-258.
Jakobovits, A. et al. (Mar. 1993). "Analysis of Homozygous Mutant Chimeric Mice: Deletion of the Immunoglobulin Heavy-chain Joining Region Blocks B-Cell Development and Antibody Production," *Proceedings of the National Academy of Sciences* 90(6):2551-2555.
Jansen, P. et al. (Nov. 2007; e-pub. Oct. 14, 2007). "Roles for the Pro-Neurotrophin Receptor Sortilin in Neuronal Development, Aging and Brain Injury," *Nature Neuroscience* 10(11):1449-1457.
Jay, T.R. et al. (Mar. 9, 2015; e-pub. Mar. 2, 2015). "TREM2 Deficiency Eliminates TREM2+ Inflammatory Macrophages and Ameliorates Pathology in Alzheimer's Disease Mouse Models," *J Exp Med* 212(3):287-295.
Johnson, K.S. et al. (Aug. 1993). "Human Antibody Engineering: Current Opinion in Structural Biology," *Curr. Opin Struct. Biol.* 3(4):564-571.
Johnson, L.A. et al. (Sep. 2011). "Apolipoprotein E4 Exaggerates Diabetic Dyslipidemia and Atherosclerosis in Mice Lacking the LDL Receptor," *Diabetes* 60(9):2285-2294.
Jones, P.T. et al. (May 29, 1986). "Replacing the Complementarity-Determining Regions in a Human Antibody with Those from a Mouse," *Nature* 321(6069):522-525.

(56) References Cited

OTHER PUBLICATIONS

Jonsson, T. et al. (Jan. 10, 2013). "Variant of *TREM2* Associated with the Risk of Alzheimer's Disease," *The New England Journal of Medicine* 368(2):107-116.
Kelker, M.S. et al. (Dec. 10, 2004). "Crystal Structure of Mouse Triggering Receptor Expressed on Myeloid Cells 1 (TREM-1) at 1.76 Å," *Journal of Molecular Biology* 344(5):1175-1181.
Kelker, M.S. et al. (Sep. 24, 2004). "Crystal Structure of Human Triggering Receptor Expressed on Myeloid Cells 1 (TREM-1) at 1.47 Å," *Journal of Molecular Biology* 342(4):1237-1248.
Kjolby et al. (2010). "*Sort1*, Encoded by the CardiovascularRisk Locus 1p13.3, Is a Regulator of Hepatic Lipoprotein Export," *Cell Metabolism* 12(3):213-223.
Kleinberg, G. et al. (Jul. 2, 2014). "TREM2 Mutations Implicated in Neurodegeneration Impair Cell Surface Transport and Phagocytosis," *Sci Transl Med*. 6(243):243ra86, pp. 1-12.
Koga, T. et al. (Apr. 15, 2004). "Costimulatory Signals Mediated by the ITAM Motif Cooperate with RANKL for Bone Homeostasis," *Nature* 428(6984):758-763.
Köhler, G. et al. (Aug. 7, 1975). "Continuous Cultures of Fused Cells Secreting Antibody of Predefined Specificity," *Nature* 256(5517):495-497.
Kostelny, S.A. et al. (Mar. 1, 1992). "Formation of a Bispecific Antibody by the Use of Leucine Zippers," *The Journal of Immunology* 148(5):1547-1553.
Kozbor, D. et al. (Dec. 1984). "A Human Hybrid Myeloma for Production of Human Monoclonal Antibodies," *The Journal of Immunology* 133(6):3001-3005.
Kuroda, R. et al. (2007; e-pub. Nov. 27, 2006). "A Novel Compound Heterozygous Mutation in the *DAP12* Gene in a Patient with Nasu-Hakola Disease," *J Neurol Sci*. 252(1):88-91.
Labrijn, A.F. et al. (Oct. 2014; e-pub. Sep. 25, 2014). "Controlled Fab-arm exchange for the generation of stable bispecific IgG1," *Nature Protocols* 9(10):2450-2463.
Laird, A.S. et al. (Oct. 13, 2010). "Progranulin is Neurotrophic in Vivo and Protects against a Mutant TDP-43 Induced Axonopathy," *PLOS ONE* 5(10):e1336 8, seven pages.
Langer, R. (Sep. 28, 1990). "New Methods of Drug Delivery," *Science* 249(4976):1527-1533.
Lartigue, J.D. (Jul. 5, 2012). "Antibody-Drug Conjugates: Guided Missiles Deployed Against Cancerous Cells," *OncLive* located at <https://www.onclive.com/printer?url=/publications/oncology-live/2012/june-2012/antibody-drug-conjugates-guided-missiles-deployed-against-cancerous-cells>, last visited on Nov. 27, 2018, four pages.
Lavail, M.M. (Jun. 30, 2011). "Retinal Degeneration Rat Model Resource—Availability of P23H and S334ter Mutant Rhodopsin Transgenic Rats and RCS Inbred and RCS Congenic Strains of Rats," University of California, San Francisco, 12 pages.
Lazar, G.A. et al. (Mar. 14, 2006). "Engineered Antibody Fc variants with Enhanced Effector Function," *PNAS* 103(11):4005-4010.
Lazar, G.A. et al. (Mar. 2007; e-pub. Oct. 31, 2006). "A Molecular Immunology Approach to Antibody Humanization and Functional Optimization," *Molecular Immunol* 44(8):1986-1998.
Lee, C.V. et al. (2004). "Bivalent Antibody Phage Display Mimics Natural Immunoglobulin," *Journal of Immunological Methods* 284(1-2):119-132.
Lee, C.V. et al. (2004). "High-affinity Human Antibodies from Phage-displayed Synthetic Fab Libraries with a Single Framework Scaffold," *Journal of Molecular Biology* 340(5):1073-1093.
Li, F. et al. (Aug. 19, 2011). "Inhibitory Fcγ Receptor Engagement Drives Adjuvant and Anti-Tumor Activities of Agonistic CD40 Antibodies," *Science* 333(6045):1030-1034.
Li, H. et al. (Feb. 2006). "Optimization of Humanized IgGs in Glycoengineered *Pichia pastoris*," *Nature Biotechnology* 24(2):210-215.
Li, J. et al. (Mar. 7, 2006). "Human Antibodies for Immunotherapy Development Generated via a Human B Cell Hybridoma Technology," *PNAS* 103(10):3557-3562.

Lightle, S. et al. (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," *Protein Science* 19(4):753-762.
Lipovsek, D. et al. (Jul. 2004, e-pub. May 31, 2004). "In-Vitro Protein Evolution by Ribosome Display and mRNA Display," *J. Immunological Methods* 290(1-2):51-67.
Lloyd, C. et al. (Mar. 2009; e-pub. Oct. 29, 2008). "Modelling the Human Immune Response: Performance of a $10^{11}$ Human Antibody Repertoire Against a Broad Panel of Therapeutically Relevant Antigens," *Protein Engineering, Design & Selection* 22(3):159-168.
Lonberg, N. et al. (1995). "Human Antibodies from Transgenic Mice," *International Reviews of Immunology*. 13(1):65-93.
Lonberg, N. et al. (Apr. 28, 1994). "Antigen-Specific Human Antibodies from Mice Comprising Four Distinct Genetic Modifications," *Nature* 368(6474):856-859.
Low, D. et al. (2013). "Animal Models of Ulcerative Colitis and their Application in Drug Research," *Drug Design, Development and Therapy* 7:1341-1357.
Luigi Poliani, P. et al. (2015). "TREM2 Sustains Microglial Expansion During Aging and Response to Demyelination," *J Clin Invest*. 125(5):2161-2170.
Ma, J. et al. (Apr. 2015; e-pub. Jul. 23, 2014). "TYROBP in Alzheimer's Disease," *Mol. Neurobiol*. 51(2):820-826.
Malm, T.M. et al. (Jan. 2015; e-pub. Nov. 18, 2014). "The Evolving Biology of Microglia in Alzheimer's Disease," *Neurotherapeutics* 12(1):81-93.
Marks, J.D. et al. (1991). "By-passing immunization: Human antibodies from V-gene libraries displayed on phage," *Journal of Molecular Biology* 222(3): 581-597.
Marks, J.D. et al. (Jul. 1992)."By-Passing Immunization: Building High Affinity Human Antibodies by Chain Shuffling," *Bio/Technology* 10(7):779-782.
Martens, L.H. et al. (Nov. 2012; e-pub. Oct. 8, 2012). "Progranulin Deficiency Promotes Neuroinflammation and Neuron Loss Following Toxin-Induced Injury," *The Journal of Clinical Investigation* 122(11):3955-3959.
Mather, J.P. (Aug. 1980). "Establishment and Characterization of Two Distinct Mouse Testicular Epithelial Cell Lines," *Biology of Reproduction* 23(1):243-252.
Mather, J.P. et al. (1982). "Culture of Testicular Cells in Hormone-Supplemented Serum-Free Medium," *Annals of the New York Academy of Sciences, Testicular Cell Culture* 383:44-68.
McCafferty, J. et al. (Dec. 6, 1990). "Phage Antibodies: Filamentous Phage Displaying Antibody Variable Domains," *Nature* 348(6301):552-554.
McEarchern, J.A. et al. (Feb. 1, 2007). "Engineered Anti-CD70 Antibody with Multiple Effector Functions Exhibits in Vitro and in Vivo Antitumor Activities," *Blood* 109(3):1185-1192.
Melchior, B. et al. (Jul. 12, 2010). "Dual Induction of TREM2 and Tolerance-Related Transcript, Tmem176b, in amyloid transgenic Mice: Implications for Vaccine-Based therapies for Alzheimer's Disease," *ASN Neuro* 2(3) e0037:157-170.
Milstein, C. et al. (Oct. 6, 1983). "Hybrid Hybridomas and Their Use in Immunohistochemistry," *Nature* 305(5934):537-540.
Mizoguchi, A. (2012). "Animal Models of Inflammatory Bowel Disease," *Progress in Molecular Biology and Translational Science* 105:263-320, fifty eight pages.
Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24(1-2):107-117.
Morrison, S.L. (Apr. 28, 1994). "Success in Specification," *Nature* 368(6474):812-813.
Morrison, S.L. et al. (Nov. 1984). "Chimeric Human Antibody Molecules: Mouse Antigen-binding Domains with Human Constant Region Domains," *Proc. Nat'l Acad. Sci* 81(21):6851-6855.
Munson, P.J. et al. (Sep. 1, 1980). "Ligand: A Versatile Computerized Approach for Characterization of Ligand-binding Systems," *Analytical Biochemistry* 107:220-239.
N.N., "Datasheet: anti-TREM-2 monoclonal antibody clone 78," Online catalogue Merck, Jan. 1, 2016 (Jan. 1, 2016), pp. 1-3, located

(56) References Cited

OTHER PUBLICATIONS at https://www.merckmillipore.com/DE/en/product/Anti-TREM-2-Antibody%2C-clone-78,MMNF-MABN755, three pages.
Naidoo, J. et al. (Dec. 9, 2014; e-pub. Sep. 11, 2014). "Immune Modulation for Cancer Therapy," *British Journal of Cancer* 111(12):2214-2219.
Nair, D.T. et al. (Mar. 1, 2002). "Epitome Recognition by Diverse Antibodies Suggests Conformational Convergence in an Antibody Response," *J Immunol.* 168(5):2371-2382.
Naito, K. et al. (2000). "Calicheamicin-Conjugated Humanized Anti-CD33 Monoclonal Antibody (gemtuzumab zogamicin, CMA-676) Shows Cytocidal effect on CD33-Positive Leukemia Cell Lines, But is Inactive on P-glycoprotein-Expressing sublines," *Leukemia* 14(8):1436-1443.
Nakamura, K. et al. (2007)."Intracellular Sortilin Expression Pattern Regulates proNGF-Induced Naturally Occurring Cell Death during Development," *Cell Death and Differentiation* 14(8):1552-1554.
Neary, D. et al. (Dec. 1998). "Frontotemporal Lobar Degeneration: A Consensus on Clinical Diagnostic Criteria," *Neurology* 51(6):1546-1554.
Neuberger, M. (Jul. 1996). "Generating high-avidity human Mabs in mice," *Nature Biotechnology* 14(7):826, one page.
Neumann, H. et al. (Jan. 10, 2013; e-pub. Nov. 14, 2012). "Variant TREM2 as Risk Factor for Alzheimer's Disease," *The New England Journal of Medicine* 368(2):182-184.
Neumann, H. et al. (Mar. 2007; e-pub. Jan. 18, 2007). "Essential Role of the Microglial Triggering Receptor Expressed on Myeloid Cells-2 (TREM2) for Central Nervous Tissue Immune Homeostasis," *Journal of Neuroimmunology* 184(1-2):92-99.
Neumann, M. et al. (Oct. 2007). "TDP-43 Proteinopathy in Frontotemporal Lobar Degeneration and Amyotrophic Lateral Sclerosis," *Arch Neurol.* 64(10):1388-1394.
Novack, D.V. et al. (2008, e-pub. Oct. 15, 2007). "The Osteoclast: Friend or Foe?," *Annu. Rev. Pathol. Mech. Dis.* 3:457-484.
Nykjaer, A. et al. (2005, e-pub. Jan. 26, 2005). "$p75^{NTR}$—Live or Let Die," *Current Opinion in Neurobiology* 15(1):49-57.
Nykjaer, A. et al. (Feb. 26, 2004). "Sortilin is Essential for proNGF Induced Neuronal Cell Death," *Nature* 427(6977):843-848.
Oganesyan, V. et al. (Jun. 2008). "Structural characterization of a Human Fc Fragment Engineered for Lack of Effector Functions," *Acta Crystallography* 64(6):700-704.
Otero, K. et al. (2012; e-published on Feb. 6, 2012). "TREM2 and β-Catenin Regulate Bone Homeostasis by Controlling the Rate of Osteoclastogenesis," *J Immunol* 188(6):2612-2621.
Otero, K. et al. (Jul. 2009; e-pub. Jun. 7, 2009). "Macrophage Colony-Stimulating Factor Induces the Proliferation and Survival of Macrophages via a Pathway Involving DAP12 and β-Catenin," *Nat Immunol.* 10(7):734-743.
Paloneva, J. et al. (Aug. 18, 2003). "DAP12/TREM2 Deficiency Results in Impaired Osteoclast Differentiation and Osteoporotic Features," *The Journal of Experimental Medicine* 198(4):669-675.
Paloneva, J. et al. (Sep. 2002; e-pub. Jun. 21, 2002). "Mutations in Two Genes Encoding Different Subunits of a Receptor Signaling Complex Result in an Identical Disease Phenotype," *American Journal of Human Genetics* 71(3):656-662.
Park, M. et al. (Jan. 2015). "Triggering Receptor Expressed on Myeloid Cells 2 (TREM2) Promotes Adipogenesis and Diet-Induced Obesity," *Diabetes* 64(1):117-127.
Peng, Q. et al. (May 18, 2010). "TREM2- and DAP12-Dependent Activation of PI3K Requires DAP10 and Is Inhibited by SHIP1," *Science Signaling* 3(122):ra38, pp. 1-15.
Pennesi, M.E. et al. (Aug. 2012). "Animal Models of Age Related Macular Degeneration," *Molecular Aspects of Medicine* 33(4):487-509, forty pages.
Peters, S.J. et al. (Jul. 13, 2012). "Engineering an Improved IgG4 Molecule with Reduced Disulfide Bond Heterogeneity and Increased Fab Domain Thermal Stability," *The Journal of Biological Chemistry* 287(29):24525-24533.
Piccio, L. et al. (May 2007). "Blockade of TREM-2 Exacerbates Experimental Autoimmune Encephalomyelitis," *European Journal of Immunology* 37(5):1290-1301.
Plückthun, A. (Dec. 1992). "Mono- and Bivalent Antibody Fragments Produced in *Escherichia coli*: Engineering, Folding and Antigen Binding," *Immunological Reviews*130:151-188.
Poliani, P.L. et al. (May 2015). "TREM2 Sustains Microglial Expansion During Aging and Response to Demyelination," *J. Clin. Invest.* 125(5):2161-2170.
Presta, L.G. (1992). "Antibody Engineering," *Current Opinion in Structural Biology* 2:593-596.
Presta, L.G. et al. (Sep. 1, 1993). "Humanization of an Antibody Directed Against IgE," *The Journal of Immunology* 151(5):2623-2632.
Provenzano, M.J. (2008). "p75NTR and Sortilin Increase After Facial Nerve Injury," *Laryngoscope* 118(1):87-93.
Radaev, S. et al. (Dec. 2003). "Crystal Structure of the Human Myeloid Cell Activating Receptor TREM-1," *Structure* 11(12):1527-1535.
Rajagopalan, P. et al. (Oct. 17, 2013). "*TREM2* Risk Variant and Loss of Brain Tissue," *N Engl J Med* 369(16):1565-1567.
Ratnavalli, E. et al. (Jun. 2002). "The Prevalence of Frontotemporal Dementia," *Neurology* 58(1 of 2):1615-1621.
Ravetch, J.V. et al. (1991). "Fe Receptors," *Annual Review Immunology* 9:457-492.
Rayaprolu, S. et al. (Jun. 21, 2013). "TREM2 in neurodegeneration: evidence for association of the p. R47H variant with frontotemporal dementia and Parkinson's disease," *Mol Neurodegener.* 8:19, pp. 1-5.
Reddy, M.P. et al. (2000). "Elimination of Fc Receptor-Dependent Effector Functions of a Modified IgG4 Monoclonal Antibody to Human CD4," *The Journal of Immunology* 164(4):1925-1933.
Ricart, A.D. (Oct. 15, 2011). "Antibody-Drug Conjugates of Calicheamicin Derivative: Gemtuzumab Ozogamicin and Inotuzumab Ozogamicin," *Clin Cancer Res* 17(20):6417-6427.
Riechmann, L. et al. (Mar. 24, 1988). "Reshaping Human Antibodies for Therapy," *Nature* 332(6162):323-327.
Rizo, J. et al. (1992). "Constrained Peptides: Models of Bioactive Peptides and Protein Substructures," *Ann Rev Biochem.* 61:387-418.
Roberts, R.W. et al. (Nov. 1997). "RNA-Peptide Fusions for the in vitro Selection of Peptides and Proteins," *Proc Natl Acad Sci* 94(23):12297-12302.
Rosok, M.J. et al. (Sep. 13, 1996). "Combinatorial Library Strategy for the Rapid Humanization of Anticarcinoma BR96 Fab," *The Journal of Biological Chemistry* 271(37):22611-22618.
Sazinsky, S.L. et al. (Dec. 23, 2008). "Aglycosylated Immunoglobulin G1 Variants Productively Engage Activating Fc Receptors," *PNAS* 105(51):20167-20172.
Schabbauer, G. et al. (Jul. 2010). "Myeloid PTEN Promotes Inflammation but Impairs Bactericidal Activities During Murine Pneumococcal Pneumonia," *The Journal of Immunology* 185(1):468-476.
Schaffitzel, C. et al. (Dec. 10, 1999). "Ribosome Display: An In Vitro Method for Selection and Evolution of Antibodies From Libraries," *J Immunolical Methods* 231(1-2):119-135.
Schier, R. et al. (1996). "Identification of Functional and Structural Amino-Acid Residues by Parsimonious Mutagenesis," *Gene* 169(2):147-155.
Schleinitz, N. et al. (Jul. 16, 2009). "Pattern of DAP12 Expression in Leukocytes from Both Healthy and Systemic Lupus Erythematosus Patients," *PLoS ONE* 4(7):e6264, pp. 1-7.
Schymick, J.C. et al. (Jul. 2007). "Progranulin Mutations and Amyotrophic Lateral Sclerosis or Amyotrophic Lateral Sclerosis-Frontotemporal Dementia Phenotypes," *Journal of Neurology, Neurosurgery and Psychiatry* 78(7):754-756.
Seno, H. et al. (Jan. 6, 2009). "Efficient Colonic Mucosal Wound Repair Requires Trem2 Signaling," *PNAS* 106(1):256-261.
Shalaby, M.F. et al. (Jan. 1992). "Development of Humanized Bispecitic Antibodies Reactive with Cytotoxic Lymphocytes and Tumor Cells Overexpressing the HER2 Protooncogene," *The Journal of Experimental Medicine* 175(1):217-225.
Sharif, O. et al. (2008; e-pub. Sep. 7, 2008). "From Expression to Signaling: Roles of TREM-1 and TREM-2 in Innate Immunity and Bacterial Infection," *Immunobiology* 213(9-10):701-713.

(56) References Cited

OTHER PUBLICATIONS

Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," *PLoS Pathogen* 10(6):e1004167, sixteen pages.

Sheriff, S. et al. (Sep. 1996). "Redefining the Minimal Antigen-binding Fragment," *Nature Structural & Molecular Biology* 3(9):733-736.

Shields, R.L. et al. (Mar. 2, 2001). "High Resolution Mapping of the Binding Site on Human IgG1 for FcγRI, FcγγRII, FcγRII, and FcRn and Design of IgG1 Variants with Improved Binding to the FcγR," The *Journal of Biological Chemistry* 276(9):6591-6604.

Sidhu, S.S. et al. (Apr. 2004). "Phage-displayed Antibody Libraries of Synthetic Heavy Chain Complementarity Determining Regions," *Journal of Molecular Biology* 338(2):299-310.

Sieber, M.W. et al. (Jan. 3, 2013). "Attenuated Inflammatory Response in Triggering Receptor Expressed on Myeloid Cells 2 (TREM2) Knock-Out Mice following Stroke," *PLoS ONE* 8(1):e52982, ten pages.

Siegel, R.W. et al. (Mar. 2004). "High Efficiency Recovery and Epitope-Specific Sorting of an scFv Yeast Display Library," *Journal of Immunological Methods* 286(1-2):141-153.

Sims, M.J. et al. (Aug. 15, 1993). "A Humanized CD18 Antibody Can Block Function Without Cell Destruction," *The Journal of Immunology* 151(4):2296-2308.

Skerra, A. (1993). "Bacterial Expression of Immunoglobulin Fragments," *Current Opinion in Immunology* 5:256-262.

Sollid, L.M. et al. (Sep. 2008). "Animal Models of Inflammatory Bowel Disease at the Dawn of the New Genetics Era," *PLoS Med* 5(9)(e198):1338-1342.

Stefano, L. et al. (Jul. 2009; e-pub. Apr. 29, 2009). "The Surface-Exposed Chaperone. Hsp60, is an Agonist of the Microglial TREM2 Receptor," *Journal of Neurochemistry* 110(1):284-294.

Streit, W.J. et al. (2004). "Dystrophic Microglia in the Aging Human Brain," *GLIA* 45:208-212.

Streit, W.J. et al. (2009; e-pub. Jun. 10, 2009). "Dystrophic (Senescent) Rather than Activated Microglial Cells are Associated with Tau Pathology and Likely Precede Neurodegeneration in Alzheimer's Disease," *Acta Neuropathol* 118:475-485.

Strohl, W.R. (2009; e-published on Nov. 4, 2009). "Optimization of Fc-mediated Effector Functions of Monoclonal Antibodies," *Current Opinion in Biotechnology* 20(6):685-691.

Sudduth, T. L. et al. (Jun. 5, 2013). "Intracranial Injection of Gammagard, a Human IVIg, Modulates the Inflammatory Response of the Brain and Lowers Aβ in APP/PS1 Mice Along a Different Time Course than Anti-Aβ Antibodies," *J. Neurosc* 33(23):9684-9692.

Sun, M. et al. (May 2013). "TREM-2 Promotes Host Resistance Against *Pseudomonas aeruginosa* Infection by Suppressing Corneal Inflammation via a PI3K/Akt Signaling Pathway," *Investigative Ophthalmology & Visual Science* 54(5):3451-3462.

Suresh, M.R. et al. (1986). "Bispecific Monoclonal Antibodies from Hybrid Hybridomas," *Methods in Enzymology* 121:210-228.

Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," *Plos Med* 4(4):e124, pp. 0675-0689.

Takahashi, K. et al. (Feb. 21, 2005). "Clearance of Apoptotic Neurons Without Inflammation by Microglial Triggering Receptor Expressed on Myeloid Cells-2," *Journal of Experimental Medicine* 201(4):647-657.

Takai, T. et al. (Feb. 11, 1994). "FcR γ Chain Deletion Results in Pleiotrophic Effector Cell Defects," *Cell* 76(3):519-529.

Takaki, R. et al. (Dec. 2006). "DAP12: An Adapter Protein with Dual Functionality," *Immunological Reviews* 214:118-129.

Tanaka, Y. et al. (2013). "Exacerbated Inflammatory Responses Related to Activated Microglia After Traumatic Brain Injury in Progranulin-Deficient Mice," *Neuroscience* 231:49-60.

Teng, H.K. et al. (Jun. 1, 2005). "ProBDNF Induces Neuronal Apoptosis via Activation of a Receptor Complex of p75 $^{NTR}$ and Sortilin," *The Journal of Neuroscience* 25(22):5455-5463.

Thornton, P. et al. (Oct. 2017; e-pub. Aug. 30, 2017). "TREM2 Shedding by Cleavage at the H157-S158 Bond is Accelerated for the Alzheimer's Disease-Associated H157Y Variant," *EMBO Molecular Medicine* 9(10):1366-1378.

Traunecker, A. et al. (1991). "Bispecific Single Chain Molecules (Janusins) Target Cytotoxic Lymphocytes on HIV Infected Cells," *The EMBO Journal* 10(12):3655-3659.

Tsenter, J. et al. (Apr. 2008). "Dynamic Changes in the Recovery After Traumatic Brain Injury in Mice: Effect of Injury Severity on T2-Weighted MRO Abnormalities, and Motor and Cognitive Functions," *J. Neurotrauma* 25(4):324-333.

Turnbull, I.R. et al. (Feb. 2007; e-pub. Jan. 15, 2007). "Activating and Inhibitory Functions of DAP12," *Nature Reviews Immunology* 7(2):155-161.

Turnbull, I.R. et al. (Sep. 15, 2006). "Cutting Edge: TREM-2 Attenuates Macrophage Activation," *The Journal of Immunology* 177(6):3520-3524.

Tutt, A. et al. (Jul. 1, 1991). "Trispecific F(ab')$_3$ Derivatives that Use Cooperative Signaling Via the TCR/CD3 Complex and CD2 to Activate and Redirect Resting Cytotoxic T Cells1," *The Journal of Immunology* 147(1):60-69.

Ulland, T.K. et al. (Aug. 10, 2017). "TREM2 Maintains Microglial Metabolic Fitness in Alzheimer's Disease," *Cell* 170(4):649-663.

Ulland, T.K. et al. (Dec. 2015). "Regulation of Microglial Survival and Proliferation in Health and Diseases," *Semin Immunol.* 27(6):410-415, twelve pages.

Urlaub, G. et al. (Jul. 1980). "Isolation of Chinese Hamster Cell Mutants Deficient in Dihydrofolate Reductase Activity," *Proc. Natl. Acad. Sci.* 77(7):4216-4220.

Van Dijk, M.A et al. (2001)."Human Antibodies as Next Generation Therapeutics," *Current Opinion in Chemical Biology* 5:368-374.

Vaswani, S.K. et al. (Aug. 1998). "Humanized Antibodies as Potential Therapeutic Drugs," *Annals of Allergy, Asthma & Immunology* 81(2):105-119.

Verhoeyen, M. et al. (1988). "Reshaping Human Antibodies: Grafting an Antilysozyme Activity," *Science* 239:1534-1536.

Vetrano, S. et al. (2008). "Unique Role of Junctional Adhesion Molecule-A in Maintaining Mucosal Homeostasis in Inflammatory Bowel Disease," *Gastroenterology* 135(1):173-184.

Vincent K.J. et al. (Dec. 2012). "Current Strategies in Antibody Engineering: Fc Engineering and pH-Dependent Antigen Binding, Bispecific Antibodies and Antibody Drug Conjugates," *Biotechnol J.* 7(12):1444-1450.

Volosin, M. et al. (Jul. 19, 2006). "Interaction of Survival and Death Signaling in Basal Forebrain Neurons: Roles of Neurotrophins and Proneurotrophins," *The Journal of Neuroscience* 26(29):7756-7766.

Volosin, M. et al. (Sep. 24, 2008). "Induction of Proneurotrophins and Activation of P75ntr-Mediated Apoptosis Via Neurotrophin Receptor-Interacting Factor in Hippocampal Neurons After Seizures," *The Journal of Neuroscience* 28(39):9870-9879, twenty five pages.

Wang, Y. et al. (Mar. 12, 2015; e-published on Feb. 26, 2015). "TREM2 Lipid Sensing Sustains the Microglial Response in an Alzheimer's Disease Model," *Cell* 160(6):1061-1071.

Wark, K.L. et al. (Aug. 7, 2006; e-pub. May 22, 2006). "Latest Technologies for the Enhancement of Antibody Affinity," *Advanced Drug Delivery Reviews* 58(5-6):657-670.

Waterhouse, P. et al. (1993). "Combinatorial Infection and In Vivo Recombination: A Strategy for Making Large Phage Antibody Repertoires," *Nucleic Acids Research* 21(9):2265-2266.

Wei, Y. et al. (2007). "Enhanced Protein Expressions of Sortilin and p75$^{NTR}$ in Retina of Rat Following Elevated Intraocular Pressure-Induced Retinal Ischemia," *Neuroscience Letters* 429(2-3):169-174.

White, A.L. et al. (Jan. 12, 2015). "Conformation of the Human Immunoglobulin G2 Hinge Imparts Superagonistic Properties to Immunostimulatory Anticancer Antibodies," *Cancer Cell* 27(1):138-148.

White, A.L. et al. (May 2013; e-pub. Mar. 31, 2013). "FcγRIIB Controls the Potency of Agonistic Anti-TNFR mAbs," *Cancer Immunol. Immunother.* 62(5):941-948.

(56) References Cited

OTHER PUBLICATIONS

Whittaker, G.C. et al. (Jan. 29, 2010; e-pub. Nov. 30, 2009). "The Linker for Activation of B Cells (LAB)/Non-T Cell Activation Linker (NTAL) Regulates Triggering Receptor Expressed on Myeloid Cells (TREM)-2 Signaling and Macrophage Inflammatory Responses Independently of the Linker for Activation of T Cells," *The Journal of Biological Chemistry* 285(5):2976-2985.

Wilcock, D.M. et al. (Dec. 8, 2004). "Passive Immunotherapy Against Aβ in Aged APP-Transgenic Mice Reverses Cognitive Deficits and Depletes Parenchymal Amyloid Deposits in Spite of Increased Vascular Amyloid and Microhemorrhage," *J. Neuroinflammation* 1(1): 24, 11 pages.

Wilcock, D.M. et al. (Feb. 2004). "Microglial activation facilitates Aβ plaque removal following intracranial anti-Aβ antibody administration," *Neurobiology of Disease* 15(1):11-20.

Wilcock, D.M. et al. (May 1, 2003). "Intracranially Administered Anti-Aβ Antibodies Reduce β-Amyloid Deposition by Mechanisms Both Independent of and Associated with Microglial Activation," *J Neurosci* 23(9):3745-3751.

Wilkinson, I.C. et al. (2013). "Monovalent IgG4 Molecules: Immunoglobulin Fc Mutations that Result in a Monomeric Structure," *mAbs* 5(3):406-417.

Wilson, N.S. et al. (Jan. 18, 2011). "An Fcγ Receptor-Dependent Mechanism Drives Antibody-Mediated Target-Receptor Signaling in Cancer Cells," *Cancer Cell* 19(1):101-113.

Xu, D. et al. (2000). "In Vitro Characterization of Five Humanized OKT3 Effector Function Variant Antibodies," *Cellular Immunology* 200(1):16-26.

Xu, J. et al. (Jul. 2000). "Diversity in the CDR3 Region of $V_H$ Is Sufficient for Most Antibody Specificities," *Immunity* 13(1):37-45.

Xu, Y. et al. (Oct. 2013). "Addressing Polyspecificity of Antibodies Selected from an in Vitro Yeast presentation system: a FACS-based, High-throughput Selection and Analytical Tool," *Protein Engineering, Design & Selection* 26(10):663-670.

Yano, H. et al. (Nov. 25, 2009)."Proneurotrophin-3 Is a Neuronal Apoptotic Ligand: Evidence for Retrograde-Directed Cell Killing," *The Journal of Neuroscience* 29(47):14790-14802.

Yelton, D.E. et al. (1995). "Affinity maturation of the BR96 anticarcinoma antibody by codon-based mutagenesis," *The Journal of Immunology* 155(4):1994-2004.

Yin, F. et al. (Jan. 18, 2010; e-pub. Dec. 21, 2009). "Exaggerated Inflammation, Impaired Host Defense, and Neuropathology in Progranulin-Deficient Mice," *J. Exp. Med*. 207(1):117-128.

Zapata, G. et al. (1995). "Engineering Linear F(ab')₂ Fragments for Efficient Production in *Escherichia coli* and Enhanced Antiproliferative Activity," *Protein Engineering Designs and Selections* 8(10):1057-1062.

Zhang, B. et al. (Apr. 25, 2013). "Integrated Systems Approach Identifies Genetic Nodes and Networks in Late-Onset Alzheimer's Disease," *Cell* 153(3):707-720.

Zhao, Y. (2013). "TREM-2 (B-3): sc-373828," Santa Cruz Biotechnology, Inc., Located at <http://datasheets.scbt.com/sc-373828.pdf>, one page.

Zhao, Y. et al. (Apr. 17, 2013). "Regulation of TREM2 Expression by an NF-κB-Sensitive miRNA-34a," *Neuroreport* 24(16):318-323, twelve pages.

Zheng, H. et al. (Feb. 15, 2017; e-pub. Jan. 11, 2017). "TREM2 Promotes Microglial Survival by Activating Wnt/β-Catenin Pathway," *J Neurosci*. 37(7):1772-1784.

Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," *Cancer Research* 74(18):5057-5069.

European Search Report (Partial) dated Mar. 6, 2018 for EP Application No. 15830235.6 filed on Aug. 8, 2015, six pages.

European Search Report and Search Opinion dated Jun. 18, 2018 for EP Application No. 15830235.6 filed on Aug. 8, 2015, fourteen pages.

International Preliminary Report on Patentability dated Apr. 19, 2018 for PCT Application No. PCT/US2016/055828 filed on Oct. 6, 2016, twelve pages.

International Preliminary Report on Patentability dated Feb. 23, 2017 for PCT Patent Application No. PCT/US2015/044396, filed on Aug. 8, 2015, nine pages.

International Search Report and Written Opinion dated Dec. 10, 2018 for PCT Application No. PCT/US2018/045068, filed on Aug. 2, 2018, twenty four pages.

International Search Report and Written Opinion dated Jun. 3, 2016 for PCT Patent Application No. PCT/US2015/044396, filed on Aug. 8, 2015, thirteen pages.

International Search Report dated Mar. 31, 2017 for PCT Application No. PCT/US2016/055828 filed on Oct. 6, 2016, nine pages.

Invitation to Pay Additional Fees and, where Applicable Protest Fee dated Feb. 8, 2017 for PCT Patent Application No. PCT/US2016/055828, filed on Oct. 6, 2016, twelve pages.

Invitation to Pay Additional Fees and, where Applicable Protest Fee dated Mar. 28, 2016 for PCT Patent Application No. PCT/US2015/044396, filed on Aug. 8, 2015, three pages.

Invitation to Pay Additional Fees and, where Applicable Protest Fee dated Oct. 10, 2018 for PCT Patent Application No. PCT/US2018/045068, filed on Aug. 2, 2018, fifteen pages.

Singaporean Search Report and Written Opinion dated Apr. 5, 2018, for SG Application No. 11201700901S filed on Feb. 6, 2017, thirteen pages.

Singaporean Search Report and Written Opinion dated Jan. 7, 2019, for SG Application No. 11201802114S filed on Mar. 14, 2018, fourteen pages.

Written Opinion of the International Searching Authority dated Mar. 31, 2017 for PCT Application No. PCT/US2016/055828 filed on Oct. 6, 2016, ten pages.

U.S. Appl. No. 15/766,363, filed Apr. 5, 2018. (Copy not submitted herewith pursuant to the waiver of 37 C.F.R. § 1.98(a)(2)(iii) issued by the Office on Sep. 21, 2004).

Gonzales et al., (2005). "Minimizing the Immunogenicity of Antibodies for Clinical Application," Tumour Biol., 26(1):31-43.

Hickman, S.E. et al. (2014). "TREM2 and the neuroimmunology of Alzheimers disease," Biochemical Pharmacology, 88:495-498, 9 pages.

Krieg et al., (2005). "Functional analysis of B and T lymphocyte attenuator engagement on CD4+ and CD8+ T cells," Journal of Immunology, 175(10):6420-6427.

Biotechne, May 2020. "Datasheet: Human/Mouse TREM2 Antibody: Monoclonal Rat IgG2B Clone #237920," Online catalogue number: MAB17291, Available online at <https://resources.rndsystems.com/pdfs/datasheets/mab17291.pdf>, 2 pages.

Satoh et al. (2013). "A Survey of TREM2 Antibodies Reveals Neuronal but Not Microglial Staining in Formalin-Fixed Paraffin-Embedded Postmortem Alzheimer's Brain Tissues," Alzheimers Res Ther., 5:30, 3 pages.

Sela-Culang et al., (2013). "The Structural Basis of Antibody-Antigen Recognition," Frontiers in Immunology, 4:302, 13 pages.

Sessa et al., (2004). "Distribution and signaling of TREM2/DAP12, the receptor system mutated in human polycystic lipomembraneous osteodysplasia with sclerosing leukoencephalopathy dementia," European Journal of Neuroscience, 20(10):2617-2628.

Wu et al., (1999). "Humanization of a Murine Monoclonal Antibody by Simultaneous Optimization of Framework and CDR Residues". J. Mol. Biol., 294:151-162.

International Preliminary Report on Patentability dated Feb. 13, 2020 for PCT Application No. PCT/US2018/045068 filed on Aug. 2, 2018, 15 pages.

```
1    MEPLRLLILLFVTELSGAHNTTVFQGVAGQSLQVSCPYDSMKHWGRRKAWCRQLGEKGPC    60
     + PL LL+LLF     + +     V Q VAGQ+L V C Y        +K WC++     C
6    LHPLLLLLLFPGSQAQS-KAQVLQSVAGQTLTVRCQYPPTGSLYEKKGWCKEASAL-VC    63

61   QRVVSTHNLWLLSFLRRWNGSTAITDDTLGGTLTITLRNLQPHDAGLYQCQSLHGSEADT   120
     R+V++       ++     W    I DD    G   T+T+ +L+    D+G Y C+    S+
64   IRLVTSSKPRTMA----WTSRFTIWDDPDAGFFTVTMTDLREEDSGHYWCRIYRPSDNSV   119

121  LRKVLVEVLADP    132  TREM-2 Human
     + V        ++  P
120  SKSVRFYLVVSP    131  NCTR2_HUMAN
```

FIG. 1A sp|Q9NZC2|TREM2_HUMAN Triggering receptor expressed on myeloid cells 2 OS=Homo sapiens GN=TREM2 PE=1 SV=1
Sequence ID: lcl|35715 Length: 230 Number of Matches: 1
Range 1: 6 to 110

| Score | Expect | Method | Identities | Positives | Gaps | Frame |
|---|---|---|---|---|---|---|
| 42.7 bits(99) | 1e-09() | Compositional matrix adjust. | 34/107(32%) | 49/107(45%) | 4/107(3%) | |

Features:

```
TREM1   9    LLWMLFVSBLRAATKLTEEKYBLKEGQTLDVKCDYTLEKFASSQKAW--QIIRDGENPKT   66
             LL +LPV+BL   A    T   ++    GQ+L V C Y    K   +KAW  Q+    G +
TREM2   6    LLILLPVTBLSGAHNTT--VFQGVAGQSLQVSCPYDSMKHWGRRKAWCRQLGEKGPCQRV   63

TREM1   67   LACTERPSKNSHPVQVGRIILEDYHDHGLLRVRMVNLQVEDSGLYQC   113
             +                  G   + D        G L  +  NLQ  D+GLYQC
TREM2   64   VSTHNLWLLSPLRRWNGSTAITDDTLGGTLTITLRNLQPHDAGLYQC   110
```

FIG. 2A

Ab21
EVQLVQSGAEVKKPGESLKISCKGSGYSFTTYWIGWVRQMPGKGLEWMGIIYPGDSDTRYSPSFQGQVTISADKSISTAYLQWSSLKASDTAMYYC
ARAGHYDGGHLGMDYWGQGTTVTVSS (SEQ ID NO:414)

Ab52
QVQLVQSGAEVKKPGASVKVSCKASGYTFTSYYIHWVRQAPGQGLEWMGIINPSGGSTSYAQKFQGRVTMTRDTSTSTVYMELSSLRSEDTAVYY
CAREADDSSGYPLGLDVWGQGTMVTVSS (SEQ ID NO:415)

FIG. 2B

Ab21
EIVMTQSPGTLSLSPGERATLSCRASQSVSSSYLAWYQQKPGQAPRLLIYGASNRATGIPDRFSGSGSGTDFTLTISRLEPEDFAVYYCQQDDSAPYTF
GGGTKVEIK (SEQ ID NO:416)

Ab52
EIVMTQSPATLSVSPGERATLSCRASQSVSSNLAWYQQKPGQAPRLLIYGASTRATGIPARFSGSGSGTEFTLTISSLQSEDFAVYYCQQVNSLPPTFG
GGTKVEIK (SEQ ID NO:417)

FIG. 2C

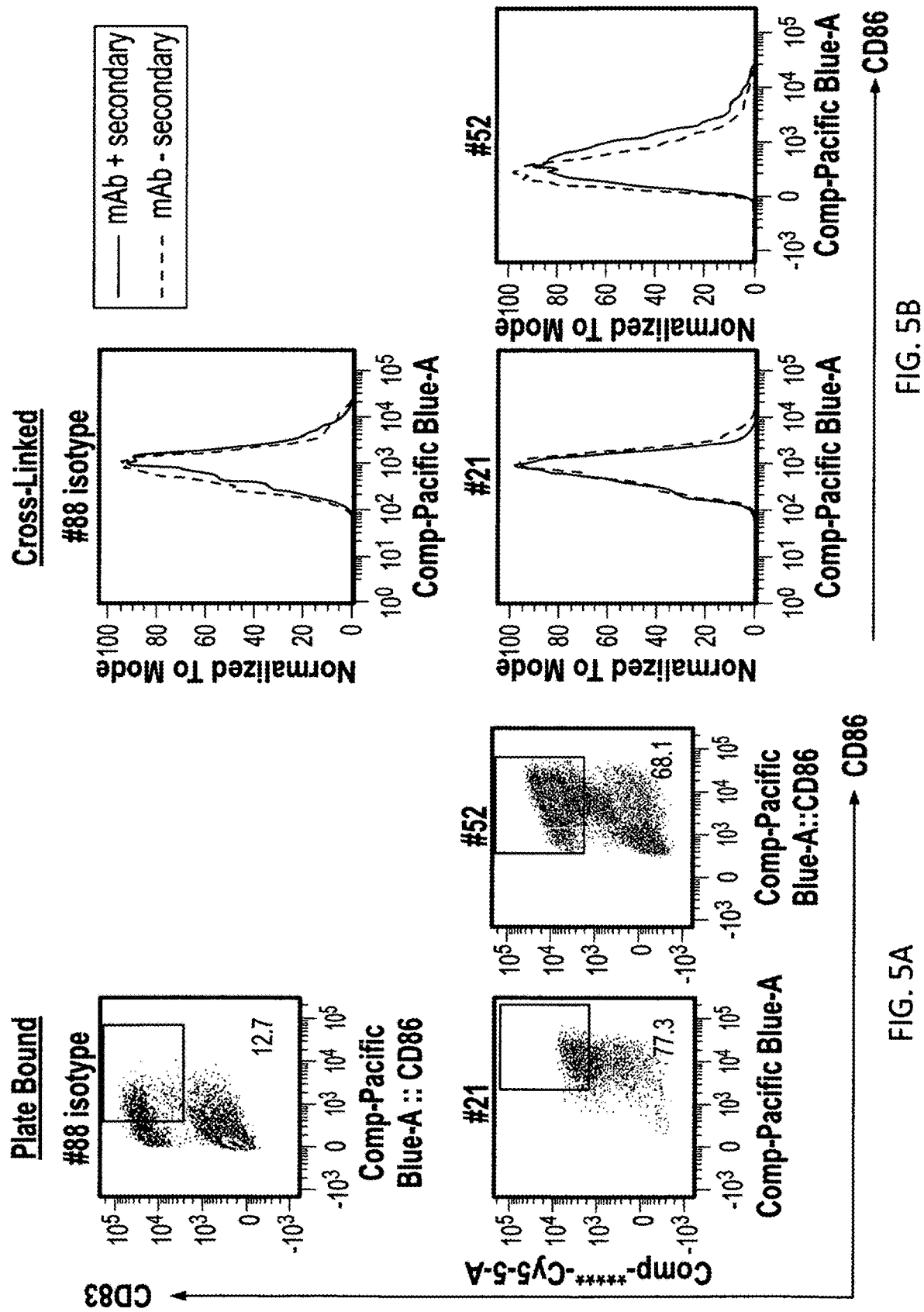

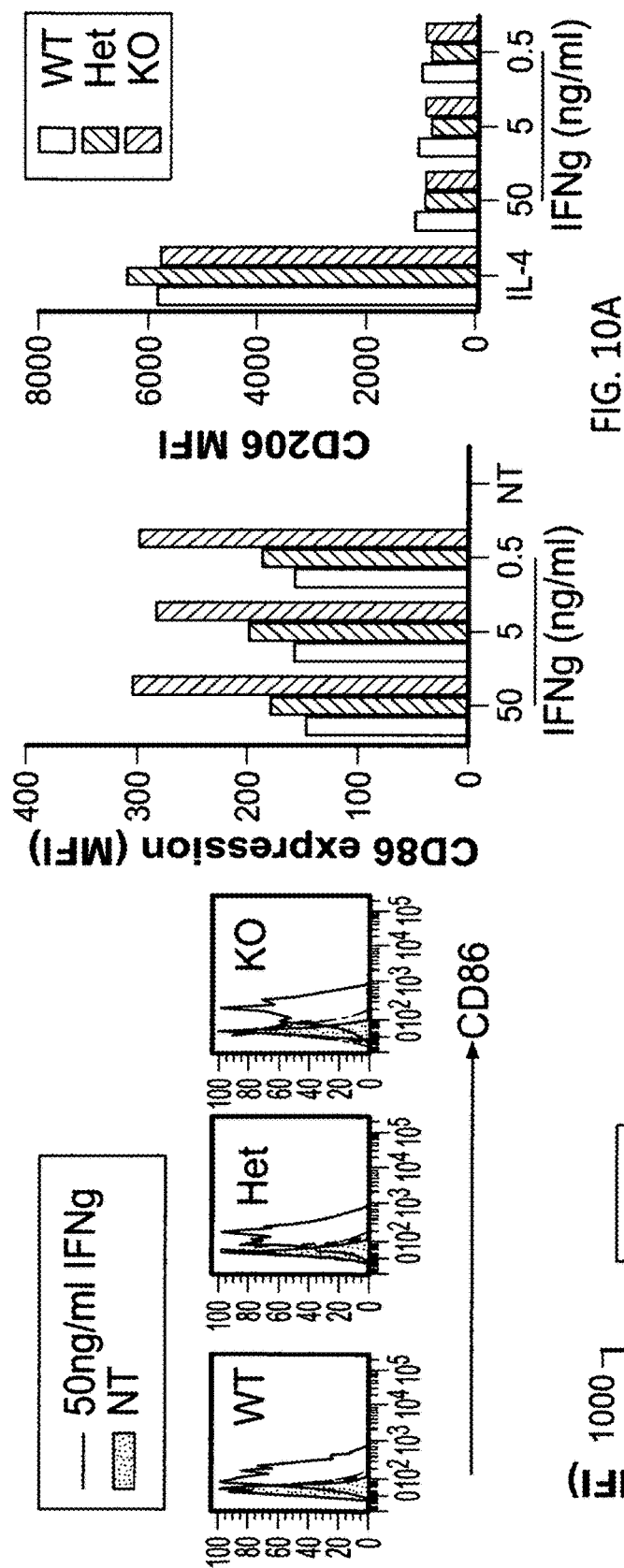
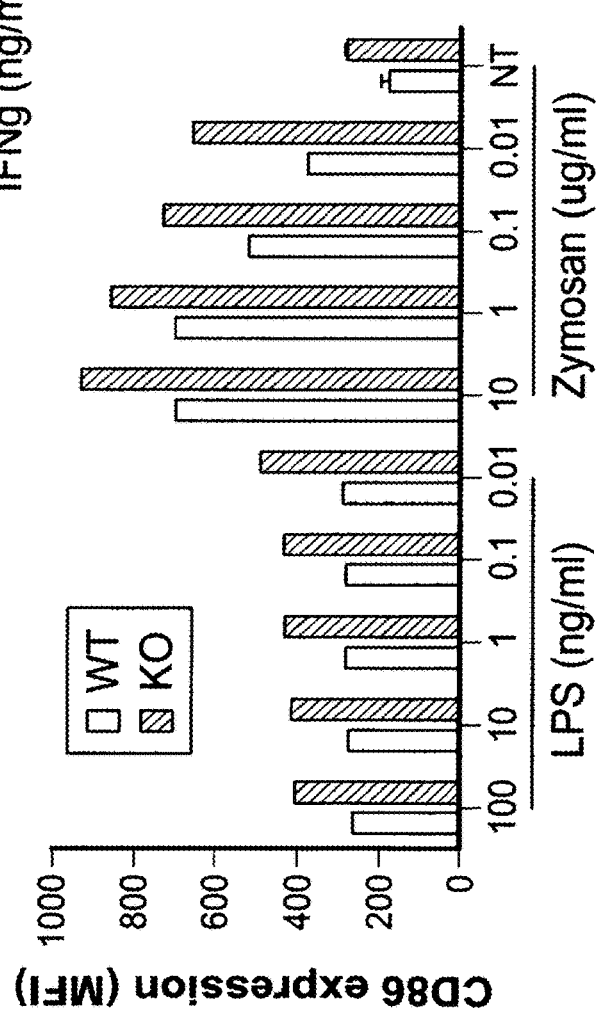
FIG. 10A
FIG. 10B

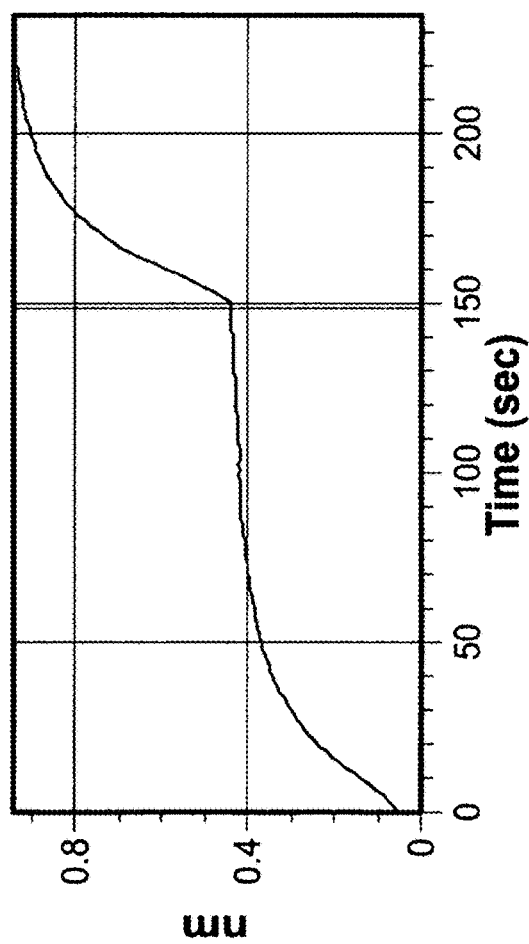
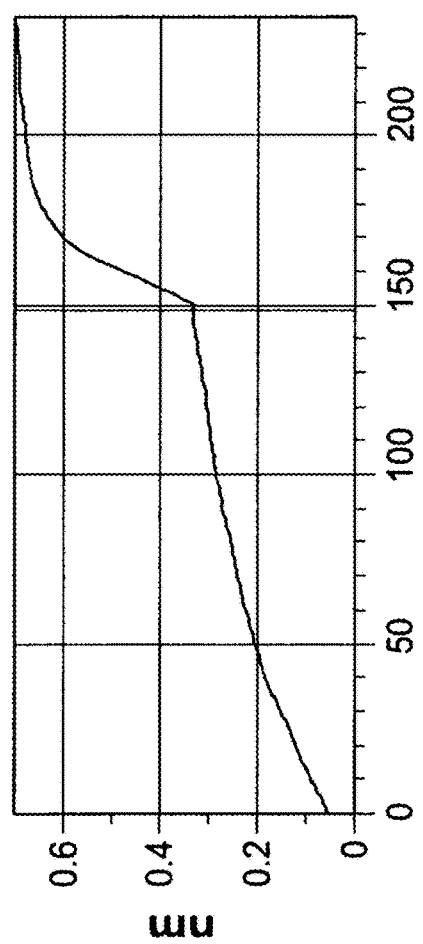
FIG. 15A
FIG. 15B

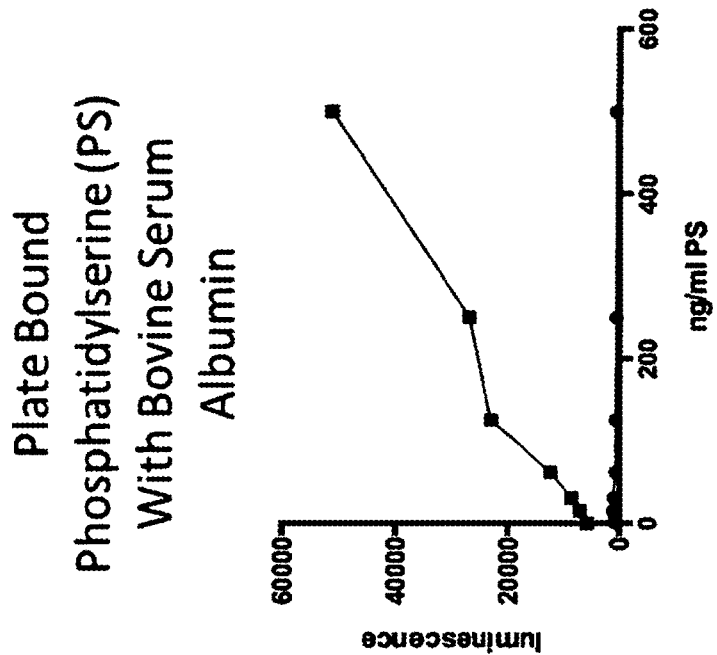
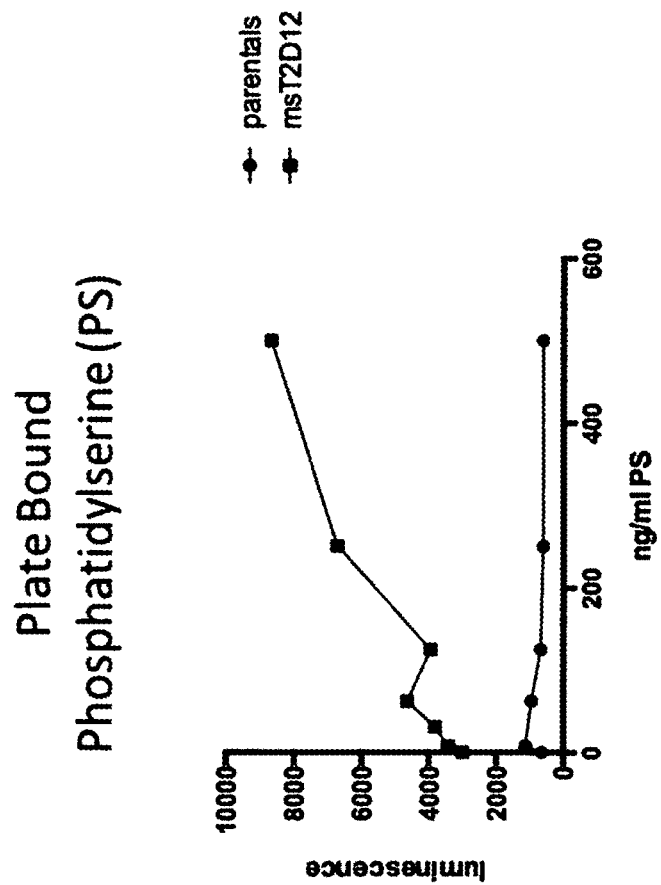
FIG. 18B

Ab1 – Heavy chain variable region (SEQ ID NO:242)
EVQLLESGGGLVQPGGSLRLSCAASGFTSSYAMSWVRQAPGKGLEWVSVISGSGGSTYYADSVKGRFTISRDNSKNTLYLQMNSLRAEDTAVYYCAKGTPTLLFQH
WGQGTLVTVSS Ab2 – Heavy chain variable region (SEQ ID NO:244)
EVQLLESGGGLVQPGGSLRLSCAASGFTFSSSAMSWVRQAPGKGLEWVSAISGSGGSTYYADSVKGRFTISRDNSKNTLYLQMNSLRAEDTAVYYCAKVPSYDYWS
GYSNYYYMDVWGKGTTVTVSS Ab3 – Heavy chain variable region (SEQ ID NO:246)
QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAREQYHVGMD
YWGKGTTVTVSS Ab4 – Heavy chain variable region (SEQ ID NO:248)
QVQLVQSGAEVKKPGSSVKVSCKASGGTFSSYAISWVRQAPGQGLEWMGGIIPIFGTASYAQKFQGRVTITADESTSTAYMELSSLRSEDTAVYYCARGVDSMDYW
GQGTLVTVSS Ab5 – Heavy chain variable region (SEQ ID NO:250)
QVQLVQSGAEVKKPGASVKVSCKASGYTFTSYYIHWVRQAPGQGLEWMGIINPSGGSTSYAQKFQGRVTMTRDTSTSTVYMELSSLRSEDTAVYYCARAPQESPYV
FDIWGQGTMVTVSS Ab6 – Heavy chain variable region (SEQ ID NO:252)
QVQLVQSGAEVKKPGASVKVSCKASGYTFTSYYMHWVRQAPGQGLEWMGIINPGGGSTSYAQKFQGRVTMTRDTSTSTVYMELSSLRSEDTAVYYCARGSPTYGY
LYDPWGQGTLVTVSS Ab7 – Heavy chain variable region (SEQ ID NO:254)
QVQLVQSGAEVKKPGASVKVSCKASGYTFTSYYMHWVRQAPGQGLEWMGIINPSGGSTIYAQKFQGRVTMTRDTSTSTVYMELSSLRSEDTAVYYCARISSKERD
YWGQGTLVTVSS Ab8 – Heavy chain variable region (SEQ ID NO:256)
QLQLQESGPGLVKPSETLSLTCTVSGGSISSSSYYWGWIRQPPGKGLEWIGSISYSGSTYYNPSLKSRVTISVDTSKNQFSLKLSSVTAADTAVYYCARGPYRLLLGMD
VWGQGTTVTVSS Ab9 – Heavy chain variable region (SEQ ID NO:258)
EVQLVQSGAEVKKPGESLKISCKGSGYSFTSYWIGWVRQMPGKGLEWMGIIYPGDSDTTYSPSFQGQVTISADKSISTAYLQWSSLKASDTAMYYCARLHISGEVNW
FDPWGQGTLVTVSS Ab10 – Heavy chain variable region (SEQ ID NO:260)
EVQLVQSGAEVKKPGESLKISCKGSGYSFTSNWIGWVRQMPGKGLEWMGIIYPGDSDTRYSPSFQGQVTISADKSISTAYLQWSSLKASDTAMYYCAREAGYDYGEL
AFDIWGQGTMVTVSS

FIG. 20A

Ab11 – Heavy chain variable region (SEQ ID NO:262)
EVQLVQSGAEVKKPGESLKISCKGSGYSFITYWIGWVRQMPGKGLEWMGIIYPGDSDTRYSPSFQGQVTISADKSISTAYLQWSSLKASDTAMYYCARAGHYDGGHLGMD
YWGQGTTVTVSS Ab12 – Heavy chain variable region (SEQ ID NO:264)
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARLGHYSGTVSSYGM
DYWGQGTTVSS Ab13 – Heavy chain variable region (SEQ ID NO:266)
QVQLVQSGAEVKKPGASVKVSCKASGYTFTSYGISWVRQAPGQGLEWMGWISAYNGNTNYAQKLQGRVTMTDTSTSTAYMELRSLRSDDTAVYYCARGPSHYDLA
WGQGTLVTVSS Ab14 – Heavy chain variable region (SEQ ID NO:268)
QVQLQESGPGLVKPSQTLSLTCTVSGGSITSGGYYWSWIRQHPGKGLEWIGNIYYSGSTYYNPSLKSRVTISVDTSKNQFSLKLSSVTAADTAVYYCARGLYGYGVLDVWG
QGTMVTVSS Ab15 – Heavy chain variable region (SEQ ID NO:268)
QVQLQESGPGLVKPSQTLSLTCTVSGGSITSGGYYWSWIRQHPGKGLEWIGNIYYSGSTYYNPSLKSRVTISVDTSKNQFSLKLSSVTAADTAVYYCARGLYGYGVLDVWG
QGTMVTVSS Ab16 – Heavy chain variable region (SEQ ID NO:271)
QLQLQESGPGLVKPSETLSLTCTVSGGSISSGGYYWSWIRQPPGKGLEWIGSIYYSGSTYYNPSLKSRVTISVDTSKNQFSLKLSSVTAADTAVYYCARGVLGYVFDYWGQ
GTLVTVSS Ab17 – Heavy chain variable region (SEQ ID NO:271)
QLQLQESGPGLVKPSETLSLTCTVSGGSISSGGYYWSWIRQPPGKGLEWIGSIYYSGSTYYNPSLKSRVTISVDTSKNQFSLKLSSVTAADTAVYYCARGVLGYVFDYWGQ
GTLVTVSS Ab18 – Heavy chain variable region (SEQ ID NO:274)
QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARDGGGEYPSGTPFDIWG
QGTMVTVSS Ab19 – Heavy chain variable region (SEQ ID NO:274)
QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARDGGGEYPSGTPFDIWG
QGTMVTVSS Ab20 – Heavy chain variable region (SEQ ID NO:277)
QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARSGMASFFDYWGQGTL
VTVSS

FIG. 20A (Cont.)

Ab22 – Heavy chain variable region (SEQ ID NO:262)
EVQLVQSGAEVKKPGESLKISCKGSGYSFTTYWIGWVRQMPGKGLEWMGIIYPGDSDTRYSPSFQGQVTISADKSISTAYLQWSSLKASDTAMYYCARAGHYDGGHLGMD
YWGQGTTVTVSS Ab23 – Heavy chain variable region (SEQ ID NO:280)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKLGGHSMDVWGQ
GTTVTVSS Ab24 – Heavy chain variable region (SEQ ID NO:282)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKPLKRGRGFYWG
QGTLVTVSS Ab25 – Heavy chain variable region (SEQ ID NO:284)
EVQLLESGGGLVQPGGSLRLSCAASGFTFSSYAMSWVRQAPGKGLEWVSVISGSGGSTYYADSVKGRFTISRDNSKNTLYLQMNSLRAEDTAVYYCAKEGRTIFMDWGQG
TLVTVSS Ab26 – Heavy chain variable region (SEQ ID NO:286)
EVQLLESGGGLVQPGGSLRLSCAASGFTFSSYAMSWVRQAPGKGLEWVSVISGSGGSTYYADSVKGRFTISRDNSKNTLYLQMNSLRAEDTAVYYCAKDQYSVLDYWGQ
GTLVTVSS Ab27 – Heavy chain variable region (SEQ ID NO:288)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKKYSSRGVYFDY
WGQGTLVTVSS Ab28 – Heavy chain variable region (SEQ ID NO:290)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLGGAVGARHVI
YFDYWGQGTLVTVSS Ab29 – Heavy chain variable region (SEQ ID NO:292)
QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARGQYYGGSGWF
DPWGQGTLVTVSS Ab30 – Heavy chain variable region (SEQ ID NO:294)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLGQEYAYFQHW
GQGTLVTVSS

FIG. 20A (Cont.)

Ab31 – Heavy chain variable region (SEQ ID NO:296)
QVQLVESGGGVVQPGRSLRLSCAASGFTFSSYGMHWVRQAPGKGLEWVALIWYDGSNKYYADSVKGRFTISRDNSKNTLYLQMNSLRAEDTAVYYCARRRDGYYDEVF
DIWGQGTMVTVSS Ab32 – Heavy chain variable region (SEQ ID NO:298)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVPKHYVVLDYW
GQGTLVTVSS Ab33 – Heavy chain variable region (SEQ ID NO:300)
QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARAGGHLFDYWG
QGTILVTVSS Ab34 – Heavy chain variable region (SEQ ID NO:302)
QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARDRGGEYVDFAF
DIWGQGTLVTVSS Ab35 – Heavy chain variable region (SEQ ID NO:304)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARTRSGYGASNYFD
YWGQGTLVTVSS Ab36 – Heavy chain variable region (SEQ ID NO:306)
QVQLVESGGGVVQPGRSLRLSCAASGFTFSTYGMHWVRQAPGKGLEWVAVIWYDGSNKYYADSVKGRFTISRDNSKNTLYLQMNSLRAEDTAVYYCARGTGAAAASPA
FDIWGQGTMVTVSS Ab37 – Heavy chain variable region (SEQ ID NO:308)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVGQYMLGMDV
WGQGTTVTVSS Ab38 – Heavy chain variable region (SEQ ID NO:310)
QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARGAPVDYGGIE
PEYFQHWGQGTLVTVSS Ab39 – Heavy chain variable region (SEQ ID NO:312)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKHYHVGIAFDIWG
QGTMVTVSS Ab40 – Heavy chain variable region (SEQ ID NO:304)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARTRSGYGASNYFD
YWGQGTLVTVSS

FIG. 20A (Cont.)

Ab41 – Heavy chain variable region (SEQ ID NO:315)
EVQLLESGGGLVQPGGSLRLSCAASGFTFSTYAMSWVRQAPGKGLEWVSAISGSGGSTYYADSVKGRFTISRDNSKNTLYLQMNSLRAEDTAVYYCARAMARKSVAFDIW
GQGTMVTVSS Ab42 – Heavy chain variable region (SEQ ID NO:317)
EVQLLESGGGLVQPGGSLRLSCAASGFTFSSSAMSWVRQAPGKGLEWVSAISGSGGSTYYADSVKGRFTISRDNSKNTLYLQMNSLRAEDTAVYYCAKVPSYQRGIAFDP
WGQGTLVTVSS Ab43 – Heavy chain variable region (SEQ ID NO:319)
EVQLLESGGGLVQPGGSLRLSCAASGFTFSSSAMSWVRQAPGKGLEWVSAISGSGGSTYYADSVKGRFTISRDNSKNTLYLQMNSLRAEDTAVYYCAKSPAVAGIYRADY
WGQGTLVTVSS Ab44 – Heavy chain variable region (SEQ ID NO:306)
QVQLVESGGGVVQPGRSLRLSCAASGFTFSTYGMHWVRQAPGKGLEWVAVIWYDGSNKYYADSVKGRFTISRDNSKNTLYLQMNSLRAEDTAVYYCARGTGAAAASPA
EDIWGQGTMVTVSS Ab45 – Heavy chain variable region (SEQ ID NO:322)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGPGYTTALDYY
YMDVWGKGTTVTVSS Ab46 – Heavy chain variable region (SEQ ID NO:324)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARPAKTADYWGQ
GTLVTVSS Ab47 – Heavy chain variable region (SEQ ID NO:326)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARPGKSMDVWGQ
GTLVTVSS Ab48 – Heavy chain variable region (SEQ ID NO:326)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARPGKSMDVWGQ
GTLVTVSS Ab49 – Heavy chain variable region (SEQ ID NO:324)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARPAKTADYWGQ
GTLVTVSS Ab50 – Heavy chain variable region (SEQ ID NO:250)
QVQLVQSGAEVKKPGASVKVSCKASGYTFTSYYIHWVRQAPGQGLEWMGIINPSGGSTSYAQKFQGRVTMTRDTSTSTVYMELSSLRSEDTAVYYCARAPQESPYVFDIW
GQGTMVTVSS

FIG. 20A (Cont.)

Ab51 – Heavy chain variable region (SEQ ID NO:331)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGVGGQDYYYM
DVWGKGTTVTVSS Ab53 – Heavy chain variable region (SEQ ID NO:250)
QVQLVQSGAEVKKPGASVKVSCKASGYTFTSYIHWVRQAPGQGLEWMGIINPSGGSTSYAQKFQGRVTMTRDTSTSTVYMELSSLRSEDTAVYYCARAPQESPYVFDIW
GQGTMVTVSS Ab54 – Heavy chain variable region (SEQ ID NO:322)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGPGYTTALDYY
YMDVWGKGTTVTVSS Ab55 – Heavy chain variable region (SEQ ID NO:335)
QVQLVQSGAEVKKPGASVKVSCKASGYTFIGSYMHWVRQAPGQGLEWMGWINPNSGGTINYAQKFQGRVTMTRDTSISTAYMELSRLRSDDTAVYYCARGPLYHPMIFD
YWGQGTLVTVSS Ab56 – Heavy chain variable region (SEQ ID NO:337)
QVQLVQSGAEVKKPGASVKVSCKASGYTFIGYYMHWVRQAPGQGLEWMGSINPNSGGTINYAQKFQGRVTMTRDTSISTAYMELSRLRSDDTAVYYCARASSVDNWGQ
GTLVTVSS Ab57 – Heavy chain variable region (SEQ ID NO:339)
QVQLVQSGAEVKKPGASVKVSCKASGYTFINYGISWVRQAPGQGLEWMGWISAYNGNTNYAQKLQGRVTMTDTSTSTAYMELRSLRSDDTAVYYCARGPTKAYYGS
GSYVVFDPWGQGTLVTVSS Ab58 – Heavy chain variable region (SEQ ID NO:341)
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARLGIYSTGATAFDI
WGQGTMVTVSS Ab59 – Heavy chain variable region (SEQ ID NO:343)
QVQLVQSGAEVKKPGASVKVSCKASGYTFIGSYMHWVRQAPGQGLEWMGWINPNSGGTINYAQKFQGRVTMTRDTSISTAYMELSRLRSDDTAVYYCARGGVWYSLFD
IWGQGTMVTVSS Ab60 – Heavy chain variable region (SEQ ID NO:345)
QVQLVQSGAEVKKPGASVKVSCKASGYTFIGYYMHWVRQAPGQGLEWMGWINPNSGGTINYAQKFQGRVTMTRDTSISTAYMELSRLRSDDTAVYYCARASKMGDDW
GQGTLVTVSS

FIG. 20A (Cont.)

Ab61 – Heavy chain variable region (SEQ ID NO:347)
QVQLVQSGAEVKKPGASVKVSCKASGYTFTSYGIHWVRQAPGQGLEWMGWISAYNGNTNYAQKLQGRVTMTDTSTSTAYMELRSLRSDDTAVYYCARGGVPRVSFQ
HWGQGTLVTVSS Ab62 – Heavy chain variable region (SEQ ID NO:349)
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARAGHYDDWSGLGL
DVWGQGTMVTVSS Ab63 – Heavy chain variable region (SEQ ID NO:351)
QVQLVQSGAEVKKPGASVKVSCKASGYTFTSYGISWVRQAPGQGLEWMGWISTYNGNTNYAQKLQGRVTMTDTSTSTAYMELRSLRSDDTAVYYCARGSGSGYDSWY
DWGQGTLVTVSS Ab64 – Heavy chain variable region (SEQ ID NO:353)
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARLGRWSSGSTAFDI
WGQGTMVTVSS Ab65 – Heavy chain variable region (SEQ ID NO:355)
EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARLGRKPSGSVAFDI
WGQGTMVTVSS Ab66 – Heavy chain variable region (SEQ ID NO:357)
QVQLVQSGAEVKKPGASVKVSCKASGYTFTGSYMHWVRQAPGQGLEWMGWINPNSGGTNYAQKFQGRVTMTRDTSISTAYMELSRLRSDDTAVYYCARAGHKTHDY
WGQGTLVTVSS Ab67 – Heavy chain variable region (SEQ ID NO:326)
QVQLVQSGAEVKKPGASVKVSCKASGYTFTSYYMHWVRQAPGQGLEWMGIINPSGGSTIYAQKFQGRVTMTRDTSTSTVYMELSSLRSEDTAVYYCARPGKSMDVWGQ
GTTVTVSS Ab68 – Heavy chain variable region (SEQ ID NO:360)
QVQLVESGGGVVQPGRSLRLSCAASGFTFSSYGMHWVRQAPGKGLEWVALIWYDGSNKYYADSVKGRFTISRDNSKNTLYLQMNSLRAEDTAVYYCAKPGSMTDYWG
QGTLVTVSS Ab69 – Heavy chain variable region (SEQ ID NO:362)
QVQLVQSGAEVKKPGASVKVSCKASGYTFTGSYMHWVRQAPGQGLEWMGWINPNSGGTNYAQKFQGRVTMTRDTSISTAYMELSRLRSDDTAVYYCARAKSVDHDYW
GQGTLVTVSS Ab70 – Heavy chain variable region (SEQ ID NO:345)
QVQLVQSGAEVKKPGASVKVSCKASGYTFTGYYMHWVRQAPGQGLEWMGWINPNSGGTSYAQKFQGRVTMTRDTSISTAYMELSRLRSDDTAVYYCARASKMGDDW
GQGTLVTVSS

FIG. 20A (Cont.)

Ab71 – Heavy chain variable region (SEQ ID NO:365)
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDISTHDYDLAF DIWGQGTMVTVSS Ab72 – Heavy chain variable region (SEQ ID NO:367)
QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARSGTETLFDYWGQGTLV TVSS Ab73 – Heavy chain variable region (SEQ ID NO:369)
EVQLVQSGAEVKKPGESLKISCKGSGYSFTSYWIGWVRQMPGKGLEWMGIIYPGDSDTIYSPSFQGQVTISADKSISTAYLQWSSLKASDTAMYYCARAKMLDDGYAFDI WGQGTMVTVSS Ab74 – Heavy chain variable region (SEQ ID NO:357)
QVQLVQSGAEVKKPGASVKVSCKASGYTFGSYMHWVRQAPGQGLEWMGWINPNSGGTNYAQKFQGRVTMTRDTSISTAYMELSRLRSDDTAVYYCARAGHKTHDY WGQGTLVTVSS Ab75 – Heavy chain variable region (SEQ ID NO:372)
QVQLVQSGAEVKKPGASVKVSCKASGYTFIGYYMHWVRQAPGQGLEWMGWINPNSGGTNYAQKFQGRVTMTRDTSISTAYMELSRLRSDDTAVYYCARDLGYSSLLA LDIWGQGTMVTVSS Ab76 – Heavy chain variable region (SEQ ID NO:374)
EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARGGGRRGDNNWFD PWGQGTLVTVSS Ab77 – Heavy chain variable region (SEQ ID NO:376)
QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARGPPHEMDYWG QGTLVTVSS Ab78 – Heavy chain variable region (SEQ ID NO:378)
QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARTPYPWIYFDL WGRGTLVTVSS Ab79 – Heavy chain variable region (SEQ ID NO:380)
EVQLVESGGGLVQPGGSLRLSCAASGFTFSSYSMNWVRQAPGKGLEWVSYISGSSTIYYADSVKGRFTISRDNAKNSLYLQMNSLRAEDTAVYYCARGGRRHYGGMDV WGQGTTVTVSS Ab80 – Heavy chain variable region (SEQ ID NO:382)
QVQLVQSGAEVKKPGSSVKVSCKASGGTFSSYAISWVRQAPGQGLEWMGGIIPFGTANYAQKFQGRVTITADESTSTAYMELSSLRSEDTAVYYCARGGGTFWSGSWAL YWGQGTLVTVSS

FIG. 20A (Cont.)

Ab81 – Heavy chain variable region (SEQ ID NO:384)
QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARDSGNYDYWSGAL RYWGQGTLVTVSS Ab82 – Heavy chain variable region (SEQ ID NO:386)
QVQLQESGPGLVKPSQTLSLTCTVSGGSISSGGYYWSWIRQHPGKGLEWIGYIYYSGSTVYNPSLKSRVTISVDTSKNQFSLKLSSVTAADTAVYYCARVSSSWYKAWGQG TMVTVSS Ab83 – Heavy chain variable region (SEQ ID NO:388)
QVQLQQWGAGLLKPSETLSLTCAVYGGSFSGYYWSWIRQPPGKGLEWIGEIDHSGSTKYNPSLKSRVTISVDTSKNQFSLKLSSVTAADTAVYYCARVGVVGRPGYSAFD IWGQGTMVTVSS Ab84 – Heavy chain variable region (SEQ ID NO:351)
QVQLVQSGAEVKKPGASVKVSCKASGYTFTSYGISWVRQAPGQGLEWMGWISTYNGNTNYAQKLQGRVTMTDTSTSTAYMELRSLRSDDTAVYYCARGSGSGYDSWY DWGQGTLVTVSS Ab85 – Heavy chain variable region (SEQ ID NO:391)
QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAKDLGGYYGGA AYGMDVWGQGTTVTVSS Ab86 – Heavy chain variable region (SEQ ID NO:393)
QVQLVESGGGVVQPGRSLRLSCAASGFTFSSYGMHWVRQAPGKGLEWVAVISYDGSNKYYADSVKGRFTISRDNSKNTLQMNSLRAEDTAVYYCAKDGVYYGLGNW EDPWGQGTLVTVSS Ab87 – Heavy chain variable region (SEQ ID NO:395)
QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARHGWDRVGWFDPWGQ GTLVTVSS

FIG. 20A (Cont.)

Ab1 – Light chain variable region (SEQ ID NO:243)
EIVMTQSPATLSVSPGERATLSCRASQSVSSNLAWYQQKPGQAPRLLIYGASTRAIGIPARFSGSGSGTEFTLTISSLQSEDFAVYYCQQLPYWPPITFGGGTKVEIK Ab2 – Light chain variable region (SEQ ID NO:245)
EIVLIQSPATLSVSPGERATLSCRASQSVSSNLAWYQQKPGQAPRLLIYGASTRAIGIPARFSGSGSGTEFTLTISSLQSEDFAVYYCQQYFFYPPITFGGGTKVEIK Ab3 – Light chain variable region (SEQ ID NO:247)
DIQMTQSPSSLSASVGDRVTITCQASQDISNYLNWYQQKPGKAPKLLIYDASNLATGVPSRFSGSGSGTDFTFTISSLQPEDIATYYCQQPFNFPYITFGGGTKVEIK Ab4 – Light chain variable region (SEQ ID NO:249)
EIVMTQSPATLSVSPGERATLSCRASQSVSSNLAWYQQKPGQAPRLLIYSASTRATGIPARFSGSGSGTEFTLTISSLQSEDFAVYYCQQHDYPFTFGGGTKVEIK Ab5 – Light chain variable region (SEQ ID NO:251)
EIVMTQSPGTLSLSPGERATLSCRASQSVSSSYLAWYQQKPGQAPRLLIYGASSRATGIPDRFSGSGSGTDFTLTISSLEPEDFAVYYCQQYFSSPFTFGGGTKVEIK Ab6 – Light chain variable region (SEQ ID NO:253)
EIVLTQSPATLSLSPGERATLSCRASQSVSSSYLAWYQQKPGQAPRLLIYDASKRATGIPARFSGSGSGTDFTLTISSLEPEDFAVYYCQQRVNLPITFGGGTKVEIK Ab7 – Light chain variable region (SEQ ID NO:255)
EIVLTQSPATLSLSPGERATLSCRASQSVSSSYLAWYQQKPGQAPRLLIYDASKRATGIPARFSGSGSGTDFTLTISSLEPEDFAVYYCQQRISYPITFGGGTKVEIK Ab8 – Light chain variable region (SEQ ID NO:257)
EIVLTQSPATLSLSPGERATLSCRASQSISSYYLNWYQQKPGKAPKLLIYGASSLQSGVPSRFSGSGSGTDFTLTISSLQPEDFATYYCQQIDDIPITFGGGTKVEIK Ab9 – Light chain variable region (SEQ ID NO:259)
DIQMTQSPSSLSASVGDRVTITCRASQSVSSYLAWYQQKPGQAPRLLIYDASNRATGIPARFSGSGSGTDFTLTISSLEPEDFAVYYCQQFSYWPWTFGGGTKVEIK Ab10 – Light chain variable region (SEQ ID NO:261)
EIVLIQSPGTLSLSPGERATLSCRASQSVSSSYLAWYQQKPGQAPRLLIYGASSRATGIPDRFSGSGSGTDFTLTISRLEPEDFAVYYCQQHDSSPPITFGGGTKVEIK

FIG. 20B

Ab11 – Light chain variable region (SEQ ID NO:263)
EIVLTQSPGTLSLSPGERATLSCRASQSVSSSDYLAWYQQKPGQAPRLLIYGASSRATGIPDRFSGSGSGTDFTLTISRLEPEDFAVYYCQQDYSYPWTFGGGTKVEIK Ab12 – Light chain variable region (SEQ ID NO:265)
DIQMTQSPSSLSASVGDRVTITCRASQSISSYLNWYQQKPGKAPKLLIYAASSLQSGVPSRFSGSGSGTDFTLTISSLQPEDFATYYCQQEYAVPYTFGGGTKVEIK Ab13 – Light chain variable region (SEQ ID NO:267)
EIVLTQSPATLSLSPGERATLSCRASQSVSSYLAWYQQKPGQAPRLLIYDASNRATGIPARFSGSGSGTDFTLTISSLEPEDFAVYYCQQVSNYPITFGGGTKVEIK Ab14 – Light chain variable region (SEQ ID NO:269)
DIQMTQSPSSLSASVGDRVTITCQASQDISNYLNWYQQKPGKAPKLLIYDASNLETGVPSRFSGSGSGTDFTFTISSLQPEDIATYYCQQVDNIPPTFGGGTKVEIK Ab15 – Light chain variable region (SEQ ID NO:270)
DIQMTQSPSSLSASVGDRVTITCQASQDISNYLNWYQQKPGKAPKLLIYDASNLETGVPSRFSGSGSGTDFTFTISSLQPEDIATYYCQQFDIYPTFGGGTKVEIK Ab16 – Light chain variable region (SEQ ID NO:272)
DIQMTQSPSSLSASVGDRVTITCQASQDISNYLNWYQQKPGKAPKLLIYDASNLETGVPSRFSGSGSGTDFTFTISSLQPEDIATYYCQQFLNFPTFGGGTKVEIK Ab17 – Light chain variable region (SEQ ID NO:273)
DIQMTQSPSSLSASVGDRVTITCQASQDISNYLNWYQQKPGKAPKLLIYDASNLETGVPSRFSGSGSGTDFTFTISSLQPEDIATYYCQQFNFPTFGGGTKVEIK Ab18 – Light chain variable region (SEQ ID NO:275)
DIQMTQSPSSLSASVGDRVTITCQASQDISNYLNWYQQKPGKAPKLLIYDASNLETGVPSRFSGSGSGTDFTFTISSLQPEDIATYYCQQFIDLPTFGGGTKVEIK Ab19 – Light chain variable region (SEQ ID NO:276)
DIQMTQSPSSLSASVGDRVTITCQASQDISNYLNWYQQKPGKAPKLLIYDASNLETGVPSRFSGSGSGTDFTFTISSLQPEDIATYYCQQYDLPTFGGGTKVEIK Ab20 – Light chain variable region (SEQ ID NO:278)
EIVLTQSPGTLSLSPGERATLSCRASQSVSSSDYLAWYQQKPGQAPRLLIYGASSRATGIPDRFSGSGSGTDFTLTISRLEPEDFAVYYCQQFSSHPTFGGGTKVEIK

FIG. 20B (Cont.)

Ab22 – Light chain variable region (SEQ ID NO:279)
EIVMTQSPGTLSLSPGERATLSCRASQSVSSSYLAWYQQKPGQAPRLLIYGASSRATGIPDRFSGSGSGTDFTLTISRLEPEDFAVYYCQQDDRSPYTFGGGTKVEIK Ab23 – Light chain variable region (SEQ ID NO:281)
DIVMTQSPDSLAVSLGERATINCKSSQSVLYSSNNKNYLAWYQQKPGQPPKLLISWASTRESGVPDRFSGSGSGTDFTLTISSLQAEDVAVYYCQQAYLPPITFGGGTKV
EIK Ab24 – Light chain variable region (SEQ ID NO:283)
DIQMTQSPSSLSASVGDRVTITCRASQSISSYLNWYQQKPGKAPKLLIYAASSLQSGVPSRFSGSGSGTDFTLTISSLQPEDFATYYCQQAFSPPPWTFGGGTKVEIK Ab25 – Light chain variable region (SEQ ID NO:285)
EIVLTQSPGTLSLSPGERATLSCRASQSVSSSYLAWYQQKPGQAPRLLIYGASSRATGIPDRFSGSGSGTDFTLTISRLEPEDFAVYYCQQDDRSPITFGGGTKVEIK Ab26 – Light chain variable region (SEQ ID NO:287)
EIVLTQSPATLSLSPGERATLSCRASQSVSSSYLAWYQQKPGQAPRLLIYDASNRAIGIPARFSGSGSGTDFTLTISSLEPEDFAVYYCQQEFDLPFTFGGGTKVEIK Ab27 – Light chain variable region (SEQ ID NO:289)
EIVLTQSPATLSLSPGERATLSCRASQSVSSSYLAWYQQKPGQAPRLLIYDASNRAIGIPARFSGSGSGTDFTLTISSLEPEDFAVYYCQQYNNFPFTFGGGTKVEIK Ab28 – Light chain variable region (SEQ ID NO:291)
EIVLTQSPATLSLSPGERATLSCRASQSVSSSYLAWYQQKPGQAPRLLIYDASKRATGIPARFSGSGSGTDFTLTISSLEPEDFAVYYCQQRYLRPITFGGGTKVEIK Ab29 – Light chain variable region (SEQ ID NO:293)
EIVLTQSPGTLSLSPGERATLSCRASQSVSSSYLAWYQQKPGQAPRLLIYGASSRATGIPDRFSGSGSGTDFTLTISRLEPEDFAVYYCQQPGAVPTFGGGTKVEIK Ab30 – Light chain variable region (SEQ ID NO:295)
DIQMTQSPSSLSASVGDRVTITCRASQSISSYLNWYQQKPGKAPKLLIYGASSLQSGVPSRFSGSGSGTDFTLTISSLQPEDFATYYCQQVYITPITFGGGTKVEIK

FIG. 20B (Cont.)

Ab31 – Light chain variable region (SEQ ID NO:297)
DIQLTQSPSSLSASVGDRVTITCQASQDISNFLNWYQQKPGKAPKLLIYDASNLETGVPSRFSGSGSGTDFTFTISSLQPEDIATYYCQQPVDLPETFGGGTKVEIK Ab32 – Light chain variable region (SEQ ID NO:299)
EIVLTQSPATLSLSPGERATLSCRASQSVSSYLAWYQQKPGQAPRLLIYDASNRATGIPARFSGSGSGTDFTLTISSLEPEDFAVYYCQQYSFPPTFGGGTKVEIK Ab33 – Light chain variable region (SEQ ID NO:301)
EIVLTQSPATLSLSPGERATLSCRASQSVSSYLAWYQQKPGQAPRLLIYDASNRATGIPARFSGSGSGTDFTLTISSLEPEDFAVYYCQQDSFPPTFGGGTKVEIK Ab34 – Light chain variable region (SEQ ID NO:303)
DIQMTQSPSSLSASVGDRVTITCRASQSISSYLNWYQQKPGKAPKLLIYAASSLQSGVPSRFSGSGSGTDFTLTISSLQPEDFATYYCQQSDFPPWTFGGGTKVEIK Ab35 – Light chain variable region (SEQ ID NO:305)
DIQMTQSPSSLSASVGDRVTITCRASQSISSYLNWYQQKPGKAPKLLIYAASSLQSGVPSRFSGSGSGTDFTLTISSLQPEDFATYYCQQGYSAPITFGGGTKVEIK Ab36 – Light chain variable region (SEQ ID NO:307)
EIVLTQSPATLSLSPGERATLSCRASQSVSSYLAWYQQKPGQAPRLLIYDASNRATGIPARFSGSGSGTDFTLTISSLEPEDFAVYYCQQLFDWPITFGGGTKVEIK Ab37 – Light chain variable region (SEQ ID NO:309)
EIVLTQSPATLSLSPGERATLSCRASQSVSSYLAWYQQKPGQAPRLLIYDASNRATGIPARFSGSGSGTDFTLTISSLEPEDFAVYYCQQRAFLFTFGGGTKVEIK Ab38 – Light chain variable region (SEQ ID NO:311)
EIVLTQSPATLSLSPGERATLSCRASQSVSSYLAWYQQKPGQAPRLLIYDASNRATGIPARFSGSGSGTDFTLTISSLEPEDFAVYYCQQIDFLPYTFGGGTKVEIK Ab39 – Light chain variable region (SEQ ID NO:313)
DIQMTQSPSSLSASVGDRVTITCRASQSISSYLNWYQQKPGKAPKLLIYAASSLQSGVPSRFSGSGSGTDFTLTISSLQPEDFATYYCQQVYSPPITFGGGTKVEIK Ab40 – Light chain variable region (SEQ ID NO:314)
DIQMTQSPSSLSASVGDRVTITCRASQSISSYLNWYQQKPGKAPKLLIYAASSLQSGVPSRFSGSGSGTDFTLTISSLQPEDFATYYCQQGYAAPITFGGGTKVEIK

FIG. 20B (Cont.)

Ab41 – Light chain variable region (SEQ ID NO:316)
EIVLTQSPATLSLSPGERATLSCRASQSVSSYLAWYQQKPGQAPRLLIYDASNRATGIPARFSGSGSGTDFTLTISSLEPEDFTVYYCQQRYALPITFGGGTKVEIK Ab42 – Light chain variable region (SEQ ID NO:318)
EIVLTQSPGTLSLSPGERATLSCRASQSVSSYLAWYQQKPGQAPRLLIYGASSRATGIPDRFSGSGSGTDFTLTISRLEPEDFAVYYCQQYASPPITFGGGTKVEIK Ab43 – Light chain variable region (SEQ ID NO:320)
DIQMTQSPSSLSASVGDRVTITCRASQSISRYLNWYQQKPGKAPKLLIYAASSLQSGVPSRFSGSGSGTDFTLTISSLQPEDFATYYCQQVYSTPITFGGGTKVEIK Ab44 – Light chain variable region (SEQ ID NO:321)
EIVMTQSPATLSLSPGERATLSCRASQSVSSYLAWYQQKPGQAPRLLIYDSSNRATGIPARFSGSGSGTDFTLTISSLEPEDFAVYYCQQLVHWPITFGGGTKVEIK Ab45 – Light chain variable region (SEQ ID NO:323)
EIVMTQSPATLSVSPGERATLSCRASQSVSSNLAWYQQKPGQAPRLLIYGASTRATGIPARFSGSGSGTEFTLTISSLQSEDFAVYYCQQLDDWFITFGGGTKVEIK Ab46 – Light chain variable region (SEQ ID NO:325)
EIVLTQSPATLSLSPGERATLSCRASQSVSSYLAWYQQKPGQAPRLLIYDSSNRATGIPARFSGSGSGTDFTLTISSLEPEDFAVYYCQQRSNYPITFGGGTKVEIK Ab47 – Light chain variable region (SEQ ID NO:327)
EIVLTQSPGTLSLSPGERATLSCRASQSVSSYLAWYQQKPGQAPRLLIYDASNRATGIPARFSGSGSGTDFTLTISSLEPEDFAVYYCQQRILYPITFGGGTKVEIK Ab48 – Light chain variable region (SEQ ID NO:328)
EIVLTQSPATLSLSPGERATLSCRASQSVSSYLAWYQQKPGQAPRLLIYDASNRATGIPARFSGSGSGTDFTLTISSLEPEDFAVYYCQQRAAYPITFGGGTKVEIK Ab49 – Light chain variable region (SEQ ID NO:329)
EIVLTQSPATLSLSPGERATLSCRASQSVSSYLAWYQQKPGQAPRLLIYDASKRATGIPARFSGSGSGTDFTLTISSLEPEDFAVYYCQQRTSHPITFGGGTKVEIK Ab50 – Light chain variable region (SEQ ID NO:330)
EIVLTQSPGTLSLSPGERATLSCRASQSVSSYLAWYQQKPGQAPRLLIYGASSRATGIPDRFSGSGSGTDFTLTISRLEPEDFAVYYCQQYAGSPFITFGGGTKVEIK

FIG. 20B (Cont.)

Ab51 – Light chain variable region (SEQ ID NO:332)
DIQMTQSPSSLSASVGDRVTITCRASQSISSYLNWYQQKPGKAPKLLIYAASSLQSGVPSRFSGSGSGTDFTLTISSLQPEDFATYYCQQFDDVFFGGGTKVEIK Ab53 – Light chain variable region (SEQ ID NO:333)
EIVLTQSPGTLSLSPGERATLSCRASQSVSSSYLAWYQQKPGQAPRLLIYGASSRATGIPDRFSGSGSGTDFTLTISRLEPEDFAVYYCQQYVNSPFTFGGGTKVEIK Ab54 – Light chain variable region (SEQ ID NO:334)
DIQMTQSPSSLSASVGDRVTITCRASQSINSYLNWYQQKPGKAPKLLIYAASSLQSGVPSRFSGSGSGTDFTLTISSLQPEDFATYYCQQSDDPFTFGGGTKVEIK Ab55 – Light chain variable region (SEQ ID NO:336)
EIVLTQSPATLSLSPGERATLSCRASQSVSSSYLAWYQQKPGQAPRLLIYDASNRATGIPARFSGSGSGTDFTLTISSLEPEDFAVYYCQQLSTYPLIFGGGTKVEIK Ab56 – Light chain variable region (SEQ ID NO:338)
EIVMTQSPATLSLSPGERATLSCRASQSVSSSYLAWYQQKPGQAPRLLIYDASNRATGIPARFSGSGSGTDFTLTISSLEPEDFAVYYCQQRSVPIIFGGGTKVEIK Ab57 – Light chain variable region (SEQ ID NO:340)
EIVLTQSPATLSLSPGERATLSCRASQSVSSSYLAWYQQKPGQAPRLLIYDASKRATGIPARFSGSGSGTDFTLTISSLEPEDFAVYYCQQVSLFPLIFGGGTKVEIK Ab58 – Light chain variable region (SEQ ID NO:342)
DIQMTQSPSSLSASVGDRVTITCRASQSISSWLAWYQQKPGKAPKLLIYDASSLESGVPSRFSGSGSGTEFTLTISSLQPDDFATYYCLDYNSYSPITFGGGTKVEIK Ab59 – Light chain variable region (SEQ ID NO:344)
DIQMTQSPSSLSASVGDRVTITCQASQDISNYLNWYQQKPGKAPKLLIYDASNLETGVPSRFSGSGSGTDFTFTISSLQPEDIATYYCQQHIALPFTFGGGTKVEIK Ab60 – Light chain variable region (SEQ ID NO:346)
EIVLTQSPATLSLSPGERATLSCRASQSVSSSYLAWYQQKPGQAPRLLIYDASKRATGIPARFSGSGSGTDFTLTISSLEPEDFAVYYCQQRASMPITFGGGTKVEIK

FIG. 20B (Cont.)

Ab61 – Light chain variable region (SEQ ID NO:348)
EIVLTQSPATLSLSPGERATLSCRASQSVSSYLAWYQQKPGQAPRLLIYDSSNRATGIPARFSGSGSGTDFTLTISSLEPEDFAVYYCQQAFNRPPTFGGGTKVEIK Ab62 – Light chain variable region (SEQ ID NO:350)
EIVLTQSPATLSLSPGERATLSCRASQSVSSYLAWYQQKPGQAPRLLIYDASKRATGIPARFSGSGSGTDFTLTISSLEPEDFAVYYCQQSSVHPYTFGGGTKVEIK Ab63 – Light chain variable region (SEQ ID NO:352)
DIQMTQSPSSVSASVGDRVTITCRASQGIDSWLAWYQQKPGKAPKLLIYAASSLQSGVPSRFSGSGSGTDFTLTISSLQPEDFATYYCQQAYSLPPTFGGGTKVEIK Ab64 – Light chain variable region (SEQ ID NO:354)
EIVMTQSPATLSVSPGERATLSCRASQSVSSNLAWYQQKPGQAPRLLIYGASTRATGIPARFSGSGSGTEFTLTISSLQSEDFAVYYCQQDDDGYTFGGGTKVEIK Ab65 – Light chain variable region (SEQ ID NO:356)
EIVLTQSPATLSLSPGERATLSCRASQSVSSYLAWYQQKPGQAPRLLIYDASNRATGIPARFSGSGSGTDFTLTISSLEPEDFAVYYCQQDYSWPYTFGGGTKVEIK Ab66 – Light chain variable region (SEQ ID NO:358)
EIVLTQSPGTLSLSPGERATLSCRASQSVSSYLAWYQQKPGQAPRLLIYDASNRATGIPARFSGSGSGTDFTLTISSLEPEDFAVYYCQQRSAYPITFGGGTKVEIK Ab67 – Light chain variable region (SEQ ID NO:359)
EIVLTQSPATLSLSPGERATLSCRASQSVSSYLAWYQQKPGQAPRLLIYDASNRATGIPARFSGSGSGTDFTLTISSLEPEDFAVYYCQQRSHFPITFGGGTKVEIK Ab68 – Light chain variable region (SEQ ID NO:361)
EIVLTQSPATLSLSPGERATLSCRASQSVSSYLAWYQQKPGQAPRLLIYDASNRATGIPARFSGSGSGTDFTLTISSLEPEDFAVYYCQQRANYPITFGGGTKVEIK Ab69 – Light chain variable region (SEQ ID NO:363)
EIVLTQSPATLSLSPGERATLSCRASQSVSSYLAWYQQKPGQAPRLLIYDASNRATGIPARFSGSGSGTDFTLTISSLEPEDFAVYYCQQRADYPITFGGGTKVEIK Ab70 – Light chain variable region (SEQ ID NO:364)
EIVLTQSPATLSLSPGERATLSCRASQSVSSYLAWYQQKPGQAPRLLIYDASNRATGIPARFSGSGSGTDFTLTISSLEPEDFAVYYCQQRSVPITFGGGTKVEIK

FIG. 20B (Cont.)

Ab71 – Light chain variable region (SEQ ID NO:366)
EIVMTQSPGTLSLSPGERATLSCRASQSVSSSYLAWYQQKPGQAPRLLIYGASNRATGIPDRFSGSGSGTDFTLTISRLEPEDFAVYYCQQAGSHPFTFGGGTKVEIK Ab72 – Light chain variable region (SEQ ID NO:368)
DIQMTQSPSSLSASVGDRVTITCQASQDINYLNWYQQKPGKAPKLLIYDASNLETGVPSRFSGSRSGTDFTFTISSLQPEDIATYYCQQDVNYPPTFGGGTKVEIK Ab73 – Light chain variable region (SEQ ID NO:370)
EIVMTQSPATLSVSPGERATLSCRASQSVSSNLAWYQQKPGQAPRLLIYGASTRATGIPARFSGSGSGTEFTLTISSLQSEDFAVYYCQQDDNYPYTFGGGTKVEIK Ab74 – Light chain variable region (SEQ ID NO:371)
EIVLTQSPATLSLSPGERATLSCRASQSVSSYLAWYQQKPGQAPRLLIYDASNRATGIPARFSGSGSGTDFTLTISSLEPEDFAVYYCQQRSTFPITFGGGTKVEIK Ab75 – Light chain variable region (SEQ ID NO:373)
EIVLTQSPATLSLSPGERATLSCRASQSVSSYLAWYQQKPGQAPRLLIYDASNRATGIPARFSGSGSGTDFTLTISSLEPEDFAVYYCQQVSNYPFTFGGGTKVEIK Ab76 – Light chain variable region (SEQ ID NO:375)
DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYHDAPITFGGGTKVEIK Ab77 – Light chain variable region (SEQ ID NO:377)
DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQAYVVPPTFGGGTKVEIK Ab78 – Light chain variable region (SEQ ID NO:379)
EIVLTQSPATLSLSPGERATLSCRASQSVSSYLAWYQQKPGQAPRLLIYDASNRATGIPARFSGSGSGTDFTLTISSLEPEDFAVYYCQQADNWPFTFGGGTKVEIK Ab79 – Light chain variable region (SEQ ID NO:381)
DIVMTQSPLSLPVTPGEPASISCRSSQSLLHSNGYNYLDWYLQKPGQSPQLLIYLGSHRASGVPDRFSGSGSGTDFTLKISRVEAEDVGVYYCMQALESPRTFGGGTKVEIK Ab80 – Light chain variable region (SEQ ID NO:383)
EIVLTQSPATLSLSPGERATLSCRASQSVSSYLAWYQQKPGQAPRLLIYDASNRATGIPARFSGSGSGTDFTLTISSLEPEDFAVYYCQQYVNWPFTFGGGTKVEIK

FIG. 20B (Cont.)

Ab81 – Light chain variable region (SEQ ID NO:385)
EIVLTQSPATLSLSPGERATLSCRASQSVSSYLAWYQQKPGQAPRLLIYDASNRATGIPARFSGSGSGTDFTLTISSLEPEDFAVYYCQQSSNWPWTFGGGTKVEIK Ab82 – Light chain variable region (SEQ ID NO:387)
DIQMTQSPSSVSASVGDRVTITCRASQGISSWLAWYQQKPGKAPKLLIYAASSLQSGVPSRFSGSGSGTDFTLTISSLQPEDFATYYCQQASTFPITFGGGTKVEIK Ab83 – Light chain variable region (SEQ ID NO:389)
DIQMTQSPSSVSASVGDRVTITCRASQGISSWLAWYQQKPGKAPKLLIYAASSLQSGVPSRFSGSGSGTDFTLTISSLQPEDFATYYCQQRNSLPLTFGGGTKVEIK Ab84 – Light chain variable region (SEQ ID NO:390)
DIQMTQSPSSLSASVGDRVTITCRASQSISSYLNWYQQKPGKAPKLLIYAASSLQSGVPSRFSGSGSGTDFTLTISSLQPEDFATYYCQQSYDFPITFGGGTKVEIK Ab85 – Light chain variable region (SEQ ID NO:392)
DIQLTQSPSSVSASVGDRVTITCRASQDISSWLAWYQQKPGKAPKLLIYAASSLQSGVPSRFSGSGSGTDFTLTISSLQPEDFATYYCQQEVDYPPLTFGGGTKVEIK Ab86 – Light chain variable region (SEQ ID NO:394)
DIQMTQSPSTLSASVGDRVTITCRASQSISSWLAWYQQKPGKAPKLLIYKASSLESGVPSRFSGSGSGTEFTLTISSLQPDDFATYYCQQLNSYSPTFGGGTKVEIK Ab87 – Light chain variable region (SEQ ID NO:396)
EIVLTQSPATLSLSPGERATLSCRASQSVSRYLAWYQQKPGQAPRLLIYDASNRAIGIPARFSGSGSGTDFTLTISSLEPEDFAVYYCQQYIFWPPTFGGGTKVEIK

FIG. 20B (Cont.)

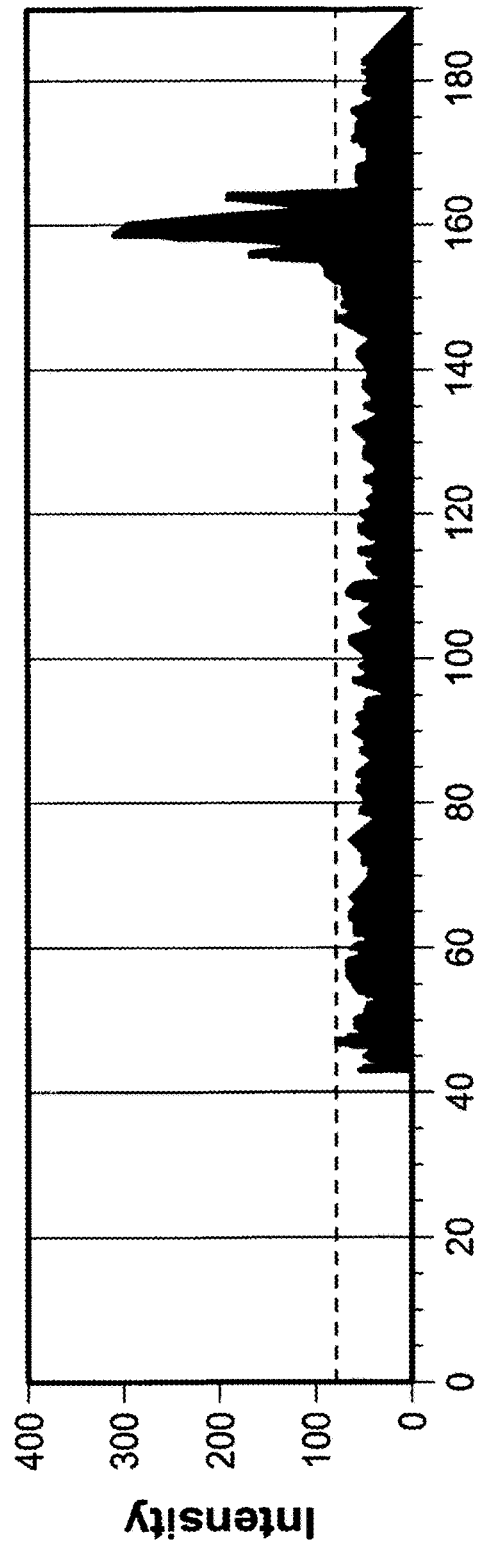
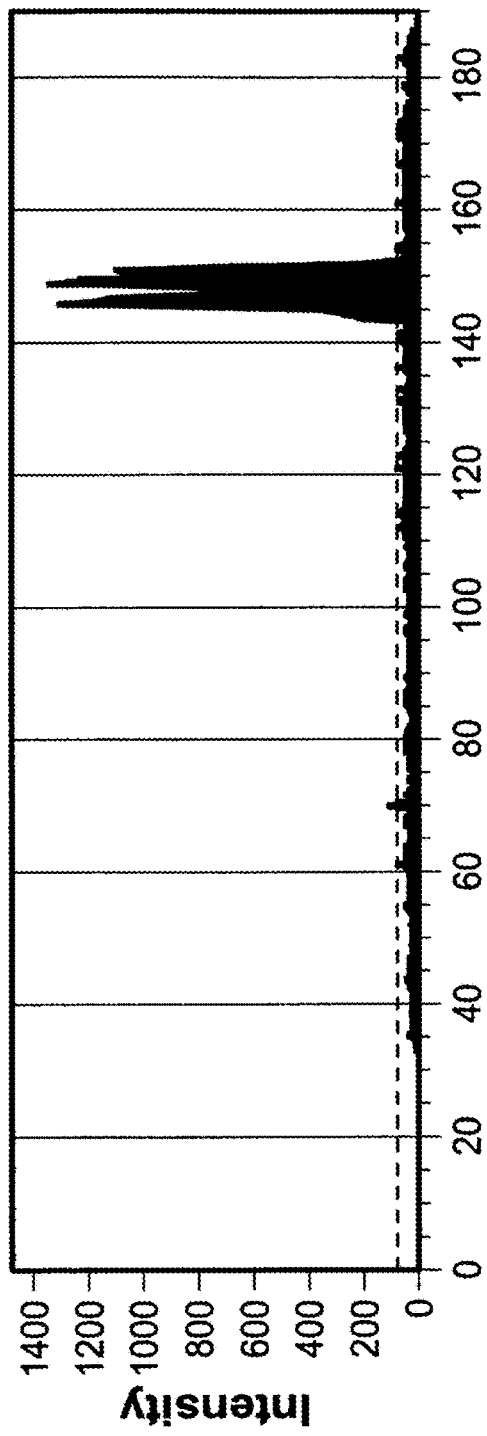
FIG. 27A
FIG. 27B

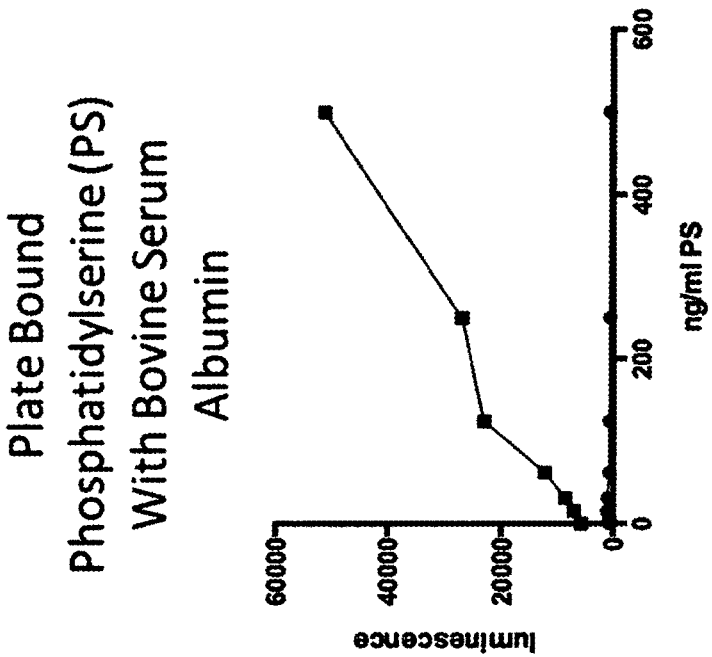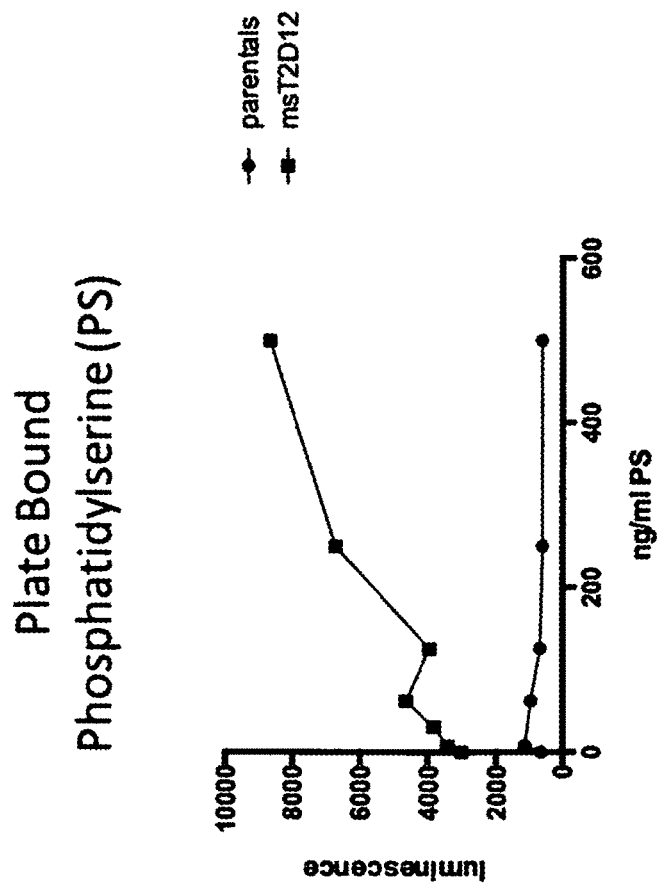
FIG. 31C

SEQUENCE LISTING

```
<160> NUMBER OF SEQ ID NOS: 447

<210> SEQ ID NO 1
<211> LENGTH: 230
<212> TYPE: PRT
<213> ORGANISM: Homo sapiens
```

<400> SEQUENCE: 1

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230

<210> SEQ ID NO 2
<211> LENGTH: 113
<212> TYPE: PRT
<213> ORGANISM: Homo sapiens

<400> SEQUENCE: 2

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

```
<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Phe Thr Phe Ser Ser Tyr Ala Met Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Phe Thr Phe Ser Ser Ser Ala Met Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gly Thr Phe Ser Ser Tyr Ala Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Tyr Thr Phe Thr Ser Tyr Tyr Ile His
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Tyr Thr Phe Thr Ser Tyr Tyr Met His
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Gly Ser Ile Ser Ser Ser Ser Tyr Tyr Trp Gly
1               5                   10

<210> SEQ ID NO 9
```

<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Tyr Ser Phe Thr Ser Tyr Trp Ile Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Tyr Ser Phe Thr Ser Asn Trp Ile Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Tyr Ser Phe Thr Thr Tyr Trp Ile Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Tyr Thr Phe Thr Ser Tyr Gly Ile Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Gly Ser Ile Ser Ser Gly Gly Tyr Tyr Trp Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Gly Ser Ile Ser Ser Asn Ser Tyr Tyr Trp Gly
1               5                   10

<210> SEQ ID NO 15
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 15

Gly Ser Ile Ser Ser Tyr Tyr Trp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Phe Thr Phe Ser Ser Tyr Gly Met His
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Phe Thr Phe Ser Thr Tyr Gly Met His
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Phe Thr Phe Ser Thr Tyr Ala Met Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Tyr Thr Phe Thr Gly Ser Tyr Met His
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Tyr Thr Phe Thr Gly Tyr Tyr Met His
1               5

<210> SEQ ID NO 21
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 21

Tyr Thr Phe Thr Asn Tyr Gly Ile Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Tyr Thr Phe Thr Ser Tyr Gly Ile His
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Phe Thr Phe Ser Ser Tyr Ser Met Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gly Ser Phe Ser Gly Tyr Tyr Trp Ser
1               5

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Val Ile Ser Gly Ser Gly Gly Ser Thr Tyr Tyr Ala Asp Ser Val Lys
1               5                   10                  15
Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Ala Ile Ser Gly Ser Gly Gly Ser Thr Tyr Tyr Ala Asp Ser Val Lys
1               5                   10                  15
Gly
```

```
<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Gly Ile Ile Pro Ile Phe Gly Thr Ala Asn Tyr Ala Gln Lys Phe Gln
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Gly Ile Ile Pro Ile Phe Gly Thr Ala Ser Tyr Ala Gln Lys Phe Gln
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Ile Ile Asn Pro Ser Gly Gly Ser Thr Ser Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Ile Ile Asn Pro Gly Gly Gly Ser Thr Ser Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Ile Ile Asn Pro Ser Gly Gly Ser Thr Thr Tyr Ala Gln Lys Phe Gln
1               5                   10                  15

Gly

<210> SEQ ID NO 32
<211> LENGTH: 16
<212> TYPE: PRT
<213> ORGANISM: Artificial Sequence
```

```
<220> FEATURE:
<223> OTHER INFORMATION: Synthetic Construct

<400> SEQUENCE: 32

Ser Ile Ser Tyr Ser Gly Ser Thr Tyr Tyr Asn Pro Ser Leu Lys Ser
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Ile Ile Tyr Pro Gly Asp Ser Asp Thr Thr Tyr Ser Pro Ser Phe Gln
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Ile Ile Tyr Pro Gly Asp Ser Asp Thr Arg Tyr Ser Pro Ser Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic Construct

<400> SEQUENCE: 35

Trp Ile Ser Ala Tyr Asn Gly Asn Thr Asn Tyr Ala Gln Lys Leu Gln
1               5                   10                  15

Gly

<210> SEQ ID NO 36
<211> LENGTH: 16
<212> TYPE: PRT
<213> ORGANISM: Artificial Sequence
<220> FEATURE:
<223> OTHER INFORMATION: Synthetic Construct

<400> SEQUENCE: 36

Asn Ile Tyr Tyr Ser Gly Ser Thr Val Tyr Asn Pro Ser Leu Lys Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic Construct

<400> SEQUENCE: 37

Ser Ile Tyr Tyr Ser Gly Ser Thr Tyr Tyr Asn Pro Ser Leu Lys Ser
1               5                   10                  15
```

<210> SEQ ID NO 38
<211> LENGTH: 16
<212> TYPE: PRT
<213> ORGANISM: Artificial Sequence
<220> FEATURE:
<223> OTHER INFORMATION: Synthetic Construct

<400> SEQUENCE: 38

Ser Ile Tyr Tyr Ser Gly Ser Thr Asn Tyr Asn Pro Ser Leu Lys Ser
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Val Ile Ser Tyr Asp Gly Ser Asn Lys Tyr Tyr Ala Asp Ser Val Lys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Leu Ile Trp Tyr Asp Gly Ser Asn Lys Tyr Tyr Ala Asp Ser Val Lys
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Val Ile Trp Tyr Asp Gly Ser Asn Lys Tyr Tyr Ala Asp Ser Val Lys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Trp Ile Asn Pro Asn Ser Gly Gly Thr Asn Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:

<223> OTHER INFORMATION: Synthetic Construct

<400> SEQUENCE: 43

Ser Ile Asn Pro Asn Ser Gly Gly Thr Asn Tyr Ala Gln Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Trp Ile Asn Pro Asn Ser Gly Gly Thr Ser Tyr Ala Gln Lys Phe Gln
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic Construct

<400> SEQUENCE: 45

Trp Ile Ser Thr Tyr Asn Gly Asn Thr Asn Tyr Ala Gln Lys Leu Gln
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Ser Ile Ser Ser Ser Ser Ser Tyr Ile Tyr Tyr Ala Asp Ser Val Lys
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic Construct

<400> SEQUENCE: 47

Tyr Ile Ser Gly Ser Ser Ser Thr Ile Tyr Tyr Ala Asp Ser Val Lys
1               5                   10                  15

Gly

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct

<400> SEQUENCE: 48

```
Tyr Ile Tyr Tyr Ser Gly Ser Thr Val Tyr Asn Pro Ser Leu Lys Ser
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct

<400> SEQUENCE: 49

Glu Ile Asp His Ser Gly Ser Thr Lys Tyr Asn Pro Ser Leu Lys Ser
1               5                   10                  15

<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Ala Lys Gly Thr Pro Thr Leu Leu Phe Gln His
1               5                   10

<210> SEQ ID NO 51
<211> LENGTH: 21
<212> TYPE: PRT
<213> ORGANISM: Artificial Sequence
<220> FEATURE:
<223> OTHER INFORMATION: Synthetic Construct

<400> SEQUENCE: 51

Ala Lys Val Pro Ser Tyr Asp Tyr Trp Ser Gly Tyr Ser Asn Tyr Tyr
1               5                   10                  15

Tyr Tyr Met Asp Val
            20

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Ala Arg Glu Gln Tyr His Val Gly Met Asp Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Ala Arg Gly Val Asp Ser Ile Met Asp Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 54

Ala Arg Ala Pro Gln Glu Ser Pro Tyr Val Phe Asp Ile
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic Construct

<400> SEQUENCE: 55

Ala Arg Gly Ser Pro Thr Tyr Gly Tyr Leu Tyr Asp Pro
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Ala Arg Thr Ser Ser Lys Glu Arg Asp Tyr
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic Construct

<400> SEQUENCE: 57

Ala Arg Gly Pro Tyr Arg Leu Leu Leu Gly Met Asp Val
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Ala Arg Leu His Ile Ser Gly Glu Val Asn Trp Phe Asp Pro
1               5                   10

<210> SEQ ID NO 59
<211> LENGTH: 15
<212> TYPE: PRT
<213> ORGANISM: Artificial Sequence
<220> FEATURE:
<223> OTHER INFORMATION: Synthetic Construct

<400> SEQUENCE: 59

Ala Arg Glu Ala Gly Tyr Asp Tyr Gly Glu Leu Ala Phe Asp Ile
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60
```

```
Ala Arg Ala Gly His Tyr Asp Gly Gly His Leu Gly Met Asp Val
1               5                   10                  15
```

<210> SEQ ID NO 61
<211> LENGTH: 17
<212> TYPE: PRT
<213> ORGANISM: Artificial Sequence
<220> FEATURE:
<223> OTHER INFORMATION: Synthetic Construct

<400> SEQUENCE: 61

```
Ala Arg Leu Gly His Tyr Ser Gly Thr Val Ser Ser Tyr Gly Met Asp
1               5                   10                  15

Val
```

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

```
Ala Arg Gly Pro Ser His Tyr Tyr Asp Leu Ala
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Synthetic Construct

<400> SEQUENCE: 63

```
Ala Arg Gly Leu Tyr Gly Tyr Gly Val Leu Asp Val
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: Synthetic Construct

<400> SEQUENCE: 64

```
Ala Arg Gly Val Leu Gly Tyr Gly Val Phe Asp Tyr
1               5                   10
```

<210> SEQ ID NO 65
<211> LENGTH: 16
<212> TYPE: PRT
<213> ORGANISM: Artificial Sequence
<220> FEATURE:
<223> OTHER INFORMATION: Synthetic Construct

<400> SEQUENCE: 65

```
Ala Arg Asp Gly Gly Gly Glu Tyr Pro Ser Gly Thr Pro Phe Asp Ile
1               5                   10                  15
```

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 66

Ala Arg Ser Gly Met Ala Ser Phe Phe Asp Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Ala Lys Leu Gly Gly His Ser Met Asp Val
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Construct

<400> SEQUENCE: 68

Ala Lys Pro Leu Lys Arg Gly Arg Gly Phe Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Ala Lys Glu Gly Arg Thr Ile Thr Met Asp
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Ala Lys Asp Gln Tyr Ser Val Leu Asp Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic Construct

<400> SEQUENCE: 71

Ala Lys Lys Tyr Ser Ser Arg Gly Val Tyr Phe Asp Tyr
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Synthetic Construct

<400> SEQUENCE: 72
```

Ala Arg Leu Gly Gly Ala Val Gly Ala Arg His Val Thr Tyr Phe Asp
1               5                   10                  15

Tyr

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

Ala Arg Gly Gln Tyr Tyr Gly Gly Ser Gly Trp Phe Asp Pro
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic Construct

<400> SEQUENCE: 74

Ala Arg Leu Gly Gln Glu Tyr Ala Tyr Phe Gln His
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Ala Arg Arg Arg Asp Gly Tyr Tyr Asp Glu Val Phe Asp Ile
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Ala Arg Val Pro Lys His Tyr Val Val Leu Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Ala Arg Ala Gly Gly His Leu Phe Asp Tyr
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 78

Ala Arg Asp Arg Gly Gly Glu Tyr Val Asp Phe Ala Phe Asp Ile
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic Construct

<400> SEQUENCE: 79

Ala Arg Thr Arg Ser Gly Tyr Gly Ala Ser Asn Tyr Phe Asp Tyr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Construct

<400> SEQUENCE: 80

Ala Arg Gly Thr Gly Ala Ala Ala Ala Ser Pro Ala Phe Asp Ile
1               5                   10                  15

<210> SEQ ID NO 81
<211> LENGTH: 12
<212> TYPE: PRT
<213> ORGANISM: Artificial Sequence
<220> FEATURE:
<223> OTHER INFORMATION: Synthetic Construct

<400> SEQUENCE: 81

Ala Arg Val Gly Gln Tyr Met Leu Gly Met Asp Val
1               5                   10

<210> SEQ ID NO 82
<211> LENGTH: 18
<212> TYPE: PRT
<213> ORGANISM: Artificial Sequence
<220> FEATURE:
<223> OTHER INFORMATION: Synthetic Construct

<400> SEQUENCE: 82

Ala Arg Gly Ala Pro Val Asp Tyr Gly Gly Ile Glu Pro Glu Tyr Phe
1               5                   10                  15

Gln His

<210> SEQ ID NO 83
<211> LENGTH: 12
<212> TYPE: PRT
<213> ORGANISM: Artificial Sequence
<220> FEATURE:
<223> OTHER INFORMATION: Synthetic Construct

<400> SEQUENCE: 83

Ala Lys His Tyr His Val Gly Ile Ala Phe Asp Ile
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 84

Ala Arg Ala Met Ala Arg Lys Ser Val Ala Phe Asp Ile
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Ala Lys Val Pro Ser Tyr Gln Arg Gly Thr Ala Phe Asp Pro
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic Construct

<400> SEQUENCE: 86

Ala Lys Ser Pro Ala Val Ala Gly Ile Tyr Arg Ala Asp Tyr
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Synthetic Construct

<400> SEQUENCE: 87

Ala Arg Gly Pro Gly Tyr Thr Thr Ala Leu Asp Tyr Tyr Tyr Met Asp
1               5                   10                  15

Val

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Ala Arg Pro Ala Lys Thr Ala Asp Tyr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Ala Arg Pro Gly Lys Ser Met Asp Val
1               5

<210> SEQ ID NO 90
<211> LENGTH: 14
<212> TYPE: PRT
<213> ORGANISM: Artificial Sequence
<220> FEATURE:
```

<223> OTHER INFORMATION: Synthetic Construct

<400> SEQUENCE: 90

Ala Arg Gly Val Gly Gly Gln Asp Tyr Tyr Tyr Met Asp Val
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic Construct

<400> SEQUENCE: 91

Ala Arg Gly Pro Leu Tyr His Pro Met Ile Phe Asp Tyr
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Ala Arg Ala Ser Ser Val Asp Asn
1               5

<210> SEQ ID NO 93
<211> LENGTH: 19
<212> TYPE: PRT
<213> ORGANISM: Artificial Sequence
<220> FEATURE:
<223> OTHER INFORMATION: Synthetic Construct

<400> SEQUENCE: 93

Ala Arg Gly Pro Thr Lys Ala Tyr Tyr Gly Ser Gly Ser Tyr Val Val
1               5                   10                  15

Phe Asp Pro

<210> SEQ ID NO 94
<211> LENGTH: 15
<212> TYPE: PRT
<213> ORGANISM: Artificial Sequence
<220> FEATURE:
<223> OTHER INFORMATION: Synthetic Construct

<400> SEQUENCE: 94

Ala Arg Leu Gly Ile Tyr Ser Thr Gly Ala Thr Ala Phe Asp Ile
1               5                   10                  15

<210> SEQ ID NO 95
<211> LENGTH: 12
<212> TYPE: PRT
<213> ORGANISM: Artificial Sequence
<220> FEATURE:
<223> OTHER INFORMATION: Synthetic Construct

<400> SEQUENCE: 95

Ala Arg Gly Gly Val Trp Tyr Ser Leu Phe Asp Ile
1               5                   10

<210> SEQ ID NO 96
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 96

Ala Arg Ala Ser Lys Met Gly Asp Asp
1               5

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Ala Arg Gly Gly Val Pro Arg Val Ser Tyr Phe Gln His
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct

<400> SEQUENCE: 98

Ala Arg Ala Gly His Tyr Asp Asp Trp Ser Gly Leu Gly Leu Asp Val
1               5                   10                  15

<210> SEQ ID NO 99
<211> LENGTH: 13
<212> TYPE: PRT
<213> ORGANISM: Artificial Sequence
<220> FEATURE:
<223> OTHER INFORMATION: Synthetic Construct

<400> SEQUENCE: 99

Ala Arg Gly Ser Gly Ser Gly Tyr Asp Ser Trp Tyr Asp
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Ala Arg Leu Gly Arg Trp Ser Ser Gly Ser Thr Ala Phe Asp Ile
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct

<400> SEQUENCE: 101

Ala Arg Leu Gly Arg Lys Pro Ser Gly Ser Val Ala Phe Asp Ile
1               5                   10                  15

<210> SEQ ID NO 102
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 102

Ala Arg Ala Gly His Lys Thr His Asp Tyr
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct

<400> SEQUENCE: 103

Ala Lys Pro Gly Ser Met Thr Asp Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Ala Arg Ala Lys Ser Val Asp His Asp Tyr
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic Construct

<400> SEQUENCE: 105

Ala Arg Asp Ile Ser Thr His Asp Tyr Asp Leu Ala Phe Asp Ile
1               5                   10                  15

<210> SEQ ID NO 106
<211> LENGTH: 11
<212> TYPE: PRT
<213> ORGANISM: Artificial Sequence
<220> FEATURE:
<223> OTHER INFORMATION: Synthetic Construct

<400> SEQUENCE: 106

Ala Arg Ser Gly Thr Glu Thr Leu Phe Asp Tyr
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Synthetic Construct

<400> SEQUENCE: 107

Ala Arg Ala Lys Met Leu Asp Asp Gly Tyr Ala Phe Asp Ile
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 108

Ala Arg Asp Leu Gly Tyr Ser Ser Leu Leu Ala Leu Asp Ile
1               5                   10

<210> SEQ ID NO 109
<211> LENGTH: 15
<212> TYPE: PRT
<213> ORGANISM: Artificial Sequence
<220> FEATURE:
<223> OTHER INFORMATION: Synthetic Construct

<400> SEQUENCE: 109

Ala Arg Gly Gly Gly Arg Arg Gly Asp Asn Asn Trp Phe Asp Pro
1               5                   10                  15

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Ala Arg Gly Pro Pro His Glu Met Asp Tyr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct

<400> SEQUENCE: 111

Ala Arg Thr Pro Tyr Pro Trp Ile Tyr Phe Asp Leu
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic Construct

<400> SEQUENCE: 112

Ala Arg Gly Gly Arg Arg His Tyr Gly Gly Met Asp Val
1               5                   10

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Ala Arg Gly Gly Gly Thr Phe Trp Ser Gly Ser Trp Ala Leu Tyr
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 114

Ala Arg Asp Ser Gly Asn Tyr Asp Tyr Trp Ser Gly Ala Leu Arg Tyr
1               5                   10                  15

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Ala Arg Val Ser Ser Ser Trp Tyr Lys Ala
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Synthetic Construct

<400> SEQUENCE: 116

Ala Arg Val Gly Val Val Val Gly Arg Pro Gly Tyr Ser Ala Phe Asp
1               5                   10                  15

Ile

<210> SEQ ID NO 117
<211> LENGTH: 17
<212> TYPE: PRT
<213> ORGANISM: Artificial Sequence
<220> FEATURE:
<223> OTHER INFORMATION: Synthetic Construct

<400> SEQUENCE: 117

Ala Lys Asp Leu Gly Gly Tyr Tyr Gly Gly Ala Ala Tyr Gly Met Asp
1               5                   10                  15

Val

<210> SEQ ID NO 118
<211> LENGTH: 15
<212> TYPE: PRT
<213> ORGANISM: Artificial Sequence
<220> FEATURE:
<223> OTHER INFORMATION: Synthetic Construct

<400> SEQUENCE: 118

Ala Lys Asp Gly Val Tyr Tyr Gly Leu Gly Asn Trp Phe Asp Pro
1               5                   10                  15

<210> SEQ ID NO 119
<211> LENGTH: 13
<212> TYPE: PRT
<213> ORGANISM: Artificial Sequence
<220> FEATURE:
<223> OTHER INFORMATION: Synthetic Construct

<400> SEQUENCE: 119

Ala Arg His Gly Trp Asp Arg Val Gly Trp Phe Asp Pro
1               5                   10

<210> SEQ ID NO 120
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 120

Arg Ala Ser Gln Ser Val Ser Asn Leu Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic Construct

<400> SEQUENCE: 121

Arg Ala Ser Gln Ser Val Gly Ser Asn Leu Ala
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic Construct

<400> SEQUENCE: 122

Gln Ala Ser Gln Asp Ile Ser Asn Tyr Leu Asn
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic Construct

<400> SEQUENCE: 123

Arg Ala Ser Gln Ser Val Ser Ser Ser Tyr Leu Ala
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic Construct

<400> SEQUENCE: 124

Arg Ala Ser Gln Ser Val Ser Ser Tyr Leu Ala
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic Construct

<400> SEQUENCE: 125

Arg Ala Ser Gln Ser Ile Ser Ser Tyr Leu Asn
1               5                   10

<210> SEQ ID NO 126
<211> LENGTH: 12
<212> TYPE: PRT
<213> ORGANISM: Artificial Sequence
<220> FEATURE:
```

<223> OTHER INFORMATION: Synthetic Construct

<400> SEQUENCE: 126

Arg Ala Ser Gln Ser Val Ser Ser Asp Tyr Leu Ala
1               5                   10

<210> SEQ ID NO 127
<211> LENGTH: 17
<212> TYPE: PRT
<213> ORGANISM: Artificial Sequence
<220> FEATURE:
<223> OTHER INFORMATION: Synthetic Construct

<400> SEQUENCE: 127

Lys Ser Ser Gln Ser Val Leu Tyr Ser Ser Asn Asn Lys Asn Tyr Leu
1               5                   10                  15

Ala

<210> SEQ ID NO 128
<211> LENGTH: 11
<212> TYPE: PRT
<213> ORGANISM: Artificial Sequence
<220> FEATURE:
<223> OTHER INFORMATION: Synthetic Construct

<400> SEQUENCE: 128

Gln Ala Ser Gln Asp Ile Ser Asn Phe Leu Asn
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Construct

<400> SEQUENCE: 129

Arg Ala Ser Gln Ser Ile Ser Arg Tyr Leu Asn
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic Construct

<400> SEQUENCE: 130

Arg Ala Ser Gln Ser Ile Asn Ser Tyr Leu Asn
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic Construct

<400> SEQUENCE: 131

Arg Ala Ser Gln Ser Ile Ser Ser Trp Leu Ala
1               5                   10

<210> SEQ ID NO 132
<211> LENGTH: 11
<212> TYPE: PRT
<213> ORGANISM: Artificial Sequence

```
<220> FEATURE:
<223> OTHER INFORMATION: Synthetic Construct

<400> SEQUENCE: 132

Arg Ala Ser Gln Gly Ile Asp Ser Trp Leu Ala
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic Construct

<400> SEQUENCE: 133

Gln Ala Ser Gln Asp Ile Thr Asn Tyr Leu Asn
1               5                   10

<210> SEQ ID NO 134
<211> LENGTH: 16
<212> TYPE: PRT
<213> ORGANISM: Artificial Sequence
<220> FEATURE:
<223> OTHER INFORMATION: Synthetic Construct

<400> SEQUENCE: 134

Arg Ser Ser Gln Ser Leu Leu His Ser Asn Gly Tyr Asn Tyr Leu Asp
1               5                   10                  15

<210> SEQ ID NO 135
<211> LENGTH: 11
<212> TYPE: PRT
<213> ORGANISM: Artificial Sequence
<220> FEATURE:
<223> OTHER INFORMATION: Synthetic Construct

<400> SEQUENCE: 135

Arg Ala Ser Gln Gly Ile Ser Ser Trp Leu Ala
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Construct

<400> SEQUENCE: 136

Arg Ala Ser Gln Asp Ile Ser Ser Trp Leu Ala
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic Construct

<400> SEQUENCE: 137

Arg Ala Ser Gln Ser Val Ser Arg Tyr Leu Ala
1               5                   10

<210> SEQ ID NO 138
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 138

Gly Ala Ser Thr Arg Ala Thr
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 139

Asp Ala Ser Asn Leu Ala Thr
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Ser Ala Ser Thr Arg Ala Thr
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic Construct

<400> SEQUENCE: 141

Gly Ala Ser Ser Arg Ala Thr
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic Construct

<400> SEQUENCE: 142

Asp Ala Ser Lys Arg Ala Thr
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 143

Gly Ala Ser Ser Leu Gln Ser
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic Construct

<400> SEQUENCE: 144

Asp Ala Ser Asn Arg Ala Thr
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 145

Ala Ala Ser Ser Leu Gln Ser
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic Construct

<400> SEQUENCE: 146

Asp Ala Ser Asn Leu Glu Thr
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic Construct

<400> SEQUENCE: 147

Trp Ala Ser Thr Arg Glu Ser
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic Construct

<400> SEQUENCE: 148

Asp Ser Ser Asn Arg Ala Thr
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 149

Asp Ala Ser Ser Leu Glu Ser
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 150

Gly Ala Ser Asn Arg Ala Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 151

Leu Gly Ser His Arg Ala Ser
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 152

Lys Ala Ser Ser Leu Glu Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Gln Gln Leu Pro Tyr Trp Pro Pro Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic Construct

<400> SEQUENCE: 154

Gln Gln Tyr Phe Phe Tyr Pro Pro Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic Construct

<400> SEQUENCE: 155

Gln Gln Pro Phe Asn Phe Pro Tyr Thr
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Construct

<400> SEQUENCE: 156
```

```
Gln Gln Asp His Asp Tyr Pro Phe Thr
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Gln Gln Tyr Phe Ser Ser Pro Phe Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Gln Gln Arg Val Asn Leu Pro Pro Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct

<400> SEQUENCE: 159

Gln Gln Arg Ile Ser Tyr Pro Ile Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct

<400> SEQUENCE: 160

Gln Gln Ile Asp Asp Thr Pro Ile Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Gln Gln Phe Ser Tyr Trp Pro Trp Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162
```

Gln Gln His Asp Ser Ser Pro Pro Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic Construct

<400> SEQUENCE: 163

Gln Gln Asp Tyr Ser Tyr Pro Trp Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Construct

<400> SEQUENCE: 164

Gln Gln Glu Tyr Ala Val Pro Tyr Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Construct

<400> SEQUENCE: 165

Gln Gln Val Ser Asn Tyr Pro Ile Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Gln Gln Val Asp Asn Ile Pro Pro Thr
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 167

Gln Gln Phe Asp Thr Tyr Pro Thr
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Gln Gln Phe Leu Asn Phe Pro Thr

```
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct

<400> SEQUENCE: 169

Gln Gln Phe Phe Asn Phe Pro Thr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Construct

<400> SEQUENCE: 170

Gln Gln Phe Ile Asp Leu Pro Phe Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic Construct

<400> SEQUENCE: 171

Gln Gln Tyr Tyr Asp Leu Pro Phe Thr
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Gln Gln Phe Ser Ser His Pro Phe Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic Construct

<400> SEQUENCE: 173

Gln Gln Asp Asp Arg Ser Pro Tyr Thr
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Construct

<400> SEQUENCE: 174

Gln Gln Ala Tyr Leu Pro Pro Ile Thr
1               5
```

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Gln Gln Ala Phe Ser Pro Pro Pro Trp Thr
1               5                   10

<210> SEQ ID NO 176
<211> LENGTH: 8
<212> TYPE: PRT
<213> ORGANISM: Artificial Sequence
<220> FEATURE:
<223> OTHER INFORMATION: Synthetic Construct

<400> SEQUENCE: 176

Gln Gln Asp Asp Arg Ser Pro Thr
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic Construct

<400> SEQUENCE: 177

Gln Gln Glu Phe Asp Leu Pro Phe Thr
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct

<400> SEQUENCE: 178

Gln Gln Tyr Asn Asn Phe Pro Pro Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Construct

<400> SEQUENCE: 179

Gln Gln Arg Tyr Leu Arg Pro Ile Thr
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic Construct

<400> SEQUENCE: 180

Gln Gln Pro Gly Ala Val Pro Thr
1               5

```
<210> SEQ ID NO 181
<211> LENGTH: 9
<212> TYPE: PRT
<213> ORGANISM: Artificial Sequence
<220> FEATURE:
<223> OTHER INFORMATION: Synthetic Construct

<400> SEQUENCE: 181

Gln Gln Val Tyr Ile Thr Pro Ile Thr
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Gln Gln Pro Val Asp Leu Pro Phe Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic Construct

<400> SEQUENCE: 183

Gln Gln Tyr Ser Phe Phe Pro Pro Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Construct

<400> SEQUENCE: 184

Gln Gln Asp Ser Ser Phe Pro Pro Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Gln Gln Ser Asp Phe Pro Pro Trp Thr
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Construct

<400> SEQUENCE: 186

Gln Gln Gly Tyr Ser Ala Pro Ile Thr
1               5
```

```
<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Gln Gln Leu Phe Asp Trp Pro Thr
1               5

<210> SEQ ID NO 188
<211> LENGTH: 8
<212> TYPE: PRT
<213> ORGANISM: Artificial Sequence
<220> FEATURE:
<223> OTHER INFORMATION: Synthetic Construct

<400> SEQUENCE: 188

Gln Gln Arg Ala Phe Leu Phe Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Gln Gln Ile Asp Phe Leu Pro Tyr Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Construct

<400> SEQUENCE: 190

Gln Gln Val Tyr Ser Pro Pro Ile Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic Construct

<400> SEQUENCE: 191

Gln Gln Gly Tyr Ala Ala Pro Ile Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic Construct

<400> SEQUENCE: 192

Gln Gln Arg Tyr Ala Leu Pro Ile Thr
1               5

<210> SEQ ID NO 193
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 193

Gln Gln Tyr Ala Ser Pro Pro Ile Thr
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Construct

<400> SEQUENCE: 194

Gln Gln Val Tyr Ser Thr Pro Ile Thr
1               5

<210> SEQ ID NO 195
<211> LENGTH: 8
<212> TYPE: PRT
<213> ORGANISM: Artificial Sequence
<220> FEATURE:
<223> OTHER INFORMATION: Synthetic Construct

<400> SEQUENCE: 195

Gln Gln Leu Val His Trp Pro Thr
1               5

<210> SEQ ID NO 196
<211> LENGTH: 8
<212> TYPE: PRT
<213> ORGANISM: Artificial Sequence
<220> FEATURE:
<223> OTHER INFORMATION: Synthetic Construct

<400> SEQUENCE: 196

Gln Gln Leu Asp Asp Trp Phe Thr
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic Construct

<400> SEQUENCE: 197

Gln Gln Arg Ser Asn Tyr Pro Ile Thr
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Construct

<400> SEQUENCE: 198

Gln Gln Arg Ile Leu Tyr Pro Ile Thr
1               5

<210> SEQ ID NO 199
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 199

Gln Gln Arg Ala Ala Tyr Pro Ile Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct

<400> SEQUENCE: 200

Gln Gln Arg Thr Ser His Pro Ile Thr
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic Construct

<400> SEQUENCE: 201

Gln Gln Tyr Ala Gly Ser Pro Phe Thr
1               5

<210> SEQ ID NO 202
<211> LENGTH: 8
<212> TYPE: PRT
<213> ORGANISM: Artificial Sequence
<220> FEATURE:
<223> OTHER INFORMATION: Synthetic Construct

<400> SEQUENCE: 202

Gln Gln Phe Asp Asp Val Phe Thr
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic Construct

<400> SEQUENCE: 203

Gln Gln Tyr Val Asn Ser Pro Phe Thr
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Construct

<400> SEQUENCE: 204

Gln Gln Ser Asp Asp Pro Phe Thr
1               5

<210> SEQ ID NO 205
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 205

Gln Gln Leu Ser Thr Tyr Pro Leu Thr
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Construct

<400> SEQUENCE: 206

Gln Gln Arg Ser Val Tyr Pro Ile Thr
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Construct

<400> SEQUENCE: 207

Gln Gln Val Ser Leu Phe Pro Leu Thr
1               5

<210> SEQ ID NO 208
<211> LENGTH: 10
<212> TYPE: PRT
<213> ORGANISM: Artificial Sequence
<220> FEATURE:
<223> OTHER INFORMATION: Synthetic Construct

<400> SEQUENCE: 208

Leu Asp Tyr Asn Ser Tyr Ser Pro Ile Thr
1               5                   10

<210> SEQ ID NO 209
<211> LENGTH: 9
<212> TYPE: PRT
<213> ORGANISM: Artificial Sequence
<220> FEATURE:
<223> OTHER INFORMATION: Synthetic Construct

<400> SEQUENCE: 209

Gln Gln His Ile Ala Leu Pro Phe Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct

<400> SEQUENCE: 210

Gln Gln Arg Ala Ser Met Pro Ile Thr
1               5

<210> SEQ ID NO 211
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 211

Gln Gln Ala Phe Asn Arg Pro Pro Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic Construct

<400> SEQUENCE: 212

Gln Gln Ser Ser Val His Pro Tyr Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Construct

<400> SEQUENCE: 213

Gln Gln Ala Tyr Ser Leu Pro Pro Thr
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic Construct

<400> SEQUENCE: 214

Gln Gln Asp Asp Asp Gly Tyr Thr
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic Construct

<400> SEQUENCE: 215

Gln Gln Asp Tyr Ser Trp Pro Tyr Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic Construct

<400> SEQUENCE: 216

Gln Gln Arg Ser Ala Tyr Pro Ile Thr
1               5

<210> SEQ ID NO 217
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 217

Gln Gln Arg Ser His Phe Pro Ile Thr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

Gln Gln Arg Ala Asn Tyr Pro Ile Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic Construct

<400> SEQUENCE: 219

Gln Gln Arg Ala Asp Tyr Pro Ile Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic Construct

<400> SEQUENCE: 220

Gln Gln Ala Gly Ser His Pro Phe Thr
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic Construct

<400> SEQUENCE: 221

Gln Gln Asp Val Asn Tyr Pro Pro Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Construct

<400> SEQUENCE: 222

Gln Gln Asp Asp Asn Tyr Pro Tyr Thr
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Construct

<400> SEQUENCE: 223

Gln Gln Arg Ser Thr Phe Pro Ile Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Gln Gln Val Ser Asn Tyr Pro Phe Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic Construct

<400> SEQUENCE: 225

Gln Gln Tyr His Asp Ala Pro Ile Thr
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic Construct

<400> SEQUENCE: 226

Gln Gln Ala Tyr Val Val Pro Pro Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Gln Gln Ala Asp Asn Trp Pro Phe Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Synthetic Construct

<400> SEQUENCE: 228

Met Gln Ala Leu Glu Ser Pro Arg Thr
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 229

Gln Gln Tyr Val Asn Trp Pro Phe Thr
1               5

<210> SEQ ID NO 230
<211> LENGTH: 9
<212> TYPE: PRT
<213> ORGANISM: Artificial Sequence
<220> FEATURE:
<223> OTHER INFORMATION: Synthetic Construct

<400> SEQUENCE: 230

Gln Gln Ser Ser Asn Trp Pro Trp Thr
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic Construct

<400> SEQUENCE: 231

Gln Gln Ala Ser Thr Phe Pro Ile Thr
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Construct

<400> SEQUENCE: 232

Gln Gln Arg Asn Ser Leu Pro Leu Thr
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic Construct

<400> SEQUENCE: 233

Gln Gln Ser Tyr Asp Phe Pro Ile Thr
1               5

<210> SEQ ID NO 234
<211> LENGTH: 10
<212> TYPE: PRT
<213> ORGANISM: Artificial Sequence
<220> FEATURE:
<223> OTHER INFORMATION: Synthetic Construct

<400> SEQUENCE: 234

Gln Gln Glu Val Asp Tyr Pro Pro Leu Thr
1               5                   10

<210> SEQ ID NO 235
<211> LENGTH: 9
<212> TYPE: PRT
<213> ORGANISM: Artificial Sequence
<220> FEATURE:
<223> OTHER INFORMATION: Synthetic Construct

<400> SEQUENCE: 235
```

```
Gln Gln Leu Asn Ser Tyr Ser Pro Thr
1               5
```

<210> SEQ ID NO 236
<211> LENGTH: 9
<212> TYPE: PRT
<213> ORGANISM: Artificial Sequence
<220> FEATURE:
<223> OTHER INFORMATION: Synthetic Construct

<400> SEQUENCE: 236

```
Gln Gln Tyr Ile Phe Trp Pro Pro Thr
1               5
```

<210> SEQ ID NO 237
<211> LENGTH: 8
<212> TYPE: PRT
<213> ORGANISM: Artificial Sequence
<220> FEATURE:
<223> OTHER INFORMATION: Synthetic Construct

<400> SEQUENCE: 237

```
Gly Asp Leu Trp Phe Pro Gly Glu
1               5
```

<210> SEQ ID NO 238
<211> LENGTH: 14
<212> TYPE: PRT
<213> ORGANISM: Artificial Sequence
<220> FEATURE:
<223> OTHER INFORMATION: Synthetic Construct

<400> SEQUENCE: 238

```
Asp Leu Trp Phe Pro Gly Glu Ser Glu Ser Phe Glu Asp Ala
1               5                   10
```

<210> SEQ ID NO 239
<211> LENGTH: 14
<212> TYPE: PRT
<213> ORGANISM: Artificial Sequence
<220> FEATURE:
<223> OTHER INFORMATION: Synthetic Construct

<400> SEQUENCE: 239

```
Asp Leu Trp Val Pro Glu Glu Ser Ser Ser Phe Glu Gly Ala
1               5                   10
```

<210> SEQ ID NO 240
<211> LENGTH: 15
<212> TYPE: PRT
<213> ORGANISM: Artificial Sequence
<220> FEATURE:
<223> OTHER INFORMATION: Synthetic Construct

<400> SEQUENCE: 240

```
Ala Asp Pro Leu Asp His Arg Asp Ala Gly Asp Leu Trp Phe Pro
1               5                   10                  15
```

<210> SEQ ID NO 241
<211> LENGTH: 13
<212> TYPE: PRT
<213> ORGANISM: Artificial Sequence
<220> FEATURE:
<223> OTHER INFORMATION: Synthetic Construct

<400> SEQUENCE: 241

Ser Ile Ser Arg Ser Leu Leu Glu Gly Glu Ile Pro Phe
1               5                   10

<210> SEQ ID NO 242
<211> LENGTH: 118
<212> TYPE: PRT
<213> ORGANISM: Artificial Sequence
<220> FEATURE:
<223> OTHER INFORMATION: Synthetic Construct

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Pro Thr Leu Leu Phe Gln His Trp Gly Gln Gly Thr
            100                 105                 110

Leu Val Thr Val Ser Ser
        115

<210> SEQ ID NO 243
<211> LENGTH: 107
<212> TYPE: PRT
<213> ORGANISM: Artificial Sequence
<220> FEATURE:
<223> OTHER INFORMATION: Synthetic Construct

<400> SEQUENCE: 243

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Pro Tyr Trp Pro Pro
                85                  90                  95

Thr Phe Gly Gly Gly Thr Lys Val Glu Ile Lys
            100                 105

<210> SEQ ID NO 244
<211> LENGTH: 128
<212> TYPE: PRT
<213> ORGANISM: Artificial Sequence
<220> FEATURE:
<223> OTHER INFORMATION: Synthetic Construct

<400> SEQUENCE: 244

Glu Val Gln Leu Leu Glu Ser Gly Gly Gly Leu Val Gln Pro Gly Gly

```
            1               5                  10                 15
Ser Leu Arg Leu Ser Cys Ala Ala Ser Gly Phe Thr Phe Ser Ser Ser
                20                  25                 30

Ala Met Ser Trp Val Arg Gln Ala Pro Gly Lys Gly Leu Glu Trp Val
                35                  40                 45

Ser Ala Ile Ser Gly Ser Gly Gly Ser Thr Tyr Tyr Ala Asp Ser Val
            50                  55                 60

Lys Gly Arg Phe Thr Ile Ser Arg Asp Asn Ser Lys Asn Thr Leu Tyr
 65                 70                  75                 80

Leu Gln Met Asn Ser Leu Arg Ala Glu Asp Thr Ala Val Tyr Tyr Cys
                85                  90                 95

Ala Lys Val Pro Ser Tyr Asp Tyr Trp Ser Gly Tyr Ser Asn Tyr Tyr
                100                 105                110

Tyr Tyr Met Asp Val Trp Gly Lys Gly Thr Thr Val Thr Val Ser Ser
                115                 120                125
```

<210> SEQ ID NO 245
<211> LENGTH: 107
<212> TYPE: PRT
<213> ORGANISM: Artificial Sequence
<220> FEATURE:
<223> OTHER INFORMATION: Synthetic Construct

<400> SEQUENCE: 245

```
            1               5                  10                 15
Glu Ile Val Leu Thr Gln Ser Pro Ala Thr Leu Ser Val Ser Pro Gly
 1                  5                  10                 15

Glu Arg Ala Thr Leu Ser Cys Arg Ala Ser Gln Ser Val Gly Ser Asn
                20                  25                 30

Leu Ala Trp Tyr Gln Gln Lys Pro Gly Gln Ala Pro Arg Leu Leu Ile
                35                  40                 45

Tyr Gly Ala Ser Thr Arg Ala Thr Gly Ile Pro Ala Arg Phe Ser Gly
            50                  55                 60

Ser Gly Ser Gly Thr Glu Phe Thr Leu Thr Ile Ser Ser Leu Gln Ser
 65                 70                  75                 80

Glu Asp Phe Ala Val Tyr Tyr Cys Gln Gln Tyr Phe Phe Tyr Pro Pro
                85                  90                 95

Thr Phe Gly Gly Gly Thr Lys Val Glu Ile Lys
                100                 105
```

<210> SEQ ID NO 246
<211> LENGTH: 118
<212> TYPE: PRT
<213> ORGANISM: Artificial Sequence
<220> FEATURE:
<223> OTHER INFORMATION: Synthetic Construct

<400> SEQUENCE: 246

```
Gln Val Gln Leu Val Gln Ser Gly Ala Glu Val Lys Lys Pro Gly Ser
 1                  5                  10                 15

Ser Val Lys Val Ser Cys Lys Ala Ser Gly Gly Thr Phe Ser Ser Tyr
                20                  25                 30

Ala Ile Ser Trp Val Arg Gln Ala Pro Gly Gln Gly Leu Glu Trp Met
                35                  40                 45

Gly Gly Ile Ile Pro Ile Phe Gly Thr Ala Asn Tyr Ala Gln Lys Phe
            50                  55                 60

Gln Gly Arg Val Thr Ile Thr Ala Asp Glu Ser Thr Ser Thr Ala Tyr
 65                 70                  75                 80
```

```
Met Glu Leu Ser Ser Leu Arg Ser Glu Asp Thr Ala Val Tyr Tyr Cys
                85                  90                  95

Ala Arg Glu Gln Tyr His Val Gly Met Asp Val Trp Gly Lys Gly Thr
            100                 105                 110

Thr Val Thr Val Ser Ser
            115

<210> SEQ ID NO 247
<211> LENGTH: 107
<212> TYPE: PRT
<213> ORGANISM: Artificial Sequence
<220> FEATURE:
<223> OTHER INFORMATION: Synthetic Construct

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Pro Phe Asn Phe Pro Tyr
                85                  90                  95

Thr Phe Gly Gly Gly Thr Lys Val Glu Ile Lys
            100                 105

<210> SEQ ID NO 248
<211> LENGTH: 117
<212> TYPE: PRT
<213> ORGANISM: Artificial Sequence
<220> FEATURE:
<223> OTHER INFORMATION: Synthetic Construct

<400> SEQUENCE: 248

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Asp Ser Ile Met Asp Tyr Trp Gly Gln Gly Thr Leu
            100                 105                 110

Val Thr Val Ser Ser
        115

<210> SEQ ID NO 249
<211> LENGTH: 107
<212> TYPE: PRT
<213> ORGANISM: Artificial Sequence
```

<220> FEATURE:
<223> OTHER INFORMATION: Synthetic Construct

<400> SEQUENCE: 249

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp His Asp Tyr Pro Phe
                85                  90                  95

Thr Phe Gly Gly Gly Thr Lys Val Glu Ile Lys
            100                 105

<210> SEQ ID NO 250
<211> LENGTH: 120
<212> TYPE: PRT
<213> ORGANISM: Artificial Sequence
<220> FEATURE:
<223> OTHER INFORMATION: Synthetic Construct

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Pro Gln Glu Ser Pro Tyr Val Phe Asp Ile Trp Gly Gln
            100                 105                 110

Gly Thr Met Val Thr Val Ser Ser
        115                 120

<210> SEQ ID NO 251
<211> LENGTH: 108
<212> TYPE: PRT
<213> ORGANISM: Artificial Sequence
<220> FEATURE:
<223> OTHER INFORMATION: Synthetic Construct

<400> SEQUENCE: 251

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Phe Ser Ser Pro
                 85                  90                  95

Phe Thr Phe Gly Gly Gly Thr Lys Val Glu Ile Lys
            100                 105

<210> SEQ ID NO 252
<211> LENGTH: 120
<212> TYPE: PRT
<213> ORGANISM: Artificial Sequence
<220> FEATURE:
<223> OTHER INFORMATION: Synthetic Construct

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ser Pro Thr Tyr Gly Tyr Leu Tyr Asp Pro Trp Gly Gln
            100                 105                 110

Gly Thr Leu Val Thr Val Ser Ser
        115                 120

<210> SEQ ID NO 253
<211> LENGTH: 107
<212> TYPE: PRT
<213> ORGANISM: Artificial Sequence
<220> FEATURE:
<223> OTHER INFORMATION: Synthetic Construct

<400> SEQUENCE: 253

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Val Asn Leu Pro Pro
                 85                  90                  95

Thr Phe Gly Gly Gly Thr Lys Val Glu Ile Lys
            100                 105

<210> SEQ ID NO 254
```

<211> LENGTH: 117
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Thr Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Thr Ser Ser Lys Glu Arg Asp Tyr Trp Gly Gln Gly Thr Leu
            100                 105                 110
Val Thr Val Ser Ser
        115

<210> SEQ ID NO 255
<211> LENGTH: 107
<212> TYPE: PRT
<213> ORGANISM: Artificial Sequence
<220> FEATURE:
<223> OTHER INFORMATION: Synthetic Construct

<400> SEQUENCE: 255

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Lys Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ile Ser Tyr Pro Ile
                85                  90                  95
Thr Phe Gly Gly Gly Thr Lys Val Glu Ile Lys
            100                 105

<210> SEQ ID NO 256
<211> LENGTH: 121
<212> TYPE: PRT
<213> ORGANISM: Artificial Sequence
<220> FEATURE:
<223> OTHER INFORMATION: Synthetic Construct

<400> SEQUENCE: 256

Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30

```
Ser Tyr Tyr Trp Gly Trp Ile Arg Gln Pro Pro Gly Lys Gly Leu Glu
            35                  40                  45

Trp Ile Gly Ser Ile Ser Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Pro Tyr Arg Leu Leu Leu Gly Met Asp Val Trp Gly
            100                 105                 110

Gln Gly Thr Thr Val Thr Val Ser Ser
            115                 120

<210> SEQ ID NO 257
<211> LENGTH: 107
<212> TYPE: PRT
<213> ORGANISM: Artificial Sequence
<220> FEATURE:
<223> OTHER INFORMATION: Synthetic Construct

<400> SEQUENCE: 257

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Asp Asp Thr Pro Ile
                 85                  90                  95

Thr Phe Gly Gly Gly Thr Lys Val Glu Ile Lys
            100                 105

<210> SEQ ID NO 258
<211> LENGTH: 121
<212> TYPE: PRT
<213> ORGANISM: Artificial Sequence
<220> FEATURE:
<223> OTHER INFORMATION: Synthetic Construct

<400> SEQUENCE: 258

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Thr Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Ile Ser Gly Glu Val Asn Trp Phe Asp Pro Trp Gly
            100                 105                 110
```

```
Gln Gly Thr Leu Val Thr Val Ser Ser
        115                 120

<210> SEQ ID NO 259
<211> LENGTH: 107
<212> TYPE: PRT
<213> ORGANISM: Artificial Sequence
<220> FEATURE:
<223> OTHER INFORMATION: Synthetic Construct

<400> SEQUENCE: 259

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Tyr Trp Pro Trp
                85                  90                  95

Thr Phe Gly Gly Gly Thr Lys Val Glu Ile Lys
            100                 105

<210> SEQ ID NO 260
<211> LENGTH: 122
<212> TYPE: PRT
<213> ORGANISM: Artificial Sequence
<220> FEATURE:
<223> OTHER INFORMATION: Synthetic Construct

<400> SEQUENCE: 260

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Ala Gly Tyr Asp Tyr Gly Glu Leu Ala Phe Asp Ile Trp
            100                 105                 110

Gly Gln Gly Thr Met Val Thr Val Ser Ser
        115                 120

<210> SEQ ID NO 261
<211> LENGTH: 108
<212> TYPE: PRT
<213> ORGANISM: Artificial Sequence
<220> FEATURE:
<223> OTHER INFORMATION: Synthetic Construct

<400> SEQUENCE: 261
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Asp Ser Ser Pro
                85                  90                  95

Pro Thr Phe Gly Gly Gly Thr Lys Val Glu Ile Lys
            100                 105

<210> SEQ ID NO 262
<211> LENGTH: 122
<212> TYPE: PRT
<213> ORGANISM: Artificial Sequence
<220> FEATURE:
<223> OTHER INFORMATION: Synthetic Construct

<400> SEQUENCE: 262

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Gly His Tyr Asp Gly Gly His Leu Gly Met Asp Val Trp
            100                 105                 110

Gly Gln Gly Thr Thr Val Thr Val Ser Ser
        115                 120

<210> SEQ ID NO 263
<211> LENGTH: 108
<212> TYPE: PRT
<213> ORGANISM: Artificial Sequence
<220> FEATURE:
<223> OTHER INFORMATION: Synthetic Construct

<400> SEQUENCE: 263

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Asp Tyr Ser Tyr Pro
                85                  90                  95

Trp Thr Phe Gly Gly Gly Thr Lys Val Glu Ile Lys
            100                 105

<210> SEQ ID NO 264
<211> LENGTH: 124
<212> TYPE: PRT
<213> ORGANISM: Artificial Sequence
<220> FEATURE:
<223> OTHER INFORMATION: Synthetic Construct

<400> SEQUENCE: 264

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly His Tyr Ser Gly Thr Val Ser Ser Tyr Gly Met Asp
                100                 105                 110

Val Trp Gly Gln Gly Thr Thr Val Thr Val Ser Ser
            115                 120

<210> SEQ ID NO 265
<211> LENGTH: 107
<212> TYPE: PRT
<213> ORGANISM: Artificial Sequence
<220> FEATURE:
<223> OTHER INFORMATION: Synthetic Construct

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ala Val Pro Tyr
                85                  90                  95

Thr Phe Gly Gly Gly Thr Lys Val Glu Ile Lys
            100                 105

<210> SEQ ID NO 266
<211> LENGTH: 118
<212> TYPE: PRT
<213> ORGANISM: Artificial Sequence
<220> FEATURE:
<223> OTHER INFORMATION: Synthetic Construct
```

<400> SEQUENCE: 266

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Ser His Tyr Tyr Asp Leu Ala Trp Gly Gln Gly Thr
            100                 105                 110

Leu Val Thr Val Ser Ser
        115

<210> SEQ ID NO 267
<211> LENGTH: 107
<212> TYPE: PRT
<213> ORGANISM: Artificial Sequence
<220> FEATURE:
<223> OTHER INFORMATION: Synthetic Construct

<400> SEQUENCE: 267

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Ser Asn Tyr Pro Ile
                85                  90                  95

Thr Phe Gly Gly Gly Thr Lys Val Glu Ile Lys
            100                 105

<210> SEQ ID NO 268
<211> LENGTH: 120
<212> TYPE: PRT
<213> ORGANISM: Artificial Sequence
<220> FEATURE:
<223> OTHER INFORMATION: Synthetic Construct

<400> SEQUENCE: 268

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Val Tyr Asn Pro Ser
    50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Leu Tyr Gly Tyr Gly Val Leu Asp Val Trp Gly Gln
            100                 105                 110

Gly Thr Met Val Thr Val Ser Ser
        115                 120

<210> SEQ ID NO 269
<211> LENGTH: 107
<212> TYPE: PRT
<213> ORGANISM: Artificial Sequence
<220> FEATURE:
<223> OTHER INFORMATION: Synthetic Construct

<400> SEQUENCE: 269

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Val Asp Asn Ile Pro Pro
                 85                  90                  95

Thr Phe Gly Gly Gly Thr Lys Val Glu Ile Lys
            100                 105

<210> SEQ ID NO 270
<211> LENGTH: 106
<212> TYPE: PRT
<213> ORGANISM: Artificial Sequence
<220> FEATURE:
<223> OTHER INFORMATION: Synthetic Construct

<400> SEQUENCE: 270

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Asp Thr Tyr Pro Thr
                 85                  90                  95

Phe Gly Gly Gly Thr Lys Val Glu Ile Lys
            100                 105

<210> SEQ ID NO 271
<211> LENGTH: 120
<212> TYPE: PRT
```

```
<213> ORGANISM: Artificial Sequence
<220> FEATURE:
<223> OTHER INFORMATION: Synthetic Construct

<400> SEQUENCE: 271

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Leu Gly Tyr Gly Val Phe Asp Tyr Trp Gly Gln
            100                 105                 110

Gly Thr Leu Val Thr Val Ser Ser
        115                 120

<210> SEQ ID NO 272
<211> LENGTH: 106
<212> TYPE: PRT
<213> ORGANISM: Artificial Sequence
<220> FEATURE:
<223> OTHER INFORMATION: Synthetic Construct

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Leu Asn Phe Pro Thr
                85                  90                  95

Phe Gly Gly Gly Thr Lys Val Glu Ile Lys
            100                 105

<210> SEQ ID NO 273
<211> LENGTH: 106
<212> TYPE: PRT
<213> ORGANISM: Artificial Sequence
<220> FEATURE:
<223> OTHER INFORMATION: Synthetic Construct

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Phe Asn Phe Pro Thr
                 85                  90                  95

Phe Gly Gly Gly Thr Lys Val Glu Ile Lys
            100                 105

<210> SEQ ID NO 274
<211> LENGTH: 122
<212> TYPE: PRT
<213> ORGANISM: Artificial Sequence
<220> FEATURE:
<223> OTHER INFORMATION: Synthetic Construct

<400> SEQUENCE: 274

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
             35                  40                  45

Gly Ser Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gly Gly Gly Glu Tyr Pro Ser Gly Thr Pro Phe Asp Ile Trp
            100                 105                 110

Gly Gln Gly Thr Met Val Thr Val Ser Ser
            115                 120

<210> SEQ ID NO 275
<211> LENGTH: 107
<212> TYPE: PRT
<213> ORGANISM: Artificial Sequence
<220> FEATURE:
<223> OTHER INFORMATION: Synthetic Construct

<400> SEQUENCE: 275

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ile Asp Leu Pro Phe
                 85                  90                  95

Thr Phe Gly Gly Gly Thr Lys Val Glu Ile Lys
            100                 105
```

<210> SEQ ID NO 276
<211> LENGTH: 107
<212> TYPE: PRT
<213> ORGANISM: Artificial Sequence
<220> FEATURE:
<223> OTHER INFORMATION: Synthetic Construct

<400> SEQUENCE: 276

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Asp Leu Pro Phe
                85                  90                  95

Thr Phe Gly Gly Gly Thr Lys Val Glu Ile Lys
            100                 105
```

<210> SEQ ID NO 277
<211> LENGTH: 117
<212> TYPE: PRT
<213> ORGANISM: Artificial Sequence
<220> FEATURE:
<223> OTHER INFORMATION: Synthetic Construct

<400> SEQUENCE: 277

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Met Ala Ser Phe Phe Asp Tyr Trp Gly Gln Gly Thr Leu
            100                 105                 110

Val Thr Val Ser Ser
        115
```

<210> SEQ ID NO 278
<211> LENGTH: 108
<212> TYPE: PRT
<213> ORGANISM: Artificial Sequence
<220> FEATURE:
<223> OTHER INFORMATION: Synthetic Construct

<400> SEQUENCE: 278

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30
```

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Ser Ser His Pro
                 85                  90                  95

Phe Thr Phe Gly Gly Gly Thr Lys Val Glu Ile Lys
            100                 105

<210> SEQ ID NO 279
<211> LENGTH: 108
<212> TYPE: PRT
<213> ORGANISM: Artificial Sequence
<220> FEATURE:
<223> OTHER INFORMATION: Synthetic Construct

<400> SEQUENCE: 279

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Asp Arg Ser Pro
                 85                  90                  95

Tyr Thr Phe Gly Gly Gly Thr Lys Val Glu Ile Lys
            100                 105

<210> SEQ ID NO 280
<211> LENGTH: 117
<212> TYPE: PRT
<213> ORGANISM: Artificial Sequence
<220> FEATURE:
<223> OTHER INFORMATION: Synthetic Construct

<400> SEQUENCE: 280

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Gly His Ser Met Asp Val Trp Gly Gln Gly Thr Thr
            100                 105                 110

Val Thr Val Ser Ser

<210> SEQ ID NO 281
<211> LENGTH: 113
<212> TYPE: PRT
<213> ORGANISM: Artificial Sequence
<220> FEATURE:
<223> OTHER INFORMATION: Synthetic Construct

<400> SEQUENCE: 281

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Ser Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ala Tyr Leu Pro Pro Ile Thr Phe Gly Gly Gly Thr Lys Val Glu Ile
            100                 105                 110
Lys
```

<210> SEQ ID NO 282
<211> LENGTH: 118
<212> TYPE: PRT
<213> ORGANISM: Artificial Sequence
<220> FEATURE:
<223> OTHER INFORMATION: Synthetic Construct

<400> SEQUENCE: 282

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Pro Leu Lys Arg Gly Arg Gly Phe Tyr Trp Gly Gln Gly Thr
            100                 105                 110
Leu Val Thr Val Ser Ser
        115
```

<210> SEQ ID NO 283
<211> LENGTH: 108
<212> TYPE: PRT
<213> ORGANISM: Artificial Sequence
<220> FEATURE:
<223> OTHER INFORMATION: Synthetic Construct

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser Pro Pro Pro
                85                  90                  95

Trp Thr Phe Gly Gly Gly Thr Lys Val Glu Ile Lys
            100                 105

<210> SEQ ID NO 284
<211> LENGTH: 117
<212> TYPE: PRT
<213> ORGANISM: Artificial Sequence
<220> FEATURE:
<223> OTHER INFORMATION: Synthetic Construct

<400> SEQUENCE: 284

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Arg Thr Ile Thr Met Asp Trp Gly Asn Gly Thr Leu
            100                 105                 110

Val Thr Val Ser Ser
        115

<210> SEQ ID NO 285
<211> LENGTH: 107
<212> TYPE: PRT
<213> ORGANISM: Artificial Sequence
<220> FEATURE:
<223> OTHER INFORMATION: Synthetic Construct

<400> SEQUENCE: 285

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Arg Ser Pro
                85                  90                  95

Thr Phe Gly Gly Gly Thr Lys Val Glu Ile Lys
            100                 105

<210> SEQ ID NO 286
<211> LENGTH: 117
<212> TYPE: PRT
<213> ORGANISM: Artificial Sequence
<220> FEATURE:
<223> OTHER INFORMATION: Synthetic Construct

<400> SEQUENCE: 286

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Tyr Ser Val Leu Asp Tyr Trp Gly Gln Gly Thr Leu
            100                 105                 110

Val Thr Val Ser Ser
        115

<210> SEQ ID NO 287
<211> LENGTH: 107
<212> TYPE: PRT
<213> ORGANISM: Artificial Sequence
<220> FEATURE:
<223> OTHER INFORMATION: Synthetic Construct

<400> SEQUENCE: 287

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Glu Phe Asp Leu Pro Phe
                85                  90                  95

Thr Phe Gly Gly Gly Thr Lys Val Glu Ile Lys
            100                 105

<210> SEQ ID NO 288
<211> LENGTH: 120
<212> TYPE: PRT
<213> ORGANISM: Artificial Sequence
<220> FEATURE:
<223> OTHER INFORMATION: Synthetic Construct

<400> SEQUENCE: 288

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Tyr Ser Ser Arg Gly Val Tyr Phe Asp Tyr Trp Gly Gln
            100                 105                 110

Gly Thr Leu Val Thr Val Ser Ser
            115                 120

<210> SEQ ID NO 289
<211> LENGTH: 107
<212> TYPE: PRT
<213> ORGANISM: Artificial Sequence
<220> FEATURE:
<223> OTHER INFORMATION: Synthetic Construct

<400> SEQUENCE: 289

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Asn Phe Pro Pro
                85                  90                  95

Thr Phe Gly Gly Gly Thr Lys Val Glu Ile Lys
            100                 105

<210> SEQ ID NO 290
<211> LENGTH: 124
<212> TYPE: PRT
<213> ORGANISM: Artificial Sequence
<220> FEATURE:
<223> OTHER INFORMATION: Synthetic Construct

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Ala Val Gly Ala Arg His Val Thr Tyr Phe Asp
            100                 105                 110

Tyr Trp Gly Gln Gly Thr Leu Val Thr Val Ser Ser
        115                 120

<210> SEQ ID NO 291
<211> LENGTH: 107
<212> TYPE: PRT
<213> ORGANISM: Artificial Sequence
<220> FEATURE:
<223> OTHER INFORMATION: Synthetic Construct

<400> SEQUENCE: 291

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Leu Arg Pro Ile
                85                  90                  95

Thr Phe Gly Gly Gly Thr Lys Val Glu Ile Lys
            100                 105

<210> SEQ ID NO 292
<211> LENGTH: 121
<212> TYPE: PRT
<213> ORGANISM: Artificial Sequence
<220> FEATURE:
<223> OTHER INFORMATION: Synthetic Construct

<400> SEQUENCE: 292

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Tyr Tyr Gly Ser Gly Trp Phe Asp Pro Trp Gly
            100                 105                 110

Gln Gly Thr Leu Val Thr Val Ser Ser
        115                 120

<210> SEQ ID NO 293
<211> LENGTH: 107
<212> TYPE: PRT
<213> ORGANISM: Artificial Sequence
<220> FEATURE:
<223> OTHER INFORMATION: Synthetic Construct

<400> SEQUENCE: 293

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Pro Gly Ala Val Pro
                85                  90                  95

Thr Phe Gly Gly Gly Thr Lys Val Glu Ile Lys
            100                 105

<210> SEQ ID NO 294
<211> LENGTH: 119
<212> TYPE: PRT
<213> ORGANISM: Artificial Sequence
<220> FEATURE:
<223> OTHER INFORMATION: Synthetic Construct

<400> SEQUENCE: 294

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gln Glu Tyr Ala Tyr Phe Gln His Trp Gly Gln Gly
            100                 105                 110

Thr Leu Val Thr Val Ser Ser
        115

<210> SEQ ID NO 295
<211> LENGTH: 107
<212> TYPE: PRT
<213> ORGANISM: Artificial Sequence
<220> FEATURE:
<223> OTHER INFORMATION: Synthetic Construct

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Tyr Ile Thr Pro Ile
                85                  90                  95

Thr Phe Gly Gly Gly Thr Lys Val Glu Ile Lys
                100                 105
```

<210> SEQ ID NO 296
<211> LENGTH: 121
<212> TYPE: PRT
<213> ORGANISM: Artificial Sequence
<220> FEATURE:
<223> OTHER INFORMATION: Synthetic Construct

<400> SEQUENCE: 296

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Arg Asp Gly Tyr Tyr Asp Glu Val Phe Asp Ile Trp Gly
                100                 105                 110

Gln Gly Thr Met Val Thr Val Ser Ser
        115                 120
```

<210> SEQ ID NO 297
<211> LENGTH: 107
<212> TYPE: PRT
<213> ORGANISM: Artificial Sequence
<220> FEATURE:
<223> OTHER INFORMATION: Synthetic Construct

<400> SEQUENCE: 297

```
Asp Ile Gln Leu Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Phe
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Pro Val Asp Leu Pro Phe
                85                  90                  95

Thr Phe Gly Gly Gly Thr Lys Val Glu Ile Lys
```

<210> SEQ ID NO 298
<211> LENGTH: 119
<212> TYPE: PRT
<213> ORGANISM: Artificial Sequence
<220> FEATURE:
<223> OTHER INFORMATION: Synthetic Construct

<400> SEQUENCE: 298

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Pro Lys His Tyr Val Val Leu Asp Tyr Trp Gly Gln Gly
            100                 105                 110

Thr Leu Val Thr Val Ser Ser
        115

<210> SEQ ID NO 299
<211> LENGTH: 107
<212> TYPE: PRT
<213> ORGANISM: Artificial Sequence
<220> FEATURE:
<223> OTHER INFORMATION: Synthetic Construct

<400> SEQUENCE: 299

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Phe Phe Pro Pro
                85                  90                  95

Thr Phe Gly Gly Gly Thr Lys Val Glu Ile Lys
            100                 105

<210> SEQ ID NO 300
<211> LENGTH: 117
<212> TYPE: PRT
<213> ORGANISM: Artificial Sequence
<220> FEATURE:
<223> OTHER INFORMATION: Synthetic Construct

<400> SEQUENCE: 300

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Gly Gly His Leu Phe Asp Tyr Trp Gly Gln Gly Thr Leu
                100                 105                 110

Val Thr Val Ser Ser
            115

<210> SEQ ID NO 301
<211> LENGTH: 107
<212> TYPE: PRT
<213> ORGANISM: Artificial Sequence
<220> FEATURE:
<223> OTHER INFORMATION: Synthetic Construct

<400> SEQUENCE: 301

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asp Ser Ser Phe Pro Pro
                85                  90                  95

Thr Phe Gly Gly Gly Thr Lys Val Glu Ile Lys
                100                 105

<210> SEQ ID NO 302
<211> LENGTH: 122
<212> TYPE: PRT
<213> ORGANISM: Artificial Sequence
<220> FEATURE:
<223> OTHER INFORMATION: Synthetic Construct

<400> SEQUENCE: 302

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
            85                  90                  95
Ala Arg Asp Arg Gly Gly Glu Tyr Val Asp Phe Ala Phe Asp Ile Trp
            100                 105                 110

Gly Gln Gly Thr Met Val Thr Val Ser Ser
        115                 120

<210> SEQ ID NO 303
<211> LENGTH: 107
<212> TYPE: PRT
<213> ORGANISM: Artificial Sequence
<220> FEATURE:
<223> OTHER INFORMATION: Synthetic Construct

<400> SEQUENCE: 303

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Phe Pro Pro Trp
                85                  90                  95

Thr Phe Gly Gly Gly Thr Lys Val Glu Ile Lys
            100                 105

<210> SEQ ID NO 304
<211> LENGTH: 122
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Ser Gly Tyr Gly Ala Ser Asn Tyr Phe Asp Tyr Trp
            100                 105                 110

Gly Gln Gly Thr Leu Val Thr Val Ser Ser
        115                 120

<210> SEQ ID NO 305
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ala Pro Ile
                85                  90                  95

Thr Phe Gly Gly Gly Thr Lys Val Glu Ile Lys
            100                 105

<210> SEQ ID NO 306
<211> LENGTH: 122
<212> TYPE: PRT
<213> ORGANISM: Artificial Sequence
<220> FEATURE:
<223> OTHER INFORMATION: Synthetic Construct

<400> SEQUENCE: 306

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Ala Ala Ala Ser Pro Ala Phe Asp Ile Trp
            100                 105                 110

Gly Gln Gly Thr Met Val Thr Val Ser Ser
        115                 120

<210> SEQ ID NO 307
<211> LENGTH: 106
<212> TYPE: PRT
<213> ORGANISM: Artificial Sequence
<220> FEATURE:
<223> OTHER INFORMATION: Synthetic Construct

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Leu Phe Asp Trp Pro Thr
                 85                  90                  95

Phe Gly Gly Gly Thr Lys Val Glu Ile Lys
            100                 105
```

<210> SEQ ID NO 308
<211> LENGTH: 119
<212> TYPE: PRT
<213> ORGANISM: Artificial Sequence
<220> FEATURE:
<223> OTHER INFORMATION: Synthetic Construct

<400> SEQUENCE: 308

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Gln Tyr Met Leu Gly Met Asp Val Trp Gly Gln Gly
            100                 105                 110

Thr Thr Val Thr Val Ser Ser
        115
```

<210> SEQ ID NO 309
<211> LENGTH: 106
<212> TYPE: PRT
<213> ORGANISM: Artificial Sequence
<220> FEATURE:
<223> OTHER INFORMATION: Synthetic Construct

<400> SEQUENCE: 309

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ala Phe Leu Phe Thr
                 85                  90                  95

Phe Gly Gly Gly Thr Lys Val Glu Ile Lys
            100                 105
```

<210> SEQ ID NO 310
<211> LENGTH: 125

<212> TYPE: PRT
<213> ORGANISM: Artificial Sequence
<220> FEATURE:
<223> OTHER INFORMATION: Synthetic Construct

<400> SEQUENCE: 310

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Asp Tyr Gly Ile Glu Pro Glu Tyr Phe
            100                 105                 110

Gln His Trp Gly Gln Gly Thr Leu Val Thr Val Ser Ser
        115                 120                 125

<210> SEQ ID NO 311
<211> LENGTH: 107
<212> TYPE: PRT
<213> ORGANISM: Artificial Sequence
<220> FEATURE:
<223> OTHER INFORMATION: Synthetic Construct

<400> SEQUENCE: 311

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ile Asp Phe Leu Pro Tyr
                85                  90                  95

Thr Phe Gly Gly Gly Thr Lys Val Glu Ile Lys
            100                 105

<210> SEQ ID NO 312
<211> LENGTH: 119
<212> TYPE: PRT
<213> ORGANISM: Artificial Sequence
<220> FEATURE:
<223> OTHER INFORMATION: Synthetic Construct

<400> SEQUENCE: 312

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
            35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys His Tyr His Val Gly Ile Ala Phe Asp Ile Trp Gly Gln Gly
                100                 105                 110
Thr Met Val Thr Val Ser Ser
            115

<210> SEQ ID NO 313
<211> LENGTH: 107
<212> TYPE: PRT
<213> ORGANISM: Artificial Sequence
<220> FEATURE:
<223> OTHER INFORMATION: Synthetic Construct

<400> SEQUENCE: 313

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Val Tyr Ser Pro Pro Ile
                 85                  90                  95
Thr Phe Gly Gly Gly Thr Lys Val Glu Ile Lys
                100                 105

<210> SEQ ID NO 314
<211> LENGTH: 107
<212> TYPE: PRT
<213> ORGANISM: Artificial Sequence
<220> FEATURE:
<223> OTHER INFORMATION: Synthetic Construct

<400> SEQUENCE: 314

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Tyr Ala Ala Pro Ile
                 85                  90                  95
Thr Phe Gly Gly Gly Thr Lys Val Glu Ile Lys
                100                 105
```

<210> SEQ ID NO 315
<211> LENGTH: 120
<212> TYPE: PRT
<213> ORGANISM: Artificial Sequence
<220> FEATURE:
<223> OTHER INFORMATION: Synthetic Construct

<400> SEQUENCE: 315

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Met Ala Arg Lys Ser Val Ala Phe Asp Ile Trp Gly Gln
            100                 105                 110

Gly Thr Met Val Thr Val Ser Ser
        115                 120

<210> SEQ ID NO 316
<211> LENGTH: 107
<212> TYPE: PRT
<213> ORGANISM: Artificial Sequence
<220> FEATURE:
<223> OTHER INFORMATION: Synthetic Construct

<400> SEQUENCE: 316

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Thr Val Tyr Tyr Cys Gln Gln Arg Tyr Ala Leu Pro Ile
                85                  90                  95

Thr Phe Gly Gly Gly Thr Lys Val Glu Ile Lys
            100                 105

<210> SEQ ID NO 317
<211> LENGTH: 121
<212> TYPE: PRT
<213> ORGANISM: Artificial Sequence
<220> FEATURE:
<223> OTHER INFORMATION: Synthetic Construct

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser

```
            20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Val Pro Ser Tyr Gln Arg Gly Thr Ala Phe Asp Pro Trp Gly
                100                 105                 110
Gln Gly Thr Leu Val Thr Val Ser Ser
                115                 120

<210> SEQ ID NO 318
<211> LENGTH: 108
<212> TYPE: PRT
<213> ORGANISM: Artificial Sequence
<220> FEATURE:
<223> OTHER INFORMATION: Synthetic Construct

<400> SEQUENCE: 318

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Ala Ser Pro Pro
                85                  90                  95
Ile Thr Phe Gly Gly Gly Thr Lys Val Glu Ile Lys
                100                 105

<210> SEQ ID NO 319
<211> LENGTH: 121
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Ser
            20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Lys Ser Pro Ala Val Ala Gly Ile Tyr Arg Ala Asp Tyr Trp Gly
                100                 105                 110
Gln Gly Thr Leu Val Thr Val Ser Ser
        115                 120
```

<210> SEQ ID NO 320
<211> LENGTH: 107
<212> TYPE: PRT
<213> ORGANISM: Artificial Sequence
<220> FEATURE:
<223> OTHER INFORMATION: Synthetic Construct

<400> SEQUENCE: 320

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Arg Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Val Tyr Ser Thr Pro Ile
                85                  90                  95
Thr Phe Gly Gly Gly Thr Lys Val Glu Ile Lys
            100                 105
```

<210> SEQ ID NO 321
<211> LENGTH: 106
<212> TYPE: PRT
<213> ORGANISM: Artificial Sequence
<220> FEATURE:
<223> OTHER INFORMATION: Synthetic Construct

<400> SEQUENCE: 321

```
Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ser Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Leu Val His Trp Pro Thr
                85                  90                  95
Phe Gly Gly Gly Thr Lys Val Glu Ile Lys
            100                 105
```

<210> SEQ ID NO 322
<211> LENGTH: 124
<212> TYPE: PRT
<213> ORGANISM: Artificial Sequence
<220> FEATURE:
<223> OTHER INFORMATION: Synthetic Construct

<400> SEQUENCE: 322

```
Gln Val Gln Leu Val Gln Ser Gly Ala Glu Val Lys Lys Pro Gly Ala
```

-continued

```
                1               5                  10                  15
            Ser Val Lys Val Ser Cys Lys Ala Ser Gly Tyr Thr Phe Thr Ser Tyr
                            20                  25                  30

Tyr Met His Trp Val Arg Gln Ala Pro Gly Gln Gly Leu Glu Trp Met
                            35                  40                  45

Gly Ile Ile Asn Pro Ser Gly Gly Ser Thr Ser Tyr Ala Gln Lys Phe
                            50                  55                  60

Gln Gly Arg Val Thr Met Thr Arg Asp Thr Ser Thr Ser Thr Val Tyr
             65                 70                  75                  80

Met Glu Leu Ser Ser Leu Arg Ser Glu Asp Thr Ala Val Tyr Tyr Cys
                            85                  90                  95

Ala Arg Gly Pro Gly Tyr Thr Ala Leu Asp Tyr Tyr Met Asp
                            100                 105                 110

Val Trp Gly Lys Gly Thr Thr Val Thr Val Ser Ser
                            115                 120

<210> SEQ ID NO 323
<211> LENGTH: 106
<212> TYPE: PRT
<213> ORGANISM: Artificial Sequence
<220> FEATURE:
<223> OTHER INFORMATION: Synthetic Construct

<400> SEQUENCE: 323

1               5                  10                  15
            Glu Ile Val Met Thr Gln Ser Pro Ala Thr Leu Ser Val Ser Pro Gly

Glu Arg Ala Thr Leu Ser Cys Arg Ala Ser Gln Ser Val Ser Ser Asn
                            20                  25                  30

Leu Ala Trp Tyr Gln Gln Lys Pro Gly Gln Ala Pro Arg Leu Leu Ile
                            35                  40                  45

Tyr Gly Ala Ser Thr Arg Ala Thr Gly Ile Pro Ala Arg Phe Ser Gly
                            50                  55                  60

Ser Gly Ser Gly Thr Glu Phe Thr Leu Thr Ile Ser Ser Leu Gln Ser
             65                 70                  75                  80

Glu Asp Phe Ala Val Tyr Tyr Cys Gln Gln Leu Asp Asp Trp Phe Thr
                            85                  90                  95

Phe Gly Gly Gly Thr Lys Val Glu Ile Lys
                            100                 105

<210> SEQ ID NO 324
<211> LENGTH: 116
<212> TYPE: PRT
<213> ORGANISM: Artificial Sequence
<220> FEATURE:
<223> OTHER INFORMATION: Synthetic Construct

<400> SEQUENCE: 324

1               5                  10                  15
            Gln Val Gln Leu Val Gln Ser Gly Ala Glu Val Lys Lys Pro Gly Ala

Ser Val Lys Val Ser Cys Lys Ala Ser Gly Tyr Thr Phe Thr Ser Tyr
                            20                  25                  30

Tyr Met His Trp Val Arg Gln Ala Pro Gly Gln Gly Leu Glu Trp Met
                            35                  40                  45

Gly Ile Ile Asn Pro Ser Gly Gly Ser Thr Ser Tyr Ala Gln Lys Phe
                            50                  55                  60

Gln Gly Arg Val Thr Met Thr Arg Asp Thr Ser Thr Ser Thr Val Tyr
             65                 70                  75                  80
```

Met Glu Leu Ser Ser Leu Arg Ser Glu Asp Thr Ala Val Tyr Tyr Cys
                85                  90                  95

Ala Arg Pro Ala Lys Thr Ala Asp Tyr Trp Gly Gln Gly Thr Leu Val
            100                 105                 110

Thr Val Ser Ser
        115

<210> SEQ ID NO 325
<211> LENGTH: 107
<212> TYPE: PRT
<213> ORGANISM: Artificial Sequence
<220> FEATURE:
<223> OTHER INFORMATION: Synthetic Construct

<400> SEQUENCE: 325

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Tyr Pro Ile
                85                  90                  95

Thr Phe Gly Gly Gly Thr Lys Val Glu Ile Lys
            100                 105

<210> SEQ ID NO 326
<211> LENGTH: 116
<212> TYPE: PRT
<213> ORGANISM: Artificial Sequence
<220> FEATURE:
<223> OTHER INFORMATION: Synthetic Construct

<400> SEQUENCE: 326

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Lys Ser Met Asp Val Trp Gly Gln Gly Thr Thr Val
            100                 105                 110

Thr Val Ser Ser
        115

<210> SEQ ID NO 327
<211> LENGTH: 107
<212> TYPE: PRT
<213> ORGANISM: Artificial Sequence
<220> FEATURE:
<223> OTHER INFORMATION: Synthetic Construct

<400> SEQUENCE: 327

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Leu Tyr Pro Ile
                85                  90                  95

Thr Phe Gly Gly Gly Thr Lys Val Glu Ile Lys
            100                 105

<210> SEQ ID NO 328
<211> LENGTH: 107
<212> TYPE: PRT
<213> ORGANISM: Artificial Sequence
<220> FEATURE:
<223> OTHER INFORMATION: Synthetic Construct

<400> SEQUENCE: 328

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Ala Tyr Pro Ile
                85                  90                  95

Thr Phe Gly Gly Gly Thr Lys Val Glu Ile Lys
            100                 105

<210> SEQ ID NO 329
<211> LENGTH: 107
<212> TYPE: PRT
<213> ORGANISM: Artificial Sequence
<220> FEATURE:
<223> OTHER INFORMATION: Synthetic Construct

<400> SEQUENCE: 329

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Ser His Pro Ile
                 85                  90                  95

Thr Phe Gly Gly Gly Thr Lys Val Glu Ile Lys
            100                 105
```

<210> SEQ ID NO 330
<211> LENGTH: 108
<212> TYPE: PRT
<213> ORGANISM: Artificial Sequence
<220> FEATURE:
<223> OTHER INFORMATION: Synthetic Construct

<400> SEQUENCE: 330

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Gly Ser Pro
                 85                  90                  95

Phe Thr Phe Gly Gly Gly Thr Lys Val Glu Ile Lys
            100                 105
```

<210> SEQ ID NO 331
<211> LENGTH: 121
<212> TYPE: PRT
<213> ORGANISM: Artificial Sequence
<220> FEATURE:
<223> OTHER INFORMATION: Synthetic Construct

<400> SEQUENCE: 331

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Val Gly Gly Gln Asp Tyr Tyr Tyr Met Asp Val Trp Gly
            100                 105                 110

Lys Gly Thr Thr Val Thr Val Ser Ser
            115                 120
```

<210> SEQ ID NO 332
<211> LENGTH: 106
<212> TYPE: PRT
<213> ORGANISM: Artificial Sequence

```
<220> FEATURE:
<223> OTHER INFORMATION: Synthetic Construct

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Asp Val Phe Thr
                85                  90                  95

Phe Gly Gly Gly Thr Lys Val Glu Ile Lys
            100                 105

<210> SEQ ID NO 333
<211> LENGTH: 108
<212> TYPE: PRT
<213> ORGANISM: Artificial Sequence
<220> FEATURE:
<223> OTHER INFORMATION: Synthetic Construct

<400> SEQUENCE: 333

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Asn Ser Pro
                85                  90                  95

Phe Thr Phe Gly Gly Gly Thr Lys Val Glu Ile Lys
            100                 105

<210> SEQ ID NO 334
<211> LENGTH: 107
<212> TYPE: PRT
<213> ORGANISM: Artificial Sequence
<220> FEATURE:
<223> OTHER INFORMATION: Synthetic Construct

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Asp Pro Phe
            85                  90                  95

Thr Phe Gly Gly Gly Thr Lys Val Glu Ile Lys
            100                 105

<210> SEQ ID NO 335
<211> LENGTH: 120
<212> TYPE: PRT
<213> ORGANISM: Artificial Sequence
<220> FEATURE:
<223> OTHER INFORMATION: Synthetic Construct

<400> SEQUENCE: 335

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gly Pro Leu Tyr His Pro Met Ile Phe Asp Tyr Trp Gly Gln
            100                 105                 110

Gly Thr Leu Val Thr Val Ser Ser
        115                 120

<210> SEQ ID NO 336
<211> LENGTH: 107
<212> TYPE: PRT
<213> ORGANISM: Artificial Sequence
<220> FEATURE:
<223> OTHER INFORMATION: Synthetic Construct

<400> SEQUENCE: 336

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Leu Ser Thr Tyr Pro Leu
            85                  90                  95

Thr Phe Gly Gly Gly Thr Lys Val Glu Ile Lys
            100                 105

<210> SEQ ID NO 337
<211> LENGTH: 115
<212> TYPE: PRT
<213> ORGANISM: Artificial Sequence

```
<220> FEATURE:
<223> OTHER INFORMATION: Synthetic Construct

<400> SEQUENCE: 337

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ser Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Ser Ser Val Asp Asn Trp Gly Gln Gly Thr Leu Val Thr
            100                 105                 110

Val Ser Ser
        115

<210> SEQ ID NO 338
<211> LENGTH: 107
<212> TYPE: PRT
<213> ORGANISM: Artificial Sequence
<220> FEATURE:
<223> OTHER INFORMATION: Synthetic Construct

<400> SEQUENCE: 338

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Val Tyr Pro Ile
                85                  90                  95

Thr Phe Gly Gly Gly Thr Lys Val Glu Ile Lys
            100                 105

<210> SEQ ID NO 339
<211> LENGTH: 126
<212> TYPE: PRT
<213> ORGANISM: Artificial Sequence
<220> FEATURE:
<223> OTHER INFORMATION: Synthetic Construct

<400> SEQUENCE: 339

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45
```

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Thr Lys Ala Tyr Tyr Gly Ser Gly Ser Tyr Val Val
            100                 105                 110

Phe Asp Pro Trp Gly Gln Gly Thr Leu Val Thr Val Ser Ser
            115                 120                 125

<210> SEQ ID NO 340
<211> LENGTH: 107
<212> TYPE: PRT
<213> ORGANISM: Artificial Sequence
<220> FEATURE:
<223> OTHER INFORMATION: Synthetic Construct

<400> SEQUENCE: 340

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Ser Leu Phe Pro Leu
                85                  90                  95

Thr Phe Gly Gly Gly Thr Lys Val Glu Ile Lys
            100                 105

<210> SEQ ID NO 341
<211> LENGTH: 122
<212> TYPE: PRT
<213> ORGANISM: Artificial Sequence
<220> FEATURE:
<223> OTHER INFORMATION: Synthetic Construct

<400> SEQUENCE: 341

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ile Tyr Ser Thr Gly Ala Thr Ala Phe Asp Ile Trp
            100                 105                 110

Gly Gln Gly Thr Met Val Thr Val Ser Ser
            115                 120

<210> SEQ ID NO 342
<211> LENGTH: 108
<212> TYPE: PRT
<213> ORGANISM: Artificial Sequence
<220> FEATURE:
<223> OTHER INFORMATION: Synthetic Construct

<400> SEQUENCE: 342

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Asp Tyr Asn Ser Tyr Ser Pro
                85                  90                  95

Ile Thr Phe Gly Gly Gly Thr Lys Val Glu Ile Lys
            100                 105

<210> SEQ ID NO 343
<211> LENGTH: 119
<212> TYPE: PRT
<213> ORGANISM: Artificial Sequence
<220> FEATURE:
<223> OTHER INFORMATION: Synthetic Construct

<400> SEQUENCE: 343

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Trp Tyr Ser Leu Phe Asp Ile Trp Gly Gln Gly
            100                 105                 110

Thr Met Val Thr Val Ser Ser
        115

<210> SEQ ID NO 344
<211> LENGTH: 107
<212> TYPE: PRT
<213> ORGANISM: Artificial Sequence
<220> FEATURE:
<223> OTHER INFORMATION: Synthetic Construct

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ile Ala Leu Pro Phe
                 85                  90                  95

Thr Phe Gly Gly Gly Thr Lys Val Glu Ile Lys
            100                 105

<210> SEQ ID NO 345
<211> LENGTH: 116
<212> TYPE: PRT
<213> ORGANISM: Artificial Sequence
<220> FEATURE:
<223> OTHER INFORMATION: Synthetic Construct

<400> SEQUENCE: 345

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Ser Tyr Ala Gln Lys Phe
     50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                 85                  90                  95

Ala Arg Ala Ser Lys Met Gly Asp Asp Trp Gly Gln Gly Thr Leu Val
            100                 105                 110

Thr Val Ser Ser
        115

<210> SEQ ID NO 346
<211> LENGTH: 107
<212> TYPE: PRT
<213> ORGANISM: Artificial Sequence
<220> FEATURE:
<223> OTHER INFORMATION: Synthetic Construct

<400> SEQUENCE: 346

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
         35                  40                  45

Tyr Asp Ala Ser Lys Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Ser Met Pro Ile
                 85                  90                  95

```
Thr Phe Gly Gly Gly Thr Lys Val Glu Ile Lys
                100                 105
```

<210> SEQ ID NO 347
<211> LENGTH: 120
<212> TYPE: PRT
<213> ORGANISM: Artificial Sequence
<220> FEATURE:
<223> OTHER INFORMATION: Synthetic Construct

<400> SEQUENCE: 347

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile His Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Pro Arg Val Ser Tyr Phe Gln His Trp Gly Gln
                100                 105                 110

Gly Thr Leu Val Thr Val Ser Ser
            115                 120
```

<210> SEQ ID NO 348
<211> LENGTH: 107
<212> TYPE: PRT
<213> ORGANISM: Artificial Sequence
<220> FEATURE:
<223> OTHER INFORMATION: Synthetic Construct

<400> SEQUENCE: 348

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ser Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Phe Asn Arg Pro Pro
                85                  90                  95

Thr Phe Gly Gly Gly Thr Lys Val Glu Ile Lys
                100                 105
```

<210> SEQ ID NO 349
<211> LENGTH: 123
<212> TYPE: PRT
<213> ORGANISM: Artificial Sequence
<220> FEATURE:
<223> OTHER INFORMATION: Synthetic Construct

<400> SEQUENCE: 349

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Gly His Tyr Asp Asp Trp Ser Gly Leu Gly Leu Asp Val
            100                 105                 110

Trp Gly Gln Gly Thr Met Val Thr Val Ser Ser
        115                 120

<210> SEQ ID NO 350
<211> LENGTH: 107
<212> TYPE: PRT
<213> ORGANISM: Artificial Sequence
<220> FEATURE:
<223> OTHER INFORMATION: Synthetic Construct

<400> SEQUENCE: 350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Val His Pro Tyr
                85                  90                  95

Thr Phe Gly Gly Gly Thr Lys Val Glu Ile Lys
            100                 105

<210> SEQ ID NO 351
<211> LENGTH: 120
<212> TYPE: PRT
<213> ORGANISM: Artificial Sequence
<220> FEATURE:
<223> OTHER INFORMATION: Synthetic Construct

<400> SEQUENCE: 351

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

```
Met Glu Leu Arg Ser Leu Arg Ser Asp Asp Thr Ala Val Tyr Tyr Cys
                85                  90                  95

Ala Arg Gly Ser Gly Ser Gly Tyr Asp Ser Trp Tyr Asp Trp Gly Gln
            100                 105                 110

Gly Thr Leu Val Thr Val Ser Ser
        115                 120

<210> SEQ ID NO 352
<211> LENGTH: 107
<212> TYPE: PRT
<213> ORGANISM: Artificial Sequence
<220> FEATURE:
<223> OTHER INFORMATION: Synthetic Construct

<400> SEQUENCE: 352

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Leu Pro Pro
                85                  90                  95

Thr Phe Gly Gly Gly Thr Lys Val Glu Ile Lys
            100                 105

<210> SEQ ID NO 353
<211> LENGTH: 122
<212> TYPE: PRT
<213> ORGANISM: Artificial Sequence
<220> FEATURE:
<223> OTHER INFORMATION: Synthetic Construct

<400> SEQUENCE: 353

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Arg Trp Ser Ser Gly Ser Thr Ala Phe Asp Ile Trp
            100                 105                 110

Gly Gln Gly Thr Met Val Thr Val Ser Ser
        115                 120

<210> SEQ ID NO 354
<211> LENGTH: 106
<212> TYPE: PRT
```

<213> ORGANISM: Artificial Sequence
<220> FEATURE:
<223> OTHER INFORMATION: Synthetic Construct

<400> SEQUENCE: 354

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Gly Tyr Thr
                85                  90                  95

Phe Gly Gly Gly Thr Lys Val Glu Ile Lys
            100                 105

<210> SEQ ID NO 355
<211> LENGTH: 122
<212> TYPE: PRT
<213> ORGANISM: Artificial Sequence
<220> FEATURE:
<223> OTHER INFORMATION: Synthetic Construct

<400> SEQUENCE: 355

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Arg Lys Pro Ser Gly Ser Val Ala Phe Asp Ile Trp
            100                 105                 110

Gly Gln Gly Thr Met Val Thr Val Ser Ser
        115                 120

<210> SEQ ID NO 356
<211> LENGTH: 107
<212> TYPE: PRT
<213> ORGANISM: Artificial Sequence
<220> FEATURE:
<223> OTHER INFORMATION: Synthetic Construct

<400> SEQUENCE: 356

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asp Tyr Ser Trp Pro Tyr
                 85                  90                  95

Thr Phe Gly Gly Gly Thr Lys Val Glu Ile Lys
            100                 105

<210> SEQ ID NO 357
<211> LENGTH: 117
<212> TYPE: PRT
<213> ORGANISM: Artificial Sequence
<220> FEATURE:
<223> OTHER INFORMATION: Synthetic Construct

<400> SEQUENCE: 357

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Gly His Lys Thr His Asp Tyr Trp Gly Gln Gly Thr Leu
            100                 105                 110

Val Thr Val Ser Ser
        115

<210> SEQ ID NO 358
<211> LENGTH: 107
<212> TYPE: PRT
<213> ORGANISM: Artificial Sequence
<220> FEATURE:
<223> OTHER INFORMATION: Synthetic Construct

<400> SEQUENCE: 358

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ala Tyr Pro Ile
                85                  90                  95

Thr Phe Gly Gly Gly Thr Lys Val Glu Ile Lys
            100                 105

```
<210> SEQ ID NO 359
<211> LENGTH: 107
<212> TYPE: PRT
<213> ORGANISM: Artificial Sequence
<220> FEATURE:
<223> OTHER INFORMATION: Synthetic Construct

<400> SEQUENCE: 359

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser His Phe Pro Ile
                85                  90                  95

Thr Phe Gly Gly Gly Thr Lys Val Glu Ile Lys
            100                 105

<210> SEQ ID NO 360
<211> LENGTH: 116
<212> TYPE: PRT
<213> ORGANISM: Artificial Sequence
<220> FEATURE:
<223> OTHER INFORMATION: Synthetic Construct

<400> SEQUENCE: 360

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Ser Met Thr Asp Tyr Trp Gly Gln Gly Thr Leu Val
            100                 105                 110

Thr Val Ser Ser
        115

<210> SEQ ID NO 361
<211> LENGTH: 107
<212> TYPE: PRT
<213> ORGANISM: Artificial Sequence
<220> FEATURE:
<223> OTHER INFORMATION: Synthetic Construct

<400> SEQUENCE: 361

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Tyr Pro Ile
                85                  90                  95

Thr Phe Gly Gly Gly Thr Lys Val Glu Ile Lys
            100                 105

<210> SEQ ID NO 362
<211> LENGTH: 117
<212> TYPE: PRT
<213> ORGANISM: Artificial Sequence
<220> FEATURE:
<223> OTHER INFORMATION: Synthetic Construct

<400> SEQUENCE: 362

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Lys Ser Val Asp His Asp Tyr Trp Gly Gln Gly Thr Leu
            100                 105                 110

Val Thr Val Ser Ser
        115

<210> SEQ ID NO 363
<211> LENGTH: 107
<212> TYPE: PRT
<213> ORGANISM: Artificial Sequence
<220> FEATURE:
<223> OTHER INFORMATION: Synthetic Construct

<400> SEQUENCE: 363

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asp Tyr Pro Ile
                85                  90                  95

Thr Phe Gly Gly Gly Thr Lys Val Glu Ile Lys

<210> SEQ ID NO 364
<211> LENGTH: 107
<212> TYPE: PRT
<213> ORGANISM: Artificial Sequence
<220> FEATURE:
<223> OTHER INFORMATION: Synthetic Construct

<400> SEQUENCE: 364

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Val Tyr Pro Ile
                85                  90                  95

Thr Phe Gly Gly Gly Thr Lys Val Glu Ile Lys
            100                 105

<210> SEQ ID NO 365
<211> LENGTH: 122
<212> TYPE: PRT
<213> ORGANISM: Artificial Sequence
<220> FEATURE:
<223> OTHER INFORMATION: Synthetic Construct

<400> SEQUENCE: 365

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Thr His Asp Tyr Asp Leu Ala Phe Asp Ile Trp
            100                 105                 110

Gly Gln Gly Thr Met Val Thr Val Ser Ser
        115                 120

<210> SEQ ID NO 366
<211> LENGTH: 108
<212> TYPE: PRT
<213> ORGANISM: Artificial Sequence
<220> FEATURE:
<223> OTHER INFORMATION: Synthetic Construct

<400> SEQUENCE: 366

Glu Ile Val Met Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Ser His Pro
                85                  90                  95

Phe Thr Phe Gly Gly Gly Thr Lys Val Glu Ile Lys
                100                 105
```

<210> SEQ ID NO 367
<211> LENGTH: 117
<212> TYPE: PRT
<213> ORGANISM: Artificial Sequence
<220> FEATURE:
<223> OTHER INFORMATION: Synthetic Construct

<400> SEQUENCE: 367

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
                35                  40                  45

Gly Ser Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Thr Glu Thr Leu Phe Asp Tyr Trp Gly Gln Gly Thr Leu
                100                 105                 110

Val Thr Val Ser Ser
        115
```

<210> SEQ ID NO 368
<211> LENGTH: 107
<212> TYPE: PRT
<213> ORGANISM: Artificial Sequence
<220> FEATURE:
<223> OTHER INFORMATION: Synthetic Construct

<400> SEQUENCE: 368

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
                20                  25                  30

Leu Asn Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Phe Ser Gly
    50                  55                  60

Ser Arg Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Val Asn Tyr Pro Pro
```

```
                85                  90                  95

Thr Phe Gly Gly Gly Thr Lys Val Glu Ile Lys
                100                 105

<210> SEQ ID NO 369
<211> LENGTH: 121
<212> TYPE: PRT
<213> ORGANISM: Artificial Sequence
<220> FEATURE:
<223> OTHER INFORMATION: Synthetic Construct

<400> SEQUENCE: 369

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Thr Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Lys Met Leu Asp Asp Gly Tyr Ala Phe Asp Ile Trp Gly
                100                 105                 110

Gln Gly Thr Met Val Thr Val Ser Ser
            115                 120

<210> SEQ ID NO 370
<211> LENGTH: 107
<212> TYPE: PRT
<213> ORGANISM: Artificial Sequence
<220> FEATURE:
<223> OTHER INFORMATION: Synthetic Construct

<400> SEQUENCE: 370

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Asn Tyr Pro Tyr
                85                  90                  95

Thr Phe Gly Gly Gly Thr Lys Val Glu Ile Lys
                100                 105

<210> SEQ ID NO 371
<211> LENGTH: 107
<212> TYPE: PRT
<213> ORGANISM: Artificial Sequence
<220> FEATURE:
<223> OTHER INFORMATION: Synthetic Construct

<400> SEQUENCE: 371
```

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Thr Phe Pro Ile
                85                  90                  95

Thr Phe Gly Gly Gly Thr Lys Val Glu Ile Lys
            100                 105

<210> SEQ ID NO 372
<211> LENGTH: 121
<212> TYPE: PRT
<213> ORGANISM: Artificial Sequence
<220> FEATURE:
<223> OTHER INFORMATION: Synthetic Construct

<400> SEQUENCE: 372

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Tyr Ser Ser Leu Leu Ala Leu Asp Ile Trp Gly
            100                 105                 110

Gln Gly Thr Met Val Thr Val Ser Ser
        115                 120

<210> SEQ ID NO 373
<211> LENGTH: 107
<212> TYPE: PRT
<213> ORGANISM: Artificial Sequence
<220> FEATURE:
<223> OTHER INFORMATION: Synthetic Construct

<400> SEQUENCE: 373

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro

```
65                  70                  75                  80
Glu Asp Phe Ala Val Tyr Tyr Cys Gln Gln Val Ser Asn Tyr Pro Phe
                85                  90                  95
Thr Phe Gly Gly Gly Thr Lys Val Glu Ile Lys
            100                 105
```

<210> SEQ ID NO 374
<211> LENGTH: 122
<212> TYPE: PRT
<213> ORGANISM: Artificial Sequence
<220> FEATURE:
<223> OTHER INFORMATION: Synthetic Construct

<400> SEQUENCE: 374

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Gly Arg Arg Gly Asp Asn Asn Trp Phe Asp Pro Trp
            100                 105                 110
Gly Gln Gly Thr Leu Val Thr Val Ser Ser
        115                 120
```

<210> SEQ ID NO 375
<211> LENGTH: 113
<212> TYPE: PRT
<213> ORGANISM: Artificial Sequence
<220> FEATURE:
<223> OTHER INFORMATION: Synthetic Construct

<400> SEQUENCE: 375

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr His Asp Ala Pro Ile Thr Phe Gly Gly Gly Thr Lys Val Glu Ile
            100                 105                 110
Lys
```

<210> SEQ ID NO 376
<211> LENGTH: 117
<212> TYPE: PRT

<213> ORGANISM: Artificial Sequence
<220> FEATURE:
<223> OTHER INFORMATION: Synthetic Construct

<400> SEQUENCE: 376

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Pro His Glu Met Asp Tyr Trp Gly Gln Gly Thr Leu
            100                 105                 110

Val Thr Val Ser Ser
        115
```

<210> SEQ ID NO 377
<211> LENGTH: 113
<212> TYPE: PRT
<213> ORGANISM: Artificial Sequence
<220> FEATURE:
<223> OTHER INFORMATION: Synthetic Construct

<400> SEQUENCE: 377

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ala Tyr Val Val Pro Pro Thr Phe Gly Gly Gly Thr Lys Val Glu Ile
            100                 105                 110

Lys
```

<210> SEQ ID NO 378
<211> LENGTH: 119
<212> TYPE: PRT
<213> ORGANISM: Artificial Sequence
<220> FEATURE:
<223> OTHER INFORMATION: Synthetic Construct

<400> SEQUENCE: 378

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Pro Tyr Pro Trp Ile Tyr Phe Asp Leu Trp Gly Arg Gly
            100                 105                 110

Thr Leu Val Thr Val Ser Ser
            115

<210> SEQ ID NO 379
<211> LENGTH: 107
<212> TYPE: PRT
<213> ORGANISM: Artificial Sequence
<220> FEATURE:
<223> OTHER INFORMATION: Synthetic Construct

<400> SEQUENCE: 379

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ala Asp Asn Trp Pro Phe
                 85                  90                  95

Thr Phe Gly Gly Gly Thr Lys Val Glu Ile Lys
            100                 105

<210> SEQ ID NO 380
<211> LENGTH: 120
<212> TYPE: PRT
<213> ORGANISM: Artificial Sequence
<220> FEATURE:
<223> OTHER INFORMATION: Synthetic Construct

<400> SEQUENCE: 380

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Gly Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Arg Arg His Tyr Gly Gly Met Asp Val Trp Gly Gln
            100                 105                 110
```

Gly Thr Thr Val Thr Val Ser Ser
        115                 120

<210> SEQ ID NO 381
<211> LENGTH: 112
<212> TYPE: PRT
<213> ORGANISM: Artificial Sequence
<220> FEATURE:
<223> OTHER INFORMATION: Synthetic Construct

<400> SEQUENCE: 381

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Ser Pro Arg Thr Phe Gly Gly Gly Thr Lys Val Glu Ile Lys
            100                 105                 110

<210> SEQ ID NO 382
<211> LENGTH: 122
<212> TYPE: PRT
<213> ORGANISM: Artificial Sequence
<220> FEATURE:
<223> OTHER INFORMATION: Synthetic Construct

<400> SEQUENCE: 382

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Thr Phe Trp Ser Gly Ser Trp Ala Leu Tyr Trp
            100                 105                 110

Gly Gln Gly Thr Leu Val Thr Val Ser Ser
        115                 120

<210> SEQ ID NO 383
<211> LENGTH: 107
<212> TYPE: PRT
<213> ORGANISM: Artificial Sequence
<220> FEATURE:
<223> OTHER INFORMATION: Synthetic Construct

<400> SEQUENCE: 383

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Val Asn Trp Pro Phe
                85                  90                  95

Thr Phe Gly Gly Gly Thr Lys Val Glu Ile Lys
            100                 105
```

<210> SEQ ID NO 384
<211> LENGTH: 123
<212> TYPE: PRT
<213> ORGANISM: Artificial Sequence
<220> FEATURE:
<223> OTHER INFORMATION: Synthetic Construct

<400> SEQUENCE: 384

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Asn Tyr Asp Tyr Trp Ser Gly Ala Leu Arg Tyr
            100                 105                 110

Trp Gly Gln Gly Thr Leu Val Thr Val Ser Ser
        115                 120
```

<210> SEQ ID NO 385
<211> LENGTH: 107
<212> TYPE: PRT
<213> ORGANISM: Artificial Sequence
<220> FEATURE:
<223> OTHER INFORMATION: Synthetic Construct

<400> SEQUENCE: 385

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Ser Ser Asn Trp Pro Trp
                85                  90                  95

Thr Phe Gly Gly Gly Thr Lys Val Glu Ile Lys
            100                 105

<210> SEQ ID NO 386
<211> LENGTH: 118
<212> TYPE: PRT
<213> ORGANISM: Artificial Sequence
<220> FEATURE:
<223> OTHER INFORMATION: Synthetic Construct

<400> SEQUENCE: 386

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Val Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Ser Ser Ser Trp Tyr Lys Ala Trp Gly Gln Gly Thr
            100                 105                 110

Met Val Thr Val Ser Ser
        115

<210> SEQ ID NO 387
<211> LENGTH: 107
<212> TYPE: PRT
<213> ORGANISM: Artificial Sequence
<220> FEATURE:
<223> OTHER INFORMATION: Synthetic Construct

<400> SEQUENCE: 387

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Thr Phe Pro Ile
                85                  90                  95

Thr Phe Gly Gly Gly Thr Lys Val Glu Ile Lys
            100                 105

<210> SEQ ID NO 388
<211> LENGTH: 123
<212> TYPE: PRT
<213> ORGANISM: Artificial Sequence
<220> FEATURE:
<223> OTHER INFORMATION: Synthetic Construct

<400> SEQUENCE: 388

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Lys Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Val Val Gly Arg Pro Gly Tyr Ser Ala Phe Asp Ile
            100                 105                 110

Trp Gly Gln Gly Thr Met Val Thr Val Ser Ser
        115                 120

<210> SEQ ID NO 389
<211> LENGTH: 107
<212> TYPE: PRT
<213> ORGANISM: Artificial Sequence
<220> FEATURE:
<223> OTHER INFORMATION: Synthetic Construct

<400> SEQUENCE: 389

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asn Ser Leu Pro Leu
                85                  90                  95

Thr Phe Gly Gly Gly Thr Lys Val Glu Ile Lys
            100                 105

<210> SEQ ID NO 390
<211> LENGTH: 107
<212> TYPE: PRT
<213> ORGANISM: Artificial Sequence
<220> FEATURE:
<223> OTHER INFORMATION: Synthetic Construct

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Ile
                85                  90                  95

Thr Phe Gly Gly Gly Thr Lys Val Glu Ile Lys
            100                 105

<210> SEQ ID NO 391
<211> LENGTH: 124
<212> TYPE: PRT
<213> ORGANISM: Artificial Sequence
<220> FEATURE:
<223> OTHER INFORMATION: Synthetic Construct

<400> SEQUENCE: 391

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Gly Tyr Gly Gly Ala Ala Tyr Gly Met Asp
            100                 105                 110

Val Trp Gly Gln Gly Thr Thr Val Thr Val Ser Ser
        115                 120

<210> SEQ ID NO 392
<211> LENGTH: 108
<212> TYPE: PRT
<213> ORGANISM: Artificial Sequence
<220> FEATURE:
<223> OTHER INFORMATION: Synthetic Construct

<400> SEQUENCE: 392

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Val Asp Tyr Pro Pro
                85                  90                  95

Leu Thr Phe Gly Gly Gly Thr Lys Val Glu Ile Lys
            100                 105

<210> SEQ ID NO 393
<211> LENGTH: 122
<212> TYPE: PRT

<213> ORGANISM: Artificial Sequence
<220> FEATURE:
<223> OTHER INFORMATION: Synthetic Construct

<400> SEQUENCE: 393

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val Tyr Gly Leu Gly Asn Trp Phe Asp Pro Trp
            100                 105                 110

Gly Gln Gly Thr Leu Val Thr Val Ser Ser
        115                 120
```

<210> SEQ ID NO 394
<211> LENGTH: 107
<212> TYPE: PRT
<213> ORGANISM: Artificial Sequence
<220> FEATURE:
<223> OTHER INFORMATION: Synthetic Construct

<400> SEQUENCE: 394

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Asn Ser Tyr Ser Pro
                85                  90                  95

Thr Phe Gly Gly Gly Thr Lys Val Glu Ile Lys
            100                 105
```

<210> SEQ ID NO 395
<211> LENGTH: 119
<212> TYPE: PRT
<213> ORGANISM: Artificial Sequence
<220> FEATURE:
<223> OTHER INFORMATION: Synthetic Construct

<400> SEQUENCE: 395

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45
```

Gly Ser Ile Tyr Tyr Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Trp Asp Arg Val Gly Trp Phe Asp Pro Trp Gly Gln Gly
                100                 105                 110

Thr Leu Val Thr Val Ser Ser
            115

<210> SEQ ID NO 396
<211> LENGTH: 107
<212> TYPE: PRT
<213> ORGANISM: Artificial Sequence
<220> FEATURE:
<223> OTHER INFORMATION: Synthetic Construct

<400> SEQUENCE: 396

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Phe Trp Pro Pro
                85                  90                  95

Thr Phe Gly Gly Gly Thr Lys Val Glu Ile Lys
            100                 105

<210> SEQ ID NO 397
<211> LENGTH: 110
<212> TYPE: PRT
<213> ORGANISM: Artificial Sequence
<220> FEATURE:
<223> OTHER INFORMATION: Synthetic Construct

<400> SEQUENCE: 397

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

```
<210> SEQ ID NO 398
<211> LENGTH: 9
<212> TYPE: PRT
<213> ORGANISM: Artificial Sequence
<220> FEATURE:
<223> OTHER INFORMATION: Synthetic Construct

<400> SEQUENCE: 398

Tyr Thr Phe Thr Ser Tyr Tyr Ile His
1               5

<210> SEQ ID NO 399
<211> LENGTH: 17
<212> TYPE: PRT
<213> ORGANISM: Artificial Sequence
<220> FEATURE:
<223> OTHER INFORMATION: Synthetic Construct

<400> SEQUENCE: 399

Ile Ile Asn Pro Ser Gly Gly Ser Thr Ser Tyr Ala Gln Lys Phe Gln
1               5                   10                  15

Gly

<210> SEQ ID NO 400
<211> LENGTH: 16
<212> TYPE: PRT
<213> ORGANISM: Artificial Sequence
<220> FEATURE:
<223> OTHER INFORMATION: Synthetic Construct

<400> SEQUENCE: 400

Ala Arg Glu Ala Asp Asp Ser Ser Gly Tyr Pro Leu Gly Leu Asp Val
1               5                   10                  15

<210> SEQ ID NO 401
<211> LENGTH: 11
<212> TYPE: PRT
<213> ORGANISM: Artificial Sequence
<220> FEATURE:
<223> OTHER INFORMATION: Synthetic Construct

<400> SEQUENCE: 401

Arg Ala Ser Gln Ser Val Ser Ser Asn Leu Ala
1               5                   10

<210> SEQ ID NO 402
<211> LENGTH: 7
<212> TYPE: PRT
<213> ORGANISM: Artificial Sequence
<220> FEATURE:
<223> OTHER INFORMATION: Synthetic Construct

<400> SEQUENCE: 402

Gly Ala Ser Thr Arg Ala Thr
1               5

<210> SEQ ID NO 403
<211> LENGTH: 9
<212> TYPE: PRT
<213> ORGANISM: Artificial Sequence
<220> FEATURE:
<223> OTHER INFORMATION: Synthetic Construct

<400> SEQUENCE: 403

Gln Gln Val Asn Ser Leu Pro Pro Thr
1               5
```

<210> SEQ ID NO 404
<211> LENGTH: 9
<212> TYPE: PRT
<213> ORGANISM: Artificial Sequence
<220> FEATURE:
<223> OTHER INFORMATION: Synthetic Construct

<400> SEQUENCE: 404

Tyr Ser Phe Thr Thr Tyr Trp Ile Gly
1               5

<210> SEQ ID NO 405
<211> LENGTH: 17
<212> TYPE: PRT
<213> ORGANISM: Artificial Sequence
<220> FEATURE:
<223> OTHER INFORMATION: Synthetic Construct

<400> SEQUENCE: 405

Ile Ile Tyr Pro Gly Asp Ser Asp Thr Arg Tyr Ser Pro Ser Phe Gln
1               5                   10                  15

Gly

<210> SEQ ID NO 406
<211> LENGTH: 15
<212> TYPE: PRT
<213> ORGANISM: Artificial Sequence
<220> FEATURE:
<223> OTHER INFORMATION: Synthetic Construct

<400> SEQUENCE: 406

Ala Arg Ala Gly His Tyr Asp Gly Gly His Leu Gly Met Asp Val
1               5                   10                  15

<210> SEQ ID NO 407
<211> LENGTH: 12
<212> TYPE: PRT
<213> ORGANISM: Artificial Sequence
<220> FEATURE:
<223> OTHER INFORMATION: Synthetic Construct

<400> SEQUENCE: 407

Arg Ala Ser Gln Ser Val Ser Ser Ser Tyr Leu Ala
1               5                   10

<210> SEQ ID NO 408
<211> LENGTH: 7
<212> TYPE: PRT
<213> ORGANISM: Artificial Sequence
<220> FEATURE:
<223> OTHER INFORMATION: Synthetic Construct

<400> SEQUENCE: 408

Gly Ala Ser Asn Arg Ala Thr
1               5

<210> SEQ ID NO 409
<211> LENGTH: 9
<212> TYPE: PRT
<213> ORGANISM: Artificial Sequence
<220> FEATURE:
<223> OTHER INFORMATION: Synthetic Construct

<400> SEQUENCE: 409

Gln Gln Asp Asp Ser Ala Pro Tyr Thr
1               5

-continued

```
<210> SEQ ID NO 410
<211> LENGTH: 122
<212> TYPE: PRT
<213> ORGANISM: Artificial Sequence
<220> FEATURE:
<223> OTHER INFORMATION: Synthetic Construct

<400> SEQUENCE: 410

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Gly His Tyr Asp Gly Gly His Leu Gly Met Asp Val Trp
            100                 105                 110

Gly Gln Gly Thr Thr Val Thr Val Ser Ser
        115                 120

<210> SEQ ID NO 411
<211> LENGTH: 108
<212> TYPE: PRT
<213> ORGANISM: Artificial Sequence
<220> FEATURE:
<223> OTHER INFORMATION: Synthetic Construct

<400> SEQUENCE: 411

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Asn Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Asp Ser Ala Pro
                85                  90                  95

Tyr Thr Phe Gly Gly Gly Thr Lys Val Glu Ile Lys
            100                 105

<210> SEQ ID NO 412
<211> LENGTH: 123
<212> TYPE: PRT
<213> ORGANISM: Artificial Sequence
<220> FEATURE:
<223> OTHER INFORMATION: Synthetic Construct

<400> SEQUENCE: 412

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Asp Asp Ser Ser Gly Tyr Pro Leu Gly Leu Asp Val
            100                 105                 110

Trp Gly Gln Gly Thr Met Val Thr Val Ser Ser
        115                 120

<210> SEQ ID NO 413
<211> LENGTH: 107
<212> TYPE: PRT
<213> ORGANISM: Artificial Sequence
<220> FEATURE:
<223> OTHER INFORMATION: Synthetic Construct

<400> SEQUENCE: 413

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Val Asn Ser Leu Pro Pro
                85                  90                  95

Thr Phe Gly Gly Gly Thr Lys Val Glu Ile Lys
            100                 105

<210> SEQ ID NO 414
<211> LENGTH: 17
<212> TYPE: PRT
<213> ORGANISM: Artificial Sequence
<220> FEATURE:
<223> OTHER INFORMATION: Synthetic Construct

<400> SEQUENCE: 414

Leu Gln Val Thr Asp Ser Gly Leu Tyr Arg Cys Val Ile Tyr His Pro
1               5                   10                  15

Pro

<210> SEQ ID NO 415
<211> LENGTH: 21
<212> TYPE: PRT
<213> ORGANISM: Artificial Sequence
<220> FEATURE:
<223> OTHER INFORMATION: Synthetic Construct

<400> SEQUENCE: 415

Met Glu Val Gly Trp Tyr Arg Ser Pro Phe Ser Arg Val Val His Leu
1               5                   10                  15

Tyr Arg Asn Gly Lys
         20

<210> SEQ ID NO 416
<211> LENGTH: 21
<212> TYPE: DNA
<213> ORGANISM: Artificial Sequence
<220> FEATURE:
<223> OTHER INFORMATION: Synthetic Construct

<400> SEQUENCE: 416
ctccactcac ggcaaattca a                                      21

<210> SEQ ID NO 417
<211> LENGTH: 22
<212> TYPE: DNA
<213> ORGANISM: Artificial Sequence
<220> FEATURE:
<223> OTHER INFORMATION: Synthetic Construct

<400> SEQUENCE: 417
gatgacaagc ttcccattct cg                                     22

<210> SEQ ID NO 418
<211> LENGTH: 21
<212> TYPE: DNA
<213> ORGANISM: Artificial Sequence
<220> FEATURE:
<223> OTHER INFORMATION: Synthetic Construct

<400> SEQUENCE: 418
ccgtcagccg atttgctatc t                                      21

<210> SEQ ID NO 419
<211> LENGTH: 22
<212> TYPE: DNA
<213> ORGANISM: Artificial Sequence
<220> FEATURE:
<223> OTHER INFORMATION: Synthetic Construct

<400> SEQUENCE: 419
acggcagaga ggaggttgac tt                                     22

<210> SEQ ID NO 420
<211> LENGTH: 22
<212> TYPE: DNA
<213> ORGANISM: Artificial Sequence
<220> FEATURE:
<223> OTHER INFORMATION: Synthetic Construct

<400> SEQUENCE: 420
acaacaaaaa agcctcgtgc tg                                     22

<210> SEQ ID NO 421
<211> LENGTH: 22
<212> TYPE: DNA
<213> ORGANISM: Artificial Sequence
<220> FEATURE:
<223> OTHER INFORMATION: Synthetic Construct

<400> SEQUENCE: 421
ccattgaggt ggagagcttt ca                                     22

<210> SEQ ID NO 422
<211> LENGTH: 22

```
<212> TYPE: DNA
<213> ORGANISM: Artificial Sequence
<220> FEATURE:
<223> OTHER INFORMATION: Synthetic Construct

<400> SEQUENCE: 422
ggcaaaccca aggtctacgt tc                                              22

<210> SEQ ID NO 423
<211> LENGTH: 21
<212> TYPE: DNA
<213> ORGANISM: Artificial Sequence
<220> FEATURE:
<223> OTHER INFORMATION: Synthetic Construct

<400> SEQUENCE: 423
tacctcattg gccagctgct t                                               21

<210> SEQ ID NO 424
<211> LENGTH: 20
<212> TYPE: DNA
<213> ORGANISM: Artificial Sequence
<220> FEATURE:
<223> OTHER INFORMATION: Synthetic Construct

<400> SEQUENCE: 424
aggacctggg ttggaagtgg                                                 20

<210> SEQ ID NO 425
<211> LENGTH: 20
<212> TYPE: DNA
<213> ORGANISM: Artificial Sequence
<220> FEATURE:
<223> OTHER INFORMATION: Synthetic Construct

<400> SEQUENCE: 425
agttggcatg gtagcccttg                                                 20

<210> SEQ ID NO 426
<211> LENGTH: 132
<212> TYPE: PRT
<213> ORGANISM: Homo sapiens

<400> SEQUENCE: 426

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro
    130
```

```
<210> SEQ ID NO 427
<211> LENGTH: 126
<212> TYPE: PRT
<213> ORGANISM: Homo sapiens

<400> SEQUENCE: 427

Leu His Pro Leu Leu Leu Leu Leu Phe Pro Gly Ser Gln Ala
1               5                   10                  15

Gln Ser Lys Ala Gln Val Leu Gln Ser Val Ala Gly Gln Thr Leu Thr
            20                  25                  30

Val Arg Cys Gln Tyr Pro Pro Thr Gly Ser Leu Tyr Glu Lys Lys Gly
        35                  40                  45

Trp Cys Lys Glu Ala Ser Ala Leu Val Cys Ile Arg Leu Val Thr Ser
    50                  55                  60

Ser Lys Pro Arg Thr Met Ala Trp Thr Ser Arg Phe Thr Ile Trp Asp
65                  70                  75                  80

Asp Pro Asp Ala Gly Phe Phe Thr Val Thr Met Thr Asp Leu Arg Glu
                85                  90                  95

Glu Asp Ser Gly His Tyr Trp Cys Arg Ile Tyr Arg Pro Ser Asp Asn
            100                 105                 110

Ser Val Ser Lys Ser Val Arg Phe Tyr Leu Val Val Ser Pro
        115                 120                 125

<210> SEQ ID NO 428
<211> LENGTH: 105
<212> TYPE: PRT
<213> ORGANISM: Homo sapiens

<400> SEQUENCE: 428

Leu Leu Trp Met Leu Phe Val Ser Glu Leu Arg Ala Ala Thr Lys Leu
1               5                   10                  15

Thr Glu Glu Lys Tyr Glu Leu Lys Glu Gly Gln Thr Leu Asp Val Lys
            20                  25                  30

Cys Asp Tyr Thr Leu Glu Lys Phe Ala Ser Ser Gln Lys Ala Trp Gln
        35                  40                  45

Ile Ile Arg Asp Gly Glu Met Pro Lys Thr Leu Ala Cys Thr Glu Arg
    50                  55                  60

Pro Ser Lys Asn Ser His Pro Val Gln Val Gly Arg Ile Ile Leu Glu
65                  70                  75                  80

Asp Tyr His Asp His Gly Leu Leu Arg Val Arg Met Val Asn Leu Gln
                85                  90                  95

Val Glu Asp Ser Gly Leu Tyr Gln Cys
            100                 105

<210> SEQ ID NO 429
<211> LENGTH: 118
<212> TYPE: PRT
<213> ORGANISM: Homo sapiens

<400> SEQUENCE: 429

Glu Leu Arg Ala Ala Thr Lys Leu Thr Gly Glu Lys Tyr Glu Leu Lys
1               5                   10                  15

Glu Gly Gln Thr Leu Asp Val Lys Cys Asp Tyr Thr Leu Glu Lys Phe
            20                  25                  30

Ala Ser Ser Gln Lys Ala Trp Gln Ile Ile Arg Asp Gly Glu Met Pro
        35                  40                  45
```

```
Lys Thr Leu Ala Cys Thr Glu Arg Pro Ser Lys Asn Ser His Pro Val
 50                  55                  60

Gln Val Gly Arg Ile Ile Leu Glu Asp Tyr His Asp His Gly Leu Leu
 65                  70                  75                  80

Arg Val Arg Met Val Asn Leu Gln Val Glu Asp Ser Gly Leu Tyr Gln
                 85                  90                  95

Cys Val Ile Tyr Gln Pro Pro Lys Glu Pro His Met Leu Phe Asp Arg
                100                 105                 110

Ile Arg Leu Val Val Thr
                115

<210> SEQ ID NO 430
<211> LENGTH: 121
<212> TYPE: PRT
<213> ORGANISM: Homo sapiens

<400> SEQUENCE: 430

Val Thr Glu Leu Ser Gly Ala His Asn Thr Thr Val Phe Gln Gly Val
 1               5                  10                  15

Ala Gly Gln Ser Leu Gln Val Ser Cys Pro Tyr Asp Ser Met Lys His
                 20                  25                  30

Trp Gly Arg Arg Lys Ala Trp Cys Arg Gln Leu Gly Glu Lys Gly Pro
             35                  40                  45

Cys Gln Arg Val Val Ser Thr His Asn Leu Trp Leu Leu Ser Phe Leu
 50                  55                  60

Arg Arg Trp Asn Gly Ser Thr Ala Ile Thr Asp Asp Thr Leu Gly Gly
 65                  70                  75                  80

Thr Leu Thr Ile Thr Leu Arg Asn Leu Gln Pro His Asp Ala Gly Leu
                 85                  90                  95

Tyr Gln Cys Gln Ser Leu His Gly Ser Glu Ala Asp Thr Leu Arg Lys
                100                 105                 110

Val Leu Val Glu Val Leu Ala Asp Pro
                115                 120

<210> SEQ ID NO 431
<211> LENGTH: 120
<212> TYPE: PRT
<213> ORGANISM: Mus musculus

<400> SEQUENCE: 431

Glu Val Lys Ala Ala Ile Val Leu Glu Glu Arg Tyr Asp Leu Val
 1               5                  10                  15

Glu Gly Gln Thr Leu Thr Val Lys Cys Pro Phe Asn Ile Met Lys Tyr
                 20                  25                  30

Ala Asn Ser Gln Lys Ala Trp Gln Arg Leu Pro Asp Gly Lys Glu Pro
             35                  40                  45

Leu Thr Leu Val Val Thr Gln Arg Pro Phe Thr Arg Pro Ser Glu Val
 50                  55                  60

His Met Gly Lys Phe Thr Leu Lys His Asp Pro Ser Glu Ala Met Leu
 65                  70                  75                  80

Gln Val Gln Met Thr Asp Leu Gln Val Thr Asp Ser Gly Leu Tyr Arg
                 85                  90                  95

Cys Val Ile Tyr His Pro Pro Asn Asp Pro Val Val Leu Phe His Pro
                100                 105                 110

Val Arg Leu Val Val Thr Lys Gly
                115                 120
```

<210> SEQ ID NO 432
<211> LENGTH: 121
<212> TYPE: PRT
<213> ORGANISM: Mus musculus

<400> SEQUENCE: 432

Ile Thr Ala Leu Ser Gln Ala Leu Asn Thr Thr Val Leu Gln Gly Met
1               5                   10                  15

Ala Gly Gln Ser Leu Arg Val Ser Cys Thr Tyr Asp Ala Leu Lys His
            20                  25                  30

Trp Gly Arg Arg Lys Ala Trp Cys Arg Gln Leu Gly Glu Glu Gly Pro
        35                  40                  45

Cys Gln Arg Val Val Ser Thr His Gly Val Trp Ala Ala Gly Leu Pro
    50                  55                  60

Glu Glu Ala Asp Gly Ser Thr Val Ile Ala Asp Thr Leu Ala Gly
65                  70                  75                  80

Thr Val Thr Ile Thr Leu Lys Asn Leu Gln Ala Gly Asp Ala Gly Leu
                85                  90                  95

Tyr Gln Cys Gln Ser Leu Arg Gly Arg Glu Arg Glu Val Leu Gln Lys
            100                 105                 110

Val Leu Val Glu Val Leu Glu Asp Pro
            115                 120

<210> SEQ ID NO 433
<211> LENGTH: 121
<212> TYPE: PRT
<213> ORGANISM: Mus musculus

<400> SEQUENCE: 433

Leu Cys Val Ser Gly Leu Gln Ala Gly Asp Glu Glu His Lys Cys
1               5                   10                  15

Phe Leu Glu Gly Glu Asn Leu Thr Leu Thr Cys Pro Tyr Asn Ile Met
            20                  25                  30

Leu Tyr Ser Leu Ser Leu Lys Ala Trp Gln Arg Val Arg Ser His Gly
        35                  40                  45

Ser Pro Glu Thr Leu Val Leu Thr Asn Thr Arg Lys Ala Asp Phe Asn
    50                  55                  60

Val Ala Arg Ala Gly Lys Tyr Leu Leu Glu Asp Tyr Pro Thr Glu Ser
65                  70                  75                  80

Val Val Lys Val Thr Val Thr Gly Leu Gln Arg Gln Asp Val Gly Leu
                85                  90                  95

Tyr Gln Cys Val Val Tyr Leu Ser Pro Asp Asn Val Ile Ile Leu Arg
            100                 105                 110

Gln Arg Ile Arg Leu Ala Trp Cys Gln
            115                 120

<210> SEQ ID NO 434
<211> LENGTH: 112
<212> TYPE: PRT
<213> ORGANISM: Homo sapiens

<400> SEQUENCE: 434

Ser Gln Ala Gln Ser Lys Ala Gln Val Leu Gln Ser Val Ala Gly Gln
1               5                   10                  15

Thr Leu Thr Val Arg Cys Gln Tyr Pro Pro Thr Gly Ser Leu Tyr Glu
            20                  25                  30

Lys Lys Gly Trp Cys Lys Glu Ala Ser Ala Leu Val Cys Ile Arg Leu

```
                 35                   40                  45
Val Thr Ser Ser Lys Pro Arg Thr Met Ala Trp Thr Ser Arg Phe Thr
 50                      55                  60

Ile Trp Asp Asp Pro Asp Ala Gly Phe Phe Thr Val Thr Met Thr Asp
 65                  70                  75                  80

Leu Arg Glu Glu Asp Ser Gly His Tyr Trp Cys Arg Ile Tyr Arg Pro
                 85                  90                  95

Ser Asp Asn Ser Val Ser Lys Ser Val Arg Phe Tyr Leu Val Val Ser
                100                 105                 110

<210> SEQ ID NO 435
<211> LENGTH: 109
<212> TYPE: PRT
<213> ORGANISM: Homo sapiens

<400> SEQUENCE: 435

Glu Val Glu Gln Asn Ser Gly Pro Leu Ser Val Pro Glu Gly Ala Ile
 1               5                  10                  15

Ala Ser Leu Asn Cys Thr Tyr Ser Asp Arg Gly Ser Gln Ser Phe Phe
                20                  25                  30

Trp Tyr Arg Gln Tyr Ser Gly Lys Ser Pro Glu Leu Ile Met Ser Ile
                35                  40                  45

Tyr Ser Asn Gly Asp Lys Glu Asp Gly Arg Phe Thr Ala Gln Leu Asn
 50                      55                  60

Lys Ala Ser Gln Tyr Val Ser Leu Leu Ile Arg Asp Ser Gln Pro Ser
 65                  70                  75                  80

Asp Ser Ala Thr Tyr Leu Cys Ala Val Thr Thr Asp Ser Trp Gly Lys
                 85                  90                  95

Leu Gln Phe Gly Ala Gly Thr Gln Val Val Val Thr Pro
                100                 105

<210> SEQ ID NO 436
<211> LENGTH: 114
<212> TYPE: PRT
<213> ORGANISM: Homo sapiens

<400> SEQUENCE: 436

Gly Val Thr Gln Thr Pro Lys Phe Gln Val Leu Lys Thr Gly Gln Ser
 1               5                  10                  15

Met Thr Leu Gln Cys Ala Gln Asp Met Asn His Glu Tyr Met Ser Trp
                20                  25                  30

Tyr Arg Gln Asp Pro Gly Met Gly Leu Arg Leu Ile His Tyr Ser Val
                35                  40                  45

Gly Ala Gly Ile Thr Asp Gln Gly Glu Val Pro Asn Gly Tyr Asn Val
 50                      55                  60

Ser Arg Ser Thr Thr Glu Asp Phe Pro Leu Arg Leu Leu Ser Ala Ala
 65                  70                  75                  80

Pro Ser Gln Thr Ser Val Tyr Phe Cys Ala Ser Arg Pro Gly Leu Ala
                 85                  90                  95

Gly Gly Arg Pro Glu Gln Tyr Phe Gly Pro Gly Thr Arg Leu Thr Val
                100                 105                 110

Thr Glu

<210> SEQ ID NO 437
<211> LENGTH: 121
<212> TYPE: PRT
<213> ORGANISM: Homo sapiens
```

<400> SEQUENCE: 437

His Leu Glu Gln Pro Gln Ile Ser Ser Thr Lys Thr Leu Ser Lys Thr
1               5                   10                  15

Ala Arg Leu Glu Cys Val Val Ser Gly Ile Thr Ile Ser Ala Thr Ser
            20                  25                  30

Val Tyr Trp Tyr Arg Glu Arg Pro Gly Glu Val Ile Gln Phe Leu Val
        35                  40                  45

Ser Ile Ser Tyr Asp Gly Thr Val Arg Lys Glu Ser Gly Ile Pro Ser
    50                  55                  60

Gly Lys Phe Glu Val Asp Arg Ile Pro Glu Thr Ser Thr Ser Thr Leu
65                  70                  75                  80

Thr Ile His Asn Val Glu Lys Gln Asp Ile Ala Thr Tyr Tyr Cys Ala
                85                  90                  95

Leu Trp Glu Ala Gln Gln Glu Leu Gly Lys Lys Ile Lys Val Phe Gly
            100                 105                 110

Pro Gly Thr Lys Leu Ile Ile Thr Asp
            115                 120

<210> SEQ ID NO 438
<211> LENGTH: 119
<212> TYPE: PRT
<213> ORGANISM: Homo sapiens

<400> SEQUENCE: 438

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95

Leu Gly Met Gly Gly Tyr Thr Asp Lys Leu Ile Phe Gly Lys Gly
            100                 105                 110

Thr Arg Val Thr Val Glu Pro
            115

<210> SEQ ID NO 439
<211> LENGTH: 116
<212> TYPE: PRT
<213> ORGANISM: Homo sapiens

<400> SEQUENCE: 439

Asp Lys Val Thr Gln Ser Ser Pro Asp Gln Thr Val Ala Ser Gly Ser
1               5                   10                  15

Glu Val Val Leu Leu Cys Thr Tyr Asp Thr Val Tyr Ser Asn Pro Asp
            20                  25                  30

Leu Phe Trp Tyr Arg Ile Arg Pro Asp Tyr Ser Phe Gln Phe Val Phe
        35                  40                  45

Tyr Gly Asp Asp Ser Arg Ser Glu Gly Ala Asp Phe Thr Gln Gly Arg
    50                  55                  60

Phe Ser Val Lys His Ile Leu Thr Gln Lys Ala Phe His Leu Val Ile
65                  70                  75                  80

Ser Pro Val Arg Thr Glu Asp Ser Ala Thr Tyr Tyr Cys Ala Phe Thr
                85                  90                  95

Leu Pro Pro Thr Asp Lys Leu Ile Phe Gly Lys Gly Thr Arg Val
            100                 105                 110

Thr Val Glu Pro
        115

<210> SEQ ID NO 440
<211> LENGTH: 115
<212> TYPE: PRT
<213> ORGANISM: Mus musculus

<400> SEQUENCE: 440

Gln Leu Gln Gln Ser Gly Ala Glu Leu Met Lys Pro Gly Ala Ser Val
1               5                   10                  15

Lys Ile Ser Cys Lys Ala Ser Gly Tyr Thr Phe Ser Asp Tyr Trp Ile
                20                  25                  30

Glu Trp Val Lys Gln Arg Pro Gly His Gly Leu Glu Trp Ile Gly Glu
            35                  40                  45

Ile Leu Pro Gly Ser Gly Ser Thr Asn Tyr His Glu Arg Phe Lys Gly
50                  55                  60

Lys Ala Thr Phe Thr Ala Asp Thr Ser Ser Thr Ala Tyr Met Gln
65                  70                  75                  80

Leu Asn Ser Leu Thr Ser Glu Asp Ser Gly Val Tyr Tyr Cys Leu His
                85                  90                  95

Gly Asn Tyr Asp Phe Asp Gly Trp Gly Gln Gly Thr Thr Leu Thr Val
            100                 105                 110

Ser Ser Ala
        115

<210> SEQ ID NO 441
<211> LENGTH: 103
<212> TYPE: PRT
<213> ORGANISM: Mus musculus

<400> SEQUENCE: 441

Val Leu Thr Gln Ser Pro Ala Ile Met Ser Ala Ser Pro Gly Glu Lys
1               5                   10                  15

Val Thr Met Thr Cys Ser Ala Ser Ser Val Asn Tyr Met Tyr Trp
                20                  25                  30

Tyr Gln Gln Lys Ser Gly Thr Pro Lys Arg Trp Ile Tyr Asp Thr Ser
            35                  40                  45

Lys Leu Ala Ser Gly Val Pro Val Arg Phe Ser Gly Ser Gly Ser Gly
50                  55                  60

Thr Ser Tyr Ser Leu Thr Ile Ser Ser Met Glu Thr Glu Asp Ala Ala
65                  70                  75                  80

Thr Tyr Tyr Cys Gln Gln Trp Gly Arg Asn Pro Thr Phe Gly Gly Gly
                85                  90                  95

Thr Lys Leu Glu Ile Lys Arg
            100

<210> SEQ ID NO 442
<211> LENGTH: 113
<212> TYPE: PRT
<213> ORGANISM: Homo sapiens

<400> SEQUENCE: 442

Gln Phe Arg Val Ser Pro Leu Asp Arg Thr Trp Asn Leu Gly Glu Thr
1               5                   10                  15

Val Glu Leu Lys Cys Gln Val Leu Leu Ser Asn Pro Thr Ser Gly Cys
            20                  25                  30

Ser Trp Leu Phe Gln Pro Arg Gly Ala Ala Ala Ser Pro Thr Phe Leu
        35                  40                  45

Leu Tyr Leu Ser Gln Asn Lys Pro Lys Ala Ala Glu Gly Leu Asp Thr
    50                  55                  60

Gln Arg Phe Ser Gly Lys Arg Leu Gly Asp Thr Phe Val Leu Thr Leu
65                  70                  75                  80

Ser Asp Phe Arg Arg Glu Asn Glu Gly Tyr Tyr Phe Cys Ser Ala Leu
                85                  90                  95

Ser Asn Ser Ile Met Tyr Phe Ser His Phe Val Pro Val Phe Leu Pro
            100                 105                 110

Ala

<210> SEQ ID NO 443
<211> LENGTH: 115
<212> TYPE: PRT
<213> ORGANISM: Homo sapiens

<400> SEQUENCE: 443

His Val Ala Gln Pro Ala Val Val Leu Ala Ser Ser Arg Gly Ile Ala
1               5                   10                  15

Ser Phe Val Cys Glu Tyr Ala Ser Pro Gly Lys Ala Thr Glu Val Arg
            20                  25                  30

Val Thr Val Leu Arg Gln Ala Asp Ser Gln Val Thr Glu Val Cys Ala
        35                  40                  45

Ala Thr Tyr Met Met Gly Asn Glu Leu Thr Phe Leu Asp Asp Ser Ile
    50                  55                  60

Cys Thr Gly Thr Ser Ser Gly Asn Gln Val Asn Leu Thr Ile Gln Gly
65                  70                  75                  80

Leu Arg Ala Met Asp Thr Gly Leu Tyr Ile Cys Lys Val Glu Leu Met
                85                  90                  95

Tyr Pro Pro Pro Tyr Tyr Leu Gly Ile Gly Asn Gly Thr Gln Ile Tyr
            100                 105                 110

Val Ile Asp
        115

<210> SEQ ID NO 444
<211> LENGTH: 9
<212> TYPE: PRT
<213> ORGANISM: Artificial Sequence
<220> FEATURE:
<223> OTHER INFORMATION: Synthetic Construct

<400> SEQUENCE: 444

Ala Trp Cys Arg Gln Leu Gly Glu Lys
1               5

<210> SEQ ID NO 445
<211> LENGTH: 7
<212> TYPE: PRT
<213> ORGANISM: Artificial Sequence
<220> FEATURE:
<223> OTHER INFORMATION: Synthetic Construct

<400> SEQUENCE: 445

His Trp Gly Arg Arg Ala Trp
1               5

<210> SEQ ID NO 446
<211> LENGTH: 132
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 1, 2, 5, 8, 12, 13, 14, 15, 16, 17, 18, 19, 20, 21, 22,
      24, 26, 31, 33, 35, 37, 39, 40, 41, 42, 43, 44, 45, 46, 47,
      49, 52, 53, 54, 55, 56, 57, 58, 59, 61, 63, 65, 66, 67,
      68, 69, 70, 71, 72, 73, 74, 75, 76, 77, 79, 80, 81, 82,
      83
<223> OTHER INFORMATION: Xaa = Any Amino Acid
<220> FEATURE:
<221> NAME/KEY: VARIANT
<222> LOCATION: 85, 88, 89, 90, 92, 93, 95, 97, 98, 99, 101, 102, 103,
      105, 107, 109, 111, 112, 113, 114, 115, 117, 118, 119, 120, 121,
      122, 123, 125, 126, 127, 128, 129, 130, 131
<223> OTHER INFORMATION: Xaa = Any Amino Acid

<400> SEQUENCE: 446

Xaa Xaa Pro Leu Xaa Leu Leu Xaa Leu Leu Phe Xaa Xaa Xaa Xaa Xaa
1               5                   10                  15

Xaa Xaa Xaa Xaa Xaa Xaa Val Xaa Gln Xaa Val Ala Gly Gln Xaa Leu
                20                  25                  30

Xaa Val Xaa Cys Xaa Tyr Xaa Xaa Xaa Xaa Xaa Xaa Xaa Xaa Xaa Lys
            35                  40                  45

Xaa Trp Cys Xaa Xaa Xaa Xaa Xaa Xaa Xaa Cys Xaa Arg Xaa Val
    50                  55                  60

Xaa Xaa Xaa Xaa Xaa Xaa Xaa Xaa Xaa Xaa Xaa Xaa Xaa Trp Xaa Xaa
65                  70                  75                  80

Xaa Xaa Xaa Ile Xaa Asp Asp Xaa Xaa Xaa Gly Xaa Xaa Thr Xaa Thr
                85                  90                  95

Xaa Xaa Xaa Leu Xaa Xaa Xaa Xaa Asp Xaa Gly Xaa Tyr Xaa Cys Xaa Xaa
            100                 105                 110

Xaa Xaa Xaa Ser Xaa Xaa Xaa Xaa Xaa Xaa Xaa Val Xaa Xaa Xaa Xaa
            115                 120                 125

Xaa Xaa Xaa Pro
        130

<210> SEQ ID NO 447
<211> LENGTH: 107
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 3, 4, 8, 11, 12, 14, 15, 16, 18, 19, 20, 21, 22, 23, 24,
      25, 28, 30, 32, 34, 36, 37, 38, 40, 41, 42, 43, 44
<223> OTHER INFORMATION: Xaa = Any Amino Acid
<220> FEATURE:
<221> NAME/KEY: VARIANT
<222> LOCATION: 48, 49
<223> OTHER INFORMATION: Xaa = Any Amino Acid and can be present or
      absent
<220> FEATURE:
<221> NAME/KEY: VARIANT
<222> LOCATION: 51, 52, 53, 54, 56, 57, 58, 59, 60, 61, 62, 63, 64,
      65, 66, 67, 68, 69, 70, 71, 72, 73, 74, 75, 76, 78, 79,
      80, 81
<223> OTHER INFORMATION: Xaa = Any Amino Acid
<220> FEATURE:

```
<221> NAME/KEY: VARIANT
<222> LOCATION: 82, 84, 85, 86, 87, 89, 91, 92, 93, 94, 95, 99, 100, 102
<223> OTHER INFORMATION: Xaa = Any Amino Acid

<400> SEQUENCE: 447

Leu Leu Xaa Xaa Leu Phe Val Xaa Glu Leu Xaa Xaa Ala Xaa Xaa Xaa
1               5                   10                  15

Thr Xaa Xaa Xaa Xaa Xaa Xaa Xaa Gly Gln Xaa Leu Xaa Val Xaa
            20                  25                  30

Cys Xaa Tyr Xaa Xaa Xaa Lys Xaa Xaa Xaa Xaa Lys Ala Trp Xaa
        35                  40                  45

Xaa Gln Xaa Xaa Xaa Xaa Gly Xaa Xaa Xaa Xaa Xaa Xaa Xaa Xaa
    50                  55                  60

Xaa Xaa Xaa Xaa Xaa Xaa Xaa Xaa Xaa Xaa Xaa Gly Xaa Xaa Xaa
65                  70                  75                  80

Xaa Xaa Asp Xaa Xaa Xaa Xaa Gly Xaa Leu Xaa Xaa Xaa Xaa Asn
            85                  90                  95

Leu Gln Xaa Xaa Asp Xaa Gly Leu Tyr Gln Cys
            100                 105
```

ANTI-TREM2 ANTIBODIES AND METHODS OF USE THEREOF

CROSS-REFERENCE TO RELATED APPLICATIONS

This application is a Continuation of U.S. application Ser. No. 15/502,766, filed Aug. 8, 2015, which is a U.S. National Phase patent application of PCT/US2015/044396, filed Aug. 8, 2015, which claims the benefit of U.S. Provisional Application No. 62/035,336, filed Aug. 8, 2014, U.S. Provisional Application No. 62/135,110, filed Mar. 18, 2015, and U.S. Provisional Application No. 62/135,122, filed Mar. 18, 2015, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022000401SEQLIST.TXT, date recorded: Apr. 10, 2019, size: 241 KB).

FIELD OF THE INVENTION

This invention relates to anti-TREM2 and anti-DAP12 antibodies and therapeutic uses of such antibodies.

BACKGROUND OF THE INVENTION

Triggering receptor expressed on myeloid cells-2 (TREM2) is an immunoglobulin-like receptor that is expressed primarily on myeloid lineage cells, such as macrophages, dendritic cells, monocytes, Langerhans cells of skin, Kupffer cells, osteoclasts, and microglia; and is required for modulation (e.g., suppression) of Toll-like receptor (TLR) signaling, the modulation of inflammatory cytokines, as well as for normal osteoclast development. TREM2 was discovered as a member of the TREM transmembrane glycoproteins, which belong to the single immunoglobulin variable (IgV) domain receptor family. The genes encoding human and mouse TREMs map to human chromosome 6p21.1 and mouse chromosome 17C3, respectively. The TREM cluster includes genes encoding TREM1, TREM2, TREM4, and TREM5, as well as the TREM-like genes in both human and mouse. Additionally TREM3 and plasmocytoid dendritic cell (pDC)-TREM were identified in mouse. The TREM-like genes, TREML1 and TREML2 in humans, and Treml1 and Treml2 in mouse, encode TLT-1 and TLT-2 respectively. The two best characterized of these receptors, TREM1 and TREM2, display some sequence homology with other members of the Ig-SF such as activating NK cells receptors (20% identity with NKp44) and act through association with a DAP12-mediated pathway for signaling.

TREM2 was originally cloned as a cDNA encoding a TREM1 homologue (Bouchon, A et al., J Exp Med, 2001, 194(8): p. 1111-22). This receptor is a glycoprotein of about 40 kDa, which is reduced to 26 kDa after N-deglycosylation. The TREM2 gene encodes a 230 amino acid-length protein that includes an extracellular domain, a transmembrane region and a short cytoplasmic tail. The extracellular region, encoded by exon 2, is composed of a single type V Ig-SF domain, containing three potential N-glycosylation sites. The putative transmembrane region contains a charged lysine residue. The cytoplasmic tail of TREM2 lacks signaling motifs and is thought to signal through the signaling adaptor molecule DAP12/TRYROBP.

The signaling adaptor molecule DAP12 is expressed as a homodimer at the surface of a variety of cells participating in innate immune response, including microglia, macrophages, granulocytes, NK cells, and dendritic cells (DC). DAP12 is a member of the type I transmembrane adapter protein family on the basis of homology with the human T-cell receptor (TCR)-associated CD3 chains and the Fc receptor (FcR) γ-chain (Turnbull, I R and Colonna, M, Nat Rev Immunol, 2007. 7(2): p. 155-61). These proteins share many structural and functional characteristics, including one or more ITAM motifs in their cytoplasmic domain, charged acidic residue in transmembrane region (critical for interaction with its partner chain) and the ability to recruit Src homology domain-2 (SH2)-containing proteins following tyrosine phosphorylation. The ITAM motif mediates signal propagation by activation of the ZAP70 or Syk tyrosine kinase. Both kinases phosphorylate several substrates, thereby facilitating the formation of a signaling complex leading to cellular activation. Interestingly, some B-cells and T-cells also express DAP12 under inflammatory conditions. In humans, subsets of $CD4^+CD28^-$ T-cells, $\alpha\beta TCR^+CD4^+$ T-cells, and $CD8^+$ T-cells expressing this protein have been described in patients suffering from chronic inflammatory diseases, in the context of autoimmune T cells (Schleinitz, N. et al., PLoS ONE, 4 (2009), p. e6264). In view of the significant level of DAP12 expression in mouse peritoneal macrophages, this protein is believed to be expressed in other macrophage-related cells, such as osteoclasts in the bone marrow, Kupffer cells in the liver, alveolar macrophages of the lung, Langerhans cells of skin, and microglial cells in the brain (Takaki, R et al., Immunol Rev, 2006. 214: p. 118-29).

TREM2 has been identified as expressed on the surface of human monocyte-derived dendritic cells and as an mRNA transcript in the mouse macrophage cell line RAW264 (Bouchon, A et al., J Exp Med, 2001. 194(8): p. 1111-22). Human TREM2 was the first DAP12-associated receptor described on the surface of DCs. Studies have demonstrated that TREM2 cell surface expression is reduced in DAP12-deficient bone marrow-derived dendritic cells (BMDCs) and in DAP12-deficient macrophages, as compared to wild-type cells (Ito, H and Hamerman, J A, Eur J Immunol. 42(1): p. 176-85; Hamerman, J A et al., J Immunol, 2006. 177(4): p. 2051-5; and Hamerman, J A et al., Nat Immunol, 2005. 6(6): p. 579-86). This indicates that formation of the TREM2/DAP12 complex is needed for maximal TREM2 surface expression.

Recent studies have also shown cell-surface expression of TREM2 on macrophages infiltrating tissue from the circulation, as well as on macrophages activated by IL-4 or IL-13 (Turnbull, I R et al., J Immunol, 2006. 177(6): p. 3520-4). However, TREM2 expression was not always found in other cell populations, such as tissue-resident macrophages, circulating monocytes, or the corresponding progenitor cells in the bone marrow, suggesting that TREM2 expression is not induced centrally, but locally during tissue infiltration or by cytokine-mediated activation. Moreover, it has also been observed that IFN-γ and LPS reduce or otherwise abrogate TREM2 expression. Further, it has been recently reported that TREM2 is highly expressed on microglia and infiltrating macrophages in the central nervous system during experimental autoimmune encephalomyelitis or Alzheimer's disease (Piccio, L et al., Eur J Immunol, 2007. 37(5): p. 1290-301; and Wang Y, Cell. 2015 Mar. 12; 160(6):1061-71).

It has been shown that TREM2 signals through DAP12. Downstream this leads to activation of the Syk/Zap70 tyrosine kinase family, PI3K, and other intracellular signals. On myeloid cells, TLR signals are important for activation, such as with infection response, but also play a key role in the pathological inflammatory response, such as with macrophages and dendritic cells (Hamerman, J A et al., (2006) J Immunol 177: 2051-2055; Ito, H et al., Eur J Immunol 42: 176-185; Neumann, H et al., (2007) J Neuroimmunol 184: 92-99; Takahashi, K et al., (2005) J Exp Med 201: 647-657; and Takahashi, K et al., (2007) PLoS Med 4: e124). Deficiency of either TREM2 or DAP12 is thought to lead to increased pro-inflammatory signaling. The impact of TREM2-deficiency in vitro has been shown in the context of stimulation with typical TLR ligands, such as LPS, CpG DNA, and Zymosan. TREM-2-deficient dendritic cells show increased release of IL-12p70, TNF, IL-6, and IL-10 in the presence, but not in the absence of stimulation.

Several recent studies have explored the intracellular signaling events induced by the activation of the TREM2/DAP12 pathway. For example, TREM2 is thought to activate signaling pathways involved in cell survival (e.g., protein kinase B-Akt), cell activation and differentiation (e.g., Syk, Erk1/2, PLC-γ, etc.), and in the control of the actin cytoskeleton (e.g., Syk, Vav, etc.) (Peng, Q et al., Sci Signal. 3(122): p. ra38; and Whittaker, G C et al., J Biol Chem. 285(5): p. 2976-85). After ligation of TREM2, the ITAM tyrosines in DAP12 are phosphorylated by SRC-family kinases leading to the recruitment and activation of the Syk kinase and/or ZAP70 kinase. In the mouse, Syk may be the predominant kinase involved, whereas in humans both Syk and ZAP70 appear to couple efficiently with such ITAM-containing subunits, binding them through their tandem SH2 domains.

Studies on TREM2 signaling have shown that, like TREM1, TREM2-mediated signaling through DAP12 also leads to an increase in intracellular calcium ion levels and ERK1/2 phosphorylation of ERK1/2 (Bouchon, A et al., J Exp Med, 2001. 194(8): p. 1111-22; and Sharif, O and Knapp, S, Immunobiology, 2008. 213(9-10): p. 701-13). Importantly, TREM2 receptor ligation does not induce the degradation of IkB-a and the subsequent nuclear translocation of NF-kB, which points to a possible difference between TREM2 and TREM1 signaling (Bouchon, A et al., J Exp Med, 2001. 194(8): p. 1111-22). Receptor cross-linking of TREM2 on immature dendritic cells triggers the up-regulation of molecules involved in T-cell co-stimulation, such as CD86, CD40, and MHC class II, as well as the up-regulation of the chemokine receptor CCR7 (Bouchon, A et al., J Exp Med, 2001. 194(8): p. 1111-22). TREM2 is also expressed on microglia, where receptor cross-linking results in an increase in ERK1/2 phosphorylation and CCR7, but not an increase in CD86 or MHC class II expression, suggesting possible cell type-specific differences in TREM2 signaling. Additionally, over-expression of TREM2 in myeloid cells resulted in an increase in phagocytosis of degenerated myelin (Takahashi, K et al., PLoS Med, 2007. 4(4): p. e124; and Neumann, H and Takahashi, K, J Neuroimmunol, 2007. 184(1-2): p. 92-9).

It has also been shown that bone marrow-derived macrophages (BMDM) that have been silenced for TREM2 using shRNAi display increased secretion of TNF in response to the TLR2/6 ligand zymosan and the TLR9 ligand CpG, as compared to control BMDM cells that were treated with a non-specific shRNAi, indicating that TREM2 negatively regulates cytokine synthesis in macrophages (Ito, H and Hamerman, J A, Eur J Immunol. 42(1): p. 176-85; Hamerman, J A et al., J Immunol, 2006. 177(4): p. 2051-5; and Hamerman, J A et al., Nat Immunol, 2005. 6(6): p. 579-86). These results have been confirmed using BMDM cells from TREM2 knockout mice, and have further shown that levels of TNF and IL-6 were also higher in TREM2$^{-/-}$ BMDM cells in response to LPS, as compared to wild-type BMDM cells (Turnbull, I R, et al., J Immunol, 2006. 177(6): p. 3520-4; and Turnbull, I R and Colonna, M, Nat Rev Immunol, 2007. 7(2): p. 155-61). Additionally, TREM2 overexpression in microglia has been demonstrated to lead to a decrease in TNF and inducible nitric oxide (iNOS) mRNA after culture of these cells with apoptotic neurons, whereas TREM2 knockdown resulted in a modest increase in TNF and iNOS mRNA levels. This indicates that, in contrast to TREM1, which is a positive regulator of cytokine synthesis, TREM2 is a negative regulator of cytokine synthesis. This effect of TREM2 on inflammation may be independent of the type of macrophage as it occurs in both microglia and BMDM cells.

It has also been shown that in resident myeloid cells of the central nervous system, activation of microglia can lead to inflammation (Neumann, H et al., (2007) J Neuroimmunol 184: 92-99; Takahashi, K et al., (2005) J Exp Med 201: 647-657; Takahashi, K et al., (2007) PLoS Med 4: e124; and Hsieh, C L et al., (2009) J Neurochem 109: 1144-1156). Moreover, microglia activation has also been implicated in frontotemporal dementia (FTD), Alzheimer's disease, Parkinson's disease, stroke/ischemic brain injury, and multiple sclerosis. Whereas reduced TREM2 activation leads to increases in certain activation and inflammation markers, such as NOS2 gene transcription in myeloid cells, increased TREM2 activation leads to reduced NOS2 transcription. It is thought that dying neurons express an endogenous ligand for TREM2. HSP60 has been implicated as a ligand of TREM2 on neuroblastoma cells (Stefani, L et al., (2009) Neurochem 110: 284-294). TREM2 over-expression also leads to increased phagocytosis of dying neurons by microglia, and similarly increases phagocytosis by other myeloid lineage cells.

In humans, the complete absence of TREM2 has been shown to cause Nasu-Hakola disease, a rare neurodegenerative disease with late-onset dementia, demyelination, and cerebral atrophy (Paloneva, J et al., (2002) Am J Hum Genet 71: 656-662; and Paloneva, J et al., (2003) J Exp Med 198: 669-675). Nasu-Hakola disease can also be caused by DAP12-deficiency.

TREM2 gene expression has also been shown to be increased in APP23 transgenic mice, an Alzheimer's disease model in which the mice express a mutant form of the amyloid precursor protein that is associated with familial Alzheimer's disease (Melchior, B et al., ASN Neuro 2: e00037). Uptake of Amyloid 1-42 has also been shown to be increased in BV-2 microglial cell lines that overexpress TREM2.

TREM2 has further been shown to be upregulated in the EAE mouse model of multiple sclerosis (Neumann, H et al., (2007) J Neuroimmunol 184: 92-99; Takahashi, K et al., (2005) J Exp Med 201: 647-657; and Takahashi, K et al., (2007) PLoS Med 4: e124). The transduction of bone marrow-derived myeloid precursor cells (BM-DC) in vitro with TREM2 leads to increased phagocytosis of degenerated myelin. In response to LPS, these cells show increased IL-10 and decreased IL-1β. Intravenous transplantation of myeloid cells overexpressing TREM2 can suppress EAE in vivo.

Further, exome sequencing of individuals with frontotemporal dementia (FTD) presentation has identified homozygous mutations in TREM2 (Guerreiro, R J et al., JAMA Neurol 70: 78-84; and Guerreiro, R J et al., Arch Neurol: 1-7). Some of these mutations lead to truncation and likely loss-of-function of TREM2. These same TREM2 mutations can also cause Naku-Hakula disease in some individuals. Imaging analysis in certain individuals with TREM2 homozygous mutations has also shown evidence of demyelination.

Heterozygous mutations in TREM2, which are the same as the mutation that cause Naku-Hakula and FTD, also increase the risk of Alzheimer's disease (Guerreiro, R et al., N Engl J Med 368: 117-127; Jonsson, T et al., N Engl J Med 368: 107-116; and Neumann, H et al., N Engl J Med 368: 182-184). Although these TREM2 mutations are rarer than the known risk variants of Alzheimer's disease (e.g., APOE4), the effect of carrying these mutations is just as serious; around a 3 fold increase in the risk of developing Alzheimer's disease. Moreover, even individuals without Alzheimer's disease who carry a heterozygous TREM2 mutation show worse cognition as compared to individuals with two normal TREM2 alleles. Further, it has been shown that the R47H variant of TREM2 (arginine to histidine amino acid substitution at position 47 of TREM2), which is most common TREM2 mutation (up to 1 in 200 individuals) is located within the immunoglobulin domain of TREM2, and may thus alter ligand binding (Wang Y, Cell. 2015 Mar. 12; 160(6):1061-71).

In addition an integrative network-based approach to rank-ordered organized structure of molecular networks of gene expression for relevance to late onset developing Alzheimer's disease (LOAD) identified TYROBP/DAP12 as the signaling molecule for TREM2 as a key regulator of the immune/microglia gene modules that is associated with LOAD. TYROBP was found to be the causal regulator of the highest scoring immune/microglia module as rank-ordered based on the number of other genes that TREM2 regulated and the magnitude of loss of regulation, as well as differential expression in LOAD brains. TYROBP was significantly upregulated in LOAD brains and there was a progression of TYROBP expression changes across mild cognitive impairment (MCI), which often precedes LOAD (Zhang et al., (2013) Cell 153, 707-720). Targeting such causal networks in ways that restore them to a normal state may be a way to treat disease.

Accordingly, there is a need for antibodies that specifically bind TREM2 and/or its signaling adapter molecule DAP12/TRYROBP on a cell surface and that modulate (e.g., activate or inhibit) one or more TREM2 and/or DAP12 activities in order to treat one or more diseases, disorders, and conditions associated with decreased TREM2 and/or DAP12 activity, as well as conditions associated with undesired TREM2 and/or DAP12 activity.

Moreover, the tumor microenvironment is composed of a heterogeneous immune infiltrate, which include T lymphocytes, macrophages and cells of myeloid/granulocytic lineage. Therapeutic approaches that modulate specific subsets of immune cells are changing the standard of care. "Checkpoint blocking" antibodies targeting immune-modulatory molecules expressed on T cells (such as CTLA-4 and PD-1) have demonstrated clinical activity across a variety of tumor types (Naidoo-et al., (2014) *British Journal of Cancer* 111, 2214-2219).

Cancer immune-therapy targeting tumor-associated macrophages (e.g., M2-type macrophages) is an intense area of research. The presence of M2-macrophages in tumors is associated with poor prognosis. Accordingly, there is a need for antibodies that specifically bind TREM2 and/or DAP12 and (e.g., activate or inhibit) one or more TREM2 and/or DAP12 activities in tumor-associated immune cells, such as macrophages, dendritic cells, myeloid/granulocytic cells, T cells, and monocytes.

All references cited herein, including patent applications and publications, are hereby incorporated by reference in their entirety.

SUMMARY OF THE INVENTION

The invention is generally directed to methods and compositions that include antibodies, e.g., monoclonal antibodies, chimeric antibodies, bispecific antibodies, humanized antibodies, antibody fragments, etc., that specifically bind a TREM2 protein and/or its signaling adaptor molecule DAP12, e.g., a mammalian TREM2, a human TREM2, a mammalian DAP12, or a human DAP12, including wild-type proteins and naturally occurring variants thereof. The antibodies of the present disclosure may include agonist antibodies, inert antibodies, and/or antagonist antibodies. The methods provided herein find use in preventing, reducing risk, or treating an individual having dementia, frontotemporal dementia, Alzheimer's disease, Nasu-Hakola disease, or multiple sclerosis; in inducing or promoting innate immune cell survival in an individual in need thereof, and/or in decreasing innate immune cell survival in an individual in need thereof.

Certain aspect of the present disclosure relate to different classes of anti-TREM2 antibodies. In some embodiments, anti-TREM2 antibodies are agonist antibodies that bind to TREM2 and activate, induce, promote, stimulate, or otherwise increase one or more TREM2 activities, survival of one or more innate immune cells, and/or expression of IL-6. In some embodiments, agonist anti-TREM2 antibodies of the present disclosure compete with TREM2 ligands for binding to TREM2 expressed on a cell surface. In some embodiments, agonist anti-TREM2 antibodies of the present disclosure do not compete with TREM2 ligands for binding to TREM2 expressed on a cell surface. In some embodiments, anti-TREM2 antibodies are inert or antagonist antibodies that bind to TREM2 and decrease, inhibit, or otherwise reduce one or more TREM2 activities and/or survival of one or more innate immune cells. In some embodiments, inert or antagonist anti-TREM2 antibodies of the present disclosure block or otherwise inhibit ligand binding to TREM2 expressed on a cell surface.

Other aspects of the present disclosure relate to an isolated agonist antibody that binds to a TREM2 protein, a DAP12 protein, or both, wherein the antibody induces one or more TREM2 activities, DAP12 activities, or both.

In certain embodiments that may be combined with any of the preceding embodiments, the TREM2 protein, the DAP12 protein, or both is a mammalian protein or a human protein. In certain embodiments that may be combined with any of the preceding embodiments, the TREM2 protein, the DAP12 protein, or both is a wild-type protein. In certain embodiments that may be combined with any of the preceding embodiments, the TREM2 protein, the DAP12 protein, or both is a naturally occurring variant. In certain embodiments that may be combined with any of the preceding embodiments, the TREM2 protein, the DAP12 protein, or both is expressed on human dendritic cells, human macrophages, human monocytes, human osteoclasts, human Langerhans cells of skin, human Kupffer cells, and/or human microglia. In certain embodiments that may be combined with any of the preceding embodiments, the isolated antibody induces or retains TREM2 clustering, DAP12 clustering, or both on a cell surface. In certain embodiments that may be combined with any of the preceding embodiments, the one or more TREM2 activities comprise TREM2 binding to DAP12. In certain embodiments that may be combined with any of the preceding embodiments, the one or more DAP12 activities comprise DAP12 binding to TREM2. In certain embodiments that may be combined with any of the preceding embodiments, the one or more TREM2 activities, DAP12 activities, or both comprise DAP12 phosphorylation, TREM2 phosphorylation, or both. In certain embodiments that may be combined with any of the preceding embodiments, DAP12 phosphorylation, TREM2 phosphorylation, or both is induced by one or more SRC family tyrosine kinases. In certain embodiments that may be combined with any of the preceding embodiments, the one or more SRC family tyrosine kinases comprise a Syk kinase. In certain embodiments that may be combined with any of the preceding embodiments, the one or more TREM2 activities, DAP12 activities, or both comprise PI3K activation. In certain embodiments that may be combined with any of the preceding embodiments, the one or more TREM2 activities, DAP12 activities, or both comprise increased expression of one or more anti-inflammatory cytokines. In certain embodiments that may be combined with any of the preceding embodiments, the one or more TREM2 activities, DAP12 activities, or both comprise increased expression of one or more anti-inflammatory mediators (e.g., cytokines) selected from the group consisting of IL-12p70, IL-6, and IL-10. In certain embodiments that may be combined with any of the preceding embodiments, the increased expression occurs in one or more cells selected from the group consisting of macrophages, dendritic cells, monocytes, osteoclasts, Langerhans cells of skin, Kupffer cells, and microglial cells. In certain embodiments that may be combined with any of the preceding embodiments, the one or more TREM2 activities, DAP12 activities, or both comprise reduced expression of one or more pro-inflammatory cytokines. In certain embodiments that may be combined with any of the preceding embodiments, the one or more TREM2 activities, DAP12 activities, or both comprise reduced expression of one or more pro-inflammatory mediators selected from the group consisting of IFN-a4, IFN-b, IL-6, IL-12 p70, IL-1β, TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP. In certain embodiments that may be combined with any of the preceding embodiments, the one or more TREM2 activities, DAP12 activities, or both comprise reduced expression of TNF-α, IL-6, or both. In certain embodiments that may be combined with any of the preceding embodiments, the reduced expression of the one or more pro-inflammatory mediators occurs in one or more cells selected from the group consisting of macrophages, dendritic cells, monocytes, osteoclasts, Langerhans cells of skin, Kupffer cells, and microglial cells. In certain embodiments that may be combined with any of the preceding embodiments, the one or more TREM2 activities, DAP12 activities, or both comprise extracellular signal-regulated kinase (ERK) phosphorylation. In certain embodiments that may be combined with any of the preceding embodiments, the one or more TREM2 activities, DAP12 activities, or both comprise increased expression of C—C chemokine receptor 7 (CCR7). In certain embodiments that may be combined with any of the preceding embodiments, the one or more TREM2 activities, DAP12 activities, or both comprise induction of microglial cell chemotaxis toward CCL19 and CCL21 expressing cells. In certain embodiments that may be combined with any of the preceding embodiments, the one or more TREM2 activities, DAP12 activities, or both comprise an enhancement, normalization, or both of the ability of bone marrow-derived dendritic cells to induce antigen-specific T-cell proliferation. In certain embodiments that may be combined with any of the preceding embodiments, the one or more TREM2 activities, DAP12 activities, or both comprise induction of osteoclast production, increased rate of osteoclastogenesis, or both. In certain embodiments that may be combined with any of the preceding embodiments, the one or more TREM2 activities, DAP12 activities, or both comprise increasing the survival of macrophages, microglial cells, or both. In certain embodiments that may be combined with any of the preceding embodiments, the one or more TREM2 activities, DAP12 activities, or both comprise increasing the function of macrophages, microglial cells, dendritic cells, monocytes, osteoclasts, Langerhans cells of skin, and/or Kupffer cells. In certain embodiments that may be combined with any of the preceding embodiments, the macrophages are M1 macrophages and/or microglia, M2 macrophages and/or microglia, or both. In certain embodiments that may be combined with any of the preceding embodiments, the M1 macrophages and/or microglia are activated M1 macrophages and/or microglia. In certain embodiments that may be combined with any of the preceding embodiments, the one or more TREM2 activities, DAP12 activities, or both comprise induction of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance. In certain embodiments that may be combined with any of the preceding embodiments, the one or more TREM2 activities, DAP12 activities, or both comprise induction of phagocytosis of one or more of apoptotic neurons, nerve tissue debris, non-nerve tissue debris, bacteria, other foreign bodies, disease-causing proteins, disease-causing peptides, or disease-causing nucleic acid. In certain embodiments that may be combined with any of the preceding embodiments, the disease-causing protein is selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides. In certain embodiments that may be combined with any of the preceding embodiments, the disease-causing nucleic acid is antisense GGCCCC (G2C4) repeat-expansion RNA. In certain embodiments that may be combined with any of the preceding embodiments, the one or more TREM2 activities, DAP12 activities, or both comprise normalization of disrupted TREM2/DAP12-dependent gene expression. In certain embodiments that may be combined with any of the preceding embodiments, the one or more TREM2 activities, DAP12 activities, or both comprise recruitment of Syk, ZAP70, or both to a DAP12/TREM2 complex. In certain embodiments that may be combined with any of the preceding embodiments, the one or more TREM2 activities, DAP12 activities, or both comprise Syk phosphorylation. In certain embodiments that may be combined with any of the preceding embodiments, the one or more TREM2 activities, DAP12 activities, or both comprise increased expression of CD83 and/or CD86 on dendritic cells, macrophages, and/or monocytes. In certain embodiments that may be combined with any of the preceding embodiments, the one or more TREM2 activities, DAP12 activities, or both comprise reduced secretion of one or more inflammatory cytokines. In certain embodiments that may be combined with any of the preceding embodiments, the one or more inflammatory cytokines are selected from the group consisting of TNF-α, IL-10, IL-6, MCP-1, IFN-a4, IFN-b, IL-1β, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP. In certain embodiments that may be combined with any of the preceding embodiments, the one or more TREM2 activities, DAP12 activities, or both comprise reduced expression of one or more inflammatory receptors. In certain embodiments that may be combined with any of the preceding embodiments, the one or more inflammatory receptors comprise CD86. In certain embodiments that may be combined with any of the preceding embodiments, the one or more TREM2 activities, DAP12 activities, or both comprise increasing phagocytosis by macrophages, dendritic cells, monocytes, and/or microglia under conditions of reduced levels of MCSF. In certain embodiments that may be combined with any of the preceding embodiments, the one or more TREM2 activities, DAP12 activities, or both comprise decreasing phagocytosis by macrophages, dendritic cells, monocytes, and/or microglia in the presence of normal levels of MCSF. In certain embodiments that may be combined with any of the preceding embodiments, the one or more TREM2 activities, DAP12 activities, or both comprise increasing activity of one or more TREM2-dependent genes. In certain embodiments that may be combined with any of the preceding embodiments, the one or more TREM2-dependent genes comprise one or more nuclear factor of activated T-cells (NFAT) transcription factors. In certain embodiments that may be combined with any of the preceding embodiments, the antibody is of the IgG class the IgM class, or the IgA class. In certain embodiments that may be combined with any of the preceding embodiments, the antibody is of the IgG class and has an IgG1, IgG2, IgG3, or IgG4 isotype. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the e human IgG2 constant region comprises an Fc region. In certain embodiments that may be combined with any of the preceding embodiments, the antibody induces the one or more TREM2 activities, DAP12 activities, or both independently of binding to an Fc receptor. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments, the human IgG2 constant region comprises an Fc region that comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU or Kabat numbering. In certain embodiments that may be combined with any of the preceding embodiments, the human IgG2 constant region comprises a light chain constant region comprising a C214S amino acid substitution, wherein the numbering of the residues is according to EU or Kabat numbering. In certain embodiments that may be combined with any of the preceding embodiments, the antibody has an IgG1 isotype. In certain embodiments that may be combined with any of the preceding embodiments, the antibody comprises a human IgG1 constant region. In certain embodiments that may be combined with any of the preceding embodiments, the human IgG1 constant region comprises an Fc region. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγRIIB). In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to EU or Kabat numbering. In certain embodiments that may be combined with any of the preceding embodiments, the antibody comprises an IgG2 isotype heavy chain constant domain 1(CH1) and hinge region. In certain embodiments that may be combined with any of the preceding embodiments, the IgG2 isotype CH1 and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397). In certain embodiments that may be combined with any of the preceding embodiments, the antibody Fc region comprises a S267E amino acid substitution, a L328F a L328F amino acid substitution, or both, and/or a N297A or N297Q amino acid substitution, wherein the numbering of the residues on IgG1 is according to EU or Kabat numbering. In certain embodiments that may be combined with any of the preceding embodiments, the antibody comprises a mouse IgG1 constant region. In certain embodiments that may be combined with any of the preceding embodiments, the antibody has an IgG4 isotype. In certain embodiments that may be combined with any of the preceding embodiments, the antibody comprises a human IgG4 constant region. In certain embodiments that may be combined with any of the preceding embodiments, the human IgG4 constant region comprises an Fc region. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU or Kabat numbering. In certain embodiments that may be combined with any of the preceding embodiments, the antibody has a hybrid IgG2/4 isotype. In certain embodiments that may be combined with any of the preceding embodiments, the antibody comprises an amino acid sequence comprising amino acids 118 to 260 of human IgG2 and amino acids 261 to 447 of human IgG4, wherein the numbering of the residues is according to EU or Kabat numbering. In certain embodiments that may be combined with any of the preceding embodiments, the antibody comprises a mouse IgG4 constant region. In certain embodiments that may be combined with any of the preceding embodiments, the isolated antibody is an antibody fragment that binds to one or more human proteins selected from the group consisting of human TREM2, a naturally occurring variant of human TREM2, human DAP12, and naturally occurring variant of human DAP12, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the fragment is an Fab, Fab', Fab'-SH, F(ab')2, Fv or scFv fragment.

Other aspects of the present disclosure relate to an isolated inert antibody that binds to a TREM2 protein. Other aspects of the present disclosure relate to an isolated antagonist antibody that binds to a TREM2 protein.

In certain embodiments that may be combined with any of the preceding embodiments, the TREM2 protein, the DAP12 protein, or both is a mammalian protein or a human protein. In certain embodiments that may be combined with any of the preceding embodiments, the TREM2 protein, the DAP12 protein, or both is a wild-type protein. In certain embodiments that may be combined with any of the preceding embodiments, the TREM2 protein, the DAP12 protein, or both is a naturally occurring variant. In certain embodiments that may be combined with any of the preceding embodiments, the isolated antibody inhibits one or more TREM2 activities, DAP12 activities, or both. In certain embodiments that may be combined with any of the preceding embodiments, the one or more TREM2 activities, DAP12 activities, or both comprise decreasing activity of one or more TREM2-dependent genes. In certain embodiments that may be combined with any of the preceding embodiments, the one or more TREM2-dependent genes comprise one or more nuclear factor of activated T-cells (NFAT) transcription factors. In certain embodiments that may be combined with any of the preceding embodiments, the one or more TREM2 activities, DAP12 activities, or both comprise decreasing the survival of macrophages, microglial cells, M1 macrophages, M1 microglial cells, M2 macrophages, M2 microglial cells, osteoclasts, Langerhans cells of skin, Kupffer cells, and/or dendritic cells. In certain embodiments that may be combined with any of the preceding embodiments, the isolated antibody inhibits interaction between TREM2 and one or more TREM2 ligands, inhibits TREM2 signal transduction, or both. In certain embodiments that may be combined with any of the preceding embodiments, the antibody is incapable of binding an Fc-gamma receptor (FcγR). In certain embodiments that may be combined with any of the preceding embodiments, the antibody has an IgG1 isotype. In certain embodiments that may be combined with any of the preceding embodiments, the antibody comprises a human IgG1 constant region. In certain embodiments that may be combined with any of the preceding embodiments, the human IgG1 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering. In certain embodiments that may be combined with any of the preceding embodiments, the Fc region further comprises an amino acid deletion at a position corresponding to glycine 236 according to EU or Kabat numbering. In certain embodiments that may be combined with any of the preceding embodiments, the antibody comprises a mouse IgG1 constant region. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the e human IgG2 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU or Kabat numbering. In certain embodiments that may be combined with any of the preceding embodiments, the antibody has an IgG4 isotype. In certain embodiments that may be combined with any of the preceding embodiments, the antibody comprises a human IgG4 constant region. In certain embodiments that may be combined with any of the preceding embodiments, the human IgG4 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, the isolated antibody is an antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the fragment is an Fab, Fab', Fab'-SH, F(ab')2, Fv or scFv fragment.

In certain embodiments that may be combined with any of the preceding embodiments, the Fc region further comprises one or more additional amino acid substitutions at a position selected from the group consisting of A330L, L234F; L235E, P331S, and any combination thereof, w wherein the numbering of the residues is according to EU or Kabat numbering. In certain embodiments that may be combined with any of the preceding embodiments, the Fc region further comprises one or more additional amino acid substitutions at a position selected from the group consisting of M252Y, S254T, T256E, and any combination thereof, wherein the numbering of the residues is according to EU or Kabat numbering. In certain embodiments that may be combined with any of the preceding embodiments, the Fc region further comprises a S228P amino acid substitution according to EU or Kabat numbering. In certain embodiments that may be combined with any of the preceding embodiments, the isolated antibody competes for binding of TREM2 with one or more TREM2 ligands. In certain embodiments that may be combined with any of the preceding embodiments, the one or more TREM2 ligands are selected from the group consisting of E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide. In certain embodiments that may be combined with any of the preceding embodiments, the isolated antibody is a human antibody, a humanized antibody, a bispecific antibody, a multivalent antibody, a conjugated antibody, or a chimeric antibody. In certain embodiments that may be combined with any of the preceding embodiments, the isolated antibody is a bispecific antibody recognizing a first antigen and a second antigen. In certain embodiments that may be combined with any of the preceding embodiments, the first antigen is human TREM2 or a naturally occurring variant thereof, and the second antigen is a disease-causing protein selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides; a blood brain barrier targeting protein selected from the group consisting of: trasnferin receptor, insulin receptor, insulin like growth factor receptor, LRP-1, and LRP1; or ligands and/or proteins expressed on immune cells. In certain embodiments that may be combined with any of the preceding embodiments, the isolated antibody is an antibody fragment that binds to one or more human proteins selected from the group consisting of human TREM2, a naturally occurring variant of human TREM2, human DAP12, and naturally occurring variant of human DAP12; and wherein the antibody is used in combination with one or more antibodies that specifically bind a disease-causing protein selected from the group consisting of: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, and any combination thereof. In certain embodiments that may be combined with any of the preceding embodiments, the antibody is a monoclonal antibody.

In certain embodiments that may be combined with any of the preceding embodiments, the isolated antibody binds to a linear epitope on TREM2. In certain embodiments that may be combined with any of the preceding embodiments, the linear epitope on TREM2 is located within the extracellular domain of TREM2. In certain embodiments that may be combined with any of the preceding embodiments, the linear epitope on TREM2 is located within the extracellular immunoglobulin-like variable-type (IgV) domain of TREM2. In certain embodiments that may be combined with any of the preceding embodiments, the isolated antibody binds to a TREM2 protein, and wherein the isolated antibody binds to one or more amino acids within amino acid residues selected from the group consisting of: i. amino acid residues 29-112 of SEQ ID NO: 1, or amino acid residues on a TREM2 protein corresponding to amino acid residues 29-112 of SEQ ID NO: 1; ii amino acid residues 29-41 of SEQ ID NO: 1, or amino acid residues on a TREM2 protein corresponding to amino acid residues 29-41 of SEQ ID NO: 1; iii. amino acid residues 40-44 of SEQ ID NO: 1, or amino acid residues on a TREM2 protein corresponding to amino acid residues 40-44 of SEQ ID NO: 1; iv. amino acid residues 47-69 of SEQ ID NO: 1, or amino acid residues on a TREM2 protein corresponding to amino acid residues 47-69 of SEQ ID NO: 1; v. amino acid residues 67-76 of SEQ ID NO: 1, or amino acid residues on a TREM2 protein corresponding to amino acid residues 67-76 of SEQ ID NO: 1; vi. amino acid residues 76-86 of SEQ ID NO: 1, or amino acid residues on a TREM2 protein corresponding to amino acid residues 76-86 of SEQ ID NO: 1; vii. amino acid residues 91-100 of SEQ ID NO: 1, or amino acid residues on a TREM2 protein corresponding to amino acid residues 91-100 of SEQ ID NO: 1; viii. amino acid residues 99-115 of SEQ ID NO: 1, or amino acid residues on a TREM2 protein corresponding to amino acid residues 99-115 of SEQ ID NO: 1; ix. amino acid residues 104-112 of SEQ ID NO: 1, or amino acid residues on a TREM2 protein corresponding to amino acid residues 104-112 of SEQ ID NO: 1; and x. amino acid residues 114-118 of SEQ ID NO: 1, or amino acid residues on a TREM2 protein corresponding to amino acid residues 114-118 of SEQ ID NO: 1. In certain embodiments that may be combined with any of the preceding embodiments, the isolated antibody binds to one or more amino acids within amino acid residues 43-50 of SEQ ID NO: 1, or amino acid residues on a TREM2 protein corresponding to amino acid residues 43-50 of SEQ ID NO: 1. In certain embodiments that may be combined with any of the preceding embodiments, the isolated antibody binds to one or more amino acids within amino acid residues 49-57 of SEQ ID NO: 1, or amino acid residues on a TREM2 protein corresponding to amino acid residues 49-57 of SEQ ID NO: 1. In certain embodiments that may be combined with any of the preceding embodiments, the isolated antibody binds to an epitope comprising one or more amino acids within amino acid residues 43-50 of SEQ ID NO: 1. In certain embodiments that may be combined with any of the preceding embodiments, the isolated antibody binds to an epitope comprising one or more amino acids within amino acid residues 43-50 of SEQ ID NO: 1. In certain embodiments that may be combined with any of the preceding embodiments, the isolated antibody binds to an epitope comprising one or more amino acid residues selected from the group consisting of: i. amino acid residue Arg47 or Asp87 of SEQ ID NO: 1; ii. amino acid residues 40-44 of SEQ ID NO: 1; iii. amino acid residues 67-76 of SEQ ID NO: 1; and iv. amino acid residues 114-118 of SEQ ID NO: 1. In certain embodiments that may be combined with any of the preceding embodiments, the isolated antibody binds to one or more amino acids within amino acid residues 22-40 of SEQ ID NO: 2, or amino acid residues on a DAP12 protein corresponding to amino acid residues 22-40 of SEQ ID NO: 2. In certain embodiments that may be combined with any of the preceding embodiments, the isolated antibody is a bispecific antibody that binds to one or more amino acids selected from the group consisting of: i. one or more amino acid residues of SEQ ID NO: 1, or amino acid residues on a TREM2 protein corresponding to amino acid residues of SEQ ID NO: 1; and ii. one or more amino acid residues of SEQ ID NO: 2, or amino acid residues on a DAP12 protein corresponding to amino acid residues of SEQ ID NO: 2.

In certain embodiments that may be combined with any of the preceding embodiments, the isolated antibody comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52. In certain embodiments that may be combined with any of the preceding embodiments, the HVR-H1 comprises the amino acid sequence of SEQ ID NO:398. In certain embodiments that may be combined with any of the preceding embodiments, the HVR-H2 comprises the amino acid sequence of SEQ ID NO:399. In certain embodiments that may be combined with any of the preceding embodiments, the HVR-H3 comprises the amino acid sequence of SEQ ID NO:400. In certain embodiments that may be combined with any of the preceding embodiments, the HVR-L1 comprises the amino acid sequence of SEQ ID NO:401. In certain embodiments that may be combined with any of the preceding embodiments, the HVR-L2 comprises the amino acid sequence of SEQ ID NO:402. In certain embodiments that may be combined with any of the preceding embodiments, the HVR-L3 comprises the amino acid sequence of SEQ ID NO:403. In certain embodiments that may be combined with any of the preceding embodiments, the isolated antibody comprises a heavy chain variable domain and a light chain variable domain, wherein the heavy chain variable domain comprises: (a) an HVR-H1 comprising the amino acid sequence of SEQ ID NO:398, or an amino acid sequence with at least about 95% homology to the amino acid sequence of SEQ ID NO:398; (b) an HVR-H2 comprising the amino acid sequence of SEQ ID NO:399, or an amino acid sequence with at least about 95% homology to the amino acid sequence of SEQ ID NO:399; and; and/or (c) an HVR-H3 comprising the amino acid sequence of SEQ ID NO:400, or an amino acid sequence with at least about 95% homology to the amino acid sequence of SEQ ID NO:400; and/or wherein the light chain variable domain comprises: (a) an HVR-L1 comprising the amino acid sequence of SEQ ID NO:401, or an amino acid sequence with at least about 95% homology to the amino acid sequence of SEQ ID NO:401; (b) an HVR-L2 comprising the amino acid sequence of SEQ ID NO:402, or an amino acid sequence with at least about 95% homology to the amino acid sequence of SEQ ID NO:402; and/or (c) an HVR-L3 comprising the amino acid sequence of SEQ ID NO:403, or an amino acid sequence with at least about 95% homology to the amino acid sequence of SEQ ID NO:403. In certain embodiments that may be combined with any of the preceding embodiments, the isolated antibody comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L1, HVR-L2, and/or HVR-L3 of the monoclonal antibody Ab21. In certain embodiments that may be combined with any of the preceding embodiments, the HVR-H1 comprises the amino acid sequence of SEQ ID NO:404. In certain embodiments that may be combined with any of the preceding embodiments, the HVR-H2 comprises the amino acid sequence of SEQ ID NO:405. In certain embodiments that may be combined with any of the preceding embodiments, the HVR-H3 comprises the amino acid sequence of SEQ ID NO:406. In certain embodiments that may be combined with any of the preceding embodiments, the HVR-L1 comprises the amino acid sequence of SEQ ID NO:407. In certain embodiments that may be combined with any of the preceding embodiments, the HVR-L2 comprises the amino acid sequence of SEQ ID NO:408. In certain embodiments that may be combined with any of the preceding embodiments, the HVR-L3 comprises the amino acid sequence of SEQ ID NO:409. In certain embodiments that may be combined with any of the preceding embodiments, the isolated antibody comprises a heavy chain variable domain and a light chain variable domain, wherein the heavy chain variable domain comprises: (a) n HVR-H1 comprising the amino acid sequence of SEQ ID NO:404, or an amino acid sequence with at least about 95% homology to the amino acid sequence of SEQ ID NO:404; (b) an HVR-H2 comprising the amino acid sequence of SEQ ID NO:405, or an amino acid sequence with at least about 95% homology to the amino acid sequence of SEQ ID NO:405; and/or (c) an HVR-H3 comprising the amino acid sequence of SEQ ID NO:406, or an amino acid sequence with at least about 95% homology to the amino acid sequence of SEQ ID NO:406, and/or wherein the light chain variable domain comprises: (a) an HVR-L1 comprising the amino acid sequence of SEQ ID NO:407, or an amino acid sequence with at least about 95% homology to the amino acid sequence of SEQ ID NO:407; (b) an HVR-L2 comprising the amino acid sequence of SEQ ID NO:408, or an amino acid sequence with at least about 95% homology to the amino acid sequence of SEQ ID NO:408; and/or (c) an HVR-L3 comprising the amino acid sequence of SEQ ID NO:409, or an amino acid sequence with at least about 95% homology to the amino acid sequence of SEQ ID NO:409.

Other aspects of the present disclosure relate to an isolated anti-human TREM2 antibody, wherein the isolated antibody comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52. In certain embodiments that may be combined with any of the preceding embodiments, the HVR-H1 comprises the amino acid sequence of SEQ ID NO:398. In certain embodiments that may be combined with any of the preceding embodiments, the HVR-H2 comprises the amino acid sequence of SEQ ID NO:399. In certain embodiments that may be combined with any of the preceding embodiments, the HVR-H3 comprises the amino acid sequence of SEQ ID NO:400. In certain embodiments that may be combined with any of the preceding embodiments, the HVR-L1 comprises the amino acid sequence of SEQ ID NO:401. In certain embodiments that may be combined with any of the preceding embodiments, the HVR-L2 comprises the amino acid sequence of SEQ ID NO:402. In certain embodiments that may be combined with any of the preceding embodiments, the HVR-L3 comprises the amino acid sequence of SEQ ID NO:403. In certain embodiments that may be combined with any of the preceding embodiments, the isolated antibody comprises a heavy chain variable domain and a light chain variable domain, wherein the heavy chain variable domain comprises an HVR-H1 comprising the amino acid sequence of SEQ ID NO:398, an HVR-H2 comprising the amino acid sequence of SEQ ID NO:399, and an HVR-H3 comprising the amino acid sequence of SEQ ID NO:400, and/or wherein the light chain variable domain comprises an HVR-L1 comprising the amino acid sequence of SEQ ID NO:401, an HVR-L2 comprising the amino acid sequence of SEQ ID NO:402, and an HVR-L3 comprising the amino acid sequence of SEQ ID NO:403.

Other aspects of the present disclosure relate to an isolated anti-human TREM2 antibody, wherein the isolated antibody comprises a heavy chain variable domain and a light chain variable domain, wherein the heavy chain variable domain comprises: (a) an HVR-H1 comprising the amino acid sequence of SEQ ID NO:398, or an amino acid sequence with at least about 95% homology to the amino acid sequence of SEQ ID NO:398; (b) an HVR-H2 comprising the amino acid sequence of SEQ ID NO:399, or an amino acid sequence with at least about 95% homology to the amino acid sequence of SEQ ID NO:399; and; and/or (c) an HVR-H3 comprising the amino acid sequence of SEQ ID NO:400, or an amino acid sequence with at least about 95% homology to the amino acid sequence of SEQ ID NO:400; and/or wherein the light chain variable domain comprises: (a) an HVR-L1 comprising the amino acid sequence of SEQ ID NO:401, or an amino acid sequence with at least about 95% homology to the amino acid sequence of SEQ ID NO:401; (b) an HVR-L2 comprising the amino acid sequence of SEQ ID NO:402, or an amino acid sequence with at least about 95% homology to the amino acid sequence of SEQ ID NO:402; and/or (c) an HVR-L3 comprising the amino acid sequence of SEQ ID NO:403, or an amino acid sequence with at least about 95% homology to the amino acid sequence of SEQ ID NO:403.

Other aspects of the present disclosure relate to an isolated anti-human TREM2 antibody, wherein the isolated antibody comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L1, HVR-L2, and/or HVR-L3 of the monoclonal antibody Ab21. In certain embodiments that may be combined with any of the preceding embodiments, the HVR-H1 comprises the amino acid sequence of SEQ ID NO:404. In certain embodiments that may be combined with any of the preceding embodiments, the HVR-H2 comprises the amino acid sequence of SEQ ID NO:405. In certain embodiments that may be combined with any of the preceding embodiments, the HVR-H3 comprises the amino acid sequence of SEQ ID NO:406. In certain embodiments that may be combined with any of the preceding embodiments, the HVR-L1 comprises the amino acid sequence of SEQ ID NO:407. In certain embodiments that may be combined with any of the preceding embodiments, the HVR-L2 comprises the amino acid sequence of SEQ ID NO:408. In certain embodiments that may be combined with any of the preceding embodiments, the HVR-L3 comprises the amino acid sequence of SEQ ID NO:409. In certain embodiments that may be combined with any of the preceding embodiments, the isolated antibody comprises a heavy chain variable domain and a light chain variable domain, wherein the heavy chain variable domain comprises an HVR-H1 comprising the amino acid sequence of SEQ ID NO:404, an HVR-H2 comprising the amino acid sequence of SEQ ID NO:405, and an HVR-H3 comprising the amino acid sequence of SEQ ID NO:406, and/or wherein the light chain variable domain comprises an HVR-L1 comprising the amino acid sequence of SEQ ID NO:407, an HVR-L2 comprising the amino acid sequence of SEQ ID NO:408, and an HVR-L3 comprising the amino acid sequence of SEQ ID NO:409.

Other aspects of the present disclosure relate to an isolated anti-human TREM2 antibody, wherein the isolated antibody comprises a heavy chain variable domain and a light chain variable domain, wherein the heavy chain variable domain comprises: (a) n HVR-H1 comprising the amino acid sequence of SEQ ID NO:404, or an amino acid sequence with at least about 95% homology to the amino acid sequence of SEQ ID NO:404; (b) an HVR-H2 comprising the amino acid sequence of SEQ ID NO:405, or an amino acid sequence with at least about 95% homology to the amino acid sequence of SEQ ID NO:405; and/or (c) an HVR-H3 comprising the amino acid sequence of SEQ ID NO:406, or an amino acid sequence with at least about 95% homology to the amino acid sequence of SEQ ID NO:406, and/or wherein the light chain variable domain comprises: (a) an HVR-L1 comprising the amino acid sequence of SEQ ID NO:407, or an amino acid sequence with at least about 95% homology to the amino acid sequence of SEQ ID NO:407; (b) an HVR-L2 comprising the amino acid sequence of SEQ ID NO:408, or an amino acid sequence with at least about 95% homology to the amino acid sequence of SEQ ID NO:408; and/or (c) an HVR-L3 comprising the amino acid sequence of SEQ ID NO:409, or an amino acid sequence with at least about 95% homology to the amino acid sequence of SEQ ID NO:409.

Other aspects of the present disclosure relate to an isolated anti-human TREM2 antibody which binds essentially the same TREM2 epitope as the antibody Ab52. Other aspects of the present disclosure relate to an isolated anti-human TREM2 antibody which binds essentially the same TREM2 epitope as the antibody Ab21.

In certain embodiments that may be combined with any of the preceding embodiments, the antibody is an agonist antibody, and wherein the antibody induces one or more TREM2 activities, DAP12 activities, or both. In certain embodiments that may be combined with any of the preceding embodiments, the isolated antibody induces or retains TREM2 clustering, DAP12 clustering, or both on a cell surface. In certain embodiments that may be combined with any of the preceding embodiments, the one or more TREM2 activities, DAP12 activities, or both are selected from the group consisting of TREM2 binding to DAP12; DAP12 binding to TREM2; TREM2 phosphorylation, DAP12 phosphorylation; PI3K activation; increased expression of one or more anti-inflammatory mediators (e.g., cytokines) selected from the group consisting of IL-12p70, IL-6, and IL-10; reduced expression of one or more pro-inflammatory mediators selected from the group consisting of IFN-a4, IFN-b, IL-6, IL-12 p70, IL-1β, TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP; reduced expression of TNF-α, IL-6, or both; extracellular signal-regulated kinase (ERK) phosphorylation; increased expression of C—C chemokine receptor 7 (CCR7); induction of microglial cell chemotaxis toward CCL19 and CCL21 expressing cells; an increase, normalization, or both of the ability of bone marrow-derived dendritic cells to induce antigen-specific T-cell proliferation; induction of osteoclast production, increased rate of osteoclastogenesis, or both; increasing the survival and/or function of one or more of dendritic cells, macrophages, microglial cells, M1 macrophages and/or microglial cells, activated M1 macrophages and/or microglial cells, M2 macrophages and/or microglial cells, monocytes, osteoclasts, Langerhans cells of skin, and Kupffer cells; induction of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance; induction of phagocytosis of one or more of apoptotic neurons, nerve tissue debris, non-nerve tissue debris, bacteria, other foreign bodies, disease-causing proteins, disease-causing peptides, or disease-causing nucleic acids; normalization of disrupted TREM2/DAP12-dependent gene expression; recruitment of Syk, ZAP70, or both to the TREM2/DAP12 complex; Syk phosphorylation; increased expression of CD83 and/or CD86 on dendritic cells, macrophages, monocytes, and/or microglia; reduced secretion of one or more inflammatory cytokines selected from the group consisting of TNF-α, IL-10, IL-6, MCP-1, IFN-a4, IFN-b, IL-1β, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP; reduced expression of one or more inflammatory receptors; increasing phagocytosis by macrophages, dendritic cells, monocytes, and/or microglia under conditions of reduced levels of MCSF; decreasing phagocytosis by macrophages, dendritic cells, monocytes, and/or microglia in the presence of normal levels of MCSF; increasing activity of one or more TREM2-dependent genes; and any combination thereof. In certain embodiments that may be combined with any of the preceding embodiments, the antibody is of the IgG class the IgM class, or the IgA class. In certain embodiments that may be combined with any of the preceding embodiments, the antibody is of the IgG class and has an IgG1, IgG2, IgG3, or IgG4 isotype. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the human IgG2 constant region comprises an Fc region. In certain embodiments that may be combined with any of the preceding embodiments, the antibody induces the one or more TREM2 activities, DAP12 activities, or both independently of binding to an Fc receptor. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU or Kabat numbering. In certain embodiments that may be combined with any of the preceding embodiments, the human IgG2 constant region comprises a light chain constant region comprising a C214S amino acid substitution, wherein the numbering of the residues is according to EU or Kabat numbering. In certain embodiments that may be combined with any of the preceding embodiments, the antibody has an IgG1 isotype. In certain embodiments that may be combined with any of the preceding embodiments, the antibody comprises a human IgG1 constant region. In certain embodiments that may be combined with any of the preceding embodiments, the human IgG1 constant region comprises an Fc region. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγRIIB). In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to EU or Kabat numbering. In certain embodiments that may be combined with any of the preceding embodiments, the antibody comprises an IgG2 isotype heavy chain constant domain 1(CH1) and hinge region. In certain embodiments that may be combined with any of the preceding embodiments, the IgG2 isotype CH1 and hinge region comprise the amino acid sequence of ASTKGPSVFP LAPCSRSTSE STAALGCLVK DYFPEPVTVS WNSGALT-SGVHTFPAVLQSS GLYSLSSVVT VPSSNFGTQT YTCNVDHKPS NTKVDKTVERKCCVECPPCP (SEQ ID NO: 397). In certain embodiments that may be combined with any of the preceding embodiments, the antibody Fc region comprises a S267E amino acid substitution, a L328F amino acid substitution, or both, and/or a N297A or N297Q amino acid substitution, wherein the numbering of the residues is according to EU or Kabat numbering. In certain embodiments that may be combined with any of the preceding embodiments, the antibody comprises a mouse IgG1 constant region. In certain embodiments that may be combined with any of the preceding embodiments, the antibody has an IgG4 isotype. In certain embodiments that may be combined with any of the preceding embodiments, the antibody comprises a human IgG4 constant region. In certain embodiments that may be combined with any of the preceding embodiments, the human IgG4 constant region comprises an Fc region. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU or Kabat numbering. In certain embodiments that may be combined with any of the preceding embodiments, the antibody has a hybrid IgG2/4 isotype. In certain embodiments that may be combined with any of the preceding embodiments, the antibody comprises an amino acid sequence comprising amino acids 118 to 260 of human IgG2 and amino acids 261 to 447 of human IgG4, wherein the numbering of the residues is according to EU or Kabat numbering. In certain embodiments that may be combined with any of the preceding embodiments, the antibody comprises a mouse IgG4 constant region. In certain embodiments that may be combined with any of the preceding embodiments, the isolated antibody is an antibody fragment that binds to one or more human proteins selected from the group consisting of human TREM2, a naturally occurring variant of human TREM2, human DAP12, and naturally occurring variant of human DAP12, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the fragment is an Fab, Fab', Fab'-SH, F(ab')2, Fv or scFv fragment. In certain embodiments that may be combined with any of the preceding embodiments, the isolated antibody is an inert antibody. In certain embodiments that may be combined with any of the preceding embodiments, the isolated antibody is an antagonist antibody. In certain embodiments that may be combined with any of the preceding embodiments, the isolated antibody inhibits one or more TREM2 activities. In certain embodiments that may be combined with any of the preceding embodiments, the one or more TREM2 activities are selected from the group consisting of decreasing activity of one or more TREM2-dependent genes; decreasing activity of one or more nuclear factor of activated T-cells (NFAT) transcription factors; decreasing the survival of macrophages, microglial cells, monocytes, osteoclasts, Langerhans cells of skin, Kupffer cells, and/or dendritic cells; and any combination thereof. In certain embodiments that may be combined with any of the preceding embodiments, the isolated antibody inhibits interaction between TREM2 and one or more TREM2 ligands, inhibits TREM2 signal transduction, or both. In certain embodiments that may be combined with any of the preceding embodiments, the antibody is incapable of binding an Fc-gamma receptor (FcγR). In certain embodiments that may be combined with any of the preceding embodiments, the antibody has an IgG1 isotype. In certain embodiments that may be combined with any of the preceding embodiments, the antibody comprises a human IgG1 constant region. In certain embodiments that may be combined with any of the preceding embodiments, the human IgG1 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof, wherein the numbering of the residues is according to EU or Kabat numbering. In certain embodiments that may be combined with any of the preceding embodiments, the Fc region further comprises an amino acid deletion at a position corresponding to glycine 236 according to EU or Kabat numbering. In certain embodiments that may be combined with any of the preceding embodiments, the antibody comprises a mouse IgG1 constant region. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the human IgG2 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU or Kabat numbering. In certain embodiments that may be combined with any of the preceding embodiments, the antibody has an IgG4 isotype. In certain embodiments that may be combined with any of the preceding embodiments, the antibody comprises a human IgG4 constant region. In certain embodiments that may be combined with any of the preceding embodiments, the human IgG4 constant region comprises an Fc region. In certain embodiments that may be combined with any of the preceding embodiments, the Fc region comprises one or more modifications. In certain embodiments that may be combined with any of the preceding embodiments, the Fc region comprises one or more amino acid substitutions. In certain embodiments that may be combined with any of the preceding embodiments, the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, the isolated antibody is an antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the fragment is an Fab, Fab', Fab'-SH, F(ab')2, Fv or scFv fragment. In certain embodiments that may be combined with any of the preceding embodiments, the Fc region further comprises one or more additional amino acid substitutions at a position selected from the group consisting of A330L, L234F; L235E, P331S, and any combination thereof, wherein the numbering of the residues is according to EU or Kabat numbering. In certain embodiments that may be combined with any of the preceding embodiments, the Fc region further comprises one or more additional amino acid substitutions at a position selected from the group consisting of M252Y, S254T, T256E, and any combination thereof, wherein the numbering of the residues is according to EU or Kabat numbering. In certain embodiments that may be combined with any of the preceding embodiments, the Fc region further comprises a S228P amino acid substitution according to EU or Kabat numbering. In certain embodiments that may be combined with any of the preceding embodiments, the antibody is a human antibody, a humanized antibody, a bispecific antibody, a multivalent antibody, or a chimeric antibody. In certain embodiments that may be combined with any of the preceding embodiments, the antibody is a bispecific antibody recognizing a first antigen and a second antigen. In certain embodiments that may be combined with any of the preceding embodiments, the antibody is a monoclonal antibody.

Other aspects of the present disclosure relate to an isolated antibody that binds to a TREM2 protein, wherein the isolated antibody promotes survival of one or more innate immune cells. Other aspects of the present disclosure relate to an isolated antibody that binds to a TREM2 protein, wherein the isolated antibody increases expression of IL-6. Other aspects of the present disclosure relate to an isolated antibody that binds to a TREM2 protein, wherein the isolated antibody promotes survival of one or more innate immune cells or increases expression of IL-6. Other aspects of the present disclosure relate to an isolated antibody that binds to a TREM2 protein, wherein the isolated antibody promotes survival of one or more innate immune cells and increases expression of IL-6. In certain embodiments, the one or more innate immune cells are selected from the group consisting of macrophages, microglial cells, M1 microglial cells, activated M1 microglial cells, M2 microglial cells, dendritic cells, M1 macrophages, activated M1 macrophages, M2 macrophages, monocytes, osteoclasts, Langerhans cells of skin, Kupffer cells, and any combination thereof. In certain embodiments, the one or more innate immune cells are macrophages. In certain embodiments, the one or more innate immune cells are microglial cells. In certain embodiments, the one or more innate immune cells are M1 microglial cells. In certain embodiments, the one or more innate immune cells are activated M1 microglial cells. In certain embodiments, the one or more innate immune cells are M2 microglial cells. In certain embodiments, the one or more innate immune cells are dendritic cells (DCs). In certain embodiments, the one or more innate immune cells are M1 macrophages. In certain embodiments, the one or more innate immune cells are activated M1 macrophages. In certain embodiments, the one or more innate immune cells are M2 macrophages. In certain embodiments, the one or more innate immune cells are monocytes. In certain embodiments, the one or more innate immune cells are osteoclasts. In certain embodiments, the one or more innate immune cells are Langerhans cells of skin. In certain embodiments, the one or more innate immune cells are Kupffer cells.

Other aspects of the present disclosure relate to an isolated antibody that binds to a TREM2 protein, wherein the isolated antibody binds to one or more amino acids within amino acid residues selected from the group consisting of: i. amino acid residues 29-112 of SEQ ID NO: 1, or amino acid residues on a TREM2 protein corresponding to amino acid residues 29-112 of SEQ ID NO: 1; ii. amino acid residues 29-41 of SEQ ID NO: 1, or amino acid residues on a TREM2 protein corresponding to amino acid residues 29-41 of SEQ ID NO: 1; iii. amino acid residues 40-44 of SEQ ID NO: 1, or amino acid residues on a TREM2 protein corresponding to amino acid residues 40-44 of SEQ ID NO: 1; iv. amino acid residues 43-50 of SEQ ID NO: 1, or amino acid residues on a TREM2 protein corresponding to amino acid residues 43-50 of SEQ ID NO: 1; v. amino acid residues 49-57 of SEQ ID NO: 1, or amino acid residues on a TREM2 protein corresponding to amino acid residues 49-57 of SEQ ID NO: 1; vi. amino acid residues 47-69 of SEQ ID NO: 1, or amino acid residues on a TREM2 protein corresponding to amino acid residues 47-69 of SEQ ID NO: 1; vii. amino acid residues 67-76 of SEQ ID NO: 1, or amino acid residues on a TREM2 protein corresponding to amino acid residues 67-76 of SEQ ID NO: 1; viii. amino acid residues 76-86 of SEQ ID NO: 1, or amino acid residues on a TREM2 protein corresponding to amino acid residues 76-86 of SEQ ID NO: 1; ix. amino acid residues 91-100 of SEQ ID NO: 1, or amino acid residues on a TREM2 protein corresponding to amino acid residues 91-100 of SEQ ID NO: 1; x. amino acid residues 99-115 of SEQ ID NO: 1, or amino acid residues on a TREM2 protein corresponding to amino acid residues 99-115 of SEQ ID NO: 1; xi. amino acid residues 104-112 of SEQ ID NO: 1, or amino acid residues on a TREM2 protein corresponding to amino acid residues 104-112 of SEQ ID NO: 1; xii. amino acid residues 114-118 of SEQ ID NO: 1, or amino acid residues on a TREM2 protein corresponding to amino acid residues 114-118 of SEQ ID NO: 1; xiii. amino acid residues 130-171 of SEQ ID NO: 1, or amino acid residues on a TREM2 protein corresponding to amino acid residues 130-171 of SEQ ID NO: 1; xiv. amino acid residues 139-146 of SEQ ID NO: 1, or amino acid residues on a TREM2 protein corresponding to amino acid residues 139-146 of SEQ ID NO: 1; xv. amino acid residues 140-153 of SEQ ID NO: 1, or amino acid residues on a TREM2 protein corresponding to amino acid residues 140-153 of SEQ ID NO: 1; xvi. amino acid residues 130-144 of SEQ ID NO: 1, or amino acid residues on a TREM2 protein corresponding to amino acid residues 130-144 of SEQ ID NO: 1; and xvii. amino acid residues 158-171 of SEQ ID NO: 1, or amino acid residues on a TREM2 protein corresponding to amino acid residues 158-171 of SEQ ID NO: 1. In certain embodiments, the isolated antibody binds to one or more amino acids within amino acid residues 43-50 of SEQ ID NO: 1, or amino acid residues on a TREM2 protein corresponding to amino acid residues 43-50 of SEQ ID NO: 1. In certain embodiments, the isolated antibody binds to one or more amino acids within amino acid residues 49-57 of SEQ ID NO: 1, or amino acid residues on a TREM2 protein corresponding to amino acid residues 49-57 of SEQ ID NO: 1. In certain embodiments, the isolated antibody binds to one or more amino acids within amino acid residues 139-146 of SEQ ID NO: 1, or amino acid residues on a TREM2 protein corresponding to amino acid residues 49-57 of SEQ ID NO: 1. In certain embodiments, the isolated antibody binds to one or more amino acids within amino acid residues 140-153 of SEQ ID NO: 1, or amino acid residues on a TREM2 protein corresponding to amino acid residues 140-153 of SEQ ID NO: 1. In certain embodiments, the isolated antibody binds to an epitope comprising one or more amino acids within amino acid residues 43-50 of SEQ ID NO: 1. In certain embodiments, the isolated antibody binds to an epitope comprising one or more amino acids within amino acid residues 49-57 of SEQ ID NO: 1. In certain embodiments, the isolated antibody binds to an epitope comprising one or more amino acids within amino acid residues 139-146 of SEQ ID NO: 1. In certain embodiments, the isolated antibody binds to an epitope comprising one or more amino acids within amino acid residues 140-153 of SEQ ID NO: 1.

In certain embodiments that may be combined with any of the preceding embodiments, the TREM2 protein is a mammalian protein or a human protein. In certain embodiments that may be combined with any of the preceding embodiments, the TREM2 protein is a wild-type protein. In certain embodiments that may be combined with any of the preceding embodiments, the TREM2 protein is a naturally occurring variant. In certain embodiments that may be combined with any of the preceding embodiments, the antibody is an agonist antibody, and wherein the antibody induces one or more TREM2 activities. In certain embodiments that may be combined with any of the preceding embodiments, the isolated antibody induces or retains TREM2 clustering on a cell surface. In certain embodiments that may be combined with any of the preceding embodiments, the one or more TREM2 activities are selected from the group consisting of: i. TREM2 binding to DAP12; ii. DAP12 phosphorylation; iii. increasing the survival of macrophages, microglial cells, M1 microglial cells, activated M1 microglial cells, M2 microglial cells, dendritic cells, macrophages, M1 macrophages, activated M1 macrophages, M2 macrophages, monocytes, osteoclasts, Langerhans cells of skin, and/or Kupffer cells; iv. Syk phosphorylation; v. increased expression of CD83 and/or CD86 on dendritic cells; vi. increasing phagocytosis by macrophages, dendritic cells, monocytes, and/or microglia; vii. increasing activity of one or more TREM2-dependent genes, optionally wherein the one or more TREM2-dependent genes comprise one or more nuclear factor of activated T-cells (NFAT) transcription factors; and viii. increasing expression of one or more mediators selected from the group consisting of IL-12p70, IL-6, and IL-10. In certain embodiments that may be combined with any of the preceding embodiments, the antibody is of the IgG class the IgM class, or the IgA class. In certain embodiments that may be combined with any of the preceding embodiments, the antibody is of the IgG class and has an IgG1, IgG2, IgG3, or IgG4 isotype. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the human IgG2 constant region comprises an Fc region. In certain embodiments that may be combined with any of the preceding embodiments, the antibody induces the one or more TREM2 activities independently of binding to an Fc receptor. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments: i. the isolated antibody has a human IgG2 isotype and comprises one or more amino acid substitutions in the Fc region at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU or Kabat numbering; ii. the isolated antibody has a human IgG2 isotype, wherein the human IgG2 comprises a constant region, and wherein the human IgG2 constant region comprises a light chain constant region comprising a C214S amino acid substitution, wherein the numbering of the residues is according to EU or Kabat numbering; iii. the isolated antibody has a human or mouse IgG1 isotype and comprises one or more amino acid substitutions in the Fc region at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to EU or Kabat numbering; iv. the isolated antibody has an IgG1 isotype and comprises an IgG2 isotype heavy chain constant domain 1(CH1) and hinge region, optionally wherein the IgG2 isotype CH1 and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397), and optionally wherein the antibody Fc region comprises a S267E amino acid substitution, a L328F amino acid substitution, or both, and/or a N297A or N297Q amino acid substitution, wherein the numbering of the residues is according to EU or Kabat numbering; v. the isolated antibody has a human or mouse IgG4 isotype and comprises one or more amino acid substitutions in the Fc region at a residue position selected from the group consisting of L235A, G237A, S228P, L236E, S267E, E318A, L328F, M252Y, S254T, T256E, and any combination thereof, wherein the numbering of the residues is according to EU or Kabat numbering; or vi. the isolated antibody has a hybrid IgG2/4 isotype, optionally wherein the antibody comprises an amino acid sequence comprising amino acids 118 to 260 of human IgG2 and amino acids 261 to 447 of human IgG4, wherein the numbering of the residues is according to EU or, Kabat numbering. In certain embodiments that may be combined with any of the preceding embodiments, the isolated antibody is an inert antibody. In certain embodiments that may be combined with any of the preceding embodiments, the isolated antibody is an antagonist antibody. In certain embodiments that may be combined with any of the preceding embodiments, the isolated antibody inhibits one or more TREM2 activities. In certain embodiments that may be combined with any of the preceding embodiments, the inhibited one or more TREM2 activities are selected from the group consisting of decreasing activity of one or more TREM2-dependent genes; decreasing activity of one or more nuclear factor of activated T-cells (NFAT) transcription factors; decreasing the survival of macrophages, microglial cells, M1 macrophages, M1 microglial cells, M2 macrophages, M2 microglial cells, osteoclasts, Langerhans cells of skin, Kupffer cells, and/or dendritic cells; decreased expression of one or more mediators selected from the group consisting of IL-12p70, IL-6, and IL-10; and any combination thereof. In certain embodiments that may be combined with any of the preceding embodiments, the isolated antibody inhibits interaction between TREM2 and one or more TREM2 ligands, inhibits TREM2 signal transduction, or both. In certain embodiments that may be combined with any of the preceding embodiments, the antibody is incapable of binding an Fc-gamma receptor (FcγR). In certain embodiments that may be combined with any of the preceding embodiments: i. the isolated antibody has a human or mouse IgG1 isotype and comprises one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU or Kabat numbering, optionally wherein the Fc region further comprises an amino acid deletion at a position corresponding to glycine 236 according to EU or Kabat numbering; ii. the isolated antibody has a human IgG2 isotype and comprises one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU or Kabat numbering; or iii. the isolated antibody has a human or mouse IgG4 isotype and comprises one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, the Fc region further comprises one or more additional amino acid substitutions at a position selected from the group consisting of A330L, L234F; L235E, P331S, and any combination thereof, wherein the numbering of the residues is according to EU or Kabat numbering. In certain embodiments that may be combined with any of the preceding embodiments, the Fc region further comprises a S228P amino acid substitution according to EU or Kabat numbering. In certain embodiments that may be combined with any of the preceding embodiments, the Fc region further comprises one or more additional amino acid substitutions at a position selected from the group consisting of M252Y, S254T, T256E, and any combination thereof, wherein the numbering of the residues is according to EU or Kabat numbering. In certain embodiments that may be combined with any of the preceding embodiments, the isolated antibody is an antibody fragment that binds to one or more human proteins selected from the group consisting of human TREM2, and a naturally occurring variant of human TREM2, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the isolated antibody is an antibody fragment, and wherein the antibody fragment is an Fab, Fab', Fab'-SH, F(ab')2, Fv or scFv fragment. In certain embodiments that may be combined with any of the preceding embodiments, the isolated antibody competes for binding of TREM2 with one or more TREM2 ligands. In certain embodiments that may be combined with any of the preceding embodiments, the one or more TREM2 ligands are selected from the group consisting of E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide. In certain embodiments that may be combined with any of the preceding embodiments, the isolated antibody is a human antibody, a humanized antibody, a bispecific antibody, a multivalent antibody, or a chimeric antibody. In certain embodiments that may be combined with any of the preceding embodiments, the isolated antibody is a bispecific antibody recognizing a first antigen and a second antigen. In certain embodiments that may be combined with any of the preceding embodiments, the first antigen is human TREM2 or a naturally occurring variant thereof, and the second antigen is a disease-causing protein selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides; or a blood brain barrier targeting protein selected from the group consisting of: trasnferin receptor, insulin receptor, insulin like growth factor receptor, LRP-1, and LRP1. In certain embodiments that may be combined with any of the preceding embodiments, the isolated antibody is an antibody fragment that binds to one or more human proteins selected from the group consisting of human TREM2, and a naturally occurring variant of human TREM2; and wherein the antibody is used in combination with one or more antibodies that specifically bind a disease-causing protein selected from the group consisting of: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, and any combination thereof. In certain embodiments that may be combined with any of the preceding embodiments, the antibody is a monoclonal antibody. In certain embodiments that may be combined with any of the preceding embodiments, the isolated antibody is a bispecific antibody that binds to TREM2 and DAP12.

In certain embodiments that may be combined with any of the preceding embodiments, the isolated antibody comprises a heavy chain variable domain and a light chain variable domain, wherein the heavy chain variable domain comprises: (a) an HVR-H1 comprising an amino acid sequence selected from the group consisting of SEQ ID NOs:3-24, 398, and 404; an HVR-H2 comprising an amino acid sequence selected from the group consisting of SEQ ID NOs:25-49, 399, and 405; and (c) an HVR-H3 c comprising an amino acid sequence selected from the group consisting of SEQ ID NOs:50-119, 400, and 406; and/or wherein the light chain variable domain comprises: (a) an HVR-L1 c comprising an amino acid sequence selected from the group consisting of SEQ ID NOs: 120-137, 401, and 407; (b) an HVR-L2 comprising an amino acid sequence selected from the group consisting of SEQ ID NOs:138-152, 402, and 408; and (c) an HVR-L3 comprising an amino acid sequence selected from the group consisting of SEQ ID NOs:153-236, 403, and 409.

Other aspects of the present disclosure relate to an isolated anti-human TREM2 antibody, wherein the isolated antibody comprises a heavy chain variable domain and a light chain variable domain, wherein the heavy chain variable domain comprises: (a) an HVR-H1 comprising an amino acid sequence selected from the group consisting of SEQ ID NOs:3-24, 398, and 404; an HVR-H2 comprising an amino acid sequence selected from the group consisting of SEQ ID NOs:25-49, 399, and 405; and (c) an HVR-H3 c comprising an amino acid sequence selected from the group consisting of SEQ ID NOs:50-119, 400, and 406; and/or wherein the light chain variable domain comprises: (a) an HVR-L1 c comprising an amino acid sequence selected from the group consisting of SEQ ID NOs: 120-137, 401, and 407; (b) an HVR-L2 comprising an amino acid sequence selected from the group consisting of SEQ ID NOs:138-152, 402, and 408; and (c) an HVR-L3 comprising an amino acid sequence selected from the group consisting of SEQ ID NOs:153-236, 403, and 409. Other aspects of the present disclosure relate to an isolated anti-human TREM2 antibody which binds essentially the same TREM2 epitope as a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. Other aspects of the present disclosure relate to an isolated anti-human TREM2 antibody which competes with a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87 for binding to TREM2.

In certain embodiments that may be combined with any of the preceding embodiments, the antibody is an agonist antibody, and wherein the antibody induces one or more TREM2 activities. In certain embodiments that may be combined with any of the preceding embodiments, the isolated antibody induces or retains TREM2 clustering on a cell surface. In certain embodiments that may be combined with any of the preceding embodiments, the one or more TREM2 activities are selected from the group consisting of TREM2 binding to DAP12; DAP12 phosphorylation; increasing the survival of macrophages, microglial cells, M1 microglial cells, activated M1 microglial cells, M2 microglial cells, dendritic cells, macrophages, M1 macrophages, activated M1 macrophages, M2 macrophages, monocytes, osteoclasts, Langerhans cells of skin, and/or Kupffer cells; increased expression of IL-6; Syk phosphorylation; increased expression of CD83 and/or CD86 on dendritic cells; increasing phagocytosis by macrophages, dendritic cells, monocytes, and/or microglia; and increasing activity of one or more TREM2-dependent genes, optionally wherein the one or more TREM2-dependent genes comprise one or more nuclear factor of activated T-cells (NFAT) transcription factors; and any combination thereof. In certain embodiments that may be combined with any of the preceding embodiments, the antibody is of the IgG class the IgM class, or the IgA class. In certain embodiments that may be combined with any of the preceding embodiments, the antibody is of the IgG class and has an IgG1, IgG2, IgG3, or IgG4 isotype. In certain embodiments that may be combined with any of the preceding embodiments, the antibody has an IgG2 isotype. In certain embodiments that may be combined with any of the preceding embodiments, the antibody comprises a human IgG2 constant region. In certain embodiments that may be combined with any of the preceding embodiments, the human IgG2 constant region comprises an Fc region. In certain embodiments that may be combined with any of the preceding embodiments, the antibody induces the one or more TREM2 activities independently of binding to an Fc receptor. In certain embodiments that may be combined with any of the preceding embodiments, the antibody binds an inhibitory Fc receptor. In certain embodiments that may be combined with any of the preceding embodiments, the inhibitory Fc receptor is inhibitory Fc-gamma receptor IIB (FcγIIB). In certain embodiments that may be combined with any of the preceding embodiments: i. the isolated antibody has a human IgG2 isotype and comprises one or more amino acid substitutions in the Fc region at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU or Kabat numbering; ii. the isolated antibody has a human IgG2 isotype, wherein the human IgG2 comprises a constant region, and wherein the human IgG2 constant region comprises a light chain constant region comprising a C214S amino acid substitution, wherein the numbering of the residues is according to EU or Kabat numbering; iii. the isolated antibody has a human or mouse IgG1 isotype and comprises one or more amino acid substitutions in the Fc region at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to EU or Kabat numbering; iv. the isolated antibody has an IgG1 isotype and comprises an IgG2 isotype heavy chain constant domain 1(CH1) and hinge region, optionally wherein the IgG2 isotype CH1 and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397), and optionally wherein the antibody Fc region comprises a S267E amino acid substitution, a L328F amino acid substitution, or both, and/or a N297A or N297Q amino acid substitution, wherein the numbering of the residues is according to EU or Kabat numbering; v. the isolated antibody has a human or mouse IgG1 isotype and comprises one or more amino acid substitutions in the Fc region at a residue position selected from the group consisting of L235A, G237A, S228P, L236E, S267E, E318A, L328F, M252Y, S254T, T256E, and any combination thereof, wherein the numbering of the residues is according to EU or Kabat numbering; or vi. the isolated antibody has a hybrid IgG2/4 isotype, optionally wherein the antibody comprises an amino acid sequence comprising amino acids 118 to 260 of human IgG2 and amino acids 261 to 447 of human IgG4, wherein the numbering of the residues is according to EU or, Kabat numbering. In certain embodiments that may be combined with any of the preceding embodiments, the isolated antibody is an antibody fragment that binds to one or more human proteins selected from the group consisting of human TREM2, and a naturally occurring variant of human TREM2, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12. In certain embodiments that may be combined with any of the preceding embodiments, the isolated antibody is an antibody fragment, and wherein the antibody fragment is an Fab, Fab', Fab'-SH, F(ab')2, Fv or scFv fragment. In certain embodiments that may be combined with any of the preceding embodiments, the isolated antibody is an inert antibody. In certain embodiments that may be combined with any of the preceding embodiments, the isolated antibody is an antagonist antibody. In certain embodiments that may be combined with any of the preceding embodiments, the isolated antibody inhibits one or more TREM2 activities. In certain embodiments that may be combined with any of the preceding embodiments, the inhibited one or more TREM2 activities are selected from the group consisting of decreasing activity of one or more TREM2-dependent genes; decreasing activity of one or more nuclear factor of activated T-cells (NFAT) transcription factors; decreasing the survival of macrophages, microglial cells, monocytes, osteoclasts, Langerhans cells of skin, Kupffer cells, and/or dendritic cells; decreased expression of one or more mediators selected from the group consisting of IL-12p70, IL-6, and IL-10; and any combination thereof. In certain embodiments that may be combined with any of the preceding embodiments, the isolated antibody inhibits interaction between TREM2 and one or more TREM2 ligands, inhibits TREM2 signal transduction, or both. In certain embodiments that may be combined with any of the preceding embodiments, the antibody is incapable of binding an Fc-gamma receptor (FcγR). In certain embodiments that may be combined with any of the preceding embodiments: i. the isolated antibody has a human or mouse IgG1 isotype and comprises one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU or Kabat numbering, optionally wherein the Fc region further comprises an amino acid deletion at a position corresponding to glycine 236 according to EU or Kabat numbering; ii. the isolated antibody has a human IgG2 isotype and comprises one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU or Kabat numbering; or iii. the isolated antibody has a human or mouse IgG4 isotype and comprises one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, the isolated antibody is an antibody fragment that binds to one or more human proteins selected from the group consisting of human TREM2, and a naturally occurring variant of human TREM2. In certain embodiments that may be combined with any of the preceding embodiments, the isolated antibody is an antibody fragment, and wherein the antibody fragment is an Fab, Fab', Fab'-SH, F(ab')2, Fv or scFv fragment. In certain embodiments that may be combined with any of the preceding embodiments, the Fc region further comprises one or more additional amino acid substitutions at a position selected from the group consisting of A330L, L234F; L235E, P331 S, and any combination thereof, wherein the numbering of the residues is according to EU or Kabat numbering. In certain embodiments that may be combined with any of the preceding embodiments, the Fc region further comprises a S228P amino acid substitution according to EU or Kabat numbering. In certain embodiments that may be combined with any of the preceding embodiments, the Fc region further comprises one or more additional amino acid substitutions at a position selected from the group consisting of M252Y, S254T, T256E, and any combination thereof, wherein the numbering of the residues is according to EU or Kabat numbering. In certain embodiments that may be combined with any of the preceding embodiments, the antibody is a human antibody, a humanized antibody, a bispecific antibody, a multivalent antibody, or a chimeric antibody. In certain embodiments that may be combined with any of the preceding embodiments, the antibody is a bispecific antibody recognizing a first antigen and a second antigen. In certain embodiments that may be combined with any of the preceding embodiments, the antibody is a monoclonal antibody.

In certain embodiments that may be combined with any of the preceding embodiments, the isolated antibody binds specifically to both human TREM2 and mouse TREM2. In certain embodiments that may be combined with any of the preceding embodiments, the isolated antibody has dissociation constant ($K_D$) for human TREM2 and mouse TREM2 that ranges from less than about 5.75 nM to less than about 0.09 nM. In certain embodiments that may be combined with any of the preceding embodiments, the isolated antibody has dissociation constant ($K_D$) for human TREM2-Fc fusion protein that ranges from less than about 1.51 nM to less than about 0.35 nM. In certain embodiments that may be combined with any of the preceding embodiments, the isolated antibody has dissociation constant ($K_D$) for human monomeric TREM2 protein that ranges from less than about 5.75 nM to less than about 1.15 nm. In certain embodiments that may be combined with any of the preceding embodiments, the isolated antibody has dissociation constant ($K_D$) for mouse TREM2-Fc fusion protein that ranges from less than about 0.23 nM to less than about 0.09 nM. In certain embodiments that may be combined with any of the preceding embodiments, the isolated antibody has dissociation constant ($K_D$) for human TREM2 and mouseTREM2 that ranges from less than about 6.70 nM to less than about 0.23 nM. In certain embodiments that may be combined with any of the preceding embodiments, the isolated antibody has dissociation constant ($K_D$) for human TREM2-Fc fusion protein that ranges from less than about 0.71 nM to less than about 0.23 nM. In certain embodiments that may be combined with any of the preceding embodiments, the isolated antibody has dissociation constant ($K_D$) for human monomeric TREM2 protein that ranges from less than about 6.70 nM to less than about 0.66 nM. In certain embodiments that may be combined with any of the preceding embodiments, the isolated antibody has dissociation constant ($K_D$) for mouse TREM2-Fc fusion protein that ranges from less than about 4.90 nM to less than about 0.35 nM.

Other aspects of the present disclosure relate to an isolated nucleic acid encoding the antibody of any one of the preceding embodiments. Other aspects of the present disclosure relate to a vector comprising the nucleic acid of any one of the preceding embodiments. Other aspects of the present disclosure relate to a host cell comprising the vector of any one of the preceding embodiments. Other aspects of the present disclosure relate to an isolated host cell comprising the vector of any one of the preceding embodiments. Other aspects of the present disclosure relate to a method of producing an antibody, comprising culturing the cell of any one of the preceding embodiments so that the antibody is produced. In certain embodiments, the method further comprises recovering the antibody produced by the cell. Other aspects of the present disclosure relate to an isolated antibody produced by any of the preceding methods of producing an antibody. Other aspects of the present disclosure relate to a pharmaceutical composition comprising the antibody of any one of the preceding embodiments and a pharmaceutically acceptable carrier.

Other aspects of the present disclosure relate to a method of preventing, reducing risk, or treating an individual having a disease, disorder, or injury selected from the group consisting of dementia, frontotemporal dementia, Alzheimer's disease, Nasu-Hakola disease, and multiple sclerosis, comprising administering to the individual a therapeutically effective amount of an isolated agonist antibody of any one of the preceding embodiments. Other aspects of the present disclosure relate to an isolated agonist antibody of any one of the preceding embodiments for use in preventing, reducing risk, or treating an individual having a disease, disorder, or injury selected from the group consisting of dementia, frontotemporal dementia, Alzheimer's disease, Nasu-Hakola disease, and multiple sclerosis. Other aspects of the present disclosure relate to use of an isolated agonist antibody of any one of the preceding embodiments in the manufacture of a medicament for preventing, reducing risk, or treating an individual having a disease, disorder, or injury selected from the group consisting of dementia, frontotemporal dementia, Alzheimer's disease, Nasu-Hakola disease, and multiple sclerosis. In certain embodiments that may be combined with any of the preceding embodiments, the individual has a heterozygous variant of TREM2, wherein the variant comprises one or more substitutions selected from the group consisting of: i. a glutamic acid to stop codon substitution in the nucleic acid sequence encoding amino acid residue Glu14 of SEQ ID NO: 1; ii. a glutamine to stop codon substitution in the nucleic acid sequence encoding amino acid residue Gln33 of SEQ ID NO: 1; iii. a tryptophan to stop codon substitution in the nucleic acid sequence encoding amino acid residue Trp44 of SEQ ID NO: 1; iv. an arginine to histidine amino acid substitution at an amino acid corresponding to amino acid residue Arg47 of SEQ ID NO: 1; v. a tryptophan to stop codon substitution in the nucleic acid sequence encoding amino acid residue Trp78 of SEQ ID NO: 1; vi. a valine to glycine amino acid substitution at an amino acid corresponding to amino acid residue Val126 of SEQ ID NO: 1; vii. an aspartic acid to glycine amino acid substitution at an amino acid corresponding to amino acid residue Asp134 of SEQ ID NO: 1; and viii. a lysine to asparagine amino acid substitution at an amino acid corresponding to amino acid residue Lys186 of SEQ ID NO: 1. In certain embodiments that may be combined with any of the preceding embodiments, the individual has a heterozygous variant of TREM2, wherein the variant comprises a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; or both. In certain embodiments that may be combined with any of the preceding embodiments, the individual has a heterozygous variant of DAP12, wherein the variant comprises one or more variants selected from the group consisting of: i. a methionine to threonine substitution at an amino acid corresponding to amino acid residue Met1 of SEQ ID NO: 2; ii. a glycine to arginine amino acid substitution at an amino acid corresponding to amino acid residue Gly49 of SEQ ID NO: 2; iii. a deletion within exons 1-4 of the nucleic acid sequence encoding SEQ ID NO: 2; iv. an insertion of 14 amino acid residues at exon 3 of the nucleic acid sequence encoding SEQ ID NO: 2; and v. a guanine nucleotide deletion at a nucleotide corresponding to nucleotide residue G141 of the nucleic acid sequence encoding SEQ ID NO: 2.

Other aspects of the present disclosure relate to a method of inducing or promoting innate immune cell survival in an individual in need thereof, comprising administering to the individual a therapeutically effective amount of an isolated agonist antibody of any one of the preceding embodiments. Other aspects of the present disclosure relate to an isolated agonist antibody of any one of the preceding embodiments for use in inducing or promoting innate immune cell survival in an individual in need thereof. Other aspects of the present disclosure relate to use of an isolated agonist antibody of any one of the preceding embodiments in the manufacture of a medicament for inducing or promoting innate immune cell survival in an individual in need thereof. Other aspects of the present disclosure relate to a method of inducing or promoting wound healing in an individual in need thereof, comprising administering to the individual a therapeutically effective amount of an isolated agonist antibody that binds to a TREM2 protein. Other aspects of the present disclosure relate to an isolated agonist antibody that binds to a TREM2 protein for use in inducing or promoting wound healing in an individual in need thereof. Other aspects of the present disclosure relate to use of an isolated agonist antibody that binds to a TREM2 protein in the manufacture of a medicament for inducing or promoting wound healing in an individual in need thereof.

Other aspects of the present disclosure relate to a method of decreasing innate immune cell survival in an individual in need thereof, comprising administering to the individual a therapeutically effective amount of an isolated antagonist antibody of any one of the preceding embodiments. Other aspects of the present disclosure relate to an isolated antagonist antibody of any one of the preceding embodiments for use in decreasing innate immune cell survival in an individual in need thereof. Other aspects of the present disclosure relate to use of an isolated antagonist antibody of any one of the preceding embodiments in the manufacture of a medicament for decreasing innate immune cell survival in an individual in need thereof.

Other aspects of the present disclosure relate to a method of preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, comprising administering to the individual a therapeutically effective amount of an isolated antibody of any one of the preceding embodiments. Other aspects of the present disclosure relate to an isolated antibody of any one of the preceding embodiments for use in preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. Other aspects of the present disclosure relate to use of an isolated antibody of any one of the preceding embodiments in the manufacture of a medicament for preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer.

In certain embodiments that may be combined with any of the preceding embodiments, the isolated antibody is: (a) an agonist antibody; (b) an inert antibody; or an (c) an antagonist antibody. In certain embodiments that may be combined with any of the preceding embodiments, (a) the antibody is of the IgG class the IgM class, or the IgA class; and/or (b) the antibody has an IgG1, IgG2, IgG3, or IgG4 isotype. In certain embodiments that may be combined with any of the preceding embodiments, the antibody comprises one or more amino acid substitutions in the Fc region are at a residue position selected from the group consisting of: (a) V234A, G237A, H268Q, V309L, A330S, P331S, C232S, C233S, S267E, L328F, M252Y, S254T, T256E, and any combination thereof; (b) N297A, D265A, L234A, L235A, G237A, C226S, C229S, E233P, L234V, L234F, L235E, P331S, S267E, L328F, A330L, M252Y, S254T, T256E, and any combination thereof; (c) L235A, G237A, S228P, L236E, S267E, E318A, L328F, M252Y, S254T, T256E, and any combination thereof; (d) N297A, N297Q, D265A, L234A, L235A, C226S, C229S, P238S, E233P, L234V, P238A, A327Q, A327G, P329A, K322A, L234F, L235E, P331S, T394D, A330L, M252Y, S254T, T256E, and any combination thereof; (e) V234A, G237A, H268E, V309L, N297A, N297Q, A330S, P331S, C232S, C233S, M252Y, S254T, T256E, and any combination thereof; or (f) E233P, F234V, L235A, G237A, E318A, S228P, L236E, S241P, L248E, T394D, M252Y, S254T, T256E, N297A, N297Q, and any combination thereof, wherein the numbering of the residues is according to EU or Kabat numbering. In certain embodiments that may be combined with any of the preceding embodiments, the isolated antibody: (a) binds to one or more amino acids within amino acid residues 43-50 of SEQ ID NO: 1, or amino acid residues on a TREM2 protein corresponding to amino acid residues 43-50 of SEQ ID NO: 1; or (b) one or more amino acids within amino acid residues 49-57 of SEQ ID NO: 1, or amino acid residues on a TREM2 protein corresponding to amino acid residues 49-57 of SEQ ID NO: 1. In certain embodiments that may be combined with any of the preceding embodiments, the isolated antibody: (a) binds essentially the same TREM2 epitope as the antibody Ab52; (b) comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52; (c) comprises a heavy chain variable domain and a light chain variable domain, wherein the heavy chain variable domain comprises an HVR-H1 comprising the amino acid sequence of SEQ ID NO:398, or an amino acid sequence with at least about 95% homology to the amino acid sequence of SEQ ID NO:398, an HVR-H2 comprising the amino acid sequence of SEQ ID NO:399, or an amino acid sequence with at least about 95% homology to the amino acid sequence of SEQ ID NO:399, and an HVR-H3 comprising the amino acid sequence of SEQ ID NO:400, or an amino acid sequence with at least about 95% homology to the amino acid sequence of SEQ ID NO:400, and/or wherein the light chain variable domain comprises an HVR-L1 comprising the amino acid sequence of SEQ ID NO:401, or an amino acid sequence with at least about 95% homology to the amino acid sequence of SEQ ID NO:401, an HVR-L2 comprising the amino acid sequence of SEQ ID NO:402, or an amino acid sequence with at least about 95% homology to the amino acid sequence of SEQ ID NO:402, and an HVR-L3 comprising the amino acid sequence of SEQ ID NO:403, or an amino acid sequence with at least about 95% homology to the amino acid sequence of SEQ ID NO:403; (d) binds essentially the same TREM2 epitope as the antibody Ab21; (e) comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L1, HVR-L2, and/or HVR-L3 of the monoclonal antibody Ab21; or (f) comprises a heavy chain variable domain and a light chain variable domain, wherein the heavy chain variable domain comprises an HVR-H1 comprising the amino acid sequence of SEQ ID NO:404, or an amino acid sequence with at least about 95% homology to the amino acid sequence of SEQ ID NO:404, an HVR-H2 comprising the amino acid sequence of SEQ ID NO:405, or an amino acid sequence with at least about 95% homology to the amino acid sequence of SEQ ID NO:405, and an HVR-H3 comprising the amino acid sequence of SEQ ID NO:406, or an amino acid sequence with at least about 95% homology to the amino acid sequence of SEQ ID NO:406, and/or wherein the light chain variable domain comprises an HVR-L1 comprising the amino acid sequence of SEQ ID NO:407, or an amino acid sequence with at least about 95% homology to the amino acid sequence of SEQ ID NO:407, an HVR-L2 comprising the amino acid sequence of SEQ ID NO:408, or an amino acid sequence with at least about 95% homology to the amino acid sequence of SEQ ID NO:408, and an HVR-L3 comprising the amino acid sequence of SEQ ID NO:409, or an amino acid sequence with at least about 95% homology to the amino acid sequence of SEQ ID NO:409. In certain embodiments that may be combined with any of the preceding embodiments, the isolated antibody is the isolated antibody of any one of the preceding embodiments. In certain embodiments that may be combined with any of the preceding embodiments, the isolated agonist antibody is the isolated agonist antibody of any one of the preceding embodiments. In certain embodiments that may be combined with any of the preceding embodiments, the individual has a heterozygous variant of TREM2, wherein the variant comprises one or more substitutions selected from the group consisting of: i. a glutamic acid to stop codon substitution in the nucleic acid sequence encoding amino acid residue Glu14 of SEQ ID NO: 1; ii. a glutamine to stop codon substitution in the nucleic acid sequence encoding amino acid residue Gln33 of SEQ ID NO: 1; iii. a tryptophan to stop codon substitution in the nucleic acid sequence encoding amino acid residue Trp44 of SEQ ID NO: 1; iv. an arginine to histidine amino acid substitution at an amino acid corresponding to amino acid residue Arg47 of SEQ ID NO: 1; v. a tryptophan to stop codon substitution in the nucleic acid sequence encoding amino acid residue Trp78 of SEQ ID NO: 1; vi. a valine to glycine amino acid substitution at an amino acid corresponding to amino acid residue Val1126 of SEQ ID NO: 1; vii. an aspartic acid to glycine amino acid substitution at an amino acid corresponding to amino acid residue Asp134 of SEQ ID NO: 1; and viii. a lysine to asparagine amino acid substitution at an amino acid corresponding to amino acid residue Lys186 of SEQ ID NO: 1. In certain embodiments that may be combined with any of the preceding embodiments, the individual has a heterozygous variant of TREM2, wherein the variant comprises a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; or both. In certain embodiments that may be combined with any of the preceding embodiments, the individual has a heterozygous variant of DAP12, wherein the variant comprises one or more variants selected from the group consisting of: i. a methionine to threonine substitution at an amino acid corresponding to amino acid residue Met1 of SEQ ID NO: 2; ii. a glycine to arginine amino acid substitution at an amino acid corresponding to amino acid residue Gly49 of SEQ ID NO: 2; iii. a deletion within exons 1-4 of the nucleic acid sequence encoding SEQ ID NO: 2; iv. an insertion of 14 amino acid residues at exon 3 of the nucleic acid sequence encoding SEQ ID NO: 2; and v. a guanine nucleotide deletion at a nucleotide corresponding to nucleotide residue G141 of the nucleic acid sequence encoding SEQ ID NO: 2.

In certain embodiments that may be combined with any of the preceding embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer. In certain embodiments that may be combined with any of the preceding embodiments, the method further comprises administering to the individual at least one antibody that specifically binds to an inhibitory checkpoint molecule, and/or another standard or investigational anti-cancer therapy. In certain embodiments that may be combined with any of the preceding embodiments, the at least one antibody that specifically binds to an inhibitory checkpoint molecule is administered in combination with the isolated antibody. In certain embodiments that may be combined with any of the preceding embodiments, the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In certain embodiments that may be combined with any of the preceding embodiments, the standard or investigational anti-cancer therapy is one or more therapies selected from the group consisting of radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy. In certain embodiments that may be combined with any of the preceding embodiments, the method further comprises administering to the individual at least one antibody that specifically binds to an inhibitory cytokine. In certain embodiments that may be combined with any of the preceding embodiments, the at least one antibody that specifically binds to an inhibitory cytokine is administered in combination with the isolated antibody. In certain embodiments that may be combined with any of the preceding embodiments, the at least one antibody that specifically binds to an inhibitory cytokine is selected from the group consisting of an anti-CCL2 antibody, an anti-CSF-1 antibody, an anti-IL-2 antibody, and any combination thereof. In certain embodiments that may be combined with any of the preceding embodiments, the method further comprises administering to the individual at least one agonistic antibody that specifically binds to a stimulatory checkpoint protein. In certain embodiments that may be combined with any of the preceding embodiments, the at least one agonistic antibody that specifically binds to a stimulatory checkpoint protein is administered in combination with the isolated antibody. In certain embodiments that may be combined with any of the preceding embodiments, the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof. In certain embodiments that may be combined with any of the preceding embodiments, the method further comprises administering to the individual at least one stimulatory cytokine. In certain embodiments that may be combined with any of the preceding embodiments, the at least one stimulatory cytokine is administered in combination with the isolated antibody. In certain embodiments that may be combined with any of the preceding embodiments, the at least one stimulatory cytokine is selected from the group consisting of TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, CRP, IFN-α, IFN-β3, IL-2, IL-18, GM-CSF, G-CSF, and any combination thereof.

BRIEF DESCRIPTION OF THE DRAWINGS

FIG. 1A shows an amino acid sequence alignment between the human TREM2 protein (SEQ ID NO: 426) and the human NCTR2 protein (SEQ ID NO: 427), depicting the homology between the two proteins. The consensus sequence is SEQ ID NO: 446.

FIG. 2A shows an amino acid sequence alignment between the human TREM1 protein (SEQ ID NO: 428) and the human TREM2 protein (SEQ ID NO: 426), depicting the homology between the two proteins. The consensus sequence is SEQ ID NO: 447. FIG. 2B shows the amino acid sequences of the heavy chain variable regions of antibodies Ab21 and Ab52. The CDR sequences are underlined in each sequence. Sequence regions in-between each underlined CDR sequence correspond to the framework regions. FIG. 2C shows the amino acid sequences of the light chain variable regions of antibodies Ab21 and Ab52. The CDR sequences are underlined in each sequence. Sequence regions in-between each underlined CDR sequence correspond to the framework regions.

FIG. 5A shows FACS dot plots demonstrating expression of cell surface markers CD83 and CD86 on human dendritic cells (DCs) after incubation with plate-bound TREM2 antibodies Ab21 or Ab52. Antibody Ab88 represents the negative isotype control. Plots were gated on CD11c$^+$HLA-DR$^+$ LIN$^-$ DCs. Percentage of cells within the CD83+CD86+ gate is displayed on each plot. FIG. 5B shows FACS histograms demonstrating expressing of cell surface marker CD86 on human dendritic cells (DCs) after incubation with cross-linked TREM2 antibodies Ab21 or Ab52. Antibodies were cross-linked with anti-human secondary antibody. Antibody Ab88 represents the negative isotype control.

FIG. 10A shows FACS data demonstrating expression of cell surface markers CD86 and CD206 on WT, TREM2 heterozygous (Het), and TREM2 KO macrophages after stimulation with the cytokines IL-4 or IFNg. FIG. 10B shows expression of cell surface marker CD86 on WT and TREM2 KO macrophages after stimulation with the inflammatory mediators LPS or Zymosan.

FIG. 15A shows Fortebio analysis demonstrating simultaneous binding of antibody MAB17291 and antibody Ab21 to TREM2-Fc. FIG. 15B shows Fortebio analysis demonstrating simultaneous binding of antibody MAB17291 and antibody Ab52 to TREM2-Fc.

FIG. 18B shows induction of TREM2-dependent gene expression by plate bound phosphatidylserine (PS). In FIGS. 18C and 18D "no Ab" indicates negative control with no antibody treatment, "21" indicates treatment with Ab21 Fab, "52" indicates treatment with Ab52 Fab, and "ctr" indicates treatment with control antibody Fab.

FIG. 20A shows the amino acid sequences of the heavy chain variable regions of TREM2 antibodies. The CDR sequences are underlined in each sequence. Sequence regions in-between each underlined CDR sequence correspond to the framework regions. FIG. 20B shows the amino acid sequences of the light chain variable regions of TREM2 antibodies. The CDR sequences are underlined in each sequence. Sequence regions in-between each underlined CDR sequence correspond to the framework regions.

FIG. 27A shows an epitope map of TREM2 antibodies Ab1 and Ab9. FIG. 27B shows an epitope map of TREM2 antibodies Ab45 and Ab65.

FIG. 31C shows induction of TREM2-dependent gene expression by plate bound phosphatidylserine (PS).

In FIGS. 34A and 34B "no Ab" indicates negative control with no antibody treatment, "22" indicates treatment with Ab22 Fab, "65" indicates treatment with Ab65 Fab, and "ctr" indicates treatment with control antibody Fab.

DETAILED DESCRIPTION OF THE INVENTION

General Techniques

Figure 1B:
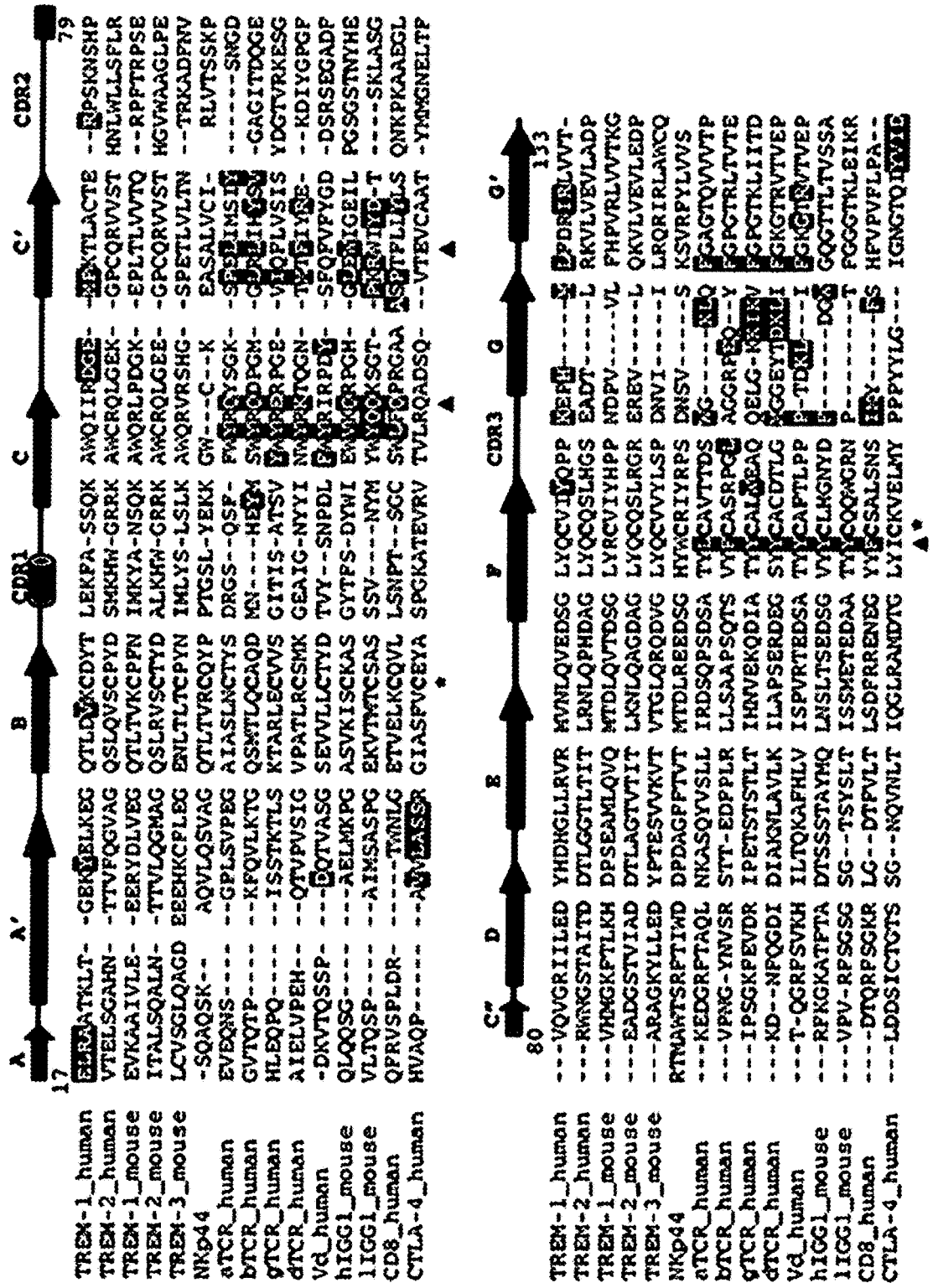
FIG. 1B shows a structure-based sequence alignment between several TREM proteins and other members of the IgV family, TREM-1_human (SEQ ID NO: 429), TREM-2_human (SEQ ID NO: 430), TREM-1_mouse (SEQ ID NO: 431), TREM-2_mouse (SEQ ID NO: 432), TREM-3_mouse (SEQ ID NO: 433), NKp44 (SEQ ID NO: 434), aTCR_human (SEQ ID NO: 435), bTCR_human (SEQ ID NO: 436), gTCR_human (SEQ ID NO: 437), dTCR_human (SEQ ID NO: 438), Vd_human (SEQ ID NO: 439), hIGG1_mouse (SEQ ID NO: 440), lIGG1_mouse (SEQ ID NO: 441), CD8_human (SEQ ID NO: 442), and CTLA4_human (SEQ ID NO: 443). The amino acid residue numbering is consistent with the mature sequence of the human TREM1 protein. The secondary structure elements of TREM1 are illustrated as arrows for the β strands and cylinders for a helices. Amino acid residues involved in homo- and heterodimer formation are shown on black background. Cysteine residues that form disulfide bonds and that are conserved for the V-type Ig fold, are depicted in bold and marked with asterisks. Gaps are indicated by "-". M-1 residues violating antibody-like dimer formation mode are marked with closed triangles as (e.g., Radaev et al., (2003) Structure. 11(12):1527-1535).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the anti-TREM2 and/or anti-DAP12 antibody to elicit a desired response in the individual. A therapeutically effective amount is also one in which any toxic or detrimental effects of the anti-TREM2 and/or anti-DAP12 antibody are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology,* 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("K") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an isolated anti-TREM2 and/or anti-DAP12 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-TREM2 and/or anti-DAP12 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-TREM2 and/or anti-DAP12 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-TREM2 and/or anti-DAP12 antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5): 1073-1093 (2004); Fellouse, *Proc. Nat'l Acad. Sci. USA* 101(34): 12467-472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/ 24893; WO 1996/34096; WO 1996/33735; WO 1991/ 10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633, 425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-TREM2 and/or anti-DAP12 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-TREM2 and/ or anti-DAP12 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding. For a review of the sFv, see Plückthun in *The Pharmacology of Monoclonal Antibodies*, vol. 113, Rosenburg and Moore eds., Springer-Verlag, New York, pp. 269-315 (1994).

"Functional fragments" of antibodies, such as anti-TREM2 and/or anti-DAP12 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as a chimeric anti-TREM2 and/or anti-DAP12 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-TREM2 and/or anti-DAP12 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-TREM2 and/or anti-DAP12 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA*, 103:3557-3562 (2006) regarding human antibodies generated via a human B-cell hybridoma technology.

The term "hypervariable region," "HVR," or "HV," when used herein refers to the regions of an antibody-variable domain, such as that of an anti-TREM2 and/or anti-DAP12 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact | |
|------|-------|-----|---------|---------|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat numbering) |
| H1 | H31-H35 | H26-H35 | H26-H32 | H30-H35 | (Chothia numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. References to residue numbers in the variable domain of antibodies means residue numbering by the Kabat numbering system. References to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-TREM2 and/or anti-DAP12 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-TREM2 and/or anti-DAP12 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7): 3310-9 (1995); and Hawkins et al, *J Mol. Biol.* 226:889-896 (1992).

As use herein, the term "specifically recognizes" or "specifically binds" refers to measurable and reproducible interactions such as attraction or binding between a target and an antibody, such as between an anti-TREM2 antibody and TREM2, or an anti-DAP12 antibody and DAP12 that is determinative of the presence of the target in the presence of a heterogeneous population of molecules including biological molecules. For example, an antibody, such as an anti-TREM2 and/or anti-DAP12 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3 M^{-1}$ or $10^4 M^{-1}$, sometimes about $10^5 M^{-1}$ or $10^6 M^{-1}$, in other instances about $10^6 M^{-1}$ or $10^7 M^{-1}$, about $10^8 M^{-1}$ to $10^9 M^{-1}$, or about $10^{10} M^{-1}$ to $10^{11} M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a TREM2 protein, or DAP12 protein, and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-TREM2 antibody or an agonist anti-DAP12 antibody of the present disclosure, that induces (e.g., increases) one or more activities or functions of the antigen after the antibody binds the antigen.

An "antagonist" antibody or a "blocking" antibody is an antibody, such as an antagonist anti-TREM2 antibody or an antagonist anti-DAP12 antibody of the present disclosure, that reduces or eliminates (e.g., decreases) antigen binding to one or more ligand after the antibody binds the antigen, and/or that reduces or eliminates (e.g., decreases) one or more activities or functions of the antigen after the antibody binds the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daeron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" nucleic acid molecule encoding an antibody, such as an anti-TREM2 and/or anti-DAP12 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the invention described herein include "comprising," "consisting," and "consisting essentially of" aspects and embodiments.

Overview

The present disclosure relates to anti-TREM2 antibodies and/or anti-DAP12 antibodies with one or more agonist or antagonist activities; methods of making and using such antibodies; pharmaceutical compositions containing such antibodies; nucleic acids encoding such antibodies; and host cells containing nucleic acids encoding such antibodies.

In some embodiments, and without wishing to be bound by theory, it is believed that the agonistic activities of the anti-TREM2 and/or anti-DAP12 antibodies of the present disclosure are due, at least in part, to the ability of the antibodies to induce or retain TREM2 receptor clustering on the surface of cells. In some embodiments, it is believed that anti-TREM2 and/or anti-DAP12 antibodies can induce or retain TREM2 receptor clustering in vivo by not only binding specifically to TREM2, but by also binding to Fc receptors on adjacent cells, which leads to antibody aggregation that in turn aggregates TREM2. Advantageously, certain immunoglobulin isotypes, including without limitation, IgG2 and IgM, have an intrinsic ability to induce or retain clustering of target antigens (e.g., TREM2) without binding Fc receptors on adjacent cells. In some embodiments, agonistic TREM2 activities can be determined or tested in vitro by any of several techniques disclosed herein (see, e.g., Examples 23-26, 34-37, 41-44, 52-55, and 67-68), including, without limitation, plate-binding full-length anti-TREM2 antibodies to increase the density of antibodies exposed to TREM2 and cross-linking anti-TREM2 antibodies.

Accordingly, certain aspects of the present disclosure are based, at least in part, on the identification of anti-TREM2 and/or anti-DAP12 antibodies that are capable of binding to both human and mouse TREM2 with high affinity (see, e.g., Examples 1and 40); that compete with TREM2-ligand for binding to the ligand-binding site on human and mouse TREM2 (see, e.g., Examples 26 and 43); and that exhibit one or more agonistic TREM2 activities, including, without limitation, induction of CD83$^+$CD86$^+$ dendritic cells (see, e.g., Examples 23 and 41), induction of the TREM2 downstream signaling molecule Syk in macrophages and dendritic cells (see, e.g., Examples 24 and 42), induction of the TREM2 signaling adaptor molecule DAP12 in macrophages (see, e.g., Examples 25 and 44), induction of cell survival of innate immune cells, such as macrophages (see, e.g., Examples 34 and 52), and activation of TREM2-dependent gene expression (see, e.g., Examples 36, 38, 54, 56, and 68).

Further aspects of the present disclosure are based, at least in part, on the surprising discovery that the anti-TREM2 and/or anti-DAP12 antibodies of the present disclosure can also induce antagonistic activities when the antibody is produced or otherwise formatted such that it is incapable of inducing or retaining TREM2 receptor clustering. In some embodiments, anti-TREM2 and/or anti-DAP12 antibodies of the present disclosure exhibit one or more antagonistic TREM2 activities, including, without limitation, inhibition of cell survival of innate immune cells ((see, e.g., Examples 35 and 53), and inhibition of TREM2-dependent gene expression (see, e.g., Examples 37, 55, and 67).

TREM2 Proteins

In one aspect, the invention provides antibodies that bind to a TREM2 protein of the present disclosure and modulate one or more TREM2 activities after binding to a TREM2 protein expressed in a cell.

TREM2 proteins of the present disclosure include, without limitation, a mammalian TREM2 protein, human TREM2 protein (Uniprot Accession No. Q9NZC2), mouse TREM2 protein (Uniprot Accession No. Q99NH8), rat TREM2 protein (Uniprot Accession No. D3ZZ89), Rhesus monkey TREM2 protein (Uniprot Accession No. F6QVF2), bovine TREM2 protein (Uniprot Accession No. Q05B59), equine TREM2 protein (Uniprot Accession No. F7D6L0), pig TREM2 protein (Uniprot Accession No. H2EZZ3), and dog TREM2 protein (Uniprot Accession No. E2RP46). As used herein "TREM2 protein" refers to both wild-type sequences and naturally occurring variant sequences.

Triggering receptor expressed on myeloid cells-2 (TREM2) is variously referred to as TREM-2, Trem2a, Trem2b, Trem2c, triggering receptor expressed on myeloid cells-2a, and triggering receptor expressed on monocytes-2. TREM2 is a 230 amino acid membrane protein. TREM2 is an immunoglobulin-like receptor primarily expressed on myeloid lineage cells, including without limitation, macrophages, dendritic cells, osteoclasts, microglia, monocytes, Langerhans cells of skin, and Kupffer cells. In some embodiments, TREM2 forms a receptor-signaling complex with DAP12. In some embodiments, TREM2 phosphorylates and signals through DAP12 (an ITAM domain adaptor protein). In some embodiments TREM2 signaling results in the downstream activation of PI3K or other intracellular signals. On Myeloid cells, Toll-like receptor (TLR) signals are important for the activation of TREM2 activities, e.g., in the context of an infection response. TLRs also play a key role in the pathological inflammatory response, e.g., TLRs expressed in macrophages and dendritic cells.

In some embodiments, an example of a human TREM2 amino acid sequence is set forth below as SEQ ID NO: 1:

```
        10         20         30         40
MEPLRLLILL FVTELSGAHN TTVFQGVAGQ SLQVSCPYDS 50         60         70         80
MKHWGRRKAW CRQLGEKGPC QRVVSTHNLW LLSFLRRWNG 90        100        110        120
STAITDDTLG GTLTITLRNL QPHDAGLYQC QSLHGSEADT 130        140        150        160
LRKVLVEVLA DPLDHRDAGD LWFPGESESF EDAHVEHSIS 170        180        190        200
RSLLEGEIPF PPTSILLLLA CIFLIKILAA SALWAAAWHG 210        220        230
QKPGTHPPSE LDCGHDPGYQ LQTLPGLRDT
```

In some embodiments, the human TREM2 is a preprotein that includes a signal peptide. In some embodiments, the human TREM2 is a mature protein. In some embodiments, the mature TREM2 protein does not include a signal peptide. In some embodiments, the mature TREM2 protein is expressed on a cell. In some embodiments, TREM2 contains a signal peptide located at amino acid residues 1-18 of human TREM2 (SEQ ID NO: 1); an extracellular immunoglobulin-like variable-type (IgV) domain located at amino acid residues 29-112 of human TREM2 (SEQ ID NO: 1);

additional extracellular sequences located at amino acid residues 113-174 of human TREM2 (SEQ ID NO: 1); a transmembrane domain located at amino acid residues 175-195 of human TREM2 (SEQ ID NO: 1); and an intracellular domain located at amino acid residues 196-230 of human TREM2 (SEQ ID NO: 1).

The transmembrane domain of human TREM2 contains a lysine at amino acid residue 186 that can interact with an aspartic acid in DAP12, which is a key adaptor protein that transduces signaling from TREM2, TREM1, and other related IgV family members.

Homologues of human TREM2 include, without limitation, the natural killer (NK) cell receptor NK-p44 (NCTR2), the polymeric immunoglobulin receptor (pIgR), CD300E, CD300A, CD300C, and TREML1/TLT1. In some embodiments, NCTR2 has similarity with TREM2 within the IgV domain.

DAP12 Proteins

In one aspect, the invention provides antibodies that bind to a DAP12 protein of the present disclosure and modulate one or more DAP12 activities after binding to a DAP12 protein expressed in a cell.

DAP12 proteins of the present disclosure include, without limitation, a mammalian DAP12 protein, human DAP12 protein (Uniprot Accession No. O43914), mouse DAP12 protein (Uniprot Accession No. O54885), rat DAP12 protein (Uniprot Accession No. Q6X9T7), Rhesus monkey DAP12 protein (Uniprot Accession No. Q8WNQ8), bovine DAP12 protein (Uniprot Accession No. Q95J80), and pig DAP12 protein (Uniprot Accession No. Q9TU45). As used herein "DAP12 protein" refers to both wild-type sequences and naturally occurring variant sequences.

DNAX-activation protein 12 (DAP12) is variously referred to as Killer-activating receptor-associated protein, KAR-associated protein (KARAP), PLOSL, PLO-SL, TYRO protein, and tyrosine kinase-binding protein. DAP12 is a 113 amino acid membrane protein. In some embodiments, DAP12 functions as a transmembrane signaling polypeptide, which contains an immunoreceptor tyrosine-based activation motif (ITAM) in its cytoplasmic domain. It may associate with the killer-cell inhibitory receptor (KIR) family of membrane glycoproteins and may act as an activating signal transduction element. In other embodiments, the DAP12 protein may bind zeta-chain (TCR) associated protein kinase 70 kDa (ZAP-70) and spleen tyrosine kinase (SYK), and play a role in signal transduction, bone modeling, brain myelination, and inflammation.

Mutations within the DAP12-encoding gene have been associated with polycystic lipomembranous osteodysplasia with sclerosing leukoencephalopathy (PLOSL), also known as Nasu-Hakola disease. Without wishing to be bound by theory, it is believed that the DAP12 receptor is TREM2, which also causes PLOSL. Multiple alternative transcript variants encoding distinct isoforms of DAP12 have been identified. DAP12 non-covalently associates with activating receptors of the CD300 family. Cross-linking of CD300-TYROBP/DAP12 complexes results in cellular activation, such as neutrophil activation mediated by integrin. DAP12 is a homodimer; disulfide-linked protein. In some embodiments, DAP12 interacts with SIRPB1, TREM1, CLECSF5, SIGLEC14, CD300LB, CD300E, and CD300D by similarity and via ITAM domain, as well as with SYK via SH2 domain. In other embodiments, DAP12 activates SYK, which mediates neutrophils and macrophages integrin-mediated activation. In other embodiments, DAP12 interacts with KLRC2 and KIR2DS3.

In some embodiments, an example of a human DAP12 amino acid sequence is set forth below as SEQ ID NO: 2:

```
        10         20         30         40
MGGLEPCSRL LLLPLLLAVS GLRPVQAQAQ SDCSCSTVSP 50         60         70         80
GVLAGIVMGD LVLTVLIALA VYFLGRLVPR GRGAAEAATR 90        100        110
KQRITETESP YQELQGQRSD VYSDLNTQRP YYK
```

In some embodiments, the human DAP12 is a preprotein that includes a signal peptide. In some embodiments, the human DAP12 is a mature protein. In some embodiments, the mature DAP12 protein does not include a signal peptide. In some embodiments, the mature DAP12 protein is expressed on a cell. DAP12 is a single-pass type I membrane protein. It contains an extracellular domain located at amino acid residues 22-40 of human DAP12 (SEQ ID NO: 2); a transmembrane domain located at amino acid residues 41-61 of human DAP12 (SEQ ID NO: 2); and an intracellular domain located at amino acid residues 62-113 of human DAP12 (SEQ ID NO: 2). The immunoreceptor tyrosine-based activation motif (ITAM) domain is located at amino acid residues 80-118 of human DAP12 (SEQ ID NO: 2).

In some embodiments, an aspartic acid residue in DAP12 interacts with the transmembrane domain of human TREM2 containing a lysine at amino acid residue 186, and transduces signaling from TREM2, TREM1, and other related IgV family member proteins.

Anti-TREM2 and Anti-DAP12 Antibodies

Certain aspects of the present disclosure relate to antibodies that specifically bind to TREM2 and/or DAP12. In some embodiments, antibodies of the present disclosure bind a mature TREM2 protein and/or DAP12 protein. In some embodiments, antibodies of the present disclosure bind a mature TREM2 protein and/or DAP12 protein, wherein the mature TREM2 protein and/or DAP12 protein is expressed on a cell. In some embodiments, antibodies of the present disclosure bind a TREM2 protein and/or DAP12 protein expressed on one or more human cells selected from human dendritic cells, human macrophages, human monocytes, human osteoclasts, human Langerhans cells of skin, human Kupffer cells, human microglia, and any combinations thereof. In some embodiments, antibodies of the present disclosure are agonist antibodies. In some embodiments, antibodies of the present disclosure are inert antibodies. In some embodiments, antibodies of the present disclosure are antagonist antibodies.

Agonist Antibodies

Anti-TREM2 and/or anti-DAP12 antibodies of the present disclosure generally bind to one or more TREM2 proteins and/or DAP12 proteins expressed in a cell. One class of antibodies is agonist antibodies. For example, the TREM2 receptor is thought to require clustering on the cell surface in order to transduce a signal. Thus agonist antibodies may have unique features to stimulate, for example, the TREM2 receptor. For example, they may have the correct epitope specificity that is compatible with receptor activation, as well as the ability to induce or retain receptor clustering on the cell surface.

In vivo, antibodies may cluster receptors by multiple potential mechanisms. Some isotypes of human antibodies such as IgG2 have, due to their unique structure, an intrinsic ability to cluster receptors, or retain receptors in a clustered configuration, thereby activating receptors such as TREM2 without binding to an Fc receptor (e.g., White et al., (2015) Cancer Cell 27, 138-148).

Other antibodies cluster receptors (e.g., TREM2) by binding to Fcg receptors on adjacent cells. Binding of the constant IgG Fc part of the antibody to Fcg receptors leads to aggregation of the antibodies, and the antibodies in turn aggregate the receptors to which they bind through their variable region (Chu et al (2008) Mol Immunol, 45:3926-3933; and Wilson et al., (2011) Cancer Cell 19, 101-113). Binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is often a preferred way to cluster antibodies in vivo, since binding to FcgRIIB is not associated with immune adverse effects.

Other mechanisms may also be used to cluster receptors (e.g., TREM2). For example, antibody fragments (e.g., Fab fragments) that are cross-linked together may be used to cluster receptors (e.g., TREM2) in a manner similar to antibodies with Fc regions that bind Fcg receptors, as described above. Without wishing to be bound to theory, it is thought that cross-linked antibody fragments (e.g., Fab fragments) may function as agonist antibodies if they induce receptor clustering on the cell surface and bind an appropriate epitope on the target (e.g., TREM2).

Therefore, in some embodiments, antibodies that bind a TREM2 protein and/or a DAP12 protein may include agonist antibodies that due to their epitope specificity bind TREM2 and/or DAP12 and activate one or more TREM2 and/or DAP12 activities. Without wishing to be bound to theory, such antibodies may bind to the ligand-binding site on the target antigen (e.g., TREM2 and/or DAP12) and mimic the action of a natural ligand, or stimulate the target antigen to transduce signal by binding to one or more domains that are not the ligand-binding sites. Such antibodies would not interfere with ligand binding and may act additively or synergistically with the natural ligands.

In some embodiments, an antibody of the present disclosure is an agonist antibody that induces one or more TREM2 activities, one or more DAP12 activities, or one or more TREM2 activities and one or more DAP12 activities. In some embodiments the antibody induces one or more activities of TREM2 and/or DAP12 after binding to a TREM2 and/or DAP12 protein that is expressed in a cell. In certain embodiments, the one or more TREM2 activities, the one or more DAP12 activities, or both are selected from TREM2 binding to DAP12; DAP12 binding to TREM2; DAP12 phosphorylation; TREM2 phosphorylation; PI3K activation; increased expression of one or more anti-inflammatory cytokines, increased expression of one or more anti-inflammatory mediators (e.g., cytokines) selected from IL-12p70, IL-6, and IL-10; reduced expression of one or more pro-inflammatory cytokines; reduced expression of one or more pro-inflammatory mediators selected from the group consisting of IFN-a4, IFN-b, IL-6, IL-12 p70, IL-1β, TNG, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, mCP-1, and CRP; reduced expression of TNF-α; reduced expression of IL-6; extracellular signal-regulated kinase (ERK) phosphorylation; increased expression of C—C chemokine receptor 7 (CCR7); induction of microglial cell chemotaxis toward CCL19 and CCL21 expressing cells; an enhancement, normalization, or both of the ability of bone marrow-derived dendritic cells to induce antigen-specific T-cell proliferation; induction of osteoclast production, increased rate of osteoclastogenesis, or both; increasing the survival and/or function of one or more of macrophages, microglial cells, M1 macrophages and/or microglial cells, activated M1 macrophages and/or microglial cells, M2 macrophages and/or microglial cells, monocytes, osteoclasts, Langerhans cells of skin, and Kupffer cells; induction of one or more types of clearance selected from apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance; induction of phagocytosis of one or more of apoptotic neurons, nerve tissue debris, non-nerve tissue debris, bacteria, other foreign bodies, disease-causing proteins, disease-causing proteins, disease-causing peptides, or disease-causing nucleic acids (e.g., antisense GGCCCC (G2C4) repeat-expansion RNA); normalization of disrupted TREM2/DAP12-dependent gene expression; recruitment of Syk, ZAP70, or both to a DAP12/TREM2 complex; Syk phosphorylation; increased expression of CD83 and/or CD86 on dendritic cells, macrophages, monocytes, and/or microglia; reduced secretion of one or more inflammatory cytokines; reduced secretion of one or more inflammatory cytokines selected from TNF-α, IL-10, IL-6, MCP-1, FN-a4, IFN-b, IL-10. IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18; reduced expression of one or more inflammatory receptors; increasing phagocytosis by macrophages, dendritic cells, monocytes, and/or microglia under conditions of reduced levels of MCSF; decreasing phagocytosis by macrophages, dendritic cells, monocytes, and/or microglia in the presence of normal levels of MCSF; increasing activity of one or more TREM2-dependent genes (e.g., transcription factors of the nuclear factor of activated T-cells (NFAT) family of transcription factors).

An antibody dependent on binding to FcgR receptor to activate targeted receptors may lose its agonist activity if engineered to eliminate FcgR binding (see, e.g., Wilson et al., (2011) Cancer Cell 19, 101-113; Armour at al., (2003) Immunology 40 (2003) 585-593); and White et al., (2015) Cancer Cell 27, 138-148). As such, it is thought that an antibody of the present disclosure with the correct epitope specificity can be an agonist antibody and activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

Exemplary agonist antibody Fc isotypes and modifications are provided in Table 2 below. In some embodiments, the agonist antibody has an Fc isotype listed in Table 2 below.

TABLE 2

Exemplary anti-TREM2 agonist antibody Fc isotypes

| Fc Isotype | Mutation (EU or Kabat numbering scheme) |
|---|---|
| IgG1 | N297A |
| IgG1 | D265A and N297A |
| IgG1 | L234A and L235A<br>L234A and G237A<br>L234A and L235A and G237A |
| IgG2 | V234A and G237A |
| IgG4 | L235A and G237A and E318A |
| IgG4 | S228P and L236E |
| IgG2/4 hybrid | IgG2 aa 118-260 and IgG4 aa 261 to 447 |
| IgG2 | H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E, and L328F<br>S267E alone |
| IgG2 | S267E and L328F |
| IgG4 | S267E and L328F |
| IgG2 | WT HC with Kappa (light chain) LC<br>HC C127S with Kappa LC<br>Kappa LC C214S<br>Kappa LC C214S and HC C233S<br>Kappa LC C214S and HC C232S<br>Any of the above listed mutations together with P330S and P331S mutations<br>F(ab')2 fragment of WT IgG1 and any of the above listed mutations |
| IgG1 | Substitute the Constant Heavy 1 (CH1) and hinge region of IgG1 With CH1 and hinge region of IGg2<br>ASTKGPSVFP LAPCSRSTSE STAALGCLVK<br>DYFPEPVTVS WNSGALTSGV HTFPAVLQSS<br>GLYSLSSVVT VPSSNFGTQT YTCNVDHKPS<br>NTKVDKTVER KCCVECPPCP (SEQ ID NO: 397)<br>With a Kappa LC |
| IgG1 | Any of the above listed mutations together with A330L and/or L234F and/or L235E and/or P331S |
| IgG1, IgG2, or IgG4 | Any of the above listed mutations together with M252Y and/or S254T and/or T256E |
| Mouse IgG1 | For mouse disease models |
| IgG4 | WT |

In addition to the isotypes described in Table 2, and without wishing to be bound to theory, it is thought that antibodies with human IgG1 or IgG3 isotypes and mutants thereof (e.g. Strohl (2009) Current Opinion in Biotechnology 2009, 20:685-691) that bind the activating Fcg Receptors I, IIA, IIC, IIIA, IIIB in human and/or Fcg Receptors I, III and IV in mouse, may also act as agonist antibodies in vivo but may be associated with adverse effects related to ADCC. However, such Fcg receptors appear to be less available for antibody binding in vivo, as compared to the Inhibitory Fcg receptor FcgRIIB (see, e.g., White, et al., (2013) Cancer Immunol. Immunother. 62, 941-948; and Li et al., (2011) IScience 333(6045):1030-1034).

In some embodiments, the agonist antibody is of the IgG class, the IgM class, or the IgA class. In some embodiments, the agonist antibody has an IgG1, IgG2, IgG3, or IgG4 isotype.

In certain embodiments, the agonist antibody has an IgG2 isotype. In some embodiments, the agonist antibody contains a human IgG2 constant region. In some embodiments, the human IgG2 constant region includes an Fc region. In some embodiments, the agonist antibody induces the one or more TREM2 activities, the DAP12 activities, or both independently of binding to an Fc receptor. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543. 31; Xu et al., (2000) *Cell Immunol*, 200:16-26), G237A (Cole et al. (1999) *Transplantation*, 68:563-571), H268Q, V309L, A330S, P331S (US 2007/0148167; Armour et al. (1999) *Eur J Immunol* 29: 2613-2624; Armour et al. (2000) *The Haematology Journal* 1(Suppl. 1):27; Armour et al. (2000) *The Haematology Journal* 1(Suppl. 1):27), C232S, and/or C233S (White et al. (2015) *Cancer Cell* 27, 138-148), S267E, L328F (Chu et al., (2008) *Mol Immunol*, 45:3926-3933), M252Y, S254T, and/or T256E, where the amino acid position is according to the EU or Kabat numbering convention.

In some embodiments, the agonist antibody has an IgG2 isotype with a heavy chain constant domain that contains a C127S amino acid substitution, where the amino acid position is according to the EU or Kabat numbering convention (White et al., (2015) *Cancer Cell* 27, 138-148; Lightle et al., (2010) *PROTEIN SCIENCE* 19:753-762; and WO2008079246).

In some embodiments, the agonist antibody has an IgG2 isotype with a Kappa light chain constant domain that contains a C214S amino acid substitution, where the amino acid position is according to the EU or Kabat numbering convention (White et al., (2015) *Cancer Cell* 27, 138-148; Lightle et al., (2010) *PROTEIN SCIENCE* 19:753-762; and WO2008079246).

In certain embodiments, the agonist antibody has an IgG1 isotype. In some embodiments, the agonist antibody contains a mouse IgG1 constant region. In some embodiments, the agonist antibody contains a human IgG1 constant region. In some embodiments, the human IgG1 constant region includes an Fc region. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA*, 92:11980-11984; Alegre et al., (1994) *Transplantation* 57:1537-1543. 31; Xu et al., (2000) *Cell Immunol*, 200:16-26), G237A (Alegre et al. (1994) *Transplantation* 57:1537-1543. 31; Xu et al. (2000) *Cell Immunol*, 200:16-26), C226S, C229S, E233P, L234V, L234F, L235E (McEarchern et al., (2007) *Blood*, 109:1185-1192), P331 S (Sazinsky et al., (2008) *Proc Natl Acad Sci USA* 2008, 105:20167-20172), S267E, L328F, A330L, M252Y, S254T, and/or T256E, where the amino acid position is according to the EU or Kabat numbering convention.

In some embodiments, the antibody includes an IgG2 isotype heavy chain constant domain 1(CH1) and hinge region (White et al., (2015) *Cancer Cell* 27, 138-148). In certain embodiments, the IgG2 isotype CH1 and hinge region contain the amino acid sequence of ASTKGPSVF-PLAPCSRSTSESTAALGCLVKDYF-PEPVTVSWNSGALTSGVHTFPAVLQSS GLYSLSSVVT VPSSNFGTQT YTCNVDHKPS NTKVDKTVERKCCVECPPCP (SEQ ID NO: 397). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the agonist antibody has an IgG4 isotype. In some embodiments, the agonist antibody contains a human IgG4 constant region. In some embodiments, the human IgG4 constant region includes an Fc region. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol*, 164:1925-1933), S267E, E318A, L328F, M252Y, S254T, and/or T256E, where the amino acid position is according to the EU or Kabat numbering convention.

In certain embodiments, the agonist antibody has a hybrid IgG2/4 isotype. In some embodiments, the agonist antibody includes an amino acid sequence containing amino acids 118 to 260 according to Kabat numbering convention of human IgG2 and amino acids 261 to 447 according to EU or Kabat numbering convention of human IgG4 (WO 1997/11971; WO 2007/106585).

In certain embodiments, the antibody contains a mouse IgG4 constant region (Bartholomaeus, et al. (2014). *J. Immunol.* 192, 2091-2098).

In some embodiments, the Fc region further contains one or more additional amino acid substitutions selected from the group consisting of A330L, L234F, L235E, and/or P331 S, where the amino acid position is according to the EU or Kabat numbering convention.

Inert Antibodies

Another class of antibodies of the present disclosure includes inert antibodies. As used herein, "inert" antibodies refer to antibodies that specifically bind their target antigen but do not modulate (e.g., decrease/inhibit or activate/induce) antigen function. For example, in the case of TREM2, inert antibodies do not modulate ligand binding and/or TREM2 activities. Without wishing to be bound to theory, it is thought that antibodies that do not have the ability to cluster TREM2 on the cell surface may be inert antibodies even if they have an epitope specificity that is compatible with receptor activation.

In some embodiments, antibodies that bind a TREM2 protein and/or a DAP12 protein may include antibodies that bind TREM2 and/or DAP12 but, due to their epitope specificity, do not modulate protein function. Such functionally inert antibodies can be used as cargo to transport toxins as described for the CD33 antibody Gemtuzumab zogamicin, (marketed as Mylotarg) which is conjugated to the cytotoxic agent from the class of calicheamicins and is used to target and kill acute myelogenous leukemia tumors (Naito et al., (2000), Leukemia, 14, 1436-1443; Ricart (2011) Clin Cancer Res 17; 6417-6436; Hamann et al., (2002) Journal: Bioconjugate Chemistry, 13, 47-58; and Beitz et al., (2001) Clin Cancer Res 7; 1490-6). Therefore, in some embodiments, antibodies of the present disclosure are inert antibodies that bind TREM2 and/or DAP12 but are incapable of inducing one or more TREM2 activities (e.g., a TREM2 activity described herein) and/or DAP12 activities (e.g., a DAP12 activity described herein).

Exemplary inert antibody Fc isotypes and modifications are provided in Table 3 below. In some embodiments, the inert antibody has an Fc isotype listed in Table 3 below.

Antagonist Antibodies

A third class of antibodies of the present disclosure includes antagonist antibodies. In some embodiments, antibodies that bind a TREM2 protein and/or a DAP12 protein may include antagonist antibodies that bind TREM2 and/or DAP12 and inhibit one or more TREM2 activities and/or DAP12 activities, either by preventing interaction between TREM2 and/or DAP12 and its ligand(s), or by preventing the transduction of signal from the extracellular domain of TREM2 and/or DAP12 into the cell cytoplasm in the presence of ligand. In some embodiments, antagonist antibodies of the present disclosure may have the epitope specificity of an agonist antibody of the present disclosure, but have an Fc domain that is not capable of binding Fcg receptors and thus is unable to, for example, cluster DAP12 and/or the TREM2 receptor.

In some embodiments, an antibody of the present disclosure is an antagonist antibody. In some embodiments, the antagonist antibody inhibits one or more TREM2 and/or DAP12 activities. In some embodiments, the antagonist antibody decreases activity of one or more TREM2-dependent genes. In some embodiments, the one or more TREM2-dependent genes include, without limitation, one or more nuclear factor of activated T-cells (NFAT) transcription factors. In some embodiments, the antagonist antibody decreases the survival of macrophages, microglial cells, M1 macrophages, M1 microglial cells, M2 macrophages, M2 microglial cells, osteoclasts, Langerhans cells of skin, Kupffer cells, and/or dendritic cell. In some embodiments, the antagonist antibody inhibits interaction between TREM2 and/or DAP12 and one or more TREM2 and/or DAP12 ligands. In some embodiments, the antagonist antibody inhibits TREM2 and/or DAP12 signal transduction. In some embodiments, the antagonist antibody inhibits interaction between TREM2 and/or DAP12 and one or more TREM2 and/or DAP12 ligands and inhibits TREM2 and/or DAP12 signal transduction.

In some embodiments, antibody cross-linking is required for agonist antibody function. Antibody cross-linking can occur through binding to a secondary antibody in vitro or through binding to Fc receptors in vivo. For example, antagonistic antibodies can be converted to agonistic antibodies via biotin/streptavidin cross-linking or secondary antibody binding in vitro (see for example Gravestein et al., (1996) J. Exp. Med. 184:675-685; Gravestein et al., (1994) International Immunol. 7:551-557). Agonistic antibodies may exert their activity by mimicking the biological activity of the receptor ligand or by enhancing receptor aggregation, thereby activating receptor signaling. In some embodiments, the absence of antibody cross-linking is required for antagonistic activity. Antagonistic antibodies may exert their activity by blocking receptor-ligand interactions.

Exemplary antagonist antibody Fc isotypes and modifications are provided in Table 3 below. In some embodiments, the antagonist antibody has an Fc isotype listed in Table 3 below.

Inert and Antagonist Antibody Fc Isotypes

In some embodiments, inert and/or antagonist anti-TREM antibodies of the present disclosure include one or more of the Fc isotypes and modifications listed in Table 3.

TABLE 3

Exemplary inert and antagonist anti-TREM2 antibody Fc isotypes

| Fc Isotype | Mutation (EU or Kabat numbering scheme) |
|---|---|
| IgG1 | N297A or N297Q |
| IgG1 | D265A and N297A |
| IgG1 | L234A and L235A |
| IgG2 | V234A and G237A |
| IgG4 | L235A and G237A and E318A |
| | E233P and/or F234V |
| | N297A or N297Q |
| IgG4 | S228P and L236E |
| | S241P |
| | S241P and L248E |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
| | P238A |
| | D265A |
| | N297A |
| | A327Q or A327G |
| | P329A |
| IgG1 | K322A and L234A and L235A |
| IgG1 | L234F and L235E and P331S |
| IgG1 or IgG4 | T394D |
| IgG2 | C232S or C233S |
| | N297A or N297Q |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) Eur J Immunol 23:403-411), D265A, L234A, L235A (McEarchern et al., (2007) Blood, 109:1185-1192), C226S, C229S (McEarchern et al., (2007) Blood, 109:1185-1192), P238S (Davis et al., (2007) J Rheumatol, 34:2204-2210), E233P, L234V (McEarchern et al., (2007) Blood, 109:1185-1192), P238A, A327Q, A327G, P329A (Shields R L. et al., (2001) J Biol Chem. 276(9):6591-604), K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the antibody has an IgG1 isotype with a heavy chain constant region that contains a C220S amino acid substitution according to the EU or Kabat numbering convention.

In some embodiments, the Fc region further contains one or more additional amino acid substitutions selected from A330L, L234F; L235E, and/or P331S according to EU or Kabat numbering convention.

In certain embodiments, the antibody has an IgG2 isotype. In some embodiments, the antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A, G237A, H268E, V309L, N297A, N297Q, A330S, P331S, C232S, C233S, M252Y, S254T, and/or T256E, where the amino acid position is according to the EU or Kabat numbering convention.

In certain embodiments, the antibody has an IgG4 isotype. In some embodiments, the antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA*, 92:11980-11984), S228P, L236E, S241P, L248E (Reddy et al., (2000) *J Immunol,* 164:1925-1933; Angal et al., (1993) *Mol Immunol.* 30(1): 105-8; U.S. Pat. No. 8,614,299 B2), T394D, M252Y, S254T, T256E, N297A, and/or N297Q, where the amino acid position is according to the EU or Kabat numbering convention.

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) *Proc Natl Acad Sci USA,* 103:4005-4010), or one or more of L234F, L235E, and/or P331S mutations (Sazinsky et al., (2008) *Proc Natl Acad Sci USA,* 105:20167-20172), where the amino acid position is according to the EU or Kabat numbering convention, to eliminate complement activation. In some embodiments, the IgG variants described herein may be combined with one or more mutations to enhance the antibody half-life in human serum (e.g. M252Y, S254T, T256E mutations according to the EU or Kabat numbering convention) (Dall'Acqua et al., (2006) *J Biol Chem,* 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) *Mol Immunol,* 30:105-108) and/or with one or more mutations described in Peters et al., (2012) *J Biol Chem.* 13; 287(29):24525-33) to enhance antibody stabilization.

Anti-TREM2 Antibodies

Certain aspects of the present disclosure related to anti-TREM2 antibodies.

In certain embodiments, anti-TREM2 antibodies of the present disclosure are agonist antibodies that induce one or more TREM2 activities. In some embodiments, anti-TREM2 antibodies of the present disclosure are agonist antibodies that promote survival of one or more innate immune cells. In some embodiments, anti-TREM2 antibodies of the present disclosure promote survival of macrophages, microglial cells, M1 microglial cells, activated M1 microglial cells, M2 microglial cells, dendritic cells, M1 macrophages, activated M1 macrophages, M2 macrophages, monocytes, osteoclasts, Langerhans cells of skin, and/or Kupffer cells. In some embodiments, promoting survival of one or more innate immune cells encompasses prolonging cell survival or otherwise delaying cell death. Accordingly, in some embodiments, anti-TREM2 antibodies of the present disclosure prolong cell survival of one or more innate immune cells. In some embodiments, anti-TREM2 antibodies of the present disclosure delay cell death of one or more innate immune cells. In some embodiments, promoting cell survival and/or prolonging cell survival is determined by measuring cell survival of one or more innate immune cells in the presence of the anti-TREM2 antibody as compared to cell survival of corresponding one or more innate immune cells in the absence of the anti-TRME2 antibody. In some embodiments, delay in cell death is determined by measuring cell death of one or more innate immune cells in the presence of the anti-TREM2 antibody as compared to cell death of corresponding one or more innate immune cells in the absence of the anti-TRME2 antibody. Any suitable methods of measuring cell survival or cell death known in the art and disclosed herein may be used (see, e.g., Examples 30, 34, 35, 38, 52, 53, and 56). In some embodiments, anti-TREM2 antibodies of the present disclosure are agonist antibodies that increase IL-6 expression. In some embodiments, anti-TREM2 antibodies of the present disclosure are agonist antibodies that promote survival of one or more innate immune cells and increase expression of IL-6. Any suitable methods known in the art and disclosed herein for measuring IL-6 expression in a cell may be used (see, e.g., Examples 28, 38, and 68).

In certain embodiments, anti-TREM2 antibodies of the present disclosure are inert or antagonist antibodies that inhibit one or more TREM2 activities. In some embodiments, anti-TREM2 antibodies of the present disclosure are inert or antagonist antibodies that decrease survival of one or more innate immune cells. In some embodiments, anti-TREM2 antibodies of the present disclosure decrease survival of macrophages, microglial cells, M1 microglial cells, activated M1 microglial cells, M2 microglial cells, dendritic cells, M1 macrophages, activated M1 macrophages, M2 macrophages, monocytes, osteoclasts, Langerhans cells of skin, and/or Kupffer cells. In some embodiments, decreasing cell survival is determined by measuring cell survival of one or more innate immune cells in the presence of the antagonist anti-TREM2 antibody as compared to cell survival of corresponding one or more innate immune cells in the absence of the antagonist anti-TRME2 antibody. Any suitable methods of measuring cell survival or cell death known in the art and disclosed herein may be used (see, e.g., Examples 30, 34, 35, 38, 52, 53, and 56).

In some embodiments, an isolated anti-TREM2 antibody of the present disclosure competes for binding of TREM2 with one or more TREM2 ligands. In some embodiments, the antibody is a human antibody, a humanized antibody, a bispecific antibody, a multivalent antibody, or a chimeric antibody. Exemplary descriptions of such antibodies are found throughout the present disclosure. In some embodiments, the antibody is a bispecific antibody recognizing a first antigen and a second antigen.

In certain embodiments the TREM2 protein is expressed on a cell surface. In some embodiment anti-TREM2 antibodies of the present disclosure modulate (e.g., induce or inhibit) one or more TREM2 activities. The TREM2 activities modulated (e.g., induced or inhibited) by the anti-TREM2 antibodies may include, without limitation, DAP12 phosphorylation; TREM2 phosphorylation; recruitment of Syk, ZAP70, or both to a DAP12/TREM2 complex; PI3K activation; increased expression of anti-inflammatory mediators (e.g. cytokines); reduced expression of pro-inflammatory mediators; ERK phosphorylation; increased expression of CCR7, induction of microglial cell chemotaxis toward CCL19 and CCL21 expressing cells; enhancement, normalization, or both of the ability of bone marrow-derived dendritic cells to induce antigen-specific T-cell proliferation; induction of osteoclast production, increased rate of osteoclastogenesis, or both; increased survival and function of microglial cells and/or macrophages (such as M1 macrophages and/or microglial cells, activated M1 macrophages and/or microglial cells, and/or M2 macrophages and/or microglial cells), dendritic cells, monocytes, osteoclasts, Langerhans cells of skin, and/or Kupffer cells; induction of apoptotic neuron clearance; reduced expression of TNF-α; SYK phosphorylation; increased expression of CD83 and/or CD86 on dendritic cells, monocytes, macrophages, and/or microglia; reduced secretion of one or more inflammatory cytokines (such as TNF-α, IL-10, IL-6, and/or MCP-1); reduced expression of one or more inflammatory receptors (such as CD86); increased phagocytosis by macrophages, dendritic cells, monocytes, and/or microglia under conditions of reduced levels of MCSF; reduced phagocytosis by macrophages, dendritic cells, monocytes, and/or microglia in the presence of normal levels of MCSF; and/or increased activity of one or more TREM2-dependent genes (e.g., transcription factors of the nuclear factor of activated T-cells (NFAT) family of transcription factors). The anti-TREM2 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer. The anti-TREM2 antibodies of the present disclosure may also be used in advanced wound care. In some embodiments, the anti-TREM2 antibodies of the present disclosure are monoclonal antibodies. Anti-TREM2 antibodies of the present disclosure may be tested for inducing one or more TREM2 activities (e.g., TREM2 autophosphorylation; DAP12 phosphorylation; Syk phosphorylation; recruitment of Syk, ZAP70, or both to a DAP12/TREM2 complex; PI3K activation; increased expression of cytokines; reduced expression of pro-inflammatory mediators; ERK phosphorylation; increased expression of CCR7; induction of microglial cell chemotaxis toward CCL19 and CCL21 expressing cells; maturation of bone marrow-derived dendritic cells; enhancement or normalization of the ability of bone marrow-derived dendritic cells to induce antigen-specific T-cell proliferation; increased ability of dendritic cells, monocytes, microglia, and/or macrophages to induce T-cell proliferation; induction of osteoclast production, increased rate of osteoclastogenesis, or both; increased survival and function of dendritic cells, macrophages, monocytes, osteoclasts, Langerhans cells of skin, Kupffer cells, and/or microglia; induction of one or more types of clearance; induction of phagocytosis of one or more of apoptotic neurons, nerve tissue debris, non-nerve tissue debris, bacteria, other foreign bodies, disease-causing proteins, disease-causing peptides, disease-causing nucleic acid, or tumor cells; reduced secretion of one or more inflammatory cytokines; reduced expression of one or more inflammatory receptors; increased phagocytosis by macrophages, dendritic cells, monocytes, and/or microglial cells under conditions of reduced levels of MCSF; reduced phagocytosis by macrophages, dendritic cells, monocytes, and/or microglial cells in the presence of normal levels of MCSF; normalization of disrupted TREM2/DAP12-dependent gene expression; and increased activity of one or more TREM2-dependent genes) using any suitable method known in the art and/or described herein. For example, the anti-TREM2 antibodies can be assayed in vitro for tyrosine phosphorylation of, TREM2, DAP12, Syk and/or ERK, by assaying for recruitment of Syk and/or ZAP70 to DAP12, by assaying for PI3K activation, by assaying for induction of expression of cytokines (e.g., IL-12p70, IL-6, and IL-10) or CCR7, or by assaying for reduced expression of pro-inflammatory mediators (e.g., IL1-β and TNF) with TLR stimulation (e.g., LPS, CpG DNA, or Zymosan). Useful assays may include western blots (e.g., for tyrosine-phosphorylated DAP12 or threonine/serine-phosphorylated PI3K-kinase substrates), ELISA (e.g., for secreted interleukin or cytokine secretion), FACS (e.g., for anti-TREM2 binding to TREM2), immunocytochemistry (e.g., for e.g., for tyrosine-phosphorylated DAP12 or threonine/serine-phosphorylated PI3K-kinase substrates), reporter-gene assays (e.g., for TLR activation), increased survival and/or function of dendritic cells, macrophages, monocytes, osteoclasts, Langerhans cells of skin, Kupffer cells, and/or microglia, increased phagocytosis of apoptotic neurons, damaged synapses, amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, nerve tissue debris, non-nerve tissue debris, bacteria, other foreign bodies, disease-causing proteins, disease-causing peptides, disease-causing nucleic acid, or tumor cells by macrophages, dendritic cells, Langerhans cells of skin, Kupffer cells, monocytes, osteoclasts, and/or microglial cells, increased cytoskeleton reorganization, and decreased microglial pro-inflammatory responses, or other assays known in the art.

In some embodiments, anti-TREM2 antibodies of the present disclosure modulate (i.e., increase or decrease) the expression and/or secretion of one or more inflammatory cytokines (e.g., TNF-α, IL-10, IL-6, MCP-1, IFN-a4, IFN-b, IL-1β, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18). In some embodiments, anti-TREM2 antibodies of the present disclosure increase the expression and/or secretion of one or more inflammatory cytokines. In some embodiments, anti-TREM2 antibodies of the present disclosure decrease the expression and/or secretion of one or more inflammatory cytokines. In some embodiments, anti-TREM2 antibodies of the present disclosure modulate (i.e., increase or decrease) the expression and/or secretion of one or more inflammatory receptors (e.g., CD86). In some embodiments, anti-TREM2 antibodies of the present disclosure increase the expression and/or secretion of one or more inflammatory receptors. In some embodiments, anti-TREM2 antibodies of the present disclosure decrease the expression and/or secretion of one or more inflammatory receptors.

In some embodiments, anti-TREM2 antibodies of the present disclosure bind to a human TREM2, or a homolog thereof, including without limitation a mammalian TREM2 protein, mouse TREM2 protein (Uniprot Accession No. Q99NH8), rat TREM2 protein (Uniprot Accession No. D3ZZ89), Rhesus monkey TREM2 protein (Uniprot Accession No. F6QVF2), bovine TREM2 protein (Uniprot Accession No. Q05B59), equine TREM2 protein (Uniprot Accession No. F7D6L0), pig TREM2 protein (Uniprot Accession No. H2EZZ3), and dog TREM2 protein (Uniprot Accession No. E2RP46). In some embodiments, anti-TREM2 antibodies of the present disclosure specifically bind to human TREM2. In some embodiments, anti-TREM2 antibodies of the present disclosure specifically bind to mouse TREM2. In some embodiments, anti-TREM2 antibodies of the present disclosure specifically bind to both human TREM2 and mouse TREM2. In some embodiments, anti-TREM2 antibodies of the present disclosure modulate (e.g., induce or inhibit) at least one TREM2 activity. In some embodiments, the at least one TREM2 activity is DAP12 phosphorylation, TREM2 phosphorylation, PI3K activation, increased expression of one or more anti-inflammatory mediators (e.g., cytokines), reduced expression of one or more pro-inflammatory mediators, increased survival and/or function of microglial cells, dendritic cells, macrophages, monocytes, osteoclasts, Langerhans cells of skin, and/or Kupffer cells, reduced expression of TNF-α, SYK phosphorylation, increased expression of CD83 and/or CD86 on dendritic cells, macrophages, monocytes, and/or macrophages, reduced secretion of one or more inflammatory cytokines, reduced expression of one or more inflammatory receptors, increased phagocytosis by macrophages, dendritic cells, monocytes, and/or microglia under conditions of reduced levels of MCSF, reduced phagocytosis by macrophages, dendritic cells, monocytes, and/or microglia in the presence of normal levels of MCSF, and/or increased activity of one or more TREM2-dependent genes (e.g., transcription factors of the nuclear factor of activated T-cells (NFAT) family of transcription factors).

In some embodiments, anti-TREM2 antibodies of the present disclosure bind to a TREM2 protein of the present disclosure and/or naturally occurring variants. In certain preferred embodiments, the anti-TREM2 antibodies bind to human TREM2.

In some embodiments, anti-TREM2 antibodies of the present disclosure are agonist antibodies, or antagonist antibodies that bind to a TREM2 protein of the present disclosure expressed on the surface of a cell and modulate (e.g., induce or inhibit) at least one TREM2 activity of the present disclosure after binding to the surface-expressed TREM2 protein. In some embodiments, anti-TREM2 antibodies of the present disclosure are inert antibodies.

In certain embodiments, anti-TREM2 antibodies of the present disclosure bind to one or more amino acids within amino acid residues 29-112 of human TREM 2 (SEQ ID NO: 1), or within amino acid residues on a TREM2 protein corresponding to amino acid residues 29-112 of SEQ ID NO: 1. In some embodiments, anti-TREM2 antibodies of the present disclosure bind to one or more amino acids within amino acid residues 29-41 of human TREM 2 (SEQ ID NO: 1), or within amino acid residues on a TREM2 protein corresponding to amino acid residues 29-41 of SEQ ID NO: 1. In some embodiments, anti-TREM2 antibodies of the present disclosure bind to one or more amino acids within amino acid residues 47-69 of human TREM 2 (SEQ ID NO: 1), or within amino acid residues on a TREM2 protein corresponding to amino acid residues 47-69 of SEQ ID NO: 1. In some embodiments, anti-TREM2 antibodies of the present disclosure bind to one or more amino acids within amino acid residues 76-86 of human TREM 2 (SEQ ID NO: 1), or within amino acid residues on a TREM2 protein corresponding to amino acid residues 76-86 of SEQ ID NO: 1. In some embodiments, anti-TREM2 antibodies of the present disclosure bind to one or more amino acids within amino acid residues 91-100 of human TREM 2 (SEQ ID NO: 1), or within amino acid residues on a TREM2 protein corresponding to amino acid residues 91-100 of SEQ ID NO: 1. In some embodiments, anti-TREM2 antibodies of the present disclosure bind to one or more amino acids within amino acid residues 99-115 of human TREM 2 (SEQ ID NO: 1), or within amino acid residues on a TREM2 protein corresponding to amino acid residues 99-115 of SEQ ID NO: 1. In some embodiments, anti-TREM2 antibodies of the present disclosure bind to one or more amino acids within amino acid residues 104-112 of human TREM 2 (SEQ ID NO: 1), or within amino acid residues on a TREM2 protein corresponding to amino acid residues 104-112 of SEQ ID NO: 1. In some embodiments, anti-TREM2 antibodies of the present disclosure bind to one or more amino acids within amino acid residues 114-118 of human TREM 2 (SEQ ID NO: 1), or within amino acid residues on a TREM2 protein corresponding to amino acid residues 114-118 of SEQ ID NO: 1. In some embodiments, anti-TREM2 antibodies of the present disclosure bind to one or more amino acids within amino acid residues 130-171 of human TREM 2 (SEQ ID NO: 1), or within amino acid residues on a TREM2 protein corresponding to amino acid residues 130-171 of SEQ ID NO: 1. In some embodiments, anti-TREM2 antibodies of the present disclosure bind to one or more amino acids within amino acid residues 139-153 of human TREM 2 (SEQ ID NO: 1), or within amino acid residues on a TREM2 protein corresponding to amino acid residues 139-153 of SEQ ID NO: 1. In some embodiments, anti-TREM2 antibodies of the present disclosure bind to one or more amino acids within amino acid residues 139-146 of human TREM 2 (SEQ ID NO: 1), or within amino acid residues on a TREM2 protein corresponding to amino acid residues 139-146 of SEQ ID NO: 1. In some embodiments, anti-TREM2 antibodies of the present disclosure bind to one or more amino acids within amino acid residues 130-144 of human TREM 2 (SEQ ID NO: 1), or within amino acid residues on a TREM2 protein corresponding to amino acid residues 130-144 of SEQ ID NO: 1. In some embodiments, anti-TREM2 antibodies of the present disclosure bind to one or more amino acids within amino acid residues 158-171 of human TREM 2 (SEQ ID NO: 1), or within amino acid residues on a TREM2 protein corresponding to amino acid residues 158-171 of SEQ ID NO: 1.

In some embodiments, anti-TREM2 antibodies of the present disclosure bind to one or more amino acids within amino acid residues 43-50 of human TREM 2 (SEQ ID NO: 1), or within amino acid residues on a TREM2 protein corresponding to amino acid residues 43-50 of SEQ ID NO:

1. In some embodiments, anti-TREM2 antibodies of the present disclosure bind to one or more amino acids within amino acid residues 49-57 of human TREM 2 (SEQ ID NO: 1), or within amino acid residues on a TREM2 protein corresponding to amino acid residues 49-57 of SEQ ID NO: 1. In some embodiments, anti-TREM2 antibodies of the present disclosure bind to one or more amino acids within amino acid residues 139-146 of human TREM 2 (SEQ ID NO: 1), or within amino acid residues on a TREM2 protein corresponding to amino acid residues 139-146 of SEQ ID NO: 1. In some embodiments, anti-TREM2 antibodies of the present disclosure bind to one or more amino acids within amino acid residues 140-153 of human TREM 2 (SEQ ID NO: 1), or within amino acid residues on a TREM2 protein corresponding to amino acid residues 140-153 of SEQ ID NO: 1.

TREM2 proteins of the present disclosure include a complementary determining region 1 (CDR1) located at amino acid residues corresponding to amino acid residues 40-44 of human TREM2 (SEQ ID NO: 1); a complementary determining region 2 (CDR2) located at amino acid residues corresponding to amino acid residues 67-76 of human TREM2 (SEQ ID NO: 1); and a complementary determining region 3 (CDR3) located at amino acid residues corresponding to amino acid residues 114-118 of human TREM2 (SEQ ID NO: 1). Accordingly, in some embodiments, anti-TREM2 antibodies of the present disclosure bind to one or more amino acids within amino acid residues 40-44 of human TREM 2 (SEQ ID NO: 1), or within amino acid residues on a TREM2 protein corresponding to amino acid residues 40-44 of SEQ ID NO: 1. In some embodiments, anti-TREM2 antibodies of the present disclosure bind to one or more amino acids within amino acid residues 67-76 of human TREM 2 (SEQ ID NO: 1), or within amino acid residues on a TREM2 protein corresponding to amino acid residues 67-76 of SEQ ID NO: 1. In some embodiments, anti-TREM2 antibodies of the present disclosure bind to one or more amino acids within amino acid residues 114-118 of human TREM 2 (SEQ ID NO: 1), or within amino acid residues on a TREM2 protein corresponding to amino acid residues 114-118 of SEQ ID NO: 1.

In other embodiments, anti-TREM2 antibodies of the present disclosure bind to an epitope that includes amino acid residue Arg47 or Asp87 of human TREM 2 (SEQ ID NO: 1). In some embodiments, anti-TREM2 antibodies of the present disclosure bind to an epitope that includes amino acid residues 40-44 of human TREM 2 (SEQ ID NO: 1). In some embodiments, anti-TREM2 antibodies of the present disclosure bind to an epitope that includes amino acid residues 67-76 of human TREM 2 (SEQ ID NO: 1). In some embodiments, anti-TREM2 antibodies of the present disclosure bind to an epitope that includes amino acid residues 114-118 of human TREM 2 (SEQ ID NO: 1).

In some embodiments, anti-TREM2 antibodies of the present disclosure competitively inhibit binding of at least one antibody selected from any of the antibodies listed in Table 1and/or Table 8. In some embodiments, anti-TREM2 antibodies of the present disclosure competitively inhibit binding of at least one antibody selected from Ab, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. In some embodiments, anti-TREM2 antibodies of the present disclosure competitively inhibit binding of at least one of the following anti-TREM2 antibodies: Ab1, Ab9, Ab14, Ab22, Ab45, and Ab65. In some embodiments, anti-TREM2 antibodies of the present disclosure bind to an epitope of human TREM2 that is the same as or overlaps with the TREM2 epitope bound by at least one antibody selected from any of the antibodies listed in Table 1and/or Table 8. In some embodiments, anti-TREM2 antibodies of the present disclosure bind to an epitope of human TREM2 that is the same as or overlaps with the TREM2 epitope bound by at least one antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. In some embodiments, anti-TREM2 antibodies of the present disclosure bind to an epitope of human TREM2 that is the same as or overlaps with the TREM2 epitope bound by at least one of the following anti-TREM2 antibodies: Ab1, Ab9, Ab14, Ab22, Ab45, and Ab65. In some embodiments, anti-TREM2 antibodies of the present disclosure bind essentially the same TREM2 epitope bound by at least one antibody selected from any of the antibodies listed in Table 1and/or Table 8. In some embodiments, anti-TREM2 antibodies of the present disclosure bind essentially the same TREM2 epitope bound by at least one antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. In some embodiments, anti-TREM2 antibodies of the present disclosure bind essentially the same TREM2 epitope bound by at least one of the following anti-TREM2 antibodies: Ab1, Ab9, Ab14, Ab22, Ab45, and Ab65. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TREM2 or cells expressing TEM2 on the cell surface are incubated in a solution comprising a first labeled antibody that binds to TREM2 (e.g., human or non-human primate) and a second unlabeled antibody that is being tested for its ability to compete with the first antibody for binding to TREM2. The second antibody may be present in a hybridoma supernatant. As a control, immobilized TREM2 or cells expressing TREM2 is incubated in a solution comprising the first labeled antibody but not the second unlabeled antibody. After incubation under conditions permissive for binding of the first antibody to TREM2, excess unbound antibody is removed, and the amount of label associated with immobilized TREM2 or cells expressing TREM2 is measured. If the amount of label associated with immobilized TREM2 or cells expressing TREM2 is substantially reduced in the test sample relative to the control sample, then that indicates that the second antibody is competing with the first antibody for binding to TREM2. See, Harlow and Lane (1988) *Antibodies: A Laboratory Manual* ch. 14 (Cold Spring Harbor Laboratory, Cold Spring Harbor, N.Y.).

In some embodiments, anti-TREM2 antibodies of the present disclosure comprise (a) a heavy chain variable region comprising at least one, two, or three HVRs selected from HVR-H1, HVR-H2, and HVR-H3 of any one of the antibodies listed in Table 1 and/or Table 8 or selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; and/or (b) a light chain variable region comprising at least one, two, or three HVRs selected from HVR-L1, HVR-L2, and HVR-L3 of any one of the antibodies listed in Table 1 and/or Table 8 or selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. In some embodiments, the HVR-H1, HVR-H2, HVR-H3, HVR-L1, HVR-L2, and HVR-L3 comprise Kabat CDR, Chothia CDR, or Contact CDR sequences as shown in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

In some embodiments, anti-TREM2 antibodies of the present disclosure comprise at least one, two, three, four, five, or six HVRs selected from (i) HVR-H1 comprising the amino acid sequence of any of the HVR-H1 sequences listed in Table 1 and/or Table 8 or from an antibody selected from Ab1, Ab2, Ab3, Ab4, Ab5, Ab6, Ab7, Ab8, Ab9, Ab10, Ab1, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; (ii) HVR-H2 comprising the amino acid sequence of any of the HVR-H2 sequences listed in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; (iii) HVR-H3 comprising the amino acid sequence of any of the HVR-H3 sequences listed in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; (iv) HVR-L1 comprising the amino acid sequence of any of the HVR-L1 sequences listed in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; (v) HVR-L2 comprising the amino acid sequence of any of the HVR-L2 sequences listed in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; and (vi) HVR-L3 comprising the amino acid sequence of any of the HVR-L3 sequences listed in Table 1 and/or Table 8 or from an antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

In some embodiments, anti-TREM2 antibodies of the present disclosure comprise a heavy chain variable domain and a light chain variable domain, wherein the heavy chain variable domain comprises one or more of: (a) an HVR-H1 comprising an amino acid sequence selected from the group consisting of SEQ ID NOs:3-24, or an amino acid sequence with at least about 95% homology to an amino acid sequence selected from the group consisting of SEQ ID NOs:3-24; (b) an HVR-H2 comprising an amino acid sequence selected from the group consisting of SEQ ID NOs:25-49, or an amino acid sequence with at least about 95% homology to an amino acid sequence selected from the group consisting of SEQ ID NOs: 25-49; and (c) an HVR-H3 comprising an amino acid sequence selected from the group consisting of SEQ ID NOs:50-119, or an amino acid sequence with at least about 95% homology to an amino acid sequence selected from the group consisting of SEQ ID NOs: 50-119; and/or wherein the light chain variable domain comprises one or more of: (a) an HVR-L1 comprising an amino acid sequence selected from the group consisting of SEQ ID NOs: 120-137, or an amino acid sequence with at least about 95% homology to an amino acid sequence selected from the group consisting of SEQ ID NOs:120-137; (b) an HVR-L2 comprising an amino acid sequence selected from the group consisting of SEQ ID NOs:138-152, or an amino acid sequence with at least about 95% homology to an amino acid sequence selected from the group consisting of SEQ ID NOs: 138-152; and (c) an HVR-L3 comprising an amino acid sequence selected from the group consisting of SEQ ID NOs:153-236 or an amino acid sequence with at least about 95% homology to an amino acid sequence selected from the group consisting of SEQ ID NOs: 138-152.

In some embodiments, anti-TREM2 antibodies of the present disclosure comprise a heavy chain variable region of any one of the antibodies listed in Table 1and/or Table 8 or selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87; and/or a light chain variable region of any one of the antibodies listed in Table 1and/or Table 8 or selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

Any of the antibodies of the present disclosure may be produced by a cell line. In some embodiments, the cell line may be a yeast cell line. In other embodiments, the cell line may be a mammalian cell line. In certain embodiments, the cell line may be a hybridoma cell line. Any cell line known in the art suitable for antibody production may be used to produce an antibody of the present disclosure. Exemplary cell lines for antibody production are described throughout the present disclosure.

In some embodiments, the anti-TREM2 antibody is an anti-TREM2 monoclonal antibody selected from Ab1, Ab2, Ab3, Ab4, Ab5, Ab6, Ab7, Ab8, Ab9, Ab10, Ab1, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87. In certain embodiments, the anti-TREM2 antibody is an agonist antibody. In other embodiments, the anti-TREM2 antibody is an antagonist antibody.

In some embodiments, the anti-TREM2 antibody is anti-TREM2 monoclonal antibody Ab1. In some embodiments, the anti-TREM2 antibody is an isolated antibody which binds essentially the same TREM2 epitope as Ab1. In some embodiments, the anti-TREM2 antibody is an isolated antibody comprising the HVR-H1, HVR-H2, and HVR-H3 of the heavy chain variable domains of monoclonal antibody Ab1. In some embodiments, the anti-TREM2 antibody is an isolated antibody comprising the HVR-L1, HVR-L2, and HVR-L3 of the light chain variable domains of monoclonal antibody Ab1. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab1. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:3, or an amino acid sequence with at least about 95% homology to the amino acid sequence of SEQ ID NO:3; (ii) HVR-H2 comprising the amino acid sequence of SEQ ID NO: 25, or an amino acid sequence with at least about 95% homology to the amino acid sequence of SEQ ID NO:25; (iii) HVR-H3 comprising the amino acid sequence of SEQ ID NO:50, or an amino acid sequence with at least about 95% homology to the amino acid sequence of SEQ ID NO:50; (iv) HVR-L1 comprising the amino acid sequence of SEQ ID NO: 120 or an amino acid sequence with at least about 95% homology to the amino acid sequence of SEQ ID NO: 120; (v) HVR-L2 comprising the amino acid sequence of SEQ ID NO: 138 or an amino acid sequence with at least about 95% homology to the amino acid sequence of SEQ ID NO: 138; and (vi) HVR-L3 comprising the amino acid sequence of SEQ ID NO:153, or an amino acid sequence with at least about 95% homology to the amino acid sequence of SEQ ID NO: 153.

In some embodiments, the anti-TREM2 antibody is anti-TREM2 monoclonal antibody Ab9. In some embodiments, the anti-TREM2 antibody is an isolated antibody which binds essentially the same TREM2 epitope as Ab9. In some embodiments, the anti-TREM2 antibody is an isolated antibody comprising the HVR-H1, HVR-H2, and HVR-H3 of the heavy chain variable domains of monoclonal antibody Ab9. In some embodiments, the anti-TREM2 antibody is an isolated antibody comprising the HVR-L1, HVR-L2, and HVR-L3 of the light chain variable domains of monoclonal antibody Ab9. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab9. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:9, or an amino acid sequence with at least about 95% homology to the amino acid sequence of SEQ ID NO:9; (ii) HVR-H2 comprising the amino acid sequence of SEQ ID NO: 33, or an amino acid sequence with at least about 95% homology to the amino acid sequence of SEQ ID NO:33; (iii) HVR-H3 comprising the amino acid sequence of SEQ ID NO:58, or an amino acid sequence with at least about 95% homology to the amino acid sequence of SEQ ID NO:58; (iv) HVR-L1 comprising the amino acid sequence of SEQ ID NO: 124 or an amino acid sequence with at least about 95% homology to the amino acid sequence of SEQ ID NO: 124; (v) HVR-L2 comprising the amino acid sequence of SEQ ID NO: 144 or an amino acid sequence with at least about 95% homology to the amino acid sequence of SEQ ID NO: 144; and (vi) HVR-L3 comprising the amino acid sequence of SEQ ID NO: 161, or an amino acid sequence with at least about 95% homology to the amino acid sequence of SEQ ID NO: 161.

In some embodiments, the anti-TREM2 antibody is anti-TREM2 monoclonal antibody Ab14. In some embodiments, the anti-TREM2 antibody is an isolated antibody which binds essentially the same TREM2 epitope as Ab14. In some embodiments, the anti-TREM2 antibody is an isolated antibody comprising the HVR-H1, HVR-H2, and HVR-H3 of the heavy chain variable domains of monoclonal antibody Ab14. In some embodiments, the anti-TREM2 antibody is an isolated antibody comprising the HVR-L1, HVR-L2, and HVR-L3 of the light chain variable domains of monoclonal antibody Ab14. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab14. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:13, or an amino acid sequence with at least about 95% homology to the amino acid sequence of SEQ ID NO: 13; (ii) HVR-H2 comprising the amino acid sequence of SEQ ID NO: 36, or an amino acid sequence with at least about 95% homology to the amino acid sequence of SEQ ID NO:36; (iii) HVR-H3 comprising the amino acid sequence of SEQ ID NO:63, or an amino acid sequence with at least about 95% homology to the amino acid sequence of SEQ ID NO:63; (iv) HVR-L1 comprising the amino acid sequence of SEQ ID NO: 122 or an amino acid sequence with at least about 95% homology to the amino acid sequence of SEQ ID NO: 122; (v) HVR-L2 comprising the amino acid sequence of SEQ ID NO: 146 or an amino acid sequence with at least about 95% homology to the amino acid sequence of SEQ ID NO: 146; and (vi) HVR-L3 comprising the amino acid sequence of SEQ ID NO: 166, or an amino acid sequence with at least about 95% homology to the amino acid sequence of SEQ ID NO: 166.

In some embodiments, the anti-TREM2 antibody is anti-TREM2 monoclonal antibody Ab22. In some embodiments, the anti-TREM2 antibody is an isolated antibody which binds essentially the same TREM2 epitope as Ab22. In some embodiments, the anti-TREM2 antibody is an isolated antibody comprising the HVR-H1, HVR-H2, and HVR-H3 of the heavy chain variable domains of monoclonal antibody Ab22. In some embodiments, the anti-TREM2 antibody is an isolated antibody comprising the HVR-L1, HVR-L2, and HVR-L3 of the light chain variable domains of monoclonal antibody Ab22. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab22. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:11, or an amino acid sequence with at least about 95% homology to the amino acid sequence of SEQ ID NO: 11; (ii) HVR-H2 comprising the amino acid sequence of SEQ ID NO: 34, or an amino acid sequence with at least about 95% homology to the amino acid sequence of SEQ ID NO:34; (iii) HVR-H3 comprising the amino acid sequence of SEQ ID NO:60, or an amino acid sequence with at least about 95% homology to the amino acid sequence of SEQ ID NO:60; (iv) HVR-L1 comprising the amino acid sequence of SEQ ID NO: 123 or an amino acid sequence with at least about 95% homology to the amino acid sequence of SEQ ID NO: 123; (v) HVR-L2 comprising the amino acid sequence of SEQ ID NO: 141 or an amino acid sequence with at least about 95% homology to the amino acid sequence of SEQ ID NO: 141; and (vi) HVR-L3 comprising the amino acid sequence of SEQ ID NO: 173, or an amino acid sequence with at least about 95% homology to the amino acid sequence of SEQ ID NO: 173.

In some embodiments, the anti-TREM2 antibody is anti-TREM2 monoclonal antibody Ab45. In some embodiments, the anti-TREM2 antibody is an isolated antibody which binds essentially the same TREM2 epitope as Ab45. In some embodiments, the anti-TREM2 antibody is an isolated antibody comprising the HVR-H1, HVR-H2, and HVR-H3 of the heavy chain variable domains of monoclonal antibody Ab45. In some embodiments, the anti-TREM2 antibody is an isolated antibody comprising the HVR-L1, HVR-L2, and HVR-L3 of the light chain variable domains of monoclonal antibody Ab45. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab45. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:7, or an amino acid sequence with at least about 95% homology to the amino acid sequence of SEQ ID NO:7; (ii) HVR-H2 comprising the amino acid sequence of SEQ ID NO: 29, or an amino acid sequence with at least about 95% homology to the amino acid sequence of SEQ ID NO:29; (iii) HVR-H3 comprising the amino acid sequence of SEQ ID NO:87, or an amino acid sequence with at least about 95% homology to the amino acid sequence of SEQ ID NO:87; (iv) HVR-L1 comprising the amino acid sequence of SEQ ID NO: 120 or an amino acid sequence with at least about 95% homology to the amino acid sequence of SEQ ID NO: 120; (v) HVR-L2 comprising the amino acid sequence of SEQ ID NO: 138 or an amino acid sequence with at least about 95% homology to the amino acid sequence of SEQ ID NO: 138; and (vi) HVR-L3 comprising the amino acid sequence of SEQ ID NO: 196, or an amino acid sequence with at least about 95% homology to the amino acid sequence of SEQ ID NO: 196.

In some embodiments, the anti-TREM2 antibody is anti-TREM2 monoclonal antibody Ab65. In some embodiments, the anti-TREM2 antibody is an isolated antibody which binds essentially the same TREM2 epitope as Ab65. In some embodiments, the anti-TREM2 antibody is an isolated antibody comprising the HVR-H1, HVR-H2, and HVR-H3 of the heavy chain variable domains of monoclonal antibody Ab65. In some embodiments, the anti-TREM2 antibody is an isolated antibody comprising the HVR-L1, HVR-L2, and HVR-L3 of the light chain variable domains of monoclonal antibody Ab65. In some embodiments, the anti-TREM2 antibody is an isolated antibody comprising the HVR-H1, HVR-H2, and HVR-H3 of the heavy chain variable domains and the HVR-L1, HVR-L2, and HVR-L3 of the light chain variable domains of monoclonal antibody Ab65. In certain embodiments, the anti-TREM2 antibody is an agonist antibody. In other embodiments, the anti-TREM2 antibody is an antagonist antibody. In some embodiments, anti-TREM2 antibodies of the present disclosure comprise at least one, two, three, four, five, or six HVRs selected from (i) HVR-H1 comprising the amino acid sequence of SEQ ID NO:9, or an amino acid sequence with at least about 95% homology to the amino acid sequence of SEQ ID NO:9; (ii) HVR-H2 comprising the amino acid sequence of SEQ ID NO: 34, or an amino acid sequence with at least about 95% homology to the amino acid sequence of SEQ ID NO:34; (iii) HVR-H3 comprising the amino acid sequence of SEQ ID NO: 101, or an amino acid sequence with at least about 95% homology to the amino acid sequence of SEQ ID NO: 101; (iv) HVR-L1 comprising the amino acid sequence of SEQ ID NO: 124 or an amino acid sequence with at least about 95% homology to the amino acid sequence of SEQ ID NO: 124; (v) HVR-L2 comprising the amino acid sequence of SEQ ID NO: 144 or an amino acid sequence with at least about 95% homology to the amino acid sequence of SEQ ID NO: 144; and (vi) HVR-L3 comprising the amino acid sequence of SEQ ID NO:215, or an amino acid sequence with at least about 95% homology to the amino acid sequence of SEQ ID NO:215.

In some embodiments, anti-TREM2 antibodies of the present disclosure bind to one or more amino acids within amino acid residues 43-50 of human TREM 2 (SEQ ID NO: 1), or within amino acid residues on a TREM2 protein corresponding to amino acid residues 43-500 of SEQ ID NO: 1. In some embodiments, anti-TREM2 antibodies of the present disclosure bind to one or more amino acids within amino acid residues 49-57 of human TREM 2 (SEQ ID NO: 1), or within amino acid residues on a TREM2 protein corresponding to amino acid residues 49-57 of SEQ ID NO: 1. In some embodiments, anti-TREM2 antibodies of the present disclosure bind to an epitope that includes one or more amino acid residues within amino acid residues 43-50 of human TREM 2 (SEQ ID NO: 1). In some embodiments, anti-TREM2 antibodies of the present disclosure bind to an epitope that includes one or more amino acid residues within amino acid residues 49-57 of human TREM 2 (SEQ ID NO: 1). In some embodiments, anti-TREM2 antibodies of the present disclosure competitively inhibit binding of at least one of the following anti-TREM2 antibodies: Ab21 and Ab52. In some embodiments, anti-TREM2 antibodies of the present disclosure bind to an epitope of human TREM2 that is the same as or overlaps with the TREM2 epitope bound by at least one of the following anti-TREM2 antibodies: Ab21 and Ab52. In some embodiments, anti-TREM2 antibodies of the present disclosure comprise (a) a heavy chain variable region comprising at least one, two, or three HVRs selected from HVR-H1, HVR-H2, and HVR-H3 of any one of antibodies Ab21 and Ab52; and/or (b) a light chain variable region comprising at least one, two, or three HVRs selected from HVR-L1, HVR-L2, and HVR-L3 of any one of antibodies Ab21 and Ab52. In some embodiments, the HVR-H1, HVR-H2, HVR-H3, HVR-L1, HVR-L2, and HVR-L3 comprise Kabat CDR, Chothia CDR, or Contact CDR sequences as shown in Table 1and/or Table 8. In some embodiments, anti-TREM2 antibodies of the present disclosure comprise a heavy chain variable region of any one of antibodies Ab21 and Ab52; and/or a light chain variable region of any one of antibodies Ab21 and Ab52. In some embodiments, the anti-TREM2 antibody is anti-TREM2 monoclonal antibody Ab52 or Ab21. In some embodiments, the anti-TREM2 antibody is an isolated antibody which binds essentially the same TREM2 epitope as Ab52 or Ab21. In certain embodiments, the anti-TREM2 antibody is an agonist antibody. In other embodiments, the anti-TREM2 antibody is an antagonist antibody.

In some embodiments, the anti-TREM2 antibody is an isolated antibody comprising the HVR-H1, HVR-H2, and HVR-H3 of the heavy chain variable domains of monoclonal antibody Ab52 or Ab21. In some embodiments, the anti-TREM2 antibody is an isolated antibody comprising the HVR-L1, HVR-L2, and HVR-L3 of the light chain variable domains of monoclonal antibody Ab52 or Ab21. In some embodiments, the anti-TREM2 antibody is an isolated antibody comprising the HVR-H1, HVR-H2, and HVR-H3 of the heavy chain variable domains and the HVR-L 1, HVR-L2, and HVR-L3 of the light chain variable domains of monoclonal antibody Ab52 or Ab21. In some embodiments, anti-TREM2 antibodies of the present disclosure comprise at least one, two, three, four, five, or six HVRs selected from (i) HVR-H1 comprising the amino acid sequence of SEQ ID NO:398, or an amino acid sequence with at least about 95% homology to the amino acid sequence of SEQ ID NO:398; (ii) HVR-H2 comprising the amino acid sequence of SEQ ID NO: 399, or an amino acid sequence with at least about 95% homology to the amino acid sequence of SEQ ID NO:399; (iii) HVR-H3 comprising the amino acid sequence of SEQ ID NO:400, or an amino acid sequence with at least about 95% homology to the amino acid sequence of SEQ ID NO:400; (iv) HVR-L1 comprising the amino acid sequence of SEQ ID NO:401 or an amino acid sequence with at least about 95% homology to the amino acid sequence of SEQ ID NO:401; (v) HVR-L2 comprising the amino acid sequence of SEQ ID NO:402 or an amino acid sequence with at least about 95% homology to the amino acid sequence of SEQ ID NO:402; and (vi) HVR-L3 comprising the amino acid sequence of SEQ ID NO:403, or an amino acid sequence with at least about 95% homology to the amino acid sequence of SEQ ID NO:403. In some embodiments, anti-TREM2 antibodies of the present disclosure comprise at least one, two, three, four, five, or six HVRs selected from (i) HVR-H1 comprising the amino acid sequence of SEQ ID NO:404, or an amino acid sequence with at least about 95% homology to the amino acid sequence of SEQ ID NO:404; (ii) HVR-H2 comprising the amino acid sequence of SEQ ID NO: 405, or an amino acid sequence with at least about 95% homology to the amino acid sequence of SEQ ID NO:405; (iii) HVR-H3 comprising the amino acid sequence of SEQ ID NO:406, or an amino acid sequence with at least about 95% homology to the amino acid sequence of SEQ ID NO:406; (iv) HVR-L1 comprising the amino acid sequence of SEQ ID NO:407, or an amino acid sequence with at least about 95% homology to the amino acid sequence of SEQ ID NO:407; (v) HVR-L2 comprising the amino acid sequence of SEQ ID NO:408, or an amino acid sequence with at least about 95% homology to the amino acid sequence of SEQ ID NO:408; and (vi) HVR-L3 comprising the amino acid sequence of SEQ ID NO:409, or an amino acid sequence with at least about 95% homology to the amino acid sequence of SEQ ID NO:409.

In some embodiments, anti-TREM2 antibodies of the present disclosure comprise a heavy chain variable region, and the heavy chain variable region comprises at least one, at least two, or three HVR sequences selected from those listed in Table 1and/or Table 8; and/or comprise a light chain variable region, and the light chain variable region comprises at least one, at least two, or three HVR sequences selected from those listed in Table 1and/or Table 8.

In some embodiments, anti-TREM2 antibodies of the present disclosure compete for binding of TREM2 with one or more TREM2 ligands. Examples of suitable TREM2 ligands include, without limitation, TREM2 ligands expressed by E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide. Accordingly, in certain embodiments, the one or more TREM2 ligands comprise E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and/or lipidated amyloid beta peptide. In certain embodiments, the anti-TREM2 antibody is an agonist antibody. In other embodiments, the anti-TREM2 antibody is an antagonist antibody.

The dissociation constants ($K_D$) of anti-TREM2 antibodies for human TREM2 (e.g., human TREM2-Fc fusion proteins and human monomeric TREM2 proteins) and mouse TREM2 (e.g., mouse TREM2-Fc fusion proteins) may be less than 10 nM, less than 9.5 nM, less than 9 nM, less than 8.5 nM, less than 8 nM, less than 7.5 nM, less than 7 nM, ess than 7 nM, less than 6.9 nM, less than 6.8 nM, less than 6.7 nM, less than 6.6 nM, less than 6.5 nM, less than 6.4 nM, less than 6.3 nM, less than 6.2 nM, less than 6.1 nM, less than 6 nM, less than 5.9 nM, less than 5.8 nM, less than 5.75 nM, less than 5.7 nM, less than 5.6 nM, less than 5.5 nM, less than 5.4 nM, less than 5.3 nM, less than 5.2 nM, less than 5.1 nM, less than 5 nM, less than 4.5 nM, less than 4 nM, less than 3.5 nM, less than 3 nM, less than 2.5 nM, less than 2 nM, less than 1.5 nM, less than 1 nM, less than 0.95 nM, less than 0.9 nM, less than 0.85 nM, less than 0.8 nM, less than 0.75 nM, less than 0.7 nM, less than 0.65 nM, less than 0.6 nM, less than 0.55 nM, less than 0.5 nM, less than 0.45 nM, less than 0.4 nM, less than 0.35 nM, less than 0.3 nM, less than 0.29 nM, less than 0.28 nM, less than 0.27 nM, less than 0.26 nM, less than 0.25 nM, less than 0.24 nM, less than 0.23 nM, less than 0.22 nM, less than 0.21 nM, less than 0.2 nM, less than 0.15 nM, less than 0.1 nM, less than 0.095 nM, less than 0.09 nM, less than 0.085 nM, less than 0.08 nM, less than 0.075 nM, less than 0.07 nM, less than 0.065 nM, less than 0.06 nM, less than 0.055 nM, or less than 0.05 nM. In some embodiments, dissociation constants range from less than about 5.75 nM to less than about 0.09 nM. In some embodiments, dissociation constants of anti-TREM2 antibodies for human TREM2-Fc fusion proteins range from less than about 1.51 nM to less than about 0.35 nM. In some embodiments, dissociation constants of anti-TREM2 antibodies for human monomeric TREM2 proteins range from less than about 5.75 nM to less than about 1.15 nM. In some embodiments, dissociation constants of anti-TREM2 antibodies for mouse TREM2-Fc fusion proteins range from less than about 0.23 nM to less than about 0.09 nM. In some embodiments, dissociation constants range from less than about 6.70 nM to less than about 0.23 nM. In some embodiments, dissociation constants of anti-TREM2 antibodies for human TREM2-Fc fusion proteins range from less than about 0.71 nM to less than about 0.23 nM. In some embodiments, dissociation constants of anti-TREM2 antibodies for human monomeric TREM2 proteins range from less than about 6.70 nM to less than about 0.66 nM. In some embodiments, dissociation constants of anti-TREM2 antibodies for mouse TREM2-Fc fusion proteins range from less than about 4.90 nM to less than about 0.35 nM. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In certain embodiments, the anti-TREM2 antibody is an agonist antibody. In other embodiments, the anti-TREM2 antibody is an antagonist antibody.

Additional anti-TREM2 antibodies, e.g., antibodies that specifically bind to a TREM2 protein of the present disclosure, may be identified, screened, and/or characterized for their physical/chemical properties and/or biological activities by various assays known in the art.

Anti-DAP12 Antibodies

Certain aspects of the present disclosure related to anti-DAP12 antibodies.

Anti-DAP12 antibodies of the present disclosure generally bind to one or more DAP12 proteins expressed in a cell. In certain embodiments the DAP12 protein is expressed on a cell surface.

In some embodiments, anti-DAP12 antibodies of the present disclosure are agonist antibodies or antagonist antibodies that bind to a DAP12 protein of the present disclosure expressed on the surface of a cell and modulate (e.g., induce or inhibit) at least one DAP12 activity of the present disclosure after binding to the surface-expressed DAP12 protein. In some embodiments, anti-DAP12 antibodies of the present disclosure are inert antibodies.

In certain embodiments the DAP12 protein is expressed on a cell surface. In some embodiment anti-DAP12 antibodies of the present disclosure modulate (e.g., induce or inhibit) one or more DAP12 activities. The DAP12 activities modulated (e.g., induced or inhibited) by the anti-DAP12 antibodies may include, without limitation, binding to TREM2; DAP12 phosphorylation; TREM2 phosphorylation; recruitment of Syk, ZAP70, or both to a DAP12/TREM2 complex; PI3K activation; increased expression of anti-inflammatory mediators (e.g. cytokines); reduced expression of pro-inflammatory mediators; ERK phosphorylation; increased expression of CCR7, induction of microglial cell chemotaxis toward CCL19 and CCL21 expressing cells; enhancement, normalization, or both of the ability of bone marrow-derived dendritic cells to induce antigen-specific T-cell proliferation; induction of osteoclast production, increased rate of osteoclastogenesis, or both; increased survival and function of microglial cells and/or macrophages (such as M1 macrophages and/or microglial cells, activated M1 macrophages and/or microglial cells, and/or M2 macrophages and/or microglial cells), dendritic cells, monocytes, osteoclasts, Langerhans cells of skin, and/or Kupffer cells; induction of apoptotic neuron clearance; reduced expression of TNF-α; SYK phosphorylation; increased expression of CD83 and/or CD86 on dendritic cells, monocytes, macrophages, and/or microglia; reduced secretion of one or more inflammatory cytokines (such as TNF-α, IL-10, IL-6, and/or MCP-1); reduced expression of one or more inflammatory receptors (such as CD86); increased phagocytosis by macrophages, dendritic cells, monocytes, and/or microglia under conditions of reduced levels of MCSF; reduced phagocytosis by macrophages, dendritic cells, monocytes, and/or microglia in the presence of normal levels of MCSF; and/or increased activity of one or more TREM2-dependent genes (e.g., transcription factors of the nuclear factor of activated T-cells (NFAT) family of transcription factors). The anti-TREM2 antibodies of the present disclosure can be used to prevent, reduce risk of, or treat dementia, frontotemporal dementia, Alzheimer's disease, Nasu-Hakola disease, and multiple sclerosis. In some embodiments, the anti-TREM2 antibodies of the present disclosure are monoclonal antibodies. Anti-TREM2 antibodies of the present disclosure may be tested for inducing one or more TREM2 activities (e.g., DAP12 phosphorylation; recruitment of Syk, ZAP70, or both to DAP12; PI3K activation; increased expression of anti-inflammatory mediators; reduced expression of pro-inflammatory mediators; ERK phosphorylation; increased expression of CCR7, induction of microglial cell chemotaxis toward CCL19 and CCL21 expressing cells; enhancement, normalization, or both of the ability of bone marrow-derived dendritic cells to induce antigen-specific T-cell proliferation; induction of osteoclast production, increased rate of osteoclastogenesis, or both; induction of apoptotic neuron clearance; reduced expression of TNF-α; SYK phosphorylation; increased expression of CD83 and/or CD86 on dendritic cells; reduced secretion of one or more inflammatory cytokines; reduced expression of one or more inflammatory receptors; increased survival and/or function of dendritic cells, macrophages and/or microglial cells; increased phagocytosis by macrophages, dendritic cells, and/or microglia under conditions of reduced levels of MCSF; reduced phagocytosis by macrophages, dendritic cells, and/or microglia in the presence of normal levels of MCSF, and increased activity of one or more TREM2-dependent genes (e.g., transcription factors of the nuclear factor of activated T-cells (NFAT) family of transcription factors) using any suitable method known in the art and/or described herein. For example, the anti-TREM2 antibodies can be assayed in vitro for tyrosine phosphorylation of TREM2, DAP12 and/or ERK, by assaying for recruitment of Syk and/or ZAP70 to a Dap12/TREM2 complex, by assaying for PI3K activation, by assaying for induction of expression of anti-inflammatory mediators (e.g., IL-12p70, IL-6, and IL-10) or CCR7, or by assaying for reduced expression of pro-inflammatory mediators (e.g., IL1-3 and TNF) with TLR stimulation (e.g., LPS, CpG DNA, or Zymosan). Useful assays may include western blots (e.g., for tyrosine-phosphorylated DAP12 or threonine/serine-phosphorylated PI3K-kinase substrates), ELISA (e.g., for secreted interleukin or cytokine secretion), FACS (e.g., for anti-TREM2 binding to TREM2), immunocytochemistry (e.g., for e.g., for tyrosine-phosphorylated DAP12 or threonine/serine-phosphorylated PI3K-kinase substrates), reporter-gene assays (e.g., for TLR activation), increased survival and/or function of microglial cells, dendritic cells, monocytes, and/or macrophages, increased phagocytosis of apoptotic neurons, damaged synapses, A beta, and/or other cellular debris by macrophages, dendritic cells, osteoclasts, and/or microglial cells, increased cytoskeleton reorganization, and decreased microglial pro-inflammatory responses, or other assays known in the art.

Certain aspects of the present disclosure provide anti-DAP12 antibodies that bind to a human DAP12, or a homolog thereof, including without limitation a mammalian DAP12 protein, mouse DAP12 protein (Uniprot Accession No. Q99NH8), rat DAP12 protein (Uniprot Accession No. D3ZZ89), Rhesus monkey DAP12 protein (Uniprot Accession No. F6QVF2), bovine DAP12 protein (Uniprot Accession No. Q05B59), equine DAP12 protein (Uniprot Accession No. F7D6L0), pig DAP12 protein (Uniprot Accession No. H2EZZ3), and dog DAP12 protein (Uniprot Accession No. E2RP46); and induce at least one DAP12 activity. In some embodiments, the at least one DAP12 activity is DAP12 phosphorylation, TREM2 phosphorylation, PI3K activation, increased expression of one or more anti-inflammatory mediators, and/or reduced expression of one or more pro-inflammatory mediators.

In some embodiments, anti-DAP12 antibodies of the present disclosure bind to a DAP12 protein of the present disclosure and/or naturally occurring variants. In certain preferred embodiments, the anti-DAP12 antibodies bind to human DAP12.

In some embodiments, anti-DAP12 antibodies of the present disclosure bind to a DAP12 protein of the present disclosure expressed on the surface of a cell and induce at least one DAP12 activity of the present disclosure after binding to the surface expressed DAP12 protein.

In certain embodiments, anti-DAP12 antibodies of the present disclosure bind to one or more amino acids within amino acid residues 22-40 of human DAP12 (SEQ ID NO: 2), or within amino acid residues on a DAP12 protein corresponding to amino acid residues 22-40 of SEQ ID NO: 2.

The dissociation constants ($K_D$) of anti-DAP12 antibodies for human DAP12 and mouse DAP12 may be less than 10 nM, less than 9.5 nM, less than 9 nM, less than 8.5 nM, less than 8 nM, less than 7.5 nM, less than 7 nM, less than 6.5 nM, less than 6 nM, less than 5.9 nM, less than 5.8 nM, less than 5.75 nM, less than 5.7 nM, less than 5.6 nM, less than 5.5 nM, less than 5.4 nM, less than 5.3 nM, less than 5.2 nM, less than 5.1 nM, less than 5 nM, less than 4.5 nM, less than 4 nM, less than 3.5 nM, less than 3 nM, less than 2.5 nM, less than 2 nM, less than 1.5 nM, less than 1 nM, less than 0.95 nM, less than 0.9 nM, less than 0.85 nM, less than 0.8 nM, less than 0.75 nM, less than 0.7 nM, less than 0.65 nM, less than 0.6 nM, less than 0.55 nM, less than 0.5 nM, less than 0.45 nM, less than 0.4 nM, less than 0.35 nM, less than 0.3 nM, less than 0.25 nM, less than 0.2 nM, less than 0.15 nM, less than 0.1 nM, less than 0.095 nM, less than 0.09 nM, less than 0.085 nM, less than 0.08 nM, less than 0.075 nM, less than 0.07 nM, less than 0.065 nM, less than 0.06 nM, less than 0.055 nM, or less than 0.05 nM. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses.

Additional anti-DAP12 antibodies, e.g., antibodies that specifically bind to a DAP12 protein of the present disclosure, may be identified, screened, and/or characterized for their physical/chemical properties and/or biological activities by various assays known in the art.

Bispecific Antibodies

Certain aspects of the present disclosure relate to bispecific antibodies that bind to both TREM2 and DAP12 proteins of the present disclosure. Methods of generating bispecific antibodies are well known in the art and described herein. In some embodiments, bispecific antibodies of the present disclosure bind to one or more amino acid residues of human TREM2 (SEQ ID NO: 1), or amino acid residues on a TREM2 protein corresponding to amino acid residues of SEQ ID NO: 1. In other embodiments, bispecific antibodies of the present disclosure also bind to one or more amino acid residues of human DAP12 (SEQ ID NO: 2), or amino acid residues on a DAP12 protein corresponding to amino acid residues of SEQ ID NO: 2.

In some embodiments, bispecific antibodies of the present disclosure recognize a first antigen and a second antigen. In some embodiments, the first antigen is human TREM2 or a naturally occurring variant thereof, or human DAP12 or a naturally occurring variant thereof. In some embodiments, the second antigen is a disease-causing protein selected from amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides. In some embodiments, the second antigen is a blood brain barrier targeting protein selected from trasnferin receptor, insulin receptor, insulin like growth factor receptor, LRP-1, and LRP1; or ligands and/or proteins expressed on immune cells, wherein the ligands and/or proteins selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine. Alternatively, the second antigen may be, without limitation, a protein expressed on one or more tumor cells.

Antibody Fragments

Certain aspects of the present disclosure relate to antibody fragments that bind to one or more human proteins selected from human TREM2, a naturally occurring variant of human TREM2, a disease variant of human TREM2, human DAP12, and naturally occurring variant of human DAP12. In some embodiments, the antibody fragment is an Fab, Fab', Fab'-SH, F(ab')2, Fv or scFv fragment. In some embodiments, the antibody fragment is used in combination with one or more antibodies that specifically bind a disease-causing protein selected from: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, proline-arginine (PR) repeat peptides, and any combination thereof, and/or one or more antibodies that specifically bind a cancer-associated protein selected from: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, phosphatidylserine, and any combination thereof.

Antibody Frameworks

Any of the antibodies described herein further include a framework. In some embodiments, the framework is a human immunoglobulin framework. For example, in some embodiments, an antibody (e.g., an anti-TREM2 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In some embodiments, an antibody comprises a heavy chain variable region comprising an HVR-H1, an HVR-H2, and an HVR-H3 of the present disclosure and one, two, three or four of the heavy chain framework regions as shown in FIG. 2B and/or FIG. 20A. In some embodiments, an antibody comprises a light chain variable region comprising an HVR-L1, an HVR-L2, and an HVR-L3 of the present disclosure and one, two, three or four of the light chain framework regions as shown in FIG. 2C and/or FIG. 20B. In some embodiments, an antibody comprises a heavy chain variable region comprising an HVR-H1, an HVR-H2, and an HVR-H3 of the present disclosure and one, two, three or four of the heavy chain framework regions as shown in FIG. 2B and/or FIG. 20A and further comprises a light chain variable region comprising an HVR-L1, an HVR-L2, and an HVR-L3 of the present disclosure and one, two, three or four of the light chain framework regions as shown in FIG. 2C and/or FIG. 20B.

TREM2 and/or DAP12 Binding and Phosphorylation

In some embodiments, the anti-TREM2 and/or anti-DAP12 antibodies of the present disclosure may induce binding of TREM2 to DAP12 and/or DAP12 binding to TREM2. In other embodiments, the anti-TREM2 and/or anti-DAP12 antibodies of the present disclosure may induce TREM2 phosphorylation after binding to a TREM2 and/or DAP12 protein expressed in a cell. In other embodiments, the anti-TREM2 and/or anti-DAP12 antibodies of the present disclosure may induce DAP12 phosphorylation after binding to a TREM2 and/or DAP12 protein expressed in a cell. In other embodiments, TREM2-mediated TREM2 and/or DAP12 phosphorylation is induced by one or more SRC family tyrosine kinases. Examples of Src family tyrosine kinases include, without limitation, Src, Yes, Fyn, Fgr, Lck, Hck, Blk, Lyn, and Frk.

DAP12 is variously referred to as TYRO protein tyrosine kinase-binding protein, TYROBP, KARAP, and PLOSL. DAP12 is a transmembrane signaling protein that contains an immunoreceptor tyrosine-based activation motif (ITAM) in its cytoplasmic domain. In certain embodiments, the anti-TREM2 and/or anti-DAP12 antibody may induce DAP12 phosphorylation in its ITAM motif. Any method known in the art for determining protein phosphorylation, such as DAP12 phosphorylation, may be used.

In some embodiments, DAP12 is phosphorylated by SRC family kinases, resulting in the recruitment and activation of the Syk kinase, ZAP70 kinase, or both, to DAP12. Thus, in certain embodiments, the anti-TREM2 and/or anti-DAP12 antibodies of the present disclosure may recruit Syk, ZAP70, or both to a DAP12/TREM2 complex.

Without wishing to be bound by theory, it is believed that anti-TREM2 and/or anti-DAP12 antibodies of the present disclosure are useful for preventing, lowering the risk of, or treating conditions and/or diseases associated with decreased levels of DAP12 activity, DAP12 phosphorylation, or recruitment of Syk, ZAP70, or both to a DAP12/TREM2 complex, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

PI3K Activation

In some embodiments, the anti-TREM2 and/or anti-DAP12 antibodies of the present disclosure may induce PI3K activation after binding to a TREM2 and/or DAP12 protein expressed in a cell.

PI3Ks are a family of related intracellular signal transducer kinases capable of phosphorylating the 3-position hydroxyl group of the inositol ring of phosphatidylinositol (PtdIns). The PI3K family is divided into three different classes (Class I, Class II, and Class III) based on primary structure, regulation, and in vitro lipid substrate specificity.

Activated PI3K produces various 3-phosphorylated phosphoinositides, including without limitation, PtdIns3P, PtdIns(3,4)P2, PtdIns(3,5)P2, and PtdIns(3,4,5)P3. These 3-phosphorylated phosphoinositides function in a mechanism by which signaling proteins are recruited to various cellular membranes. These signaling proteins contain phosphoinositide-binding domains, including without limitation, PX domains, pleckstrin homology domains (PH domains), and FYVE domains. Any method known in the art for determining PI3K activation may be used.

Without wishing to be bound by theory, it is believed that anti-TREM2 and/or anti-DAP12 antibodies of the present disclosure are beneficial for preventing, lowering the risk of, or treating conditions and/or diseases associated with decreased levels of PI3K activity, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Increased Expression of Anti-Inflammatory Mediators

In some embodiments, the anti-TREM2 and/or anti-DAP12 antibodies of the present disclosure have an anti-inflammatory activity in the brain after binding to a TREM2 and/or DAP12 protein expressed on a cell surface. It has recently been reported that TREM2 has an anti-inflammatory role in the brain. In certain embodiments, the anti-TREM2 and/or anti-DAP12 antibodies of the present disclosure increase the expression of anti-inflammatory mediators (e.g., cytokines) and/or reduce the expression of pro-inflammatory mediators after binding to a TREM2 and/or DAP12 protein expressed in a cell.

Inflammation is part of a complex biological response of vascular tissues to harmful stimuli, such as pathogens, damaged cells, and irritants. The classical signs of acute inflammation are pain, heat, redness, swelling, and loss of function. Inflammation is a protective attempt by an organism to remove the injurious stimuli and to initiate the healing process. Inflammation can be classified as either acute inflammation or chronic inflammation. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Chronic inflammation is prolonged inflammation that leads to a progressive shift in the type of cells present at the site of inflammation and is characterized by simultaneous destruction and healing of the tissue from the inflammatory process.

As used herein, anti-inflammatory mediators are proteins involved either directly or indirectly (e.g., by way of an anti-inflammatory signaling pathway) in a mechanism that reduces, inhibits, or inactivates an inflammatory response. Any method known in the art for identifying and characterizing anti-inflammatory mediators may be used. Examples of anti-inflammatory mediators include, without limitation, cytokines, such as IL-12p70, IL-6, and IL-10.

In some embodiments, the anti-TREM2 and/or anti-DAP12 antibodies of the present disclosure may increase expression of anti-inflammatory mediators, such as IL-12p70, IL-6, and IL-10. In certain embodiments, increased expression of the anti-inflammatory mediators occurs in macrophages, dendritic cells, and/or microglial cells. Increased expression may include, without limitation, in increase in gene expression, an increase in transcriptional expression, or an increase in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, an anti-inflammatory mediator may have increased expression if its expression in one or more cells of a subject treated with an anti-TREM2 and/or anti-DAP12 antibody of the present disclosure is greater than the expression of the same anti-inflammatory mediator expressed in one or more cells of a corresponding subject that is not treated with the anti-TREM2 and/or anti-DAP12 antibody. In some embodiments, an anti-TREM2 and/or anti-DAP12 antibody of the present disclosure may increase anti-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to anti-inflammatory mediator expression in one or more cells of a corresponding subject that is not treated with the anti-TREM2 and/or anti-DAP12 antibody. In other embodiments, an anti-TREM2 and/or anti-DAP12 antibody of the present disclosure increases anti-inflammatory mediator expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to anti-inflammatory mediator expression in one or more cells of a corresponding subject that is not treated with the anti-TREM2 and/or anti-DAP12 antibody.

Without wishing to be bound by theory, it is believed that, in some embodiments, anti-TREM2 and/or anti-DAP12 antibodies of the present disclosure are useful for preventing, lowering the risk of, or treating conditions and/or diseases associated with decreased levels of one or more anti-inflammatory mediators, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Reduced Expression of Pro-Inflammatory Mediators

In some embodiments, the anti-TREM2 and/or anti-DAP12 antibodies of the present disclosure may decrease the expression of pro-inflammatory mediators after binding to a TREM2 and/or DAP12 protein expressed in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used. Examples of pro-inflammatory mediators include, without limitation, cytokines, such as IIFN-a4, IFN-b, IL-1β, TNF-α, IL-10, IL-6, IL-12 p70, IL-8, CRP, TNF, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP.

In some embodiments, the anti-TREM2 and/or anti-DAP12 antibodies of the present disclosure may decrease functional expression and/or secretion of pro-inflammatory mediators, such as IFN-a4, IFN-b, IL-6, IL-12 p70, IL-1β and TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP. In certain embodiments, decreased expression of the pro-inflammatory mediators occurs in macrophages, dendritic cells, monocytes, osteoclasts, Langerhans cells of skin, Kupffer cells, and/or microglial cells. Decreased expression may include, without limitation, a decrease in gene expression, a decrease in transcriptional expression, or a decrease in protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, the anti-TREM2 and/or anti-DAP12 antibodies of the present disclosure may reduce secretion of one or more inflammatory cytokines. Examples of inflammatory cytokines whose secretion may be reduced by the anti-TREM2 and/or anti-DAP12 antibodies of the present disclosure include, without limitation, TNF-α, IL-10, IL-6, MCP-1, IFN-a4, IFN-b, IL-1β. IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18.

In certain embodiments, pro-inflammatory mediators include inflammatory receptors. Accordingly, in certain embodiments, the anti-TREM2 and/or anti-DAP12 antibodies of the present disclosure may reduce expression of one or more inflammatory receptors. Examples of inflammatory receptors whose expression may be reduced by the anti-TREM2 and/or anti-DAP12 antibodies of the present disclosure include, without limitation, CD86.

As used herein, a pro-inflammatory mediator may have decreased expression if its expression in one or more cells of a subject treated with an agonist anti-TREM2 and/or anti-DAP12 antibody of the present disclosure is less than the expression of the same pro-inflammatory mediator expressed in one or more cells of a corresponding subject that is not treated with the agonist anti-TREM2 and/or anti-DAP12 antibody. In some embodiments, the agonist anti-TREM2 and/or anti-DAP12 antibody of the present disclosure may decrease pro-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the agonist anti-TREM2 and/or anti-DAP12 antibody. In other embodiments, the agonist anti-TREM2 and/or anti-DAP12 antibody may decrease pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-TREM2 and/or anti-DAP12 antibody.

Without wishing to be bound by theory, it is believed that some anti-TREM2 and/or anti-DAP12 antibodies of the present disclosure may be useful for preventing, lowering the risk of, or treating conditions and/or diseases associated with increased levels of one or more pro-inflammatory mediators, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

ERK Phosphorylation

In some embodiments, the anti-TREM2 and/or anti-DAP12 antibodies of the present disclosure may induce extracellular signal-regulated kinase (ERK) phosphorylation after binding to a TREM2 and/or DAP12 protein expressed in a cell.

Extracellular-signal-regulated kinases (ERKs) are widely expressed protein kinase intracellular signaling kinases that are involved in, for example, the regulation of meiosis, mitosis, and postmitotic functions in differentiated cells. Various stimuli, such as growth factors, cytokines, virus infection, ligands for heterotrimeric G protein-coupled receptors, transforming agents, and carcinogens, activate ERK pathways. Phosphorylation of ERKs leads to the activation of their kinase activity.

Without wishing to be bound by theory, it is believed that anti-TREM2 and/or anti-DAP12 antibodies of the present disclosure are beneficial for preventing, lowering the risk of, or treating conditions and/or diseases associated with decreased levels of ERK phosphorylation, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Increased Expression of C—C Chemokine Receptor 7

In some embodiments, the anti-TREM2 and/or anti-DAP12 antibodies of the present disclosure may increase expression of C—C chemokine receptor 7 (CCR7) after binding to a TREM2 and/or DAP12 protein expressed in a cell. Increased expression may include, without limitation, in increase in gene expression, an increase in transcriptional expression, or an increase in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

C—C chemokine receptor 7 (CCR7) is a member of the G protein-coupled receptor family. CCR7 is expressed in various lymphoid tissues and can activate B-cells and T-cells. In some embodiments, CCR7 may modulate the migration of memory T-cells to secondary lymphoid organs, such as lymph nodes. In other embodiments, CCR7 may stimulate dendritic cell maturation. CCR7 is a receptor protein that can bind the chemokine (C—C motif) ligands CCL19/ELC and CCL21.

As used herein, CCR7 may have increased expression if its expression in one or more cells of a subject treated with an anti-TREM2 and/or anti-DAP12 antibody of the present disclosure is greater than the expression of CCR7 expressed in one or more cells of a corresponding subject that is not treated with the anti-TREM2 and/or anti-DAP12 antibody. In some embodiments, an anti-TREM2 and/or anti-DAP12 antibody of the present disclosure may increase CCR7 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to CCR7 expression in one or more cells of a corresponding subject that is not treated with the anti-TREM2 and/or anti-DAP12 antibody. In other embodiments, an anti-TREM2 and/or anti-DAP12 antibody of the present disclosure increases CCR7 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to CCR7 expression in one or more cells of a corresponding subject that is not treated with the anti-TREM2 and/or anti-DAP12 antibody.

In some embodiments, increased expression of CCR7 occurs in macrophages, dendritic cells, and/or microglial cells. Increased expression of CCR7 may induce microglial cell chemotaxis toward cells expressing the chemokines CCL19 and CCL21. Accordingly, in certain embodiments, anti-TREM2 and/or anti-DAP12 antibodies of the present disclosure may induce microglial cell chemotaxis toward CCL19 and CCL21 expressing cells.

Without wishing to be bound by theory, it is believed that, in some embodiments, anti-TREM2 and/or anti-DAP12 antibodies of the present disclosure are useful for preventing, lowering the risk of, or treating conditions and/or diseases associated with decreased levels of CCR7, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Enhancement or Normalization of the Ability of Bone Marrow-Derived Dendritic Cells to Induce Antigen-Specific T-Cell Proliferation In some embodiments, the anti-TREM2 and/or anti-DAP12 antibodies of the present disclosure may enhance and/or normalize the ability of bone marrow-derived dendritic cells to induce antigen-specific T-cell proliferation after binding to a TREM2 and/or DAP12 protein expressed in a cell.

In some embodiments, agonist anti-TREM2 and/or anti-DAP12 antibodies of the present disclosure may enhance and/or normalize the ability of bone marrow-derived dendritic cells to induce antigen-specific T-cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to induce antigen-specific T-cell proliferation in one or more bone marrow-derived dendritic cells of a corresponding subject that is not treated with the agonist anti-TREM2 and/or anti-DAP12 antibody. In other embodiments, the agonist anti-TREM2 and/or anti-DAP12 antibody may enhance and/or normalize the ability of bone marrow-derived dendritic cells to induce antigen-specific T-cell proliferation in one or more bone marrow-derived dendritic cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T-cell proliferation in one or more bone marrow-derived dendritic cells of a corresponding subject that is not treated with the agonist anti-TREM2 and/or anti-DAP12 antibody.

Without wishing to be bound by theory, it is believed that anti-TREM2 and/or anti-DAP12 antibodies of the present disclosure are beneficial for preventing, lowering the risk of, or treating conditions and/or diseases associated with an increased or disregulated ability of bone marrow-derived dendritic cells to induce antigen-specific T-cell proliferation, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Osteoclast Production

In some embodiments, the anti-TREM2 and/or anti-DAP12 antibodies of the present disclosure may induce osteoclast production and/or increase the rate of osteoclastogenesis after binding to a TREM2 and/or DAP12 protein expressed in a cell.

As used herein, an osteoclast is a type of bone cell that can remove bone tissue by removing its mineralized matrix and breaking up the organic bone (e.g., bone resorption). Osteoclasts can be formed by the fusion of cells of the monocyte-macrophage cell line. In some embodiments, osteoclasts may be characterized by high expression of tartrate resistant acid phosphatase (TRAP) and cathepsin K.

As used herein, the rate of osteoclastogenesis may be increased if the rate of osteoclastogenesis in a subject treated with an agonist anti-TREM2 and/or anti-DAP12 antibody of the present disclosure is greater than the rate of osteoclastogenesis in a corresponding subject that is not treated with the agonist anti-TREM2 and/or anti-DAP12 antibody. In some embodiments, an agonist anti-TREM2 and/or anti-DAP12 antibody of the present disclosure may increase the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the agonist anti-TREM2 and/or anti-DAP12 antibody. In other embodiments, an agonist anti-TREM2 and/or anti-DAP12 antibody of the present disclosure may increase the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the agonist anti-TREM2 and/or anti-DAP12 antibody.

As used herein, the rate of osteoclastogenesis may be decreased if the rate of osteoclastogenesis in a subject treated with an antagonist anti-TREM2 antibody and/or anti-DAP12 antibody of the present disclosure is smaller than the rate of osteoclastogenesis in a corresponding subject that is not treated with the antagonist anti-TREM2 antibody and/or anti-DAP12 antibody. In some embodiments, an antagonist anti-TREM2 antibody and/or anti-DAP12 antibody of the present disclosure may decrease the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the antagonist anti-TREM2 antibody and/or anti-DAP12 antibody. In other embodiments, an antagonist anti-TREM2 antibody and/or anti-DAP12 antibody of the present disclosure may decrease the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the antagonist anti-TREM2 antibody and/or anti-DAP12 antibody.

Without wishing to be bound by theory, it is believed that anti-TREM2 and/or anti-DAP12 antibodies of the present disclosure are beneficial for preventing, lowering the risk of, or treating conditions and/or diseases associated with a reduction in osteoclast production and/or the rate of osteoclastogenesis, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis; or associated with abnormal bone formation and maintenance including osteoporosis, which is associated with pathological decrease in bone density and osteoporotic diseases which are associated with pathological increase in bone density.

Proliferation and Survival of Macrophages, Microglial Cells, Dendritic Cells Monocytes, Osteoclasts, Langerhans Cells of Skin, and Kupffer Cells In some embodiments, the anti-TREM2 and/or anti-DAP12 antibodies of the present disclosure may increase the proliferation, survival, and/or function of macrophages, microglial cells (microglia), dendritic cells monocytes, osteoclasts, Langerhans cells of skin, and Kupffer cells after binding to TREM2 and/or DAP12 protein expressed in a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most infections from reaching the vulnerable nervous tissue. In the case where infectious agents are directly introduced to the brain or cross the blood-brain barrier, microglial cells must react quickly to decrease inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T-cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial 1 cells.

In some embodiments, anti-TREM2 and/or anti-DAP12 antibodies of the present disclosure may increase the expression of CD83 and/or CD86 on dendritic cells monocytes, and/or macrophages.

As used herein, the rate of proliferation, survival, and/or function of macrophages microglia, monocytes, and/or dendritic cells may include increased expression if the rate of proliferation, survival, and/or function of macrophages, microglia, dendritic cells monocytes, osteoclasts, Langerhans cells of skin, and/or Kupffer cells in a subject treated with an anti-TREM2 and/or anti-DAP12 antibody of the present disclosure is greater than the rate of proliferation, survival, and/or function of macrophages, microglia, dendritic cells monocytes, osteoclasts, Langerhans cells of skin, and/or Kupffer cells in a corresponding subject that is not treated with the anti-TREM2 and/or anti-DAP12 antibody. In some embodiments, an anti-TREM2 and/or anti-DAP12 antibody of the present disclosure may increase the rate of proliferation, survival, and/or function of macrophages, microglia, dendritic cells monocytes, osteoclasts, Langerhans cells of skin, and/or Kupffer cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of macrophages, microglia, dendritic cells monocytes, osteoclasts, Langerhans cells of skin, and/or Kupffer cells in a corresponding subject that is not treated with the anti-TREM2 and/or anti-DAP12 antibody. In other embodiments, an anti-TREM2 and/or anti-DAP12 antibody of the present disclosure may increase the rate of proliferation, survival, and/or function of macrophages, microglia, dendritic cells monocytes, osteoclasts, Langerhans cells of skin, and/or Kupffer cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of macrophages, microglia, dendritic cells monocytes, osteoclasts, Langerhans cells of skin, and/or Kupffer cells in a corresponding subject that is not treated with the anti-TREM2 and/or anti-DAP12 antibody.

Without wishing to be bound by theory, it is believed that anti-TREM2 and/or anti-DAP12 antibodies of the present disclosure are beneficial for preventing, lowering the risk of, or treating conditions and/or diseases associated with a reduction in proliferation, survival, and/or function of macrophages, microglia, dendritic cells monocytes, osteoclasts, Langerhans cells of skin, and/or Kupffer cells, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Clearance and Phagocytosis

In some embodiments, the anti-TREM2 and/or anti-DAP12 antibodies of the present disclosure may induce clearance and/or phagocytosis after binding to a TREM2 and/or DAP12 protein expressed in a cell of one or more of apoptotic neurons, nerve tissue debris of the nervous system, non-nerve tissue debris of the nervous system, bacteria, other foreign bodies, disease-causing proteins, disease-causing peptides, and/or disease-causing nucleic acids. In certain embodiments, disease-causing protein include, without limitation, amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides. In certain embodiments, disease-causing nucleic acids include, without limitation, antisense GGCCCC (G2C4) repeat-expansion RNA.

In some embodiments, the anti-TREM2 and/or anti-DAP12 antibodies of the present disclosure may induce of one or more types of clearance, including without limitation, apoptotic neuron clearance, nerve tissue debris clearance, non-nerve tissue debris clearance, bacteria or other foreign body clearance, disease-causing protein clearance, disease-causing peptide clearance, disease-causing nucleic acid clearance, and tumor cell clearance.

In some embodiments, the anti-TREM2 and/or anti-DAP12 antibodies of the present disclosure may induce phagocytosis of one or more of apoptotic neurons, nerve tissue debris, non-nerve tissue debris, bacteria, other foreign bodies, disease-causing proteins, disease-causing peptides, disease-causing nucleic acid, and/or tumor cells.

In some embodiments, the anti-TREM2 and/or anti-DAP12 antibodies of the present disclosure may increase phagocytosis by macrophages, dendritic cells, monocytes, and/or microglia under conditions of reduced levels of macrophage colony-stimulating factor (MCSF). Alternatively, in some embodiments, the anti-TREM2 and/or anti-DAP12 antibodies of the present disclosure may decrease phagocytosis by macrophages, dendritic cells, monocytes, and/or microglia in the presence of normal levels of macrophage colony-stimulating factor (MCSF).

Without wishing to be bound by theory, it is believed that anti-TREM2 and/or anti-DAP12 antibodies of the present disclosure are beneficial for preventing, lowering the risk of, or treating conditions and/or diseases associated with apoptotic neurons, nerve tissue debris of the nervous system, non-nerve tissue debris of the nervous system, bacteria, other foreign bodies, or disease-causing proteins, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Syk Phosphorylation

In some embodiments, the anti-TREM2 and/or anti-DAP12 antibodies of the present disclosure may induce spleen tyrosine kinase (Syk) phosphorylation after binding to a TREM2 and/or DAP12 protein expressed in a cell.

Spleen tyrosine kinase (Syk) is an intracellular signaling molecule that functions downstream of TREM2 by phosphorylating several substrates, thereby facilitating the formation of a signaling complex leading to cellular activation and inflammatory processes.

Without wishing to be bound by theory, it is believed that anti-TREM2 and/or anti-DAP12 antibodies of the present disclosure are beneficial for preventing, lowering the risk of, or treating conditions and/or diseases associated with decreased levels of Syk phosphorylation, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

TREM2-Dependent Gene Expression

In some embodiments, agonist anti-TREM2 and/or anti-DAP12 antibodies of the present disclosure may increase the activity and/or expression of TREM2-dependent genes, such as one or more transcription factors of the nuclear factor of activated T-cells (NFAT) family of transcription factors. Alternatively, antagonistic anti-TREM2 and/or anti-DAP12 antibodies of the present disclosure may inhibit the activity and/or expression of TREM2-dependent genes, such as one or more transcription factors of the NFAT family of transcription factors.

Without wishing to be bound by theory, it is believed that agonist anti-TREM2 and/or anti-DAP12 antibodies of the present disclosure are beneficial for preventing, lowering the risk of, or treating conditions and/or diseases associated with decreased levels of TREM2-dependent genes, including dementia, frontotemporal dementia, Alzheimer's disease, Nasu-Hakola disease, Parkinson's disease, Amyotrophic lateral sclerosis, Huntington's disease, Taupathy disease, and/or multiple sclerosis.

Antibody Preparation

Anti-TREM2 and/or anti-DAP12 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')2), bispecific and polyspecific antibodies, multivalent antibodies, library derived antibodies, antibodies having modified effector functions, fusion proteins containing an antibody portion, and any other modified configuration of the immunoglobulin molecule that includes an antigen recognition site, such as an epitope having amino acid residues of a TREM2 and/or DAP12 protein of the present disclosure, including glycosylation variants of antibodies, amino acid sequence variants of antibodies, and covalently modified antibodies. The anti-TREM2 and/or anti-DAP12 antibodies may be human, murine, rat, or of any other origin (including chimeric or humanized antibodies).

(1) Polyclonal Antibodies

Polyclonal antibodies, such as anti-TREM2 and/or anti-DAP12 polyclonal antibodies, are generally raised in animals by multiple subcutaneous (sc) or intraperitoneal (ip) injections of the relevant antigen and an adjuvant. It may be useful to conjugate the relevant antigen (e.g., a purified or recombinant TREM2 and/or DAP12 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies, such as anti-TREM2 and/or anti-DAP12 monoclonal antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the anti-TREM2 and/or anti-DAP12 monoclonal antibodies may be made using the hybridoma method first described by Köhler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant TREM2 and/or DAP12 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant TREM2 and/or DAP12 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a TREM2 and/or DAP12 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a TREM2 and/or DAP12 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-TREM2 and/or anti-DAP12 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host-cells such as *E. coli* cells, simian COS cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., *Curr. Opin. Immunol.*, 5:256-262 (1993) and Plickthun, *Immunol. Rev.* 130:151-188 (1992).

In certain embodiments, anti-TREM2 and/or anti-DAP12 antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222: 581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a TREM2 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-TREM2 and/or anti-DAP12 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-TREM2 and/or anti-DAP12 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-TREM2 and/or anti-DAP12 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')2 or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human anti-TREM2 and/or anti-DAP12 antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332:323-327 (1988); Verhoeyen et al., Science 239: 1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et al., Proc. Nat'l Acad. Sci. USA 89:4285 (1992); Presta et al., J. Immunol. 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., TREM2 proteins of the present disclosure), is achieved. In general, the CDR residues are directly and most substantially involved in influencing antigen binding.

Various forms of the humanized anti-TREM2 and/or anti-DAP12 antibody are contemplated. For example, the humanized anti-TREM2 and/or anti-DAP12 antibody may be an antibody fragment, such as an Fab, which is optionally conjugated with one or more TREM2 ligand, such as HSP60. Alternatively, the humanized anti-TREM2 and/or anti-DAP12 antibody may be an intact antibody, such as an intact IgG1 antibody.

(4) Human Antibodies

Alternatively, human anti-TREM2 and/or anti-DAP12 antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Nat'l Acad. Sci. USA, 90:2551 (1993); Jakobovits et al., Nature, 362:255-258 (1993); Bruggermann et al., Year in Immunol., 7:33 (1993); U.S. Pat. No. 5,591,669 and WO 97/17852.

Alternatively, phage display technology can be used to produce human anti-TREM2 and/or anti-DAP12 antibodies and antibody fragments in vitro, from immunoglobulin variable (V) domain gene repertoires from unimmunized donors. McCafferty et al., Nature 348:552-553 (1990); Hoogenboom and Winter, J. Mol. Biol. 227: 381 (1991). According to this technique, antibody V domain genes are cloned in-frame into either a maj or or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., EMBO J. 12:725-734 (1993). See also U.S. Pat. Nos. 5,565,332 and 5,573,905. Additionally, yeast display technology can be used to produce human anti-TREM2 and/or anti-DAP12 antibodies and antibody fragments in vitro (e.g., WO 2009/036379; WO 2010/105256; WO 2012/009568; US 2009/0181855; US 2010/0056386; and Feldhaus and Siegel (2004) J. Immunological Methods 290:69-80). In other embodiments, ribosome display technology can be used to produce human anti-TREM2 and/or anti-DAP12 antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Plickthun (2004) J. Immunological Methods 290:51-67).

The techniques of Cole et al., and Boerner et al., are also available for the preparation of human anti-TREM2 and/or anti-DAP12 monoclonal antibodies (Cole et al., *Monoclonal Antibodies and Cancer Therapy*, Alan R. Liss, p. 77 (1985) and Boerner et al., *J. Immunol.* 147(1): 86-95 (1991). Similarly, human anti-TREM2 and/or anti-DAP12 antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human anti-TREM2 and/or anti-DAP12 antibodies may also be generated in vitro by activated B-cells (see U.S. Pat. Nos. 5,567,610 and 5,229,275).

(5) Antibody Fragments

In certain embodiments there are advantages to using anti-TREM2 and/or anti-DAP12 antibody fragments, rather than whole anti-TREM2 and/or anti-DAP12 antibodies. In some embodiments, smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., Science 229:81 (1985)). However, these fragments can now be produced directly by recombinant host-cells, for example, using nucleic acids encoding anti-TREM2 and/or anti-DAP12 antibodies of the present disclosure. Fab, Fv and scFv antibody fragments can all be expressed in and secreted from *E. coli*, thus allowing the straightforward production of large amounts of these fragments. Anti-TREM2 and/or anti-DAP12 antibody fragments can also be isolated from the antibody phage libraries as discussed above. Alternatively, Fab'-SH fragments can be directly recovered from *E. coli* and chemically coupled to form F(ab')2 fragments (Carter et al., *Bio/Technology* 10:163-167 (1992)). According to another approach, F(ab')2 fragments can be isolated directly from recombinant host-cell culture. Production of Fab and F(ab')2 antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-TREM2 and/or anti-DAP12 antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more TREM2 proteins of the present disclosure). Alternatively, one part of a BsAb can be armed to bind to the target TREM2 and/or DAP12 antigen, and another can be combined with an arm that binds to a second protein. Such antibodies can be derived from full-length antibodies or antibody fragments (e.g., F(ab')2 bispecific antibodies).

Methods for making bispecific antibodies are known in the art. Traditional production of full-length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986); and Garber, *Nature Reviews Drug Discovery* 13, 799-801 (2014).

According to another approach described in WO 96/27011 or U.S. Pat. No. 5,731,168, the interface between a pair of antibody molecules can be engineered to maximize the percentage of heterodimers which are recovered from recombinant-cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175: 217-225 (1992) describes the production of fully humanized bispecific antibody F(ab')2 molecules. Each Fab' fragment was separately secreted from E. coli and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Nat'l Acad. Sci. USA, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., J. Immunol., 152:5368 (1994).

Another method to generate bispecific antibodies is controlled Fab-arm exchange (cFAE), which is an easy-to-use method to generate bispecific IgG1 (bsIgG1). The protocol involves the following: (i) separate expression of two parental IgG1s containing single matching point mutations in the $C_H3$ domain; (ii) mixing of parental IgG1s under permissive redox conditions in vitro to enable recombination of half-molecules; (iii) removal of the reductant to allow reoxidation of interchain disulfide bonds; and (iv) analysis of exchange efficiency and final product using chromatography-based or mass spectrometry (MS)-based methods. The protocol generates bsAbs with regular IgG architecture, characteristics and quality attributes both at bench scale (micrograms to milligrams) and at a mini-bioreactor scale (milligrams to grams) that is designed to model large-scale manufacturing (kilograms). Starting from good-quality purified proteins, exchange efficiencies of >95% can be obtained within 2-3 days (including quality control). See Labrijn et al., Nature Protocols 9, 2450-2463 (2014); and Garber, Nature Reviews Drug Discovery 13, 799-801 (2014).

Antibodies with more than two valencies are also contemplated. For example, trispecific antibodies can be prepared. Tutt et al., J. Immunol. 147:60 (1991).

Exemplary bispecific antibodies may bind to two different epitopes on a given molecule (e.g., a TREM2 and/or DAP12 protein of the present disclosure). In some embodiments a bispecific antibody binds to a first antigen, such as a TREM2 or DAP12 protein of the present disclosure, and a second antigen facilitating transport across the blood-brain barrier. Numerous antigens are known in the art that facilitate transport across the blood-brain barrier (see, e.g., Gabathuler R., Approaches to transport therapeutic drugs across the blood-brain barrier to treat brain diseases, Neurobiol. Dis. 37 (2010) 48-57). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, second antigens for an anti-TREM2 antibody may include, without limitation, a DAP12 antigen of the present disclosure. In other embodiments, second antigens for an anti-DAP12 antibody may include, without limitation, a TREM2 antigen of the present disclosure. In other embodiments, bispecific antibodies that bind to both TREM2 and DAP12 may facilitate and enhance one or more TREM2 and/or DAP12 activities. In other embodiments, second antigens for an TREM2 and/or DAP12 antibody may include, without limitation, A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR).

(7) Multivalent Antibodies

A multivalent antibody may be internalized (and/or catabolized) faster than a bivalent antibody by a cell expressing an antigen to which the antibodies bind. The anti-TREM2 and/or anti-DAP12 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multiivalent antibodies may recognize a TREM2 angigen as well as without limitation additional antigens A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-ariginine (GR), proline-alanine (PA), or proline-arginine (PR), Isnulin receptor, insulin like growth factor receptor. Transferrin receptor or any other antigen that facilitate antibody transfer across the blood brain barrier.

(8) Effector Function Engineering

It may also be desirable to modify an anti-TREM2 and/or anti-DAP12 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII (e.g., to reduce antibody-dependent cell-mediated cytotoxicity. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000). In some embodiments, it may also be desirable to modify an anti-TREM2 and/or anti-DAP12 antibody of the present disclosure to modify effector function to increase selectivity toward the ITIM-containing FcgRIIb (CD32b) to increase clustering of antibodies on adjacent cells without activating humoral responses including antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(9) Other Amino Acid Sequence Modifications

Amino acid sequence modifications of anti-TREM2 and/or anti-DAP12 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a TREM2 and/or DAP12 protein of the present disclosure). The amino acid changes also may alter post-translational processes of the antibody, such as changing the number or position of glycosylation sites.

A useful method for identification of certain residues or regions of the anti-TREM2 and/or anti-DAP12 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-TREM2 and/or anti-DAP12 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a TREM2 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-TREM2 and/or anti-DAP12 antibodies of the present disclosure) or antibody fragments.

(10) Other Antibody Modifications

Anti-TREM2 and/or anti-DAP12 antibodies of the present disclosure, or antibody fragments thereof, can be further modified to contain additional non-proteinaceous moieties that are known in the art and readily available, or to contain different types of drug conjugates that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and *Science* (2000).

Drug conjugtation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

Binding Assays and Other Assays

Anti-TREM2 and/or anti-DAP12 antibodies of the present disclosure (e.g., antibody activity of anti-TREM2 antibodies) may be identified, screened for, and/or characterized for their physical/chemical properties and/or biological activities by various assays known in the art or assays described in the Examples herein, such as, for example, radiolabeled immunoassays, optical assays, protein binding assays, biochemical screening assays, immunoassays, fluorescence assays, and/or cell survival assays.

In some embodiments, anti-TREM2 and/or anti-DAP12 antibodies of the present disclosure may be tested for antigen binding activity, e.g., by known methods such as ELISA, Western blot, etc.

In some embodiments, competition assays may be used to identify an antibody that competes with any of the antibodies listed in Table 1and/or Table 8, selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, and Ab87, and/or human and/or humanized MAB17291 for binding to TREM2. In certain embodiments, such a competing antibody binds to the same epitope (e.g., a linear or a conformational epitope) that is bound by any of the antibodies listed in Table 1and/or Table 8, selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87, and/or human and/or humanized MAB17291. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TREM2 or cells expressing TREM2 on cell surface are incubated in a solution comprising a first labeled antibody that binds to TREM2 (e.g., human or non-human primate) and a second unlabeled antibody that is being tested for its ability to compete with the first antibody for binding to TREM2. The second antibody may be present in a hybridoma supernatant. As a control, immobilized TREM2 or cells expressing TREM2 is incubated in a solution comprising the first labeled antibody but not the second unlabeled antibody. After incubation under conditions permissive for binding of the first antibody to TREM2, excess unbound antibody is removed, and the amount of label associated with immobilized TREM2 or cells expressing TREM2 is measured. If the amount of label associated with immobilized TREM2 or cells expressing TREM2 is substantially reduced in the test sample relative to the control sample, then that indicates that the second antibody is competing with the first antibody for binding to TREM2. See Harlow and Lane (1988) *Antibodies: A Laboratory Manual* ch. 14 (Cold Spring Harbor Laboratory, Cold Spring Harbor, N.Y.).

In some embodiments, assays are provided for identifying agonist anti-TRME2 and/or anti-DAP12 antibodies of the present disclosure having biological activity. Biological activity may include, e.g., inducing, promoting, stimulating, or otherwise increasing one more activities of TREM2 and/or DAP12. Agonist anti-TRME2 and/or anti-DAP12 antibodie antibodies having such biological activity in vivo and/or in vitro are also provided.

Assays known in the art and described herein (see, e.g., Examples 23-27, 33-38, 41-44, 52-55, and 67-68) can be used for identifying and testing biological activities of anti-TRME2 and/or anti-DAP12 antibodies that induce, promote, stimulate, or otherwise increase one more activities of TREM2 and/or DAP12. In some embodiments, assays for testing one or more activities of an agonist anti-TRME2 and/or anti-DAP12 antibody are provided. An exemplary test for biological activity may include, e.g., treating a population of immune cells, such as an innate immune cells expressing TREM2 and/or DAP12 with an agonist anti-TRME2 and/or anti-DAP12 antibody candidate for sufficient time to allow binding to, and activation of, the TREM2 and/or DAP12 protein, and measuring cell survival (or cell death) as compared to cell survival (or cell death) in a corresponding population in the absence of the antibody candidate. Methods for measuring cell survival or cell death are well known in the art and described herein. Agonist anti-TRME2 and/or anti-DAP12 antibodies may be identified by their ability to promote or prolong cell survival or delay cell death in a cell population relative to a control cell population, e.g., a cell population that was not treated with the agonist antibody candidate. Certain aspects of the present disclosure provide methods for identifying a candidate agonist antibody that specifically binds to TREM2 and/or DAP12. In certain embodiments, the method for identifying a candidate agonist antibody that specifically binds to TREM2 and/or DAP12 comprises a. contacting an innate immune cell population expressing TREM2 and/or DAP12 on its surface with a candidate agonist antibody that specifically binds to the TREM2 and/or DAP12 for a period of time sufficient for the candidate agonist antibody to promote cell survival in the innate immune cell population; and b. comparing cell survival of the contacted innate immune cell population contacted cell with cell survival from a corresponding innate immune cell population not contacted with the candidate agonist antibody that specifically binds to the TREM2 and/or DAP12, wherein increased cell survival from the contacted innate immune cell population indicates that the candidate antibody is an agonist. Other aspects of the present disclosure provide an isolated antibody that specifically binds to TREM2 and/or DAP12 identified by any of the disclosed methods for identifying an antibody that specifically binds to TREM2 and/or DAP12.

Nucleic Acids, Vectors, and Host Cells

Anti-TREM2 and/or anti-DAP12 antibodies of the present disclosure may be produced using recombinant methods and compositions, e.g., as described in U.S. Pat. No. 4,816,567. In some embodiments, isolated nucleic acids having a nucleotide sequence encoding any of the anti-TREM2 and/or anti-DAP12 antibodies of the present disclosure are provided. Such nucleic acids may encode an amino acid sequence containing the VL and/or an amino acid sequence containing the VH of the anti-TREM2 and/or anti-DAP12 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell is an isolated host cell. As used herein, an "isolated cell" is a a cell that is identified and separated from at least one contaminant cell with which it is ordinarily associated in the environment in which it was produced. In some embodiments, the isolated cell is free of association with all components associated with the production environment. The isolated cell is in a form other than in the form or setting in which it is found in nature. Isolated cells are distinguished from cells existing naturally in tissues, organs, or individuals. In some embodiments, the isolated cell is a host cell of the present disclosure. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-TREM2 and/or anti-DAP12 antibody of the present disclosure are provided. In some embodiments, the method includes culturing a host cell of the present disclosure containing a nucleic acid encoding the anti-TREM2 and/or anti-DAP12 antibody, under conditions suitable for expression of the antibody. In some embodiments, the antibody is subsequently recovered from the host cell (or host cell culture medium).

For recombinant production of an anti-TREM2 and/or anti-DAP12 antibody of the present disclosure, a nucleic acid encoding the anti-TREM2 and/or anti-DAP12 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-TREM2 and/or anti-DAP12 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-TREM2 and/or anti-DAP12 antibody of the present disclosure.

Suitable host cells for cloning or expression of antibody-encoding vectors include prokaryotic or eukaryotic cells. For example, anti-TREM2 and/or anti-DAP12 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789, 199, and 5,840,523; and Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compositions

Anti-TREM2 and/or anti-DAP12 antibodies of the present disclosure can be incorporated into a variety of formulations for therapeutic administration by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-TREM2 and/or anti-DAP12 antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions that may be employed include, without limitation, organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-TREM2 and/or anti-DAP12 antibody of the present disclosure may be administered to an individual in need of treatment with the anti-TREM2 and/or anti-DAP12 antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-TREM2 and/or anti-DAP12 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-TREM2 and/or anti-DAP12 antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-TREM2 and/or anti-DAP12 antibody administered, can vary over time independently of the dose used.

Dosages for a particular anti-TREM2 and/or anti-DAP12 antibody may be determined empirically in individuals who have been given one or more administrations of the anti-TREM2 and/or anti-DAP12 antibody. Individuals are given incremental doses of an anti-TREM2 and/or anti-DAP12 antibody. To assess efficacy of an anti-TREM2 and/or anti-DAP12 antibody, a clinical symptom of ay of the diseases, disorders, or conditions of the present disclosure (e.g., dementia, frontotemporal dementia, Alzheimer's disease, Nasu-Hakola disease, and multiple sclerosis) can be monitored.

Administration of an anti-TREM2 and/or anti-DAP12 antibody of the present disclosure can be continuous or intermittent, depending, for example, on the recipient's physiological condition, whether the purpose of the administration is therapeutic or prophylactic, and other factors known to skilled practitioners. The administration of an anti-TREM2 and/or anti-DAP12 antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

Further aspects of the present disclosure provide methods for modulating (e.g., activating or inhibiting) TREM2, modulating (e.g., activating or inhibiting) DAP12, modulating (e.g., activating or inhibiting) PI3K, modulating (e.g., increasing or reducing) expression of one or more anti-inflammatory mediators (e.g., IL-12p70, IL-6, and IL-10), or modulating (e.g., increasing or reducing) expression of one or more pro-inflammatory mediators (e.g., L-1β and TNF) in an individual in need thereof, by administering to the individual a therapeutically effective amount of an anti-TREM2 and/or anti-DAP12 antibody of the present disclosure to modulate (e.g., induce or inhibit) one or more TREM2 and/or DAP12 activities in the individual.

As disclosed herein, anti-TREM2 and/or anti-DAP12 antibodies of the present disclosure may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and/or, cancer (e.g., bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer). In some embodiments, the anti-TREM2 and/or anti-DAP12 antibodies are agonist antibodies. In some embodiments, the anti-TREM2 and/or anti-DAP12 antibodies are inert antibodies. In some embodiments, the anti-TREM2 and/or anti-DAP12 antibodies are antagonist antibodies.

In some embodiments, the present disclosure provides methods of preventing, reducing risk, or treating an individual having dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, by administering to the individual a therapeutically effective amount of an anti-TREM2 and/or anti-DAP12 antibody of the present disclosure to modulate (e.g., induce or inhibit) one or more TREM2 activities, including without limitation, DAP12 phosphorylation, PI3K activation, expression of one or more anti-inflammatory mediators (e.g., IL-12p70, IL-6, and IL-10), or expression of one or more pro-inflammatory mediators (e.g., L-1β and TNF). In some embodiments, the anti-TREM2 and/or anti-DAP12 antibody is an agonist antibody. In some embodiments, the anti-TREM2 and/or anti-DAP12 antibody is an inert antibody. In some embodiments, the anti-TREM2 and/or anti-DAP12 antibody is an antagonist antibody. In certain embodiments, the individual has a heterozygous TREM2 variant allele having an glutamic acid to stop codon substitution in the nucleic acid sequence encoding amino acid residue 14 of the human TREM2 protein (SEQ ID NO: 1). In certain embodiments, the individual has a heterozygous TREM2 variant allele having a glutamine to stop codon substitution in the nucleic acid sequence encoding amino acid residue 33 of the human TREM2 protein (SEQ ID NO: 1). In certain embodiments, the individual has a heterozygous TREM2 variant allele having a tryptophan to stop codon substitution in the nucleic acid sequence encoding amino acid residue 44 of the human TREM2 protein (SEQ ID NO: 1). In certain embodiments, the individual has a heterozygous TREM2 variant allele having an arginine to histidine amino acid substitution at amino acid residue 47 of the human TREM2 protein (SEQ ID NO: 1). In certain embodiments, the individual has a heterozygous TREM2 variant allele having a tryptophan to stop codon substitution in the nucleic acid sequence encoding amino acid residue 78 of the human TREM2 protein (SEQ ID NO: 1). In certain embodiments, the individual has a heterozygous TREM2 variant allele having a valine to glycine amino acid substitution at an amino acid corresponding to amino acid residue 126 of the human TREM2 protein (SEQ ID NO: 1). In certain embodiments, the individual has a heterozygous TREM2 variant allele having an aspartic acid to glycine amino acid substitution at an amino acid corresponding to amino acid residue 134 of the human TREM2 protein (SEQ ID NO: 1). In certain embodiments, the individual has a heterozygous TREM2 variant allele having a lysine to asparagine amino acid substitution at an amino acid corresponding to amino acid residue 186 of the human TREM2 protein (SEQ ID NO: 1).

In some embodiments, the individual has a heterozygous TREM2 variant allele having a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; a threonine to methionine amino acid substitution at an amino acid corresponding to amino acid residue Thr66 of SEQ ID NO: 1; and/or a serine to cysteine amino acid substitution at an amino acid corresponding to amino acid residue Ser116 of SEQ ID NO: 1.

In some embodiments, the individual has a heterozygous DAP12 variant allele having a methionine to threonine substitution at an amino acid corresponding to amino acid residue Met1 of SEQ ID NO: 2, a glycine to arginine amino acid substitution at an amino acid corresponding to amino acid residue Gly49 of SEQ ID NO: 2, a deletion within exons 1-4 of the nucleic acid sequence encoding SEQ ID NO: 2, an insertion of 14 amino acid residues at exon 3 of the nucleic acid sequence encoding SEQ ID NO: 2, and/or a guanine nucleotide deletion at a nucleotide corresponding to nucleotide residue G141 of the nucleic acid sequence encoding SEQ ID NO: 2.

As disclosed herein, anti-TREM2 and/or anti-DAP12 antibodies of the present disclosure may also be used for inducing and/or promoting innate immune cell survival. In some embodiments, the present disclosure provides methods of inducing or promoting innate immune cell survival in an individual in need thereof, by administering to the individual a therapeutically effective amount of an agonist anti-TREM2 and/or anti-DAP12 antibody of the present disclosure.

As disclosed herein, anti-TREM2 and/or anti-DAP12 antibodies of the present disclosure may also be used for inducing and/or promoting wound healing, such as after injury. In some embodiments, the wound healing may be colonic wound repair following injury. In some embodiments, the present disclosure provides methods of inducing or promoting wound healing in an individual in need thereof, by administering to the individual a therapeutically effective amount of an agonist anti-TREM2 and/or anti-DAP12 antibody of the present disclosure.

As disclosed herein, anti-TREM2 and/or anti-DAP12 antibodies of the present disclosure may also be used for inhibiting innate immune cell survival. In some embodiments, the present disclosure provides methods of i inhibiting innate immune cell survival in an individual in need thereof, by administering to the individual a therapeutically effective amount of an antagonist anti-TREM2 and/or anti-DAP12 antibody of the present disclosure.

In some embodiments, the methods of the present disclosure may involve the coadministration of anti-TREM2 and/or anti-DAP12 antibodies, or bispecific antibodies that bind to both TREM2 and DAP12, with TLR antagonists or with agents neutralizing TLR agonist (e.g., neutralizing cytokine or interleukin antibodies).

In some embodiments, the methods of the present disclosure may involve the administration of chimeric constructs, including an anti-TREM2 and/or anti-DAP12 antibody of the present disclosure in conjunction with a TREM2 ligand, such as HSP60.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Without wishing to be bound by theory, it is believed that administering an anti-TREM2 and/or anti-DAP12 antibody of the present disclosure can prevent, reduce the risk, and/or treat dementia. In some embodiments, administering an anti-TREM2 and/or anti-DAP12 antibody may induce one or more TREM2 and/or DAP12 activities in an individual having dementia (e.g., DAP12 phosphorylation, PI3K activation, increased expression of one or more anti-inflammatory mediators, or reduced expression of one or more pro-inflammatory mediators).

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the progranulin gene.

Without wishing to be bound by theory, it is believed that administering an anti-TREM2 and/or anti-DAP12 antibody of the present disclosure can prevent, reduce the risk, and/or treat FTD. In some embodiments, administering an anti-TREM2 and/or anti-DAP12 antibody may induce one or more TREM2 and/or DAP12 activities in an individual having FTD (e.g., DAP12 phosphorylation, PI3K activation, increased expression of one or more anti-inflammatory mediators, or reduced expression of one or more pro-inflammatory mediators).

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

Without wishing to be bound by theory, it is believed that administering an anti-TREM2 and/or anti-DAP12 antibody of the present disclosure can prevent, reduce the risk, and/or treat Alzheimer's disease. In some embodiments, administering an anti-TREM2 and/or anti-DAP12 antibody may induce one or more TREM2 and/or DAP12 activities in an individual having Alzheimer's disease (e.g., DAP12 phosphorylation, PI3K activation, increased expression of one or more anti-inflammatory mediators, or reduced expression of one or more pro-inflammatory mediators).

Nasu-Hakola Disease

Nasu-Hakola disease (NHD), which may alternatively be referred to as polycystic lipomembranous osteodysplasia with sclerosing leukoencephalopathy (PLOSL), is a rare inherited leukodystrophy characterized by progressive presenile dementia associated with recurrent bone fractures due to polycystic osseous lesions of the lower and upper extremities. NHD disease course is generally divided into four stages: latent, osseous, early neurologic, and late neurologic. After a normal development during childhood (latent stage), NHD starts manifesting during adolescence or young adulthood (typical age of onset 20-30 years) with pain in the hands, wrists, ankles, and feet. Patients then start suffering from recurrent bone fractures due to polycystic osseous and osteoporotic lesions in the limb bones (osseous stage). During the third or fourth decade of life (early neurologic stage), patients present with pronounced personality changes (e.g., euphoria, lack of concentration, loss of judgment, and social inhibitions) characteristic of a frontal lobe syndrome. Patients also typically suffer from progressive memory disturbances. Epileptic seizures are also frequently observed. Finally (late neurologic stage), patients progress to a profound dementia, are unable to speak and move, and usually die by the age of 50.

Without wishing to be bound by theory, it is believed that administering an anti-TREM2 and/or anti-DAP12 antibody of the present disclosure can prevent, reduce the risk, and/or treat Nasu-Hakola disease (NHD). In some embodiments, administering an anti-TREM2 and/or anti-DAP12 antibody may induce one or more TREM2 and/or DAP12 activities in an individual having NHD (e.g., DAP12 phosphorylation, PI3K activation, increased expression of one or more anti-inflammatory mediators, or reduced expression of one or more pro-inflammatory mediators).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

Without wishing to be bound by theory, it is believed that administering an anti-TREM2 antibody of the present disclosure can prevent, reduce the risk, and/or treat Parkinson's disease. In some embodiments, administering an anti-TREM2 and/or anti-DAP12 antibody may induce one or more TREM2 and/or DAP12 activities in an individual having Parkinson's disease (e.g., DAP12 phosphorylation, PI3K activation, increased expression of one or more anti-inflammatory mediators, or reduced expression of one or more pro-inflammatory mediators).

Amyotrophic Lateral Sclerosis

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that progranulin play a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

Without wishing to be bound by theory, it is believed that administering an anti-TREM2 antibody of the present disclosure can prevent, reduce the risk, and/or treat ALS. In some embodiments, administering an anti-TREM2 and/or anti-DAP12 antibody may induce one or more TREM2 and/or DAP12 activities in an individual having ALS (e.g., DAP12 phosphorylation, PI3K activation, increased expression of one or more anti-inflammatory mediators, or reduced expression of one or more pro-inflammatory mediators).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

Without wishing to be bound by theory, it is believed that administering an anti-TREM2 antibody of the present disclosure can prevent, reduce the risk, and/or treat Huntington's disease (HD). In some embodiments, administering an anti-TREM2 and/or anti-DAP12 antibody may induce one or more TREM2 and/or DAP12 activities in an individual having HD (e.g., DAP12 phosphorylation, PI3K activation, increased expression of one or more anti-inflammatory mediators, or reduced expression of one or more pro-inflammatory mediators).

Taupathy Disease

Taupathy diseases, or Tauopathies, are a class of neurodegenerative disease caused by aggregation of the microtubule-associated protein tau within the brain. Alzheimer's disease (AD) is the most well-known Taupathy disease, and involves an accumulation of tau protein within neurons in the form of insoluble neurofibrillary tangles (NFTs). Other Taupathy diseases and disorders include progressive supranuclear palsy, dementia pugilistica (chromic traumatic encephalopathy), Frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, frontotemporal dementia, and frontotemporal lobar degeneration.

Without wishing to be bound by theory, it is believed that administering an anti-TREM2 antibody of the present disclosure can prevent, reduce the risk, and/or treat Taupathy disease. In some embodiments, administering an anti-TREM2 and/or anti-DAP12 antibody may induce one or more TREM2 and/or DAP12 activities in an individual having Taupathy disease (e.g., DAP12 phosphorylation, PI3K activation, increased expression of one or more anti-inflammatory mediators, or reduced expression of one or more pro-inflammatory mediators).

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

Without wishing to be bound by theory, it is believed that administering an anti-TREM2 and/or anti-DAP12 antibody of the present disclosure can prevent, reduce the risk, and/or treat multiple sclerosis. In some embodiments, administering an anti-TREM2 and/or anti-DAP12 antibody may induce one or more TREM2 and/or DAP12 activities in an individual having multiple sclerosis (e.g., DAP12 phosphorylation, PI3K activation, increased expression of one or more anti-inflammatory mediators, and reduced expression of one or more pro-inflammatory mediators).

Cancer

Yet further aspects of the present disclosure provide methods for preventing, reducing risk, or treating an individual having cancer, comprising administering to the individual a therapeutically effective amount of an isolated anti-TREM2 and/or anti-DAP12 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure.

As described above, the tumor microenvironment is known to contain a heterogeneous immune infiltrate, which includes T lymphocytes, macrophages and cells of myeloid/granulocytic lineage. In particular, the presence of M2-macrophages in tumors is associated with poor prognosis. Therapies that reduce the number of these cells in the tumor, such as CSF1R blocking agents, are showing beneficial effects in preclinical models and early stage clinical studies. It has been shown that TREM2 synergizes with CSF1 to promote survival of macrophages in vitro, and that this effect is particularly prominent in M2-type macrophages, compared to other types of phagocytic cells. A seminal preclinical study has also shown synergies between drugs that target tumor-associated macrophages (e.g., CSF1/CSF1R blocking antibodies) and checkpoint blocking antibodies that target T cells, indicating that manipulating both cell types shows efficacy in tumor models where individual therapies are poorly effective (Zhu Y; Cancer Res. 2014 Sep. 15; 74(18): 5057-69). Therefore, without wishing to be bound by theory, it is thought that blocking TREM2 signaling in tumor associated macrophages may inhibit suppression of the immune response in the tumor microenvironment, resulting in a therapeutic anti-tumor immune response.

Due to the synergies between TREM2 and CSF1, and between targeting tumor-associated macrophages and targeting T cells, in some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with an antagonist anti-TREM2 and/or anti-DAP12 antibody of the present disclosure.

In some embodiments, a cancer to be prevented or treated by the methods of the present disclosure includes, but is not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-TREM2 and/or anti-DAP12 antibodies of the present disclosure may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of an anti-TREM2 and/or anti-DAP12 antibody of the present disclosure.

In some embodiments, the method further includes administering to the individual at least one antibody that specifically binds to an inhibitory checkpoint molecule, and/or another standard or investigational anti-cancer therapy. In some embodiments, the at least one antibody that specifically binds to an inhibitory checkpoint molecule is administered in combination with the isolated antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and an anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the isolated antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with the isolated antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the isolated antibody. In some embodiments, the at least one stimulatory cytokine is selected from TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, CRP, IFN-α, IFN-β, IL-2, IL-18, GM-CSF, G-CSF, and any combination thereof.

Kits/Articles of Manufacture

The present disclosure also provides kits containing an isolated antibody of the present disclosure (e.g., an anti-TREM2 or anti-DAP12 antibody described herein), or a functional fragment thereof. Kits of the present disclosure may include one or more containers comprising a purified antibody of the present disclosure. In some embodiments, the kits further include instructions for use in accordance with the methods of this disclosure. In some embodiments, these instructions comprise a description of administration of the isolated antibody of the present disclosure (e.g., an anti-TREM2 or anti-DAP12 antibody described herein) to prevent, reduce risk, or treat an individual having a disease, disorder, or injury selected from dementia, frontotemporal dementia, Alzheimer's disease, Nasu-Hakola disease, and multiple sclerosis, according to any methods of this disclosure.

In some embodiments, the instructions comprise a description of how to detect TREM2 and/or DAP12, for example in an individual, in a tissue sample, or in a cell. The kit may further comprise a description of selecting an individual suitable for treatment based on identifying whether that individual has the disease and the stage of the disease.

In some embodiments, the kits may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory check point protein) and/or at least one stimulatory cytokine. In some embodiments, the kits may further include instructions for using the antibody and/or stimulatory cytokine in combination with an isolated antibody of the present disclosure (e.g., an anti-TREM2 antagonist antibody described herein), instructions for using the isolated antibody of the present disclosure in combination with an antibody and/or stimulatory cytokine, or instructions for using an isolated antibody of the present disclosure and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an isolated antibody of the present disclosure (e.g., an anti-TREM2 or anti-DAP12 antibody described herein). The container may further comprise a second pharmaceutically active agent.

Kits may optionally provide additional components such as buffers and interpretive information. Normally, the kit comprises a container and a label or package insert(s) on or associated with the container.

Diagnostic Uses

The isolated antibodies of the present disclosure (e.g., an anti-TREM2 or anti-DAP12 antibody described herein) also have diagnostic utility. This disclosure therefore provides for methods of using the antibodies of this disclosure, or functional fragments thereof, for diagnostic purposes, such as the detection of TREM2 and/or DAP12 in an individual or in tissue samples derived from an individual.

In some embodiments, the individual is a human. In some embodiments, the individual is a human patient suffering from, or at risk for developing dementia, frontotemporal dementia, Alzheimer's disease, Nasu-Hakola disease, Parkinson's disease, Amyotrophic lateral sclerosis, Huntington's disease, Taupathy disease, multiple sclerosis, or cancer. In some embodiments, the diagnostic methods involve detecting TREM2 and/or DAP12 in a biological sample, such as a biopsy specimen, a tissue, or a cell. An isolated antibody of the present disclosure (e.g., an anti-TREM2 or anti-DAP12 antibody described herein) is contacted with the biological sample and antigen-bound antibody is detected. For example, a tissue sample (e.g., a biopsy specimen) may be stained with an anti-TREM2 or anti-DAP12 antibody described herein in order to detect and/or quantify disease-associated macrophages (e.g., M2-type macrophages). The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-TREM2 or anti-DAP12 antibody described herein) may be used to detect and/or quantify, for example, microglia in a brain specimen taken from a preclinical disease model (e.g., a non-human disease model). As such, an isolated antibody of the present disclosure (e.g., an anti-TREM2 or anti-DAP12 antibody described herein) may be useful in evaluating therapeutic response after treatment in a model for a nervous system disease or injury such as dementia, frontotemporal dementia, Alzheimer's disease, Nasu-Hakola disease, or multiple sclerosis, as compared to a control.

Enumerated Embodiments

The following enumerated embodiments are representative of some aspects of the invention.

1. An isolated agonist antibody that binds to a TREM2 protein, a DAP12 protein, or both, wherein the antibody induces one or more TREM2 activities, DAP12 activities, or both.
2. The isolated antibody of embodiment 1, wherein the TREM2 protein, the DAP12 protein, or both is a mammalian protein or a human protein.
3. The isolated antibody of embodiment 2, wherein the TREM2 protein, the DAP12 protein, or both is a wild-type protein.
4. The isolated antibody of embodiment 2, wherein the TREM2 protein, the DAP12 protein, or both is a naturally occurring variant.
5. The isolated antibody of any one of embodiments 1-4, wherein the one or more TREM2 activities comprise TREM2 binding to DAP12.
6. The isolated antibody of any one of embodiments 1-4, wherein the one or more DAP12 activities comprise DAP12 binding to TREM2.
7. The isolated antibody of any one of embodiments 1-6, wherein the one or more TREM2 activities, DAP12 activities, or both comprise DAP12 phosphorylation.
8. The isolated antibody of embodiment 7, wherein DAP12 phosphorylation is induced by one or more SRC family tyrosine kinases.
9. The isolated antibody of any one of embodiments 1-8, wherein the one or more TREM2 activities, DAP12 activities, or both comprise PI3K activation.
10. The isolated antibody of any one of embodiments 1-9, wherein the one or more TREM2 activities, DAP12 activities, or both comprise increased expression of one or more anti-inflammatory mediators selected from the group consisting of IL-12p70, IL-6, and IL-10.

11. The isolated antibody of embodiment 10, wherein the increased expression of the one or more anti-inflammatory mediators occurs in one or more cells selected from the group consisting of macrophages, dendritic cells, and microglial cells.

12. The isolated antibody of any one of embodiments 1-11, wherein the one or more TREM2 activities, DAP12 activities, or both comprise reduced expression of one or more pro-inflammatory mediators selected from the group consisting of IFN-a4, IFN-b, IL-6, IL-12 p70, IL-1β and TNF.

13. The isolated antibody of embodiment 12, wherein the reduced expression of the one or more pro-inflammatory mediators occurs in one or more cells selected from the group consisting of macrophages, dendritic cells, and microglial cells.

14. The isolated antibody of any one of embodiments 1-13, wherein the one or more TREM2 activities, DAP12 activities, or both comprise extracellular signal-regulated kinase (ERK) phosphorylation.

15. The isolated antibody of any one of embodiments 1-14, wherein the one or more TREM2 activities, DAP12 activities, or both comprise increased expression of C—C chemokine receptor 7 (CCR7).

16. The isolated antibody of any one of embodiments 1-15, wherein the one or more TREM2 activities, DAP12 activities, or both comprise induction of microglial cell chemotaxis toward CCL19 and CCL21 expressing cells.

17. The isolated antibody of any one of embodiments 1-16, wherein the one or more TREM2 activities, DAP12 activities, or both comprise a reduction, normalization, or both of the ability of bone marrow-derived dendritic cells to induce antigen-specific T-cell proliferation.

18. The isolated antibody of any one of embodiments 1-17, wherein the one or more TREM2 activities, DAP12 activities, or both comprise induction of osteoclast production, increased rate of osteoclastogenesis, or both.

19. The isolated antibody of any one of embodiments 1-18, wherein the one or more TREM2 activities, DAP12 activities, or both comprise of increasing the survival of macrophages, microglial cells, or both.

20. The isolated antibody of any one of embodiments 1-19, wherein the one or more TREM2 activities, DAP12 activities, or both comprise increasing the function of macrophages, microglial cells, or both.

21. The isolated antibody of any one of any one of embodiments 1-20, wherein the one or more TREM2 activities, DAP12 activities, or both comprise induction of one or more types of clearance without inflammation selected from the group consisting of apoptotic neuron clearance without inflammation, nerve tissue debris clearance without inflammation, non-nerve tissue debris clearance without inflammation, bacteria or other foreign body clearance without inflammation, and disease-causing protein clearance without inflammation.

22. The isolated antibody of any one of embodiments 1-21, wherein the one or more TREM2 activities, DAP12 activities, or both comprise induction of phagocytosis without inflammation of one or more of apoptotic neurons, nerve tissue debris, non-nerve tissue debris, bacteria, other foreign bodies, or disease-causing proteins without inflammation.

23. The isolated antibody of embodiment 21 or embodiment 22, wherein the disease-causing protein is selected from the group consisting of A beta peptide, alpha synuclain protein, Tau protein, TDP-43 protein, prion protein, and huntingtin protein.

24. The isolated antibody of any one of embodiments 1-23, wherein the one or more TREM2 activities, DAP12 activities, or both comprise normalization of disrupted TREM2/DAP12-dependent gene expression.

25. The isolated antibody of any one of embodiments 1-24, wherein the one or more TREM2 activities, DAP12 activities, or both comprise recruitment of Syk, ZAP70, or both to DAP12.

26. The isolated antibody of any one of embodiments 1-25, wherein the isolated agonist antibody that binds to a TREM2 protein binds to one or more amino acids within amino acid residues selected from the group consisting of:
 i. amino acid residues 29-112 of SEQ ID NO: 1, or amino acid residues on a TREM2 protein corresponding to amino acid residues 29-112 of SEQ ID NO: 1;
 ii. amino acid residues 29-41 of SEQ ID NO: 1, or amino acid residues on a TREM2 protein corresponding to amino acid residues 29-41 of SEQ ID NO: 1;
 iii. amino acid residues 40-44 of SEQ ID NO: 1, or amino acid residues on a TREM2 protein corresponding to amino acid residues 40-44 of SEQ ID NO: 1;
 iv. amino acid residues 47-69 of SEQ ID NO: 1, or amino acid residues on a TREM2 protein corresponding to amino acid residues 47-69 of SEQ ID NO: 1;
 v. amino acid residues 67-76 of SEQ ID NO: 1, or amino acid residues on a TREM2 protein corresponding to amino acid residues 67-76 of SEQ ID NO: 1;
 vi. amino acid residues 76-86 of SEQ ID NO: 1, or amino acid residues on a TREM2 protein corresponding to amino acid residues 76-86 of SEQ ID NO: 1;
 vii. amino acid residues 91-100 of SEQ ID NO: 1, or amino acid residues on a TREM2 protein corresponding to amino acid residues 91-100 of SEQ ID NO: 1;
 viii. amino acid residues 99-115 of SEQ ID NO: 1, or amino acid residues on a TREM2 protein corresponding to amino acid residues 99-115 of SEQ ID NO: 1;
 ix. amino acid residues 104-112 of SEQ ID NO: 1, or amino acid residues on a TREM2 protein corresponding to amino acid residues 104-112 of SEQ ID NO: 1; and
 x. amino acid residues 114-118 of SEQ ID NO: 1, or amino acid residues on a TREM2 protein corresponding to amino acid residues 114-118 of SEQ ID NO: 1.

27. The isolated antibody of any one of embodiments 1-25, wherein the isolated agonist antibody that binds to a TREM2 protein binds to an epitope comprising one or more amino acid residues selected from the group consisting of:
 i. amino acid residue Arg47 or Asp87 of SEQ ID NO: 1;
 ii. amino acid residues 40-44 of SEQ ID NO: 1;
 iii. amino acid residues 67-76 of SEQ ID NO: 1; and
 iv. amino acid residues 114-118 of SEQ ID NO: 1.

28. The isolated antibody of any one of embodiments 1-25, wherein the isolated agonist antibody that binds to a DAP12 protein binds to one or more amino acids within amino acid residues 22-40 of SEQ ID NO: 2, or amino acid residues on a DAP12 protein corresponding to amino acid residues 22-40 of SEQ ID NO: 2.

29. The isolated antibody of any one of embodiments 1-25, wherein the isolated agonist antibody is a bispecific antibody that binds to one or more amino acids selected from the group consisting of:
 i. one or more amino acid residues of SEQ ID NO: 1, or amino acid residues on a TREM2 protein corresponding to amino acid residues of SEQ ID NO: 1; and
 ii. one or more amino acid residues of SEQ ID NO: 2, or amino acid residues on a DAP12 protein corresponding to amino acid residues of SEQ ID NO: 2.

30. The isolated antibody of any of the preceding embodiments, wherein the antibody is a human antibody, a humanized antibody, a bispecific antibody, a multivalent antibody, or a chimeric antibody.

31. The isolated antibody of any of the preceding embodiments, wherein the antibody is a monoclonal antibody.

32. The isolated antibody of any of the preceding embodiments, wherein the isolated antibody is an antibody fragment that binds to one or more human proteins selected from the group consisting of human TREM2, a naturally occurring variant of human TREM2, human DAP12, and naturally occurring variant of human DAP12.

33. The isolated antibody of embodiment 32, wherein the fragment is an Fab, Fab', Fab'-SH, F(ab')2, Fv or scFv fragment.

34. An isolated nucleic acid encoding the antibody of any one of the preceding embodiments.

35. A vector comprising the nucleic acid of embodiment 34.

36. A host cell comprising the vector of embodiment 35.

37. A method of producing an antibody, comprising culturing the host cells of embodiment 36 so that the antibody is produced.

38. The method of embodiment 37, further comprising recovering the antibody produced by the host cell.

39. A pharmaceutical composition comprising the antibody of any one of embodiments 1-33, and a pharmaceutically acceptable carrier.

40. A method of preventing, reducing risk, or treating an individual having a disease, disorder, or injury selected from the group consisting of dementia, frontotemporal dementia, Alzheimer's disease, Nasu-Hakola disease, and multiple sclerosis, comprising administering to the individual a therapeutically effective amount of the isolated antibody of any one of embodiments 1-33.

41. The method of embodiment 40, wherein the individual has a heterozygous variant of TREM2, wherein the variant comprises one or more substitutions selected from the group consisting of:
  i. a glutamic acid to stop codon substitution in the nucleic acid sequence encoding amino acid residue Glu14 of SEQ ID NO: 1;
  ii. a glutamine to stop codon substitution in the nucleic acid sequence encoding amino acid residue Gln33 of SEQ ID NO: 1;
  iii. a tryptophan to stop codon substitution in the nucleic acid sequence encoding amino acid residue Trp44 of SEQ ID NO: 1;
  iv. an arginine to histidine amino acid substitution at an amino acid corresponding to amino acid residue Arg47 of SEQ ID NO: 1
  v. a tryptophan to stop codon substitution in the nucleic acid sequence encoding amino acid residue Trp78 of SEQ ID NO: 1;
  vi. a valine to glycine amino acid substitution at an amino acid corresponding to amino acid residue Val126 of SEQ ID NO: 1;
  vii. an aspartic acid to glycine amino acid substitution at an amino acid corresponding to amino acid residue Asp134 of SEQ ID NO: 1; and
  viii. a lysine to asparagine amino acid substitution at an amino acid corresponding to amino acid residue Lys186 of SEQ ID NO: 1.

42. The method of embodiment 40, wherein the individual has a heterozygous variant of TREM2, wherein the variant comprises a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; or both.

43. The method of embodiment 40, wherein the individual has a heterozygous variant of DAP12, wherein the variant comprises one or more variants selected from the group consisting of:
  i. a methionine to threonine substitution at an amino acid corresponding to amino acid residue Met1 of SEQ ID NO: 2;
  ii. a glycine to arginene amino acid substitution at an amino acid corresponding to amino acid residue Gly49 of SEQ ID NO: 2;
  iii. a deletion within exons 1-4 of the nucleic acid sequence encoding SEQ ID NO: 2;
  iv. an insertion of 14 amino acid residues at exon 3 of the nucleic acid sequence encoding SEQ ID NO: 2; and
  v. a guanine nucleotide deletion at a nucleotide corresponding to nucleotide residue G141 of the nucleic acid sequence encoding SEQ ID NO: 2.

44. An isolated agonist antibody that binds to a TREM2 protein, a DAP12 protein, or both, wherein the antibody induces one or more TREM2 activities, DAP12 activities, or both.

45. The isolated antibody of embodiment 44, wherein the TREM2 protein, the DAP12 protein, or both is a mammalian protein or a human protein.

46. The isolated antibody of embodiment 45, wherein the TREM2 protein, the DAP12 protein, or both is a wild-type protein.

47. The isolated antibody of embodiment 45, wherein the TREM2 protein, the DAP12 protein, or both is a naturally occurring variant.

48. The isolated antibody of any one of embodiments 44-47, wherein the isolated antibody induces or retains TREM2 clustering, DAP12 clustering, or both on a cell surface.

49. The isolated antibody of any one of embodiments 44-48, wherein the one or more TREM2 activities comprise TREM2 binding to DAP12.

50. The isolated antibody of any one of embodiments 44-48, wherein the one or more DAP12 activities comprise DAP12 binding to TREM2.

51. The isolated antibody of any one of embodiments 44-50, wherein the one or more TREM2 activities, DAP12 activities, or both comprise DAP12 phosphorylation, TREM2 phosphorylation, or both.

52. The isolated antibody of embodiment 51, wherein DAP12 phosphorylation, TREM2 phosphorylation, or both is induced by one or more SRC family tyrosine kinases.

53. The isolated antibody of embodiment 52, wherein the one or more SRC family tyrosine kinases comprise a Syk kinase.

54. The isolated antibody of any one of embodiments 44-53, wherein the one or more TREM2 activities, DAP12 activities, or both comprise PI3K activation.

55. The isolated antibody of any one of embodiments 44-54, wherein the one or more TREM2 activities, DAP12 activities, or both comprise increased expression of one or more anti-inflammatory cytokines.

56. The isolated antibody of any one of embodiments 44-54, wherein the one or more TREM2 activities, DAP12 activities, or both comprise increased expression of one or more anti-inflammatory mediators selected from the group consisting of IL-12p70, IL-6, and IL-10.

57. The isolated antibody of embodiment 55 or embodiment 56, wherein the increased expression occurs in one or more cells selected from the group consisting of macrophages, dendritic cells, monocytes, osteoclasts, Langerhans cells of skin, Kupffer cells, and microglial cells.

58. The isolated antibody of any one of embodiments 44-57, wherein the one or more TREM2 activities, DAP12 activities, or both comprise reduced expression of one or more pro-inflammatory cytokines.

59. The isolated antibody of any one of embodiments 44-57, wherein the one or more TREM2 activities, DAP12 activities, or both comprise reduced expression of one or more pro-inflammatory mediators selected from the group consisting of IFN-a4, IFN-b, IL-6, IL-12 p70, IL-1β TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP.

60. The isolated antibody of any one of embodiments 44-58, wherein the one or more TREM2 activities, DAP12 activities, or both comprise reduced expression of TNF-α, IL-6, or both.

61. The isolated antibody of embodiment 58 or embodiment 60, wherein the reduced expression of the one or more pro-inflammatory mediators occurs in one or more cells selected from the group consisting of macrophages, dendritic cells, dendritic cells, monocytes, osteoclasts, Langerhans cells of skin, Kupffer cells, and microglial cells.

62. The isolated antibody of any one of embodiments 44-60, wherein the one or more TREM2 activities, DAP12 activities, or both comprise extracellular signal-regulated kinase (ERK) phosphorylation.

63. The isolated antibody of any one of embodiments 44-62, wherein the one or more TREM2 activities, DAP12 activities, or both comprise increased expression of C—C chemokine receptor 7 (CCR7).

64. The isolated antibody of any one of embodiments 44-63, wherein the one or more TREM2 activities, DAP12 activities, or both comprise induction of microglial cell chemotaxis toward CCL19 and CCL21 expressing cells.

65. The isolated antibody of any one of embodiments 44-64, wherein the one or more TREM2 activities, DAP12 activities, or both comprise an enhancement, normalization, or both of the ability of bone marrow-derived dendritic cells to induce antigen-specific T-cell proliferation.

66. The isolated antibody of any one of embodiments 44-65, wherein the one or more TREM2 activities, DAP12 activities, or both comprise induction of osteoclast production, increased rate of osteoclastogenesis, or both.

67. The isolated antibody of any one of embodiments 44-66, wherein the one or more TREM2 activities, DAP12 activities, or both comprise increasing the survival of macrophages, microglial cells, dendritic cells, macrophages, monocytes, osteoclasts, Langerhans cells of skin, and/or Kupffer cells.

68. The isolated antibody of any one of embodiments 44-67, wherein the one or more TREM2 activities, DAP12 activities, or both comprise increasing the function of macrophages, microglial cells, dendritic cells, macrophages, monocytes, osteoclasts, Langerhans cells of skin, and/or Kupffer cells.

69. The isolated antibody of embodiment 67 or embodiment 68, wherein the macrophages and/or microglial cells are M1 macrophages and/or microglial cells, M2 macrophages and/or microglial cells, or both.

70. The isolated antibody of embodiment 69, wherein the M1 macrophages and/or microglial cells are activated M1 macrophages and/or microglial cells.

71. The isolated antibody of any one of any one of embodiments 44-68, wherein the one or more TREM2 activities, DAP12 activities, or both comprise induction of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance.

72. The isolated antibody of any one of embodiments 44-71, wherein the one or more TREM2 activities, DAP12 activities, or both comprise induction of phagocytosis of one or more of apoptotic neurons, nerve tissue debris, non-nerve tissue debris, bacteria, other foreign bodies, disease-causing proteins, disease-causing peptides, or disease-causing nucleic acids.

73. The isolated antibody of embodiment 71 or embodiment 72, wherein the disease-causing protein is selected from the group consisting of amyloid beta, Tau, IAPP, alpha-synuclein, TDP-43, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides.

74. The isolated antibody of embodiment 71 or embodiment 72, wherein the disease-causing nucleic acid is antisense GGCCCC (G2C4) repeat-expansion RNA.

75. The isolated antibody of any one of embodiments 44-74, wherein the one or more TREM2 activities, DAP12 activities, or both comprise normalization of disrupted TREM2/DAP12-dependent gene expression.

76. The isolated antibody of any one of embodiments 44-75, wherein the one or more TREM2 activities, DAP12 activities, or both comprise recruitment of Syk, ZAP70, or both to a DAP12/TREM2 complex.

77. The isolated antibody of any one of embodiments 44-76, wherein the one or more TREM2 activities, DAP12 activities, or both comprise Syk phosphorylation.

78. The isolated antibody of any one of embodiments 44-77, wherein the one or more TREM2 activities, DAP12 activities, or both comprise increased expression of CD83 and/or CD86 on dendritic cells.

79. The isolated antibody of any one of embodiments 44-78, wherein the one or more TREM2 activities, DAP12 activities, or both comprise reduced secretion of one or more inflammatory cytokines.

80. The isolated antibody of embodiment 79, wherein the one or more inflammatory cytokines are selected from the group consisting of TNF-α, IL-10, IL-6, MCP-1, IFN-a4, IFN-b, IL-1β, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18.

81. The isolated antibody of any one of embodiments 44-79, wherein the one or more TREM2 activities, DAP12 activities, or both comprise reduced expression of one or more inflammatory receptors.

82. The isolated antibody of embodiment 81, wherein the one or more inflammatory receptors comprise CD86.

83. The isolated antibody of any one of embodiments 44-82, wherein the one or more TREM2 activities, DAP12 activities, or both comprise increasing phagocytosis by macrophages, dendritic cells, monocytes, and/or microglia under conditions of reduced levels of MCSF.

84. The isolated antibody of any one of embodiments 44-82, wherein the one or more TREM2 activities, DAP12 activities, or both comprise decreasing phagocytosis by macrophages, dendritic cells, monocytes, and/or microglia in the presence of normal levels of MCSF.

85. The isolated antibody of any one of embodiments 44-84, wherein the one or more TREM2 activities, DAP12 activities, or both comprise increasing activity of one or more TREM2-dependent genes.

86. The isolated antibody of embodiment 85, wherein the one or more TREM2-dependent genes comprise one or more nuclear factor of activated T-cells (NFAT) transcription factors.

87. The isolated antibody of any one of embodiments 44-86, wherein the antibody is of the IgG class the IgM class, or the IgA class.

88. The isolated antibody of embodiment 87, wherein the antibody is of the IgG class and has an IgG1, IgG2, IgG3, or IgG4 isotype.

89. The isolated antibody of embodiment 87, wherein the antibody has an IgG2 isotype.

90. The isolated antibody of embodiment 89, wherein the antibody comprises a human IgG2 constant region.

91. The isolated antibody of embodiment 90, wherein the human IgG2 constant region comprises an Fc region.

92. The isolated antibody of any one of embodiments 89-91, wherein the antibody induces the one or more TREM2 activities, DAP12 activities, or both independently of binding to an Fc receptor.

93. The isolated antibody of any one of embodiments 89-91, wherein the antibody binds an inhibitory Fc receptor.

94. The isolated antibody of embodiment 93, wherein the inhibitory Fc receptor is inhibitory Fc-gamma receptor IIB (FcγIIB).

95. The isolated antibody of embodiment 93 or embodiment 94, wherein the human IgG2 constant region comprises an Fc region that comprises one or more modifications.

96. The isolated antibody of embodiment 95, wherein the Fc region comprises one or more amino acid substitutions.

97. The isolated antibody of embodiment 96, wherein the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU numbering.

98. The isolated antibody of embodiment 90, wherein the human IgG2 constant region comprises a light chain constant region comprising a C214S amino acid substitution, wherein the numbering of the residues is according to EU numbering.

99. The isolated antibody of embodiment 87, wherein the antibody has an IgG1 isotype.

100. The isolated antibody of embodiment 99, wherein the antibody comprises a human IgG1 constant region.

101. The isolated antibody of embodiment 100, wherein the human IgG1 constant region comprises an Fc region.

102. The isolated antibody of any one of embodiments 99-101, wherein the antibody binds an inhibitory Fc receptor.

103. The isolated antibody of embodiment 102, wherein the inhibitory Fc receptor is inhibitory Fc-gamma receptor IIB (FcγRIIB).

104. The isolated antibody of any one of embodiments 101-103, wherein the Fc region comprises one or more modifications.

105. The isolated antibody of embodiment 104, wherein the Fc region comprises one or more amino acid substitutions.

106. The isolated antibody of embodiment 105, wherein the one or more amino acid substitutions in the Fc region are at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to EU numbering.

107. The isolated antibody of any one of embodiments 101-103, wherein the antibody comprises an IgG2 isotype heavy chain constant domain 1($C_H1$) and hinge region.

108. The isolated antibody of embodiment 107, wherein the IgG2 isotype $C_H1$ and hinge region comprise the amino acid sequence of ASTKGPSVFP LAPCSRSTSE STAAL- GCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397).

109. The isolated antibody of embodiment 107 or embodiment 108, wherein the antibody Fc region comprises a S267E amino acid substitution, a L328F amino acid substitution, or both, and/or a N297A or N297Q amino acid substitution, wherein the numbering of the residues is according to EU numbering.

110. The isolated antibody of embodiment 99, wherein the antibody comprises a mouse IgG1 constant region.

111. The isolated antibody of embodiment 87, wherein the antibody has an IgG4 isotype.

112. The isolated antibody of embodiment 111, wherein the antibody comprises a human IgG4 constant region.

113. The isolated antibody of embodiment 112, wherein the human IgG4 constant region comprises an Fc region.

114. The isolated antibody of any one of embodiments 111-113, wherein the antibody binds an inhibitory Fc receptor.

115. The isolated antibody of embodiment 114, wherein the inhibitory Fc receptor is inhibitory Fc-gamma receptor IIB (FcγIIB).

116. The isolated antibody of any one of embodiments 113-115, wherein the Fc region comprises one or more modifications.

117. The isolated antibody of embodiment 116, wherein the Fc region comprises one or more amino acid substitutions.

118. The isolated antibody of embodiment 117, wherein the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU numbering.

119. The isolated antibody of embodiment 87, wherein the antibody has a hybrid IgG2/4 isotype.

120. The isolated antibody of embodiment 119, wherein the antibody comprises an amino acid sequence comprising amino acids 118 to 260 of human IgG2 and amino acids 261 to 447 of human IgG4, wherein the numbering of the residues is according to EU numbering.

121. The isolated antibody of embodiment 111, wherein the antibody comprises a mouse IgG4 constant region.

122. The isolated antibody of any one of embodiments 1-121, wherein the isolated antibody is an antibody fragment that binds to one or more human proteins selected from the group consisting of human TREM2, a naturally occurring variant of human TREM2, human DAP12, and naturally occurring variant of human DAP12, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12.

123. The isolated antibody of embodiment 122, wherein the fragment is an Fab, Fab', Fab'-SH, F(ab')2, Fv or scFv fragment.

124. An isolated inert antibody that binds to a TREM2 protein, a DAP12 protein, or both.

125. An isolated antagonist antibody that binds to a TREM2 protein, a DAP12 protein, or both.

126. The isolated antibody of embodiment 124 or embodiment 125, wherein the TREM2 protein, the DAP12 protein, or both is a mammalian protein or a human protein.

127. The isolated antibody of embodiment 126, wherein the TREM2 protein, the DAP12 protein, or both is a wild-type protein.

128. The isolated antibody of embodiment 126, wherein the TREM2 protein, the DAP12 protein, or both is a naturally occurring variant.

129. The isolated antibody of any one of embodiments 125-128, wherein the isolated antibody inhibits one or more TREM2 activities, DAP12 activities, or both.

130. The isolated antibody of embodiment 129, wherein the one or more TREM2 activities, DAP12 activities, or both comprise decreasing activity of one or more TREM2-dependent genes.

131. The isolated antibody of embodiment 130, wherein the one or more TREM2-dependent genes comprise one or more nuclear factor of activated T-cells (NFAT) transcription factors.

132. The isolated antibody of any one of embodiments 129-131, wherein the one or more TREM2 activities, DAP12 activities, or both comprise decreasing the survival of macrophages, microglial cells, M1 macrophages, M1 microglial cells, M2 macrophages, M2 microglial cells, osteoclasts, Langerhans cells of skin, Kupffer cells, and/or dendritic cells.

133. The isolated antibody of any one of embodiments 125-132, wherein the isolated antibody inhibits interaction between TREM2 and one or more TREM2 ligands, inhibits TREM2 signal transduction, or both.

134. The isolated antibody of any one of embodiments 124-133, wherein the antibody is incapable of binding an Fc-gamma receptor (FcγR).

135. The isolated antibody of embodiment 134, wherein the antibody has an IgG1 isotype.

136. The isolated antibody of embodiment 135, wherein the antibody comprises a human IgG1 constant region.

137. The isolated antibody of embodiment 136, wherein the human IgG1 constant region comprises an Fc region.

138. The isolated antibody of embodiment 137, wherein the Fc region comprises one or more modifications.

139. The isolated antibody of embodiment 138, wherein the Fc region comprises one or more amino acid substitutions.

140. The isolated antibody of embodiment 139, wherein the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU numbering.

141. The isolated antibody of embodiment 140, wherein the Fc region further comprises an amino acid deletion at a position corresponding to glycine 236 according to EU numbering.

142. The isolated antibody of embodiment 135, wherein the antibody comprises a mouse IgG1 constant region.

143. The isolated antibody of embodiment 134, wherein the antibody has an IgG2 isotype.

144. The isolated antibody of embodiment 143, wherein the antibody comprises a human IgG2 constant region.

145. The isolated antibody of embodiment 144, wherein the human IgG2 constant region comprises an Fc region.

146. The isolated antibody of embodiment 145, wherein the Fc region comprises one or more modifications.

147. The isolated antibody of embodiment 146, wherein the Fc region comprises one or more amino acid substitutions.

148. The isolated antibody of embodiment 147, wherein the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU numbering.

149. The isolated antibody of embodiment 134, wherein the antibody has an IgG4 isotype.

150. The isolated antibody of embodiment 149, wherein the antibody comprises a human IgG4 constant region.

151. The isolated antibody of embodiment 150, wherein the human IgG4 constant region comprises an Fc region.

152. The isolated antibody of embodiment 151, wherein the Fc region comprises one or more modifications.

153. The isolated antibody of embodiment 152, wherein the Fc region comprises one or more amino acid substitutions.

154. The isolated antibody of embodiment 153, wherein the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU numbering.

155. The isolated antibody of any one of embodiments 124-154, wherein the isolated antibody is an antibody fragment that binds to one or more human proteins selected from the group consisting of human TREM2, a naturally occurring variant of human TREM2, human DAP12, and naturally occurring variant of human DAP12.

156. The isolated antibody of embodiment 155, wherein the fragment is an Fab, Fab', Fab'-SH, F(ab')2, Fv or scFv fragment.

157. The isolated antibody of embodiment 106, embodiment 140, or embodiment 141, wherein the Fc region further comprises one or more additional amino acid substitutions at a position selected from the group consisting of A330L, L234F; L235E, P331S, and any combination thereof, wherein the numbering of the residues is according to EU numbering.

158. The isolated antibody of any one of embodiments 95-157, wherein the Fc region further comprises one or more additional amino acid substitutions at a position selected from the group consisting of M252Y, S254T, T256E, and any combination thereof, wherein the numbering of the residues is according to EU numbering.

159. The isolated antibody of embodiment 118 or embodiment 154, wherein the Fc region further comprises a S228P amino acid substitution according to EU numbering.

160. The isolated antibody of any one of embodiments 44-159, wherein the isolated antibody competes for binding of TREM2 with one or more TREM2 ligands.

161. The isolated antibody of embodiment 160, wherein the one or more TREM2 ligands are selected from the group consisting of *E. coli* cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide.

162. The isolated antibody of any one of embodiments 44-161, wherein the isolated antibody is a human antibody, a humanized antibody, a bispecific antibody, a multivalent antibody, or a chimeric antibody.

163. The isolated antibody of any one of embodiments 44-162, wherein the isolated antibody is a bispecific antibody recognizing a first antigen and a second antigen.

164. The isolated antibody of embodiment 163, wherein the first antigen is human TREM2 or a naturally occurring variant thereof, or human DAP12 or a naturally occurring variant thereof, and the second antigen is a disease-causing protein selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides; or a blood brain barrier targeting protein selected from the group consisting of: trasnferin receptor, insulin receptor, insulin like growth factor receptor, LRP-1, and LRP 1.

165. The isolated antibody of any one of embodiments 44-161, wherein the isolated antibody is an antibody fragment that binds to one or more human proteins selected from the group consisting of human TREM2, a naturally occurring variant of human TREM2, human DAP12, and naturally occurring variant of human DAP12; and wherein the antibody is used in combination with one or more antibodies that specifically bind a disease-causing protein selected from the group consisting of: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, and any combination thereof.

166. The isolated antibody of any one of embodiments 44-165, wherein the antibody is a monoclonal antibody.

167. The isolated antibody of any one of embodiments 44-166, wherein the isolated antibody binds to a TREM2 protein, and wherein the isolated antibody binds to one or more amino acids within amino acid residues selected from the group consisting of:
   i. amino acid residues 29-112 of SEQ ID NO: 1, or amino acid residues on a TREM2 protein corresponding to amino acid residues 29-112 of SEQ ID NO: 1;
   ii. amino acid residues 29-41 of SEQ ID NO: 1, or amino acid residues on a TREM2 protein corresponding to amino acid residues 29-41 of SEQ ID NO: 1;
   iii. amino acid residues 40-44 of SEQ ID NO: 1, or amino acid residues on a TREM2 protein corresponding to amino acid residues 40-44 of SEQ ID NO: 1;
   iv. amino acid residues 47-69 of SEQ ID NO: 1, or amino acid residues on a TREM2 protein corresponding to amino acid residues 47-69 of SEQ ID NO: 1;
   v. amino acid residues 67-76 of SEQ ID NO: 1, or amino acid residues on a TREM2 protein corresponding to amino acid residues 67-76 of SEQ ID NO: 1;
   vi. amino acid residues 76-86 of SEQ ID NO: 1, or amino acid residues on a TREM2 protein corresponding to amino acid residues 76-86 of SEQ ID NO: 1;
   vii. amino acid residues 91-100 of SEQ ID NO: 1, or amino acid residues on a TREM2 protein corresponding to amino acid residues 91-100 of SEQ ID NO: 1;
   viii. amino acid residues 99-115 of SEQ ID NO: 1, or amino acid residues on a TREM2 protein corresponding to amino acid residues 99-115 of SEQ ID NO: 1;
   ix. amino acid residues 104-112 of SEQ ID NO: 1, or amino acid residues on a TREM2 protein corresponding to amino acid residues 104-112 of SEQ ID NO: 1; and
   x. amino acid residues 114-118 of SEQ ID NO: 1, or amino acid residues on a TREM2 protein corresponding to amino acid residues 114-118 of SEQ ID NO: 1.

168. The isolated antibody of embodiment 167, wherein the isolated antibody binds to one or more amino acids within amino acid residues 43-50 of SEQ ID NO: 1, or amino acid residues on a TREM2 protein corresponding to amino acid residues 43-50 of SEQ ID NO: 1.

169. The isolated antibody of embodiment 167, wherein the isolated antibody binds to one or more amino acids within amino acid residues 49-57 of SEQ ID NO: 1, or amino acid residues on a TREM2 protein corresponding to amino acid residues 49-57 of SEQ ID NO: 1.

170. The isolated antibody of any one of embodiments 44-167, wherein the isolated antibody binds to an epitope comprising one or more amino acids within amino acid residues 43-50 of SEQ ID NO: 1.

171. The isolated antibody of any one of embodiments 44-167, wherein the isolated antibody binds to an epitope comprising one or more amino acids within amino acid residues 43-50 of SEQ ID NO: 1.

172. The isolated antibody of any one of embodiments 44-167, wherein the isolated antibody binds to an epitope comprising one or more amino acid residues selected from the group consisting of:
   i. amino acid residue Arg47 or Asp87 of SEQ ID NO: 1;
   ii. amino acid residues 40-44 of SEQ ID NO: 1;
   iii. amino acid residues 67-76 of SEQ ID NO: 1; and
   iv. amino acid residues 114-118 of SEQ ID NO: 1.

173. The isolated antibody of any one of embodiments 44-167, wherein the isolated antibody binds to one or more amino acids within amino acid residues 22-40 of SEQ ID NO: 2, or amino acid residues on a DAP12 protein corresponding to amino acid residues 22-40 of SEQ ID NO: 2.

174. The isolated antibody of any one of embodiments 44-167, wherein the isolated antibody is a bispecific antibody that binds to one or more amino acids selected from the group consisting of:
  i. one or more amino acid residues of SEQ ID NO: 1, or amino acid residues on a TREM2 protein corresponding to amino acid residues of SEQ ID NO: 1; and
  ii. one or more amino acid residues of SEQ ID NO: 2, or amino acid residues on a DAP12 protein corresponding to amino acid residues of SEQ ID NO: 2.

175. The isolated antibody of any one of embodiments 44-174, wherein the isolated antibody comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52.

176. The isolated antibody of embodiment 175, wherein the HVR-H1 comprises the amino acid sequence of SEQ ID NO:398.

177. The isolated antibody of embodiment 175 or embodiment 176, wherein the HVR-H2 comprises the amino acid sequence of SEQ ID NO:399.

178. The isolated antibody of any one of embodiments 175-177, wherein the HVR-H3 comprises the amino acid sequence of SEQ ID NO:400.

179. The isolated antibody of any one of embodiments 175-178, wherein the HVR-L1 comprises the amino acid sequence of SEQ ID NO:401.

180. The isolated antibody of any one of embodiments 175-179, wherein the HVR-L2 comprises the amino acid sequence of SEQ ID NO:402.

181. The isolated antibody of any one of embodiments 175-180, wherein the HVR-L3 comprises the amino acid sequence of SEQ ID NO:403.

182. The isolated antibody of any one of embodiments 44-174, wherein the isolated antibody comprises a heavy chain variable domain and a light chain variable domain, wherein the heavy chain variable domain comprises
  (a) an HVR-H1 comprising the amino acid sequence of SEQ ID NO:398, or an amino acid sequence with at least about 95% homology to the amino acid sequence of SEQ ID NO:398;
  (b) an HVR-H2 comprising the amino acid sequence of SEQ ID NO:399, or an amino acid sequence with at least about 95% homology to the amino acid sequence of SEQ ID NO:399; and
  (c) an HVR-H3 comprising the amino acid sequence of SEQ ID NO:400, or an amino acid sequence with at least about 95% homology to the amino acid sequence of SEQ ID NO:400; and/or wherein the light chain variable domain comprises:
  (a) an HVR-L1 comprising the amino acid sequence of SEQ ID NO:401, or an amino acid sequence with at least about 95% homology to the amino acid sequence of SEQ ID NO:401;
  (b) an HVR-L2 comprising the amino acid sequence of SEQ ID NO:402, or an amino acid sequence with at least about 95% homology to the amino acid sequence of SEQ ID NO:402; and
  (c) an HVR-L3 comprising the amino acid sequence of SEQ ID NO:403, or an amino acid sequence with at least about 95% homology to the amino acid sequence of SEQ ID NO:403.

183. The isolated antibody of any one of embodiments 44-174, wherein the isolated antibody comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L1, HVR-L2, and/or HVR-L3 of the monoclonal antibody Ab21.

184. The isolated antibody of embodiment 183, wherein the HVR-H1 comprises the amino acid sequence of SEQ ID NO:404.

185. The isolated antibody of embodiment 183 or 184, wherein the HVR-H2 comprises the amino acid sequence of SEQ ID NO:405.

186. The isolated antibody of any one of embodiments 183-185, wherein the HVR-H3 comprises the amino acid sequence of SEQ ID NO:406.

187. The isolated antibody of any one of embodiments 183-186, wherein the HVR-L1 comprises the amino acid sequence of SEQ ID NO:407.

188. The isolated antibody of any one of embodiments 183-187, wherein the HVR-L2 comprises the amino acid sequence of SEQ ID NO:408.

189. The isolated antibody of any one of embodiments 183-188, wherein the HVR-L3 comprises the amino acid sequence of SEQ ID NO:409.

190. The isolated antibody of any one of embodiments 44-174, wherein the isolated antibody comprises a heavy chain variable domain and a light chain variable domain, wherein the heavy chain variable domain comprises
  (a) an HVR-H1 comprising the amino acid sequence of SEQ ID NO:404, or an amino acid sequence with at least about 95% homology to the amino acid sequence of SEQ ID NO:404;
  (b) an HVR-H2 comprising the amino acid sequence of SEQ ID NO:405, or an amino acid sequence with at least about 95% homology to the amino acid sequence of SEQ ID NO:405; and
  (c) an HVR-H3 comprising the amino acid sequence of SEQ ID NO:406, or an amino acid sequence with at least about 95% homology to the amino acid sequence of SEQ ID NO:406; and/or
wherein the light chain variable domain comprises:
  (a) an HVR-L1 comprising the amino acid sequence of SEQ ID NO:407, or an amino acid sequence with at least about 95% homology to the amino acid sequence of SEQ ID NO:407;
  (b) an HVR-L2 comprising the amino acid sequence of SEQ ID NO:408, or an amino acid sequence with at least about 95% homology to the amino acid sequence of SEQ ID NO:408; and
  (c) an HVR-L3 comprising the amino acid sequence of SEQ ID NO:409, or an amino acid sequence with at least about 95% homology to the amino acid sequence of SEQ ID NO:409.

191. An isolated anti-human TREM2 antibody, wherein the isolated antibody comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52.

192. The isolated antibody of embodiment 191, wherein the HVR-H1 comprises the amino acid sequence of SEQ ID NO:398.

193. The isolated antibody of embodiment 191 or embodiment 192, wherein the HVR-H2 comprises the amino acid sequence of SEQ ID NO:399.

194. The isolated antibody of any one of embodiments 191-193, wherein the HVR-H3 comprises the amino acid sequence of SEQ ID NO:400.

195. The isolated antibody of any one of embodiments 191-194, wherein the HVR-L1 comprises the amino acid sequence of SEQ ID NO:401.

196. The isolated antibody of any one of embodiments 191-195, wherein the HVR-L2 comprises the amino acid sequence of SEQ ID NO:402.

197. The isolated antibody of any one of embodiments 191-196, wherein the HVR-L3 comprises the amino acid sequence of SEQ ID NO:403.

198. The isolated antibody of embodiment 191, wherein the isolated antibody comprises a heavy chain variable domain and a light chain variable domain, wherein the heavy chain variable domain comprises an HVR-H1 comprising the amino acid sequence of SEQ ID NO:398, an HVR-H2 comprising the amino acid sequence of SEQ ID NO:399, and an HVR-H3 comprising the amino acid sequence of SEQ ID NO:400, and/or wherein the light chain variable domain comprises an HVR-L1 comprising the amino acid sequence of SEQ ID NO:401, an HVR-L2 comprising the amino acid sequence of SEQ ID NO:402, and an HVR-L3 comprising the amino acid sequence of SEQ ID NO:403.

199. An isolated anti-human TREM2 antibody, wherein the isolated antibody comprises a heavy chain variable domain and a light chain variable domain, wherein the heavy chain variable domain comprises
   (a) an HVR-H1 comprising the amino acid sequence of SEQ ID NO:398, or an amino acid sequence with at least about 95% homology to the amino acid sequence of SEQ ID NO:398;
   (b) an HVR-H2 comprising the amino acid sequence of SEQ ID NO:399, or an amino acid sequence with at least about 95% homology to the amino acid sequence of SEQ ID NO:399; and
   (c) an HVR-H3 comprising the amino acid sequence of SEQ ID NO:400, or an amino acid sequence with at least about 95% homology to the amino acid sequence of SEQ ID NO:400; and/or
wherein the light chain variable domain comprises:
   (a) an HVR-L1 comprising the amino acid sequence of SEQ ID NO:401, or an amino acid sequence with at least about 95% homology to the amino acid sequence of SEQ ID NO:401;
   (b) an HVR-L2 comprising the amino acid sequence of SEQ ID NO:402, or an amino acid sequence with at least about 95% homology to the amino acid sequence of SEQ ID NO:402; and
   (c) an HVR-L3 comprising the amino acid sequence of SEQ ID NO:403, or an amino acid sequence with at least about 95% homology to the amino acid sequence of SEQ ID NO:403.

200. An isolated anti-human TREM2 antibody, wherein the isolated antibody comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L1, HVR-L2, and/or HVR-L3 of the monoclonal antibody Ab21.

201. The isolated antibody of embodiment 200, wherein the HVR-H1 comprises the amino acid sequence of SEQ ID NO:404.

202. The isolated antibody of embodiment 200 or embodiment 201, wherein the HVR-H2 comprises the amino acid sequence of SEQ ID NO:405.

203. The isolated antibody of any one of embodiments 200-202, wherein the HVR-H3 comprises the amino acid sequence of SEQ ID NO:406.

204. The isolated antibody of any one of embodiments 200-203, wherein the HVR-L1 comprises the amino acid sequence of SEQ ID NO:407.

205. The isolated antibody of any one of embodiments 200-204, wherein the HVR-L2 comprises the amino acid sequence of SEQ ID NO:408.

206. The isolated antibody of any one of embodiments 200-205, wherein the HVR-L3 comprises the amino acid sequence of SEQ ID NO:409.

207. The isolated antibody of embodiment 200, wherein the isolated antibody comprises a heavy chain variable domain and a light chain variable domain, wherein the heavy chain variable domain comprises an HVR-H1 comprising the amino acid sequence of SEQ ID NO:404, an HVR-H2 comprising the amino acid sequence of SEQ ID NO:405, and an HVR-H3 comprising the amino acid sequence of SEQ ID NO:406, and/or wherein the light chain variable domain comprises an HVR-L1 comprising the amino acid sequence of SEQ ID NO:407, an HVR-L2 comprising the amino acid sequence of SEQ ID NO:408, and an HVR-L3 comprising the amino acid sequence of SEQ ID NO:409.

208. An isolated anti-human TREM2 antibody, wherein the isolated antibody comprises a heavy chain variable domain and a light chain variable domain, wherein the heavy chain variable domain comprises
   (a) an HVR-H1 comprising the amino acid sequence of SEQ ID NO:404, or an amino acid sequence with at least about 95% homology to the amino acid sequence of SEQ ID NO:404;
   (b) an HVR-H2 comprising the amino acid sequence of SEQ ID NO:405, or an amino acid sequence with at least about 95% homology to the amino acid sequence of SEQ ID NO:405; and
   (c) an HVR-H3 comprising the amino acid sequence of SEQ ID NO:406, or an amino acid sequence with at least about 95% homology to the amino acid sequence of SEQ ID NO:406; and/or
wherein the light chain variable domain comprises:
   (a) an HVR-L1 comprising the amino acid sequence of SEQ ID NO:407, or an amino acid sequence with at least about 95% homology to the amino acid sequence of SEQ ID NO:407;
   (b) an HVR-L2 comprising the amino acid sequence of SEQ ID NO:408, or an amino acid sequence with at least about 95% homology to the amino acid sequence of SEQ ID NO:408; and
   (c) an HVR-L3 comprising the amino acid sequence of SEQ ID NO:409, or an amino acid sequence with at least about 95% homology to the amino acid sequence of SEQ ID NO:409.

209. An isolated anti-human TREM2 antibody which binds essentially the same TREM2 epitope as the antibody Ab52.

210. An isolated anti-human TREM2 antibody which binds essentially the same TREM2 epitope as the antibody Ab21.

211. The isolated antibody of any one of embodiments 191-210, wherein the antibody is an agonist antibody, and wherein the antibody induces one or more TREM2 activities, DAP12 activities, or both.

212. The isolated antibody of embodiment 211, wherein the isolated antibody induces or retains TREM2 clustering, DAP12 clustering, or both on a cell surface.

213. The isolated antibody of embodiment 211 or embodiment 212, wherein the one or more TREM2 activities, DAP12 activities, or both are selected from the group consisting of TREM2 binding to DAP12; DAP12 binding to TREM2; TREM2 phosphorylation, DAP12 phosphorylation; PI3K activation; increased expression of one or more anti-inflammatory mediators; reduced expression of one or more pro-inflammatory mediators; reduced expression of TNF-α, IL-6, or both; extracellular signal-regulated kinase (ERK) phosphorylation; increased expression of C—C chemokine receptor 7 (CCR7); induction of microglial cell chemotaxis toward CCL19 and CCL21 expressing cells; an increase, normalization, or both of the ability of bone marrow-derived dendritic cells to induce antigen-specific T-cell proliferation; induction of osteoclast production, increased rate of osteoclastogenesis, or both; increasing the survival and/or function of one or more of dendritic cells, macrophages, microglial cells, M1 macrophages and/or microglial cells, activated M1 macrophages and/or microglial cells, M2 macrophages and/or microglial cells, osteoclasts, Langerhans cells of skin, and Kupffer cells; induction of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance; induction of phagocytosis of one or more of apoptotic neurons, nerve tissue debris, non-nerve tissue debris, bacteria, other foreign bodies, disease-causing proteins, disease-causing peptides, or disease-causing nucleic acids; normalization of disrupted TREM2/DAP12-dependent gene expression; recruitment of Syk, ZAP70, or both to the TREM2/DAP12 complex; Syk phosphorylation; increased expression of CD83 and/or CD86 on dendritic cells; reduced secretion of one or more inflammatory cytokines; reduced expression of one or more inflammatory receptors; increasing phagocytosis by macrophages, dendritic cells, monocytes, and/or microglia under conditions of reduced levels of MCSF; decreasing phagocytosis by macrophages, dendritic cells, monocytes, and/or microglia in the presence of normal levels of MCSF; increasing activity of one or more TREM2-dependent genes; and any combination thereof.

214. The isolated antibody of any one of embodiments 211-213, wherein the antibody is of the IgG class the IgM class, or the IgA class.

215. The isolated antibody of embodiment 214, wherein the antibody is of the IgG class and has an IgG1, IgG2, IgG3, or IgG4 isotype.

216. The isolated antibody of embodiment 215, wherein the antibody has an IgG2 isotype.

217. The isolated antibody of embodiment 216, wherein the antibody comprises a human IgG2 constant region.

218. The isolated antibody of embodiment 217, wherein the human IgG2 constant region comprises an Fc region.

219. The isolated antibody of any one of embodiments 216-218, wherein the antibody induces the one or more TREM2 activities, DAP12 activities, or both independently of binding to an Fc receptor.

220. The isolated antibody of any one of embodiments 216-218, wherein the antibody binds an inhibitory Fc receptor.

221. The isolated antibody of embodiment 220, wherein the inhibitory Fc receptor is inhibitory Fc-gamma receptor IIB (FcγRIIB).

222. The isolated antibody of embodiment 220 or embodiment 221, wherein the Fc region comprises one or more modifications.

223. The isolated antibody of embodiment 222, wherein the Fc region comprises one or more amino acid substitutions.

224. The isolated antibody of embodiment 223, wherein the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU numbering.

225. The isolated antibody of embodiment 217, wherein the human IgG2 constant region comprises a light chain constant region comprising a C214S amino acid substitution, wherein the numbering of the residues is according to EU numbering.

226. The isolated antibody of embodiment 215, wherein the antibody has an IgG1 isotype.

227. The isolated antibody of embodiment 226, wherein the antibody comprises a human IgG1 constant region.

228. The isolated antibody of embodiment 227, wherein the human IgG1 constant region comprises an Fc region.

229. The isolated antibody of any one of embodiments 226-228, wherein the antibody binds an inhibitory Fc receptor.

230. The isolated antibody of embodiment 229, wherein the inhibitory Fc receptor is inhibitory Fc-gamma receptor IIB (FcγRIIB).

231. The isolated antibody of any one of embodiments 228-230, wherein the Fc region comprises one or more modifications.

232. The isolated antibody of embodiment 231, wherein the Fc region comprises one or more amino acid substitutions.

233. The isolated antibody of embodiment 232, wherein the one or more amino acid substitutions in the Fc region are at a residue position selected from the group consisting of N297A, D265A, L234A, L235A, G237A, C226S, C229S, E233P, L234V, L234F, L235E, P331 S, S267E, L328F, A330L, M252Y, S254T, T256E, and any combination thereof, wherein the numbering of the residues is according to EU numbering.

234. The isolated antibody of any one of embodiments 228-230, wherein the antibody comprises an IgG2 isotype heavy chain constant domain 1(CH1) and hinge region.

235. The isolated antibody of embodiment 234, wherein the IgG2 isotype CH1 and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397).

236. The isolated antibody of embodiment 234 or embodiment 235, wherein the antibody Fc region comprises a S267E amino acid substitution, a L328F amino acid substitution, or both, and/or a N297A or N297Q amino acid substitution, wherein the numbering of the residues is according to EU numbering.

237. The isolated antibody of embodiment 226, wherein the antibody comprises a mouse IgG1 constant region.

238. The isolated antibody of embodiment 215, wherein the antibody has an IgG4 isotype.

239. The isolated antibody of embodiment 238, wherein the antibody comprises a human IgG4 constant region.

240. The isolated antibody of embodiment 239, wherein the human IgG4 constant region comprises an Fc region.

241. The isolated antibody of any one of embodiments 238-240, wherein the antibody binds an inhibitory Fc receptor.

242. The isolated antibody of embodiment 241, wherein the inhibitory Fc receptor is inhibitory Fc-gamma receptor IIB (FcγRIIB).

243. The isolated antibody of any one of embodiments 240-242, wherein the Fc region comprises one or more modifications.
244. The isolated antibody of embodiment 243, wherein the Fc region comprises one or more amino acid substitutions.
245. The isolated antibody of embodiment 244, wherein the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU numbering.
246. The isolated antibody of embodiment 214, wherein the antibody has a hybrid IgG2/4 isotype.
247. The isolated antibody of embodiment 246, wherein the antibody comprises an amino acid sequence comprising amino acids 118 to 260 of human IgG2 and amino acids 261 to 447 of human IgG4, wherein the numbering of the residues is according to EU numbering.
248. The isolated antibody of embodiment 239, wherein the antibody comprises a mouse IgG4 constant region.
249. The isolated antibody of any one of embodiments 211-248, wherein the isolated antibody is an antibody fragment that binds to one or more human proteins selected from the group consisting of human TREM2, a naturally occurring variant of human TREM2, human DAP12, and naturally occurring variant of human DAP12, and wherein the antibody fragment is cross-linked to a second antibody fragment that binds to one or more human proteins selected from the group consisting of human TREM2, a naturally occurring variant of human TREM2, human DAP12, and naturally occurring variant of human DAP12.
250. The isolated antibody of embodiment 249, wherein the fragment is an Fab, Fab', Fab'-SH, F(ab')2, Fv or scFv fragment.
251. The isolated antibody of any one of embodiments 191-210, wherein the isolated antibody is an inert antibody.
252. The isolated antibody of any one of embodiments 191-210, wherein the isolated antibody is an antagonist antibody.
253. The isolated antibody of embodiment 252, wherein the isolated antibody inhibits one or more TREM2 activities.
254. The isolated antibody of embodiment 253, wherein the one or more TREM2 activities are selected from the group consisting of decreasing activity of one or more TREM2-dependent genes; decreasing activity of one or more nuclear factor of activated T-cells (NFAT) transcription factors; decreasing the survival of macrophages, microglial cells, monocytes, osteoclasts, Langerhans cells of skin, Kupffer cells, and/or dendritic cells; and any combination thereof.
255. The isolated antibody of any one of embodiments 252-254, wherein the isolated antibody inhibits interaction between TREM2 and one or more TREM2 ligands, inhibits TREM2 signal transduction, or both.
256. The isolated antibody of any one of embodiments 251-255, wherein the antibody is incapable of binding an Fc-gamma receptor (FcγR).
257. The isolated antibody of embodiment 256, wherein the antibody has an IgG1 isotype.
258. The isolated antibody of embodiment 257, wherein the antibody comprises a human IgG1 constant region.
259. The isolated antibody of embodiment 258, wherein the human IgG1 constant region comprises an Fc region.
260. The isolated antibody of embodiment 259, wherein the Fc region comprises one or more modifications.
261. The isolated antibody of embodiment 260, wherein the Fc region comprises one or more amino acid substitutions.
262. The isolated antibody of embodiment 261, wherein the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU numbering.
263. The isolated antibody of embodiment 262, wherein the Fc region further comprises an amino acid deletion at a position corresponding to glycine 236 according to EU numbering.
264. The isolated antibody of embodiment 257, wherein the antibody comprises a mouse IgG1 constant region.
265. The isolated antibody of embodiment 256, wherein the antibody has an IgG2 isotype.
266. The isolated antibody of embodiment 264, wherein the antibody comprises a human IgG2 constant region.
267. The isolated antibody of embodiment 266, wherein the human IgG2 constant region comprises an Fc region.
268. The isolated antibody of embodiment 267, wherein the Fc region comprises one or more modifications.
269. The isolated antibody of embodiment 268, wherein the Fc region comprises one or more amino acid substitutions.
270. The isolated antibody of embodiment 269, wherein the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU numbering.
271. The isolated antibody of embodiment 256, wherein the antibody has an IgG4 isotype.
272. The isolated antibody of embodiment 271, wherein the antibody comprises a human IgG4 constant region.
273. The isolated antibody of embodiment 272, wherein the human IgG4 constant region comprises an Fc region.
274. The isolated antibody of embodiment 273, wherein the Fc region comprises one or more modifications.
275. The isolated antibody of embodiment 274, wherein the Fc region comprises one or more amino acid substitutions.
276. The isolated antibody of embodiment 275, wherein the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU numbering.
277. The isolated antibody of any one of embodiments 208-276, wherein the isolated antibody is an antibody fragment that binds to one or more human proteins selected from the group consisting of human TREM2, a naturally occurring variant of human TREM2, human DAP12, and naturally occurring variant of human DAP12.
278. The isolated antibody of embodiment 277, wherein the fragment is an Fab, Fab', Fab'-SH, F(ab')2, Fv or scFv fragment.
279. The isolated antibody of embodiment 233, embodiment 262, or embodiment 263, wherein the Fc region further comprises one or more additional amino acid substitutions at a position selected from the group consisting of A330L, L234F; L235E, P331S, and any combination thereof, wherein the numbering of the residues is according to EU numbering.
280. The isolated antibody of any one of embodiments 223-279, wherein the Fc region further comprises one or more additional amino acid substitutions at a position selected from the group consisting of M252Y, S254T, T256E, and any combination thereof, wherein the numbering of the residues is according to EU numbering.

281. The isolated antibody of embodiment 245 or embodiment 276, wherein the Fc region further comprises a S228P amino acid substitution according to EU numbering.

282. The isolated antibody of any one of embodiments 191-281, wherein the antibody is a human antibody, a humanized antibody, a bispecific antibody, a multivalent antibody, or a chimeric antibody.

283. The isolated antibody of any one of embodiments 191-282, wherein the antibody is a bispecific antibody recognizing a first antigen and a second antigen.

284. The isolated antibody of any one of embodiments 191-283, wherein the antibody is a monoclonal antibody.

285. The isolated antibody of any one of the preceding embodiments, wherein the isolated antibody binds specifically to both human TREM2 and mouse TREM2.

286. The isolated antibody of any one of the preceding embodiments, wherein the isolated antibody has dissociation constant ($K_D$) for human TREM2 and mouse TREM2 that ranges from less than about 5.75 nM to less than about 0.09 nM.

287. The isolated antibody of any one of the preceding embodiments, wherein the isolated antibody has dissociation constant ($K_D$) for human TREM2-Fc fusion protein that ranges from less than about 1.51 nM to less than about 0.35 nM.

288. The isolated antibody of any one of the preceding embodiments, wherein the isolated antibody has dissociation constant ($K_D$) for human monomeric TREM2 protein that ranges from less than about 5.75 nM to less than about 1.15 nm.

289. The isolated antibody of any one of the preceding embodiments, wherein the isolated antibody has dissociation constant ($K_D$) for mouse TREM2-Fc fusion protein that ranges from less than about 0.23 nM to less than about 0.09 nM.

290. An isolated nucleic acid encoding the antibody of any one of the preceding embodiments.

291. A vector comprising the nucleic acid of embodiment 290.

292. A host cell comprising the vector of embodiment 291.

293. A method of producing an antibody, comprising culturing the cell of embodiment 292 so that the antibody is produced.

294. The method of embodiment 293, further comprising recovering the antibody produced by the cell.

295. A pharmaceutical composition comprising the antibody of any one of embodiments 44-289 and a pharmaceutically acceptable carrier.

296. A method of preventing, reducing risk, or treating an individual having a disease, disorder, or injury selected from the group consisting of dementia, frontotemporal dementia, Alzheimer's disease, Nasu-Hakola disease, and multiple sclerosis, comprising administering to the individual a therapeutically effective amount of an isolated antibody that binds to a TREM2 protein, a DAP12 protein, or both.

297. The method of embodiment 296, wherein the isolated antibody is the isolated antibody of any one of embodiments 44-289.

298. The method of embodiment 296 or embodiment 297, wherein the individual has a heterozygous variant of TREM2, wherein the variant comprises one or more substitutions selected from the group consisting of:

i. a glutamic acid to stop codon substitution in the nucleic acid sequence encoding amino acid residue Glu14 of SEQ ID NO: 1;
ii. a glutamine to stop codon substitution in the nucleic acid sequence encoding amino acid residue Gln33 of SEQ ID NO: 1;
iii. a tryptophan to stop codon substitution in the nucleic acid sequence encoding amino acid residue Trp44 of SEQ ID NO: 1;
iv. an arginine to histidine amino acid substitution at an amino acid corresponding to amino acid residue Arg47 of SEQ ID NO: 1;
v. a tryptophan to stop codon substitution in the nucleic acid sequence encoding amino acid residue Trp78 of SEQ ID NO: 1;
vi. a valine to glycine amino acid substitution at an amino acid corresponding to amino acid residue Val126 of SEQ ID NO: 1;
vii. an aspartic acid to glycine amino acid substitution at an amino acid corresponding to amino acid residue Asp134 of SEQ ID NO: 1; and
viii. a lysine to asparagine amino acid substitution at an amino acid corresponding to amino acid residue Lys186 of SEQ ID NO: 1.

299. The method of embodiment 296, wherein the individual has a heterozygous variant of TREM2, wherein the variant comprises a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; or both.

300. The method of embodiment 296, wherein the individual has a heterozygous variant of DAP12, wherein the variant comprises one or more variants selected from the group consisting of:

i. a methionine to threonine substitution at an amino acid corresponding to amino acid residue Met1 of SEQ ID NO: 2;
ii. a glycine to arginine amino acid substitution at an amino acid corresponding to amino acid residue Gly49 of SEQ ID NO: 2;
iii. a deletion within exons 1-4 of the nucleic acid sequence encoding SEQ ID NO: 2;
iv. an insertion of 14 amino acid residues at exon 3 of the nucleic acid sequence encoding SEQ ID NO: 2; and
v. a guanine nucleotide deletion at a nucleotide corresponding to nucleotide residue G141 of the nucleic acid sequence encoding SEQ ID NO: 2.

301. A method of inducing or promoting innate immune cell survival an individual in need thereof, comprising administering to the individual a therapeutically effective amount of an isolated agonist antibody that binds to a TREM2 protein, a DAP12 protein, or both.

302. The method of embodiment 301 wherein the isolated agonist antibody is the isolated antibody of any one of embodiments 44-123, 157-250, and 277-289.

303. An isolated agonist antibody that binds to a TREM2 protein, wherein the antibody induces one or more TREM2 activities.

304. The isolated antibody of embodiment 303, wherein the TREM2 protein is a mammalian protein or a human protein.

305. The isolated antibody of embodiment 304, wherein the TREM2 protein is a wild-type protein.

306. The isolated antibody of embodiment 304, wherein the TREM2 protein is a naturally occurring variant.

307. The isolated antibody of any one of embodiments 303-306, wherein the TREM2 protein is expressed on human dendritic cells, human macrophages, human monocytes, human osteoclasts, human Langerhans cells of skin, human Kupffer cells, and/or human microglia.

308. The isolated antibody of any one of embodiments 303-307, wherein the isolated antibody induces or retains TREM2 clustering on a cell surface.

309. The isolated antibody of any one of embodiments 303-308, wherein the one or more TREM2 activities comprise TREM2 binding to DAP12.

310. The isolated antibody of any one of embodiments 303-309, wherein the one or more TREM2 activities comprise TREM2 autophosphorylation.

311. The isolated antibody of any one of embodiments 303-310, wherein the one or more TREM2 activities comprise DAP12 phosphorylation.

312. The isolated antibody of embodiment 310 or embodiment 311, wherein the TREM2 autophosphorylation, the DAP12 phosphorylation, or both is induced by one or more SRC family tyrosine kinases.

313. The isolated antibody of embodiment 312, wherein the one or more SRC family tyrosine kinases comprise a Syk kinase.

314. The isolated antibody of any one of embodiments 303-313, wherein the one or more TREM2 activities comprise PI3K activation.

315. The isolated antibody of any one of embodiments 303-314, wherein the one or more TREM2 activities comprise increased expression of one or more anti-inflammatory cytokines.

316. The isolated antibody of any one of embodiments 303-314, wherein the one or more TREM2 activities comprise increased expression of one or more cytokines selected from the group consisting of IL-12p70, IL-6, and IL-10.

317. The isolated antibody of embodiment 315 or embodiment 316, wherein the increased expression occurs in one or more cells selected from the group consisting of macrophages, dendritic cells, monocytes, osteoclasts, Langerhans cells of skin, Kupffer cells, and microglial cells.

318. The isolated antibody of any one of embodiments 303-317, wherein the one or more TREM2 activities comprise reduced expression of one or more pro-inflammatory cytokines.

319. The isolated antibody of any one of embodiments 303-317, wherein the one or more TREM2 activities comprise reduced expression of one or more pro-inflammatory mediators selected from the group consisting of IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP.

320. The isolated antibody of any one of embodiments 303-318, wherein the one or more TREM2 activities comprise reduced expression of TNF-α, IL-6, or both.

321. The isolated antibody of embodiment 319 or embodiment 320, wherein the reduced expression of the one or more pro-inflammatory mediators occurs in one or more cells selected from the group consisting of macrophages, dendritic cells, monocytes, osteoclasts, Langerhans cells of skin, Kupffer cells, and microglial cells.

322. The isolated antibody of any one of embodiments 303-320, wherein the one or more TREM2 activities comprise extracellular signal-regulated kinase (ERK) phosphorylation.

323. The isolated antibody of any one of embodiments 303-322, wherein the one or more TREM2 activities comprise increased expression of C—C chemokine receptor 7 (CCR7).

324. The isolated antibody of any one of embodiments 303-322, wherein the one or more TREM2 activities comprise induction of microglial cell chemotaxis toward CCL19 and CCL21 expressing cells.

325. The isolated antibody of any one of embodiments 303-324, wherein the one or more TREM2 activities comprise an increased ability of dendritic cells, monocytes, microglia, and/or macrophages to induce T-cell proliferation.

326. The isolated antibody of any one of embodiments 303-324, wherein the one or more TREM2 activities comprise an enhancement, normalization, or both of the ability of bone marrow-derived dendritic cells to induce antigen-specific T-cell proliferation.

327. The isolated antibody of any one of embodiments 303-326, wherein the one or more TREM2 activities comprise induction of osteoclast production, increased rate of osteoclastogenesis, or both.

328. The isolated antibody of any one of embodiments 303-327, wherein the one or more TREM2 activities comprise increasing the survival of dendritic cells, macrophages, monocytes, osteoclasts, Langerhans cells of skin, Kupffer cells, and/or microglia.

329. The isolated antibody of any one of embodiments 303-328, wherein the one or more TREM2 activities comprise increasing the function of dendritic cells, macrophages, and/or microglia.

330. The isolated antibody of any one of embodiments 303-329, wherein the one or more TREM2 activities comprise increasing phagocytosis by dendritic cells, macrophages, monocytes, and/or microglia under conditions of reduced levels of MCSF.

331. The isolated antibody of any one of embodiments 303-330, wherein the one or more TREM2 activities comprise decreasing phagocytosis by dendritic cells, macrophages, monocytes, and/or microglia in the presence of normal levels of MCSF.

332. The isolated antibody of any one of embodiments 328-331, wherein the macrophages and/or microglia are M1 macrophages and/or microglia, M2 macrophages and/or microglia, or both.

333. The isolated antibody of embodiment 332, wherein the M1 macrophages and/or microglia are activated M1 macrophages and/or microglia.

334. The isolated antibody of any one of any one of embodiments 303-333, wherein the one or more TREM2 activities comprise induction of one or more types of clearance selected from the group consisting of apoptotic neuron clearance, nerve tissue debris clearance, non-nerve tissue debris clearance, bacteria or other foreign body clearance, disease-causing protein clearance, and tumor cell clearance.

335. The isolated antibody of any one of embodiments 303-334, wherein the one or more TREM2 activities comprise induction of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells.

336. The isolated antibody of embodiment 335, wherein the disease-causing nucleic acid is antisense GGCCCC (G2C4) repeat-expansion RNA.

337. The isolated antibody of embodiment 334 or embodiment 335, wherein the disease-causing protein is selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides.

338. The isolated antibody of any one of embodiments 303-337, wherein the one or more TREM2 activities comprise normalization of disrupted TREM2/DAP12-dependent gene expression.

339. The isolated antibody of any one of embodiments 303-338, wherein the one or more TREM2 activities comprise recruitment of Syk, ZAP70, or both to a DAP12/TREM2 complex.

340. The isolated antibody of any one of embodiments 303-339, wherein the one or more TREM2 activities comprise Syk phosphorylation.

341. The isolated antibody of any one of embodiments 303-340, wherein the one or more TREM2 activities comprise increased expression of CD83 and/or CD86 on dendritic cells, monocytes, macrophages, or both.

342. The isolated antibody of embodiment 341, wherein the dendritic cells are bone marrow-derived dendritic cells.

343. The isolated antibody of any one of embodiments 303-342, wherein the one or more TREM2 activities comprise reduced secretion of one or more inflammatory cytokines.

344. The isolated antibody of 343, wherein the one or more inflammatory cytokines are selected from the group consisting of IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, CRP, and MCP-1.

345. The isolated antibody of any one of embodiments 303-344, wherein the one or more TREM2 activities comprise reduced expression of one or more inflammatory receptors.

346. The isolated antibody of embodiment 345, wherein the one or more inflammatory receptors comprise CD86.

347. The isolated antibody of any one of embodiments 303-346, wherein the one or more TREM2 activities comprise increasing activity of one or more TREM2-dependent genes.

348. The isolated antibody of embodiment 347, wherein the one or more TREM2-dependent genes comprise one or more nuclear factor of activated T-cells (NFAT) transcription factors.

349. The isolated antibody of any one of embodiments 303-348, wherein the antibody is of the IgG class the IgM class, or the IgA class.

350. The isolated antibody of embodiment 349, wherein the antibody is of the IgG class and has an IgG1, IgG2, IgG3, or IgG4 isotype.

351. The isolated antibody of embodiment 349, wherein the antibody has an IgG2 isotype.

352. The isolated antibody of embodiment 351, wherein the antibody comprises a human IgG2 constant region.

353. The isolated antibody of embodiment 352, wherein the human IgG2 constant region comprises an Fc region.

354. The isolated antibody of any one of embodiments 351-353, wherein the antibody induces the one or more TREM2 activities independently of binding to an Fc receptor.

355. The isolated antibody of any one of embodiments 351-353, wherein the antibody binds an inhibitory Fc receptor.

356. The isolated antibody of embodiment 355, wherein the inhibitory Fc receptor is inhibitory Fc-gamma receptor IIB (FcγIIB).

357. The isolated antibody of embodiment 355 or embodiment 356, wherein the human IgG2 constant region comprises an Fc region that comprises one or more modifications.

358. The isolated antibody of embodiment 357, wherein the Fc region comprises one or more amino acid substitutions.

359. The isolated antibody of embodiment 358, wherein the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU numbering.

360. The isolated antibody of embodiment 352, wherein the human IgG2 constant region comprises a light chain constant region comprising a C214S amino acid substitution, wherein the numbering of the residues is according to EU numbering.

361. The isolated antibody of embodiment 349, wherein the antibody has an IgG1 isotype.

362. The isolated antibody of embodiment 361, wherein the antibody comprises a human IgG1 constant region.

363. The isolated antibody of embodiment 362, wherein the human IgG1 constant region comprises an Fc region.

364. The isolated antibody of any one of embodiments 361-363, wherein the antibody binds an inhibitory Fc receptor.

365. The isolated antibody of embodiment 364, wherein the inhibitory Fc receptor is inhibitory Fc-gamma receptor IIB (FcγRIIB).

366. The isolated antibody of any one of embodiments 363-365, wherein the Fc region comprises one or more modifications.

367. The isolated antibody of embodiment 366, wherein the Fc region comprises one or more amino acid substitutions.

368. The isolated antibody of embodiment 367, wherein the one or more amino acid substitutions in the Fc region are at a residue position selected from the group consisting of N297A, D265A, L234A, L235A, G237A, C226S, C229S, E233P, L234V, L234F, L235E, P331 S, S267E, L328F, A330L, M252Y, S254T, T256E, and any combination thereof, wherein the numbering of the residues is according to EU numbering.

369. The isolated antibody of any one of embodiments 363-365, wherein the antibody comprises an IgG2 isotype heavy chain constant domain 1($C_H1$) and hinge region.

370. The isolated antibody of embodiment 369, wherein the IgG2 isotype $C_H1$ and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO: 397).

371. The isolated antibody of embodiment 369 or embodiment 370, wherein the antibody Fc region comprises a S267E amino acid substitution, a L328F amino acid substitution, or both, and/or a N297A or N297Q amino acid substitution, wherein the numbering of the residues is according to EU numbering.

372. The isolated antibody of embodiment 361, wherein the antibody comprises a mouse IgG1 constant region.

373. The isolated antibody of embodiment 349, wherein the antibody has an IgG4 isotype.

374. The isolated antibody of embodiment 373, wherein the antibody comprises a human IgG4 constant region.

375. The isolated antibody of embodiment 374, wherein the human IgG4 constant region comprises an Fc region.

376. The isolated antibody of any one of embodiments 373-375, wherein the antibody binds an inhibitory Fc receptor.

377. The isolated antibody of embodiment 376, wherein the inhibitory Fc receptor is inhibitory Fc-gamma receptor IIB (FcγIIB).

378. The isolated antibody of any one of embodiments 375-377, wherein the Fc region comprises one or more modifications.

379. The isolated antibody of embodiment 378, wherein the Fc region comprises one or more amino acid substitutions.

380. The isolated antibody of embodiment 379, wherein the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU numbering.

381. The isolated antibody of embodiment 349, wherein the antibody has a hybrid IgG2/4 isotype.

382. The isolated antibody of embodiment 381, wherein the antibody comprises an amino acid sequence comprising amino acids 118 to 260 of human IgG2 and amino acids 261 to 447 of human IgG4, wherein the numbering of the residues is according to EU numbering.

383. The isolated antibody of embodiment 373, wherein the antibody comprises a mouse IgG4 constant region.

384. The isolated antibody of any one of embodiments 1-383, wherein the isolated antibody is an antibody fragment that binds to one or more human proteins selected from the group consisting of human TREM2, a naturally occurring variant of human TREM2, and a disease variant of human TREM2, and wherein the antibody fragment is cross-linked to a second antibody fragment that binds to one or more human proteins selected from the group consisting of human TREM2, a naturally occurring variant of human TREM2, and a disease variant of human TREM2.

385. The isolated antibody of embodiment 384, wherein the fragment is an Fab, Fab', Fab'-SH, F(ab')2, Fv or scFv fragment.

386. An isolated inert antibody that binds to a TREM2 protein.

387. An isolated antagonist antibody that binds to a TREM2 protein.

388. The isolated antibody of embodiment 386 or embodiment 387, wherein the TREM2 protein is a mammalian protein or a human protein.

389. The isolated antibody of embodiment 388, wherein the TREM2 protein is a wild-type protein.

390. The isolated antibody of embodiment 388, wherein the TREM2 protein is a naturally occurring variant.

391. The isolated antibody of embodiment 388, wherein the TREM2 protein is a disease variant.

392. The isolated antibody of any one of embodiments 387-391, wherein the isolated antibody inhibits one or more TREM2 activities.

393. The isolated antibody of embodiment 392, wherein the one or more TREM2 activities comprise decreasing activity of one or more TREM2-dependent genes.

394. The isolated antibody of embodiment 393, wherein the one or more TREM2-dependent genes comprise one or more nuclear factor of activated T-cells (NFAT) transcription factors.

395. The isolated antibody of any one of embodiments 392-394, wherein the one or more TREM2 activities comprise decreasing the survival of macrophages, microglial cells, M1 macrophages, M1 microglial cells, M2 macrophages, M2 microglial cells, osteoclasts, Langerhans cells of skin, Kupffer cells, and/or dendritic cells.

396. The isolated antibody of any one of embodiments 387-395, wherein the isolated antibody inhibits interaction between TREM2 and one or more TREM2 ligands, inhibits TREM2 signal transduction, or both.

397. The isolated antibody of any one of embodiments 386-396, wherein the antibody is incapable of binding an Fc-gamma receptor (FcγR).

398. The isolated antibody of embodiment 397, wherein the antibody has an IgG1 isotype.

399. The isolated antibody of embodiment 398, wherein the antibody comprises a human IgG1 constant region.

400. The isolated antibody of embodiment 399, wherein the human IgG1 constant region comprises an Fc region.

401. The isolated antibody of embodiment 400, wherein the Fc region comprises one or more modifications.

402. The isolated antibody of embodiment 401, wherein the Fc region comprises one or more amino acid substitutions.

403. The isolated antibody of embodiment 402, wherein the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU numbering.

404. The isolated antibody of embodiment 403, wherein the Fc region further comprises an amino acid deletion at a position corresponding to glycine 236 according to EU numbering.

405. The isolated antibody of embodiment 398, wherein the antibody comprises a mouse IgG1 constant region.

406. The isolated antibody of embodiment 397, wherein the antibody has an IgG2 isotype.

407. The isolated antibody of embodiment 406, wherein the antibody comprises a human IgG2 constant region.

408. The isolated antibody of embodiment 407, wherein the human IgG2 constant region comprises an Fc region.

409. The isolated antibody of embodiment 408, wherein the Fc region comprises one or more modifications.

410. The isolated antibody of embodiment 409, wherein the Fc region comprises one or more amino acid substitutions.

411. The isolated antibody of embodiment 410, wherein the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU numbering.

412. The isolated antibody of embodiment 397 wherein the antibody has an IgG4 isotype.

413. The isolated antibody of embodiment 412, wherein the antibody comprises a human IgG4 constant region.

414. The isolated antibody of embodiment 413, wherein the human IgG4 constant region comprises an Fc region.

415. The isolated antibody of embodiment 414, wherein the Fc region comprises one or more modifications.

416. The isolated antibody of embodiment 415, wherein the Fc region comprises one or more amino acid substitutions.

417. The isolated antibody of embodiment 416, wherein the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU numbering.

418. The isolated antibody of any one of embodiments 386-417, wherein the isolated antibody is an antibody fragment that binds to one or more human proteins selected from the group consisting of human TREM2, a naturally occurring variant of human TREM2, and a disease variant of TREM2.

419. The isolated antibody of embodiment 418, wherein the fragment is an Fab, Fab', Fab'-SH, F(ab')2, Fv or scFv fragment.

420. The isolated antibody of embodiment 368, embodiment 403, or embodiment 404, wherein the Fc region further comprises one or more additional amino acid substitutions at a position selected from the group consisting of A330L, L234F; L235E, P331S, and any combination thereof, wherein the numbering of the residues is according to EU numbering.

421. The isolated antibody of any one of embodiments 357-420, wherein the Fc region further comprises one or more additional amino acid substitutions at a position selected from the group consisting of M252Y, S254T, T256E, and any combination thereof, wherein the numbering of the residues is according to EU numbering.

422. The isolated antibody of embodiment 380 or embodiment 417, wherein the Fc region further comprises a S228P amino acid substitution according to EU numbering.

423. The isolated antibody of any one of embodiments 303-422, wherein the antibody competes for binding of TREM2 with one or more TREM2 ligands.

424. The isolated antibody of embodiment 423, wherein the one or more TREM2 ligands are selected from the group consisting of E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide.

425. The isolated antibody of any one of embodiments 303-422, wherein the antibody does not compete for binding of TREM2 with a TREM2 ligand.

426. The isolated antibody of any one of embodiments 303-425, wherein the antibody is a human antibody, a humanized antibody, a bispecific antibody, a multivalent antibody, a conjugated antibody, or a chimeric antibody.

427. The isolated antibody of any one of embodiments 303-426, wherein the antibody is a bispecific antibody recognizing a first antigen and a second antigen.

428. The isolated antibody of embodiment 427, wherein the first antigen is human TREM2 or a naturally occurring variant thereof, and the second antigen is a disease-causing protein selected from the group consisting of: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides; a blood brain barrier targeting protein selected from the group consisting of: trasnferin receptor, insulin receptor, insulin like growth factor receptor, LRP-1, and LRP 1; or ligands and/or proteins expressed on immune cells, wherein the ligands and/or proteins selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine.

429. The isolated antibody of embodiment 427, wherein the first antigen is human TREM2 or a naturally occurring variant thereof, and the second antigen is a protein expressed on one or more tumor cells.

430. The isolated antibody of any one of embodiments 303-424, wherein the antibody is an antibody fragment that binds to one or more human proteins selected from the group consisting of human TREM2, a naturally occurring variant of human TREM2, human DAP12, and naturally occurring variant of human DAP12; and wherein the antibody is used in combination with one or more antibodies that specifically bind a disease-causing protein selected from the group consisting of: amyloid beta, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, and any combination thereof, or with one or more antibodies that specifically bind a cancer-associated protein selected from the group consisting of: CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, phosphatidylserine, and any combination thereof.

431. The isolated antibody of any one of embodiments 303-430, wherein the antibody is a monoclonal antibody.

432. The isolated antibody of any one of embodiments 303-431, wherein the antibody binds to one or more amino acids within amino acid residues selected from the group consisting of:
  xi. amino acid residues 130-171 of SEQ ID NO: 1, or amino acid residues on a TREM2 protein corresponding to amino acid residues 130-171 of SEQ ID NO: 1;
  xii. amino acid residues 140-153 of SEQ ID NO: 1, or amino acid residues on a TREM2 protein corresponding to amino acid residues 140-153 of SEQ ID NO: 1;
  xiii. amino acid residues 139-146 of SEQ ID NO: 1, or amino acid residues on a TREM2 protein corresponding to amino acid residues 139-146 of SEQ ID NO: 1;
  xiv. amino acid residues 130-144 of SEQ ID NO: 1, or amino acid residues on a TREM2 protein corresponding to amino acid residues 130-144 of SEQ ID NO: 1; and
  xv. amino acid residues 158-171 of SEQ ID NO: 1, or amino acid residues on a TREM2 protein corresponding to amino acid residues 158-171 of SEQ ID NO: 1.

433. The isolated antibody of any one of embodiments 303-431, wherein the antibody binds to an epitope comprising one or more amino acids within amino acid residues selected from the group consisting of:
  i. amino acid residues 130-171 of SEQ ID NO: 1, or amino acid residues on a TREM2 protein corresponding to amino acid residues 130-171 of SEQ ID NO: 1;
  ii. amino acid residues 140-153 of SEQ ID NO: 1, or amino acid residues on a TREM2 protein corresponding to amino acid residues 139-153 of SEQ ID NO: 1;
  iii. amino acid residues 139-146 of SEQ ID NO: 1, or amino acid residues on a TREM2 protein corresponding to amino acid residues 139-146 of SEQ ID NO: 1;
  iv. amino acid residues 130-144 of SEQ ID NO: 1, or amino acid residues on a TREM2 protein corresponding to amino acid residues 130-144 of SEQ ID NO: 1; and
  v. amino acid residues 158-171 of SEQ ID NO: 1, or amino acid residues on a TREM2 protein corresponding to amino acid residues 158-171 of SEQ ID NO: 1.

434. The isolated antibody of embodiment 432 or embodiment 433, wherein the antibody binds to an epitope further comprising one or more amino acid residues selected from the group consisting of:
  v. amino acid residue Arg47 or Asp87 of SEQ ID NO: 1;
  vi. amino acid residues 40-44 of SEQ ID NO: 1;
  vii. amino acid residues 67-76 of SEQ ID NO: 1; and
  viii. amino acid residues 114-118 of SEQ ID NO: 1.

435. The isolated antibody of any one of embodiments 303-433, wherein the isolated antibody comprises a heavy chain variable domain and a light chain variable domain, wherein the heavy chain variable domain comprises an HVR-H1, HVR-H2, and/or HVR-H3 of a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87, and/or wherein the light chain variable domain comprises an HVR-L1, HVR-L2, and/or HVR-L3 of a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

436. The isolated antibody of embodiment 435, wherein the HVR-H1 comprises an amino acid sequence selected from the group consisting of SEQ ID NOs:3-24.

437. The isolated antibody of embodiment 435 or embodiment 436, wherein the HVR-H2 comprises an amino acid sequence selected from the group consisting of SEQ ID NOs:25-49.

438. The isolated antibody of any one of embodiments 435-437, wherein the HVR-H3 comprises an amino acid sequence selected from the group consisting of SEQ ID NOs:50-119.

439. The isolated antibody of any one of embodiments 435-438, wherein the HVR-L1 comprises an amino acid sequence selected from the group consisting of SEQ ID NOs: 120-137.

440. The isolated antibody of any one of embodiments 435-439, wherein the HVR-L2 comprises an amino acid sequence selected from the group consisting of SEQ ID NOs: 138-152.

441. The isolated antibody of any one of embodiments 435-440, wherein the HVR-L3 comprises an amino acid sequence selected from the group consisting of SEQ ID NOs: 153-236.

442. The isolated antibody of any one of embodiments 303-433, wherein the isolated antibody comprises a heavy chain variable domain and a light chain variable domain, wherein the heavy chain variable domain comprises:
  (a) an HVR-H1 comprising an amino acid sequence selected from the group consisting of SEQ ID NOs:3-24, or an amino acid sequence with at least about 95% homology to an amino acid sequence selected from the group consisting of SEQ ID NOs:3-24;
  (b) an HVR-H2 comprising an amino acid sequence selected from the group consisting of SEQ ID NOs: 25-49, or an amino acid sequence with at least about 95% homology to an amino acid sequence selected from the group consisting of SEQ ID NOs: 25-49; and
  (c) an HVR-H3 comprising an amino acid sequence selected from the group consisting of SEQ ID NOs: 50-119, or an amino acid sequence with at least about 95% homology to an amino acid sequence selected from the group consisting of SEQ ID NOs: 50-119; and/or
wherein the light chain variable domain comprises:
  (a) an HVR-L1 comprising an amino acid sequence selected from the group consisting of SEQ ID NOs: 120-137, or an amino acid sequence with at least about 95% homology to an amino acid sequence selected from the group consisting of SEQ ID NOs: 120-137;
  (b) an HVR-L2 comprising an amino acid sequence selected from the group consisting of SEQ ID NOs: 138-152, or an amino acid sequence with at least about 95% homology to an amino acid sequence selected from the group consisting of SEQ ID NOs: 138-152; and
  (c) an HVR-L3 comprising an amino acid sequence selected from the group consisting of SEQ ID NOs: 153-236 or an amino acid sequence with at least about 95% homology to an amino acid sequence selected from the group consisting of SEQ ID NOs: 138-152.

443. An isolated anti-human TREM2 antibody, wherein the isolated antibody comprises a heavy chain variable domain and a light chain variable domain, wherein the heavy chain variable domain comprises the HVR-H1, HVR-H2, and/or HVR-H3 of a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87, and/or wherein the light chain variable domain comprises the HVR-L 1, HVR-L2, and/or HVR-L3 of a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

444. The isolated antibody of embodiment 443, wherein the HVR-H1 comprises an amino acid sequence selected from the group consisting of SEQ ID NOs:3-24.

445. The isolated antibody of embodiment 443 or embodiment 444, wherein the HVR-H2 comprises an amino acid sequence selected from the group consisting of SEQ ID NOs:25-49.

446. The isolated antibody of any one of embodiments 443-445, wherein the HVR-H3 comprises an amino acid sequence selected from the group consisting of SEQ ID NOs:50-119.

447. The isolated antibody of any one of embodiments 443-446, wherein the HVR-L1 comprises an amino acid sequence selected from the group consisting of SEQ ID NOs: 120-137.

448. The isolated antibody of any one of embodiments 443-447, wherein the HVR-L2 comprises an amino acid sequence selected from the group consisting of SEQ ID NOs: 138-152.

449. The isolated antibody of any one of embodiments 443-448, wherein the HVR-L3 comprises an amino acid sequence selected from the group consisting of SEQ ID NOs: 153-236.

450. The isolated antibody of embodiment 443, wherein the isolated antibody comprises a heavy chain variable domain and a light chain variable domain, wherein the heavy chain variable domain comprises an HVR-H1 comprising an amino acid sequence selected from the group consisting of SEQ ID NOs:3-24, an HVR-H2 comprising an amino acid sequence selected from the group consisting of SEQ ID NOs:25-49, and an HVR-H3 comprising an amino acid sequence selected from the group consisting of SEQ ID NOs:50-119, and/or wherein the light chain variable domain comprises an HVR-L1 comprising an amino acid sequence selected from the group consisting of SEQ ID NOs: 120-137, an HVR-L2 comprising an amino acid sequence selected from the group consisting of SEQ ID NOs:138-152, and an HVR-L3 comprising an amino acid sequence selected from the group consisting of SEQ ID NOs: 153-236.

451. An isolated anti-human TREM2 antibody which binds essentially the same TREM2 epitope as a monoclonal antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab53, Ab54, Ab55, Ab56, Ab57, Ab58, Ab59, Ab60, Ab61, Ab62, Ab63, Ab64, Ab65, Ab66, Ab67, Ab68, Ab69, Ab70, Ab71, Ab72, Ab73, Ab74, Ab75, Ab76, Ab77, Ab78, Ab79, Ab80, Ab81, Ab82, Ab83, Ab84, Ab85, Ab86, and Ab87.

452. An isolated anti-human TREM2 antibody, wherein the isolated antibody comprises a heavy chain variable domain and a light chain variable domain, wherein the heavy chain variable domain comprises:

(a) an HVR-H1 comprising an amino acid sequence selected from the group consisting of SEQ ID NOs:3-24, or an amino acid sequence with at least about 95% homology to an amino acid sequence selected from the group consisting of SEQ ID NOs:3-24;

(b) an HVR-H2 comprising an amino acid sequence selected from the group consisting of SEQ ID NOs: 25-49, or an amino acid sequence with at least about 95% homology to an amino acid sequence selected from the group consisting of SEQ ID NOs: 25-49; and (c) an HVR-H3 comprising an amino acid sequence selected from the group consisting of SEQ ID NOs: 50-119, or an amino acid sequence with at least about 95% homology to an amino acid sequence selected from the group consisting of SEQ ID NOs: 50-119; and/or wherein the light chain variable domain comprises:

(a) an HVR-L1 comprising an amino acid sequence selected from the group consisting of SEQ ID NOs: 120-137, or an amino acid sequence with at least about 95% homology to an amino acid sequence selected from the group consisting of SEQ ID NOs: 120-137;

(b) an HVR-L2 comprising an amino acid sequence selected from the group consisting of SEQ ID NOs: 138-152, or an amino acid sequence with at least about 95% homology to an amino acid sequence selected from the group consisting of SEQ ID NOs: 138-152; and (c) an HVR-L3 comprising an amino acid sequence selected from the group consisting of SEQ ID NOs: 153-236 or an amino acid sequence with at least about 95% homology to an amino acid sequence selected from the group consisting of SEQ ID NOs: 138-152.

453. The isolated antibody of any one of embodiments 443-452, wherein the antibody is an agonist antibody, and wherein the antibody induces one or more TREM2 activities.

454. The isolated antibody of embodiment 453, wherein the isolated antibody induces or retains TREM2 clustering on a cell surface.

455. The isolated antibody of embodiment 453 or embodiment 454, wherein the one or more TREM2 activities are selected from the group consisting of TREM2 binding to DAP12; DAP12 binding to TREM2; TREM2 phosphorylation, DAP12 phosphorylation; PI3K activation; increased expression of one or more cytokines selected from the group consisting of IL-12p70, IL-6, and IL-10; reduced expression of one or more pro-inflammatory mediators selected from the group consisting of IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, and CRP; reduced expression of TNF-α, IL-6, or both; extracellular signal-regulated kinase (ERK) phosphorylation; increased expression of C—C chemokine receptor 7 (CCR7); induction of microglial cell chemotaxis toward CCL19 and CCL21 expressing cells; increased ability of dendritic cells, monocytes, microglia, and/or macrophages to induce T-cell proliferation; a n increase, normalization, or both of the ability of bone marrow-derived dendritic cells to induce antigen-specific T-cell proliferation; induction of osteoclast production, increased rate of osteoclastogenesis, or both; increasing the survival and/or function of one or more of dendritic cells, macrophages, M1 macrophages, activated M1 macrophages M2 macrophages, osteoclasts, Langerhans cells of skin, Kupffer cells, microglial cells, M1 microglial cells, activated M1 microglial cells, and M2 microglial cells; induction of one or more types of clearance selected from the group consisting of cancer cells clearance, apoptotic neuron clearance, nerve tissue debris clearance, non-nerve tissue debris clearance, bacteria or other foreign body clearance, and disease-causing protein clearance; induction of phagocytosis of one or more of apoptotic neurons, nerve tissue debris, non-nerve tissue debris, bacteria, other foreign bodies, disease-causing proteins or tumor cells; normalization of disrupted TREM2/DAP12-dependent gene expression; recruitment of Syk, ZAP70, or both to the TREM2/DAP12 complex; Syk phosphorylation; increased expression of CD83 and/or CD86 on dendritic cells, microglia, monocytes, or macrophages; reduced secretion of one or more inflammatory cytokines selected from the group consisting of IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, CRP, and MCP-1; reduced expression of one or more inflammatory receptors; increasing phagocytosis by macrophages, monocytes, dendritic cells, and/or microglia under conditions of reduced levels of MCSF; decreasing phagocytosis by macrophages, monocytes, dendritic cells, and/or microglia in the presence of normal levels of MCSF; increasing activity of one or more TREM2-dependent genes; and any combination thereof.

456. The isolated antibody of any one of embodiments 453-455, wherein the antibody is of the IgG class the IgM class, or the IgA class.

457. The isolated antibody of embodiment 456, wherein the antibody is of the IgG class and has an IgG1, IgG2, IgG3, or IgG4 isotype.

458. The isolated antibody of embodiment 457, wherein the antibody has an IgG2 isotype.

459. The isolated antibody of embodiment 458, wherein the antibody comprises a human IgG2 constant region.

460. The isolated antibody of embodiment 459, wherein the human IgG2 constant region comprises an Fc region.

461. The isolated antibody of any one of embodiments 458-460, wherein the antibody induces the one or more TREM2 activities independently of binding to an Fc receptor.

462. The isolated antibody of any one of embodiments 458-461, wherein the antibody binds an inhibitory Fc receptor.

463. The isolated antibody of embodiment 462, wherein the inhibitory Fc receptor is inhibitory Fc-gamma receptor IIB (FcγIIB).

464. The isolated antibody of embodiment 462 or embodiment 463, wherein the Fc region comprises one or more modifications.

465. The isolated antibody of embodiment 464, wherein the Fc region comprises one or more amino acid substitutions.

466. The isolated antibody of embodiment 465, wherein the one or more amino acid substitutions in the Fc region are at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to EU numbering.

467. The isolated antibody of embodiment 459, wherein the human IgG2 constant region comprises a light chain constant region comprising a C214S amino acid substitution, wherein the numbering of the residues is according to EU numbering.

468. The isolated antibody of embodiment 457, wherein the antibody has an IgG1 isotype.

469. The isolated antibody of embodiment 468, wherein the antibody comprises a human IgG1 constant region.

470. The isolated antibody of embodiment 469, wherein the human IgG1 constant region comprises an Fc region.

471. The isolated antibody of any one of embodiments 468-470, wherein the antibody binds an inhibitory Fc receptor.

472. The isolated antibody of embodiment 471, wherein the inhibitory Fc receptor is inhibitory Fc-gamma receptor IIB (FcγRIIB).

473. The isolated antibody of any one of embodiments 470-472, wherein the Fc region comprises one or more modifications.

474. The isolated antibody of embodiment 473, wherein the Fc region comprises one or more amino acid substitutions.

475. The isolated antibody of embodiment 474, wherein the one or more amino acid substitutions in the Fc region are at a residue position selected from the group consisting of N297A, D265A, L234A, L235A, G237A, C226S, C229S, E233P, L234V, L234F, L235E, P331 S, S267E, L328F, A330L, M252Y, S254T, T256E, and any combination thereof, wherein the numbering of the residues is according to EU numbering.

476. The isolated antibody of any one of embodiments 470-472, wherein the antibody comprises an IgG2 isotype heavy chain constant domain 1(CH1) and hinge region.

477. The isolated antibody of embodiment 476, wherein the IgG2 isotype CH1 and hinge region comprise the amino acid sequence of ASTKGPSVFP LAPCSRSTSE STAALGCLVK DYFPEPVTVS WNSGALTSGVHTFPAVLQSS GLYSLSSVVT VPSSNFGTQT YTCNVDHKPS NTKVDKTVERKCCVECPPCP (SEQ ID NO:397).

478. The isolated antibody of embodiment 476 or embodiment 477, wherein the antibody Fc region comprises a S267E amino acid substitution, a L328F amino acid substitution, or both, and/or a N297A or N297Q amino acid substitution, wherein the numbering of the residues is according to EU numbering.

479. The isolated antibody of embodiment 468, wherein the antibody comprises a mouse IgG1 constant region.

480. The isolated antibody of embodiment 457, wherein the antibody has an IgG4 isotype.

481. The isolated antibody of embodiment 480, wherein the antibody comprises a human IgG4 constant region.

482. The isolated antibody of embodiment 481, wherein the human IgG4 constant region comprises an Fc region.

483. The isolated antibody of any one of embodiments 480-482, wherein the antibody binds an inhibitory Fc receptor.

484. The isolated antibody of embodiment 483, wherein the inhibitory Fc receptor is inhibitory Fc-gamma receptor IIB (FcγIIB).

485. The isolated antibody of any one of embodiments 482-484, wherein the Fc region comprises one or more modifications.

486. The isolated antibody of embodiment 485, wherein the Fc region comprises one or more amino acid substitutions.

487. The isolated antibody of embodiment 486, wherein the one or more amino acid substitutions in the Fc region are at a residue position selected from the group consisting of L235A, G237A, S228P, L236E, S267E, E318A, L328F, M252Y, S254T, T256E, and any combination thereof, wherein the numbering of the residues is according to EU numbering.

488. The isolated antibody of embodiment 456, wherein the antibody has a hybrid IgG2/4 isotype.

489. The isolated antibody of embodiment 488, wherein the antibody comprises an amino acid sequence comprising amino acids 118 to 260 of human IgG2 and amino acids 261 to 447 of human IgG4, wherein the numbering of the residues is according to EU numbering.

490. The isolated antibody of embodiment 481, wherein the antibody comprises a mouse IgG4 constant region.

491. The isolated antibody of any one of embodiments 451-490, wherein the isolated antibody is an antibody fragment that binds to one or more human proteins selected from the group consisting of human TREM2, a naturally occurring variant of human TREM2, and a disease variant of TREM2, and wherein the antibody fragment is cross-linked to a second antibody fragment that binds to one or more human proteins selected from the group consisting of human TREM2, a naturally occurring variant of human TREM2, and a disease variant of TREM2.

492. The isolated antibody of embodiment 491, wherein the fragment is an Fab, Fab', Fab'-SH, F(ab')2, Fv or scFv fragment.

493. The isolated antibody of any one of embodiments 443-452, wherein the isolated antibody is an inert antibody.

494. The isolated antibody of any one of embodiments 443-452, wherein the isolated antibody is an antagonist antibody.

495. The isolated antibody of embodiment 494, wherein the isolated antibody inhibits one or more TREM2 activities.

496. The isolated antibody of embodiment 495, wherein the one or more TREM2 activities are selected from the group consisting of decreasing activity of one or more TREM2-dependent genes; decreasing activity of one or more nuclear factor of activated T-cells (NFAT) transcription factors; decreasing the survival of macrophages, microglial cells, monocytes, osteoclasts, Langerhans cells of skin, Kupffer cells, and/or dendritic cells; and any combination thereof.

497. The isolated antibody of any one of embodiments 494-496, wherein the isolated antibody inhibits interaction between TREM2 and one or more TREM2 ligands, inhibits TREM2 signal transduction, or both.

498. The isolated antibody of any one of embodiments 493-497, wherein the antibody is incapable of binding an Fc-gamma receptor (FcγR).

499. The isolated antibody of embodiment 498, wherein the antibody has an IgG1 isotype.

500. The isolated antibody of embodiment 499, wherein the antibody comprises a human IgG1 constant region.

501. The isolated antibody of embodiment 500, wherein the human IgG1 constant region comprises an Fc region.

502. The isolated antibody of embodiment 501, wherein the Fc region comprises one or more modifications.

503. The isolated antibody of embodiment 502, wherein the Fc region comprises one or more amino acid substitutions.

504. The isolated antibody of embodiment 503, wherein the one or more amino acid substitutions in the Fc region are at a residue position selected from the group consisting of N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof, wherein the numbering of the residues is according to EU numbering.

505. The isolated antibody of embodiment 504, wherein the Fc region further comprises an amino acid deletion at a position corresponding to glycine 236 according to EU numbering.

506. The isolated antibody of embodiment 499, wherein the antibody comprises a mouse IgG1 constant region.

507. The isolated antibody of embodiment 498, wherein the antibody has an IgG2 isotype.

508. The isolated antibody of embodiment 507, wherein the antibody comprises a human IgG2 constant region.

509. The isolated antibody of embodiment 508, wherein the human IgG2 constant region comprises an Fc region.

510. The isolated antibody of embodiment 509, wherein the Fc region comprises one or more modifications.

511. The isolated antibody of embodiment 510, wherein the Fc region comprises one or more amino acid substitutions.

512. The isolated antibody of embodiment 511, wherein the one or more amino acid substitutions in the Fc region are at a residue position selected from the group consisting of V234A, G237A, H268E, V309L, N297A, N297Q, A330S, P331S, C232S, C233S, M252Y, S254T, T256E, and any combination thereof, wherein the numbering of the residues is according to EU numbering.

513. The isolated antibody of embodiment 498, wherein the antibody has an IgG4 isotype.

514. The isolated antibody of embodiment 513, wherein the antibody comprises a human IgG4 constant region.

515. The isolated antibody of embodiment 514, wherein the human IgG4 constant region comprises an Fc region.

516. The isolated antibody of embodiment 515, wherein the Fc region comprises one or more modifications.

517. The isolated antibody of embodiment 516, wherein the Fc region comprises one or more amino acid substitutions.

518. The isolated antibody of embodiment 517, wherein the one or more amino acid substitutions in the Fc region are at a residue position selected from the group consisting of E233P, F234V, L235A, G237A, E318A, S228P, L236E, S241P, L248E, T394D, M252Y, S254T, T256E, N297A, N297Q, and any combination thereof, wherein the numbering of the residues is according to EU numbering.

519. The isolated antibody of any one of embodiments 443-518, wherein the isolated antibody is an antibody fragment that binds to one or more human proteins selected from the group consisting of human TREM2, a naturally occurring variant of human TREM2, and a disease variant of TREM2.

520. The isolated antibody of embodiment 519, wherein the fragment is an Fab, Fab', Fab'-SH, F(ab')2, Fv or scFv fragment.

521. The isolated antibody of embodiment 475, embodiment 504, or embodiment 505, wherein the Fc region further comprises one or more additional amino acid substitutions at a position selected from the group consisting of A330L, L234F; L235E, P331S, and any combination thereof, wherein the numbering of the residues is according to EU numbering.

522. The isolated antibody of any one of embodiments 465-521, wherein the Fc region further comprises one or more additional amino acid substitutions at a position selected from the group consisting of M252Y, S254T, T256E, and any combination thereof, wherein the numbering of the residues is according to EU numbering.

523. The isolated antibody of embodiment 487 or embodiment 518, wherein the Fc region further comprises a serine to proline amino acid substitution at position 228 according to EU numbering.

524. The isolated antibody of any one of embodiments 443-523, wherein the antibody is a human antibody, a humanized antibody, a bispecific antibody, a multivalent antibody, or a chimeric antibody.

525. The isolated antibody of any one of embodiments 443-524, wherein the antibody is a bispecific antibody recognizing a first antigen and a second antigen.

526. The isolated antibody of any one of embodiments 443-525, wherein the antibody is a monoclonal antibody.
527. The isolated antibody of any one of the preceding embodiments, wherein the isolated antibody binds specifically to both human TREM2 and mouse TREM2.
528. The isolated antibody of any one of the preceding embodiments, wherein the isolated antibody has dissociation constant ($K_D$) for human TREM2 and mouseTREM2 that ranges from less than about 6.70 nM to less than about 0.23 nM.
529. The isolated antibody of any one of the preceding embodiments, wherein the isolated antibody has dissociation constant ($K_D$) for human TREM2-Fc fusion protein that ranges from less than about 0.71 nM to less than about 0.23 nM.
530. The isolated antibody of any one of the preceding embodiments, wherein the isolated antibody has dissociation constant ($K_D$) for human monomeric TREM2 protein that ranges from less than about 6.70 nM to less than about 0.66 nM.
531. The isolated antibody of any one of the preceding embodiments, wherein the isolated antibody has dissociation constant ($K_D$) for mouse TREM2-Fc fusion protein that ranges from less than about 4.90 nM to less than about 0.35 nM.
532. An isolated nucleic acid encoding the antibody of any one of the preceding embodiments.
533. A vector comprising the nucleic acid of embodiment 532.
534. A host cell comprising the vector of embodiment 533.
535. A method of producing an antibody, comprising culturing the cell of embodiment 534 so that the antibody is produced.
536. The method of embodiment 535, further comprising recovering the antibody produced by the cell.
537. A pharmaceutical composition comprising the antibody of any one of embodiments 303-531 and a pharmaceutically acceptable carrier.
538. A method of preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, comprising administering to the individual a therapeutically effective amount of an isolated antibody that binds to a TREM2 protein.
539. A method of inducing or promoting innate immune cell survival or wound healing an individual in need thereof, comprising administering to the individual a therapeutically effective amount of an isolated agonist antibody that binds to a TREM2 protein.
540. The method of embodiment 538 or embodiment 539, wherein the isolated antibody is:
  i. (a) an agonist antibody;
     (b) an inert antibody; or an
     (c) an anatagonist antibody.
541. The method of embodiment 540, wherein:
  i. (a) the antibody is of the IgG class the IgM class, or the IgA class; and/or
  ii. (b) the antibody has an IgG1, IgG2, IgG3, or IgG4 isotype
542. The method of embodiment 541, wherein the antibody comprises one or more amino acid substitutions in the Fc region are at a residue position selected from the group consisting of:
  i. (a) V234A, G237A, H268Q, V309L, A330S, P331S, C232S, C233S, S267E, L328F, M252Y, S254T, T256E, and any combination thereof;
  ii. (b) N297A, D265A, L234A, L235A, G237A, C226S, C229S, E233P, L234V, L234F, L235E, P331S, S267E, L328F, A330L, M252Y, S254T, T256E, and any combination thereof;
  iii. (c) L235A, G237A, S228P, L236E, S267E, E318A, L328F, M252Y, S254T, T256E, and any combination thereof;
  iv. (d) N297A, N297Q, D265A, L234A, L235A, C226S, C229S, P238S, E233P, L234V, P238A, A327Q, A327G, P329A, K322A, L234F, L235E, P331 S, T394D, A330L, M252Y, S254T, T256E, and any combination thereof;
  v. (e) V234A, G237A, H268E, V309L, N297A, N297Q, A330S, P331S, C232S, C233S, M252Y, S254T, T256E, and any combination thereof; or vi. (f) E233P, F234V, L235A, G237A, E318A, S228P, L236E, S241P, L248E, T394D, M252Y, S254T, T256E, N297A, N297Q, and any combination thereof, vii. wherein the numbering of the residues is according to EU numbering.
543. The method of ant one of embodiments 538-542, wherein the isolated antibody:
  i. (a) binds to one or more amino acids within amino acid residues 43-50 of SEQ ID NO: 1, or amino acid residues on a TREM2 protein corresponding to amino acid residues 43-50 of SEQ ID NO: 1; or
  ii. (b) one or more amino acids within amino acid residues 49-57 of SEQ ID NO: 1, or amino acid residues on a TREM2 protein corresponding to amino acid residues 49-57 of SEQ ID NO: 1.
544. The method of ant one of embodiments 538-543, wherein the isolated antibody:
  i. (a) binds essentially the same TREM2 epitope as the antibody Ab52;
  ii. (b) comprises a heavy chain variable domain and a light chain variable domain, wherein the heavy chain variable domain comprises the HVR-H1, HVR-H2, and/or HVR-H3 of the monoclonal antibody Ab52; and/or wherein the light chain variable domain comprises the HVR-L1, HVR-L2, and/or HVR-L3 of the monoclonal antibody Ab52;
  iii. (c) comprises a heavy chain variable domain and a light chain variable domain, wherein the heavy chain variable domain comprises an HVR-H1 comprising the amino acid sequence of SEQ ID NO:398, or an amino acid sequence with at least about 95% homology to the amino acid sequence of SEQ ID NO:398, an HVR-H2 comprising the amino acid sequence of SEQ ID NO:399 or an amino acid sequence with at least about 95% homology to the amino acid sequence of SEQ ID NO:399, and an HVR-H3 comprising the amino acid sequence of SEQ ID NO:400 or an amino acid sequence with at least about 95% homology to the amino acid sequence of SEQ ID NO:400, and/or wherein the light chain variable domain comprises an HVR-L1 comprising the amino acid sequence of SEQ ID NO:401 or an amino acid sequence with at least about 95% homology to the amino acid sequence of SEQ ID NO:401, an HVR-L2 comprising the amino acid sequence of SEQ ID NO:402 or an amino acid sequence with at least about 95% homology to the amino acid sequence of SEQ ID NO:402, and an HVR-L3 comprising the amino acid sequence of SEQ ID NO:403 or an amino acid sequence with at least about 95% homology to the amino acid sequence of SEQ ID NO:403;

iv. (d) binds essentially the same TREM2 epitope as the antibody Ab21;

v. (e) comprises a heavy chain variable domain and a light chain variable domain, wherein the heavy chain variable domain comprises the HVR-H1, HVR-H2, and/or HVR-H3 of the monoclonal antibody Ab21; and/or wherein the light chain variable domain comprises the HVR-L 1, HVR-L2, and/or HVR-L3 of the monoclonal antibody Ab21; or vi. (f) comprises a heavy chain variable domain and a light chain variable domain, wherein the heavy chain variable domain comprises an HVR-H1 comprising the amino acid sequence of SEQ ID NO:404 or an amino acid sequence with at least about 95% homology to the amino acid sequence of SEQ ID NO:404, an HVR-H2 comprising the amino acid sequence of SEQ ID NO:405 or an amino acid sequence with at least about 95% homology to the amino acid sequence of SEQ ID NO:405, and an HVR-H3 comprising the amino acid sequence of SEQ ID NO:406 or an amino acid sequence with at least about 95% homology to the amino acid sequence of SEQ ID NO:406, and/or wherein the light chain variable domain comprises an HVR-L1 comprising the amino acid sequence of SEQ ID NO:407 or an amino acid sequence with at least about 95% homology to the amino acid sequence of SEQ ID NO:407, an HVR-L2 comprising the amino acid sequence of SEQ ID NO:408 or an amino acid sequence with at least about 95% homology to the amino acid sequence of SEQ ID NO:408, and an HVR-L3 comprising the amino acid sequence of SEQ ID NO:409 or an amino acid sequence with at least about 95% homology to the amino acid sequence of SEQ ID NO:409.

545. The method of embodiment 538, wherein the isolated antibody is the isolated antibody of any one of embodiments 303-531.

546. The method of embodiment 539, wherein the isolated agonist antibody is the isolated antibody of any one of embodiments 303-385, 420-492, and 519-531.

547. The method of any one of embodiments 538 and 540-545, wherein the individual has a heterozygous variant of TREM2, wherein the variant comprises one or more substitutions selected from the group consisting of:

viii. a glutamic acid to stop codon substitution in the nucleic acid sequence encoding amino acid residue Glu14 of SEQ ID NO: 1;

ix. a glutamine to stop codon substitution in the nucleic acid sequence encoding amino acid residue Gln33 of SEQ ID NO: 1;

x. a tryptophan to stop codon substitution in the nucleic acid sequence encoding amino acid residue Trp44 of SEQ ID NO: 1;

xi. an arginine to histidine amino acid substitution at an amino acid corresponding to amino acid residue Arg47 of SEQ ID NO: 1;

xii. a tryptophan to stop codon substitution in the nucleic acid sequence encoding amino acid residue Trp78 of SEQ ID NO: 1;

xiii. a valine to glycine amino acid substitution at an amino acid corresponding to amino acid residue Val126 of SEQ ID NO: 1;

xiv. an aspartic acid to glycine amino acid substitution at an amino acid corresponding to amino acid residue Asp134 of SEQ ID NO: 1; and viii. a lysine to asparagine amino acid substitution at an amino acid corresponding to amino acid residue Lys186 of SEQ ID NO: 1.

548. The method of any one of embodiments 538, 540-545, and 547, wherein the individual has a heterozygous variant of TREM2, wherein the variant comprises a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; or both.

549. The method of any one of embodiments 538, 540-545, and 547-548, wherein the individual has a heterozygous variant of DAP12, wherein the variant comprises one or more variants selected from the group consisting of:

vi. a methionine to threonine substitution at an amino acid corresponding to amino acid residue Met1 of SEQ ID NO: 2;

vii. a glycine to arginine amino acid substitution at an amino acid corresponding to amino acid residue Gly49 of SEQ ID NO: 2;

viii. a deletion within exons 1-4 of the nucleic acid sequence encoding SEQ ID NO: 2;

ix. an insertion of 14 amino acid residues at exon 3 of the nucleic acid sequence encoding SEQ ID NO: 2; and x. a guanine nucleotide deletion at a nucleotide corresponding to nucleotide residue G141 of the nucleic acid sequence encoding SEQ ID NO: 2.

550. The method of any one of embodiments 538 and 540-545, wherein the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

551. The method of any one of embodiments 538 and 540-545, and 550, further comprising administering to the individual at least one antibody that specifically binds to an inhibitory checkpoint molecule, and/or another standard or investigational anti-cancer therapy.

552. The method of embodiment 551, wherein the at least one antibody that specifically binds to an inhibitory checkpoint molecule is administered in combination with the isolated antibody.

553. The method of embodiment 551 or embodiment 552, wherein the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof.

554. The method of embodiment 551, wherein the standard or investigational anti-cancer therapy is one or more therapies selected from the group consisting of radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

555. The method of any one of embodiments 538, 540-545, and 550, further comprising administering to the individual at least one antibody that specifically binds to an inhibitory cytokine.

556. The method of embodiment 555, wherein the at least one antibody that specifically binds to an inhibitory cytokine is administered in combination with the isolated antibody.

557. The method of embodiment 555 or embodiment 556, wherein the at least one antibody that specifically binds to an inhibitory cytokine is selected from the group consisting of an anti-CCL2 antibody, an anti-CSF-1 antibody, an anti-IL-2 antibody, and any combination thereof.

558. The method of any one of embodiments 538, 540-545, and 550, further comprising administering to the individual at least one agonistic antibody that specifically binds to a stimulatory checkpoint protein.

559. The method of embodiment 558, wherein the at least one agonistic antibody that specifically binds to a stimulatory checkpoint protein is administered in combination with the isolated antibody.

560. The method of embodiment 558 or embodiment 559, wherein the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

561. The method of any one of embodiments 538, 540-545, and 550, further comprising administering to the individual at least one stimulatory cytokine.

562. The method of embodiment 561, wherein the at least one stimulatory cytokine is administered in combination with the isolated antibody.

563. The method of embodiment 561 or embodiment 562, wherein the at least one stimulatory cytokine is selected from the group consisting of TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, CRP, IFN-α, IFN-β, IL-2, IL-18, GM-CSF, G-CSF, and any combination thereof.

The invention will be more fully understood by reference to the following Examples. They should not, however, be construed as limiting the scope of the invention. All citations throughout the disclosure are hereby expressly incorporated by reference.

EXAMPLES

Example 1: Production, Identification, and Characterization of Agonist Anti-TREM2 and Anti-DAP12 Antibodies Introduction The amino acid sequence of the human TREM2 preprotein is set forth below in SEQ ID NO: 1. Human TREM2 contains a signal peptide located at amino residues 1-18 of SEQ ID NO: 1. Human TREM2 contains an extracellular immunoglobulin-like variable-type (IgV) domain located at amino residues 29-112 of SEQ ID NO: 1; additional extracellular sequences located at amino residues 113-174 of SEQ ID NO: 1; a transmembrane domain located at amino residues 175-195 of SEQ ID NO: 1; and an intracellular domain located at amino residues 196-230 of SEQ ID NO: 1.

TREM2 amino acid sequence (SEQ ID NO: 1):

```
        10         20         30         40
MEPLRLLILL FVTELSGAHN TTVFQGVAGQ SLQVSCPYDS 50         60         70         80
MKHWGRRKAW CRQLGEKGPC QRVVSTHNLW LLSFLRRWNG 90        100        110        120
STAITDDTLG GTLTITLRNL QPHDAGLYQC QSLHGSEADT 130        140        150        160
LRKVLVEVLA DPLDHRDAGD LWFPGESESF EDAHVEHSIS 170        180        190        200
RSLLEGEIPF PPTSILLLLA CIFLIKILAA SALWAAAWHG 210        220        230
QKPGTHPPSE LDCGHDPGYQ LQTLPGLRDT
```

A known feature of human TREM2 is that the transmembrane domain contains a lysine (aa186) that can interact with an aspartic acid in DAP12, a key adaptor protein that transduces signaling from TREM2, TREM1, and other related IgV family members.

A BLAST analysis of human TREM2 identified 18 related homologues. These homologues included the Natural Killer (NK) cell receptor NK-p44 (NCTR2), the polymeric immunoglobulin receptor (pIgR), CD300E, CD300A, CD300C, and TREML1/TLT1. The closest homologue was identified as NCTR2, having similarity with TREM2 within the IgV domain (FIG. 1A). A BLAST analysis also compared TREM proteins with other IgV family proteins (FIG. 1B).

TREM2 is also closely related to TREM1. An alignment of the amino acid sequences of TREM1 and TREM2 was generated by 2-way blast (FIG. 2A). This is limited to the IgV domain as well.

Agonistic antibodies for TREM1, NK-p44, and other members of this family have been previously described. Antibodies that bind the extracellular domain of TREM2, particularly the IgV domain (amino acid residues 29-112 of SEQ ID NO: 1) are generated using mouse hybridoma technology, phage display technology, and yeast display technology. Antibodies are then screened for their ability to activate TREM2 signaling and functions in cells and in a whole animal in vivo as described in Examples 2-39 below.

For example, agonist anti-TREM2 antibodies can be produced that target the IgV domain (amino acid residues 29-112). IgV domains bind to targets, and through multimerization of receptors, such as IgG itself or NKp44, lead to activation. Thus these domains are rational targets for agonistic antibodies. They are also highly divergent.

Agonist anti-TREM2 antibodies can also be produced that target amino acid residues 99-115 of human TREM2. It is believed that amino acid residues 99-115 correspond to a peptide that block binding of TREM2 to its endogenous target, as the corresponding peptide in mouse TREM1 (amino acid residues 83-99) block binding of TREM1 to its endogenous target (Gibot et al., Infect. Immunity 2004). The mouse TREM1 peptide is called LP17 (LQVTDSG-LYRCVIYHPP (SEQ ID NO: 414)). The equivalent region in human TREM2 is located within the CD3 domain and is located at amino acid residues 99-115 of SEQ ID NO: 1 (LQPHDAGLYQCQSLHG). Antibodies that block ligand binding could activate the receptors similar to the ligand itself.

Another approach for predicting a relevant (e.g., agonistic) site within the human TREM2 protein is by targeting the sites where the mutations are found in Alzheimer's disease (e.g., R47H), Polycystic lipomembranous osteodysplasia with sclerosing leukoencephalopathy (PLOSL), or Nasu-Hakola disease. Also relevant is the site of the major mutations associated with human disease, which are generally found within the IgV domain.

The crystal structures of the TREM2-related structures of TREM1 (Kelker, M S et al., J Mol Biol, 2004. 344(5): p. 1175-81; Kelker, M S et al., J Mol Biol, 2004. 342(4): p. 1237-48; and Radaev, S et al., Structure, 2003. 11(12): p. 1527-35), TLT1 (Gattis, J L et al., *J Biol Chem*, 2006. 281(19): p. 13396-403), and NKp44 have been described, and thus structural regions/features are identified within the IgV domain that are particularly likely to play a central role in interacting with natural agonists. These studies support the belief that the complementary determining regions (CDR1, CDR2, CDR3) play a major role in ligand binding. TREM1 has been reported to be either monomeric (Gattis, J L et al., *J Biol Chem*, 2006. 281(19): p. 13396-403) or dimeric (Radaev, S et al., Structure, 2003. 11(12): p. 1527-35) in vitro under cell-free conditions, but its oligomeric state in vivo remains unclear, as well as that of TREM2.

The amino acid sequence of human DAP12 is set forth below as SEQ ID NO: 2:

```
         10         20         30         40
MGGLEPCSRL LLLPLLLAVS GLRPVQAQAQ SDCSCSTVSP 50         60         70         80
GVLAGIVMGD LVLTVLIALA VYFLGRLVPR GRGAAEAATR 90        100        110
KQRITETESP YQELQGQRSD VYSDLNTQRP YYK
```

DAP12 is a single-pass type I membrane protein. It contains an extracellular domain located at amino acid residues 22-40 of human DAP12 (SEQ ID NO: 2); a transmembrane domain located at amino acid residues 41-61 of human DAP12 (SEQ ID NO: 2); and an intracellular domain located at amino acid residues 62-113 of human DAP12 (SEQ ID NO: 2). The immunoreceptor tyrosine-based activation motif (ITAM) domain of DAP12 is located at amino acid residues 80-118 of human DAP12 (SEQ ID NO: 2). An aspartic acid in DAP12 interacts with the transmembrane domain of human TREM2 containing a lysine at amino acid residue 186, and transduces signaling from TREM2, TREM1, and other related IgV family member proteins.

Agonist anti-DAP12 antibodies can be produced that target amino acid residues 22-40 of the human DAP12. It is believed that DAP12 is a disulfide-bonded dimer, associating with TREM2, and that dimerizing DAP12 with an antibody against the extra cellular domain encompassing amino acid residues 22-40 will activate one or more TREM2 and/or DAP12 activities.

The studies discussed herein describe the generation of agonist antibodies that bind TREM2. Antibodies were screened for binding to TREM2 expressing cells and for their ability to activate TREM2 signaling and functionality.

Results

Anti-TREM2 Antibody Production

Antibodies that bind the extracellular domain of TREM2, particularly the IgV domain (amino acid residues 29-112 of SEQ ID NO: 1) were generated using the following procedure. Eight naïve human synthetic yeast libraries each of $\sim 10^9$ diversity were designed, generated, and propagated as described previously (see, e.g., WO2009036379; WO2010105256; WO2012009568; Xu et al., (2013) *Protein. Eng. Des. Sel.* 26(10):663-670). The ADIMAB yeast-based antibody discovery platform used herein allowed for the identification of fully human, full-length, monoclonal IgG1 antibodies with broad epitopic coverage. The ADIMAB yeast is engineered to transport high quality, whole IgGs through the secretory pathway, and then present them on the surface or secrete them directly into the medium.

For the first rounds of selection, a magnetic bead sorting technique utilizing the Miltenyi MACs system was performed, as previously described (Siegel et al., (2004) *J. Immunol. Methods* 286(1-2):141-53). Briefly, yeast cells ($\sim 10^{10}$ cells/library) were incubated with 3 ml of 200 nM biotinylated TREM2 antigen or 10 nM biotinylated TREM2-Fc fusion antigen for 15 min at room temperature in FACS wash buffer PBS with 0.1% BSA. Biotinylations were performed using the EZ-Link Sulfo-NHS-Biotinylation Kit (Thermo Scientific, Cat #21425). After washing once with 50 ml ice-cold wash buffer, the cell pellet was resuspended in 40 mL wash buffer, and 500 µl Streptavidin MicroBeads (Miltenyi Biotec, Bergisch Gladbach, Germany. Cat #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany. Cat. #130-042-401). After the 5 mL was loaded, the column was washed 3 times with 3 ml FACS wash buffer. The column was then removed from the magnetic field, and the yeast were eluted with 5 mL of growth media and then grown overnight. The following three rounds of sorting were performed using flow cytometry. Approximately $1 \times 10^8$ yeast were pelleted, washed three times with wash buffer, and incubated with 200 nM, 100, or 10 biotinylated TREM2 for 10 min at room temperature respectively. Yeast were then washed twice and stained with goat anti-human F(ab')2 kappa-FITC diluted 1:100 (Southern Biotech, Birmingham, Ala., Cat #2062-02) and either streptavidin-Alexa Fluor 633 (Life Technologies, Grand Island, N.Y., Cat #S21375) diluted 1:500 or Extravidin-phycoerthyrin (Sigma-Aldrich, St Louis, Cat #E4011) diluted 1:50 secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only TREM2 binding clones for two rounds and the third round was a negative sort to decrease reagent binders. After the final round of sorting, yeast were plated and individual colonies were picked for characterization.

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences, Cat #17-5458-01). Two antibodies (Ab21 and Ab52) were selected for further analysis.

Heavy Chain and Light Chain Variable Domain Sequences of Antibodies Ab21 and Ab52

Using standard techniques, the amino acid sequences encoding the heavy chain variable (FIG. 2B) and the light chain variable (FIG. 2C) domain of antibody Ab21 and antibody Ab52 were determined.

The Kabat CDR sequences of antibody Ab21 and antibody Ab52 are set forth in Table 1.

The amino acid sequence of the heavy chain variable domain of antibody Ab21 is: EVQLVQSGAEVKKPGESLKISCKGSGYSFTTYWIGWVRQMPGKGLEWMGIIYPGDSDTRYSPSFQGQVTISADKSISTAYLQWSSLKASDTAMYYCARAGHYDGGHLGMDVWGQG TTVTVSS (SEQ ID NO:410), and the amino acid sequence of the light chain variable domain of antibody 21 is: EIVMTQSPGTLSLSPGERATLSCRASQSVSSSYLAWYQQKPGQAPRLLIYGASNRATGIPDRFSGSGSGTDFTLTISRLEPEDFAVYYCQQDDSAPYTFGGGTKVEIK (SEQ ID NO:411).

The amino acid sequence of the heavy chain variable domain of antibody Ab52 is: QVQLVQSGAEVKKPGASVKVSCKASGYTFTSYYIHWVRQAPGQGLEWMGIINPSGGST SYAQKFQGRVTMTRDTSTSTVYMELSSLRSEDTAVYYCAREADDSSGYPLGLDVWGQG TMVTVSS (SEQ ID NO:412), and the amino acid sequence of the light chain variable domain of antibody 52 is: EIVMTQSPATLSVSPGERATLSCRASQSVSSNLAWYQQKPGQAPRLLIYGASTRATGIPARFSGSGSGTEFTLTISSLQSEDFAVYYCQQVNSLPPTFGGGTKVEIK (SEQ ID NO:413).

Characterization of Ab21 and Ab52 Binding

Initial characterization of TREM2 antibodies involved determining their ability to bind TREM2 expressed on dendritic and other primary human or mouse immune cells. Cells were harvested, plated at $10^5$/ml in a 96 well plate, washed, and incubated in 100 ul PBS containing 10-50 ug/ml Mab and Fc blocking reagent for 1 hour in ice. Cells were then washed twice and incubated in 100 ul PBS containing 5 ug/ml PE-conjugated secondary antibody for 30 minutes in ice. Cells were washed twice in cold PBS and acquired on a BD FACS Canto. Data analysis and calculation of MFI values was performed with FlowJo (TreeStar) software version 10.0.7.

Figure 3A:
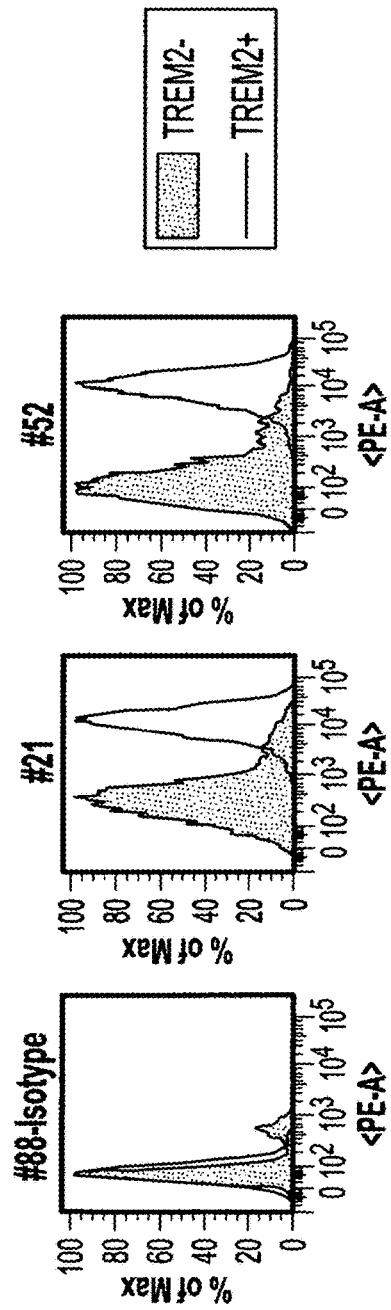
FIG. 3A shows FACS histograms demonstrating binding of TREM2 antibodies Ab21, Ab52, Ab16, Ab20, Ab66, and Ab68 to a mouse cell line (BWZ T2) expressing recombinant mouse TREM2.
Figure 3B:
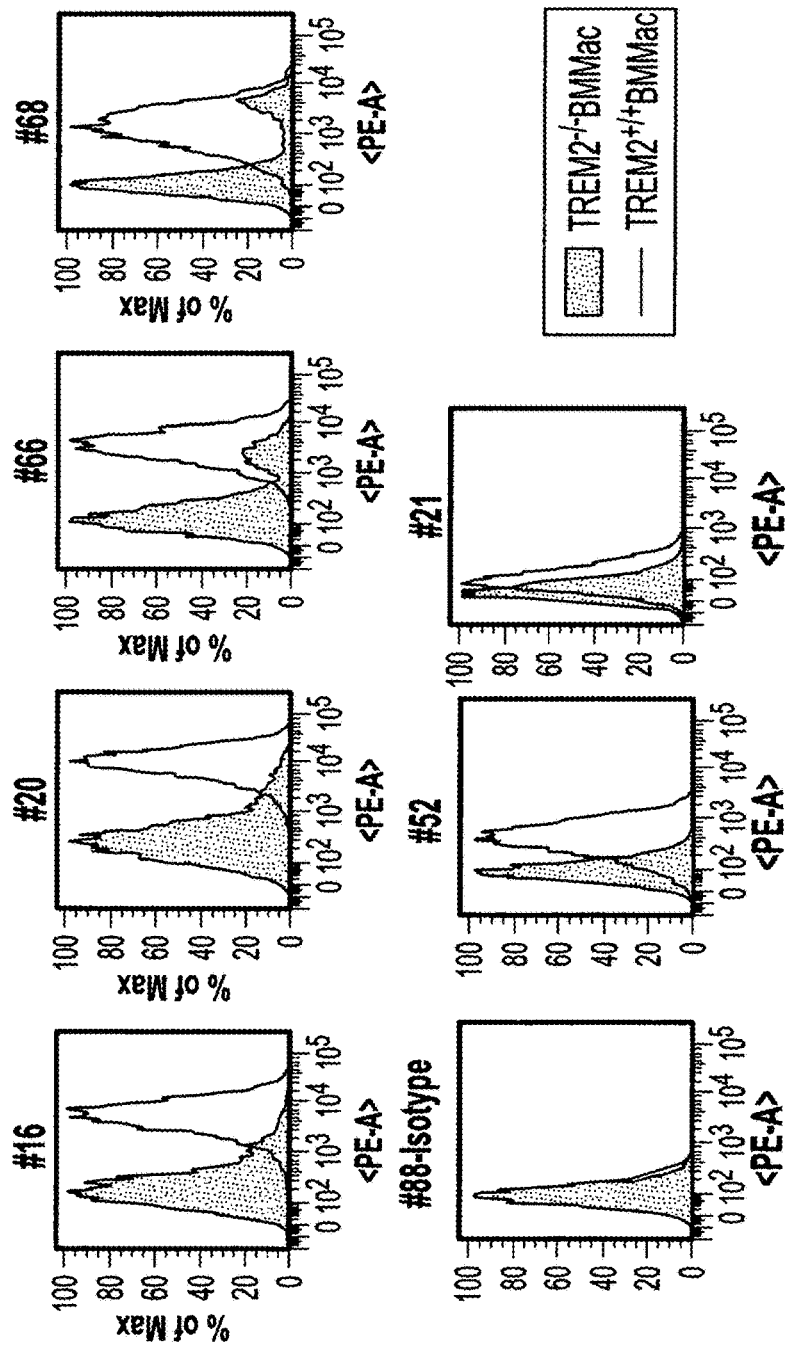
FIG. 3B shows antibodies Ab21 and Ab52 binding to WT (Trem+/+) and TREM2 deficient (TREM2−/−) bone marrow derived mouse macrophages (BMMac). Shaded histograms represent the TREM2 antibody negative population. Black outlined histograms represent the TREM2 antibody positive population.
Figure 4A:
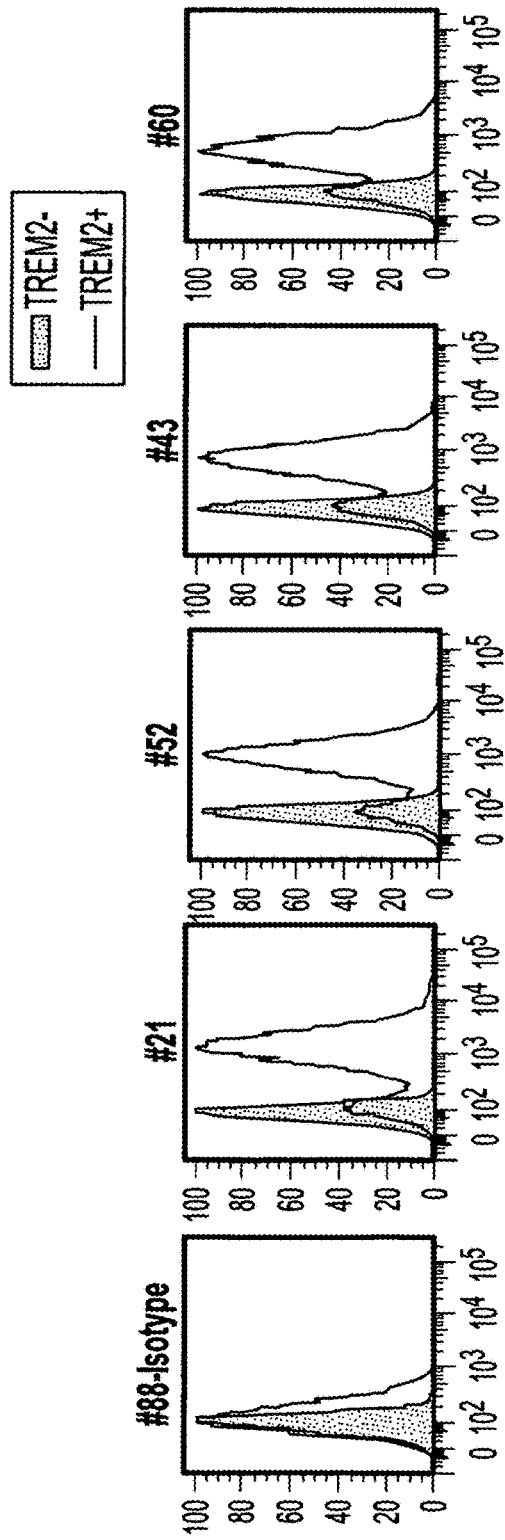
FIG. 4A shows FACS histograms demonstrating binding of TREM2 antibodies Ab21, Ab52, Ab43, and Ab60 to a human cell line (293) expressing recombinant human TREM2-DAP12 fusion protein. Shaded histograms represent a TREM2 antibody negative population. Black outlined histograms represent a TREM2 antibody positive population.
Figure 4B:
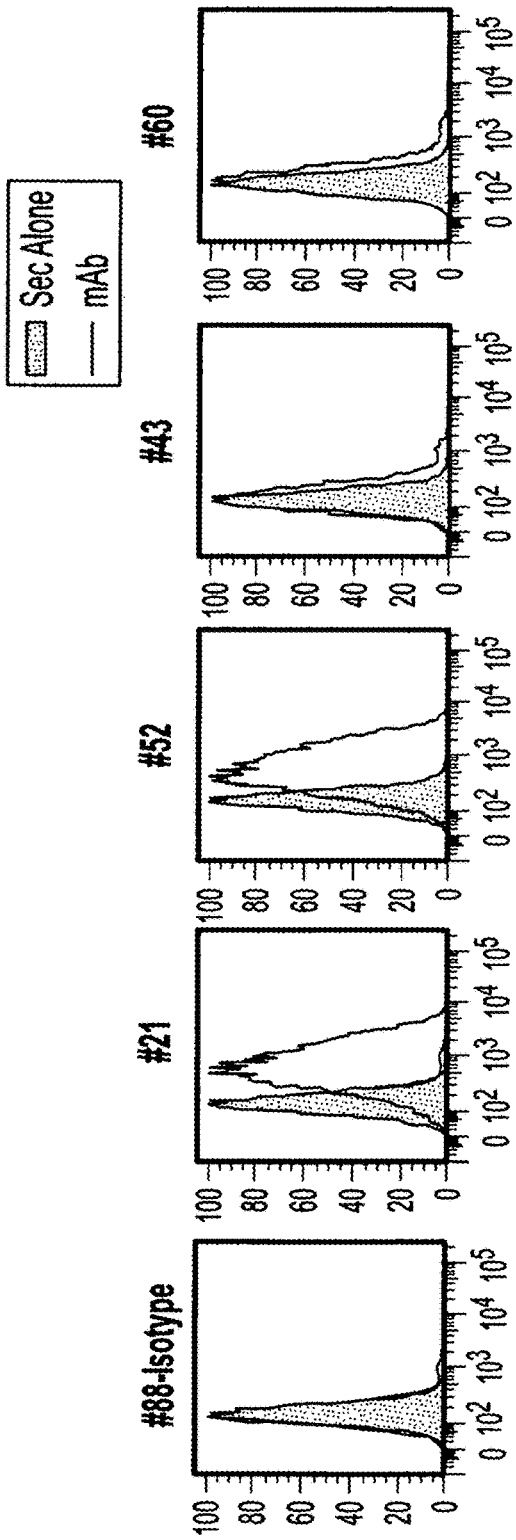
FIG. 4B shows antibodies Ab21, Ab52, Ab43, and Ab60 binding to primary human dendritic cells (hDCs). Shaded histograms represent secondary antibody alone negative control. Black outlined histograms represent the TREM2 antibody positive population.

Antibodies Ab21, Ab52, Ab16, Ab20, Ab66, and Ab68 demonstrated binding to a mouse cell line (BWZ T2) expressing recombinant mouse TREM2, as indicated by positive TREM2 antibody staining detected via FACS analysis (black outlined histograms) (FIG. 3A). Antibodies Ab21 and Ab52 demonstrated antibody binding to WT (Trem+/+) bone marrow derived mouse macrophages (BMMac, mMac), but not to TREM2 deficient (TREM2−/−) mouse macrophages (BMMac, mMacs) (FIG. 3B). Antibodies Ab21 and Ab52 demonstrated binding to both a human cell line (293) expressing recombinant Human TREM2 (FIG. 4A) and to primary human dendritic cells (hDC) (FIG. 4B). Conversely, antibodies Ab43 and ab60 bound to a human cell line expressing recombinant human TREM2 (FIG. 4A), but did not bind to primary human dendritic cells (FIG. 4B).

Mean fluorescent intensities (MFI) values for cell types bound by TREM2 antibodies Ab21 and Ab52 are listed in Table 4. Binding is compared to the parental mouse cell line (mTREM2 cell line BWZ parental), primary human cell line (hTREM2 Parental Cell line (293)), primary mouse macrophages deficient in TREM2 (mMacs KO MFI), and primary mouse dendritic cells deficient in TREM2 (mDC KO MFI).

TABLE 1A

Kabat heavy chain CDR sequences

| Antibody Name | CDR H1 | CDR H2 | CDR H3 |
|---|---|---|---|
| Ab21 | YSFTTYWIG (SEQ ID NO: 404) | IIYPGDSDTRYSPSFQG (SEQ ID NO: 405) | ARAGHYDGGHLGMDV (SEQ ID NO: 406) |
| Ab52 | YTFTSYYIH (SEQ ID NO: 398) | IINPSGGSTSYAQKFQG (SEQ ID NO: 399) | AREADDSSGYPLGLDV (SEQ ID NO: 400) |

TABLE 1B

Kabat lightchain CDR sequences

| Antibody Name | CDR L1 | CDR L2 | CDR L3 |
|---|---|---|---|
| Ab21 | RASQSVSSSYLA (SEQ ID NO: 407) | GASNRAT (SEQ ID NO: 408) | QQDDSAPYT (SEQ ID NO: 409) |
| Ab52 | RASQSVSSNLA (SEQ ID NO: 401) | GASTRAT (SEQ ID NO: 402) | QQVNSLPPT (SEQ ID NO: 403) |

TABLE 4

TREM2 Antibody Binding to Human and Mouse Cells

| Antibody | mTREM2 Cell line (BWZ-parental) MFI | mTREM2 Cell line (BWZ T2) MFI | hTREM2 Parental Cell line (293) MFI | hTREM2 Cell line (293) MFI | mMacs KO MFI | mMacs WT MFI | mDC KO MFI | mDC WT MFI | hDC % positive |
|---|---|---|---|---|---|---|---|---|---|
| Ab52 | 1021 | 15613 | 89 | 1411 | 73.3 | 174.0 | 203 | 663 | 69.1 |
| Ab21 | 1036 | 13840 | 81 | 1884 | 64.7 | 111.0 | 187 | 464 | 77.1 |

The binding affinity of each anti-TREM2 antibody was determined by measuring their $K_D$ by ForteBio or MSD-SET. ForteBio affinity measurements were performed as previously described (Estep et al, (2013) *MAbs* 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, then transferred to assay buffer for 5 min for off-rate measurement. Kinetics were analyzed using the 1:1 binding model.

Equilibrium affinity measurements were performed as previously described (Estep et al, (2013) *MAbs* 5(2):270-8). Solution equilibrium titrations (SET) were performed in PBS+0.1% IgG-Free BSA (PBSF) with antigen held constant at 50 pM and incubated with 3- to 5-fold serial dilutions of antibody starting at 10 nM. Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Table 5 lists values representing the binding affinity ($K_D$) of antibodies Ab21 and Ab52 to a human TREM2 Fc fusion protein (hTREM2-Fc), a human monomeric His tagged TREM2 protein (hTREM2-HIS), and a mouse TREM2 Fc fusion protein (mTREM2-Fc).

TABLE 5

Binding affinity of TREM2 antibodies

| Antibody | IgG $K_D$ hTREM2-Fc (M) Avid | IgG $K_D$ hTREM2-HIS (M) Monovalent | IgG $K_D$ mTREM2-Fc (M) Avid |
|---|---|---|---|
| Ab52 | 1.51E−09 | 5.75E−09 | 8.96E−11 |
| Ab21 | 3.44E−10 | 1.14E−09 | 2.27E−10 |

Example 2: Normalization and Reduction of Toll-Like Receptor (TLR) Responses in Dendritic Cells by Agonistic TREM2, DAP12, and/or TREM2/DAP12 Bispecific Antibodies Bone marrow-derived dendritic cells (BMDC) are stimulated by culturing with TLR ligands, such as LPS, CpG DNA, and zymosan, for 16 h. Conditioned media is collected and ELISA assays are performed in order to evaluate secretion of the cytokines IFN-a4, IFN-b, IL-6, IL-12 p70, and TNF. It is believed that BMDC cells that do not have active TREM2 may secrete significantly more IL-12, p70, and TNF than BMDC cells that have activated TREM2 after stimulation. It is further believed that anti-TREM2 agonistic antibodies will reduce the expression levels of IL-12, p70, and TNF. Bone marrow-derived dendritic cells from wild-type and from TREM2-hetrozyous mice, which would have partially inactive TREM2, will serve as positive controls for determining expression levels of the cytokines IL-12, p70, and TNF, as well as their modulation by agonistic anti-TREM2, anti-DAP12, and/or TREM2/DAP12 bispecific antibodies.

Cytokine concentrations in the culture supernatants are determined using mouse IFN-a4, IFN-b, IL-6, IL-12 p70, TNF, and IL-10 ELISA kits (eBioscience) and VeriKine Mouse IFN-b ELISA kit (PBL interferon source) according to manufacturer's protocol. Levels of mRNA for these cytokines are also measured by Quantitative RT-PCR (qRT-PCR). Total RNA is prepared by using RNeasy plus mini kit (QIAGEN) is reverse-transcribed with Superscript III Reverse Transcriptase (Invitrogen) using oligo dT primer according to manufacturer's protocol. Quantitative PCR is performed using the Power SYBR Green PCR Master Mix (Applied Biosystems) and 7900HT (Applied Biosystems) according to manufacturer's protocol. The sequences of IFN-a4, IFN-b, IL-6, IL-12 p70, and TNF primers are as described. (e.g., Hamerman, J A, Eur. *J. Immunol.* 2012. 42: 176-185).

Example 3: Normalization and Reduction of the Ability of BMDCs to Induce Antigen-Specific T-Cell Proliferation by Agonistic TREM2, DAP12, and/or TEM2/DAP12 Bispecific Antibodies It is believed that agonistic anti-TREM2, anti-DAP12, and/or TREM2/DAP12 bispecific antibodies may reduce and normalize the ability of bone marrow-derived dendritic cells (BMDC) to induce antigen-specific T-cell proliferation. Ovalbumin (OVA)-specific T-cell response induced by BMDCs can be determined by CFSE dilution. BMDCs are isolated by MACS after 6 days of culture and plated at $1\times10^4$ cells per well of a round bottom 96 well plate with OVA (2 or 0.5 mg/mL) and CpG DNA (100 or 25 nM) in the presence of GM-CSF (10 ng/mL) for 4 h. CD4 T-cells from the spleen and lymph nodes of OT-II transgenic mice are isolated by using Dynal Mouse CD4 Negative Isolation Kit (Invitrogen) and stained with CFSE (final 0.8 mM). After 4 h of DC culture, $1\times10^5$ CFSE-labeled CD4 OT-II T-cells are added into each well and incubated for 72 h. After culturing, cells are stained with an anti-CD4 monoclonal antibody and flow cytometry is performed to detect CFSE dilution of gated CD4 OT-II T-cells. Data analysis to calculate the percentage of divided and division index is performed by Flowjo software (Treestar) (Eur. *J. Immunol.* 2012. 42: 176-185).

Example 4: Normalization and Reduction of Toll-Like Receptor (TLR) Responses in Macrophages by Agonistic TREM2, DAP12, and/or TEM2/DAP12 Bispecific Antibodies Bone marrow-derived macrophages (BMDM) or primary peritoneal macrophage responses are altered to TLR signaling by deficiency of TREM2 (Tumbull, I R et al., *J Immunol* 2006; 177:3520-3524). It is believed that agonistic anti-TREM2, anti-DAP12, and/or TREM2/DAP12 bispecific antibodies may reduce and normalize TLR responses in macrophages.

To elicit primary macrophages, mice are treated with 1.5 ml of 2% thioglycollate medium by intraperitoneal injection, and cells are then isolated by peritoneal lavage. To generate BMDM, total bone marrow is cultured in DMEM supplemented with 10% bovine calf serum, 5% horse serum, and 6 ng/ml recombinant human CSF-1 (R&D Systems). Cells are cultured for 5-6 days, and adherent cells are detached with 1m MEDTA in PBS. Cells are stained with commercially available antibodies: anti-CD11b, anti-CD40, anti-GR1 (BD Pharmingen), and F4/80 (Caltag Laboratories). BMDM are re-plated and allowed to adhere for 4 h at 37° C., and then TLR agonists, such as LPS (*Salmonella abortus equi*), zymosan (*Saccharomyces cerevisiae*), and CpG 1826 DNA (purchased from e.g., Sigma-Aldrich) are added. Cell culture supernatant is collected 24 h after stimulation and the levels of IFN-a4, IFN-b, IL-6, IL-12 p70, and TNF cytokines are measured by ELISA or by cytometric bead array (BD Biosciences mouse inflammation kit).

Example 5: Induction of the Anti-Inflammatory Cytokine IL-10 in Bone Marrow-Derived Myeloid Precursor Cells by Agonistic TREM2, DAP12, and/or TEM2/DAP12 Bispecific Antibodies It is believed that bone marrow-derived myeloid precursor cells may show an increase in the anti-inflammatory cytokine IL-10 following treatment with agonistic anti-TREM2, anti-DAP12, and/or TREM2/DAP12 bispecific antibodies and stimulation with 100 ng/ml LPS (Sigma), by co-culturing with apoptotic cells, or by a similar stimulus.

Isolation of bone marrow-derived myeloid precursor cells is performed as follows. Bone marrow cells are isolated from adult 6-8 week-old female C57BL/6 mice (Charles River, Sulzfeld, Germany) from the medullary cavities of the tibia and femur of the hind limbs. Removal of erythrocytes is performed by lysis with hypotonic solution. Cells are cultured in DMEM medium (Invitrogen) containing 10% fetal calf serum (Pan Biotech) and 10 ng/ml of GM-CSF (R&D Systems) in 75 cm² culture flasks (Greiner Bio-One). After 24 h, non-adherent cells are collected and re-seeded in fresh 75 cm² culture flasks. Medium is changed after 5 d and cells are cultured for an additional 10-11 d. The remaining cells are bone marrow-derived myeloid precursor cells, and are transduced with TREM2 virus. The transduced cells are then examined for the level of IL-10 in conditioned media in both the presence and absence of anti-TREM2 agonistic antibodies and LPS. Supernatant is collected after 24 h, and the level of IL-10 released from the cells is determined by IL-10 ELISA according to manufacturer's instructions (QuantikineM mouse IL-10, R&D Systems) (JEM (2005), 201; 647-657; and PLoS Medicine (2004), 4 | Issue 4 | e124).

Example 6: Induction of Phagocytosis of Apoptotic Neurons, Nerve Tissue Debris, Non-Nerve Tissue Debris, Bacteria, Other Foreign Bodies, and Disease-Causing Proteins in Cells from the Myeloid Lineage by Agonistic TREM2, DAP12, and/or TEM2/DAP12 Bispecific Antibodies It is believed that agonistic anti-TREM2, anti-DAP12, and/or TREM2/DAP12 bispecific antibodies may induce phagocytosis of apoptotic neurons, nerve tissue debris, non-nerve tissue debris, bacteria, other foreign bodies, and disease-causing proteins, such as A beta peptide, alpha synuclain protein, Tau protein, TDP-43 protein, prion protein, and huntingtin protein, in cells from the myeloid lineage, such as monocytes and microglia.

Monocytes are isolated from peripheral blood that is collected from adult C57BL/6 mice. Hypotonic lysis buffer depletes erythrocytes. Cells are plated on culture dishes in RPMI medium (Invitrogen) containing 10% fetal calf serum (Pan Biotech). Cells are cultured for several hours at 37° C. in 10% CO2. After trypsinization, adherent cells are collected and used for phagocytosis experiments.

Microglial cells are prepared from the brains of post-natal day 3 to 5 (P3 to P5) C57BL/6 mice. In brief, meninges are removed mechanically, and the cells are dissociated by trituration and cultured in basal medium (BME; GIBCO BRL) supplemented with 10% FCS (PAN Biotech GmbH), 1% glucose (Sigma-Aldrich), 1% L-glutamine (GIBCO BRL), and 1% penicillin/streptomycin (GIBCO BRL), for 14 d to form a confluent glial monolayer. To collect microglial cells, the cultures are shaken on a rotary shaker (200 rpm) for 2 h. The attached astrocytes are used for immunohistochemistry. The detached microglial cells are seeded in normal culture dishes for 1 h, and then all non-adherent cells are removed and discarded. Purity of the isolated microglial cells is about 95% as determined by flow cytometry analysis with antibody directed against CD11b (BD Biosciences). Microglial cells are cultured in basal medium.

Oligodendrocytes (i.e., neurons) and neuron-enriched cells are prepared from the brain of C57BL/6 mouse embryos (E15-16). In brief, brain tissue is isolated and mechanically dispersed and seeded in culture dishes pre-coated with 0.01 mg/ml poly-L-ornithin (Sigma-Aldrich) and 10 µg/ml laminin (Sigma-Aldrich). Cells are cultured in neuronal condition medium (BME; GIBCO BRL) supplemented with 2% B-27 supplement (GIBCO BRL), 1% glucose (Sigma-Aldrich), and 1% FCS (PAN Biotech GmbH). Cells are cultured for 5-10 d to obtain morphologically mature oligodendrocytes.

To conduct phagocytosis assays of apoptotic neurons, nerve tissue debris, non-nerve tissue debris, bacteria, other foreign bodies, and disease-causing proteins, microglia are transduced with sh-TREM2 RNA, sh-control RNA, wTREM2, GFP1 control, mtDAP12-GFP, and GFP2 control vector. After transduction, microglia are cultured for 72 h to achieve effective knockdown of TREM2 by RNA interference. Neurons are cultured for 5-10 d, and okadaic acid is then added at the final concentration of 30 nM for 3 h to induce apoptosis. Neuronal cell membranes are labeled with CellTracker CM-DiI membrane dye (Molecular Probes). After incubation, apoptotic neurons or other targets of phagocytosis are washed two times and added to the transduced microglial culture at an effector/target ratio of 1:20. At 1 and 24 h after addition of apoptotic neurons, the number of microglia having phagocytosed neuronal cell membranes is counted under a confocal fluorescence microscope (Leica). Apoptotic cells are counted in three different areas at a magnification of 60. The amount of phagocytosis is confirmed by flow cytometry. Moreover, 24, 48, or 72 h after the addition of apoptotic neurons, cells are collected and used for RT-PCR of cytokines.

To conduct microsphere bead or bacterial phagocytosis assay, microglia are transduced with a TREM2 expression vector or a GFP control vector. Cells are then treated with anti-TREM2 agonistic antibodies. After 24 h, 1.00 µm of red fluorescent microsphere beads (Fluoresbrite Polychromatic Red M1-crospheres; Polysciences Inc.) or, fluorescent labeled bacteria are added for 1 h. Phagocytosis of microsphere beads or, fluorescent labeled bacteria, by microglia is analyzed by fluorescence microscopy. Furthermore, microglia are collected from the culture plates and analyzed by flow cytometry. The percentage of microglia having phagocytosed beads is determined. Because phagocytosis varies from one experiment to the other, the relative change in phagocytosis is also determined. Data are shown as the relative change in phagocytosis between microglia cultured with agonistic antibodies and control antibody.

To conduct RT-PCR for analysis of inflammatory gene transcripts, microglia are transduced with a TREM2 vector or a GFP1 control vector. Cells are then cultured on dishes and treated with anti-TREM2 agonistic antibodies. After 24, 48, and 72 h, RNA is isolated from microglia using an RNeasy Mini Kit (QIAGEN). RNA is also collected from microglia that have been transduced with sh-TREM2 RNA, sh-control RNA, wTREM2, GFP2, mtDAP12-GFP, and GFP1 vector and co-cultured with apoptotic neurons for 48 h.

Reverse transcription of RNA is then performed. Quantitative RT-PCR by SYBR Green is performed on an ABI Prism 5700 Sequence Detection System (PerkinElmer). Amplification of GAPDH is used for sample normalization. The amplification protocol followed the GeneAmp 5700 Sequence Detection System Software (version 1.3). For detection of GAPDH, TNF-alpha, IL-1, NOS2, and TGF-beta transcripts, the following forward and reverse primers were used at final concentrations of 200 nM:

```
GAPDH forward primer:
                                 (SEQ ID NO: 416)
5'-CTCCACTCACGGCAAATTCAA-3',
and GAPDH reverse primer:
                                 (SEQ ID NO: 417)
5'-GATGACAAGCTTCCCATTCTCG-3';

TNF-α forward primer:
                                 (SEQ ID NO: 418)
5'-CCGTCAGCCGATTTGCTATCT-3',
and TNF-α reverse primer:
                                 (SEQ ID NO: 419)
5'-ACGGCAGAGAGGAGGTTGACTT-3';

IL-1α forward primer:
                                 (SEQ ID NO: 420)
5'-ACAA-CAAAAAAGCCTCGTGCTG-3',
and IL-1α reverse primer:
                                 (SEQ ID NO: 421)
5'-CCATTGAGGTGGAGAGCTTTCA-3';
```

```
NOS2 forward primer:
                                 (SEQ ID NO: 422)
5'-GGCAAACCCAAGGTCTACGTTC-3', NOS2 reverse primer:
                                 (SEQ ID NO: 423)
5'-TACCTCATTGGCCAGCTGCTT-3';
and TGF-β1 forward primer:
                                 (SEQ ID NO: 424)
5'-AGGACCTGGGTTGGAAGTGG-3',
and TGF-β1 reverse primer:
                                 (SEQ ID NO: 425)
5'-AGTTGGCATGGTAGCCCTTG-3'.
```

To conduct amyloid phagocytosis assay, HiLyteFluor™ 647 (Anaspec)-Abeta-(1-40) was resuspended in Tris/EDTA (pH 8.2) at 20 mM and then incubated in the dark for 3 d at 37° C. to promote aggregation. Microglial cells are pretreated in low serum (0.5% FBS supplemented with insulin), LPS (50 ng/ml), IFNc (100 units/ml), and anti-TREM2 agonistic antibodies for 24 h prior to the addition of aggregated fluorescently labeled a beta peptide. Amyloid phagocytosis and surface expression of TREM2 are determined by flow cytometric analysis 5 h post-addition of 100 nM aggregated HiLyteFluor™ 647-Ab-(1-40) (ASN NEURO (2010) 2(3): 157-170). Phagocytosis of other disease-causing proteins is conducted in a similar manner.

Example 7: Induction of ERK Activation by Agonistic TREM2, DAP12, and/or TEM2/DAP12 Bispecific Antibodies It is believed that agonistic anti-TREM2, anti-DAP12, and/or TREM2/DAP12 bispecific antibodies may induce ERK activation.

Microglia are transduced with a TREM2 vector, and $2 \times 10^5$ cells are exposed to agonistic anti-TREM2, anti-DAP12, and/or TREM2/DAP12 bispecific antibodies for 1 h. After stimulation, cells are lysed in reducing sample buffer for Western blot analysis. Phosphorylation of ERK and total amount of ERK are determined by immuno-detection with anti-phospho-ERK and anti-ERK antibodies, respectively (both from Cell Signaling Technology) by Western blot analysis (JEM (2005), 201, 647-657).

Example 8: Induction of CCR7 and Migration Toward CCL19 and CCL21 in Microglia, Macrophages, and Dendritic Cells by Agonistic TREM2, DAP12, and/or TEM2/DAP12 Bispecific Antibodies It is believed that agonistic anti-TREM2, anti-DAP12, and/or TREM2/DAP12 bispecific antibodies may induce CCR7 and migration toward CCL19 and CCL21 in microglial cells, macrophages, and dendritic cells.

Microglial cells are transduced with a TREM2 vector or a GFP1 control vector. The transduced microglial cells are then either cultured with agonistic anti-TREM2, anti-DAP12, and/or TREM2/DAP12 bispecific antibodies, or with a control antibody. Cells are collected after 72 h, immuno-labeled with CCR7 specific anti-bodies, and analyzed by flow cytometry.

To determine any functional consequences of increased CCR7 expression, a chemotaxis assay is performed. Microglial cells are stimulated via TREM2 with the agonistic anti-TREM2, anti-DAP12, and/or TREM2/DAP12 bispecific antibodies and placed in a two-chamber system. The number of microglial cells migrating toward the chemokine ligands CCL19 and CCL21 is quantified (JEM (2005), 201, 647-657).

For the chemotaxis assay, microglial cells are exposed to the agonistic anti-TREM2, anti-DAP12, and/or TREM2/DAP12 bispecific antibodies and treated with 1 µg/ml LPS. Microglia are transferred into the upper chamber of a transwell system (3 µm pore filter; Millipore) containing 450 µl medium with 100 ng/ml CCL19 or CCL21 (both from PeproTech) in the lower chamber. After a 1 h incubation period, the number of microglial cells that have migrated to the lower chamber is counted in three independent areas by microscopy (JEM (2005), 201, 647-657).

Example 9: Induction of F-Actin in Microglia, Macrophages, and Dendritic Cells by Agonistic TREM2, DAP12, and/or TEM2/DAP12 Bispecific Antibodies It is believed that agonistic anti-TREM2, anti-DAP12, and/or TREM2/DAP12 bispecific antibodies may induce F-actin in microglial cells, macrophages, and dendritic cells.

Microglia and other cells of interest that are transduced with TREM2 or that express TREM2 are added to culture plates and then exposed to agonistic anti-TREM2, anti-DAP12, and/or TREM2/DAP12 bispecific antibodies, or a control antibody. Cells are fixed, blocked, and then stained with Alexa Fluor 546-conjugated phalloidin (Molecular Probes) after 1 h and F-actin is labeled with a fluorescence dye. Images are collected by confocal laser scanning microscopy with a 40× objective lens (Leica). (JEM (2005), 201, 647-657).

Example 10: Induction of Osteoclast Production and Increased Rate of Osteoclastogenesis by Agonistic TREM2, DAP12, and/or TEM2/DAP12 Bispecific Antibodies It is believed that agonistic anti-TREM2, anti-DAP12, and/or TREM2/DAP12 bispecific antibodies may induce osteoclast production and increase the rate of osteoclastogenesis.

RAW264.7 cells that make osteoclasts or bone marrow-derived monocyte/macrophage (BMM) precursor cells are maintained in RPMI-1640 medium (Mediatech), or another appropriate medium, supplemented with 10% FBS (Atlantic Biologics, Atlanta, Ga., USA) and penicillin-streptomycin-glutamine (Mediatech). TREM2B cDNA with a FLAG epitope added to the N terminus is inserted into the retroviral vector pMXpie upstream of an IRES, followed by an eGFP cDNA sequence. Cells are transfected with pMXpie-FLAG TREM2B, using Fugene 6 (Roche) according to manufacturer's protocol. Cells are selected in puromycin (Sigma) at 2 µg/ml. Stable puromycin-resistant clones are screened for anti-FLAG M2 monoclonal antibody (Sigma) binding by using flow cytometry, and then subcloned and maintained on puromycin selection media.

RAW264.7 cells expressing TREM2B are seeded in 96-well plates with 3000 cells/well in alpha-MEM medium supplemented with 10% FBS, penicillin-streptomycin-glutamine, 50 ng/ml RANKL, and 20 ng/ml M-CSF. The medium is changed every 3 days, exposed to anti-TREM2 agonistic antibodies and the number of multinucleated (at least three nuclei) TRACP$^+$ osteoclasts are counted and scored by light microscopy. To determine complexity and size, osteoclasts are counted by number of nuclei (>10 or 3-10 nuclei). The surface area of osteoclasts is also measured by using Image J software (NIH). In addition, expression levels of osteoclasts genes are determined. Total RNA is extracted from osteoclastogenic cultures at different time points using TRIzol reagent (Invitrogen). After first-strand cDNA synthesis using a SuperScript III kit (Invitrogen), real-time quantitative PCR reactions are performed for Nfatc1, Acp5, Ctsk, Calcr, and Ccnd1. Relative quantification of target mRNA expression is calculated and normalized to the expression of cyclophilin and expressed as (mRNA of the target gene/mRNA of cyclophilin) 3×10$^6$. (J. OF BONE AND MINERAL RESEARCH (2006), 21, 237-245; J Immunol 2012; 188:2612-2621).

Example 11: In Vivo Protection from EAE and Cuprizone in a Whole Animal

Adult 7-9 week-old female C57BL/6 mice (obtained from Charles River Laboratories) are injected in the tail base bilaterally with 200 µl of an innoculum containing 100 µg of myelin oligodendrocyte glycoprotein peptide 35-55 (amino acids MEVGWYRSPFSRVVHLYRNGK (SEQ ID NO: 415); Seqlab) and 1 mg of *Mycobacterium tuberculosis* H37 Ra (Difco) in incomplete Freund adjuvant (Difco). Pertussis toxin (200 ng; List Bio-logical Laboratories) is injected at day 0 and at day 2 after immunization. Clinical signs are scored as follows: 0, no clinical signs; 1, complete limp tail; 2, complete limp tail and abnormal gait; 3, one hind-limb paraparesis; 4, complete hindlimb paraparesis; and 5, fore- and hind-limb paralysis or moribund.

Only mice having disease onset (clinical score of 1 or more) at day 14 are used for experiments. Agonistic anti-TREM2, anti-DAP12, and/or TREM2/DAP12 bispecific antibodies are injected intraperitoneally or intravenously in EAE-diseased mice at the day of the first clinical symptoms or at any other desired time (PLoS Med (2007) 4(4): e124).

Young or aged wild-type (WT) mice are fed a standard diet (Harlan) containing 0.2% cuprizone (CPZ) powdered oxalic bis(cyclohexylidenehydrazide) (Sigma-Aldrich) for 4, 6 or 12 weeks. For Histological and immunohistochemical analyses brains are removed after mouse perfusion with 4% paraformaldehyde (PFA), fixed in 4% PFA for 24 h, followed by immersion in 30% sucrose for 24-48 h. To evaluate myelin integrity and damage, as well as cell proliferation and inflammation sections or mouse brain are stained with anti-MBP (1:100; Abcam, ab7349), -dMBP (1:2000; Millipore, ab5864), -β APP (1:100; Invitrogen, 51-2700), -SMI-31 (1:1000; Covance, smi-31R), -Iba1 (1:600; Wako, 019-19741), -BrdU (1:250; Abcam, ab1893), -GFAP (1:200; Invitrogen, 13-0300), -iNOS (1:100; BD Pharmingen, 610329), -LPL(1:400, from Dr. G. Olivecrona) and -MHC II (1:100; BD Pharmingen, 553549). For behavioral effects of the antibodies, mice are analyzed for locomotor activity using transparent polystyrene enclosures and computerized photobeam instrumentation. General activity variables (total ambulations, vertical rearings), along with indices of emotionality including time spent, distance traveled and entries, are analyzed. A battery of sensorimotor tests is performed to assess balance (ledge and platform), strength (inverted screen), coordination (pole and inclined screens) and initiation of movement (walking initiation). Motor coordination and balance are studied using a rotarod protocol (Cantoni et al., Acta Neuropathol (2015) 129 (3): 429-47).

Example 12: Characterization of the Therapeutic Use of Agonistic TREM2, DAP12, and/or TEM2/DAP12 Bispecific Antibodies in Established Animal Models of Traumatic Brain Injury The therapeutic utility of agonistic anti-TREM2, anti-DAP12, and/or TREM2/DAP12 bispecific antibodies is tested in established animal models of traumatic brain injury (Tanaka, Y et al. (2013) Neuroscience 231 49-60).

For example, a model of traumatic brain injury that induces the activation of microglia and astrocytes is used. Eight or nine week-old male C57BL/6J WT mice or progranulin heterozygous mice are used (purchased from Charles River Laboratories or Jackson Laboratories). Mice are anesthetized by intraperitoneal administration of xylazine hydrochloride (8 mg/kg) and chloral hydrate (300 mg/kg) dissolved in sterile saline, and subsequently placed in a stereotaxic apparatus (Narishige, Tokyo, Japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5 mm outer diameter, is used to make a longitudinal stab wound in the right hemisphere. The cannula is positioned at 1.3 mm lateral to the midline, and 1 mm posterior to bregma, and introduced into the brain until the tip reaches a depth of 2 mm. The cannula is then shifted 2 mm caudally (bregma 3 mm), and then shifts back 2 mm rostrally to its initial position. Finally, the cannula is removed from the brain, and the scalp wound is sutured. Mice are then treated with agonistic anti-TREM2, anti-DAP12, and/or TREM2/DAP12 bispecific antibodies according to standard procedures and then analyzed by histology and immunofluorescence staining and behavioral tests.

Example 13: Characterization of Therapeutic Use of Agonistic TREM2, DAP12, and/or TEM2/DAP12 Bispecific Antibodies in a Model of Neuro-Inflammation and Neuron Loss Following Toxin-Induced Injury The therapeutic utility of agonistic anti-TREM2, anti-DAP12, and/or TREM2/DAP12 bispecific antibodies is tested in a model of neuro-inflammation and neuron loss following toxin-induced injury (Martens, L H et al., (2012) The Journal of Clinical Investigation, 122, 3955).

Three-month-old mice are treated with 4 intraperitoneal injections of MPTP (1-methyl-4-phenyl-1,2,3,6-tetrahydropyridine) per day for 2 days (4 µg/g body weight) (Sigma-Aldrich) or PBS. Mice are treated with agonistic anti-TREM2, anti-DAP12, and/or TREM2/DAP12 bispecific antibodies according to standard protocols and then analyzed using Stereological counting to quantify dopamine neurons and microglia in the substantia nigra pars compacta (SNpc), as described.

Example 14: Characterization of the Therapeutic Use of Agonistic TREM2, DAP12, and/or TEM2/DAP12 Bispecific Antibodies in Animal Models of Aging, Seizures, Spinal Cord Injury, Retinal Dystrophy, Frontotemporal Dementia, and Alzheimer's Disease The therapeutic utility of agonistic anti-TREM2, anti-DAP12, and/or TREM2/DAP12 bispecific antibodies is tested in animal models for aging, seizures, spinal cord injury, retinal dystrophy, frontotemporal dementia, and Alzheimer's disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 15: Characterization of the Therapeutic Use of Agonistic TREM2, DAP12, and/or TEM2/DAP12 Bispecific Antibodies in Models of Atherosclerosis The therapeutic utility of agonistic anti-TREM2, anti-DAP12, and/or TREM2/DAP12 bispecific antibodies is tested in models of atherosclerosis, as previously described (e.g., Lance, A et al., (2011) Diabetes, 60, 2285; and Kjolby, M et al., (2012) Cell Metabolism 12, 213-223).

Example 16: Characterization of the Therapeutic Use of Agonistic TREM2, DAP12, and/or TEM2/DAP12 Bispecific Antibodies in a Model of Infection The therapeutic utility of agonistic anti-TREM2, anti-DAP12, and/or TREM2/DAP12 bispecific antibodies is tested in a model of infection. For example, *Listeria monocytogenes* or other infection in normal mice or progranulin heterozygous mice can be used, as previously described (e.g., Yin, F et al., (2009) J. Exp. Med, 207, 117-128).

Example 17: Characterization of the Therapeutic Use of Agonistic TREM2, DAP12, and/or TEM2/DAP12 Bispecific Antibodies in a Model of Inflammatory Diseases The therapeutic utility of agonistic anti-TREM2, anti-DAP12, and/or TREM2/DAP12 bispecific antibodies is tested in a model of inflammatory diseases. For example rheumatoid arthritis or in an established model of another inflammatory disease (Mizoguchi (2012) Prog Mol Biol Transl Sci., 105:263-320; and Asquith et al., (2009) Eur J Immunol. 39:2040-4).

Example 18: Screening for Anti-TREM2, Anti-DAP12, and/or TEM2/DAP12 Bispecific Antibodies that Induce Phosphorylation of DAP12, ERK, and AKT which Indicate Activation of the PI3K Pathway Cells (J774, RAW 264.7, BMM cells, or osteoclasts) are removed from tissue culture dishes with PBS-EDTA, washed with PBS, and counted. J774 ($40 \times 10^6$) or RAW 264.7 cells ($10 \times 10^6$ BMM or osteoclasts) are incubated with an anti-TREM2, anti-DAP12, and/or TREM2/DAP12 bispecific antibody or with an isotype-matched control antibody at 1 µg/10⁶ cells for 20 min on ice or under other conditions. Cells are lysed in ice-cold radioimmunoprecipitation assay (RIPA) buffer [50 mM tris-HCl (pH 7.4), 150 mM NaCl, 1 mM EDTA, 1% Triton-100, 1 mM NaF, 1 mM phenylmethylsulfonyl fluoride, 1 mM Na VO, 0.25% sodium deoxycholate, aprotinin (1 µg/ml), leupeptin (1 µg/ml), pepstatin (1 µg/ml)] for 20 min followed by centrifugation at 16,000 g for 10 min at 4° C. to remove insoluble materials. The resulting supernatant is subjected to immunoprecipitation reactions with the indicated antibodies (DAP12, ERK, or AKT) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate antibodies (antibodies that specifically recognize the phosphorylated form of DAP12, ERK, or AKT) and visualized with the enhanced chemiluminescence (ECL) system (Pierce), as described (e.g., Peng et al., (2010) Sci Signal., 3(122): ra38).

Example 19: Screening for Anti-TREM2, Anti-DAP12, and/or TEM2/DAP12 Bispecific Antibodies that Induce Calcium Flux BMM cells are washed twice with HEPES-containing buffer [20 mM HEPES (pH 7.3), 120 mM NaCl, 1 mM CaCl, 1 mM MgCl, 5 mM KCl, glucose (1 mg/ml), bovine serum albumin (1 mg/ml)] followed by incubation in 0.05% Pluronic F-127 (Invitrogen) and 1 µM Indo-1 AM (Invitrogen) for 20 min at 37° C. Cells are washed twice with HEPES buffer and are then stimulated with an anti-TREM2, anti-DAP12, and/or TREM2/DAP12 bispecific antibody (16 µg/ml) or with a control antibody (16 µg/ml) and monitored by spectrophotometer (PTL Photon Technology International). The Indo-1 fluorescence emission is converted to calcium ($Ca^{2+}$) according to manufacturer's instructions (e.g., Peng et al., (2010) Sci Signal., 3(122): ra38).

Example 20: Screening for Anti-TREM2, Anti-DAP12, and/or TEM2/DAP12 Bispecific Antibodies that Prevent Apoptosis Mature osteoclast cell cultures are differentiated in 24-well dishes with RANKL and M-CSF. After 4 days, complete medium is substituted with serum-free medium to induce apoptosis. Cells are treated with RANKL, PBS, and an anti-TREM2, anti-DAP12, and/or TREM2/DAP12 bispecific antibody, or an isotype-matched control antibody, during the overnight serum starvation. Cells are fixed in 1% paraformaldehyde and stained with a TUNEL-based kit (Millipore Corporation) according to manufacturer's instructions. Apoptotic nuclei are counted with a Nikon TE2000-E microscope with 20× magnification. Results are expressed as the percentage of apoptotic cells relative to the total number of cells in six randomly selected fields of the two wells, as described (e.g., Peng et al., (2010) Sci Signal., 3(122): ra38). Similar assays are performed with primary microglial cells.

Example 21: Screening for Anti-TREM2, Anti-DAP12, and/or TEM2/DAP12 Bispecific Antibodies that Induce Osteoclast Differentiation BMM cells are seeded onto the plates in triplicate wells and treated with RANKL, M-CSF, and with an anti-TREM2, anti-DAP12, and/or TREM2/DAP12 bispecific antibody, or an isotype-matched control monoclonal antibody. The medium is changed every 3 days until large multinucleated cells are visible. After 3 to 5 days in culture, cells are fixed with 3.7% formaldehyde in PBS for 10 min. Plates are then washed twice in PBS, incubated for 30 s in a solution of 50% acetone and 50% ethanol, and washed with PBS. Cells are stained for tartrate-resistant acid phosphatase (TRAP) with a kit from Sigma (product 435). Multinucleated (more than two nuclei), TRAP-positive cells are then counted by light microscopy, as described (e.g., Peng et al., (2010) Sci Signal., 3(122): ra38).

Example 22: Screening for Anti-TREM2, Anti-DAP12, and/or TEM2/DAP12 Bispecific Antibodies that Normalize TREM2/TYROBP-Dependent Changes in Gene Expression within the Immune/Microglia Regulatory Module Microglial cells derived from mouse embryonic stem cells are genetically modified by lentiviral vectors to overexpress either full-length or a truncated version of Tyrobp that lacks both intracellular immunoreceptor tyrosine-based activation motif (ITAM) motifs. Microglia cells are also derived from mouse embryonic stem cells that are heterozygous for TREM2. To assess the genome-wide gene-expression changes in response to the perturbation of Tyrobp or TREM2, gene-expression data is derived from the RNA sequencing of mouse microglial cell lines overexpressing: (1) vehicle, (2) full-length Tyrobp, or (3) dominant-negative truncated Tyrobp; or (4) overexpressing a knockdown construct for TREM2, such as SiRNA and cells which are heterozygous for TREM2. Approximately 2,638 and 3,415 differentially expressed genes for the overexpression of full-length Tyrobp and truncated Tyrob are identified, respectively (Zhang et al., (2013) Cell 153, 707-720). Approximately 99% of the differentially expressed genes from the microglia overexpressing intact Tyrobp are downregulated compared to the control vehicle. For example, 658 genes, related to the vacuole/autophagy, as well as genes involved with RNA metabolism and cell-cycle mitosis are downregulated by active Tyrobp, but upregulated in cells expressing dominant-negative truncated Tyrobp. Conversely, some 2,856 genes for the vacuole/autophagy pathway and for mitochondrion are selectively upregulated in microglia expressing the dominant-negative truncated Tyrobp.

Agonistic anti-TREM2, anti-DAP12, and/or TREM2/DAP12 bispecific antibodies are screened for their ability to elicit gene expression profiles similar to that observed in normal microglial cells and in microglial cells overexpressing intact Tyrobp in cells that express dominant-negative truncated Tyrobp (Zhang et al., (2013) Cell 153, 707-720), in cells that express the knockdown construct for TREM2, or in cells that are heterozygous for TREM2. Antibodies that are capable of changing the gene expression network are selected.

Example 23: TREM2 Antibodies Induce the Expression of CD83 and CD86 on Human Dendritic Cells (DCs)

To evaluate the ability of anti-TREM2 antibodies to modify expression of CD83 and CD86, both plate bound and soluble antibodies were incubated with dendritic cells (DCs), and the expression of CD83 and CD86 were measured.

Antibodies were plated overnight at 4° C. in 12 well plates at 2 or 5 ug/ml in PBS. Wells were washed 3× with PBS the next day. On day 5, immature human DCs were harvested and plated at 1 million cells per well and incubated at 37 C, 5% $CO_2$ in the absence of cytokine. FACS analysis of CD86, CD83, CD11c, HLA-DR, and LIN (BD Biosciences) was performed on a BD FACS Canto 48 hours later. Data analysis was performed with FlowJo (TreeStar) software version 10.0.7. Levels of CD83 and CD86 were evaluated on CD11c+HLA-DR+LIN- cell populations.

Alternatively, Day 5 immature human dendritic cells were plated at 100,000 cells per well in a U-bottom non-TC treated 96 well plate in media without cytokine. Antibodies were added at 5 ug/ml with or without LPS-removed anti-human secondary (Jackson ImmunoResearch) at 20 ug/ml. FACS analysis for CD86, CD83, CD11c, HLA-DR, and LIN (BD Biosciences) was performed 48 hrs post antibody addition as previously described.

Plate bound TREM2 antibodies Ab21 and Ab52 increased the frequency of CD83+CD86+ DCs compared to the isotype control antibody Ab88 (FIG. 5A). Soluble antibody Ab21 and Ab52, both alone and cross-linked with an anti-human secondary antibody, induced equivalent expression of CD86 on DCs to the isotype control antibody (Ab88) (FIG. 5B). Based on these results, TREM2 antibodies Ab21 and Ab52 function as agonists to induce the expression of inflammatory surface markers CD83 and CD86 on human dendritic cells.

Example 24: TREM2 Antibodies Ab21 and Ab52 Induce Syk Phosphorylation

Spleen tyrosine kinase (Syk) is an intracellular signaling molecule that functions downstream of TREM2 by phosphorylating several substrates, thereby facilitating the formation of a signaling complex leading to cellular activation and inflammatory processes. The ability of agonist TREM2 antibodies to induce Syk activation was determined by culturing human and mouse macrophages and primary human dendritic cells and measuring the phosphorylation state of Syk protein in cell extracts.

Bone marrow-derived macrophages (BMDM), WT mouse BMDM, TREM2 knockout (KO) mouse BMDM, and primary human dendritic cells were starved for 4 hours in 1% serum RPMI and then removed from tissue culture dishes with PBS-EDTA, washed with PBS, and counted. The cells were coated with the full-length agonist TREM2 antibodies Ab21 and Ab52, or control antibodies (Ab89 or Ab92) for 15 minutes on ice. After washing with cold PBS, cells were incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM MgCl2, 10% glycerol, plus protease and phosphatase inhibitors) followed by centrifugation at 16,000 g for 10 min at 4° C. to remove insoluble materials. Lysates were then immunoprecipitated with anti-Syk Ab (N-19 for BMDM or 4D10 for human DCs, Santa Cruz Biotechnology). Precipitated proteins were fractionated by SDS-PAGE, transferred to PVDF membranes and probed with anti-phosphotyrosine Ab (4G10, Millipore). To confirm that all substrates were adequately immunoprecipitated, immunoblots were reprobed with anti-Syk Ab (Abcam, for BMDM) or anti-Syk (Novus Biological, for human DCs). Visualization was performed with the enhanced chemiluminescence (ECL) system (GE healthcare), as described (e.g., Peng et al., (2010) Sci Signal., 3(122): ra38).

Figure 6A:
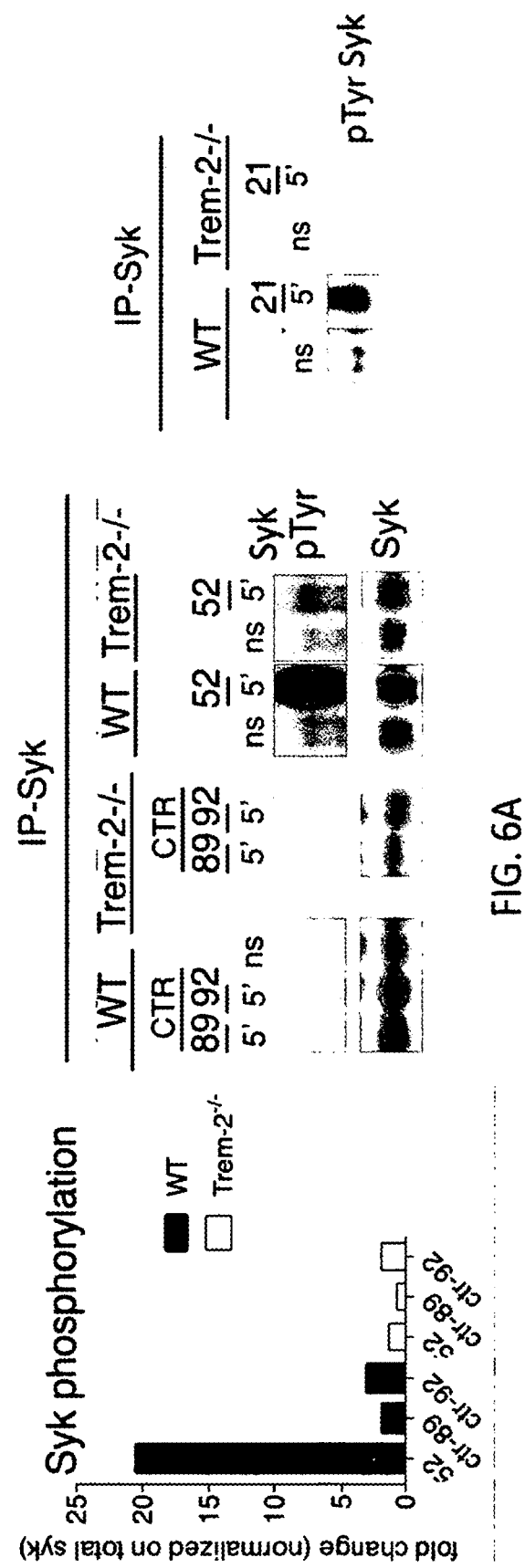
FIG. 6A shows Syk phosphorylation as determine by western blot in wild-type and TREM2 deficient (Trem2−/−) mouse (left and center panels) and human (right panel) macrophages after incubation with TREM2 antibodies Ab21 and Ab52. Antibodies Ab89 and Ab92 are non-agonistic negative controls.
Figure 6B:
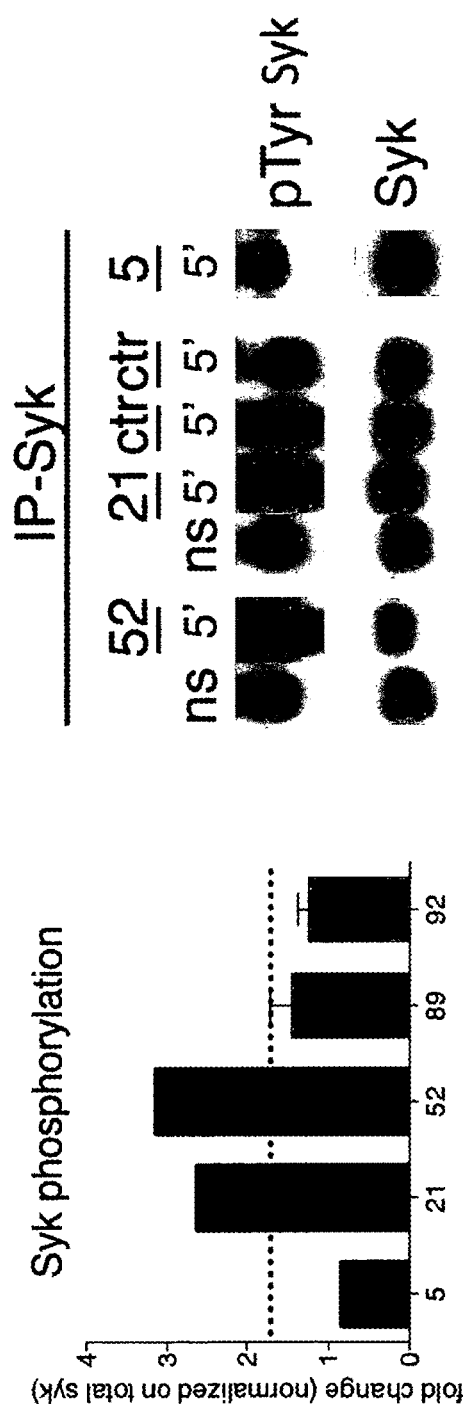
FIG. 6B shows Syk phosphorylation as determine by western blot in primary human dendritic cells after incubation with TREM2 antibodies Ab21 and Ab52.

TREM2 antibodies Ab21 and Ab51 induced Syk phosphorylation in WT TREM2 mouse BMDMs, but did not induce phosphorylation in TREM2 KO (TREM2$^{-/-}$) cells (FIG. 6A). Antibodies Ab21 and Ab51 also induced Syk phosphorylation in both human BMDM (FIG. 6A, right panel) and in primary human dendritic cells (FIG. 6B). Control antibodies Ab89 and Ab92 did not induce Syk phosphorylation. Based on these results, TREM2 antibodies Ab21 and Ab52 function as agonists to induce Syk phosphorylation in macrophages and dendritic cells.

Example 25: TREM2 Antibodies Ab21 and Ab52 Induce DAP12 Phosphorylation in Mouse Macrophages TREM2 signals through DAP12, leading downstream to activation of PI3K and other intracellular signals. The ability of agonist TREM2 antibodies to induce DAP12 activation was determined by culturing mouse macrophages and measuring the phosphorylation state of DAP12 protein in cell extracts.

Before stimulation with antibodies, mouse wild-type (WT) bone marrow-derived macrophages (BMDM) and TREM2 knockout (KO) BMDM were starved for 4h in 1% serum RPMI. 15×10$^6$ cells were incubated in ice for 15 min with full-length agonistic or control antibodies. Cells were washed and incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors), followed by centrifugation at 16,000 g for 10 min at 4° C. to remove insoluble materials. Cell lysate was immunoprecipitated with a second TREM2 antibody (R&D Systems). Precipitated proteins were fractionated by SDS-PAGE, transferred to PVDF membranes, and probed with anti-phosphotyrosine Ab (4G10, Millipore). The membrane was stripped and reprobed with anti-DAP12 antibody (Cells Signaling, D7G1X). Each cell lysate used for TREM2 immunoprecipitations contained an equal amount of proteins, as indicated by a control Ab (anti-actin, Santa Cruz).

Figure 7A:
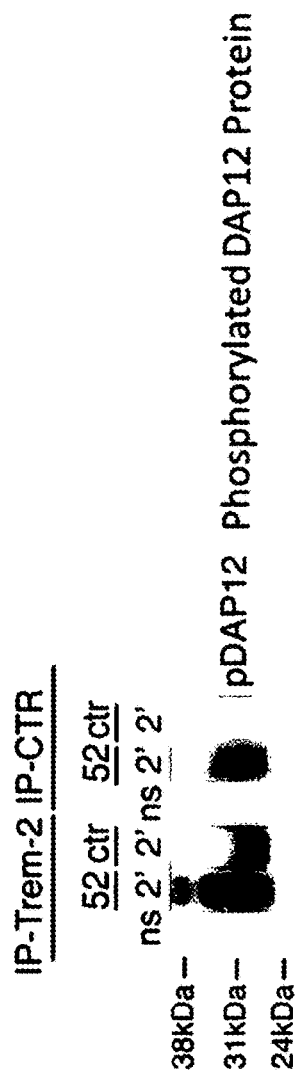
FIG. 7A shows DAP12 phosphorylation as determine by western blot in mouse macrophages after incubation with TREM2 antibody Ab52.
Figure 7B:
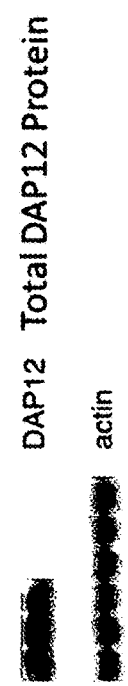
FIG. 7B shows DAP12 phosphorylation as determine by western blot in wild-type and TREM2 deficient (Trem2−/−) mouse macrophages after incubation with TREM2 antibody Ab21.

DAP12 co-precipitated with TREM2 and was phosphorylated in WT macrophages incubated with agonist TREM2 antibodies Ab52 (FIG. 7A) and Ab21 (FIG. 7B). Conversely, no DAP12 phosphorylation was observed in TREM2 KO (TREM2$^{-/-}$) macrophages incubated with antibody Ab21 (FIG. 7B). These results demonstrate that DAP12 is associated with TREM2 protein, and that agonist TREM2 antibodies are able to induce DAP12 phosphorylation in vitro.

Example 26: TREM2 Antibodies Ab21 and Ab52 Compete with TREM2 Ligand for Binding to Human and Mouse TREM2

The ability of agonist TREM2 antibodies to recognize the ligand-binding site on TREM2 was evaluated through competitive binding assays with E. coli cells expressing a putative TREM2 ligand.

E. coli were grown in 10 ml LB media O/N, harvested by centrifuging, and washed twice in 10 ml PBS. E. coli were then heat-inactivated by incubating in a 70° C. water bath for 30 min. E. coli were labeled with CellTracker DeepRed (ThermoFisher/Invitrogen, 1 uM final concentration) and subsequently washed thrice in 10 ml PBS and resuspended in 1 ml PBS at a concentration of $10^8$/ml. For competition binding, bacteria were added to a mouse TREM2 and DAP12 expressing cell line (BWZ), or to a BW cell line expressing a human TREM2/DAP12 fusion protein, together with 10 μg/ml of full-length agonist TREM2 antibodies and incubated for one hour on ice. Cells were analyzed via FACS for binding of CellTracker labeled bacteria to the cell lines.

Figure 8:
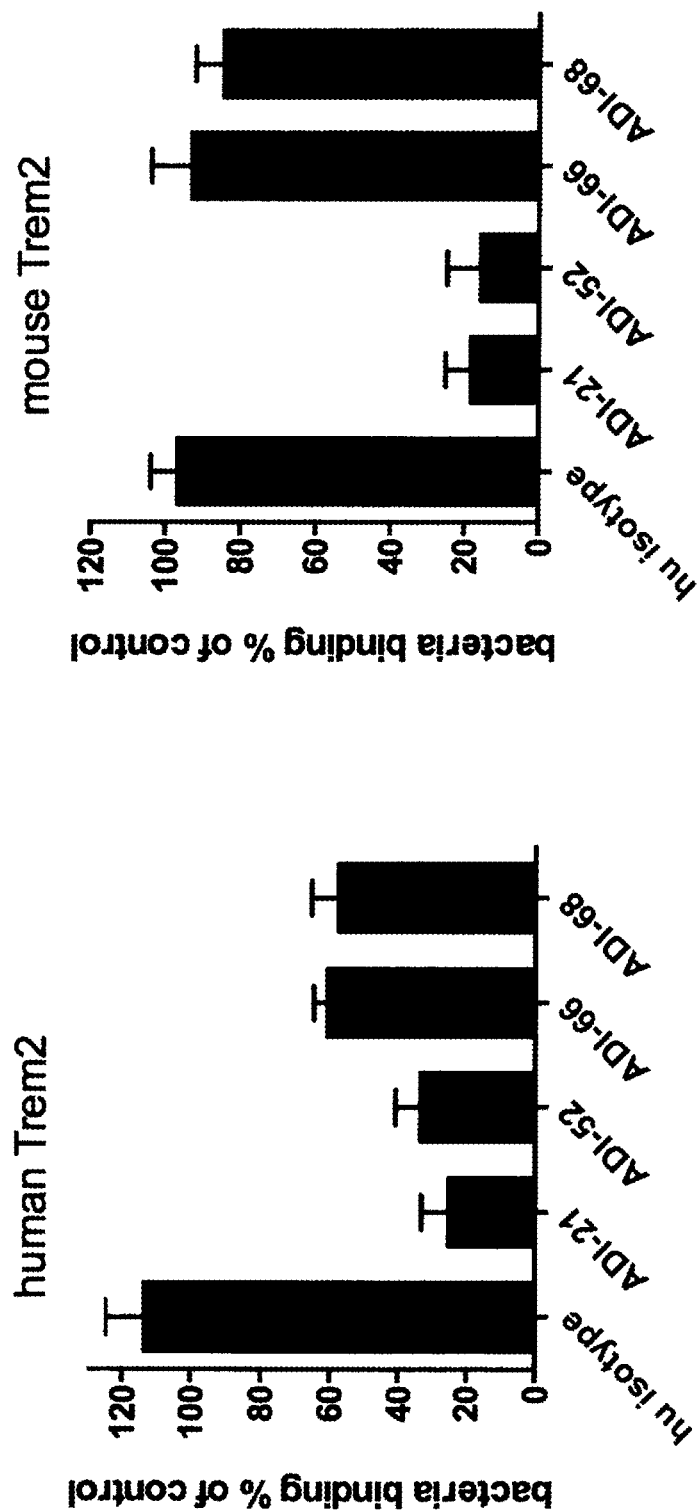
FIG. 8 shows competitive binding between TREM2 antibodies and *E. coli* bacteria expressing putative TREM2 ligand with mouse and human cell lines expressing TREM2. Bacterial binding is expressed as a percentage of control. Average of two independent experiments; black bars: no difference to isotype control, red bars: significantly different from isotype controls (ANOVA).

TREM2 antibodies Ab21 and Ab52 inhibited the binding of *E. coli* bacteria to both human and mouse cells, indicating competitive binding of the antibodies to the ligand-binding site on TREM2 (FIG. 8). Non-agonistic control TREM2 antibodies (Ab66 and Ab68) inhibited bacterial binding to human cells expressing TREM2, but did not inhibit binding to mouse TREM2.

Example 27: Summary of TREM2 Antibody Functional Studies

Table 6 summarizes results of the functional studies described in Examples 24-26 above. Antibodies Ab21 and Ab52 demonstrated induction of Syk phosphorylation in human dendritic cells (hDC), mouse dendritic cells (mDC), and mouse macrophages (mMac). However, antibody Ab52 induced higher levels of phosphorylated Syk compared to antibody Ab21 in human and mouse DCs. Both antibodies were able to mimic ligand binding to human and mouse TREM2, although antibody Ab21 demonstrated more effective binding, as indicated by a greater decrease in bacterial binding (see Example 26 above).

TABLE 6

TREM2 Antibody Functional Studies

| Antibody | Induction Phospho Syk hDC | Induction Phospho Syk mDC | Induce Phospho DAP12 mMac | Mimic ligand binding site on human Trem2 | Mimic ligand binding site on mouse Trem2 |
|---|---|---|---|---|---|
| Ab52 | +++ | +++ | +++ | ++ | +++ |
| Ab21 | ++ | ++ | +++ | +++ | +++ |
| Isotype control | – | – | – | – | – |

Example 28: TREM2 Decreases the Secretion of Inflammatory Cytokines from Mouse Macrophages In order to determine the role of TREM2 in inflammatory cytokine production, mouse wild-type (WT), TREM2 knock-out (KO), and TREM2 heterozygous (Het) macrophages were cultured with various inflammatory mediators, and cytokine levels were measured in the culture supernatants.

To generate BMDM, total bone marrow from wild-type (WT), TREM2 KO (KO), and TREM2 heterozygous (Het) mice was cultured in RPMI supplemented with 10% bovine calf serum, 5% horse serum, and 50 ng/ml recombinant mouse CSF-1 (R&D Systems). Cells were cultured for 5 days, and adherent cells were detached with 1 mM EDTA in PBS. BMDM were plated on 96-well plates at 105 cells/well and allowed to adhere for 4 h at 37° C. Cells were then stimulated with TLR agonists LPS (*Salmonella abortus* equi) or zymosan (*Saccharomyces cerevisiae*) at concentrations ranging from 0.01-100 ng/ml (LPS) or 0.01-100 μg/ml (zymosan). Alternatively, macrophages isolated from WT, KO, and Het mice were cultured in the presence of 10 ng/ml of the cytokine IL-4 or 50 ng/ml of IFN-γ. Cell culture supernatant was collected 24 or 48 h after stimulation and the levels of TNFa, IL-6, IL-10, and MCP-1 cytokines were measured by using Cytometric Bead Array Mouse Inflammation Kit (BD) according to manufacturer's protocol.

Figure 9A:
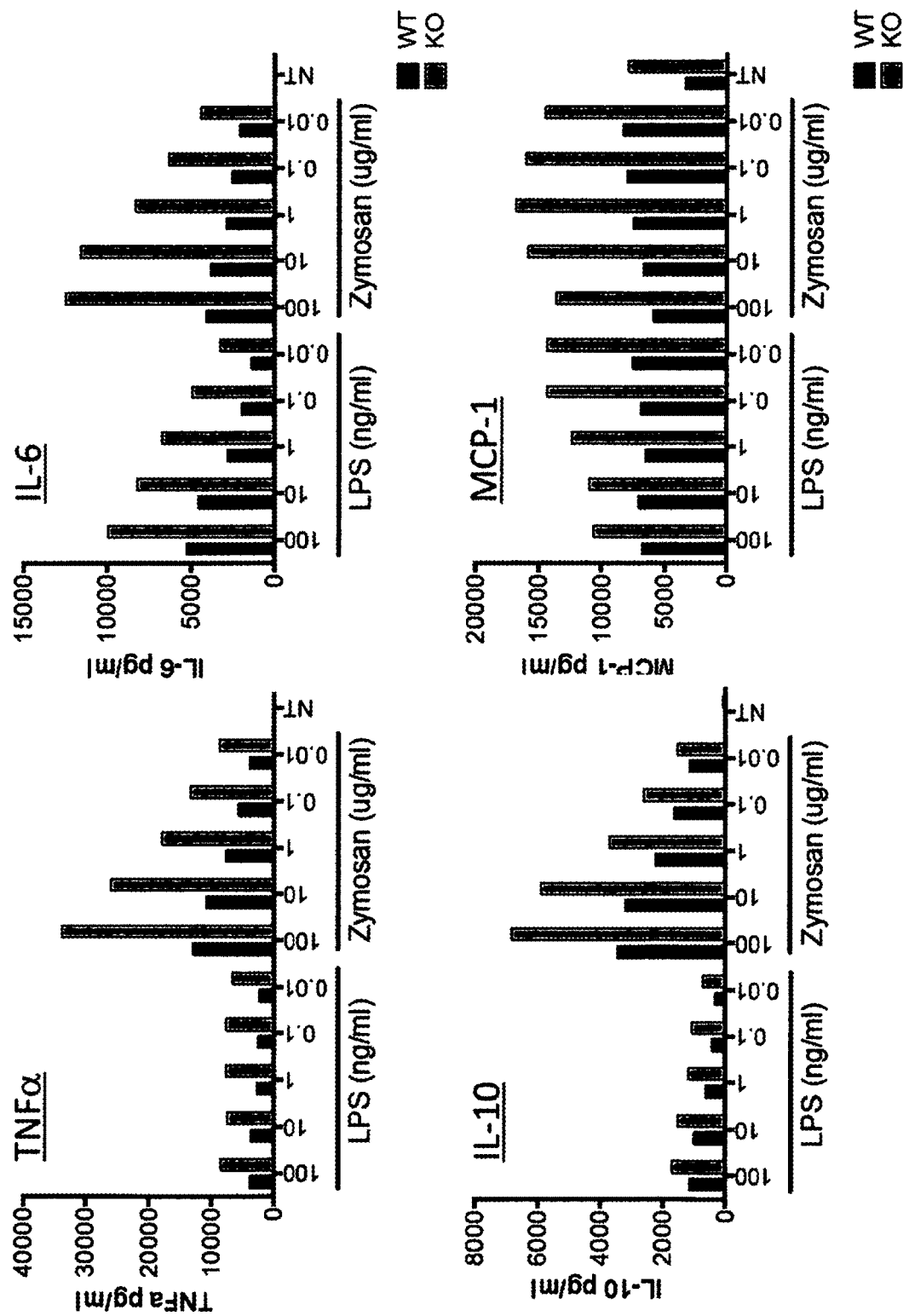
FIG. 9A shows protein levels of inflammatory cytokines TNFa, IL-6, IL-10, and MCP-1 secreted in response to stimulation of WT and TREM2 KO macrophages with inflammatory mediators LPS or Zymosan.
Figure 9B:
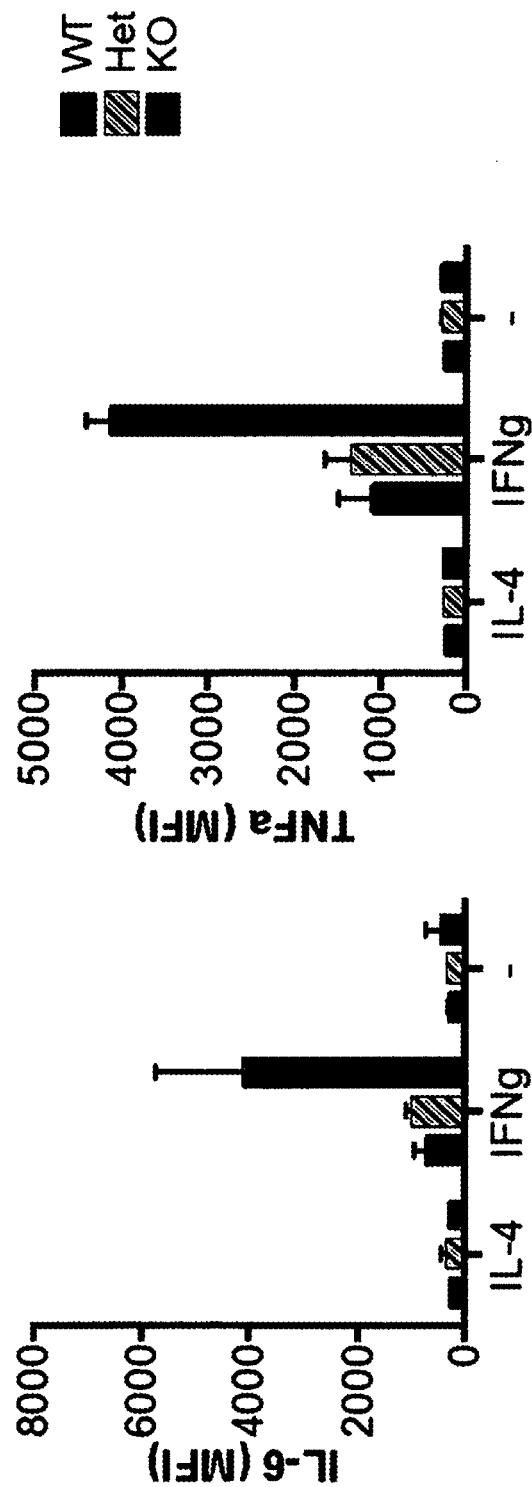
FIG. 9B shows protein levels of inflammatory cytokines IL-6 and TNFa secreted in response to stimulation of WT, TREM2 heterozygous (Het), and TREM2 KO macrophages with the cytokines IL-4 or IFNg.

Wild-type (WT) macrophages stimulated with the inflammatory mediators LPS or zymosan secreted less inflammatory cytokines TNFa, IL-6, IL-10, and MCP-1 compared to TREM2 KO (TREM2$^{-/-}$) macrophages (FIG. 9A). Similarly, WT and Het (TREM2$^{+/-}$) macrophages treated with the mediator IFNγ produced less inflammatory cytokines IL-6 and TNFa compared to TREM2 KO macrophages (FIG. 9B). WT, Het, and KO macrophages cultured in the presence of the cytokine IL-4 produced similar low levels of IL-6 and TNFa (FIG. 9B). Based on these results, TREM2 antibodies may reduce the secretion of inflammatory cytokines from macrophages.

Example 29: TREM2 Decreases the Expression of Inflammatory Cell Surface Markers on Mouse Macrophages In order to determine the role of TREM2 in inflammatory marker expression, mouse wild-type (WT), TREM2 knock-out (KO), and TREM2 heterozygous (Het) macrophages were cultured with various inflammatory mediators, and the expression of surface markers CD86 and CD206 were measured.

Macrophages isolated from WT, KO, and Het mice were plated and allowed to adhere for 4 h at 37° C., and TLR agonists LPS (*Salmonella abortus* equi) and zymosan (*Saccharomyces cerevisiae*) were added at concentrations ranging from 0.01-100 ng/ml (LPS) or 0.01-10 μg/ml (zymosan). Alternatively, macrophages isolated from WT, KO, and Het mice were cultured in the presence of the cytokines IL-4 (10 ng/ml) or IFN-γ (0.5-50 ng/ml). FACS analysis of CD86 and CD206 was performed on a BD FACS Canto 48 hours later. Data analysis was performed with FlowJo (TreeStar) software version 10.0.7.

Wild-type (WT) macrophages treated with the inflammatory mediators IFN-γ (FIG. 10A), LPS, or Zymosan (FIG. 10B) expressed lower levels of the inflammatory receptor CD86 but not of the receptor CD206 compared TREM2 KO (TREM2$^{-/-}$) macrophages. Similarly, Het (TREM2$^{-/-}$) macrophages treated with I IFN-γ expressed lower levels of CD86 but not of CD206 compared to TREM2 KO macrophages (FIG. 10A). Based on these results, TREM2 agonistic antibodies may reduce expression of inflammatory receptors on macrophages.

Example 30: TREM2 Increases the Survival of Macrophages and Dendritic Cells

To evaluate the role of TREM2 in cell survival, wild-type (WT) and TREM2 knock-out (KO) macrophages and dendritic cells were cultured in the presence of inflammatory mediators, and cell survival was measured.

Murine bone marrow precursor cells from TREM2 WT, Het, and KO mice were obtained by flushing tibial and femoral marrow cells with cold PBS. After one wash with PBS, erythrocytes were lysed using ACK Lysing Buffer (Lonza), washed twice with PBS and suspended at $0.5\times10^6$ cells/ml in complete RPMI media (10% FCS, Pen/Strep, Gln, neAA) with the indicated amounts of 50 ng/ml M-CSF to produce macrophages, or 10 ng/ml GM-CSF to produce dendritic cells. For M2-type macrophages, 10 ng/ml IL-4 was added to the cultured cells. For M1-type macrophages, 50 ng/ml IFN-γ was added. In some experiments LPS or zymosan was added to the cell culture at day 5 at a concentration range of 1 µg/ml-0.01 ng/ml. Recombinant cytokines were purchased from Peprotech.

To analyze viability of bone marrow-derived macrophages, cells were prepared as above and cultured in MCSF. Cells were either plated at $10^5/200$ µl in a 96-well plate (for viability analysis using a luciferase based-assay) or at $0.5\times10^6/1$ ml in a 6-well plate (for Tripan Blue exclusion cell count) in non-tissue culture treated plates. Media containing fresh M-CSF was added at day 3. At the indicated time points cells were gently detached from the plates with 3 mM EDTA and counted using a Burker chamber. For FACS analysis of live cells, macrophages were cultured either in 50 ng/ml MCSF for 6 days (+MCSF) or in 50 ng/ml MCSF for 4 days before MCSF was removed for an additional 36 hrs (−MCSF). Cells were stained using CD11b antibody and DAPI. For luciferase viability assays, cell viability was measured at day 5 of culture in graded concentrations of growth factors GMCSF (dendritic cells), MCSF (M1 macrophages), or MCSF+IL-4 (M2 macrophages). Cells were directly incubated with ToxGlo reagent (Promega) and luciferase activity (luminescence) was read using an XY reader. For FACS analysis of viable macrophages cultured in the presence of inflammatory mediators IFN-γ, LPS, or zymosan, cells were collected at day 5 and stained using CD11b antibody and DAPI.

Figures 11A, 11B:
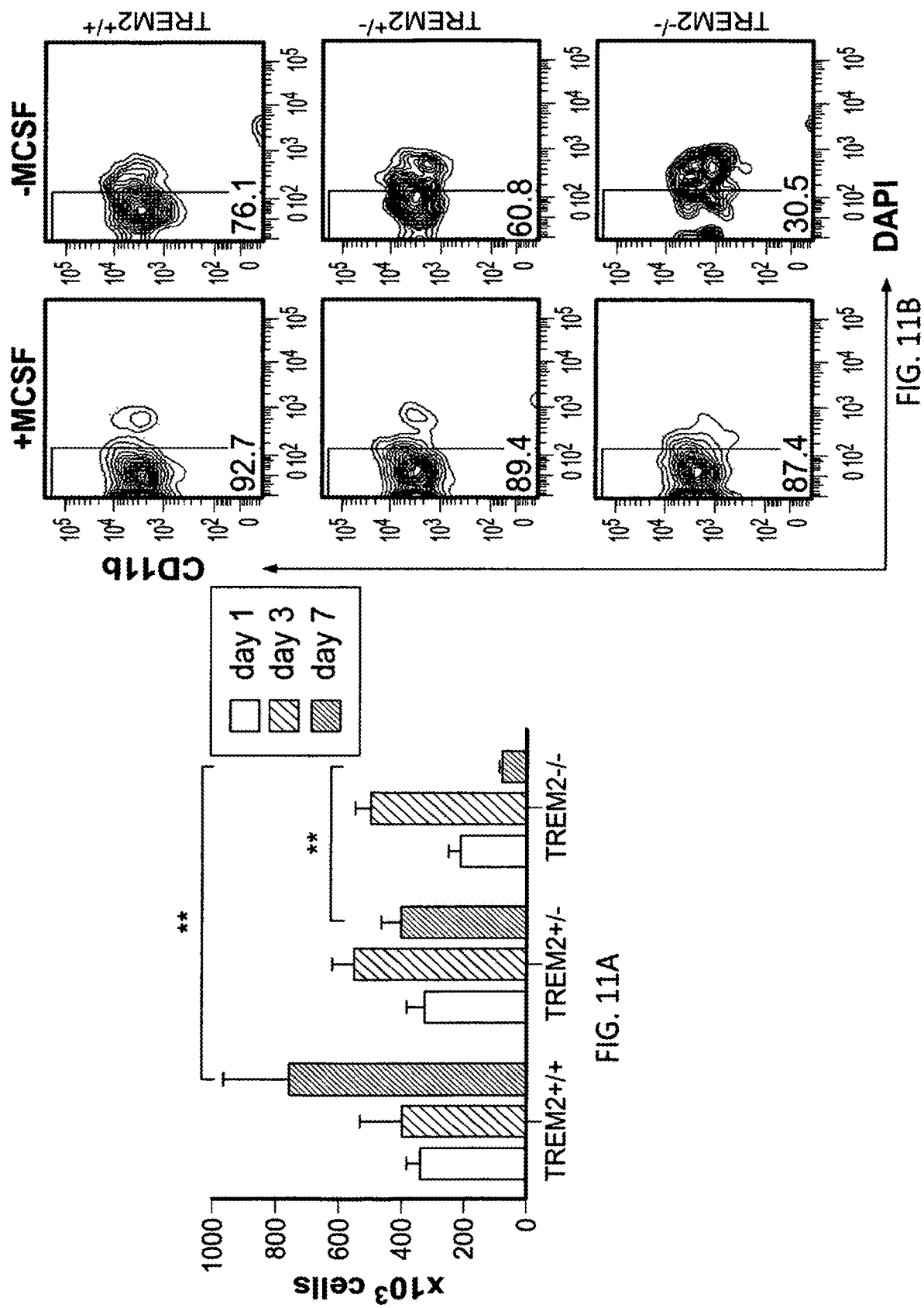
FIG. 11A shows numbers of live WT, TREM2 heterozygous (TREM2+/−), and TREM2 KO (TREM2−/−) macrophages after culture in growth factor MCSF for the indicated number of days.
FIG. 11B shows FACS plots demonstrating staining of WT, TREM2 heterozygous (TREM2+/−), and TREM2 KO (TREM2−/−) macrophages after culture in MCSF for 6 days (+MCSF) or in MCSF for 4 days, followed by no MCSF for 36 hours (−MCSF). Percentage of live macrophages within the CD11b+DAPI−gate is indicated on each plot.
Figure 11C:
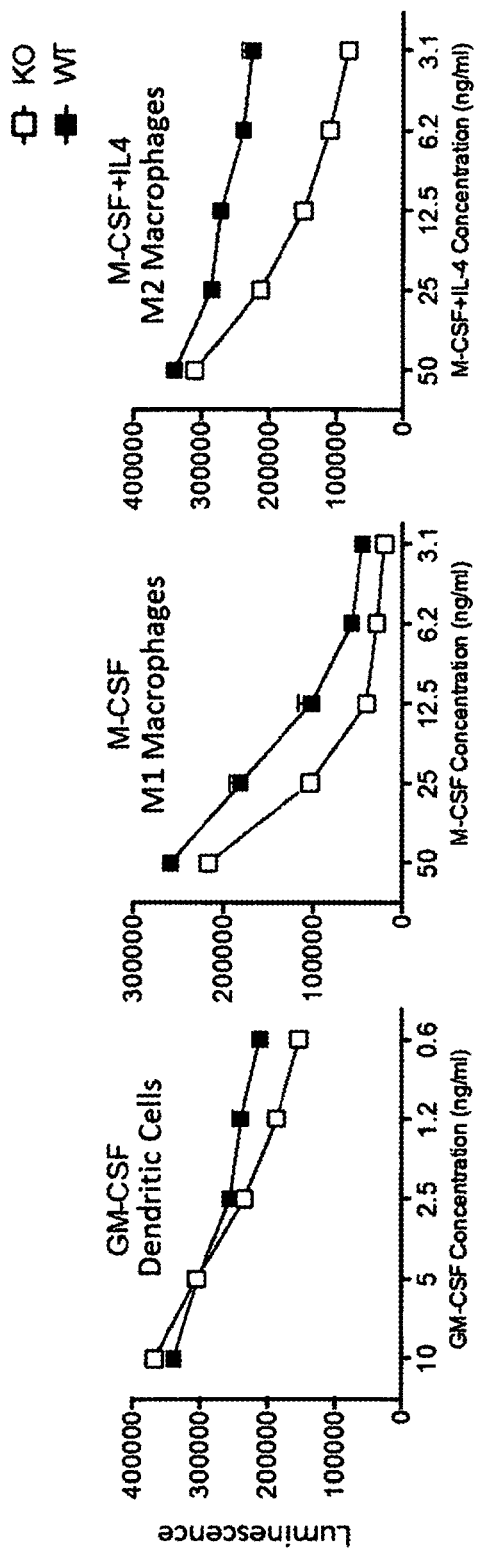
FIG. 11C shows luminescence levels detected in a luciferase viability assay after culture of WT and TREM2 KO dendritic cells, M1 macrophages, and M2 macrophages in growth factors GM-CSF, M-CSF, or M-CSF+IL-4, respectively.
Figure 11D:
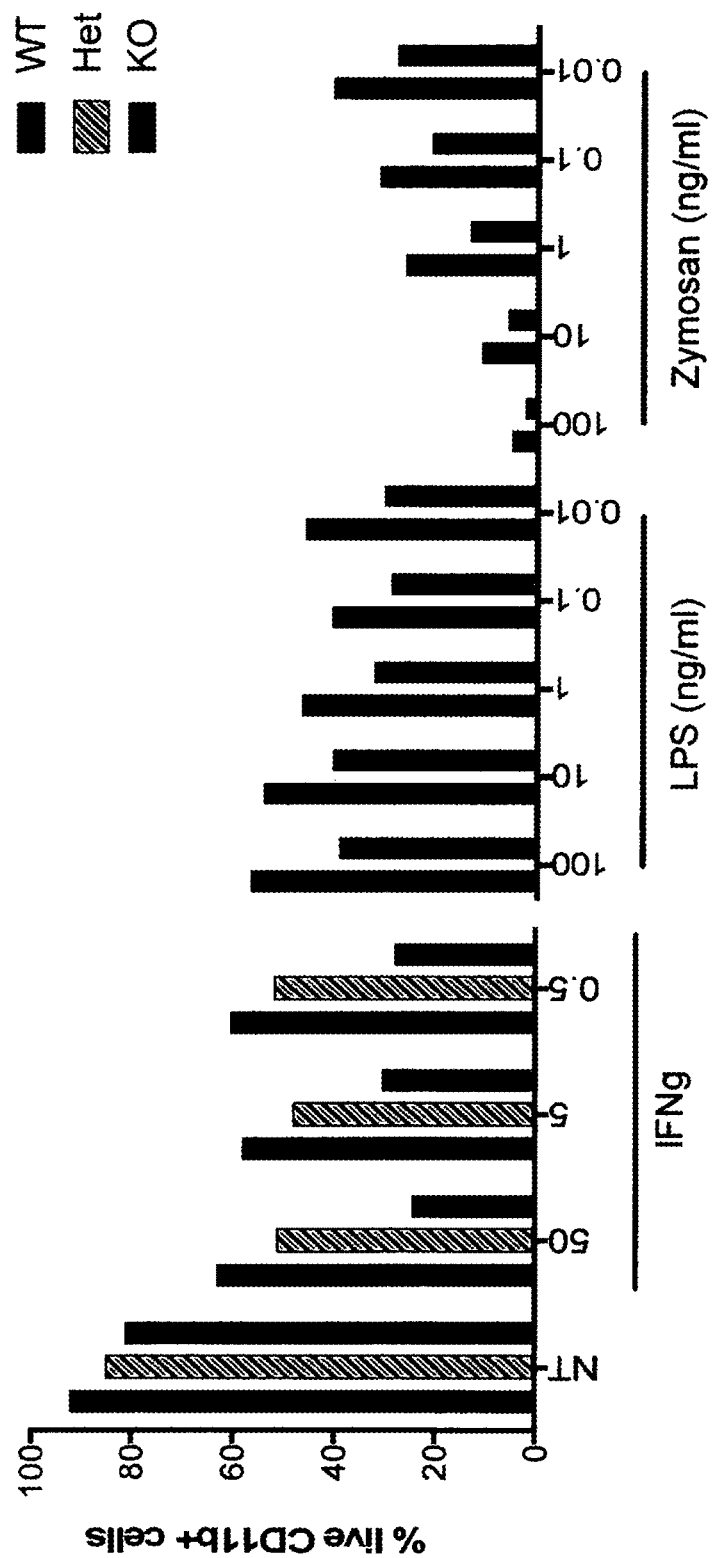
FIG. 11D shows the frequency of live WT, TREM2 heterozygous (Het), and TREM2 KO macrophages (CD11b+) after culture in inflammatory mediators IFNg, LPS, or Zymosan.

After 7 days of culture in MCSF, significantly higher numbers of viable (trypan blue excluded) TREM2 WT and Het (TREM2$^{+/-}$) macrophages were observed than TREM2 KO (TREM2$^{-/-}$) macrophages (FIG. 11A). FACS analysis revealed that WT macrophages treated with MCSF for either 6 (+MCSF) or 4 days (−MCSF) displayed increased survival compared to Het and KO macrophages, as indicated by a higher percentage of live (CD11b+DAPI−) cells (FIG. 11B). For luciferase assays, WT cells cultured in the presence of growth factors GMCSF (dendritic cells), MCSF (M1 macrophages), or MCSF+IL-4 (M2 macrophages) survived better than KO cells, as indicated by a higher luminescence reading across the range of growth factor concentrations (FIG. 11C). Wild-type macrophages cultured with inflammatory mediators (IFN-γ, LPS, or zymosan) had a higher survival rate than TREM2 Het and KO macrophages, as indicated by a higher percentage of CD11b+ live cells (FIG. 11D). Based on these results, TREM2 agonistic antibodies may increase the survival of macrophages and dendritic cells, while TREM2 antagonistic antibodies can decrease cell survival.

Example 31: TREM2 Modulates Phagocytosis

TREM2 signaling is involved in phagocytosis pathways, including bacterial clearance from the lung and phagocytosis of apoptotic neurons. The role of TREM2 in phagocytosis was evaluated by measuring the ability of wild-type (WT) and TREM2 knock-out (KO) mouse macrophages to phagocytose E. coli cells and apoptotic cells.

WT and TREM2 KO BMDM were starved in 1% serum RPMI or kept in culture in the presence of MCSF (50 ng/ml) overnight. The following day cells were plated at $2\times10^5$ in 96 well plates (round bottom non tissue culture), in the presence or absence of MCSF. Target cells (CCL119) were cultured overnight with 0.5 µM staurosporine to induce apoptosis. The day after cells were washed and labeled with 20 ng/ml of pHrodo-SE (Invitrogen). Apoptotic cells or bioparticle E. coli (pHrodo, Invitrogen) were added and the cells were incubated at 37° C. for 1h and 30 min. The assay was stopped on ice. After washing with cold PBS, cells were stained for CD11b (pacific blue-CD11b, BD) and analyzed by FACS. In all samples, BMDM were distinguished from apoptotic cells and beads by CD11b staining, and gates were drawn based on effector cells cultured without target cells. For negative controls, effector cells were incubated during the entire assay with cytochalasin D (2 µM, SIGMA). Phagocytosis was quantified as (percent or MFI of PhRodo positive cells)−(percent or MFI of PhRodo positive cytochalasin D treated negative control cells).

Figure 12:
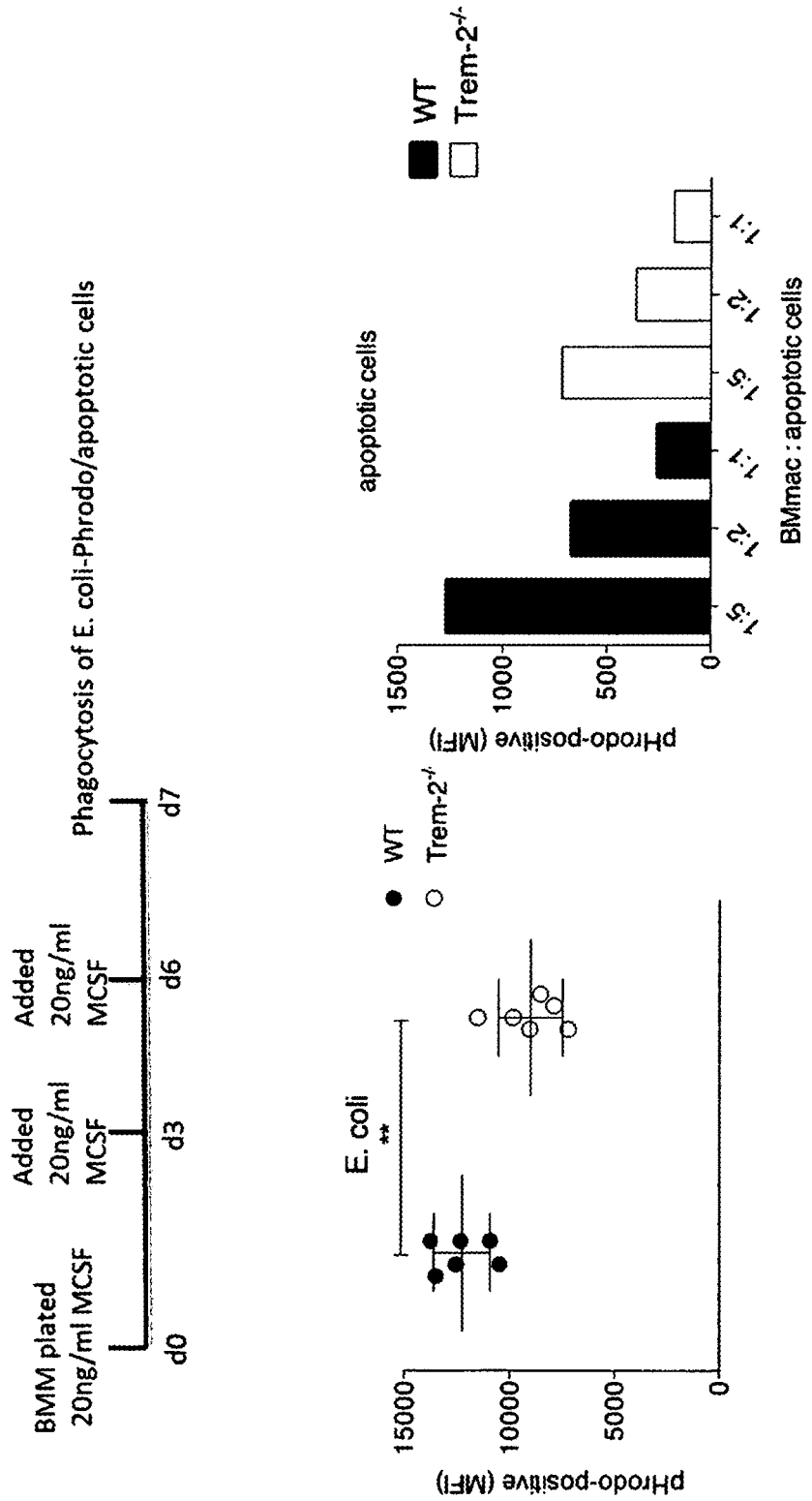
FIG. 12 shows phagocytosis of apoptotic cells and *E. coli* by wild-type (WT) and TREM2 KO (TREM2−/−) bone marrow derived macrophages (BMmacs) cultured without MCSF.

Wild-type (WT) macrophages cultured with MCSF displayed less phagocytosis of apoptotic cells and E. coli cells as compared to TREM2 KO (TREM2-) macrophages, as indicated by a lower percentage of pHrodo+ cells (FIG. 12). Conversely, WT macrophages cultured without MCSF displayed increased phagocytosis of apoptotic cells and E. coli cells as compared to TREM2 KO macrophages, as indicated by a higher percentage of pHrodo+ cells (FIG. 12). Based on these results, TREM2 agonistic antibodies may enhance phagocytosis in the absence of MCSF and reduce phagocytosis in the presence of MCSF. Conversely, it is believed that TREM2 antagonistic antibodies can enhance phagocytosis in the presence of MCSF and reduce phagocytosis in the absence of MCSF.

Example: 32: Epitope Mapping of TREM2 Antibodies

TREM2 antibodies were tested for their ability to bind 15 or 25 mer peptides spanning the entire human and mouse TREM2.

Linear 15-mer peptides were synthesized based on the sequence of human or mouse TREM2, with a 14 residue overlap. In addition, linear 25-mer peptides were synthesized based on sequence of human or mouse TREM2 with a 1 residue shift. The binding of TREM2 antibodies to each of the synthesized peptides was tested in an ELISA-based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% H2O2 were added. After one hour, the color development was measured. The color development was quantified with a charge coupled device (CCD) camera and an image processing system.

Figure 13:
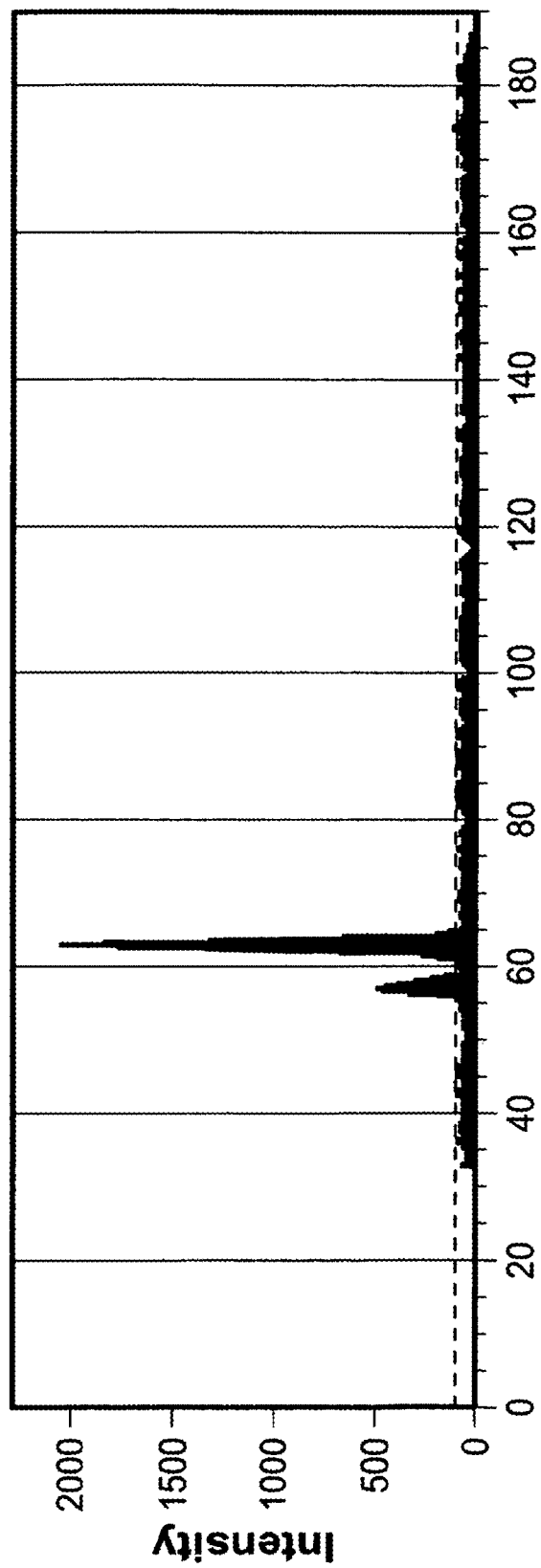
FIG. 13 shows an epitope map of TREM2 antibody Ab52.

Antibody Ab52 demonstrated reliable binding in all peptide sets. Antibody Ab52 was found to recognize an N-terminal peptide region between amino acid residues 49-57 of human and mouse TREM2 ($^{49}$AWCRQLGEK$^{57}$ (SEQ ID NO: 444)) (FIG. 13). The epitope region recognized by Ab52 corresponds to amino acid residues 49-57 of SEQ ID NO: 1 and has the amino acid sequence of: AWCRQLGEK (SEQ ID NO: 444).

Antibody Ab21 was found to recognize an N-terminal peptide region between amino acid residues 43-50 of human and mouse TREM2 ($^{43}$HWGRRAW$^{50}$ (SEQ ID NO: 445)). The epitope region recognized by Ab21 corresponds to amino acid residues 43-50 of SEQ ID NO: 1 and has the amino acid sequence of: HWGRRAW (SEQ ID NO: 445).

Example 33: Comparison of Agonistic TREM2 Antibodies Ab52 and Ab21 to Reference TREM2 Antibodies Reference TREM2 antibodies were compared to agonist antibodies Ab21 and Ab52 by evaluating their ability to induce Syk phosphorylation and by determining their TREM2 binding region.

Cells were coated with 1 Gg/10$^6$ cells of TREM2 antibody MAB17291 (R&D Systems) or monoclonal rat IgG1 antibody 78.18 (obtained from the University of California, San Francisco) and stimulated by cross-linking with a secondary antibody (goat anti-rat 1.5 g/10$^6$ cells). Syk phosphorylation was evaluated according to the methods described in Example 24 above.

To evaluate antibody binding regions, human TREM2-Fc was incubated with immobilized full-length agonist TREM2 antibodies Ab21 or Ab52, and TREM2 antibodies MAB17291 or 78.18 were subsequently added. Epitope binning of the antibodies was performed on a Forte Bio Octet Red384 system (Pall Forte Bio Corporation, Menlo Park, Calif.) using a standard sandwich format binning assay (see Estep et al, (2013) MAbs 5(2):270-8). Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor).

Figure 14:
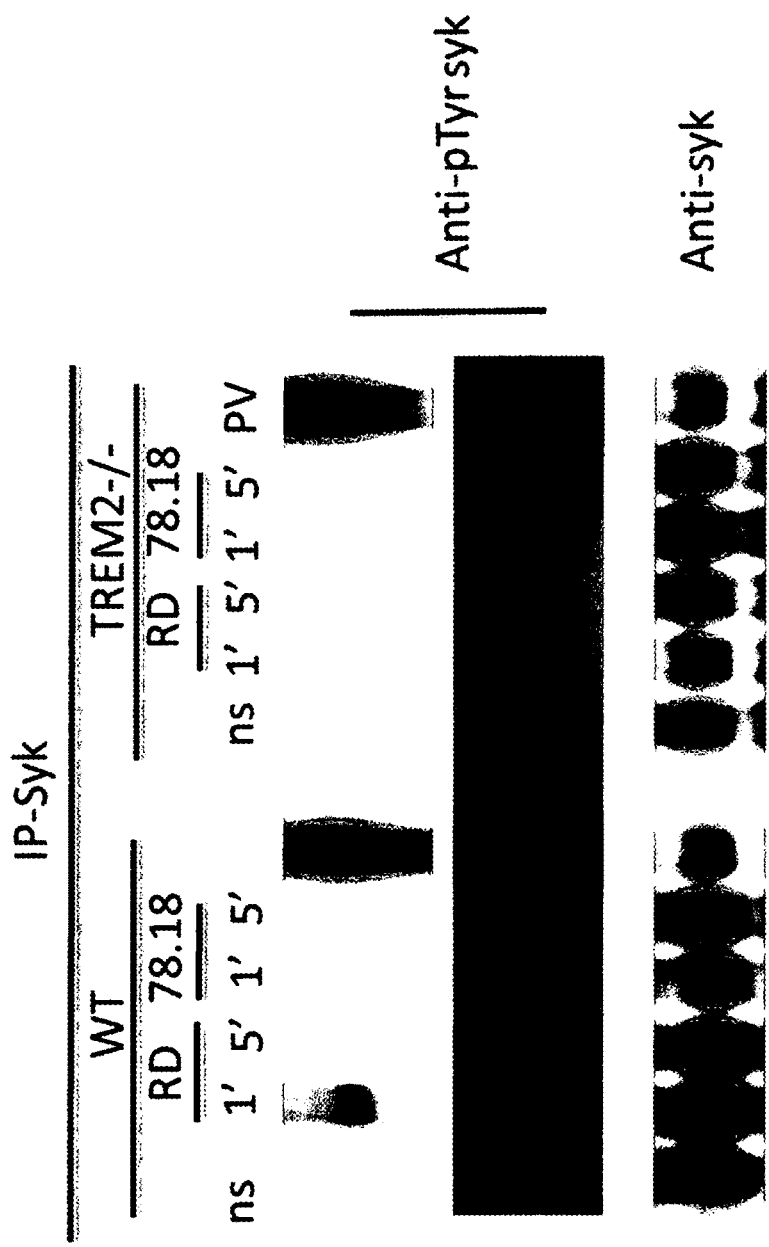
FIG. 14 shows Syk phosphorylation as determined by Western blot in wild-type and TREM2 deficient (Trem2−/−) mouse macrophages after incubation with TREM2 antibodies MAB17291 (RD) or 78.18, demonstrating that antibody 78.18 does not induce Syk phosphorylation or TREM2 signaling.

Reference TREM2 antibody MAB17291 induced Syk phosphorylation in WT, but not TREM2 KO (TREM2$^{-/-}$) cells. Reference TREM2 antibody 78.18, however, did not induce Syk phosphorylation under the experimental conditions used (FIG. 14). This is in contrast to Ab21 and Ab52, which were both able to induced Syk phosphorylation in WT TREM2 mouse BMDMs (FIG. 6).

Reference antibody MAB17291 was able to simultaneously bind TREM2 with antibody Ab21 (FIG. 15A) or antibody Ab52 (FIG. 15B). These results demonstrate that agonist TREM2 antibodies Ab21 and Ab52 bind different regions of the TREM2 protein than does reference antibody MAB17291.

Example 34: Analysis of Ability of TREM2 Antibody Fabs to Stimulate Viability of Innate Immune Cells The agonistic functionality of plate bound, cross-linked anti-TREM2 antibody Fab fragments derived from antibodies Ab21 and Ab52 was evaluated in innate immune cells (e.g., macrophages).

Wild-type (WT) and TREM2 knock-out (KO) mouse bone marrow derived macrophages were cultured in the presence of M-CSF and plate bound TREM2 antibody Fabs, and cell viability was measured.

Macrophages isolated from the bone marrow of WT and KO mice were plated on non-tissue-culture-treated 96-well plates, pre-coated with either 12.5 nM or 100 nM of cross-linked Ab21 or Ab52 Fabs. Cells were cultured for 48 hours in the presence of 10 ng/ml M-CSF. Analysis of viability was performed using Cell Titer Glo kit (Promega). Plates were read with a BioTek Synergy Microplate Reader using GEN5 2.04 software.

Figure 16:
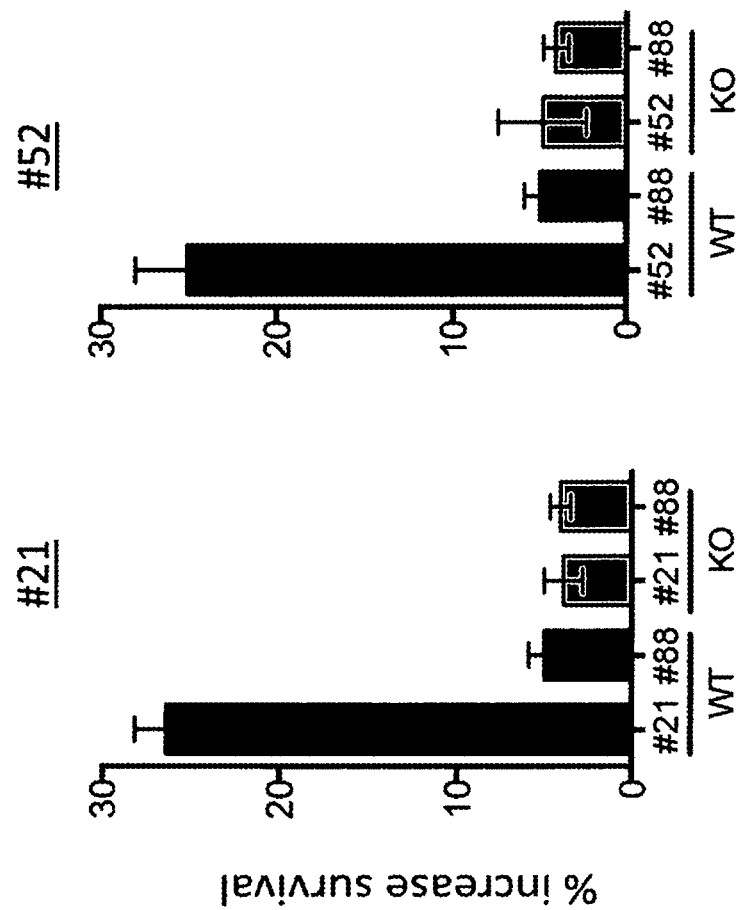
FIG. 16 shows the percent increased survival of wild-type (WT) and TREM2 knock-out (KO) mouse bone marrow derived macrophages cultured in the presence of plate bound, cross-linked TREM2 antibody Ab21 or Ab52 Fabs and M-CSF. Antibody Ab88 represents the negative isotype control.

Cross-linked TREM2 Fab fragments derived from antibodies Ab21 and Ab52 increased the number of viable mouse bone marrow-derived macrophages compared to isotype control Fab Ab88, as indicated by a higher % increased survival (FIG. 16). This enhancement in cell viability was not observed in KO mouse macrophages. These data indicate that the biological activity of TREM2 antibodies Ab21 and Ab52 is TREM2 specific, and that plate bound, cross-linked Ab21 and Ab52 Fab fragments function as agonists to increase the survival of macrophages cultured in M-CSF.

Example 35: Analysis of Ability of TREM2 Antibodies to Decrease Survival of Innate Immune Cells The antagonistic functionality of both soluble, non-cross-linked anti-TREM2 antibody Fab fragments derived from antibodies Ab21 and Ab52 and soluble, full-length anti-TREM2 antibodies Ab21 and Ab52 was evaluated in innate immune cells (e.g., macrophages).

Wild-type (WT) and TREM2 knock-out (KO) mouse bone marrow derived macrophages were cultured in the presence of M-CSF and soluble TREM2 antibody Fabs or soluble full-length antibodies, and cell viability was measured.

Macrophages isolated from the bone marrow of WT and KO mice were plated on non-tissue-culture-treated 96-well plates in the presence of 20 ng/ml M-CSF and increasing amounts of the indicated soluble, non-cross-linked TREM2 antibody Fabs or soluble, full-length antibodies. Each condition was plated in triplicate. Analysis of viability was performed using Cell Titer Glo kit (Promega) 3 days later. Plates were read with a BioTek Synergy Microplate Reader using GEN5 2.04 software.

In FIG. 17, the "NT" dotted line indicates the average cell viability obtained with untreated macrophages (no antibody added). The "no MCSF" dotted line indicates the average cell viability obtained when macrophages were cultured in the absence of M-CSF.

Figure 17A:
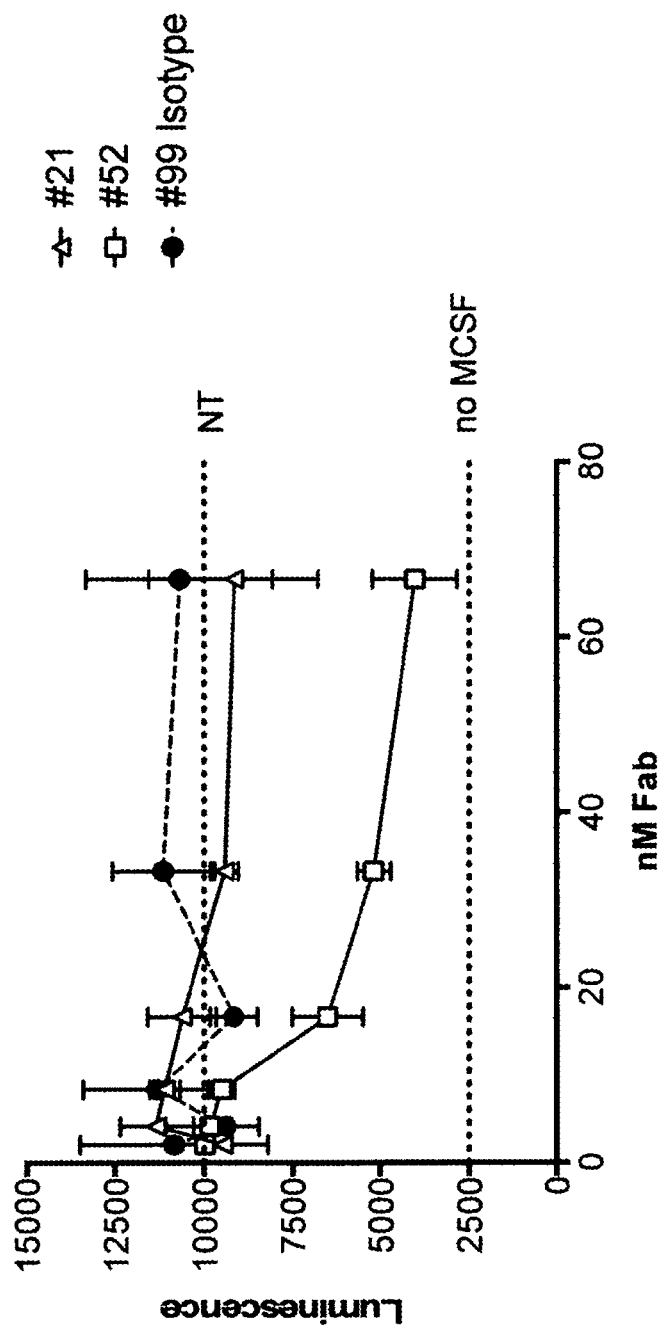
FIG. 17A shows the luminescence viability assay of mouse bone marrow derived macrophages cultured in the presence of soluble, non-cross-linked TREM2 antibody Ab21 or Ab52 Fabs and M-CSF. Antibody Ab99 represents the negative isotype control.

When macrophage cell viability was evaluated with soluble, non-cross-linked TREM2 antibody Fabs, the results indicated that soluble, non-cross-linked TREM2 Fab fragments derived from antibody Ab52 decreased cell viability (FIG. 17A). In contrast, soluble, non-cross-linked TREM2 Fab fragments derived from antibody Ab21 did not inhibit viability and had an effect comparable to the isotype control Ab99 (FIG. 17A). The results demonstrate that the soluble, non-cross-linked Fab derived from TREM2 antibody Ab52 can function as an antagonist and inhibit the survival of macrophages in vitro.

Figure 17B:
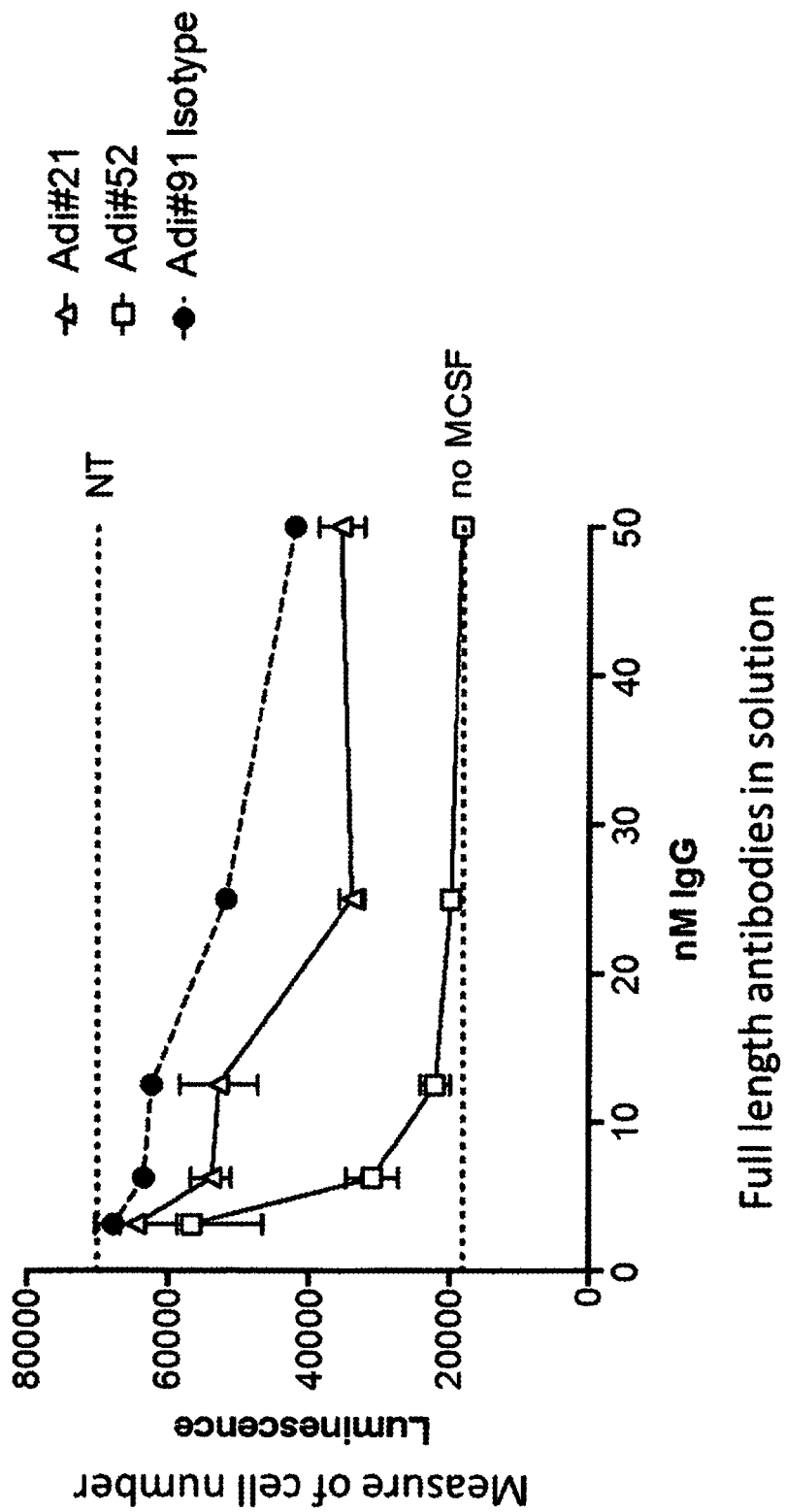
FIG. 17B shows the luminescence viability assay of mouse bone marrow derived macrophages cultured in the presence of soluble, full-length TREM2 antibody Ab21 or Ab52 and M-CSF. Antibody Ab91 represents the negative isotype control. The "NT" dotted line indicates the average viability obtained with untreated macrophages (no antibody added). The "no MCSF" dotted line indicates the average viability obtained when macrophages are cultured in the absence of M-CSF.

When macrophage cell viability was evaluated with soluble, full-length antibodies, antibody Ab52 decreased cell viability more potently than did Ab21 (FIG. 17B). Indeed, soluble, full-length antibody Ab21 had an effect on cell that was comparable to that of isotype control Ab91 (FIG. 17B). The results demonstrate that soluble, full-length TREM2 antibody Ab52 can function as antagonist, when not cross-linked or clustered, and inhibit the survival of macrophages.

The results of these experiments indicate that the TREM2 antibody Ab52, in the absence of clustering, can inhibit the survival of innate immune cells such as macrophages. In contrast, the TREM2 antibody Ab21, even in the absence of clustering, does not inhibit the survival of innate immune cells such as macrophages.

Example 36: Analysis of the Ability of TREM2 Antibodies to Induce TREM2-Dependent Genes The ability of plate bound anti-TREM2 antibodies Ab21 and Ab52 to activate TREM2-dependent genes was evaluate using a luciferase reporter gene under the control of an NFAT (nuclear factor of activated T-cells) promoter.

A cell line derived from mouse thymus lymphoma T lymphocytes BW5147.G.1.4 (ATCC® TIB48™) was infected with mouse Trem2 and Dap12, and with Cignal Lenti NFAT-Luciferase virus (Qiagen). Full-length anti-TREM2 antibodies were plate bound at 10 ug/ml in DPBS on tissue-culture treated clear bottom white 96 well plates (100 ul/well), overnight at 4° C. Wells were rinsed thrice with DPBS and subsequently were plated at 100,000 cells/well in media with 1% serum. As a positive control for signaling, PMA (0.05 ug/ml) and ionomycin (0.25 uM) were added together. Cells were incubated for 6 hours and luciferase activity was measured by adding OneGlo Reagent (Promega) to each well and incubating 3 min at RT on a plate shaker. Luciferase signal was measured using a BioTek plate reader.

Figure 18A:
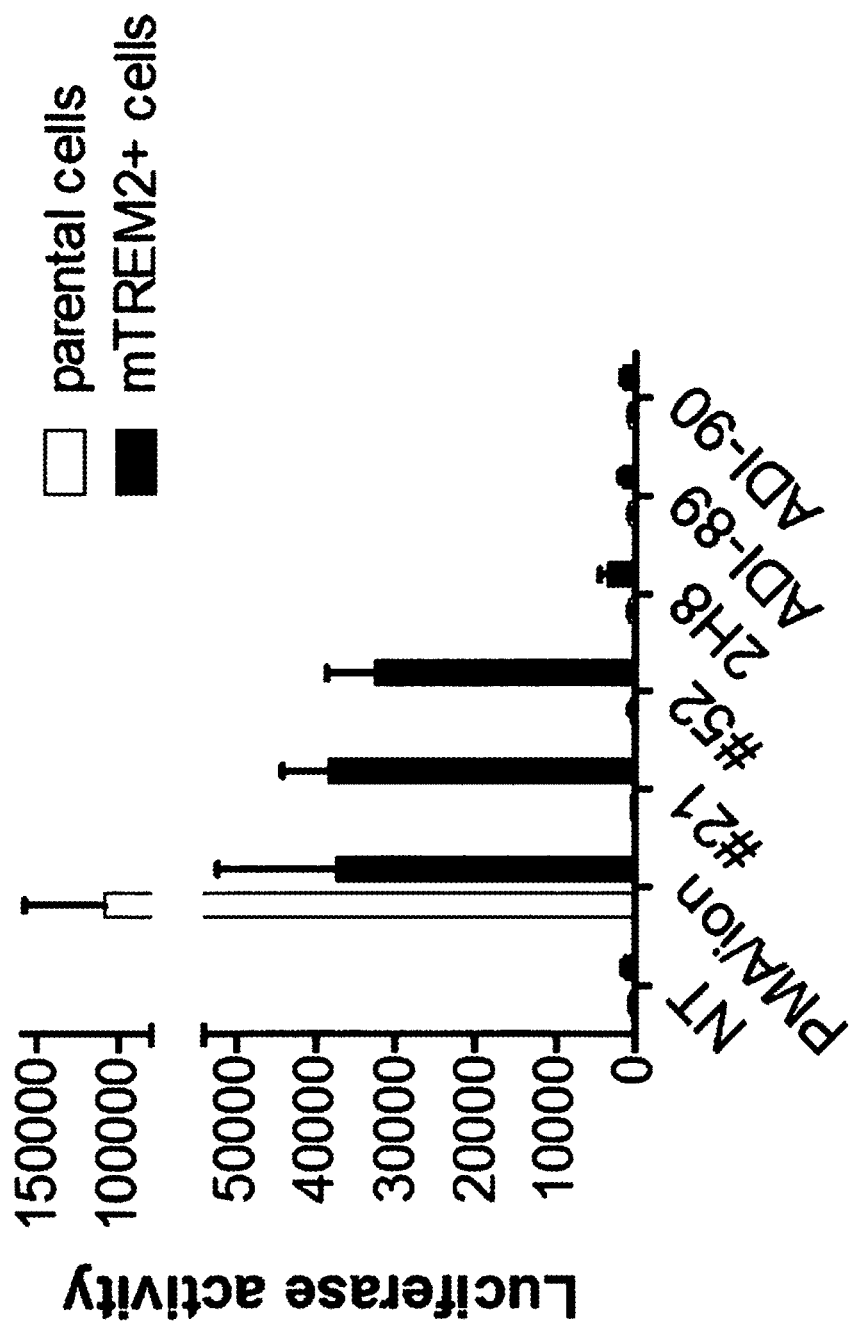
FIG. 18A shows induction of TREM2-dependent gene expression by plate bound, full-length anti-TREM2 antibodies Ab21 and Ab52 using a luciferase reporter gene in a cell-based assay.

As shown in FIG. 18A, anti-TREM2 antibodies Ab 21 and Ab52 increased luciferase activity, indicating that the antibodies were able to induce TREM2-dependent gene transcription.

As shown in FIG. 18B, plate bound phosphatidylserine (PS) induces TREM2-dependent gene expression. It is believed that PS is a natural ligand of TREM2. Thus, the results in FIG. 18 indicate that agonist anti-TREM2 antibodies can mimic a natural ligand of TREM2.

The ability of plate bound anti-TREM2 Fab antibodies Ab21 and Ab52 to activate TREM2-dependent genes was evaluated using primary mouse macrophages. Bone marrow-derived macrophages (BMM) were generated with M-CSF for 5 days. BMM ($10^5$/well) was seeded on 96 well plates that had been previously coated with the Fab portion of the antibodies Ab21 and Ab52 (50 nM). Ultrapure LPS (100 ng/ml *Escherichia coli* 0111:B4) was added after the plates were spun for 1 min at 1200 rpm. After 18 h of stimulation with LPS, cytokines present in cell supernatants were measured with cytometric bead array (CBA; BD Biosciences, CBA mouse inflammation kit).

Figures 18C, 18D:
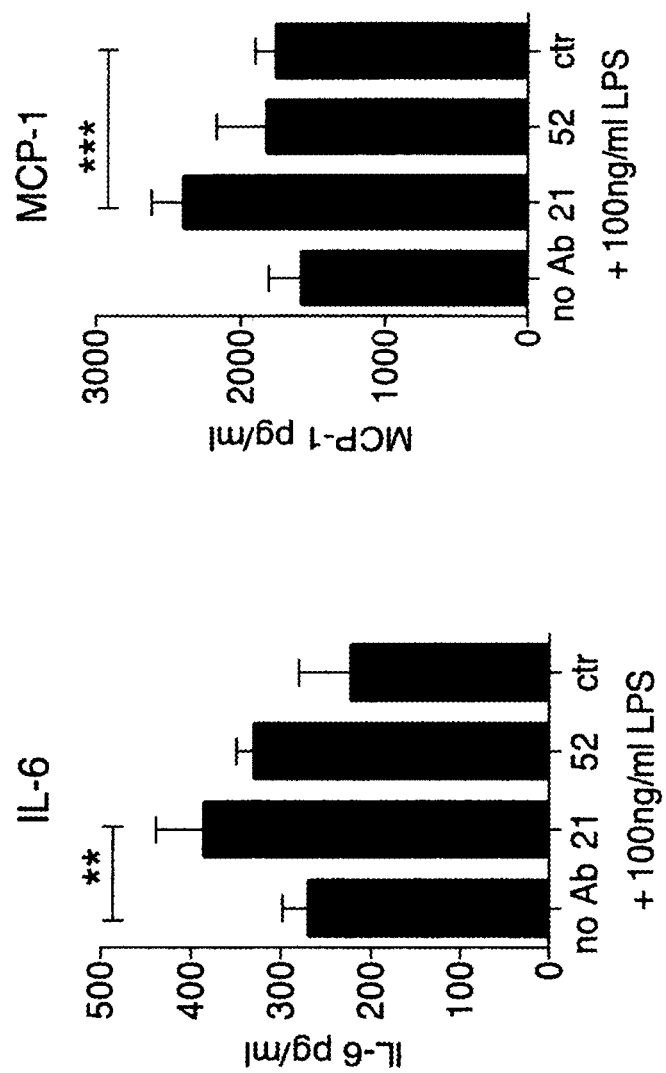
FIG. 18C shows activation of TREM2-dependent gene IL-6 in mouse macrophages by plate bound, Fab anti-TREM2 antibodies Ab21 and Ab52 Fabs.
FIG. 18D shows activation of TREM2-dependent gene MCP-1 in mouse macrophages by plate bound, Fab anti-TREM2 antibodies Ab21 and Ab52 Fabs. Data in FIGS. 18C and 18D are shown as means±SD; n=3 mice per group.

As shown in FIGS. 18C and 18D, plate bound anti-TREM2 Fab antibodies Ab 21 and Ab52 increased the levels of IL-6 and MCP-1, indicating that the antibodies were able to activate TREM2-dependent genes in primary immune cells.

Example 37: Analysis of the Ability of TREM2 Antibodies to Inhibit TREM2-Dependent Genes The ability of soluble, full-length anti-TREM2 antibodies Ab21 and Ab52 to inhibit TREM2-dependent genes was evaluate using a luciferase reporter gene under the control of an NFAT (nuclear factor of activated T-cells) promoter.

A cell line derived from mouse thymus lymphoma T lymphocytes BW5147.G.1.4 (ATCC® TIB48™) was infected with mouse Trem2 and Dap12, and with Cignal Lenti NFAT-Luciferase virus (Qiagen). Soluble, full-length anti-TREM2 antibodies Ab 21 or Ab52 were added at increasing concentration to the cells. Cells were incubated for 6 hours at 37° C. and luciferase activity was measured using OneGlo Reagent (Promega).

The cells display tonic TREM2-dependent signaling due to either the presence of an endogenous ligand or to spontaneous receptor aggregation, which leads to TREM2 signaling.

Figure 19:
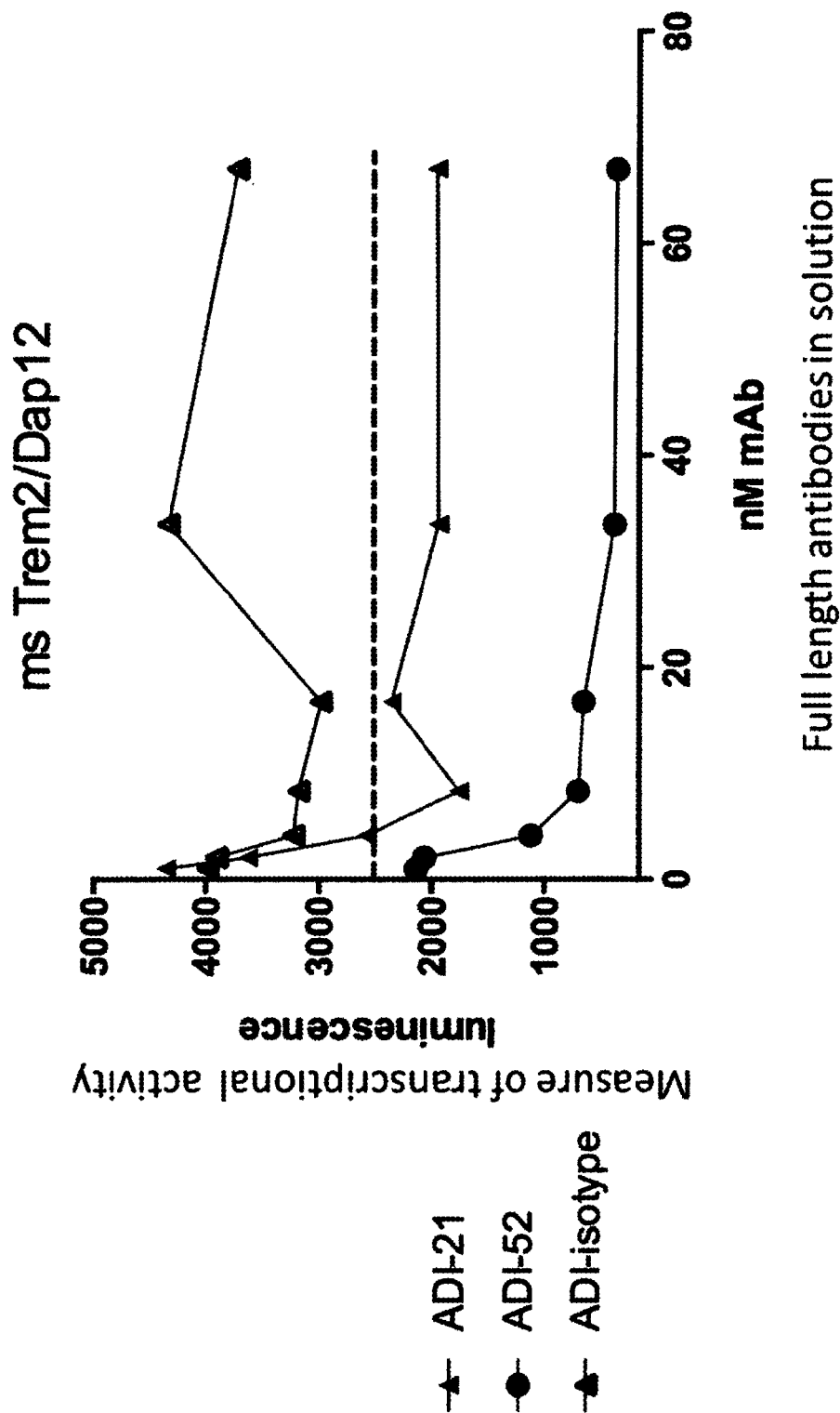
FIG. 19 shows inhibition of TREM2-dependent gene expression by soluble, full-length anti-TREM2 antibodies Ab21 and Ab52 using a luciferase reporter gene in a cell-based assay.

The dotted line in FIG. 19 indicates the levels of TREM2 activity without stimulation.

As shown in FIG. 19, soluble, full-length anti-TREM2 antibody Ab52 was able to inhibit tonic, TREM2-dependent gene expression. Soluble, full-length anti-TREM2 antibody Ab21 was able to partially inhibit tonic, TREM2-dependent gene expression; however the levels of gene expression were nearly the same as the levels of TREM2 activity without stimulation (FIG. 19).

Example 38: Summary of TREM2 Antibody Agonistic and Antagonistic Activity

Table 7 summarizes results of the functional studies described in Examples 35-37 above. Antibodies Ab21 and Ab52 demonstrated agonistic activity in activating TREM2-dependent gene expression using either a luciferase reporter gene (FIG. 18) or a beta-GAL reporter gene (Table 7). As indicated in Table 7, Ab21 showed an increased level of gene induction, compared to Ab52 when the luciferase reporter gene was used. However, Ab52 showed an increased level of gene induction, compared to Ab21 when the beta-GAL reporter gene was used (Table 7). Antibodies Ab21 and Ab52 also demonstrated agonistic activity in stimulating cell survival of innate immune cells (FIG. 16). Table 7 further summarizes results demonstrating the antagonistic effects of soluble, non-cross-linked antibody Ab52 in inhibiting cell survival of innate immune cells (FIG. 17). In contrast, soluble, non-cross-linked antibody Ab21 had minimal antagonistic activity in inhibiting cell survival (FIG. 17).

TABLE 7

TREM2 Antibody Agonist and Antagonist Activity

| Antibody | Luciferase Agonistic antibody activity | beta-GAL Agonistic antibody activity | Survival Agonistic antibody activity | Luciferase Antagonistic antibody activity in solution/antagonistic Ab format |
|---|---|---|---|---|
| Ab52 | +++ | +++ | +++ | +++ |
| Ab21 | ++++ | ++ | +++ | −/+ |
| Isotype control | − | − | − | − |

Example 39: Analysis of Anti-Alzheimer's Disease Effect of Agonist TREM2 Antibodies To evaluate the ability of agonistic anti-TREM2 antibodies to delay, prevent, or reverse the development of Alzheimer's disease (AD), 5×FAD mice are used. 5×FAD mice overexpress mutant human APP (695) with the Swedish (K670N, M671L), Florida (I716V), and London (V7171) familial Alzheimer's disease (FAD) mutations, along with human PS1 harboring two FAD mutations, M146L and L286V. Both transgenes are regulated by the mouse Thy1 promoter to drive over expression on the brain and recapitulate major features of AD. Mice treated with the agonistic anti-TREM2 antibodies or with control antibodies are tested for A beta plaque load with immunohistochemistry and by ELISA of tissue extracts. They are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mousebiology.org website; Wang et al., (2015) Cell. pii: S0092-8674(15)00127-0).

Example 40: Production, Identification, and Characterization of Agonist Anti-TREM2 Antibodies Introduction Antibodies that bind the extracellular domain of TREM2, particularly the extra cellular domain (amino acid residues 19-174 of SEQ ID NO: 1) are generated using mouse hybridoma technology, phage display technology, and yeast display technology according to the methods described in Example 1 above. Antibodies were then screened for their ability to bind cells that express TREM2 and for their ability to activate TREM2 signaling and functions in cells and in a whole animal in vivo as described in Examples 41-67 below.

Results

Anti-TREM2 Antibody Production

Antibodies that bind the extracellular domain of TREM2, particularly within the extracellular sequences located at amino residues 113-174 of SEQ ID NO: 1, were generated using the procedure described in Example 1.

A total of 87 antibodies were generated. The antibodies were then screened for TREM2 binding. Antibodies that were positive for binding to primary cells were tested for agonistic activity. From the 87 antibodies, certain antibodies (e.g., Ab1, Ab9, Ab14, Ab22, Ab45, and Ab65) were selected for further analysis.

Antibody Heavy Chain and Light Chain Variable Domain Sequences

Using standard techniques, the amino acid sequences encoding the heavy chain variable (FIG. 20A) and the light chain variable (FIG. 20B) domains of the generated antibodies were determined. The Kabat CDR sequences of the antibodies are set forth in Table 8.

TABLE 8

Kabat CDR sequences

| Antibody Name | CDR H1 | CDR H2 | CDR H3 | CDR L1 | CDR L2 | CDR L3 |
|---|---|---|---|---|---|---|
| Ab1 | FTFSSYAMS (SEQ ID NO: 3) | VISGSGGSTYYADSVKG (SEQ ID NO: 25) | AKGTPTLLFQH (SEQ ID NO: 50) | RASQSVSSNLA (SEQ ID NO: 120) | GASTRAT (SEQ ID NO: 138) | QQLPYWPPT (SEQ ID NO: 153) |
| Ab2 | FTFSSSAMS (SEQ ID NO: 4) | AISGSGGSTYYADSVKG (SEQ ID NO: 26) | AKVPSYDYWSGYSNYYYYMDV (SEQ ID NO: 51) | RASQSVGSNLA (SEQ ID NO: 121) | GASTRAT (SEQ ID NO: 138) | QQYFFYPPT (SEQ ID NO: 154) |
| Ab3 | GTFSSYAIS (SEQ ID NO: 5) | GIIPIFGTANYAQKFQG (SEQ ID NO: 27) | AREQYHVGMDV (SEQ ID NO: 52) | QASQDISNYLN (SEQ ID NO: 122) | DASNLAT (SEQ ID NO: 139) | QQPFNFPYT (SEQ ID NO: 155) |
| Ab4 | GTFSSYAIS (SEQ ID NO: 5) | GIIPIFGTASYAQKFQG (SEQ ID NO: 28) | ARGVDSIMDY (SEQ ID NO: 53) | RASQSVSSNLA (SEQ ID NO: 120) | SASTRAT (SEQ ID NO: 140) | QQDHDYPFT (SEQ ID NO: 156) |
| Ab5 | YTFTSYYIH (SEQ ID NO: 6) | IINPSGGSTSYAQKFQG (SEQ ID NO: 29) | ARAPQESPYVFDI (SEQ ID NO: 54) | RASQSVSSSYLA (SEQ ID NO: 123) | GASSRAT (SEQ ID NO: 141) | QQYFSSPFT (SEQ ID NO: 157) |
| Ab6 | YTFTSYYMH (SEQ ID NO: 7) | IINPGGGSTSYAQKFQG (SEQ ID NO: 30) | ARGSPTYGYLYDP (SEQ ID NO: 55) | RASQSVSSYLA (SEQ ID NO: 124) | DASKRAT (SEQ ID NO: 142) | QQRVNLPPT (SEQ ID NO: 158) |
| Ab7 | YTFTSYYMH (SEQ ID NO: 7) | IINPSGGSTTYAQKFQG (SEQ ID NO: 31) | ARTSSKERDY (SEQ ID NO: 56) | RASQSVSSYLA (SEQ ID NO: 124) | DASKRAT (SEQ ID NO: 142) | QQRISYPIT (SEQ ID NO: 159) |
| Ab8 | GSISSSSYYWG (SEQ ID NO: 8) | SISYSGSTYYNPSLKS (SEQ ID NO: 32) | ARGPYRLLLGMDV (SEQ ID NO: 57) | RASQSISSYLN (SEQ ID NO: 125) | GASSLQS (SEQ ID NO: 143) | QQIDDTPIT (SEQ ID NO: 160) |
| Ab9 | YSFTSYWIG (SEQ ID NO: 9) | IIYPGDSDTTYSPSFQG (SEQ ID NO: 33) | ARLHISGEVNWFDP (SEQ ID NO: 58) | RASQSVSSYLA (SEQ ID NO: 124) | DASNRAT (SEQ ID NO: 144) | QQFSYWPWT (SEQ ID NO: 161) |

TABLE 8-continued

Kabat CDR sequences

| Antibody Name | CDR H1 | CDR H2 | CDR H3 | CDR L1 | CDR L2 | CDR L3 |
|---|---|---|---|---|---|---|
| Ab10 | YSFTSNWIG (SEQ ID NO: 10) | IIYPGDSDTRYSPSFQG (SEQ ID NO: 34) | AREAGYDYGELAFDI (SEQ ID NO: 59) | RASQSVSSSYLA (SEQ ID NO: 123) | GASSRAT (SEQ ID NO: 141) | QQHDSSPPT (SEQ ID NO: 162) |
| Ab11 | YSFTTYWIG (SEQ ID NO: 11) | IIYPGDSDTRYSPSFQG (SEQ ID NO: 34) | ARAGHYDGGHLGMDV (SEQ ID NO: 60) | RASQSVSSDYLA (SEQ ID NO: 126) | GASSRAT (SEQ ID NO: 141) | QQDYSYPWT (SEQ ID NO: 163) |
| Ab12 | YSFTSYWIG (SEQ ID NO: 9) | IIYPGDSDTRYSPSFQG (SEQ ID NO: 34) | ARLGHYSGTVSSYGMDV (SEQ ID NO: 61) | RASQSISSYLN (SEQ ID NO: 125) | AASSLQS (SEQ ID NO: 145) | QQEYAVPYT (SEQ ID NO: 164) |
| Ab13 | YTFTSYGIS (SEQ ID NO: 12) | WISAYNGNTNYAQKLQG (SEQ ID NO: 35) | ARGPSHYYDLA (SEQ ID NO: 62) | RASQSVSSYLA (SEQ ID NO: 124) | DASNRAT (SEQ ID NO: 144) | QQVSNYPIT (SEQ ID NO: 165) |
| Ab14 | GSISSGGYYWS (SEQ ID NO: 13) | NIYYSGSTVYNPSLKS (SEQ ID NO: 36) | ARGLYGYGVLDV (SEQ ID NO: 63) | QASQDISNYLN (SEQ ID NO: 122) | DASNLET (SEQ ID NO: 146) | QQVDNIPPT (SEQ ID NO: 166) |
| Ab15 | GSISSGGYYWS (SEQ ID NO: 13) | NIYYSGSTVYNPSLKS (SEQ ID NO: 36) | ARGLYGYGVLDV (SEQ ID NO: 63) | QASQDISNYLN (SEQ ID NO: 122) | DASNLET (SEQ ID NO: 146) | QQFDTYPT (SEQ ID NO: 167) |
| Ab16 | GSISSNSYYWG (SEQ ID NO: 14) | SIYYSGSTYYNPSLKS (SEQ ID NO: 37) | ARGVLGYGVFDY (SEQ ID NO: 64) | QASQDISNYLN (SEQ ID NO: 122) | DASNLET (SEQ ID NO: 146) | QQFLNFPT (SEQ ID NO: 168) |
| Ab17 | GSISSNSYYWG (SEQ ID NO: 14) | SIYYSGSTYYNPSLKS (SEQ ID NO: 37) | ARGVLGYGVFDY (SEQ ID NO: 64) | QASQDISNYLN (SEQ ID NO: 122) | DASNLET (SEQ ID NO: 146) | QQFFNFPT (SEQ ID NO: 169) |
| Ab18 | GSISSYYWS (SEQ ID NO: 15) | SIYYSGSTNYNPSLKS (SEQ ID NO: 38) | ARDGGGEYPSGTPFDI (SEQ ID NO: 65) | QASQDISNYLN (SEQ ID NO: 122) | DASNLET (SEQ ID NO: 146) | QQFIDLPFT (SEQ ID NO: 170) |
| Ab19 | GSISSYYWS (SEQ ID NO: 15) | SIYYSGSTNYNPSLKS (SEQ ID NO: 38) | ARDGGGEYPSGTPFDI (SEQ ID NO: 65) | QASQDISNYLN (SEQ ID NO: 122) | DASNLET (SEQ ID NO: 146) | QQYYDLPFT (SEQ ID NO: 171) |
| Ab20 | GSISSYYWS (SEQ ID NO: 15) | SIYYSGSTNYNPSLKS (SEQ ID NO: 38) | ARSGMASFFDY (SEQ ID NO: 66) | RASQSVSSDYLA (SEQ ID NO: 126) | GASSRAT (SEQ ID NO: 141) | QQFSSHPFT (SEQ ID NO: 172) |
| Ab22 | YSFTTYWIG (SEQ ID NO: 11) | IIYPGDSDTRYSPSFQG (SEQ ID NO: 34) | ARAGHYDGGHLGMDV (SEQ ID NO: 60) | RASQSVSSSYLA (SEQ ID NO: 123) | GASSRAT (SEQ ID NO: 141) | QQDDRSPYT (SEQ ID NO: 173) |
| Ab23 | FTFSSYAMS (SEQ ID NO: 3) | AISGSGGSTYYADSVKG (SEQ ID NO: 26) | AKLGGHSMDVKNYLA (SEQ ID NO: 67) | KSSQSVLYSSNN (SEQ ID NO: 127) | WASTRES (SEQ ID NO: 147) | QQAYLPPIT (SEQ ID NO: 174) |
| Ab24 | FTFSSYAMS (SEQ ID NO: 3) | AISGSGGSTYYADSVKG (SEQ ID NO: 26) | AKPLKRGRGFY (SEQ ID NO: 68) | RASQSISSYLN (SEQ ID NO: 125) | AASSLQS (SEQ ID NO: 145) | QQAFSPPPWT (SEQ ID NO: 175) |
| Ab25 | FTFSSYAMS (SEQ ID NO: 3) | VISGSGGSTYYADSVKG (SEQ ID NO: 25) | AKEGRTITMD (SEQ ID NO: 69) | RASQSVSSSYLA (SEQ ID NO: 123) | GASSRAT (SEQ ID NO: 141) | QQDDRSPT (SEQ ID NO: 176) |
| Ab26 | FTFSSYAMS (SEQ ID NO: 3) | VISGSGGSTYYADSVKG (SEQ ID NO: 25) | AKDQYSVLDY (SEQ ID NO: 70) | RASQSVSSYLA (SEQ ID NO: 124) | DASNRAT (SEQ ID NO: 144) | QQEFDLPFT (SEQ ID NO: 177) |
| Ab27 | FTFSSYAMS (SEQ ID NO: 3) | AISGSGGSTYYADSVKG (SEQ ID NO: 26) | AKKYSSRGVYFDY (SEQ ID NO: 71) | RASQSVSSYLA (SEQ ID NO: 124) | DASNRAT (SEQ ID NO: 144) | QQYNFPPT (SEQ ID NO: 178) |
| Ab28 | FTFSSYAMS (SEQ ID NO: 3) | AISGSGGSTYYADSVKG (SEQ ID NO: 26) | ARLGGAVGARHVTYFDY (SEQ ID NO: 72) | RASQSVSSYLA (SEQ ID NO: 124) | DASKRAT (SEQ ID NO: 142) | QQRYLRPIT (SEQ ID NO: 179) |

TABLE 8-continued

Kabat CDR sequences

| Antibody Name | CDR H1 | CDR H2 | CDR H3 | CDR L1 | CDR L2 | CDR L3 |
|---|---|---|---|---|---|---|
| Ab29 | FTFSSYGMH (SEQ ID NO: 16) | VISYDGSNKYYADS VKG (SEQ ID NO: 39) | ARGQYYGGSGWFD P (SEQ ID NO: 73) | RASQSVSSSYLA (SEQ ID NO: 123) | GASSRAT (SEQ ID NO: 141) | QQPGAVPT (SEQ ID NO: 180) |
| Ab30 | FTFSSYAMS (SEQ ID NO: 3) | AISGSGGSTYYADS VKG (SEQ ID NO: 26) | ARLGQEYAYFQH (SEQ ID NO: 74) | RASQSISSYLN (SEQ ID NO: 125) | GASSLQS (SEQ ID NO: 143) | QQVYITPIT (SEQ ID NO: 181) |
| Ab31 | FTFSSYGMH (SEQ ID NO: 16) | LIWYDGSNKYYADS VKG (SEQ ID NO: 40) | ARRRDGYYDEVFDI (SEQ ID NO: 75) | QASQDISNFLN (SEQ ID NO: 128) | DASNLET (SEQ ID NO: 146) | QQPVDLPFT (SEQ ID NO: 182) |
| Ab32 | FTFSSYAMS (SEQ ID NO: 3) | AISGSGGSTYYADS VKG (SEQ ID NO: 26) | ARVPKHYVVLDY (SEQ ID NO: 76) | RASQSVSSYLA (SEQ ID NO: 124) | DASNRAT (SEQ ID NO: 144) | QQYSFFPPT (SEQ ID NO: 183) |
| Ab33 | FTFSSYGMH (SEQ ID NO: 16) | VISYDGSNKYYADS VKG (SEQ ID NO: 39) | ARAGGHLFDY (SEQ ID NO: 77) | RASQSVSSYLA (SEQ ID NO: 124) | DASNRAT (SEQ ID NO: 144) | QQDSSFPPT (SEQ ID NO: 184) |
| Ab34 | FTFSSYGMH (SEQ ID NO: 16) | VISYDGSNKYYADS VKG (SEQ ID NO: 39) | ARDRGGEYVDFAFD I (SEQ ID NO: 78) | RASQSISSYLN (SEQ ID NO: 125) | AASSLQS (SEQ ID NO: 145) | QQSDFPPWT (SEQ ID NO: 185) |
| Ab35 | FTFSSYAMS (SEQ ID NO: 3) | AISGSGGSTYYADS VKG (SEQ ID NO: 26) | ARTRSGYGASNYFD Y (SEQ ID NO: 79) | RASQSISSYLN (SEQ ID NO: 125) | AASSLQS (SEQ ID NO: 145) | QQGYSAPIT (SEQ ID NO: 186) |
| Ab36 | FTFSTYGMH (SEQ ID NO: 17) | VIWYDGSNKYYAD SVKG (SEQ ID NO: 41) | ARGTGAAAASPAFD I (SEQ ID NO: 80) | RASQSVSSYLA (SEQ ID NO: 124) | DASNRAT (SEQ ID NO: 144) | QQLFDWPT (SEQ ID NO: 187) |
| Ab37 | FTFSSYAMS (SEQ ID NO: 3) | AISGSGGSTYYADS VKG (SEQ ID NO: 26) | ARVGQYMLGMDV (SEQ ID NO: 81) | RASQSVSSYLA (SEQ ID NO: 124) | DASNRAT (SEQ ID NO: 144) | QQRAFLFT (SEQ ID NO: 188) |
| Ab38 | FTFSTYGMH (SEQ ID NO: 17) | VIWYDGSNKYYAD SVKG (SEQ ID NO: 41) | ARGAPVDYGGIEPE YFQH (SEQ ID NO: 82) | RASQSVSSYLA (SEQ ID NO: 124) | DASNRAT (SEQ ID NO: 144) | QQIDFLPYT (SEQ ID NO: 189) |
| Ab39 | FTFSSYAMS (SEQ ID NO: 3) | AISGSGGSTYYADS VKG (SEQ ID NO: 26) | AKHYHVGIAFDI (SEQ ID NO: 83) | RASQSISSYLN (SEQ ID NO: 125) | AASSLQS (SEQ ID NO: 145) | QQVYSPPIT (SEQ ID NO: 190) |
| Ab40 | FTFSSYAMS (SEQ ID NO: 3) | AISGSGGSTYYADS VKG (SEQ ID NO: 26) | ARTRSGYGASNYFD Y (SEQ ID NO: 79) | RASQSISSYLN (SEQ ID NO: 125) | AASSLQS (SEQ ID NO: 145) | QQGYAAPIT (SEQ ID NO: 191) |
| Ab41 | FTFSTYAMS (SEQ ID NO: 18) | AISGSGGSTYYADS VKG (SEQ ID NO: 26) | ARAMARKSVAFDI (SEQ ID NO: 84) | RASQSVSSYLA (SEQ ID NO: 124) | DASNRAT (SEQ ID NO: 144) | QQRYALPIT (SEQ ID NO: 192) |
| Ab42 | FTFSSSAMS (SEQ ID NO: 4) | AISGSGGSTYYADS VKG (SEQ ID NO: 26) | AKVPSYQRGTAFDP (SEQ ID NO: 85) | RASQSVSSSYLA (SEQ ID NO: 123) | GASSRAT (SEQ ID NO: 141) | QQYASPPIT (SEQ ID NO: 193) |
| Ab43 | FTFSSSAMS (SEQ ID NO: 4) | AISGSGGSTYYADS VKG (SEQ ID NO: 26) | AKSPAVAGIYRADY (SEQ ID NO: 86) | RASQSISRYLN (SEQ ID NO: 129) | AASSLQS (SEQ ID NO: 145) | QQVYSTPIT (SEQ ID NO: 194) |
| Ab44 | FTFSTYGMH (SEQ ID NO: 17) | VIWYDGSNKYYAD SVKG (SEQ ID NO: 41) | ARGTGAAAASPAFD I (SEQ ID NO: 80) | RASQSVSSYLA (SEQ ID NO: 124) | DSSNRAT (SEQ ID NO: 148) | QQLVHWPT (SEQ ID NO: 195) |
| Ab45 | YTFTSYYMH (SEQ ID NO: 7) | IINPSGGSTSYAQKF QG (SEQ ID NO: 29) | ARGPGYTTALDYYY MDV (SEQ ID NO: 87) | RASQSVSSNLA (SEQ ID NO: 120) | GASTRAT (SEQ ID NO: 138) | QQLDDWFT (SEQ ID NO: 196) |
| Ab46 | YTFTSYYMH (SEQ ID NO: 7) | IINPSGGSTSYAQKF QG (SEQ ID NO: 29) | ARPAKTADY (SEQ ID NO: 88) | RASQSVSSYLA (SEQ ID NO: 124) | DSSNRAT (SEQ ID NO: 148) | QQRSNYPIT (SEQ ID NO: 197) |

TABLE 8-continued

Kabat CDR sequences

| Antibody Name | CDR H1 | CDR H2 | CDR H3 | CDR L1 | CDR L2 | CDR L3 |
|---|---|---|---|---|---|---|
| Ab47 | YTFTSYYMH (SEQ ID NO: 7) | IINPSGGSTTYAQKFQG (SEQ ID NO: 31) | ARPGKSMDV (SEQ ID NO: 89) | RASQSVSSYLA (SEQ ID NO: 124) | DASNRAT (SEQ ID NO: 144) | QQRILYPIT (SEQ ID NO: 198) |
| Ab48 | YTFTSYYMH (SEQ ID NO: 7) | IINPSGGSTTYAQKFQG (SEQ ID NO: 31) | ARPGKSMDV (SEQ ID NO: 89) | RASQSVSSYLA (SEQ ID NO: 124) | DASNRAT (SEQ ID NO: 144) | QQRAAYPIT (SEQ ID NO: 199) |
| Ab49 | YTFTSYYMH (SEQ ID NO: 7) | IINPSGGSTSYAQKFQG (SEQ ID NO: 29) | ARPAKTADY (SEQ ID NO: 88) | RASQSVSSYLA (SEQ ID NO: 124) | DASKRAT (SEQ ID NO: 142) | QQRTSHPIT (SEQ ID NO: 200) |
| Ab50 | YTFTSYYIH (SEQ ID NO: 6) | IINPSGGSTSYAQKFQG (SEQ ID NO: 29) | ARAPQESPYVFDI (SEQ ID NO: 54) | RASQSVSSSYLA (SEQ ID NO: 123) | GASSRAT (SEQ ID NO: 141) | QQYAGSPFT (SEQ ID NO: 201) |
| Ab51 | YTFTSYYMH (SEQ ID NO: 7) | IINPSGGSTSYAQKFQG (SEQ ID NO: 29) | ARGVGGQDYYYMDV (SEQ ID NO: 90) | RASQSISSYLN (SEQ ID NO: 125) | AASSLQS (SEQ ID NO: 145) | QQFDDVFT (SEQ ID NO: 202) |
| Ab53 | YTFTSYYIH (SEQ ID NO: 6) | IINPSGGSTSYAQKFQG (SEQ ID NO: 29) | ARAPQESPYVFDI (SEQ ID NO: 54) | RASQSVSSSYLA (SEQ ID NO: 123) | GASSRAT (SEQ ID NO: 141) | QQYVNSPFT (SEQ ID NO: 203) |
| Ab54 | YTFTSYYMH (SEQ ID NO: 7) | IINPSGGSTSYAQKFQG (SEQ ID NO: 29) | ARGPGYTTALDYYYMDV (SEQ ID NO: 87) | RASQSINSYLN (SEQ ID NO: 130) | AASSLQS (SEQ ID NO: 145) | QQSDDDPFT (SEQ ID NO: 204) |
| Ab55 | YTFTGSYMH (SEQ ID NO: 19) | WINPNSGGTNYAQKFQG (SEQ ID NO: 42) | ARGPLYHPMIFDY (SEQ ID NO: 91) | RASQSVSSYLA (SEQ ID NO: 124) | DASNRAT (SEQ ID NO: 144) | QQLSTYPLT (SEQ ID NO: 205) |
| Ab56 | YTFTGYYMH (SEQ ID NO: 20) | SINPNSGGTNYAQKFQG (SEQ ID NO: 43) | ARASSVDN (SEQ ID NO: 92) | RASQSVSSYLA (SEQ ID NO: 124) | DASNRAT (SEQ ID NO: 144) | QQRSVYPIT (SEQ ID NO: 206) |
| Ab57 | YTFTNYGIS (SEQ ID NO: 21) | WISAYNGNTNYAQKLQG (SEQ ID NO: 35) | ARGPTKAYYGSGSYVVFDP (SEQ ID NO: 93) | RASQSVSSYLA (SEQ ID NO: 124) | DASKRAT (SEQ ID NO: 142) | QQVSLFPLT (SEQ ID NO: 207) |
| Ab58 | YSFTSYWIG (SEQ ID NO: 9) | IIYPGDSDTRYSPSFQG (SEQ ID NO: 34) | ARLGIYSTGATAFDI (SEQ ID NO: 94) | RASQSISSWLA (SEQ ID NO: 131) | DASSLES (SEQ ID NO: 149) | LDYNSYSPIT (SEQ ID NO: 208) |
| Ab59 | YTFTGSYMH (SEQ ID NO: 19) | WINPNSGGTNYAQKFQG (SEQ ID NO: 42) | ARGGVVVYSLFDI (SEQ ID NO: 95) | QASQDISNYLN (SEQ ID NO: 122) | DASNLET (SEQ ID NO: 146) | QQHIALPFT (SEQ ID NO: 209) |
| Ab60 | YTFTGYYMH (SEQ ID NO: 20) | WINPNSGGTSYAQKFQG (SEQ ID NO: 44) | ARASKMGDD (SEQ ID NO: 96) | RASQSVSSYLA (SEQ ID NO: 124) | DASKRAT (SEQ ID NO: 142) | QQRASMPIT (SEQ ID NO: 210) |
| Ab61 | YTFTSYGIH (SEQ ID NO: 22) | WISAYNGNTNYAQKLQG (SEQ ID NO: 35) | ARGGVPRVSYFQH (SEQ ID NO: 97) | RASQSVSSYLA (SEQ ID NO: 124) | DSSNRAT (SEQ ID NO: 148) | QQAFNRPPT (SEQ ID NO: 211) |
| Ab62 | YSFTSYWIG (SEQ ID NO: 9) | IIYPGDSDTRYSPSFQG (SEQ ID NO: 34) | ARAGHYDDWSGLGLDV (SEQ ID NO: 98) | RASQSVSSYLA (SEQ ID NO: 124) | DASKRAT (SEQ ID NO: 142) | QQSSVHPYT (SEQ ID NO: 212) |
| Ab63 | YTFTSYGIS (SEQ ID NO: 12) | WISTYNGNTNYAQKLQG (SEQ ID NO: 45) | ARGSGSGYDSWYD (SEQ ID NO: 99) | RASQGIDSWLA (SEQ ID NO: 132) | AASSLQS (SEQ ID NO: 145) | QQAYSLPPT (SEQ ID NO: 213) |
| Ab64 | YSFTSYWIG (SEQ ID NO: 9) | IIYPGDSDTRYSPSFQG (SEQ ID NO: 34) | ARLGRWSSGSTAFDI (SEQ ID NO: 100) | RASQSVSSNLA (SEQ ID NO: 120) | GASTRAT (SEQ ID NO: 138) | QQDDDGYT (SEQ ID NO: 214) |
| Ab65 | YSFTSYWIG (SEQ ID NO: 9) | IIYPGDSDTRYSPSFQG (SEQ ID NO: 34) | ARLGRKPSGSVAFDI (SEQ ID NO: 101) | RASQSVSSYLA (SEQ ID NO: 124) | DASNRAT (SEQ ID NO: 144) | QQDYSWPYT (SEQ ID NO: 215) |

TABLE 8-continued

Kabat CDR sequences

| Antibody Name | CDR H1 | CDR H2 | CDR H3 | CDR L1 | CDR L2 | CDR L3 |
|---|---|---|---|---|---|---|
| Ab66 | YTFTGSYMH (SEQ ID NO: 19) | WINPNSGGTNYAQKFQG (SEQ ID NO: 42) | ARAGHKTHDY (SEQ ID NO: 102) | RASQSVSSYLA (SEQ ID NO: 124) | DASNRAT (SEQ ID NO: 144) | QQRSAYPIT (SEQ ID NO: 216) |
| Ab67 | YTFTSYYMH (SEQ ID NO: 7) | IINPSGGSTTYAQKFQG (SEQ ID NO: 31) | ARPGKSMDV (SEQ ID NO: 89) | RASQSVSSYLA (SEQ ID NO: 124) | DASNRAT (SEQ ID NO: 144) | QQRSHFPIT (SEQ ID NO: 217) |
| Ab68 | FTFSSYGMH (SEQ ID NO: 16) | LIWYDGSNKYYADSVKG (SEQ ID NO: 40) | AKPGSMTDY (SEQ ID NO: 103) | RASQSVSSYLA (SEQ ID NO: 124) | DASNRAT (SEQ ID NO: 144) | QQRANYPIT (SEQ ID NO: 218) |
| Ab69 | YTFTGSYMH (SEQ ID NO: 19) | WINPNSGGTNYAQKFQG (SEQ ID NO: 42) | ARAKSVDHDY (SEQ ID NO: 104) | RASQSVSSYLA (SEQ ID NO: 124) | DASNRAT (SEQ ID NO: 144) | QQRADYPIT (SEQ ID NO: 219) |
| Ab70 | YTFTGYYMH (SEQ ID NO: 20) | WINPNSGGTSYAQKFQG (SEQ ID NO: 44) | ARASKMGDD (SEQ ID NO: 96) | RASQSVSSYLA (SEQ ID NO: 124) | DASNRAT (SEQ ID NO: 144) | QQRSVYPIT (SEQ ID NO: 206) |
| Ab71 | YTFTSYYMH (SEQ ID NO: 7) | IINPSGGSTSYAQKFQG (SEQ ID NO: 29) | ARDISTHDYDLAFDI (SEQ ID NO: 105) | RASQSVSSSYLA (SEQ ID NO: 123) | GASNRAT (SEQ ID NO: 150) | QQAGSHPFT (SEQ ID NO: 220) |
| Ab72 | GSISSYYWS (SEQ ID NO: 15) | SIYYSGSTNYNPSLKS (SEQ ID NO: 38) | ARSGIETLFDY (SEQ ID NO: 106) | QASQDITNYLN (SEQ ID NO: 133) | DASNLET (SEQ ID NO: 146) | QQDVNYPPT (SEQ ID NO: 221) |
| Ab73 | YSFTSYWIG (SEQ ID NO: 9) | IIYPGDSDTTYSPSFQG (SEQ ID NO: 33) | ARAKMLDDGYAFDI (SEQ ID NO: 107) | RASQSVSSNLA (SEQ ID NO: 120) | GASTRAT (SEQ ID NO: 138) | QQDDNYPYT (SEQ ID NO: 222) |
| Ab74 | YTFTGSYMH (SEQ ID NO: 19) | WINPNSGGTNYAQKFQG (SEQ ID NO: 42) | ARAGHKTHDY (SEQ ID NO: 102) | RASQSVSSYLA (SEQ ID NO: 124) | DASNRAT (SEQ ID NO: 144) | QQRSTFPIT (SEQ ID NO: 223) |
| Ab75 | YTFTGYYMH (SEQ ID NO: 20) | WINPNSGGTNYAQKFQG (SEQ ID NO: 42) | ARDLGYSSLLALDI (SEQ ID NO: 108) | RASQSVSSYLA (SEQ ID NO: 124) | DASNRAT (SEQ ID NO: 144) | QQVSNYPFT (SEQ ID NO: 224) |
| Ab76 | FTFSSYSMN (SEQ ID NO: 23) | SISSSSYIYYADSVKG (SEQ ID NO: 46) | ARGGGRRGDNNWFDP (SEQ ID NO: 109) | KSSQSVLYSSNNKNYLA (SEQ ID NO: 127) | WASTRES (SEQ ID NO: 147) | QQYHDAPIT (SEQ ID NO: 225) |
| Ab77 | FTFSSYGMH (SEQ ID NO: 16) | VISYDGSNKYYADSVKG (SEQ ID NO: 39) | ARGPPHEMDY (SEQ ID NO: 110) | KSSQSVLYSSNNKNYLA (SEQ ID NO: 127) | WASTRES (SEQ ID NO: 147) | QQAYVVPPT (SEQ ID NO: 226) |
| Ab78 | FTFSSYGMH (SEQ ID NO: 16) | VIWYDGSNKYYADSVKG (SEQ ID NO: 41) | ARTPYPWIYFDL (SEQ ID NO: 111) | RASQSVSSYLA (SEQ ID NO: 124) | DASNRAT (SEQ ID NO: 144) | QQADNWPFT (SEQ ID NO: 227) |
| Ab79 | FTFSSYSMN (SEQ ID NO: 23) | YISGSSSTIYYADSVKG (SEQ ID NO: 47) | ARGGRRHYGGMDV (SEQ ID NO: 112) | RSSQSLLHSNGYNYLD (SEQ ID NO: 134) | LGSHRAS (SEQ ID NO: 151) | MQALESPRT (SEQ ID NO: 228) |
| Ab80 | GTFSSYAIS (SEQ ID NO: 5) | GIIPIFGTANYAQKFQG (SEQ ID NO: 27) | ARGGGTFWSGSWALY (SEQ ID NO: 113) | RASQSVSSYLA (SEQ ID NO: 124) | DASNRAT (SEQ ID NO: 144) | QQYVNWPFT (SEQ ID NO: 229) |
| Ab81 | GTFSSYAIS (SEQ ID NO: 5) | GIIPIFGTANYAQKFQG (SEQ ID NO: 27) | ARDSGNYDYWSGALRY (SEQ ID NO: 114) | RASQSVSSYLA (SEQ ID NO: 124) | DASNRAT (SEQ ID NO: 144) | QQSSNWPWT (SEQ ID NO: 230) |
| Ab82 | GSISSGGYYWS (SEQ ID NO: 13) | YIYYSGSTVYNPSLKS (SEQ ID NO: 48) | ARVSSSWYKA (SEQ ID NO: 115) | RASQGISSWLA (SEQ ID NO: 135) | AASSLQS (SEQ ID NO: 145) | QQASTFPIT (SEQ ID NO: 231) |

TABLE 8-continued

Kabat CDR sequences

| Antibody Name | CDR H1 | CDR H2 | CDR H3 | CDR L1 | CDR L2 | CDR L3 |
|---|---|---|---|---|---|---|
| Ab83 | GSFSGYYWS (SEQ ID NO: 24) | EIDHSGSTKYNPSLKS (SEQ ID NO: 49) | ARVGVVVGRPGYSAFDI (SEQ ID NO: 116) | RASQGISSWLA (SEQ ID NO: 135) | AASSLQS (SEQ ID NO: 145) | QQRNSLPLT (SEQ ID NO: 232) |
| Ab84 | YTFTSYGIS (SEQ ID NO: 12) | WISTYNGNTNYAQKLQG (SEQ ID NO: 45) | ARGSGSGYDSWYD (SEQ ID NO: 99) | RASQSISSYLN (SEQ ID NO: 125) | AASSLQS (SEQ ID NO: 145) | QQSYDFPIT (SEQ ID NO: 233) |
| Ab85 | FTFSSYGMH (SEQ ID NO: 16) | VIWYDGSNKYYADSVKG (SEQ ID NO: 41) | AKDLGGYYGGAAYGMDV (SEQ ID NO: 117) | RASQDISSWLA (SEQ ID NO: 136) | AASSLQS (SEQ ID NO: 145) | QQEVDYPPLT (SEQ ID NO: 234) |
| Ab86 | FTFSSYGMH (SEQ ID NO: 16) | VISYDGSNKYYADSVKG (SEQ ID NO: 39) | AKDGVYYGLGNWFDP (SEQ ID NO: 118) | RASQSISSWLA (SEQ ID NO: 131) | KASSLES (SEQ ID NO: 152) | QQLNSYSPT (SEQ ID NO: 235) |
| Ab87 | GSISSYYWS (SEQ ID NO: 15) | SIYYSGSTNYNPSLKS (SEQ ID NO: 38) | ARHGWDRVGWFDP (SEQ ID NO: 119) | RASQSVSRYLA (SEQ ID NO: 137) | DASNRAT (SEQ ID NO: 144) | QQYIFWPPT (SEQ ID NO: 236) |

Characterization of Ab1, Ab9, Ab14, Ab22, Ab45, and Ab65 Binding

Initial characterization of TREM2 antibodies involved determining their ability to bind TREM2 expressed on dendritic and other primary human or mouse immune cells. Cells were harvested, plated at $10^5$/ml in a 96 well plate, washed, and incubated in 100 ul PBS containing 10-50 ug/ml Mab and Fc blocking reagent for 1 hour in ice. Cells were then washed twice and incubated in 100 ul PBS containing 5 ug/ml PE-conjugated secondary antibody for 30 minutes in ice. Cells were washed twice in cold PBS and acquired on a BD FACS Canto. Data analysis and calculation of MFI values was performed with FlowJo (TreeStar) software version 10.0.7.

Figure 21A:
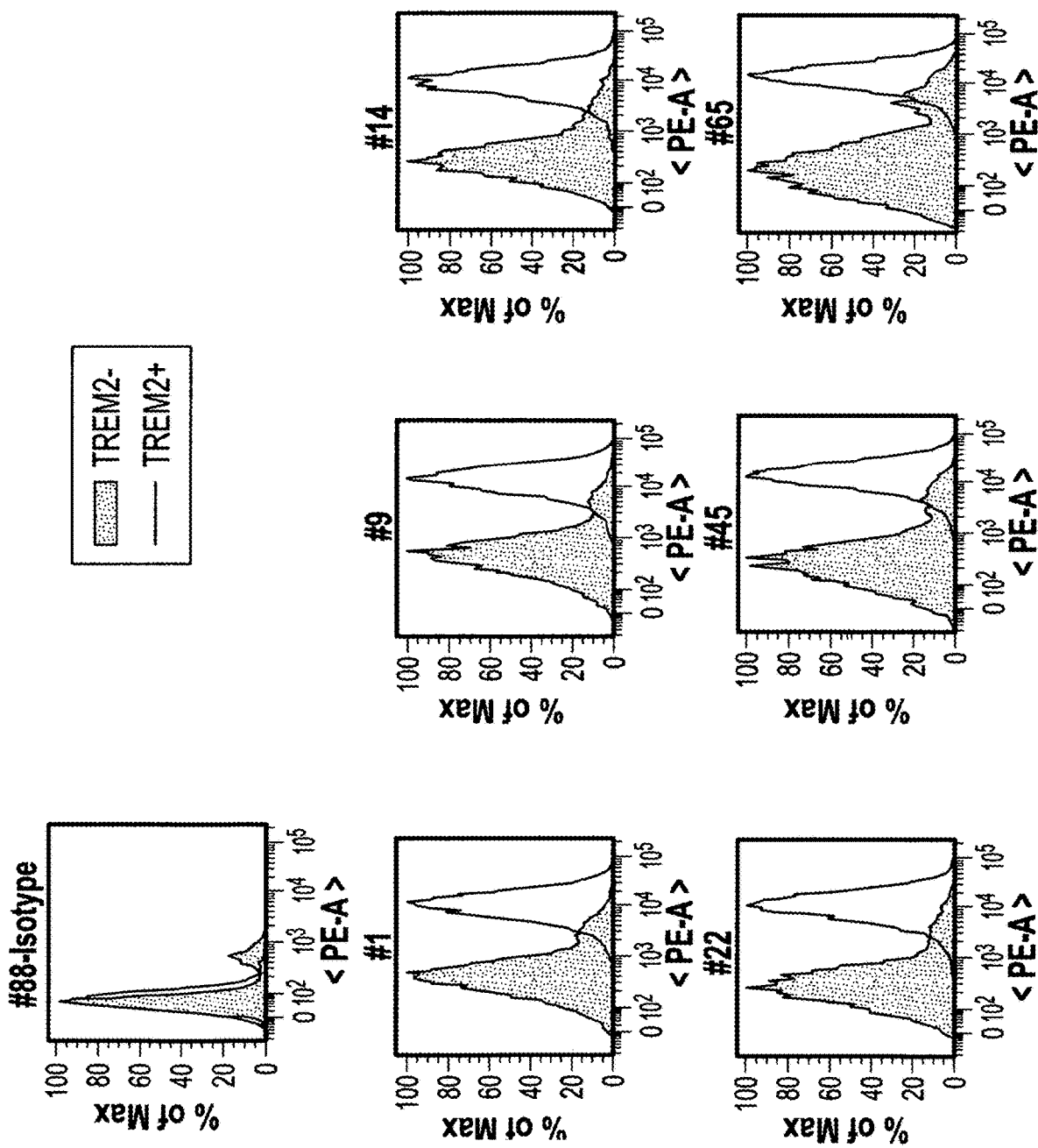
FIG. 21A shows FACS histograms demonstrating binding of TREM2 antibodies Ab1, Ab9, Ab14, Ab22, Ab45, and Ab65 to a mouse cell line (BWZ T2) expressing recombinant mouse TREM2.
Figure 21B:
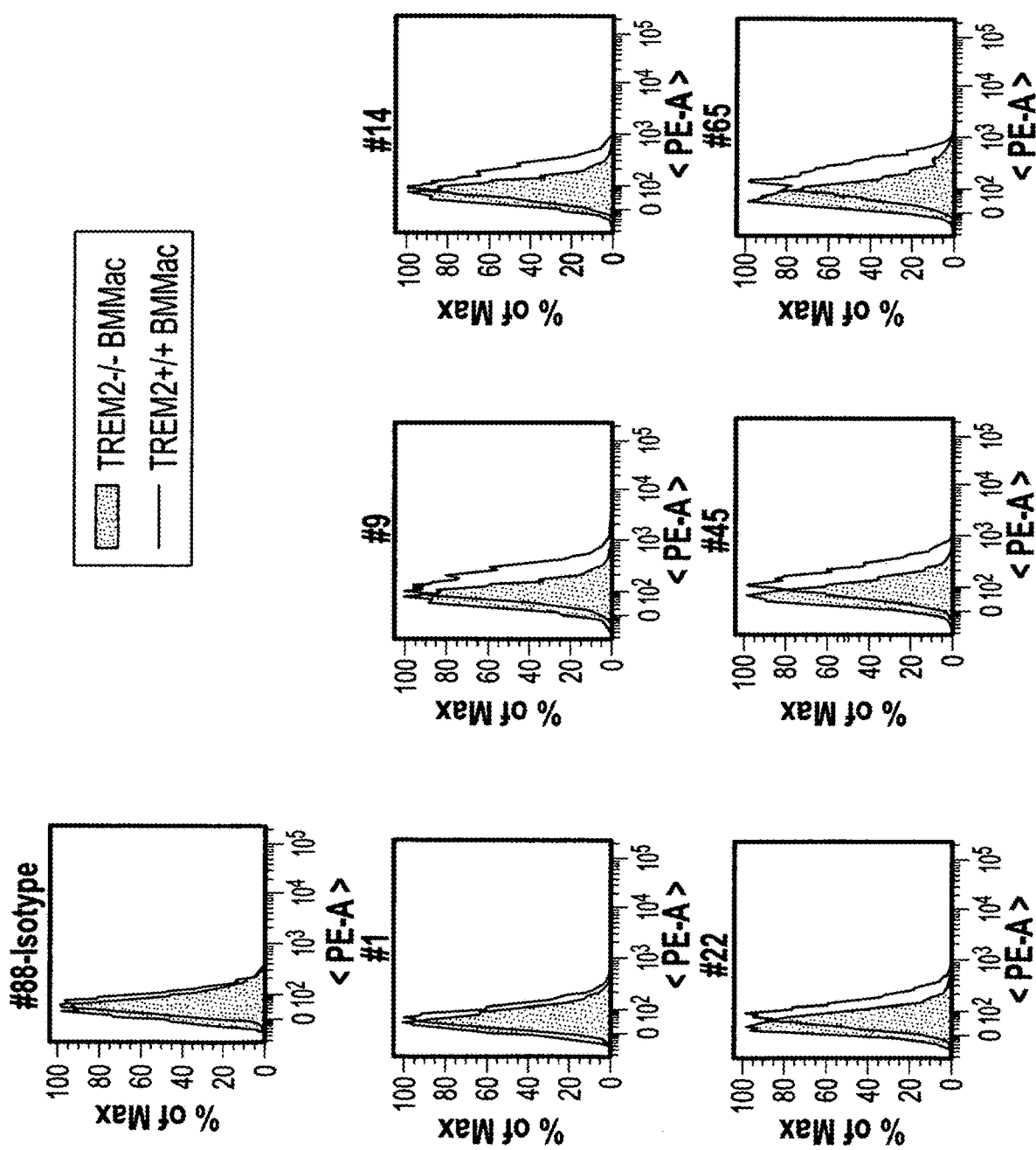
FIG. 21B shows antibodies Ab1, Ab9, Ab14, Ab22, Ab45, and Ab65 binding to WT (Trem+/+) and TREM2 deficient (TREM2−/−) bone marrow derived mouse macrophages (BMMac). Antibody Ab88 represents the negative isotype control. Shaded histograms represent the TREM2 antibody negative population. Black outlined histograms represent the TREM2 antibody positive population.
Figure 22A:
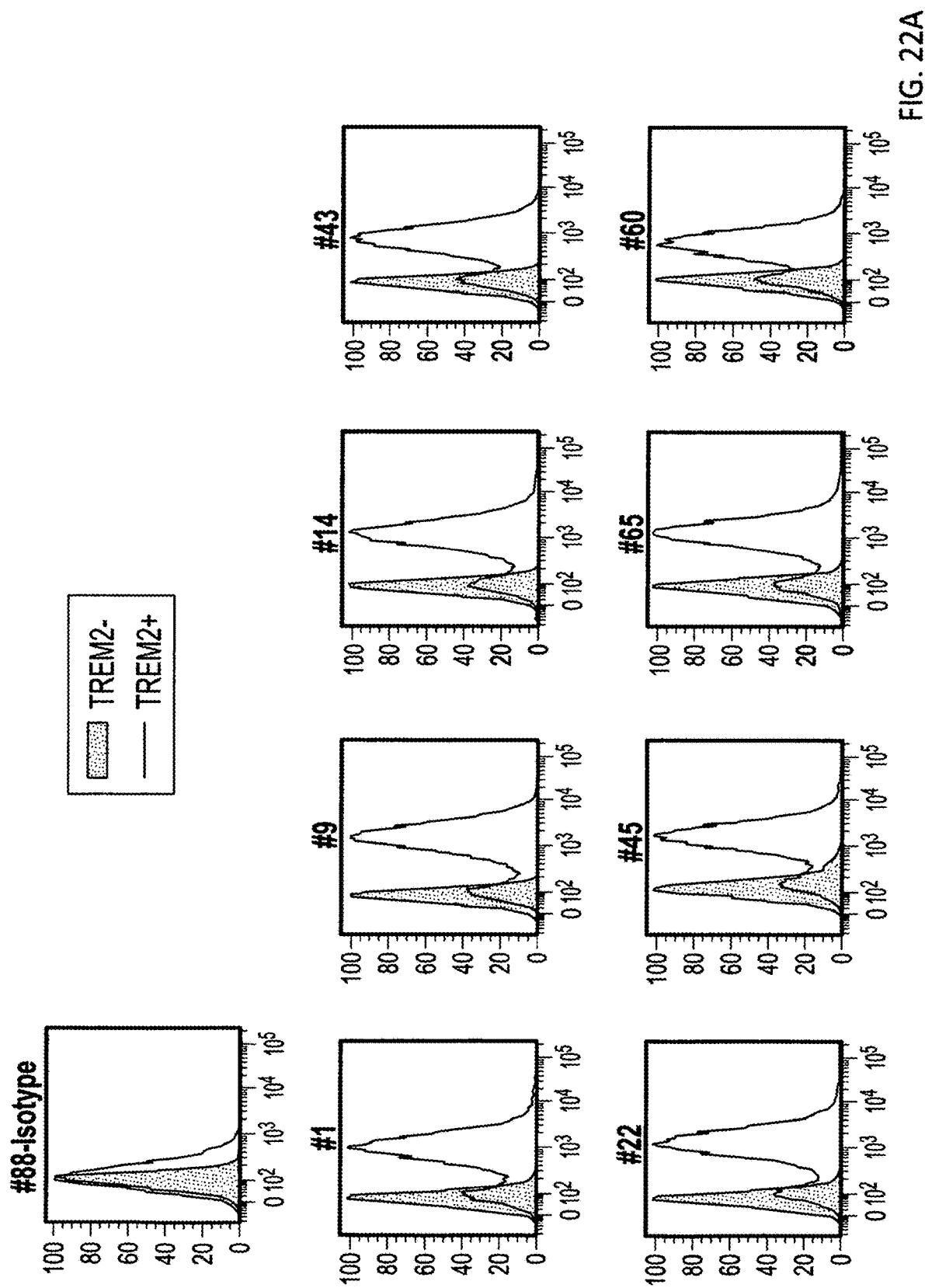
FIG. 22A shows FACS histograms demonstrating binding of TREM2 antibodies Ab1, Ab9, Ab14, Ab22, Ab43, Ab45, Ab60, and Ab65 to a human cell line (293) expressing recombinant human TREM2-DAP12 fusion protein. Shaded histograms represent a TREM2 antibody negative population. Black outlined histograms represent a TREM2 antibody positive population.
Figure 22B:
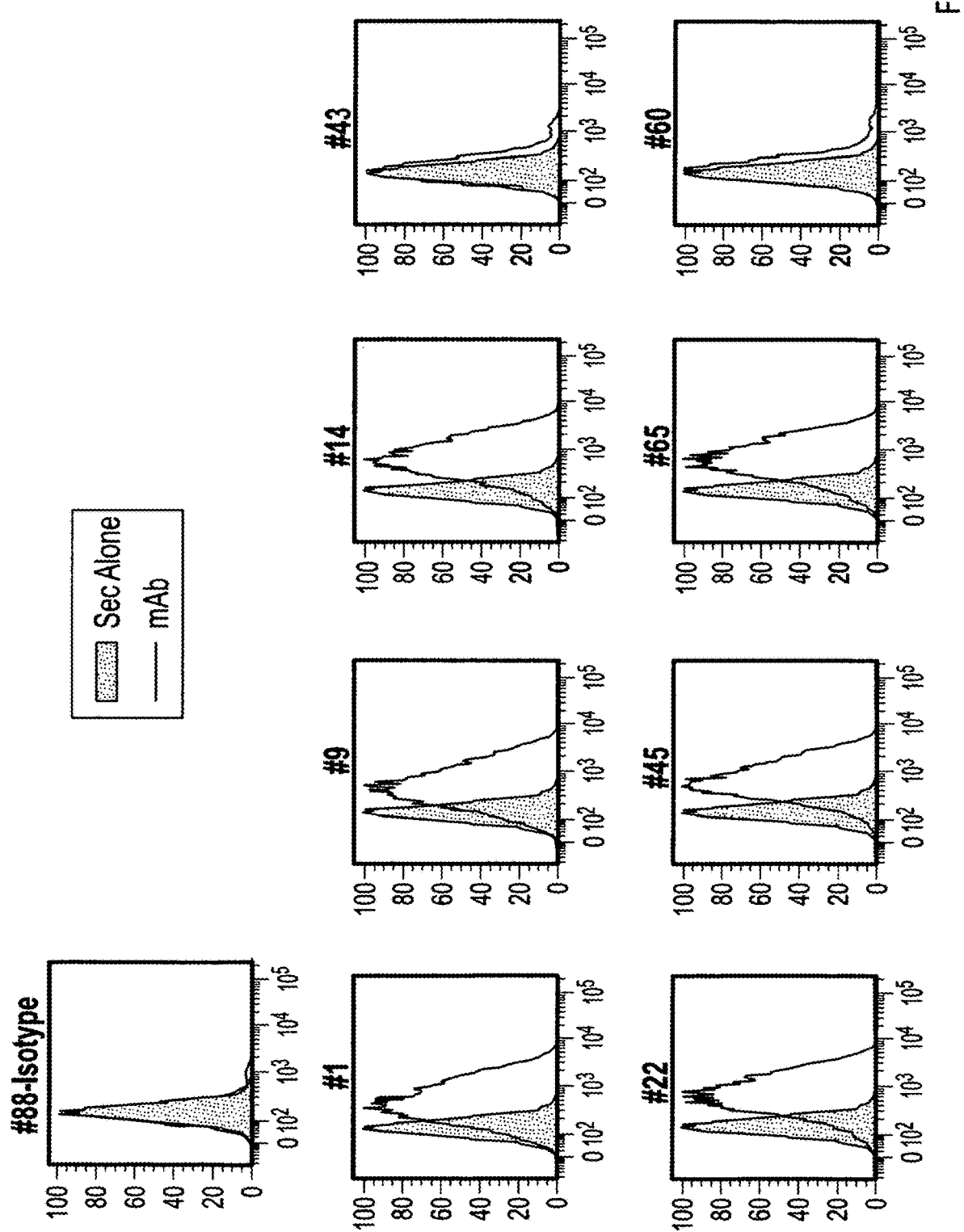
FIG. 22B shows antibodies Ab1, Ab9, Ab14, Ab22, Ab43, Ab45, Ab60, and Ab65 binding to primary human dendritic cells (hDCs). Antibody Ab88 represents the negative isotype control. Shaded histograms represent secondary antibody alone negative control. Black outlined histograms represent the TREM2 antibody positive population.

Antibodies Ab1, Ab9, Ab14, Ab22, Ab45, and Ab65 demonstrated binding to a mouse cell line (BWZ T2) expressing recombinant mouse TREM2, as indicated by positive TREM2 antibody staining detected via FACS analysis (black outlined histograms) (FIG. 21A). The negative isotype control (antibody Ab88) did not demonstrate binding. Antibodies Ab1, Ab9, Ab14, Ab22, Ab45, and Ab65 demonstrated antibody binding to WT (Trem+/+) bone marrow derived mouse macrophages (BMMac, mMac), but not to TREM2 deficient (TREM2-/-) mouse macrophages (BMMac, mMacs) (FIG. 21B). Antibodies Ab1, Ab9, Ab14, Ab22, Ab45, and Ab65 demonstrated binding to both a human cell line (293) expressing recombinant Human TREM2 (FIG. 22A) and to primary human dendritic cells (hDC) (FIG. 22B). Conversely, antibodies Ab43 and Ab60 bound to a human cell line expressing recombinant human TREM2 (FIG. 22A), but did not bind to primary human dendritic cells (FIG. 22B).

Mean fluorescent intensities (MFI) values for cell types bound by TREM2 antibodies Ab1, Ab9, Ab14, Ab22, Ab45, and Ab65 are listed in Table 9. Binding is compared to the parental mouse cell line (mTREM2 cell line BWZ parental), primary human cell line (hTREM2 Parental Cell line (293)), primary mouse macrophages deficient in TREM2 (mMacs KO MFI), and primary mouse dendritic cells deficient in TREM2 (mDC KO MFI). Results in Table 9 indicate that Ab1, Ab9, Ab14, Ab22, Ab45, and Ab65 bind specifically to cell lines overexpressing human and mouse TREM2 on the cell membrane, but not to control cell lines that do not express TREM2. The antibodies also bind to primary human macrophages and primary mouse macrophages and dendritic cells. Binding to mouse primary cells is specific, as it is not detected on primary cells derived from TREM2 KO mice.

TABLE 9

TREM2 Antibody Binding to Human and Mouse Cells

| Antibody | mTrem2 Cell line (BWZ-parental) MFI | mTrem2 Cell line (BWZ T2) MFI | hTrem2 Parental Cell line (293) MFI | hTrem2 Cell line (293) MFI | mMacs KO MFI | mMacs WT MFI | mDC KO MFI | mDC WT MFI | hDC % positive |
|---|---|---|---|---|---|---|---|---|---|
| Ab1 | 960 | 12626 | 86 | 1491 | 69.8 | 82.3 | 235 | 393 | 64.9 |
| Ab9 | 1044 | 15691 | 83 | 2126 | 97.2 | 171.0 | 200 | 538 | 65.8 |
| Ab14 | 852 | 11550 | 87 | 1656 | 77.9 | 145.0 | 218 | 529 | 75.8 |

TABLE 9-continued

TREM2 Antibody Binding to Human and Mouse Cells

| Antibody | mTrem2 Cell line (BWZ-parental) MFI | mTrem2 Cell line (BWZ T2) MFI | hTrem2 Parental Cell line (293) MFI | hTrem2 Cell line (293) MFI | mMacs KO MFI | mMacs WT MFI | mDC KO MFI | mDC WT MFI | hDC % positive |
|---|---|---|---|---|---|---|---|---|---|
| Ab22 | 828 | 12451 | 82 | 1837 | 67.2 | 110.0 | 191 | 451 | 76.9 |
| Ab45 | 1022 | 16288 | 141 | 2058 | 86.2 | 141.0 | 277 | 652 | 78.8 |
| Ab65 | 1354 | 16122 | 93 | 1734 | 92.5 | 165.0 | 260 | 642 | 76.9 |

The binding affinity of each anti-TREM2 antibody was determined by measuring their $K_D$ by ForteBio or MSD-SET. ForteBio affinity measurements were performed as previously described (Estep et al, (2013) *MAbs* 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, then transferred to assay buffer for 5 min for off-rate measurement. Kinetics were analyzed using the 1:1 binding model.

Equilibrium affinity measurements were performed as previously described (Estep et al, (2013) *MAbs* 5(2):270-8). Solution equilibrium titrations (SET) were performed in PBS+0.1% IgG-Free BSA (PBSF) with antigen held constant at 50 pM and incubated with 3- to 5-fold serial dilutions of antibody starting at 10 nM. Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Table 10 lists values representing the binding affinity ($K_D$) of antibodies Ab1, Ab9, Ab14, Ab22, Ab45, and Ab65 to a human TREM2 Fc fusion protein (hTREM2-Fc), a human monomeric His tagged TREM2 protein (hTREM2-HIS), and a mouse TREM2 Fc fusion protein (mTREM2-Fc).

TABLE 10

Binding affinity of TREM2 antibodies

| Antibody | IgG $K_D$ hTREM2-Fc (M) Avid | IgG $K_D$ hTREM2-HIS (M) Monovalent | IgG $K_D$ mTREM2-Fc (M) Avid |
|---|---|---|---|
| Ab1 | 7.05E-10 | 6.67E-09 | 4.86E-09 |
| Ab9 | 3.48E-10 | 6.32E-09 | N.B. |
| Ab14 | 5.51E-10 | 3.19E-09 | 6.20E-10 |
| Ab22 | 3.06E-10 | 1.01E-09 | 3.40E-10 |
| Ab45 | 2.29E-10 | 6.54E-10 | N.B. |
| Ab65 | 5.46E-10 | 5.01E-09 | 1.56E-09 |

Example 41: TREM2 Antibodies Induce the Expression of CD83 and CD86 on Human Dendritic Cells (DCs) and Induce T Cell Proliferation To evaluate the ability of anti-TREM2 antibodies to modify expression of CD83 and CD86, both plate bound and soluble antibodies were incubated with dendritic cells (DCs), and the expression of CD83, CD86, CCR7, and phosphorylated ERK were measured. To evaluate the ability of anti-TREM2 antibodies to modulate T cell proliferation, DCs were incubated with T cells and anti-TREM2 antibodies, and the level of T cell proliferation was measured.

Antibodies were plated overnight at 4 C in 12 well plates at 2 or 5 ug/ml in PBS. Wells were washed 3× with PBS the next day. On day 5, immature human DCs were harvested and plated at 1 million cells per well and incubated at 37 C, 5% $CO_2$ in the absence of cytokine. FACS analysis of CD86, CD83, CD11c, HLA-DR, and LIN (BD Biosciences) was performed on a BD FACS Canto 48 hours later. Data analysis was performed with FlowJo (TreeStar) software version 10.0.7. Levels of CD83, CD86, and CCR7 were evaluated for CD11c+HLA-DR+LIN− cell populations. For intracellular ERK phosphorylation, cells were fixed with 1% formaldehyde, permeabilized with cytofix/cytoperm kit (BD), and intracellular Erk phopshorylation was determined with flow cytometry after staining with PE-ERK antibody (BD).

Alternatively, Day 5 immature human dendritic cells were plated at 100,000 cells per well in a U-bottom non-TC treated 96 well plate in media without cytokine. Antibodies were added at 5 ug/ml with or without LPS-removed anti-human secondary (Jackson ImmunoResearch) at 20 ug/ml. FACS analysis for CD86, CD83, CD11c, HLA-DR, and LIN (BD Biosciences) was performed 48 hrs post antibody addition as previously described.

Additionally, Day 5 immature dendritic cells (CD14$^-$CD11c$^+$LIN$^-$) were plated in 12 well dishes coated the previous day with 2 ug/ml antibody. Plates were washed 3 times with PBS before addition of T cells. CD4$^+$ T cells from non-autologous donors were isolated and labeled with CFSE before addition to DCs in ratio of 1:10, 1:50, or 1:250. CD3/CD28 Dynal beads serve as a positive control. Day 5 post co-culture cells were analyzed by flow cytometry on a BD FACSCanto II for CFSE dilution. Percent CFSE$^{hi}$ compared to CFSE cells were calculated for each condition with FlowJo (TreeStar).

Figure 23A:
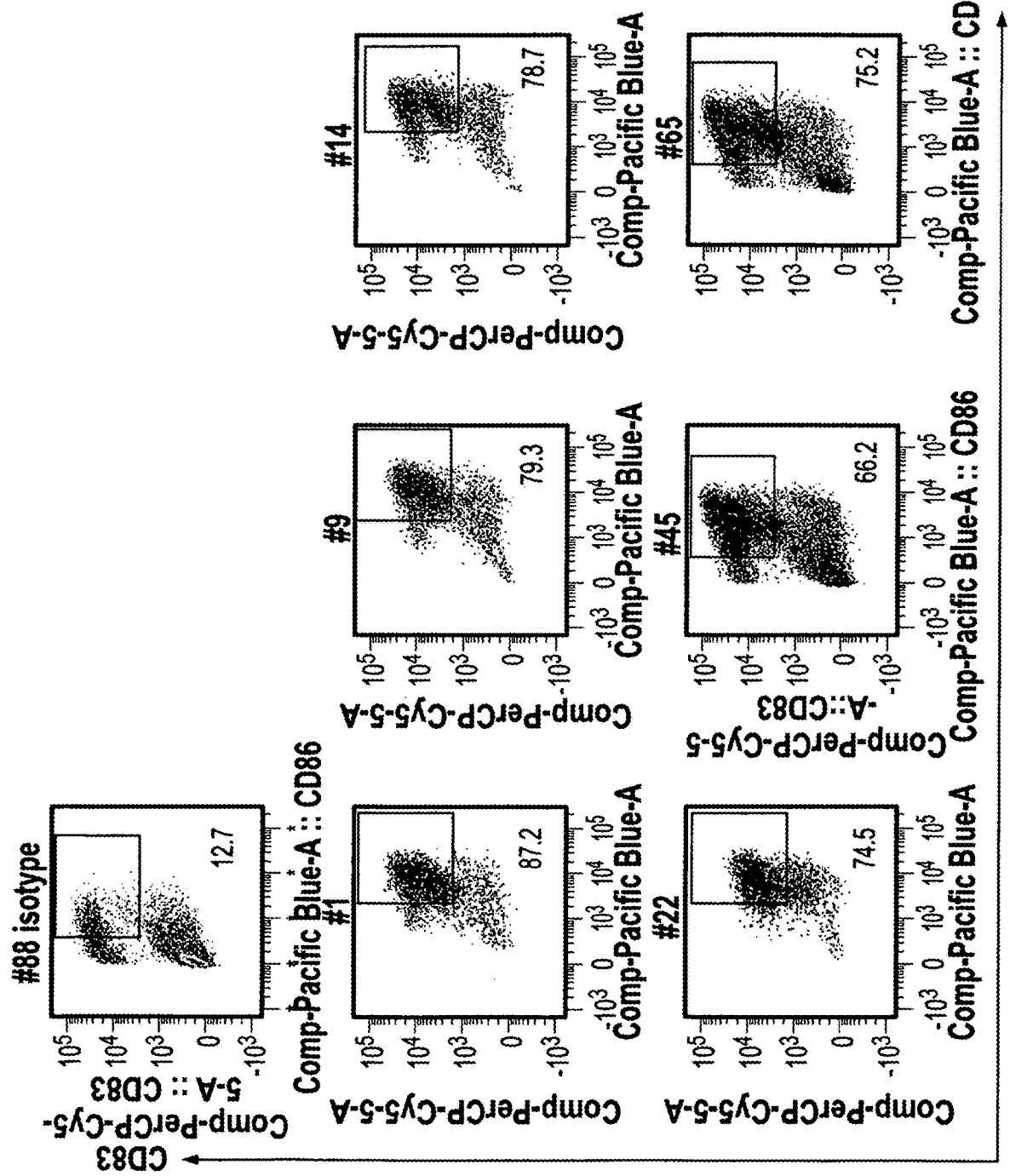
FIG. 23A shows FACS dot plots demonstrating expression of cell surface markers CD83 and CD86 on human dendritic cells (DCs) after incubation with plate-bound TREM2 antibodies Ab1, Ab9, Ab14, Ab22, Ab45, and Ab65. Antibody Ab88 represents the negative isotype control. Plots were gated on CD11c+HLA-DR+LIN− DCs. Percentage of cells within the CD83+CD86+ gate is displayed on each plot.
Figure 23B:
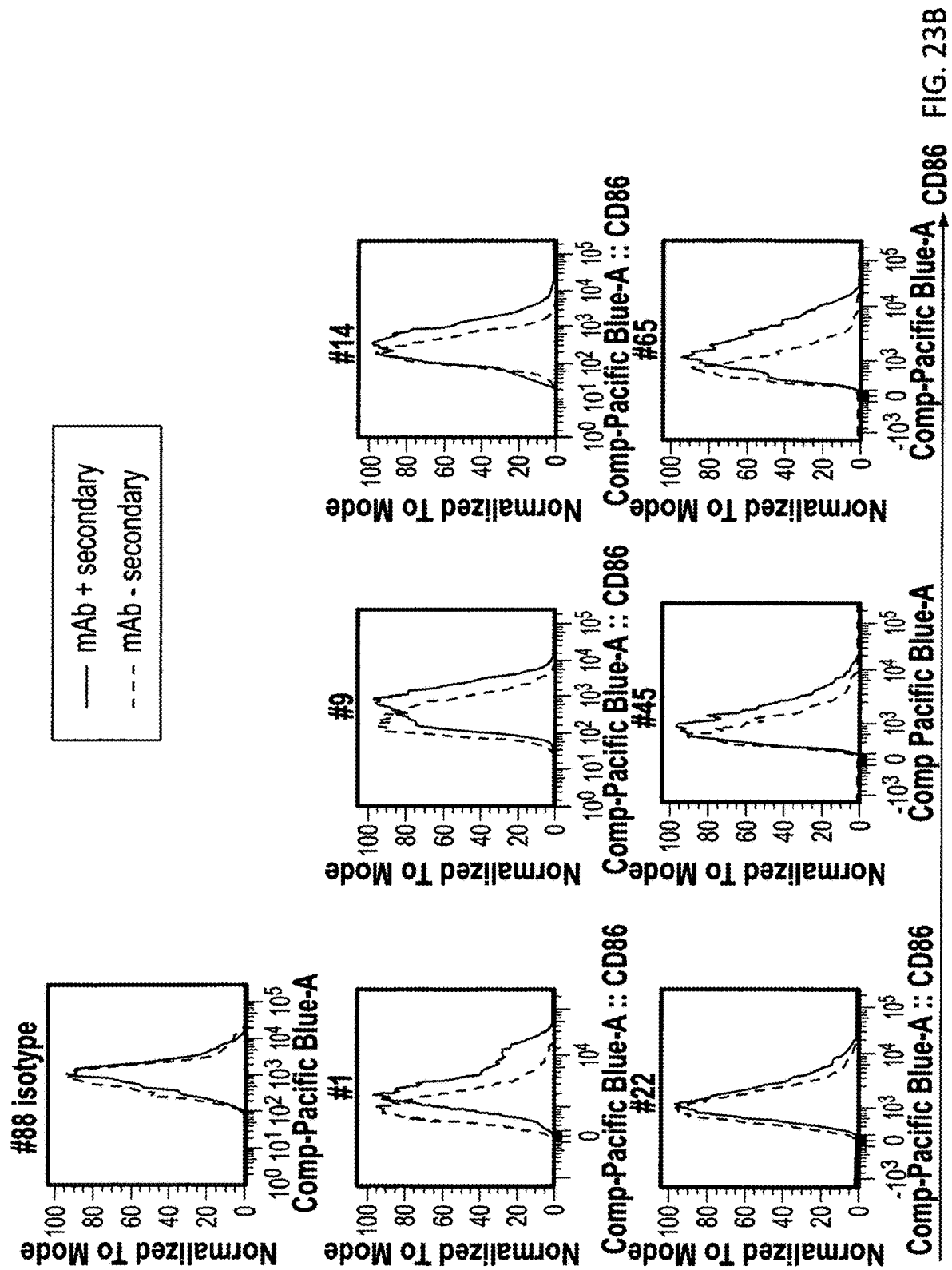
FIG. 23B shows FACS histograms demonstrating expression of cell surface marker CD86 on human dendritic cells (DCs) after incubation with cross-linked TREM2 antibodies Ab1, Ab9, Ab14, Ab22, Ab45, and Ab65. Antibodies were cross-linked with anti-human secondary antibody. Antibody Ab88 represents the negative isotype control.

Plate bound TREM2 antibodies Ab1, Ab9, Ab14, Ab22, Ab45, and Ab65 increased the frequency of CD83+CD86+ DCs compared to the isotype control antibody Ab88 (FIG. 23A). Soluble antibodies Ab1, Ab9, Ab14, Ab45, and Ab65, when cross-linked with anti-human secondary antibody, induced expression of CD86 on DCs. Conversely, cross-linked antibody Ab22 and non-cross-linked soluble antibodies did not induce CD86 expression (FIG. 23B). Based on these results, TREM2 antibodies Ab1, Ab9, Ab14, Ab22, Ab45, and Ab65 function as agonists to induce the expression of inflammatory surface markers CD83 and CD86 on human dendritic cells.

Example 42: TREM2 Antibodies Ab1, Ab9, Ab14, Ab20, Ab22, Ab45, and Ab65 Induce Syk Phosphorylation Spleen tyrosine kinase (Syk) is an intracellular signaling molecule that functions downstream of TREM2 by phosphorylating several substrates, thereby facilitating the formation of a signaling complex leading to cellular activation and inflammatory processes. The ability of agonist TREM2 antibodies to induce Syk activation was determined by culturing human and mouse macrophages and primary human dendritic cells and measuring the phosphorylation state of Syk protein in cell extracts.

Bone marrow-derived macrophages (BMDM), WT mouse BMDM, TREM2 knockout (KO) mouse BMDM, and primary human dendritic cells were starved for 4 hours in 1% serum RPMI and then removed from tissue culture dishes with PBS-EDTA, washed with PBS, and counted. The cells were coated with full-length agonist TREM2 antibodies Ab1, Ab9, Ab14, Ab20, Ab22, Ab45, Ab65, non-agonistic antibodies (Ab16, Ab77), or control antibodies (Ab89, or Ab92) for 15 minutes on ice. After washing with cold PBS, cells were incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates were then immunoprecipitated with anti-Syk Ab (N-19 for BMDM or 4D10 for human DCs, Santa Cruz Biotechnology). Precipitated proteins were fractionated by SDS-PAGE, transferred to PVDF membranes and probed with anti-phosphotyrosine Ab (4G10, Millipore). To confirm that all substrates were adequately immunoprecipitated, immunoblots were reprobed with anti-Syk Ab (Abcam, for BMDM) or anti-Syk (Novus Biological, for human DCs). Visualization was performed with the enhanced chemiluminescence (ECL) system (GE healthcare), as described (e.g., Peng et al., (2010) Sci Signal., 3(122): ra38).

Figure 24A:
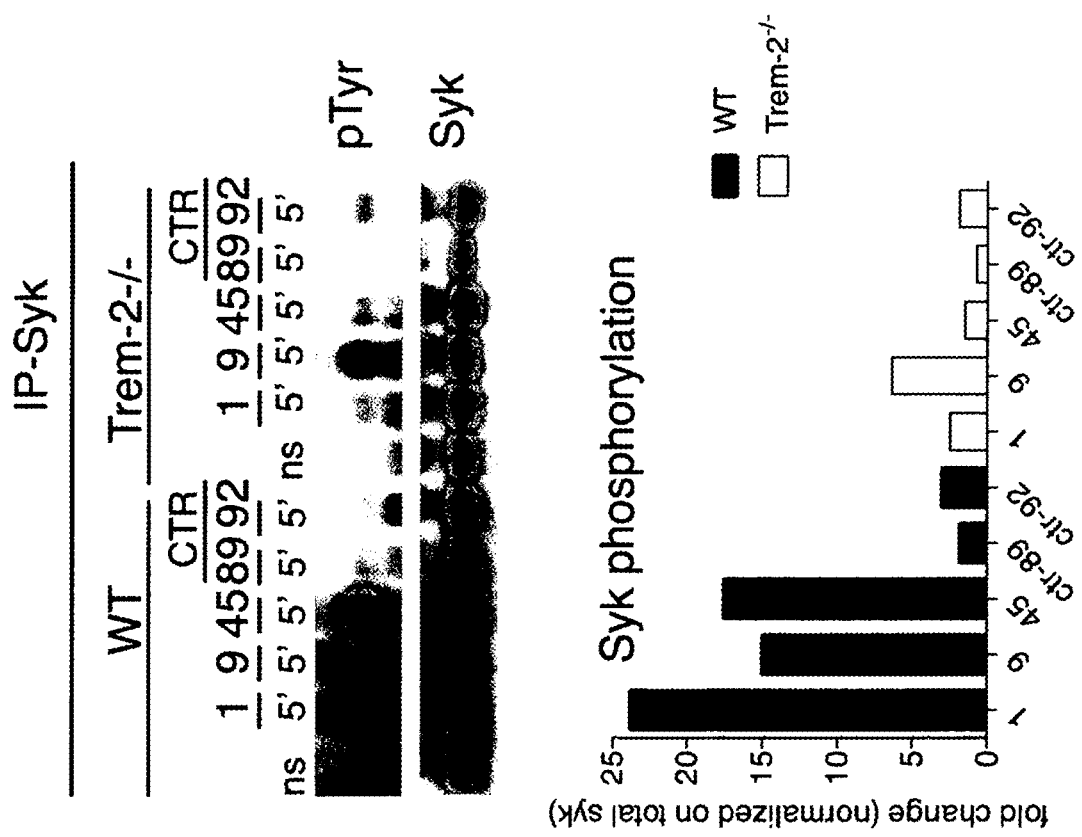
FIG. 24A shows Syk phosphorylation as determined by western blot in wild-type and TREM2 deficient (Trem2−/−) mouse macrophages after incubation with TREM2 antibodies Ab1, Ab9, or Ab45. Antibodies Ab89 and Ab92 are negative isotype controls.
Figure 24B:
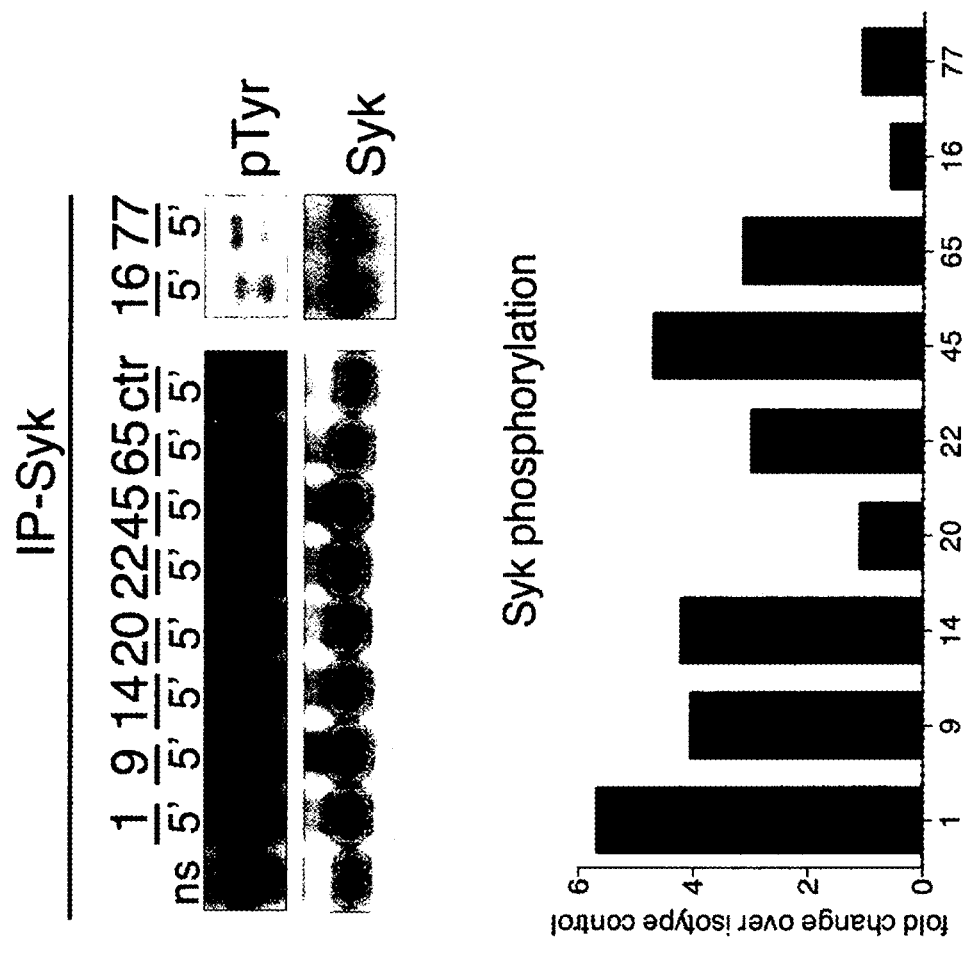
FIG. 24B shows Syk phosphorylation as determined by western blot in human macrophages after incubation with TREM2 antibodies Ab1, Ab9, Ab14, Ab20, Ab22, Ab45, and Ab65. Antibodies Ab16 and Ab77 are non-agonistic negative controls.
Figure 24C:
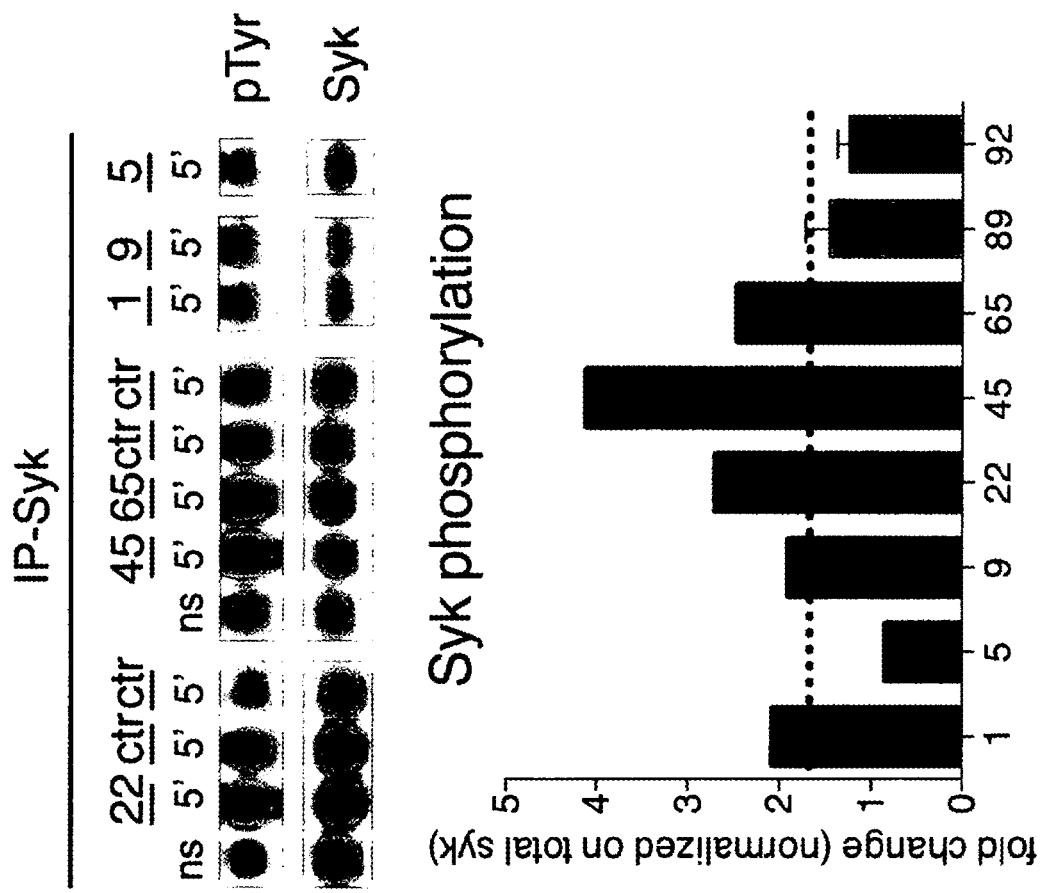
FIG. 24C shows Syk phosphorylation as determined by western blot in primary human dendritic cells after incubation with TREM2 antibodies Ab1, Ab5, Ab9, Ab22, Ab45, or Ab65.

TREM2 antibodies Ab1, Ab9, Ab14, Ab20, Ab22, Ab45, and Ab65 induced TREM-2 mediated Syk phosphorylation in BMDMs, (FIG. 24A). Syk phosphorylation induced by Antibodies Ab1, Ab9, and Ab45 is TREM-2 specific, as Syk phosphorylation is not induced when TREM2 KO BMDM are used as a control (FIG. 24B). TREM2 antibodies Ab22, Ab45, and Ab65 induce Syk phopshorylation in primary human dendritic cells (FIG. 24C). Non agonistic antibodies (Ab16 and Ab77) or control antibodies (Ab89 and Ab92) did not induce Syk phosphorylation. Based on these results, TREM2 antibodies Ab1, Ab9, Ab14, Ab20, Ab22, Ab45, Ab65 function as agonists to induce Syk phosphorylation in macrophages and dendritic cells.

Example 43: TREM2 Antibodies Ab1, Ab9, Ab14, Ab22, Ab45, and Ab65 Compete with TREM2 Ligand for Binding to Human and Mouse TREM2

The ability of agonist TREM2 antibodies to recognize the ligand-binding site on TREM2 was evaluated through competitive binding assays with E. coli cells expressing a putative TREM2 ligand.

E. coli were grown in 10 ml LB media O/N, harvested by centrifuging, and washed twice in 10 ml PBS. E. coli were then heat-inactivated by incubating in a 70° C. water bath for 30 min. Ecoli were labeled with CellTracker DeepRed (ThermoFisher/Invitrogen, 1 uM final concentration) and subsequently washed thrice in 10 ml PBS and resuspended in 1 ml PBS at a concentration of $10^8$/ml. For competition binding, bacteria were added to a mouse TREM2 and DAP12 expressing cell line (BWZ), or to a BW cell line expressing a human TREM2/DAP12 fusion protein, together with 10 μg/ml of full-length agonist TREM2 antibodies and incubated for one hour on ice. Cells were analyzed via FACS for binding of CellTracker labeled bacteria to the cell lines.

Figure 25:
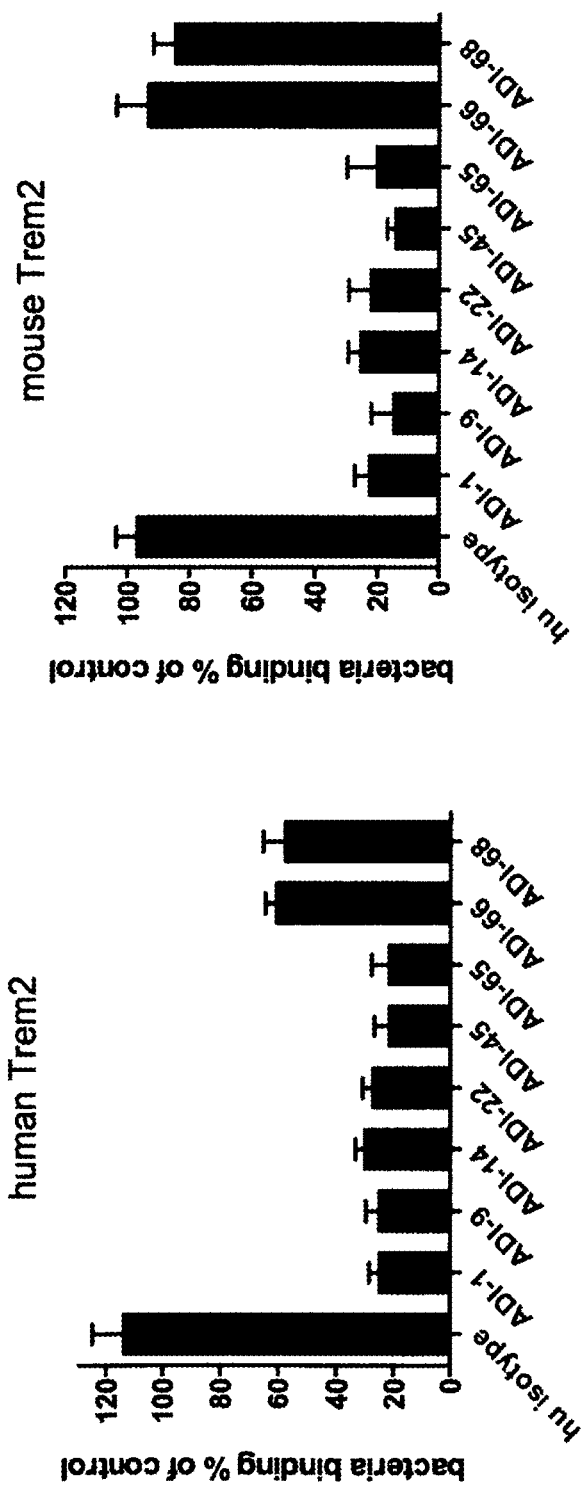
FIG. 25 shows competitive binding between TREM2 antibodies Ab1, Ab9, Ab14, Ab22, Ab45, Ab65, Ab66, and Ab68 and E. coli cells expressing putative TREM2 ligand to mouse and human cell lines expressing TREM2. Bacterial binding is expressed as a percentage of control. Average of two independent experiments; black bars: no difference to isotype control, red bars: significantly different from isotype controls (ANOVA).

TREM2 antibodies Ab1, Ab9, Ab14, Ab22, Ab45, and Ab65 inhibited the binding of E. coli bacteria to both human and mouse cells, indicating competitive binding of the antibodies to the ligand-binding site on TREM2 (FIG. 25). Non-agonistic control TREM2 antibodies (Ab66 and Ab68) partially inhibited bacterial binding to human cells expressing TREM2, but did not inhibit binding to mouse TREM2, indicating that they are weaker competitors of ligand binding.

Example 44: TREM2 Antibodies Ab1, Ab9, Ab22, Ab45, and Ab65 Induce DAP12 Phosphorylation in Mouse Macrophages TREM2 signals through DAP12, leading downstream to activation of PI3K and other intracellular signals. The ability of agonist TREM2 antibodies to induce DAP12 activation was determined by culturing mouse macrophages and measuring the phosphorylation state of DAP12 protein in cell extracts.

Before stimulation with mAbs, mouse wild-type (WT) bone marrow-derived macrophages (BMDM) and TREM2 knockout (KO) BMDM were starved for 4h in 1% serum RPMI. $15 \times 10^6$ cells were incubated in ice for 15 min with full-length agonistic or control antibodies. Cells were washed and incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors), followed by centrifugation at 16,000 g for 10 min at 4° C. to remove insoluble materials. Cell lysate was immunoprecipitated with a second TREM2 antibody (R&D Systems). Precipitated proteins were fractionated by SDS-PAGE, transferred to PVDF membranes, and probed with anti-phosphotyrosine Ab (4G10, Millipore). The membrane was stripped and reprobed with anti-DAP12 antibody (Cells Signaling, D7G1X). Each cell lysate used for TREM2 immunoprecipitations contained an equal amount of proteins, as indicated by a control Ab (anti-actin, Santa Cruz).

Figures 26A, 26B:
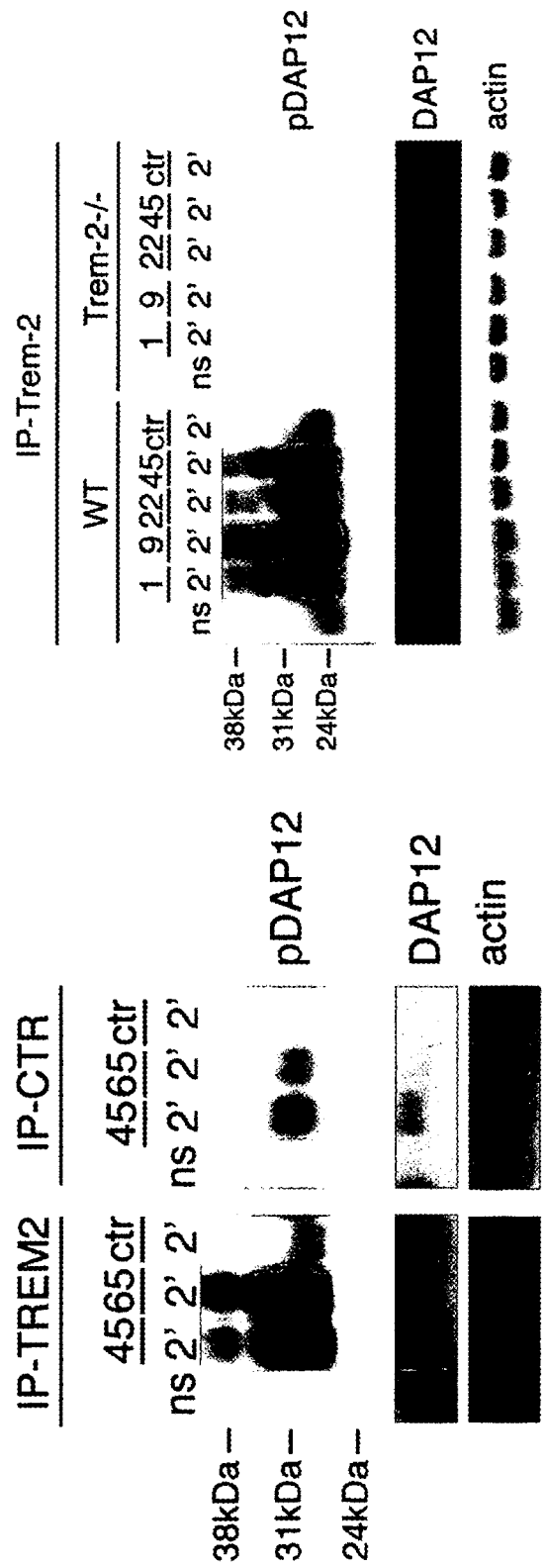
FIG. 26A shows DAP12 phosphorylation as determined by western blot in mouse macrophages after incubation with TREM2 antibody Ab45 or Ab65.
FIG. 26B shows DAP12 phosphorylation as determine by western blot in wild-type and TREM2 deficient (Trem2−/−) mouse macrophages after incubation with TREM2 antibody Ab1, Ab9, Ab22, or Ab45.

DAP12 co-precipitated with TREM2 and was phosphorylated in WT macrophages incubated with agonist TREM2 antibodies Ab1, Ab9, Ab22, Ab45, and Ab65 (FIGS. 26A and 26B). Conversely, no DAP12 phosphorylation was observed in TREM2 KO (TREM2$^{-/-}$) macrophages incubated with antibodies Ab1, Ab9, Ab22, or Ab45 (FIG. 26B). These results demonstrate that agonistic antibodies Ab1, Ab9, Ab22, and Ab45 induce phosphorylation of TREM-2-associated DAP12 in a TREM-2 specific manner, as DAP12 phosphorylation is absent in TREM-2 deficient BMDM.

Example 45: Epitope Mapping of TREM2 Antibodies and Comparison of TREM2 Antibodies to Reference TREM2 Antibodies TREM2 antibodies were tested for their ability to bind 15 or 25 mer peptides spanning the entire human and mouse TREM2. The TREM2 antibodies were also compared to a reference TREM2 antibody by determining their TREM2 binding region.

Linear 15-mer peptides were synthesized based on the sequence of human or mouse TREM2, with a 14 residue overlap. In addition, linear 25-mer peptides were synthesized based on sequence of human or mouse TREM2 with a 1 residue shift. The binding of TREM2 antibodies to each of the synthesized peptides was tested in an ELISA based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% H2O2 were added. After one hour, the color development was measured. The color development was quantified with a charge coupled device (CCD) camera and an image processing system.

To evaluate antibody binding regions, human TREM2-Fc was incubated with immobilized full-length agonist TREM2 antibodies Ab1, Ab9, Ab14, Ab22, Ab45, Ab63, Ab65, or Ab87, and TREM2 antibody MAB17291 (R&D Systems) was subsequently added. Epitope binning of the antibodies was performed on a Forte Bio Octet Red384 system (Pall Forte Bio Corporation, Menlo Park, Calif.) using a standard sandwich format binning assay (see Estep et al, (2013) MAbs 5(2):270-8). Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor).

Antibodies Ab1, Ab9, Ab28, and Ab29 yielded strong and robust binding exclusively for peptides from Set1 and Set2, which are derived from the sequence of human TREM2. All four antibodies bound peptides that contain the region between amino acid residues 139-146 of human TREM2 ($^{139}$GDLWFPGE$^{146}$ (SEQ ID NO: 237)) (FIG. 27A). The epitope region recognized by Ab1, Ab9, Ab28, and Ab29 corresponds to amino acid residues 139-146 of SEQ ID NO: 1 and has the amino acid sequence of: GDLWFPGE (SEQ ID NO: 237).

Antibodies Ab45 and Ab65 bound only to 25-mer peptides from Set2 and Set4. Both antibodies recognized a highly conserved region of TREM2 near its C-terminus between amino acid residues 140-153 of the human TREM2 ($^{140}$DLWFPGESESFEDA$^{153}$ (SEQ ID NO: 238)) and mouse TREM2 ($^{140}$DLWVPEESSSFEGA$^{153}$ (SEQ ID NO: 239)) (FIG. 27B). The epitope region recognized by Ab45 and Ab65 corresponds to amino acid residues 140-153 of SEQ ID NO: 1 and has the amino acid sequence of:

```
                                        (SEQ ID NO: 238)
             DLWFPGESESFEDA.
```

The epitope region recognized by reference antibody MAB17291 was also determined. Reference antibody MAB17291 was found to recognize a first peptide that contains the region between amino acid residues 130-144 of human TREM2 ($^{130}$ADPLDHRDAGDLWFP$^{144}$ (SEQ ID NO: 240)), and a second peptide that contains the region between amino acid residues 158-170 of human TREM2 ($^{158}$SISRSLLEGEIPF$^{170}$ (SEQ ID NO: 241)). The epitope regions recognized by MAB17291 correspond to amino acid residues 130-144 and 158-170 of SEQ ID NO: 1 and have the amino acid sequences of:

```
                                        (SEQ ID NO: 240)
             ADPLDHRDAGDLWFP
             and
                                        (SEQ ID NO: 241)
             SISRSLLEGEIPF.
```

Figure 28:
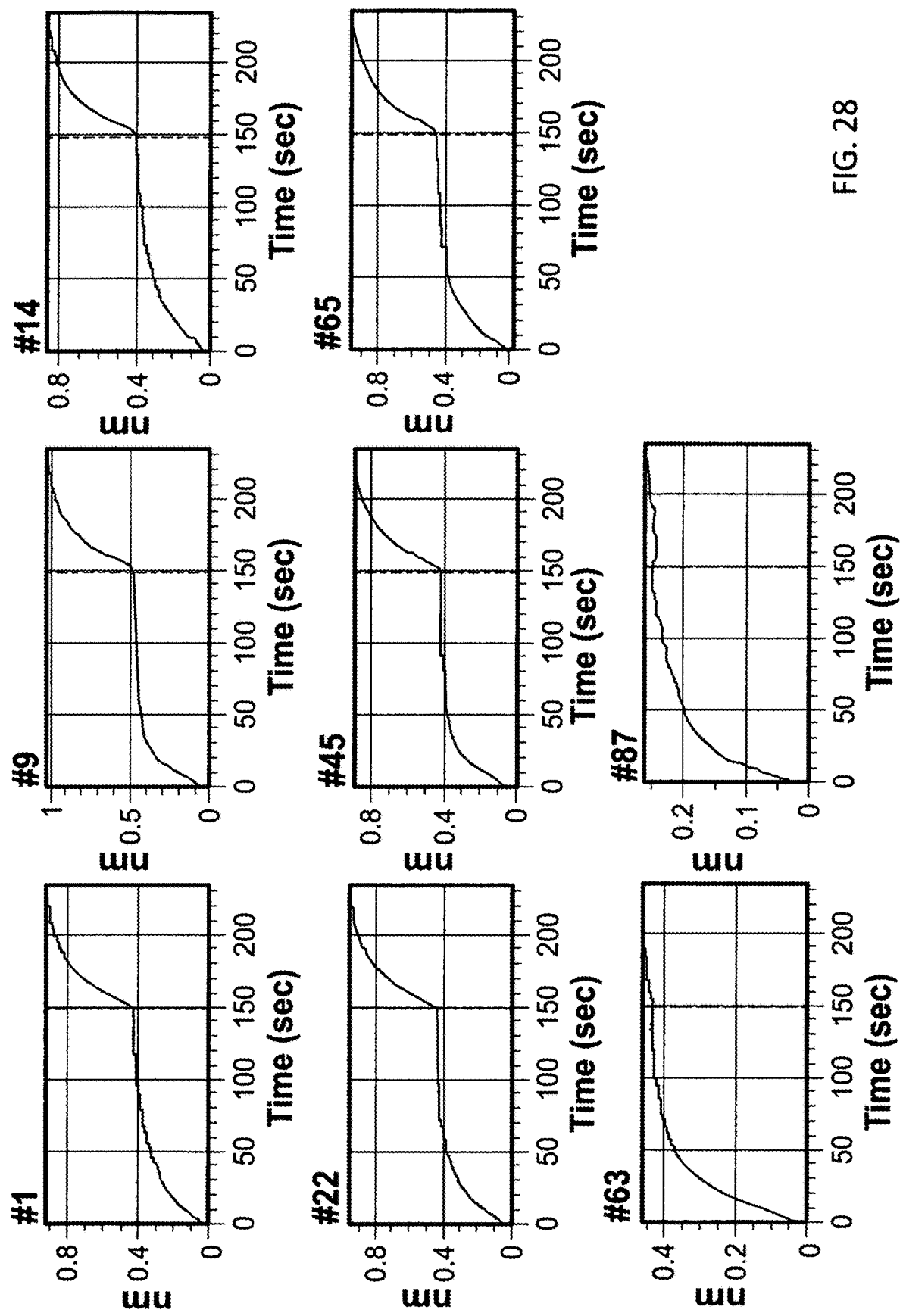
FIG. 28 shows Fortebio analysis demonstrating simultaneous binding of antibody MAB17291 and antibodies Ab1, Ab9, Ab14, Ab22, Ab45, and Ab65 to TREM2-Fc. Control antibodies Ab63 and Ab87 did not simultaneously bind to TREM2-Fc.

Reference antibody MAB17291 was able to simultaneously bind TREM2 with antibody Ab1, Ab9, Ab14, Ab22, Ab45, or Ab65, but not with antibody Ab63 or Ab87 (FIG. 28). These results demonstrate that agonist TREM2 antibodies Ab1, Ab9, Ab14, Ab22, Ab45, and Ab65 bind different regions of the TREM2 protein than does reference antibody MAB17291.

Example 46: Summary of TREM2 Antibody Functional Studies

Table 11 summarizes results of the functional studies described in Examples 41-45 above. Antibodies Ab1, Ab9, Ab14, Ab22, Ab45, and Ab65 demonstrated induction of CD83 and CD86 on human dendritic cells (hDC), with higher induction observed with plate-bound antibody compared to cross-linked soluble antibody (values in table represent percentage of CD83+CD86+ cells). Antibodies Ab1, Ab9, Ab14, Ab22, Ab45, and Ab65 induced variable levels of Syk phosphorylation in human dendritic cells (hDC), mouse dendritic cells (mDC), and mouse macrophages (mMac), and were able to mimic ligand binding (blocking bacterial binding) to human and mouse TREM2.

TABLE 11

| | | TREM2 Antibody Functional Studies | | | | | |
|---|---|---|---|---|---|---|---|
| Antibody | Induction of CD86 & CD83 Human hDC plate | Induction of CD86 & CD83 hDC solution | Induction Phospho Syk hDC | Induction Phospho Syk mDC | Induce Phospho TREM2 and DAP12 mMac | Blocking Bacterial binding hTREM2 | Blocking Bacterial mTREM2 |
| Ab1 | 87.2 | 3.0 | −/+ | ++ | ++ | +++ | +++ |
| Ab9 | 79.3 | 5.6 | −/+ | +++ | ++++ | +++ | +++ |
| Ab14 | 78.7 | 1.9 | + | ++ | N/D | +++ | +++ |
| Ab22 | 74.5 | 1.2 | ++ | ++ | ++ | +++ | +++ |

TABLE 11-continued

TREM2 Antibody Functional Studies

| Antibody | Induction of CD86 & CD83 Human hDC plate | Induction of CD86 & CD83 hDC solution | Induction Phospho Syk hDC | Induction Phospho Syk mDC | Induce Phospho TREM2 and DAP12 mMac | Blocking Bacterial binding hTREM2 | Blocking Bacterial mTREM2 |
|---|---|---|---|---|---|---|---|
| Ab45 | 65.5 | 4.3 | +++ | +++ | +++ | +++ | +++ |
| Ab65 | 74 | 1.7 | ++ | +++ | +++ | +++ | +++ |
| Isotype control | – | – | – | – | – | – | – |

Example 47: Analysis of Tumor Growth in TREM2 Deficient Mice

Groups of 10 TREM2 wild-type (WT), TREM2 heterozygous (HET), and TREM2 knock-out (KO) mice (sex and age-matched littermates, 8 weeks old (+/−2 weeks)) are challenged subcutaneously with tumor cells (for example $1 \times 10^5$-$1 \times 10^6$ MC38 colon carcinoma, Lewis Lung carcinoma, or B16 melanoma cells) suspended in 100 ul PBS. Animals are anesthetized with isoflurane prior to implant. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate and a reduced number of tumor infiltrating immune suppressor macrophages indicate increased effector T cell influx into the tumor in TREM2 KO mice.

To determine the number of infiltrating tumor associated immune suppressor macrophages and T cells, groups of 6-8 sex and age-matched littermates are used. 8 week old (+/−2 weeks) WT-HET-KO littermates are challenged subcutaneously with tumor cells (e.g. $1 \times 10^5$-$1 \times 10^6$ MC38, Lewis Lung, or B16 cells) suspended in 200 ul Matrigel (Matrigel Matrix Growth Factor Reduced; BD). Animals are anesthetized with isoflurane prior to implant. 7 and 10 days after tumor injection, the matrigel plug is resected, incubated for 1 hour at 37° C. with 1 mg/ml Collagenase D (Sigma), dissociated to obtain a single-cell suspension, and filtered through a cell strainer. To determine the amount of T cells recruited in the tumor and the ratio between effector T cells and regulatory T cells, $5 \times 10^6$ cells are stained with anti-CD45.2 PercpCy5.5, anti-CD3-FITC, anti-CD8-PECY7, anti-CD4-APC, anti-FoxP3-PE (BD), and DAPI. To determine the amount of monocyte/macrophage lineage cells recruited into the tumor, $5 \times 10^6$ cells are stained with anti-CD45.2 PercpCy5.5, anti-CD11b-PECY7, anti-F4/80-FITC, anti-Ly6C/G-APC, anti-CD86-PE, and DAPI. Cells are acquired on a BD FACS Canto. Data analysis is performed with FlowJo (TreeStar) software version 10.0.7.

Example 48: Analysis of the Anti-Cancer Effect of TREM2 Antagonistic Antibodies Groups of 10 C57B16/NTac mice at 8 weeks (+/−2 weeks) of age are challenged subcutaneously with tumor cells (e.g. $1 \times 10^5$ to $1 \times 10^6$ MC38, Lewis Lung, or B16 cells) suspended in 100 ul PBS. Animals are anesthetized with isoflurane prior to implant. Starting at day 2, groups of mice are injected i.p. every 3 days for 4 doses with 200 ug of each of anatagonisitc anti-TREM2 antibodies, such as those described in Examples 38 and 40. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate, reduced number of tumor infiltrating immune suppressor macrophages, and increased effector T cell influx into the tumor indicate the anti-cancer effects of blocking anti-TREM2 antibodies.

Example 49: Analysis of Additive Anti-Tumor Effect of Combination Therapy that Combines TREM2 Antibodies with Antibodies Against Inhibitory Checkpoint Proteins or Inhibitory Cytokines/Chemokines and their Receptors Groups of 15 C57B16/NTac mice at 8 weeks (+/−2 weeks) of age are challenged subcutaneously with tumor cells as described in Example 35. Animals are anesthetized with isoflurane prior to implant. Starting at day 2, mice are injected i.p. every 3 days for 4 doses with 200 ug anti-TREM2 antibodies alone or in combination with antibodies against checkpoint proteins (e.g. anti-PDL1 mAb clone 10F.9G2 and/or anti-CTLA4 mAb clone UC10-4F10-11) at day 3, 6, and 9. Treatment groups include anti-TREM2; anti-CTLA4; anti-PDL1; anti-TREM2+anti-CTLA4; anti-TREM2+anti-PDL1; and isotype control. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-TREM2 antibodies have additive or synergistic therapeutic effects with anti-checkpoint antibodies. Antagonistic antibodies against checkpoint molecules include antibodies against PDL1, PDL2, PD1, CTLA4, B7-H3, B7-H4, HVEM, BTLA, KIR, GAL9, TIM3, A2AR, LAG-3, and Phosphatidyl Serine. Antagonist antibodies against inhibitory cytokines include antibodies against CCL2, CSF-1, and IL-2.

Example 50: Analysis of Additive Anti-Tumor Effect of Combination Therapy that Combines TREM2 Antibodies with Antibodies that Activate Stimulatory Checkpoint Proteins Groups of 15 C57B16/NTac mice at 8 weeks (+/−2 weeks) of age are challenged subcutaneously with tumor cells as described in Example 35. Animals are anesthetized with isoflurane prior to implant. Starting at day 2, mice are injected i.p. every 3 days for 4 doses with 200 ug anti-TREM2 antibodies alone or in combination with agonistic antibodies that activate stimulatory checkpoint proteins (e.g. OX40 or ICOS mAb) at day 3, 6, and 9. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-TREM2 antibodies have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Example 51: Analysis of Additive Anti-Tumor Effect of Combination Therapy that Combines TREM2 Antibodies with Stimulatory Cytokines Groups of 15 C57B16/NTac mice at 8 weeks (+/−2 weeks) of age are challenged subcutaneously with tumor cells as described in Example 35. Animals are anesthetized with isoflurane prior to implant. Starting at day 2, mice are injected i.p. every 3 days for 4 doses with 200 ug anti-TREM2 antibodies alone or in combination with stimulatory cytokines (e.g. IL-12, IFN-α). Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in % survival with combination therapy indicate that anti-TREM2 antibodies have additive or synergistic therapeutic effects with immune-stimulatory cytokines. Stimulatory cytokines include IFN-α/b, IL-2, IL-12, IL-18, GM-CSF, and G-CSF.

Example 52: Analysis of Ability of TREM2 Antibody Fabs to Stimulate Viability of Innate Immune Cells The agonistic functionality of plate bound, cross-linked anti-TREM2 antibody Fab fragments derived from antibodies Ab22, Ab45, and Ab65 was evaluated in innate immune cells (e.g., macrophages).

Wild-type (WT) and TREM2 knock-out (KO) mouse bone marrow derived macrophages were cultured in the presence of M-CSF and plate bound TREM2 antibody Fabs, and cell viability was measured.

Macrophages isolated from the bone marrow of WT and KO mice were plated on non-tissue-culture-treated 96-well plates, pre-coated with either 12.5 nM or 100 nM of cross-linked Ab22, Ab45, or Ab65 Fabs. Cells were cultured for 48 hours in the presence of 10 ng/ml M-CSF. Analysis of viability was performed using Cell Titer Glo kit (Promega). Plates were read with a BioTek Synergy Microplate Reader using GEN5 2.04 software.

Figure 29:
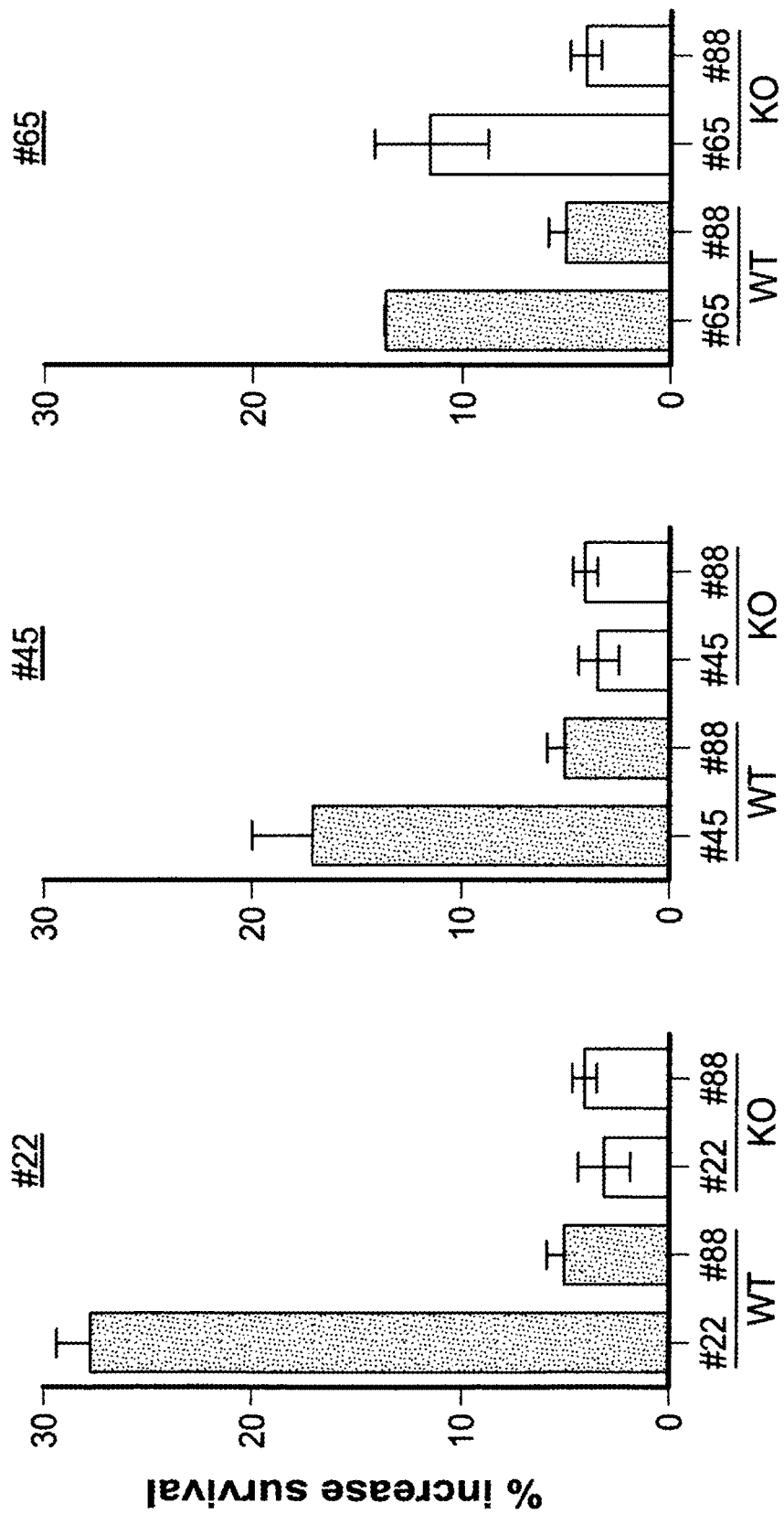
FIG. 29 shows the percent increased survival of wild-type (WT) and TREM2 knock-out (KO) mouse bone marrow derived macrophages cultured in the presence of plate bound, cross-linked TREM2 antibody Ab22, Ab45, or Ab65 Fabs and M-CSF. Antibody Ab88 represents the negative isotype control.

Cross-linked TREM2 Fab fragments derived from antibodies Ab22, Ab45, and Ab65 increased the number of viable mouse bone marrow-derived macrophages compared to isotype control Fab Ab88, as indicated by a higher % increased survival (FIG. 29). This enhancement in cell viability was not observed in KO mouse macrophages, with the exception of Ab65. These data indicate that the biological activity of Ab22 and Ab45 is TREM2 specific, and that plate bound, cross-linked Ab22 and Ab45 Fab fragments function as agonists to increase the survival of macrophages cultured in M-CSF.

Example 53: Analysis of Ability of TREM2 Antibodies to Decrease Survival of Innate Immune Cells The antagonistic functionality of both soluble, non-cross-linked anti-TREM2 antibody Fab fragments derived from antibodies and soluble, full-length anti-TREM2 antibodies was evaluated in innate immune cells (e.g., macrophages).

Wild-type (WT) and TREM2 knock-out (KO) mouse bone marrow derived macrophages were cultured in the presence of M-CSF and soluble TREM2 antibody Fabs or soluble full-length antibodies, and cell viability was measured.

Macrophages isolated from the bone marrow of WT and KO mice were plated on non-tissue-culture-treated 96-well plates in the presence of 20 ng/ml M-CSF and increasing amounts of the indicated soluble, non-cross-linked TREM2 antibody Fabs derived from antibodies Ab22, Ab45, and Ab65, or soluble, full-length antibodies Ab9, Ab14, Ab22, Ab45, and Ab65. Each condition was plated in triplicate. Analysis of viability was performed using Cell Titer Glo kit (Promega) 3 days later. Plates were read with a BioTek Synergy Microplate Reader using GEN5 2.04 software.

Figure 30A:
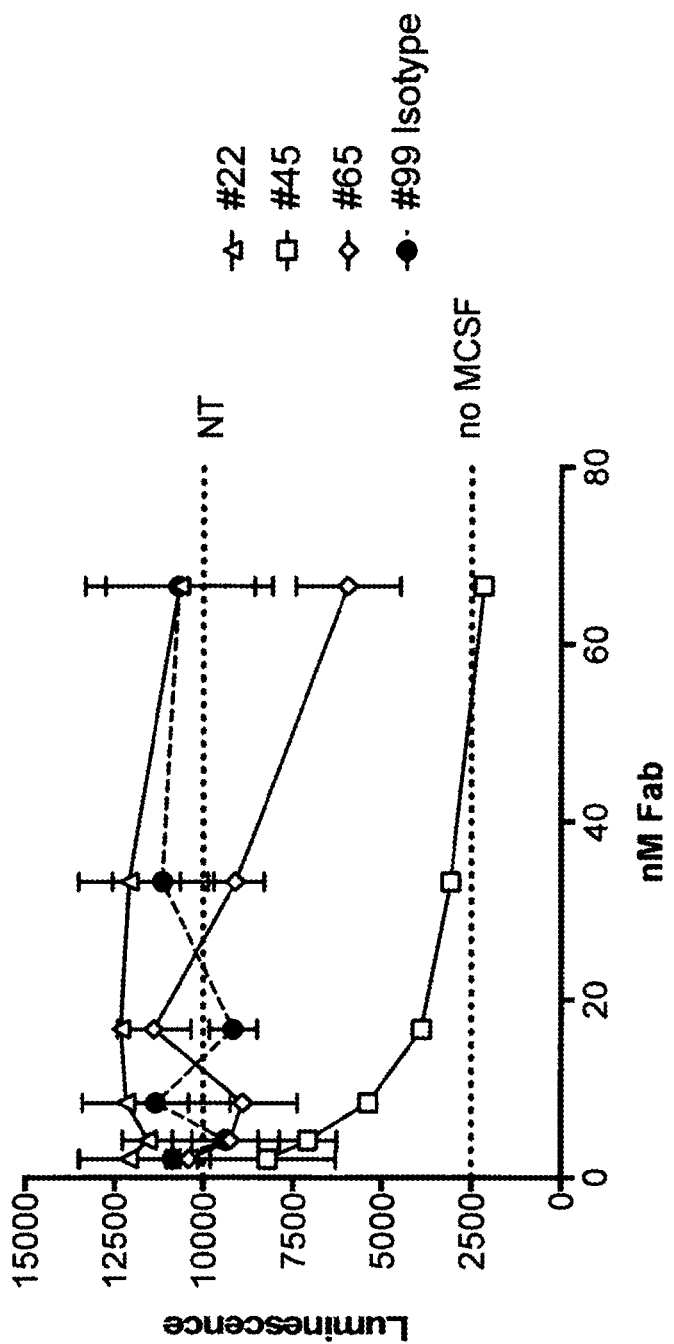
FIG. 30A shows the luminescence viability assay of mouse bone marrow derived macrophages cultured in the presence of soluble, non-cross-linked TREM2 antibody Fabs and M-CSF. Antibody Ab99 represents the negative isotype control.
Figure 30B:
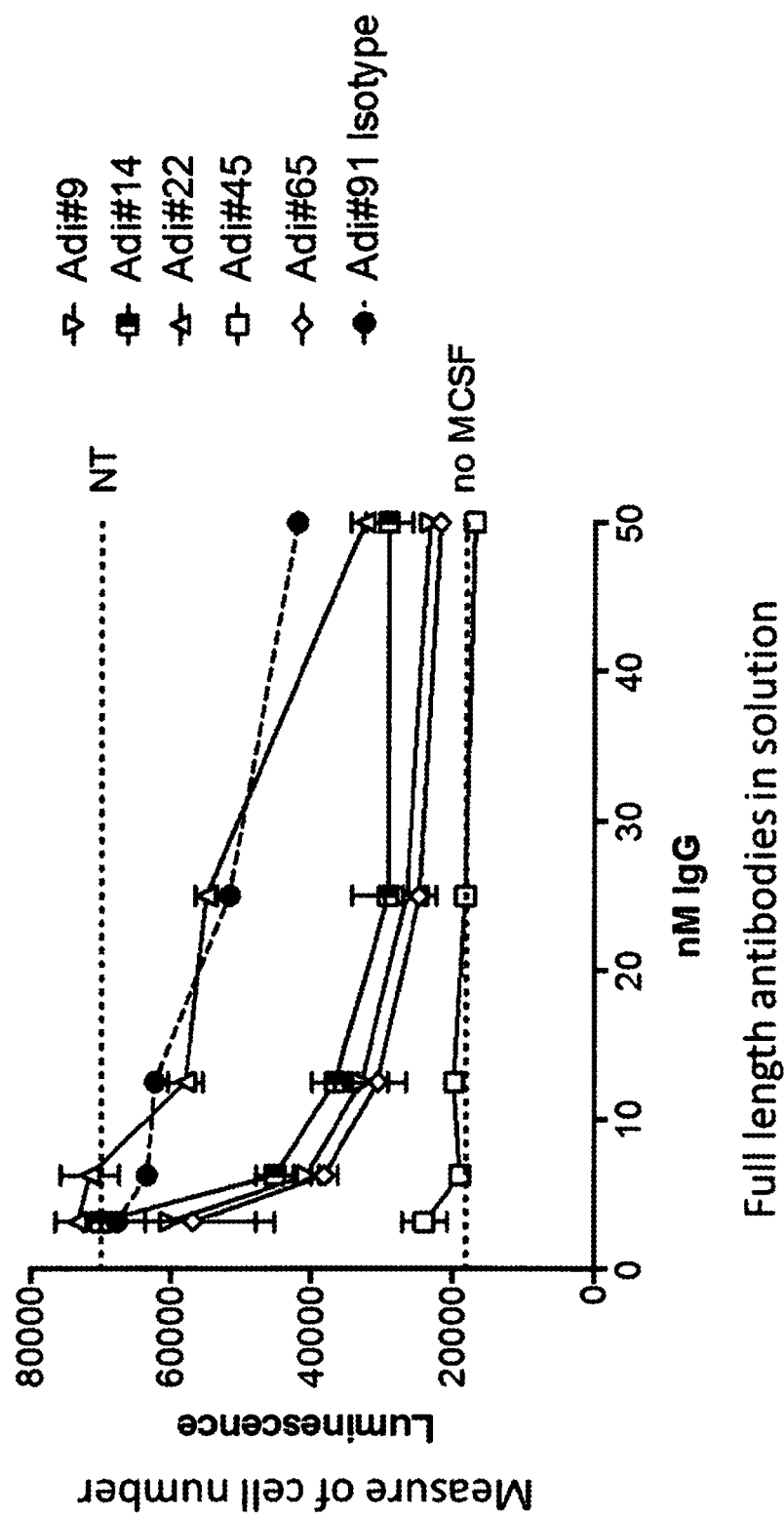
FIG. 30B shows the luminescence viability assay of mouse bone marrow derived macrophages cultured in the presence of soluble, full-length TREM2 antibodies and M-CSF. Antibody Ab91 represents the negative isotype control. The "NT" dotted line indicates the average viability obtained with untreated macrophages (no antibody added). The "no MCSF" dotted line indicates the average viability obtained when macrophages are cultured in the absence of M-CSF.

In FIGS. 30A and 30B, the "NT" dotted line indicates the average cell viability obtained with untreated macrophages (no antibody added). The "no MCSF" dotted line indicates the average cell viability obtained when macrophages were cultured in the absence of M-CSF.

When macrophage cell viability was evaluated with soluble, non-cross-linked TREM2 antibody Fabs, the results indicated that soluble, non-cross-linked TREM2 Fab fragments derived from antibody Ab45 decreased cell viability (FIG. 30A). In contrast, soluble, non-cross-linked TREM2 Fab fragments derived from antibody Ab22 did not inhibit viability and had an effect comparable to the isotype control Ab99 (FIG. 30A). Soluble, non-cross-linked TREM2 Fab fragments derived from antibody Ab65 partially inhibited cell viability (FIG. 30A). The results demonstrate that the soluble, non-cross-linked Fab derived from TREM2 antibodies Ab45 and Ab65 can function as antagonists and inhibit the survival of macrophages in vitro.

When macrophage cell viability was evaluated with soluble, full-length antibodies, antibodies Ab14, Ab45, Ab65, and Ab9 decreased cell viability (FIG. 30B). Soluble, full-length antibody Ab22 had an effect on cell viability that was nearly comparable to that of isotype control Ab91 (FIG. 30B). The results demonstrate that soluble, full-length TREM2 antibodies Ab14, Ab45, Ab65, and Ab9 can function as antagonists, when not cross-linked or clustered, and inhibit the survival of macrophages.

The results of these experiments indicate that TREM2 antibodies Ab45, Ab65, and Ab9, in the absence of clustering, can inhibit the survival of innate immune cells such as macrophages. In contrast, TREM2 antibody Ab22, even in the absence of clustering, does not inhibit the survival of innate immune cells such as macrophages.

Example 54: Analysis of the Ability of TREM2 Antibodies to Induce TREM2-Dependent Genes The ability of plate bound full-length anti-TREM2 antibodies Ab1, Ab9, Ab10, Ab14, Ab15, Ab17, Ab18, Ab20, Ab22, Ab24, Ab25, Ab28, Ab29, Ab45, Ab54, Ab51, Ab64, Ab65, and Ab66 to activate TREM2-dependent genes was evaluate using a luciferase reporter gene under the control of an NFAT (nuclear factor of activated T-cells) promoter.

A cell line derived from mouse thymus lymphoma T lymphocytes BW5147.G.1.4 (ATCC® TIB48™) was infected with mouse Trem2 and Dap12, and with Cignal Lenti NFAT-Luciferase virus (Qiagen). Full-length anti-TREM2 antibodies were plate bound at 10 ug/ml in DPBS on tissue-culture treated clear bottom white 96 well plates (100 ul/well), overnight at 4° C. Wells were rinsed thrice with DPBS and subsequently were plated at 100,000 cells/well in media with 1% serum. As a positive control for signaling, PMA (0.05 ug/ml) and ionomycin (0.25 uM) were added together. Cells were incubated for 6 hours and luciferase activity was measured by adding OneGlo Reagent (Promega) to each well and incubating 3 min at RT on a plate shaker. Luciferase signal was measured using a BioTek plate reader.

Figure 31A:
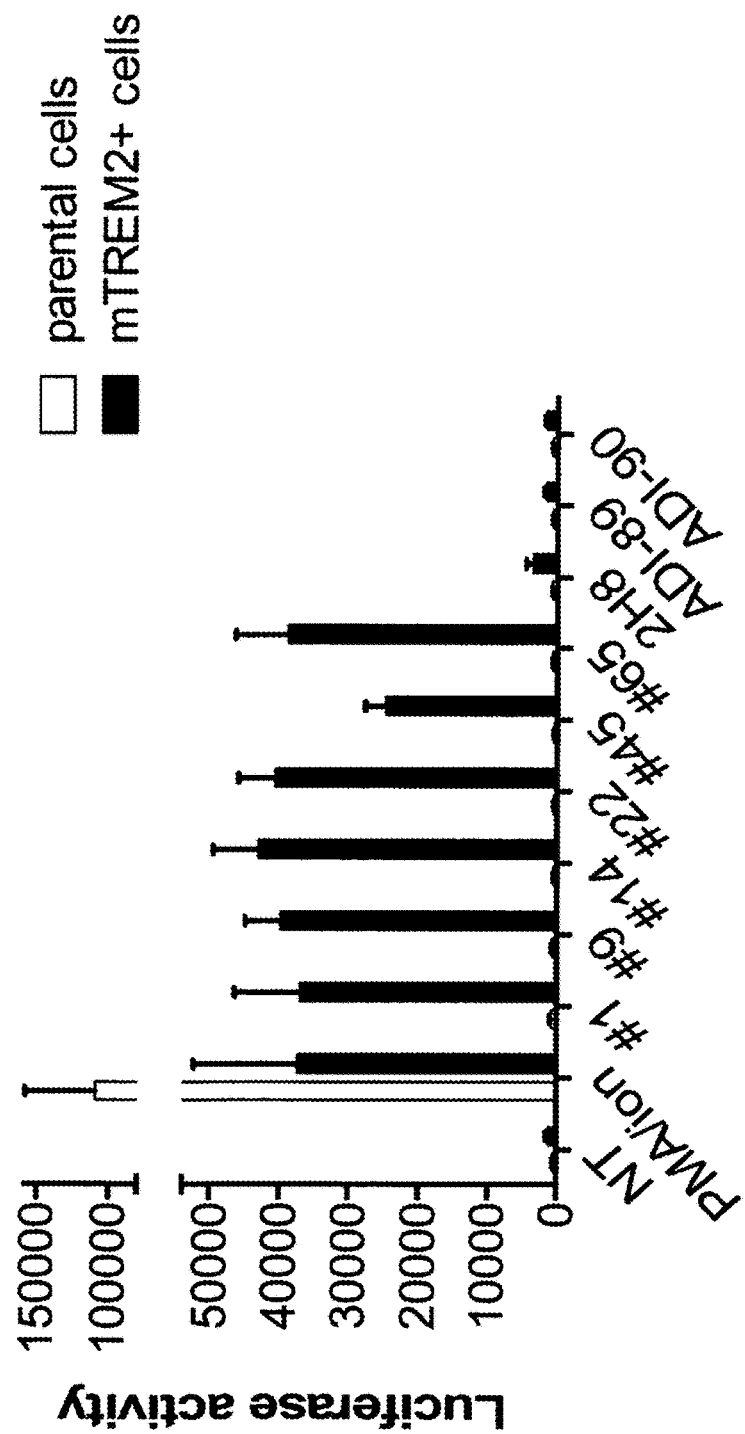
FIG. 31A shows induction of TREM2-dependent gene expression by plate bound, full-length anti-TREM2 antibodies using a luciferase reporter gene in a cell-based assay.
Figure 31B:
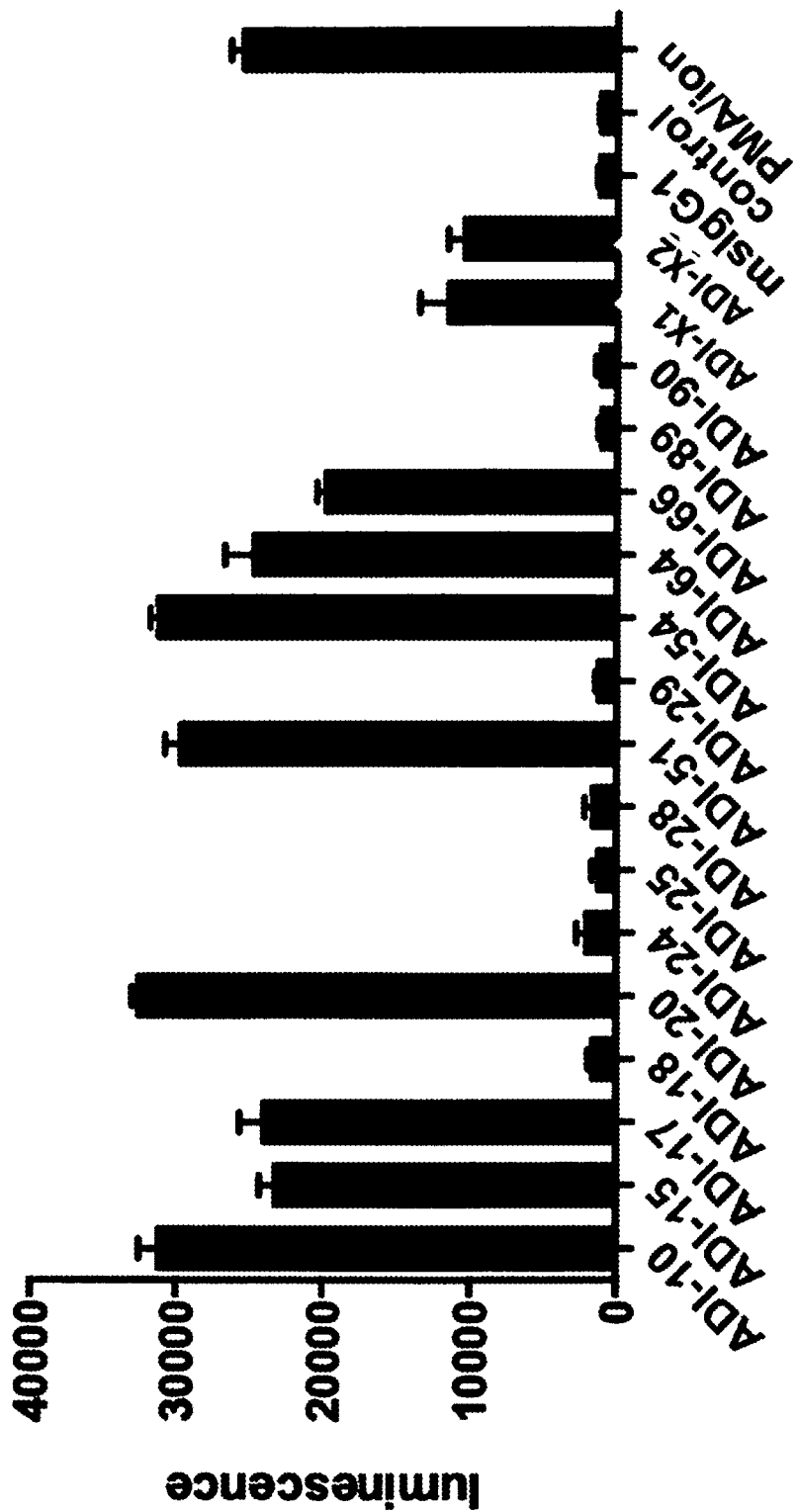
FIG. 31B shows induction of TREM2-dependent gene expression by plate bound, full-length anti-TREM2 antibodies using a luciferase reporter gene in a cell-based assay.

As shown in FIG. 31A and FIG. 31B, anti-TREM2 antibodies Ab1, Ab9, Ab10, Ab14, Ab15, Ab17, Ab20, Ab22, Ab45, Ab54, Ab64, Ab65, and Ab66 increased luciferase activity, indicating that the antibodies were able to induce TREM2-dependent gene transcription. As shown in FIG. 31C, plate bound phosphatidylserine (PS) induces TREM2-dependent gene expression. It is believed that PS is a natural ligand of TREM2. Thus, the results in FIGS. 31A-C indicate that agonist anti-TREM2 antibodies can mimic a natural ligand of TREM2.

Example 55: Analysis of the Ability of TREM2 Antibodies to Inhibit TREM2-Dependent Genes The ability of soluble, full-length anti-TREM2 antibodies Ab9, Ab14, Ab22, Ab45, and Ab65 to inhibit TREM2-dependent genes was evaluate using a luciferase reporter gene under the control of an NFAT (nuclear factor of activated T-cells) promoter.

A cell line derived from mouse thymus lymphoma T lymphocytes BW5147.G.1.4 (ATCC® TIB48™) was infected with mouse Trem2 and Dap12, and with Cignal Lenti NFAT-Luciferase virus (Qiagen). Soluble, full-length anti-TREM2 antibodies were added at increasing concentration to the cells. Cells were incubated for 6 hours at 37° C. and luciferase activity was measured using OneGlo Reagent (Promega).

The cells display tonic TREM2-dependent signaling due to either the presence of an endogenous ligand or to spontaneous receptor aggregation, which leads to TREM2 signaling.

Figure 32:
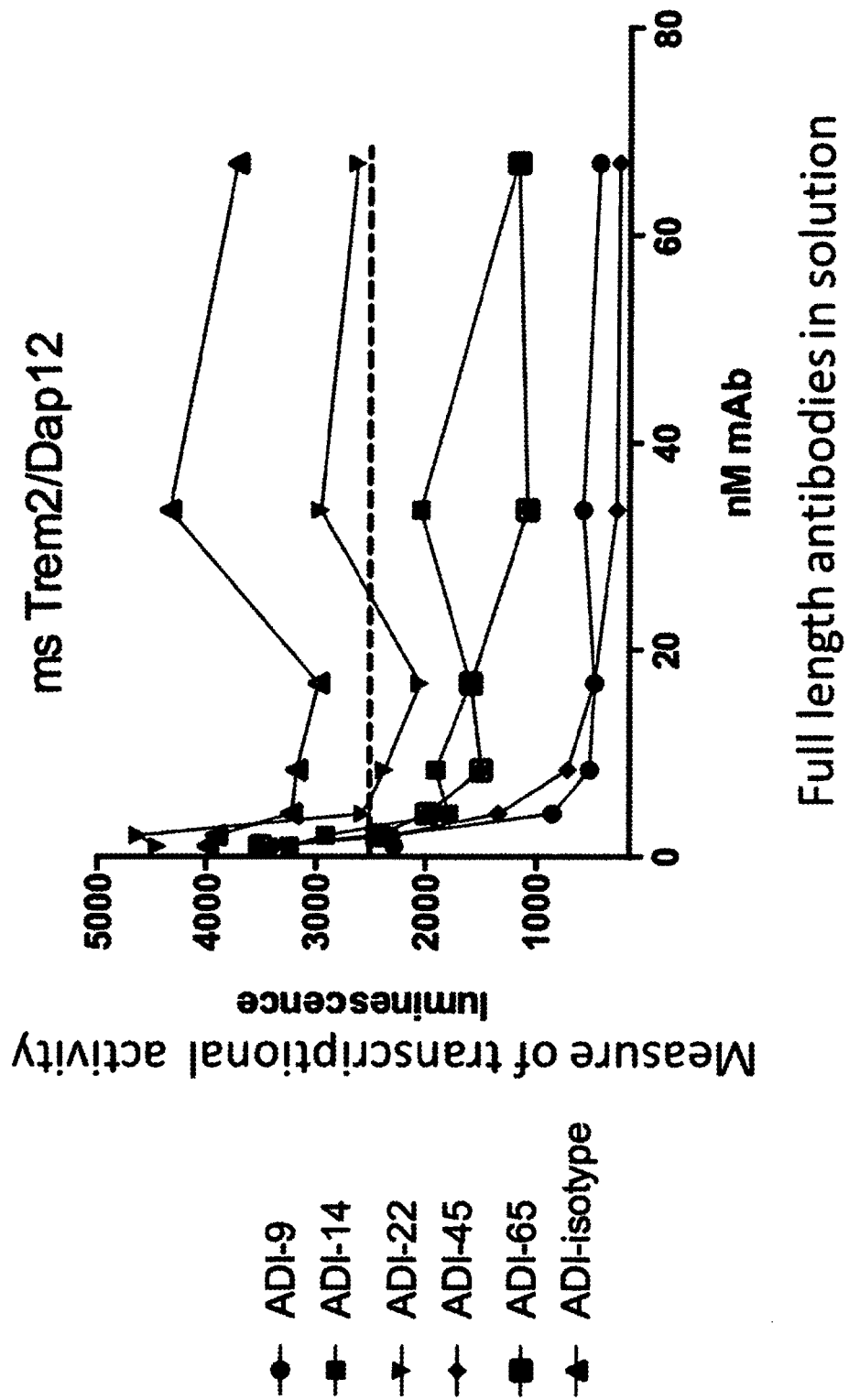
FIG. 32 shows inhibition of TREM2-dependent gene expression by soluble, full-length anti-TREM2 antibodies using a luciferase reporter gene in a cell-based assay.
Figure 33:
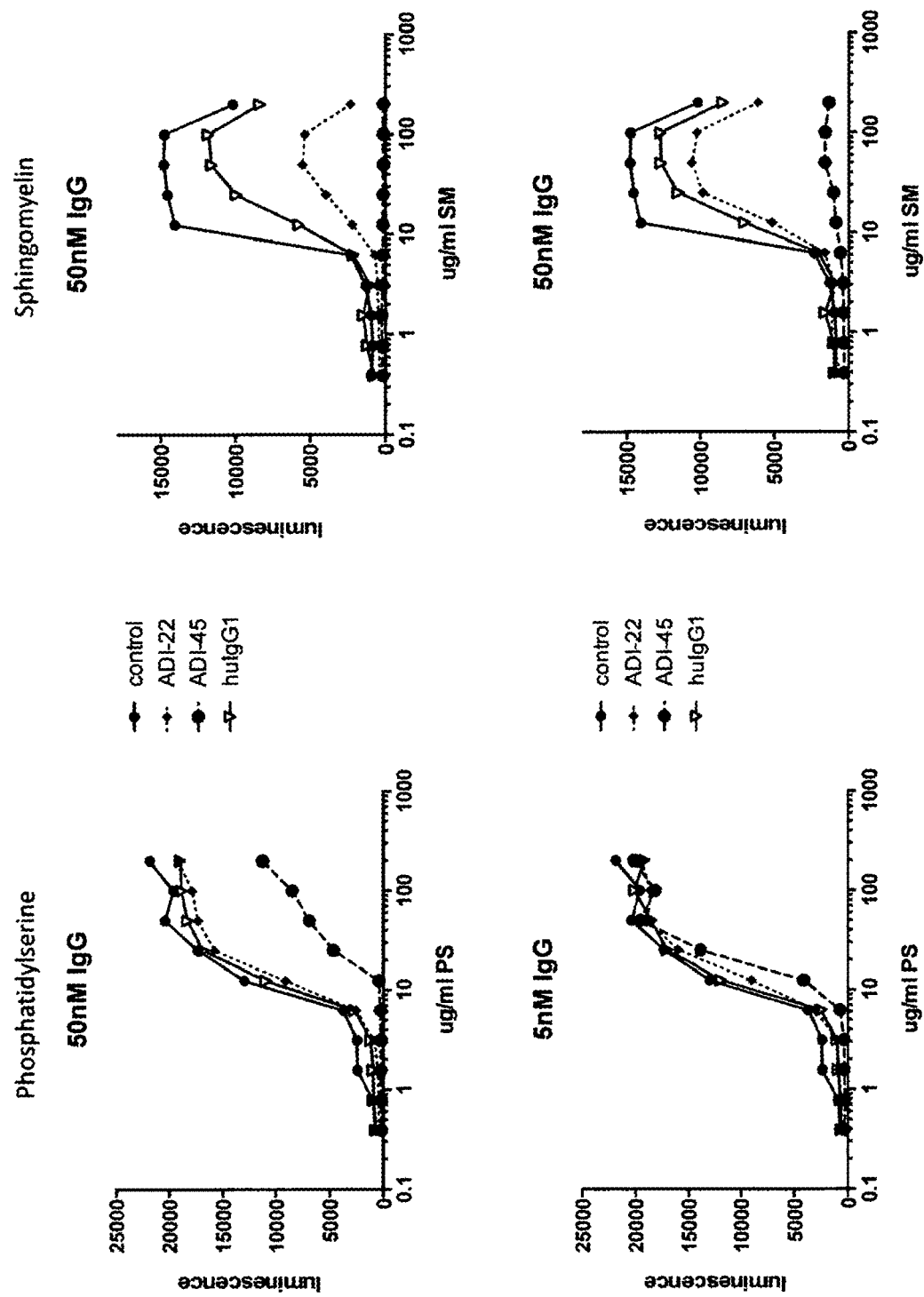
FIG. 33 shows competitive interactions between TREM2 antibodies Ab22 and Ab45 and Phosphatidylserine (PS) or Sphingomyelin (SM) in mouse and human cell lines expressing TREM2.
Figures 34A, 34B:
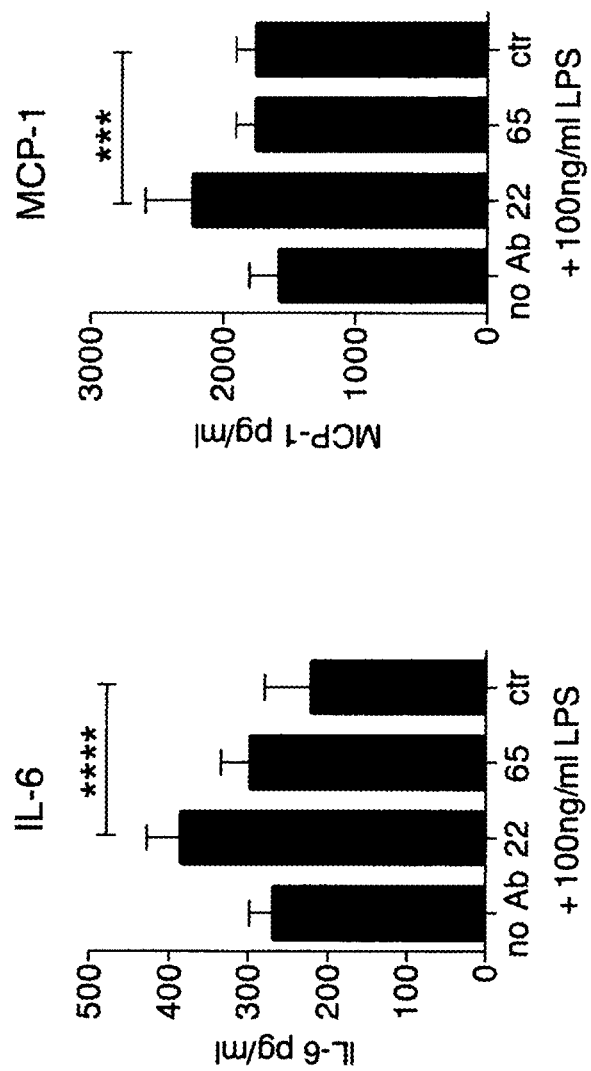
FIG. 34A shows activation of TREM2-dependent gene IL-6 in mouse macrophages by plate bound, Fab anti-TREM2 antibodies Ab22 and Ab65 Fabs.
FIG. 34B shows activation of TREM2-dependent gene MCP-1 in mouse macrophages by plate bound, Fab anti-TREM2 antibodies Ab22 and Ab65 Fabs. Data in FIGS. 34A and 34B are shown as means±SD; n=3 mice per group.

The dotted line in FIG. 32 indicates the levels of TREM2 activity without stimulation.

As shown in FIG. 32, soluble, full-length anti-TREM2 antibodies Ab9, Ab14, Ab45, and Ab65 were able to inhibit tonic, TREM2-dependent gene expression. In contrast, soluble, full-length anti-TREM2 antibody Ab22 did not appear to block tonic TREM2 signaling (FIG. 32).

Example 56: Summary of TREM2 Antibody Agonistic and Antagonistic Activity

Table 12 summarizes results of the functional studies described in Examples 52-55 above. Antibodies Ab1, Ab9, Ab14, Ab22, Ab45, and Ab65 demonstrated agonistic activity in activating TREM2-dependent gene expression using either a luciferase reporter gene (FIG. 31A) or a beta-GAL reporter gene (Table 12). As indicated in Table 12, Ab1 and Ab65 showed an increased level of gene induction, compared to Ab9, Ab22, and Ab45 when the beta-GAL reporter gene was used (Table 12). Antibodies Ab22, Ab45, and Ab65 also demonstrated agonistic activity in stimulating cell survival of innate immune cells (FIG. 29). Table 12 further summarizes results demonstrating the antagonistic effects of soluble, non-cross-linked antibodies Ab9, Ab14, Ab45, and Ab65 in inhibiting cell survival of innate immune cells (FIG. 30). In contrast, soluble, non-cross-linked antibody Ab22 had minimal antagonistic activity in inhibiting cell survival (FIG. 30).

TABLE 12

TREM2 Antibody Functional Studies

| Antibody | Luciferase Agonistic antibody activity | betaGAL Agonistic antibody activity | Survival Agonistic antibody activity | Luciferase Antagonistic antibody activity in solution/antagonistic format |
| --- | --- | --- | --- | --- |
| Ab1 | ++++ | +++ | ND | ND |
| Ab9 | ++++ | + | ND | ++++ |
| Ab14 | ++++ | ND | ND | +++ |
| Ab22 | ++++ | + | +++ | − |
| Ab45 | ++ | + | ++ | ++++ |
| Ab65 | +++ | +++ | + | +++ |
| Isotype control | − | − | − | − |

Example 57: Summary of Binding and Functional Studies for Further TREM2 Antibodies Table 13 summarizes the results of binding and functional studies for further full-length TREM2 antibodies generated as described in Example 40. The results below were obtained using the methods described in Examples 40 and 42.

TABLE 13

Binding and functional studies for other TREM2 Antibodies

| Antibody | IgG $K_D$ hTREM2-Fc (M) Avid | IgG $K_D$ hTREM2-HIS (M) t | IgG $K_D$ mTREM2-Fc (M) Avid | mTrem2 Cell binding MFI | hTrem2 Cell binding MFI | Phospho Syk hDC | Phospho Syk mDC |
|---|---|---|---|---|---|---|---|
| Ab2  | 5.92E−10 | 2.41E−08 | N.B.     | 1432  | 1407 | ND  | ND  |
| Ab3  | 4.90E−10 | 1.42E−08 | N.B.     | 488   | 1693 | ND  | ND  |
| Ab4  | 9.71E−10 | P.F.     | N.B.     | 295   | 1343 | ND  | ND  |
| Ab5  | 6.97E−10 | 3.00E−08 | N.B.     | 310   | 1336 | −   | ND  |
| Ab6  | 4.44E−09 | P.F.     | 8.51E−09 | 228   | 816  | ND  | ND  |
| Ab7  | 1.05E−09 | 3.34E−08 | 1.11E−09 | 10934 | 1249 | ND  | ND  |
| Ab8  | 7.23E−10 | 1.50E−08 | N.B.     | 523   | 1623 | ND  | ND  |
| Ab10 | 5.44E−10 | 4.79E−09 | P.F.     | 11486 | 1788 | ++  | ++  |
| Ab11 | 9.34E−10 | 7.20E−09 | 1.19E−09 | 5495  | 1909 | ND  | ND  |
| Ab12 | 1.19E−09 | 2.68E−09 | 7.91E−09 | 1552  | 1930 | −   | ND  |
| Ab13 | 1.49E−09 | 6.67E−08 | 1.71E−09 | 3246  | 971  | ND  | ND  |
| Ab15 | 6.05E−10 | 3.03E−09 | 2.80E−09 | 4755  | 1611 | ND  | +   |
| Ab16 | 1.09E−09 | 2.47E−09 | 1.36E−09 | 6382  | 1545 | ND  | −   |
| Ab17 | 7.92E−10 | 3.46E−09 | 1.67E−09 | 10312 | 1604 | ND  | +   |
| Ab18 | 5.13E−10 | 6.77E−09 | N.B.     | 5164  | 1924 | ++  | +   |
| Ab19 | 4.65E−10 | 4.49E−09 | N.B.     | 2304  | 1993 | ++  | ND  |
| Ab20 | 6.58E−10 | 3.62E−09 | N.B.     | 11245 | 1556 | ND  | +   |
| Ab23 | 9.67E−10 | P.F.     | 6.83E−09 | 919   | 2653 | ND  | ND  |
| Ab24 | 4.79E−10 | P.F.     | 9.32E−09 | 2760  | 1882 | ND  | +   |
| Ab25 | 6.84E−10 | 4.51E−09 | 5.98E−09 | 2497  | 1884 | ND  | −   |
| Ab26 | 4.81E−10 | 3.60E−09 | N.B.     | 2551  | 1421 | ND  | ND  |
| Ab27 | 1.33E−09 | P.F.     | 6.39E−09 | 2163  | 1316 | ND  | ND  |
| Ab28 | 9.15E−10 | P.F.     | 7.45E−09 | 5248  | 1487 | ND  | −   |
| Ab29 | 2.36E−09 | P.F.     | 3.27E−09 | 4518  | 1193 | ND  | −   |
| Ab30 | 1.32E−09 | P.F.     | N.B.     | 399   | 1421 | ND  | ND  |
| Ab31 | 4.51E−10 | 6.82E−09 | N.B.     | 551   | 1760 | ND  | ND  |
| Ab32 | 9.95E−10 | 2.48E−08 | 1.35E−08 | 756   | 1202 | ND  | ND  |
| Ab33 | 1.42E−09 | 1.60E−08 | N.B.     | 413   | 1352 | ND  | ND  |
| Ab34 | 7.06E−10 | 2.70E−08 | N.B.     | 395   | 1770 | ND  | ND  |
| Ab35 | 2.21E−10 | 7.82E−09 | 6.44E−09 | 931   | 1391 | ND  | ND  |
| Ab36 | 4.65E−10 | 4.01E−09 | N.B.     | 1258  | 1896 | ND  | ND  |
| Ab37 | 1.58E−09 | P.F.     | N.B.     | 1433  | 1434 | ND  | ND  |
| Ab38 | 9.60E−10 | 1.31E−08 | N.B.     | 297   | 1832 | ND  | ND  |
| Ab39 | 2.13E−09 | P.F.     | 6.41E−09 | 588   | 9029 | ND  | ND  |
| Ab40 | 1.97E−10 | 7.97E−09 | 6.03E−09 | 577   | 1452 | ND  | ND  |
| Ab41 | 2.14E−09 | P.F.     | 8.64E−09 | 373   | 1017 | ND  | ND  |
| Ab42 | 4.03E−09 | P.F.     | N.B.     | 387   | 1234 | ND  | ND  |
| Ab43 | 4.37E−09 | P.F.     | N.B.     | 418   | 918  | ND  | ND  |
| Ab44 | 5.62E−10 | 9.46E−09 | N.B.     | 1206  | 1249 | ND  | ND  |
| Ab46 | 4.45E−10 | 1.68E−08 | 2.46E−09 | 4257  | 1528 | ND  | ND  |
| Ab47 | 4.31E−10 | 7.37E−09 | 1.45E−09 | 10123 | 1833 | ND  | ND  |
| Ab48 | 3.50E−10 | 9.08E−09 | 1.41E−09 | 9770  | 1412 | ND  | ND  |
| Ab49 | 4.35E−10 | 1.74E−08 | 2.08E−09 | 4315  | 1392 | ND  | ND  |
| Ab50 | 7.29E−10 | 3.64E−08 | N.B.     | 325   | 1435 | ND  | ND  |
| Ab51 | 2.84E−10 | 1.64E−09 | N.B.     | 12077 | 1928 | ++  | +   |
| Ab52 | 1.51E−09 | 5.75E−09 | 8.96E−11 | 15613 | 1411 | +++ | +++ |
| Ab53 | 6.35E−10 | 2.16E−08 | N.B.     | 843   | 1338 | ND  | ND  |
| Ab54 | 5.00E−10 | 3.02E−09 | N.B.     | 11001 | 1931 | ND  | ++  |
| Ab55 | 2.22E−09 | 9.17E−08 | 1.17E−09 | 6221  | 911  | ND  | ND  |
| Ab56 | 1.03E−09 | 5.18E−08 | 2.71E−09 | 743   | 1157 | ND  | ND  |
| Ab57 | 4.36E−10 | 1.83E−08 | 5.98E−10 | 10226 | 1227 | ND  | ND  |
| Ab58 | 5.75E−10 | 2.73E−09 | N.B.     | 1870  | 1698 | ND  | ND  |
| Ab59 | 8.54E−10 | 5.72E−09 | N.B.     | 3901  | 1754 | ND  | ND  |
| Ab60 | 5.59E−09 | P.F.     | P.F.     | 1871  | 741  | ND  | ND  |
| Ab61 | 4.61E−09 | P.F.     | N.B.     | 10517 | 1101 | ND  | ND  |
| Ab62 | 7.72E−10 | 1.42E−08 | P.F.     | 4746  | 1647 | ND  | ND  |
| Ab63 | 1.13E−09 | 4.96E−08 | N.B.     | 1722  | 1347 | ND  | ND  |
| Ab64 | 9.45E−10 | 6.57E−08 | P.F.     | 8676  | 1458 | +++ | +   |
| Ab66 | 1.98E−09 | 6.07E−08 | 3.88E−09 | 4098  | 1161 | ND  | +   |
| Ab67 | 6.60E−10 | 3.45E−08 | 2.92E−09 | 6207  | 1118 | ND  | ND  |
| Ab68 | 6.68E−10 | 1.09E−07 | 3.26E−09 | 2103  | 1135 | ND  | ND  |
| Ab69 | 3.75E−09 | 5.97E−08 | 3.40E−09 | 629   | 957  | ND  | ND  |
| Ab70 | 6.26E−09 | P.F.     | 3.45E−09 | 3265  | 833  | ND  | ND  |
| Ab71 | 2.77E−09 | 6.47E−08 | N.B.     | 804   | 1556 | ND  | ND  |
| Ab72 | 8.39E−10 | 2.94E−08 | P.F.     | 3746  | 1500 | ND  | ND  |
| Ab73 | 4.10E−09 | P.F.     | N.B.     | 1117  | 1307 | ND  | ND  |
| Ab74 | 9.43E−09 | P.F.     | 4.91E−09 | 1360  | 645  | ND  | ND  |
| Ab75 | 5.88E−09 | P.F.     | N.B.     | 276   | 676  | ND  | ND  |
| Ab76 | 4.84E−09 | P.F.     | N.B.     | 1604  | 580  | ND  | ND  |
| Ab77 | P.F.     | P.F.     | N.B.     | 1650  | 951  | ND  | ND  |
| Ab78 | 8.51E−10 | 3.73E−08 | N.B.     | 433   | 1435 | ND  | ND  |
| Ab79 | 1.07E−08 | P.F.     | N.B.     | 738   | 900  | ND  | ND  |
| Ab80 | 5.72E−09 | P.F.     | 8.85E−09 | 593   | 897  | ND  | ND  |
| Ab81 | 1.01E−08 | P.F.     | N.B.     | 400   | 994  | ND  | ND  |

TABLE 13-continued

Binding and functional studies for other TREM2 Antibodies

| Ab82 | 1.10E−08 | N.B. | 5.82E−09 | 712 | 371 | ND | ND |
|---|---|---|---|---|---|---|---|
| Ab83 | 8.21E−09 | NB. | N.B. | 1576 | 684 | ND | ND |
| Ab84 | 1.16E−09 | 6.04E−08 | N.B. | 799 | 1148 | ND | ND |
| Ab85 | 5.72E−09 | P.F. | 2.19E−09 | 1121 | 460 | ND | ND |
| Ab86 | 3.89E−09 | P.F. | 6.55E−09 | 355 | 840 | ND | ND |
| Ab87 | 9.51E−09 | N.B. | 4.48E−09 | 1228 | 414 | ND | ND |
| 88 control | No Binding | ND | ND | 90.7 | 187 | – | – |
| 89 control | No Binding | ND | ND | 142 | 185 | – | – |

| Antibody | Luciferase Agonistic antibody activity |
|---|---|
| Ab10 | ++++ |
| Ab15 | ++++ |
| Ab17 | ++++ |
| Ab18 | – |
| Ab20 | +++ |
| Ab24 | – |
| Ab25 | – |
| Ab28 | – |
| Ab51 | +++ |
| Ab29 | – |
| Ab54 | +++ |
| Ab64 | +++ |
| Ab66 | +++ |
| Ab89 | – |
| Ab90 | – |
| Isotype Control | – |
| PMA/Ion | +++ |

Example 58: Analysis of Anti-Stroke Effect of Agonistic TREM2 Antibodies

Transient occlusion of the middle cerebral artery (MCAO)—a model that closely resembles human stroke is used to induce cerebral infarction in mice. Monofilament (70SPRe, Doccol Corp, USA) is introduced into the internal carotid artery through an incision of the right common carotid artery. The middle cerebral artery is occluded for 30 minutes with a range of reperfusion times (6 h, 12 h, 24 h, 2 d, 7 d and 28 d). The effect of surgery is controlled using sham animals at 12 h and at 7 d. Sham animals undergo the same surgical procedure without occlusion of the middle cerebral artery. MCAO animals treated with agonistic anti-TREM2 antibodies or control antibodies are tested for infarct volumetry, acute inflammatory response (12 h reperfusion), transcription of pro-inflammatory cytokines TNFa, IL-1a, and IL-1b, microglial activity (CD68, Iba1), transcription of chemokines CCL2 (MCP1), CCL3 (MIP1a and the chemokine receptor CX3CR1 and invasion of CD3-positive T-cells (Sieber et al. (2013) PLoS ONE 8(1): e52982. doi:10.1371/journal.pone.0052982).

Example 59: Analysis of the Protective Effect of Antagonist TREM2 Antibodies in Respiratory Tract Infections To evaluate the ability of antagonist TREM2 antibodies to delay, prevent, or treat bacterial respiratory tract infections, a preclinical mouse model involving challenge of C57B16 mice with *Streptococcus pneumoniae* is used. This model involves intranasal (i.n.) administration of 105 CFU *S. pneumoniae* serotype 3 (ATCC 6303) as described (see, e.g., Sharif O et al, 2014 *PLoS Pathog.* 2014 June; 10(6): e1004167; and Schabbauer G et al, 2010 *J Immunol* 185: 468-476). In this model ~90% WT C57B16 mice succumb to infection within 6 days post infection.

Ten to fifteen mice/group are challenged with *S. pneumoniae* and concomitantly are treated with antagonist anti-TREM2 antibodies every other day starting from day 0. The first dose of anti-TREM2 antibodies is administered 3 hours prior to challenge with *S. pneumonia*. Mice are monitored daily for 15 days to check for death events. % of mice surviving bacteria challenge is determined.

In separate experiments, count of bacterial load and cytokine expression in the blood and in the lungs is also determined. 24 or 48 hours after infection blood is collected in EDTA-containing tubes and plated on agar plates to enumerate bacterial CFU in the plasma. Plasma is stored at −20° C. for cytokine analysis by ELISA. Lungs are harvested, homogenized and plated on agar plates to enumerate bacterial CFU, or incubated for 30 min in lysis buffer and supernatants analyzed for cytokine measurements.

In separate experiments, lungs are collected 40 hours post bacterial infection, fixed in 10% formalin, and embedded in paraffin for H&E pathology analysis.

Example 60: Analysis of the Protective Effect of Antagonist TREM2 Antibodies in Sepsis To evaluate the ability of antagonist TREM2 antibodies to delay, prevent, or treat sepsis, a preclinical mouse model involving systemic challenge of C57B16 mice with LPS is used. This model involves intraperitoneal (i.p.) administration of 37 mg/ml LPS as described (see, e.g., Gawish R et al, 2014 *FASEB J*). In this model >95% WT C57B16 mice succumb infection within 40 hours post LPS injection.

Cohorts of mice are challenged with LPS and concomitantly are treated with antagonist anti-TREM2 antibodies every day starting from day 0. The first dose of anti-TREM2 antibodies is administered 3 hours prior to challenge with LPS. Mice are monitored every ~4 hours during daytime, to check for death events. Percentage of mice surviving LPS challenge is determined.

In separate experiments, peritoneal lavage fluid (PLF) is collected. Supernatants are stored at −20° C. for cytokine analysis by ELISA; pelleted cells are counted to quantify inflammatory cells recruited in the peritoneal cavity. Similar studies can be conducted to test the efficacy of TREM2 antibodies in other models of infection (see, e.g., Sun et al., (2013) *Invest Ophthalmol Vis Sci.* 17; 54(5):3451-62).

Example 61: Analysis of the Protective Effect of Antagonist TREM2 Antibodies in Acute and Chronic Colitis To evaluate the ability of antagonist anti-TREM2 antibodies to delay, prevent, or treat colitis, preclinical mouse models of acute or chronic colitis are used. For DSS-induced colitis, mice receive 3% DSS in drinking water ad libitum for 8 days. For TNBS-induced colitis, mice are anesthetized and treated with an intra-rectal injection of 3 mg TNBS in 20% ethanol (vol/vol) or vehicle alone as a control. For the chronic colitis model, all mice are treated with 3 cycles of 2% DSS for 5 days, followed by a 10-day recovery period. For all models, weight loss, stool consistency, and presence of fecal occult blood are monitored daily and used to calculate the disease activity index, as described (see, e.g., Correale C, 2013, *Gastroenterology*, February 2013, pp. 346-356.e3).

Cohorts of mice are treated with antagonist anti-TREM2 antibodies every day starting from day 0 and subjected to DSS or TNBS administration. Mice are monitored every day, to check for weight loss, stool consistency, and presence of fecal occult blood were monitored daily and used to calculate the disease activity index, as described (see, e.g., S. Vetrano, *Gastroenterology*, 135 (2008), pp. 173-184).

In separate experiments, endoscopic and histological images of mucosal damage are collected to evaluate inflammatory cell infiltration and mucosal damage. Similar studies can be conducted to test the benefit of TREM2 antibodies in other models of autoimmunity including Crohn's disease, inflammatory bowel disease, and ulcerative colitis (see, e.g., Low et al., (2013) *Drug Des Devel Ther.;* 7: 1341-1357; and Sollid et al., (2008) *PLoS Med* 5(9): e198).

Example 62: Analysis of the Protective Effect of Agonist TREM2 Antibodies in Wound Healing To evaluate the ability of agonistic anti-TREM2 antibodies to increase colonic wound repair following injury, a mouse model of biopsy injury in the colon is used. In this model, the endoscope with outer operating sheath is inserted to the mid-descending colon and the mucosa is surveyed to the ano-rectal junction. Then, a single full thickness area of the entire mucosa and submucosa is removed with flexible biopsy forceps with a diameter of 3 French, avoiding penetration of the muscularis propria. Each mouse is biopsy injured at 3-5 sites along the dorsal side of the colon (see, e.g., Seno H, 2008, *Proc Natl Acad Sci USA.* 2009 Jan. 6; 106(1): 256-261).

Cohorts of mice are treated with agonist anti-TREM2 antibodies 2 or 3 days after biopsy injury. Mice are monitored every day for 15 days, to check for weight loss and wound healing by measuring the surface area of lesions.

Example 63: Analysis of the Protective Effect of Antagonist TREM2 Antibodies in Retinal Degeneration Antagonist TREM2 antibodies decrease the accumulation and/or function of inflammatory macrophages, and as a result delay, prevent and/or treat age-related macular degeneration (AMD).

AMD is a degenerative disease of the outer retina. It is thought that inflammation, particularly inflammatory cytokines and macrophages, contribute to AMD disease progression.

The presence of macrophages in the proximity of AMD lesions is documented, in the drusen, Bruch's membrane, choroid and retina. Macrophages release tissue factor (TF) and vascular endothelial growth factor (VEGF), which triggers the expansion of new blood vessels formation in patients showing choroidal neovasulcarization.

The type of macrophage present in the macular choroid changes with age, displaying elevated levels of M2 macrophages in older eyes compared to younger eyes. However, advanced AMD maculae had higher M1 to M2 rations compared to normal autopsied eyes of similar age. (see, e.g., Cao X et al, (2011), *Pathol Int* 61(9): pp 528-35). This suggests a link between classical M1 macrophage activation in the eye in the late onset of AMD progression.

Retinal microglia cells are tissue-resident macrophages that are also normally present in the inner retina. In the event of damage, microglia can be activated and act as mediator of inflammation. Activated microglia has been detected in the AMD tissue samples and has been proposed as one potential contributor of inflammatory processed that lead to AMD pathogenesis (Gupta et al., (2003) *Exp Eye Res.,* 76(4):463-71). The ability of antagonist TREM2 antibodies to prevent, delay, or reverse AMD is tested in one or more of AMD models (see, e.g., Pennesi et al., (2012) *Mol Aspects Med.;* 33(4): 487-509).

Overall inflammatory macrophages (either M1 and/or activated microglia) are documented to correlate with AMD disease progression and therefore represent a therapeutic target for antagonist TREM2 antibodies. Similar therapeutic benefit can be achieved in glaucoma and genetic forms or retinal degeneration such as retinitis pigmentosa.

The ability of antagonist TREM2 antibodies to prevent, delay, or reverse retinal ganglion cell degeneration in glaucoma is tested in a glaucoma model (see, e.g., El-Danaf et al., (2015). *J Neurosci.* 11; 35(6):2329-43). Likewise, the theraputic benefit of REM2 in genetically induced retinal degeneration and retinitis pigmentosa is tested as described in Chang et al., (2002) Vision Res.; 42(4):517-25, and in "Retinal Degeneration Rat Model Resource Availability of P23H and S334ter Mutant Rhodopsin Transgenic Rats and RCS Inbred and RCS Congenic Strains of Rats," MM LaVail, Jun. 30, 2011.

Example 64: Analysis of the Protective Effect of Antagonist TREM2 Antibodies in Adipogenesis and Diet-Induced Obesity To test the effect of antagonist TREM2 antibodies in adipogenesis and obesity, a mouse model of high-fat diet (HFD) is used (see, e.g., Park et al., (2015) Diabetes. 64(1):117-27).

Example 65: Analysis of the Protective Effect of TREM2 Antibodies in Malaria TREM2 expression in the nonparenchymal liver cells closely correlates with resistance to liver stage infection with the maliaria agent *Plasmodium berghei* (Gongalves et al., (2013) *Proc Natl Acad Sci* 26; 110(48):19531-6). Without wishing to be bound to theory, it is believed that TREM2 antibodies increase resistence to liver stage infection with *P. berghei*.

The ability of TREM2 antibodies to increase resistance to malaria infection is tested as described in Goncalves et al., (2013) *Proc Natl Acad Sci* 26; 110(48):19531-6. Briefly, GFP-expressing *P. berghei* ANKA sporozoites are obtained by dissection of infected salivary glands from *Anopheles stephensi* mosquitoes. Sporozoite suspensions in RPMI medium are injected i.v. in 100 μL of inocula containing $10^4$ sporozoites per mouse. Livers are collected at 40 h after injection or survival, and parasitemia is followed for 28 days. For experimental cerebral malaria scoring, neurologic symptoms are monitored from day 5 after injection.

Example 66: Analysis of the Protective Effect of Antagonist TREM2 Antibodies in Osteoporosis Bone is a dynamic organ constantly remodeled to support calcium homeostasis and structural needs. The osteoclast is the cell responsible for removing both the organic and inorganic components of bone. The osteoclast is derived from hematopoietic progenitors in the macrophage lineage and differentiates in response to the tumor necrosis factor family cytokine receptor activators of NFκB ligand. Osteoclasts, the only bone-resorbing cells, are central to the pathogenesis of osteoporosis and osteopetrosis (Novack et al., (2008) *Annual Rev Pathol.,* 3:457-84).

Osteoporosis is a progressive bone disease that is characterized by a decrease in bone mass and density which can lead to an increased risk of fracture. It is mostly manifested in the first years following menopause, when bone turnover is accelerated, with increased activity of both osteoclasts and osteoblasts. Owing to an imbalance in the processes of resorption and synthesis, however, the net effect is bone loss, which is largely trabecular. Thus, the most prevalent sites of fracture in osteoporosis are the wrist, femoral neck, and vertebral bodies, in which the trabecular structure is key to overall bone strength. Accelerated osteoclast differentiation and increased bone resorption capacity, resulting in osteoporosis have been described in animal models lacking the expression of TREM2 (Otero et al (2012) *J Immunol.* 188, 2612-2621).

Reduced osteoclast function results in osteopetrosis, with increased bone mass and elimination of bone marrow space, as observed in animal models lacking DAP12 ITAM signaling adapter and resulting in a significant defect in differentiation of osteoclast-like cells (Koga, et al., (2004) *Nature* 428: 758-763).

Without wishing to be bound by theory, it is believed that administering an antagonist anti-TREM2 antibody of the present disclosure can prevent, reduce the risk of, and/or treat osteoporosis. In some embodiments, administering an agonist anti-TREM2 antibody may induce one or more TREM2 activities in an individual having osteopetrosis (e.g., DAP12 phosphorylation, Syk activation, and accelerated differentiation into osteoclasts) (Peng et al (2010). *Sci Signal.* 2010 18; 3 122; and Humphrey et al., (2006) *J Bone Miner Res.,* 21(2):237-45).

Example 67: Ability of Ab22 and Ab45 TREM2 Antibodies to Block Induction of TREM2-Dependent Gene Expression Antibodies Ab22 and Ab45 were tested for their ability to block induction of TREM2-dependent gene expression by lipid ligands using a Luciferase reporter system.

Phosphatidylserine (PS, Avanti Lipids) and Sphingomyelin (SM, Avanti Lipids) were dissolved in methanol and plated onto Immulon 96 well plates. Methanol was evaporated overnight at RT and cells were added the next day. BWZ cells expressing mouse TREM2 and DAP12 in conjunction with an NFAT:luciferase reporter (Qiagen) were harvested and added at 100,000 cells/well in DMEM+1% FBS. Cells were either plated alone or in combination with 50 or 5 nM human IgG. After six hours, luciferase activity was measured using OneGlo reagent (Promega) and a Biotek plate reader, according to the manufacturer's instructions.

Ab45 blocked the induction of TREM2 dependent gene expression by both PS and SM, as indicated by a decrease in luminescence (FIG. 33).

Example 68: Analysis of the Ability of TREM2 Antibodies to Induce TREM2-Dependent Cytokine Genes The ability of plate bound anti-TREM2 Fab antibodies Ab22 and Ab65 to activate TREM2-dependent genes was evaluated using primary mouse macrophages.

Bone marrow-derived macrophages (BMDM) were generated with M-CSF for 5 days. BMDM ($10^5$/well) was seeded on 96 well plates that had been previously coated with the Fab portion of the antibodies Ab22 and Ab65 (50 nM). Ultrapure LPS (100 ng/ml *Escherichia coli* 0111:B4) was added after the plates were spun for 1 min at 1200 rpm. After 18 h of stimulation with LPS, cytokines present in cell supernatants were measured with cytometric bead array (CBA; BD Biosciences, CBA mouse inflammation kit).

As shown in FIGS. 34A and 34B, plate bound anti-TREM2 Fab antibody Ab22 increased the levels of IL-6 and MCP-1, indicating that the antibodies were able to activate TREM2-dependent cytokine genes in primary immune cells.

What is claimed is:

1. An isolated antibody that binds to a TREM2 protein, wherein the isolated antibody promotes survival of one or more innate immune cells selected from the group consisting of macrophages and microglial cells, wherein the isolated antibody comprises a heavy chain variable domain and a light chain variable domain, wherein:

(a) the heavy chain variable domain comprises an HVR-H1 comprising the amino acid sequence of SEQ ID NO: 404 or the amino acid sequence of SEQ ID NO: 404 having one or more conservative amino acid substitutions, an HVR-H2 comprising the amino acid sequence of SEQ ID NO: 405 or the amino acid sequence of SEQ ID NO: 405 having one or more conservative amino acid substitutions, and an HVR-H3 comprising the amino acid sequence of SEQ ID NO: 406 or the amino acid sequence of SEQ ID NO: 406 having one or more conservative amino acid substitutions, and the light chain variable domain comprises an HVR-L1 comprising the amino acid sequence of SEQ ID NO: 407 or the amino acid sequence of SEQ ID NO: 407 having one or more conservative amino acid substitutions, an HVR-L2 comprising the amino acid sequence of SEQ ID NO: 408 or the amino acid sequence of SEQ ID NO: 408 having one or more conservative amino acid substitutions, and an HVR-L3 comprising the amino acid sequence of SEQ ID NO: 409 or the amino acid sequence of SEQ ID NO: 409 having one or more conservative amino acid substitutions;

(b) the heavy chain variable domain comprises an HVR-H1 comprising the amino acid sequence of SEQ ID NO: 11 or the amino acid sequence of SEQ ID NO: 11 having one or more conservative amino acid substitutions, an HVR-H2 comprising the amino acid sequence of SEQ ID NO: 34 or the amino acid sequence of SEQ ID NO: 34 having one or more conservative amino acid substitutions, and an HVR-H3 comprising the amino acid sequence of SEQ ID NO: 60 or the amino acid sequence of SEQ ID NO: 60 having one or more conservative amino acid substitutions, and the light chain variable domain comprises an HVR-L1 comprising the amino acid sequence of SEQ ID NO: 123 or the amino acid sequence of SEQ ID NO: 123 having one or more conservative amino acid substitutions, an HVR-L2 comprising the amino acid sequence of SEQ ID NO: 141 or the amino acid sequence of SEQ ID NO: 141 having one or more conservative amino acid substitutions, and an HVR-L3 comprising the amino acid sequence of SEQ ID NO: 173 or the amino acid sequence of SEQ ID NO: 173 having one or more conservative amino acid substitutions;

(c) the heavy chain variable domain comprises an HVR-H1 comprising the amino acid sequence of SEQ ID NO: 7 or the amino acid sequence of SEQ ID NO: 7 having one or more conservative amino acid substitutions, an HVR-H2 comprising the amino acid sequence of SEQ ID NO: 29 or the amino acid sequence of SEQ ID NO: 29 having one or more conservative amino acid substitutions, and an HVR-H3 comprising the amino acid sequence of SEQ ID NO: 87 or the amino acid sequence of SEQ ID NO: 87 having one or more conservative amino acid substitutions, and the light chain variable domain comprises an HVR-L1 comprising the amino acid sequence of SEQ ID NO: 120 or the amino acid sequence of SEQ ID NO: 120 having one or more conservative amino acid substitutions, an HVR-L2 comprising the amino acid sequence of SEQ ID NO: 138 or the amino acid sequence of SEQ ID NO: 138 having one or more conservative amino acid substitutions, and an HVR-L3 comprising the amino acid sequence of SEQ ID NO: 196 or the amino acid sequence of SEQ ID NO: 196 having one or more conservative amino acid substitutions;

(d) the heavy chain variable domain comprises an HVR-H1 comprising the amino acid sequence of SEQ ID NO: 398 or the amino acid sequence of SEQ ID NO: 398 having one or more conservative amino acid substitutions, an HVR-H2 comprising the amino acid sequence of SEQ ID NO: 399 or the amino acid sequence of SEQ ID NO: 399 having one or more conservative amino acid substitutions, and an HVR-H3 comprising the amino acid sequence of SEQ ID NO: 400 or the amino acid sequence of SEQ ID NO: 400 having one or more conservative amino acid substitutions, and the light chain variable domain comprises an HVR-L1 comprising the amino acid sequence of SEQ ID NO: 401 or the amino acid sequence of SEQ ID NO: 401 having one or more conservative amino acid substitutions, an HVR-L2 comprising the amino acid sequence of SEQ ID NO: 402 or the amino acid sequence of SEQ ID NO: 402 having one or more conservative amino acid substitutions, and an HVR-L3 comprising the amino acid sequence of SEQ ID NO: 403 or the amino acid sequence of SEQ ID NO: 403 having one or more conservative amino acid substitutions; or (e) the heavy chain variable domain comprises an HVR-H1 comprising the amino acid sequence of SEQ ID NO: 9 or the amino acid sequence of SEQ ID NO: 9 having one or more conservative amino acid substitutions, an HVR-H2 comprising the amino acid sequence of SEQ ID NO: 34 or the amino acid sequence of SEQ ID NO: 34 having one or more conservative amino acid substitutions, and an HVR-H3 comprising the amino acid sequence of SEQ ID NO: 101 or the amino acid sequence of SEQ ID NO: 101 having one or more conservative amino acid substitutions, and the light chain variable domain comprises an HVR-L1 comprising the amino acid sequence of SEQ ID NO: 124 or the amino acid sequence of SEQ ID NO: 124 having one or more conservative amino acid substitutions, an HVR-L2 comprising the amino acid sequence of SEQ ID NO: 144 or the amino acid sequence of SEQ ID NO: 144 having one or more conservative amino acid substitutions, and an HVR-L3 comprising the amino acid sequence of SEQ ID NO: 215 or the amino acid sequence of SEQ ID NO: 215 having one or more conservative amino acid substitutions.

2. The isolated antibody of claim 1, wherein:
(a) the heavy chain variable domain comprises an HVR-H1 comprising the amino acid sequence of SEQ ID NO: 404, an HVR-H2 comprising the amino acid sequence of SEQ ID NO: 405, and an HVR-H3 comprising the amino acid sequence of SEQ ID NO: 406, and the light chain variable domain comprises an HVR-L1 comprising the amino acid sequence of SEQ ID NO: 407, an HVR-L2 comprising the amino acid sequence of SEQ ID NO: 408, and an HVR-L3 comprising the amino acid sequence of SEQ ID NO: 409
(b) the heavy chain variable domain comprises an HVR-H1 comprising the amino acid sequence of SEQ ID NO: 11, an HVR-H2 comprising the amino acid sequence of SEQ ID NO: 34, and an HVR-H3 comprising the amino acid sequence of SEQ ID NO: 60, and the light chain variable domain comprises an HVR-L1 comprising the amino acid sequence of SEQ ID NO: 123, an HVR-L2 comprising the amino acid sequence of SEQ ID NO: 141, and an HVR-L3 comprising the amino acid sequence of SEQ ID NO: 173;
(c) the heavy chain variable domain comprises an HVR-H1 comprising the amino acid sequence of SEQ ID NO: 7, an HVR-H2 comprising the amino acid sequence of SEQ ID NO: 29, and an HVR-H3 comprising the amino acid sequence of SEQ ID NO: 87, and the light chain variable domain comprises an HVR-L1 comprising the amino acid sequence of SEQ ID NO: 120, an HVR-L2 comprising the amino acid sequence of SEQ ID NO: 138, and an HVR-L3 comprising the amino acid sequence of SEQ ID NO: 196;
(d) the heavy chain variable domain comprises an HVR-H1 comprising the amino acid sequence of SEQ ID NO: 398, an HVR-H2 comprising the amino acid sequence of SEQ ID NO: 399, and an HVR-H3 comprising the amino acid sequence of SEQ ID NO: 400, and the light chain variable domain comprises an HVR-L1 comprising the amino acid sequence of SEQ ID NO: 401, an HVR-L2 comprising the amino acid sequence of SEQ ID NO: 402, and an HVR-L3 comprising the amino acid sequence of SEQ ID NO: 403; or
(e) the heavy chain variable domain comprises an HVR-H1 comprising the amino acid sequence of SEQ ID NO: 9, an HVR-H2 comprising the amino acid sequence of SEQ ID NO: 34, and an HVR-H3 comprising the amino acid sequence of SEQ ID NO: 101, and the light chain variable domain comprises an HVR-L1 comprising the amino acid sequence of SEQ ID NO: 124, an HVR-L2 comprising the amino acid sequence of SEQ ID NO: 144, and an HVR-L3 comprising the amino acid sequence of SEQ ID NO: 215.

3. The isolated antibody of claim 1, wherein the antibody is an agonist antibody that induces one or more TREM2 activities, wherein the one or more TREM2 activities are selected from the group consisting of:
i) TREM2 binding to DAP12;
ii) DAP12 phosphorylation;
iii) increasing the survival of M1 microglial cells, activated M1 microglial cells, M2 microglial cells, dendritic cells, M1 macrophages, activated M1 macrophages, M2 macrophages, monocytes, osteoclasts, Langerhans cells of skin, and/or Kupffer cells;
iv) Syk phosphorylation;
v) increased expression of CD83 and/or CD86 on dendritic cells;
vi) increasing phagocytosis by macrophages, dendritic cells, monocytes, and/or microglia;
vii) increasing activity of one or more TREM2-dependent genes, optionally wherein the one or more TREM2-dependent genes comprise one or more nuclear factor of activated T-cells (NFAT) transcription factors; and
viii) increasing expression of one or more mediators selected from the group consisting of IL-12p70, IL-6, and IL-10.

4. The isolated antibody of claim 1, wherein the isolated antibody induces or retains TREM2 clustering on a cell surface.

5. The isolated antibody of claim 1, wherein the isolated antibody is of the IgG class, the IgM class, or the IgA class.

6. The isolated antibody of claim 5, wherein the isolated antibody is of the IgG class and has an IgG1, IgG2, IgG3, or IgG4 isotype.

7. The isolated antibody of claim 6, wherein:
i) the isolated antibody has a human IgG2 isotype and comprises one or more amino acid substitutions in the Fc region at a residue position selected from the group consisting of V234A, G237A, H268Q, V309L, A330S, P331S, C232S, C233S, S267E, L328F, M252Y, S254T, T256E, and any combination thereof, wherein the numbering of the residues is according to the EU numbering system;
ii) the isolated antibody has a human IgG2 isotype, wherein the human IgG2 comprises a constant region, and wherein the human IgG2 constant region comprises a light chain constant region comprising a C214S amino acid substitution, wherein the numbering of the residues is according to the EU numbering system;

iii) the isolated antibody has a human or mouse IgG1 isotype and comprises one or more amino acid substitutions in the Fc region at a residue position selected from the group consisting of N297A, D265A, L234A, L235A, G237A, C226S, C229S, E233P, L234V, L234F, L235E, P331S, S267E, L328F, A330L, M252Y, S254T, T256E, and any combination thereof, wherein the numbering of the residues is according to the EU numbering system;

iv) the isolated antibody has an IgG1 isotype and comprises an IgG2 isotype heavy chain constant domain 1(CH1) and hinge region, optionally wherein the IgG2 isotype CH1 and hinge region comprise the amino acid sequence of ASTKGPSVFP LAPCSRSTSE STAAL-GCLVK DYFPEPVTVS WNSGALT-SGVHTFPAVLQSS GLYSLSSVVT VPSSNFGTQT YTCNVDHKPS NTKVDKTVERKCCVECPPCP (SEQ ID NO: 397), and optionally wherein the antibody Fc region comprises a S267E amino acid substitution, a L328F amino acid substitution, or both, and/or a N297A or N297Q amino acid substitution, wherein the numbering of the residues is according to the EU numbering system;

v) the isolated antibody has a human or mouse IgG4 isotype and comprises one or more amino acid substitutions in the Fc region at a residue position selected from the group consisting of L235A, G237A, S228P, L236E, S267E, E318A, L328F, M252Y, S254T, T256E, and any combination thereof, wherein the numbering of the residues is according to the EU numbering system; or vi) the isolated antibody has a hybrid IgG2/4 isotype, optionally wherein the antibody comprises an amino acid sequence comprising amino acids 118 to 260 of human IgG2 and amino acids 261 to 447 of human IgG4, wherein the numbering of the residues is according to the EU numbering system.

8. The isolated antibody of claim 7, wherein the Fc region further comprises one or more additional amino acid substitutions at a position selected from the group consisting of A330L, L234F; L235E, P331S, and any combination thereof, wherein the numbering of the residues is according to the EU numbering system.

9. The isolated antibody of claim 7, wherein the Fc region further comprises a S228P amino acid substitution according to the EU numbering system.

10. The isolated antibody of claim 7, wherein the Fc region further comprises one or more additional amino acid substitutions at a position selected from the group consisting of M252Y, S254T, T256E, and any combination thereof, wherein the numbering of the residues is according to the EU numbering system.

11. The isolated antibody of claim 1, wherein the isolated antibody is an antibody fragment that binds to one or more human proteins selected from the group consisting of a wild-type human TREM2 and a naturally occurring variant of human TREM2, and wherein the antibody fragment is cross-linked to a second antibody fragment that binds to one or more human proteins selected from the group consisting of a wild-type human TREM2, a naturally occurring variant of human TREM2, a wild-type human DAP12, and naturally occurring variant of human DAP12.

12. The isolated antibody of claim 1, wherein the isolated antibody is an antibody fragment, and wherein the antibody fragment is an Fab, Fab', Fab'-SH, F(ab')2, Fv or scFv fragment.

13. The isolated antibody of claim 1, wherein the isolated antibody competes for binding of TREM2 with one or more TREM2 ligands, wherein the one or more TREM2 ligands are selected from the group consisting of E. coli cells, apoptotic cells, nucleic acids, anionic lipids, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide.

14. The isolated antibody of claim 1, wherein the isolated antibody is a human antibody, a humanized antibody, a bispecific antibody, a multivalent antibody, or a chimeric antibody.

15. The isolated antibody of claim 1, wherein the isolated antibody is a bispecific antibody recognizing a first antigen and a second antigen, wherein the first antigen is a wild-type human TREM2 or a naturally occurring variant thereof, and the second antigen is DAP12 or a disease-causing protein selected from the group consisting of amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides; or a blood brain barrier targeting protein selected from the group consisting of: transferrin receptor, insulin receptor, insulin like growth factor receptor, LRP-1, and LRP1.

16. The isolated antibody of claim 1, wherein the isolated antibody is an antibody fragment that binds to one or more human proteins selected from the group consisting of a wild-type human TREM2 and a naturally occurring variant of human TREM2; and wherein the antibody is used in combination with one or more antibodies that specifically bind a disease-causing protein selected from the group consisting of: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, and any combination thereof.

17. The isolated antibody of claim 1, wherein the isolated antibody is a monoclonal antibody.

18. The isolated antibody of claim 1, wherein the isolated antibody binds specifically to both human TREM2 and mouse TREM2.

19. The isolated antibody of claim 1, wherein the isolated antibody:
  i) has a dissociation constant (KD) for human TREM2 and mouse TREM2 that ranges from less than about 5.75 nM to less than about 0.09 nM;
  ii) has a dissociation constant (KD) for human TREM2-Fc fusion protein that ranges from less than about 1.51 nM to less than about 0.35 nM;
  iii) has a dissociation constant (KD) for human monomeric TREM2 protein that ranges from less than about 5.75 nM to less than about 1.15 nm; and/or
  iv) has a dissociation constant (KD) for mouse TREM2-Fc fusion protein that ranges from less than about 0.23 nM to less than about 0.09 nM.

20. The isolated antibody of claim 1, wherein the antibody is recombinantly produced.

21. A pharmaceutical composition comprising the antibody of claim 1 and a pharmaceutically acceptable carrier.

22. The isolated antibody of claim 1, wherein the isolated antibody does not compete for binding of TREM2 with one or more TREM2 ligands.

23. The isolated antibody of claim 1, wherein the isolated antibody binds to one or more amino acids within amino acid residues selected from the group consisting of:
  i) amino acid residues 43-50 of SEQ ID NO: 1, or amino acid residues on a TREM2 protein corresponding to amino acid residues 43-50 of SEQ ID NO: 1;
  ii) amino acid residues 49-57 of SEQ ID NO: 1, or amino acid residues on a TREM2 protein corresponding to amino acid residues 49-57 of SEQ ID NO: 1; and
  iii) amino acid residues 140-153 of SEQ ID NO: 1, or amino acid residues on a TREM2 protein corresponding to amino acid residues 140-153 of SEQ ID NO: 1.

24. The isolated antibody of claim 1, wherein the isolated antibody binds to one or more amino acids within amino acid residues 140-153 of SEQ ID NO: 1 or amino acid residues on a TREM2 protein corresponding to amino acid residues 140-153 of SEQ ID NO: 1.

25. The isolated antibody of claim 1, wherein the isolated antibody binds to an epitope of human TREM2 that is the same as the TREM2 epitope bound by a reference anti-TREM2 antibody, wherein the reference anti-TREM2 antibody comprises a light chain variable domain and a heavy chain variable domain, wherein the light chain variable domain comprises: an HVR-L1 comprising the amino acid sequence of SEQ ID NO: 120, an HVR-L2 comprising the amino acid sequence of SEQ ID NO: 138, and an HVR-L3 comprising the amino acid sequence of SEQ ID NO: 196, and wherein the heavy chain variable domain comprises: an HVR-H1 comprising the amino acid sequence of SEQ ID NO: 7, an HVR-H2 comprising the amino acid sequence of SEQ ID NO: 29, and an HVR-H3 comprising the amino acid sequence of SEQ ID NO: 87.

26. The isolated antibody of claim 1, wherein the antibody binds to an epitope of human TREM2 that is the same as the TREM2 epitope bound by a reference anti-TREM2 antibody, wherein the reference anti-TREM2 antibody comprises a light chain variable domain and a heavy chain variable domain, wherein the light chain variable domain comprises: an HVR-L1 comprising the amino acid sequence of SEQ ID NO: 124, an HVR-L2 comprising the amino acid sequence of SEQ ID NO: 144, and an HVR-L3 comprising the amino acid sequence of SEQ ID NO: 215, and wherein the heavy chain variable domain comprises: an HVR-H1 comprising the amino acid sequence of SEQ ID NO: 9, an HVR-H2 comprising the amino acid sequence of SEQ ID NO: 34, and an HVR-H3 comprising the amino acid sequence of SEQ ID NO: 101.

\* \* \* \* \*